(12) United States Patent
Lee et al.

(10) Patent No.: US 12,089,493 B2
(45) Date of Patent: Sep. 10, 2024

(54) HETEROCYCLIC COMPOUND AND ORGANIC LIGHT EMITTING DEVICE COMPRISING SAME

(71) Applicant: LT MATERIALS CO., LTD., Yongin (KR)

(72) Inventors: Nam-Jin Lee, Osan-si (KR); Young-Jin Lee, Osan-si (KR); Won-Jang Jeong, Hwaseong-si (KR)

(73) Assignee: LT MATERIALS CO., LTD., Yongin (KR)

( * ) Notice: Subject to any disclaimer, the term of this patent is extended or adjusted under 35 U.S.C. 154(b) by 672 days.

(21) Appl. No.: 17/288,746

(22) PCT Filed: Nov. 12, 2019

(86) PCT No.: PCT/KR2019/015311
§ 371 (c)(1),
(2) Date: Apr. 26, 2021

(87) PCT Pub. No.: WO2020/101316
PCT Pub. Date: May 22, 2020

(65) Prior Publication Data
US 2022/0123225 A1    Apr. 21, 2022

(30) Foreign Application Priority Data

Nov. 12, 2018   (KR) .......................... 10-2018-0138481

(51) Int. Cl.
*H10K 85/60*    (2023.01)
*C07D 471/10*    (2006.01)
(Continued)

(52) U.S. Cl.
CPC ......... *H10K 85/657* (2023.02); *C07D 471/10* (2013.01); *C07D 491/107* (2013.01);
(Continued)

(58) Field of Classification Search
CPC .............. C07D 471/10; C07D 491/107; C07D 495/10; H10K 85/657; H10K 85/6572; H10K 85/6574; H10K 85/6576
See application file for complete search history.

(56) References Cited

U.S. PATENT DOCUMENTS 4,356,429 A    10/1982    Tang
10,177,319 B2 *  1/2019    No ........................ C07D 471/04
(Continued)

FOREIGN PATENT DOCUMENTS

CN            107325084 A    11/2017
KR    10-2014-0076522 A     6/2014
(Continued)

OTHER PUBLICATIONS

International Search Report (PCT/ISA/210) issued in PCT/KR2019/015311, dated Feb. 21, 2020.
(Continued)

*Primary Examiner* — Vu A Nguyen
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

13 Claims, 3 Drawing Sheets

(51) Int. Cl.
  *C07D 491/107* (2006.01)
  *C07D 495/10* (2006.01)
  *C07D 519/00* (2006.01)
  *C07F 9/6561* (2006.01)
  *C09K 11/06* (2006.01)
  *H10K 50/18* (2023.01)
  *H10K 50/19* (2023.01)

(52) U.S. Cl.
  CPC ......... *C07D 495/10* (2013.01); *C07D 519/00* (2013.01); *C07F 9/6561* (2013.01); *C09K 11/06* (2013.01); *H10K 85/615* (2023.02); *H10K 85/622* (2023.02); *H10K 85/654* (2023.02); *H10K 85/6572* (2023.02); *H10K 85/6574* (2023.02); *H10K 85/6576* (2023.02); *C09K 2211/1018* (2013.01); *H10K 50/18* (2023.02); *H10K 50/19* (2023.02)

(56) References Cited

U.S. PATENT DOCUMENTS 10,316,013 B2  6/2019  Kim et al.
2017/0179395 A1  6/2017  Kim et al.

FOREIGN PATENT DOCUMENTS

| KR | 10-2014-0136117 A | 11/2014 |
| KR | 10-2016-0029635 A | 3/2016 |
| KR | 10-2017-0059910 A | 5/2017 |
| KR | 10-2017-0076123 A | 7/2017 |
| KR | 10-2018-0037695 A | 4/2018 |
| WO | WO 2016/068633 A2 | 5/2016 |

OTHER PUBLICATIONS

Kuwabara et al., "Thermally Stable Multilayered Organic Electroluminescent Devices Using Novel Starburst Molecules, 4,4',"-Tri(N-carbazolyl)triphenylamine (TCTA) and 4,4',4"-Tris(3-methylphenylphenyl-amino)phenylamine (m-MTDATA), as Hole-Transport Materials" Advanced Material 1994 vol. 6. No. 9. pp. 677-679.

* cited by examiner

[FIG. 1]
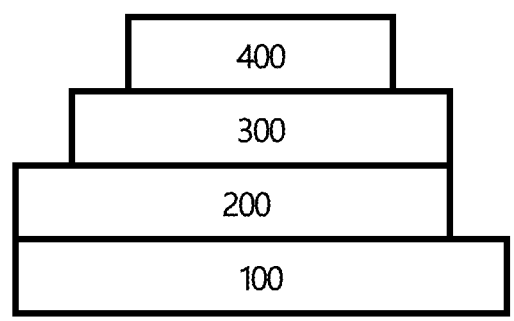
[FIG. 2]
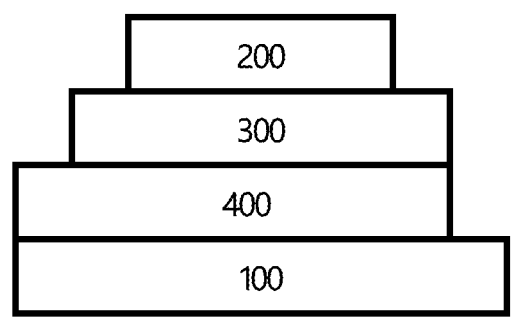

[FIG. 3]
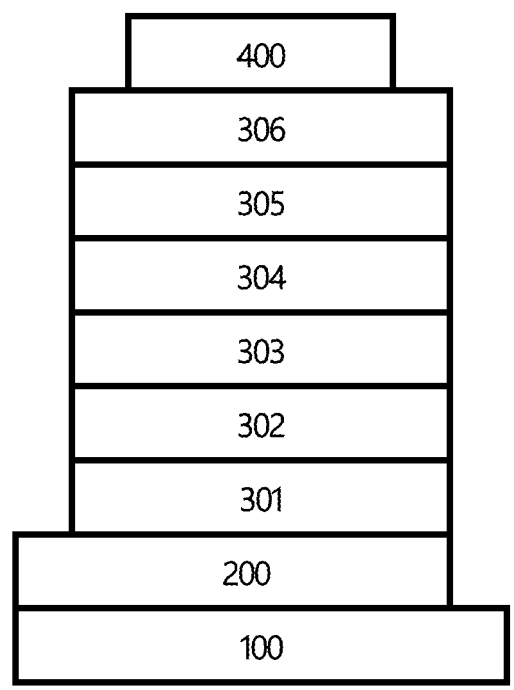

[FIG. 4]

| CATHODE |
|---|
| ELECTRON INJECTION LAYER |
| SECOND ELECTRON TRANSFER LAYER |
| SECOND HOLE BLOCKING LAYER |
| SECOND STACK LIGHT EMITTING LAYER |
| SECOND ELECTRON BLOCKING LAYER |
| SECOND HOLE TRANSFER LAYER |
| P-TYPE CHARGE GENERATION LAYER |
| N-TYPE CHARGE GENERATION LAYER |
| FIRST ELECTRON TRANSFER LAYER |
| FIRST HOLE BLOCKING LAYER |
| FIRST STACK LIGHT EMITTING LAYER |
| FIRST ELECTRON BLOCKING LAYER |
| FIRST HOLE TRANSFER LAYER |
| FIRST HOLE INJECTION LAYER |
| ANODE |
| SUBSTRATE |

HETEROCYCLIC COMPOUND AND ORGANIC LIGHT EMITTING DEVICE COMPRISING SAME

TECHNICAL FIELD

This application claims priority to and the benefits of Korean Patent Application No. 10-2018-0138481, filed with the Korean Intellectual Property Office on Nov. 12, 2018, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents (Patent Document 1) U.S. Pat. No. 4,356,429

DISCLOSURE

Technical Problem

The present specification is directed to providing a heterocyclic compound, and an organic light emitting device comprising the same.

Technical Solution

One embodiment of the present specification provides a heterocyclic compound represented by the following Chemical Formula 1.

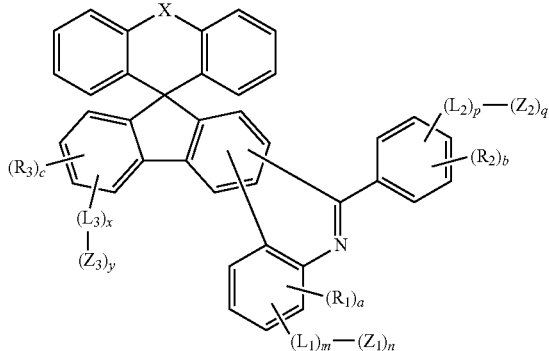

[Chemical Formula 1]

In Chemical Formula 1,

X is O; S; or $NR_{21}$, $L_1$ to $L_3$ are the same as or different from each other, and each independently a direct bond; a substituted or unsubstituted arylene group; or a substituted or unsubstituted heteroarylene group, $Z_1$ to $Z_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, $R_1$ to $R_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heterering, $R_{21}$ is hydrogen; or a substituted or unsubstituted aryl group, m, p, x, n, q and y are each an integer of 1 to 5, a is an integer of 1 to 3, b is an integer of 1 to 4, c is an integer of 1 to 3, and when m, p, x, n, q, y, a, b and c are an integer of 2 or greater, substituents in the parentheses are the same as or different from each other.

Another embodiment of the present specification provides an organic light emitting device comprising a first electrode; a second electrode; and one or more organic material layers provided between the first electrode and the second electrode, wherein one or more layers of the organic material layers comprise the heterocyclic compound represented by Chemical Formula 1.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like. Particularly, the compound can be used as an electron transfer material, a hole blocking layer material or a charge generation layer material of an organic light emitting device.

Specifically, when using the compound represented by Chemical Formula 1 in an organic material layer, a device driving voltage can be lowered, light efficiency can be enhanced, and device lifetime properties can be enhanced.

DESCRIPTION OF DRAWINGS

FIG. 1 to FIG. 4 are diagrams each illustrating a lamination structure of an organic light emitting device according to one embodiment of the present specification.

REFERENCE NUMERAL

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, the present specification will be described in more detail.

In the present specification, a certain part "comprising" certain constituents means capable of further comprising other constituents, and does not exclude other constituents unless particularly stated on the contrary.

A term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the cycloalkyl group comprises monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent comprising Si, having the Si atom directly linked as a radical, and is represented by $-SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

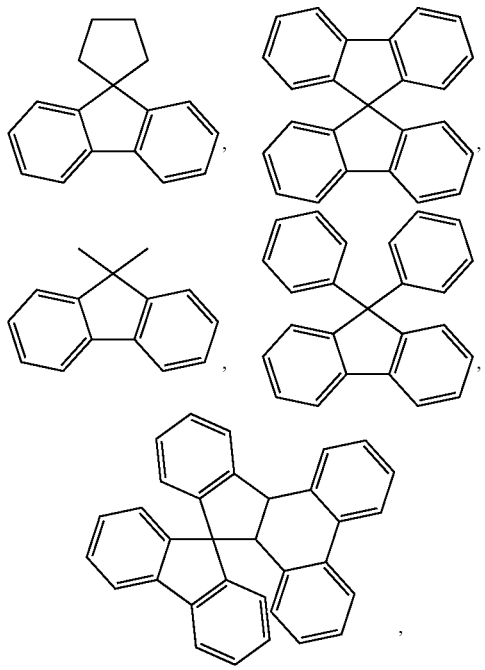

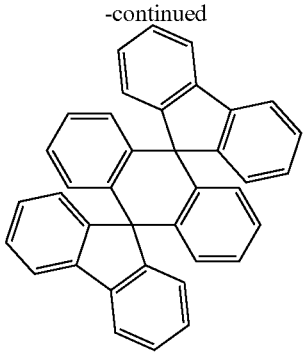

and the like may be included, however, the structure is not limited thereto.

In the present specification, the heteroaryl group comprises O, S, Se, N or Si as a heteroatom, comprises monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the phosphine oxide group may be specifically substituted with an aryl group, and as the aryl group, examples described above may be used. Examples of the phosphine oxide group may comprise a diphenylphosphine oxide group, a dinaphthylphosphine oxide group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

As the aliphatic or aromatic hydrocarbon ring or heteroring that the adjacent groups may form, the structures illustrated as the cycloalkyl group, the cycloheteroalkyl group, the aryl group and the heteroaryl group may be used except for those that are not monovalent.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(=O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted. R, R' and R" are the same as or different from each other, and each independently hydrogen; deuterium; a cyano group; a substituted or unsubstituted alkyl group; a substituted or unsubstituted cycloalkyl group; a substituted or unsubstituted aryl group; or a substituted or unsubstituted heteroaryl group.

One embodiment of the present specification provides a compound represented by Chemical Formula 1.

By having a structure in which a heteroring is fused to spirofluorene, Chemical Formula 1 has an excellent electron transfer ability as a hopping ability is enhanced by an expansion of conjugation, and as a result, driving and efficiency may be improved when used in a device.

In the heterocyclic compound provided in one embodiment of the present specification, Chemical Formula 1 is represented by any one of the following Chemical Formulae 2 to 5.

[Chemical Formula 2]

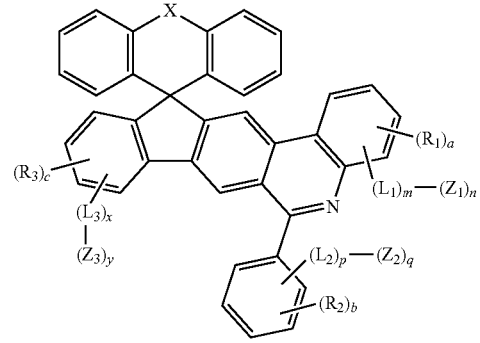

[Chemical Formula 3]

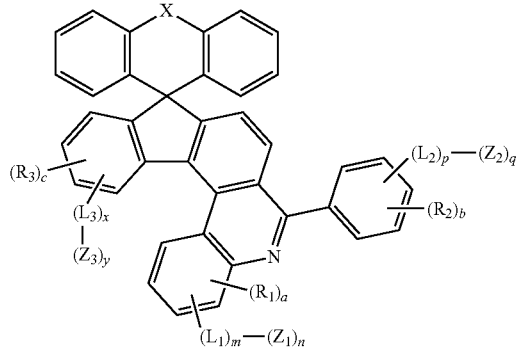

[Chemical Formula 4]

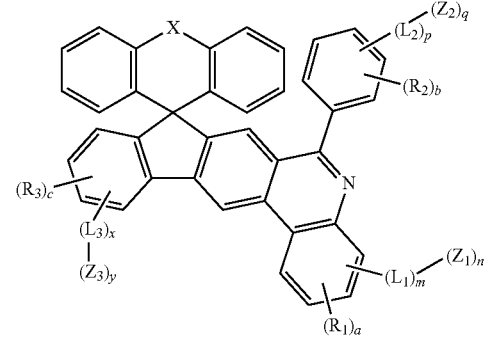

[Chemical Formula 5]

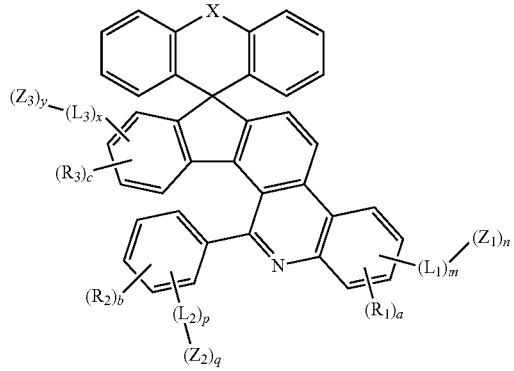

In Chemical Formula 2 to Chemical Formula 5,
each substituent has the same definition as in Chemical Formula 1.

In one embodiment of the present specification, X may be O; S; or $NR_{21}$.

In another embodiment, X may be O.

In another embodiment, X may be S.

In another embodiment, X may be $NR_{21}$.

In one embodiment of the present specification, $R_{21}$ may be hydrogen; or a substituted or unsubstituted aryl group.

In another embodiment, $R_{21}$ may be a substituted or unsubstituted aryl group.

In another embodiment, $R_{21}$ may be a phenyl group.

In one embodiment of the present specification, $L_1$ to $L_3$ are the same as or different from each other, and may be each independently a direct bond; a substituted or unsubstituted arylene group; or a substituted or unsubstituted heteroarylene group.

In another embodiment, $L_1$ to $L_3$ are the same as or different from each other, and may be each independently a direct bond; a substituted or unsubstituted C6 to C60 arylene group; or a substituted or unsubstituted C2 to C60 heteroarylene group.

In another embodiment, $L_1$ to $L_3$ are the same as or different from each other, and may be each independently a direct bond; a substituted or unsubstituted C6 to C40 arylene group; or a substituted or unsubstituted C2 to C40 heteroarylene group.

In another embodiment, $L_1$ to $L_3$ are the same as or different from each other, and may be each independently a direct bond; a substituted or unsubstituted C6 to C20 arylene group; or a substituted or unsubstituted C2 to C20 heteroarylene group.

In another embodiment, $L_1$ to $L_3$ are the same as or different from each other, and may be each independently a direct bond; a C6 to C20 arylene group; or a C2 to C20 heteroarylene group.

In another embodiment, $L_1$ to $L_3$ are the same as or different from each other, and may be each independently a direct bond; a phenylene group; a biphenylene group; a naphthylene group; an anthracene group; a phenanthrene group; a divalent pyrimidine group; a divalent triazine group; a divalent pyridine group; a divalent quinazoline group; or a divalent quinoxaline group.

In one embodiment of the present specification, $Z_1$ to $Z_3$ are the same as or different from each other, and may be each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group.

In another embodiment, $Z_1$ to $Z_3$ are the same as or different from each other, and may be each independently hydrogen; deuterium; a cyano group; a substituted or unsubstituted aryl group; a substituted or unsubstituted heteroaryl group; or a substituted or unsubstituted phosphine oxide group.

In another embodiment, $Z_1$ to $Z_3$ are the same as or different from each other, and may be each independently hydrogen; deuterium; a cyano group; a substituted or unsubstituted C6 to C60 aryl group; a substituted or unsubstituted C2 to C60 heteroaryl group; or a substituted or unsubstituted phosphine oxide group.

In another embodiment, $Z_1$ to $Z_3$ are the same as or different from each other, and may be each independently hydrogen; deuterium; a cyano group; a substituted or unsubstituted C6 to C40 aryl group; a substituted or unsubstituted C2 to C40 heteroaryl group; or a substituted or unsubstituted phosphine oxide group.

In another embodiment, $Z_1$ to $Z_3$ are the same as or different from each other, and may be each independently hydrogen; deuterium; a cyano group; a C6 to C40 aryl group unsubstituted or substituted with one or more substituents selected from the group consisting of a C6 to C40 aryl group, a C2 to C40 heteroaryl group and a C1 to C40 alkyl group; a C2 to C40 heteroaryl group unsubstituted or substituted with one or more substituents selected from the group consisting of a C6 to C40 aryl group and a C1 to C40 alkyl group; or a substituted or unsubstituted phosphine oxide group.

In another embodiment, $Z_1$ to $Z_3$ are the same as or different from each other, and may be each independently hydrogen; deuterium; a cyano group; a phenyl group; a biphenyl group; an anthracene group; a triphenylene group; a dibenzofuran group; a dibenzothiophene group; a pyrimidine group unsubstituted or substituted with one or more substituents selected from the group consisting of a phenyl group, a biphenyl group, a dibenzofuran group and a dibenzothiophene group; a triazine group unsubstituted or substituted with one or more substituents selected from the group consisting of a phenyl group, a biphenyl group, a dibenzofuran group and a dibenzothiophene group; a phenanthroline group unsubstituted or substituted with a phenyl group; a quinazoline group unsubstituted or substituted with a phenyl group; a quinoxaline group unsubstituted or substituted with a phenyl group; a carbazole group unsubstituted or substituted with one or more substituents selected from the group consisting of a phenyl group and a cyano group; an imidazole group unsubstituted or substituted with a phenyl group; a pyridine group unsubstituted or substituted with a pyridine group; a benzo[4,5]thieno[3,2-d]pyrimidine group unsubstituted or substituted with a phenyl group; or a phosphine oxide group unsubstituted or substituted with a phenyl group.

In one embodiment of the present specification, $R_1$ to $R_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other may bond to each other to form a substituted or unsubstituted aliphatic or aromatic hydrocarbon ring or heteroring.

In another embodiment, $R_1$ to $R_3$ may be hydrogen.

In the heterocyclic compound provided in one embodiment of the present specification, Chemical Formula 1 is represented by any one of the following Chemical Formulae 6 to 8.

[Chemical Formula 6]

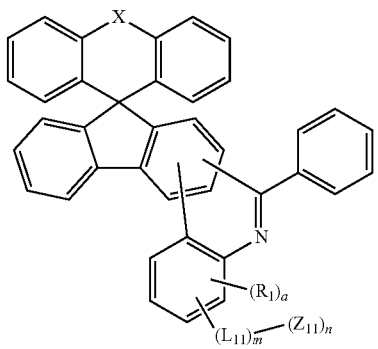

[Chemical Formula 7]

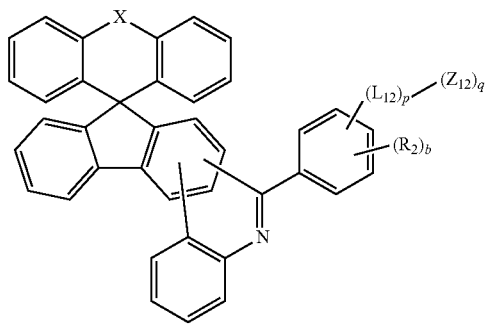

[Chemical Formula 8]

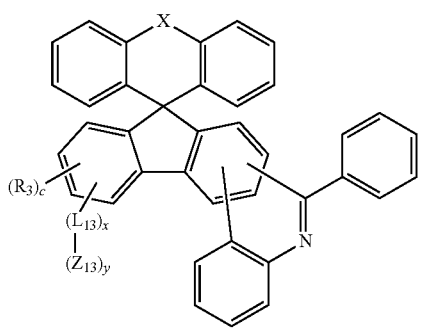

in Chemical Formulae 6 to 8,

X, $R_1$ to $R_3$, m, p, x, n, q, y, a, b and c have the same definitions as in Chemical Formula 1.

In one embodiment of the present specification, $L_{11}$ to $L_{13}$ are the same as or different from each other, and may be each independently a direct bond; a substituted or unsubstituted arylene group; or a substituted or unsubstituted heteroarylene group.

In another embodiment, $L_{11}$ to $L_{13}$ are the same as or different from each other, and may be each independently a direct bond; a substituted or unsubstituted C6 to C60 arylene group; or a substituted or unsubstituted C2 to C60 heteroarylene group.

In another embodiment, $L_{11}$ to $L_{13}$ are the same as or different from each other, and may be each independently a direct bond; a substituted or unsubstituted C6 to C40 arylene group; or a substituted or unsubstituted C2 to C40 heteroarylene group.

In another embodiment, $L_{11}$ to $L_{13}$ are the same as or different from each other, and may be each independently a direct bond; a substituted or unsubstituted C6 to C20 arylene group; or a substituted or unsubstituted C2 to C20 heteroarylene group.

In another embodiment, $L_{11}$ to $L_{13}$ are the same as or different from each other, and may be each independently a direct bond; a C6 to C20 arylene group; or a C2 to C20 heteroarylene group.

In another embodiment, $L_{11}$ to $L_{13}$ are the same as or different from each other, and may be each independently a direct bond; a phenylene group; a biphenylene group; a naphthylene group; an anthracene group; a phenanthrene group; a divalent pyrimidine group; a divalent triazine group; a divalent pyridine group; a divalent quinazoline group; or a divalent quinoxaline group.

In one embodiment of the present specification, $Z_{11}$ to $Z_{13}$ are the same as or different from each other, and may be each independently selected from the group consisting of a cyano group; a substituted or unsubstituted aryl group; a substituted or unsubstituted heteroaryl group; and a substituted or unsubstituted phosphine oxide group.

In another embodiment, $Z_{11}$ to $Z_{13}$ are the same as or different from each other, and may be each independently a cyano group; a substituted or unsubstituted C6 to C60 aryl group; a substituted or unsubstituted C2 to C60 heteroaryl group; or a substituted or unsubstituted phosphine oxide group.

In another embodiment, $Z_{11}$ to $Z_{13}$ are the same as or different from each other, and may be each independently a cyano group; a substituted or unsubstituted C6 to C40 aryl group; a substituted or unsubstituted C2 to C40 heteroaryl group; or a substituted or unsubstituted phosphine oxide group.

In another embodiment, $Z_{11}$ to $Z_{13}$ are the same as or different from each other, and may be each independently a cyano group; a C6 to C40 aryl group unsubstituted or substituted with one or more substituents selected from the group consisting of a C6 to C40 aryl group, a C2 to C40 heteroaryl group and a C1 to C40 alkyl group; a C2 to C40 heteroaryl group unsubstituted or substituted with one or more substituents selected from the group consisting of a C6 to C40 aryl group and a C1 to C40 alkyl group; or a substituted or unsubstituted phosphine oxide group.

In another embodiment, $Z_{11}$ to $Z_{13}$ are the same as or different from each other, and may be each independently a cyano group; a phenyl group; a biphenyl group; an anthracene group; a triphenylene group; a dibenzofuran group; a dibenzothiophene group; a pyrimidine group unsubstituted or substituted with one or more substituents selected from the group consisting of a phenyl group, a biphenyl group, a dibenzofuran group and a dibenzothiophene group; a triazine group unsubstituted or substituted with one or more substituents selected from the group consisting of a phenyl group, a biphenyl group, a dibenzofuran group and a dibenzothiophene group; a phenanthroline group unsubstituted or substituted with a phenyl group; a quinazoline group unsubstituted or substituted with a phenyl group; a quinoxaline group unsubstituted or substituted with a phenyl group; a carbazole group unsubstituted or substituted with one or more substituents selected from the group consisting of a phenyl group and a cyano group; an imidazole group unsubstituted or substituted with a phenyl group; a pyridine group unsubstituted or substituted with a pyridine group; a benzo[4,5]thieno[3,2-d]pyrimidine group unsubstituted or substituted with a phenyl group; or a phosphine oxide group unsubstituted or substituted with a phenyl group.

In one embodiment of the present specification, Chemical Formula 1 may be represented by any one of the following compounds, but is not limited thereto.

1
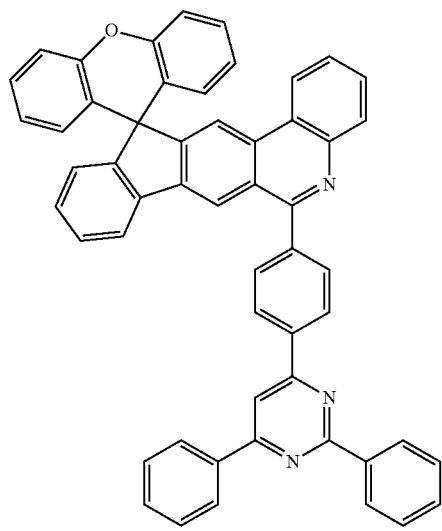
2
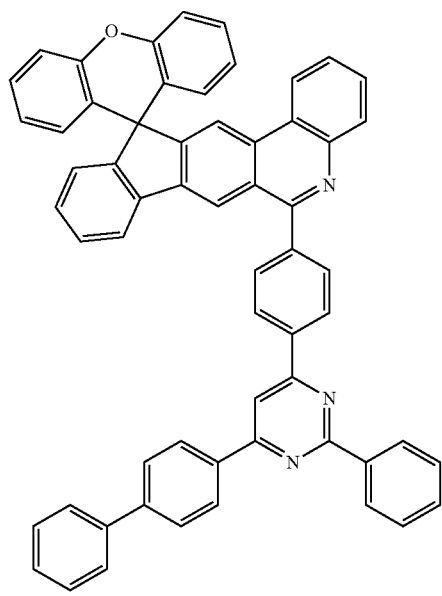
3
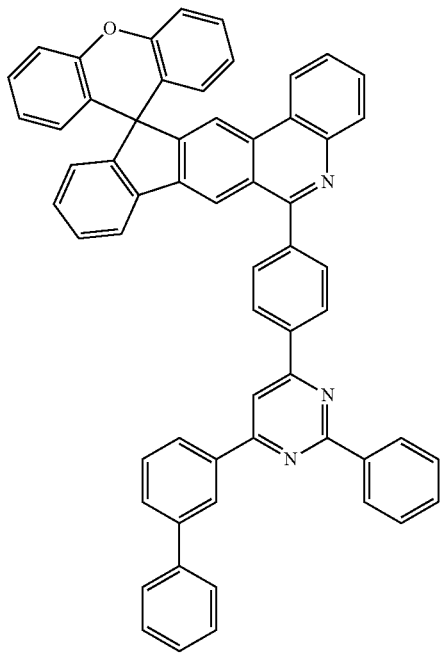
4
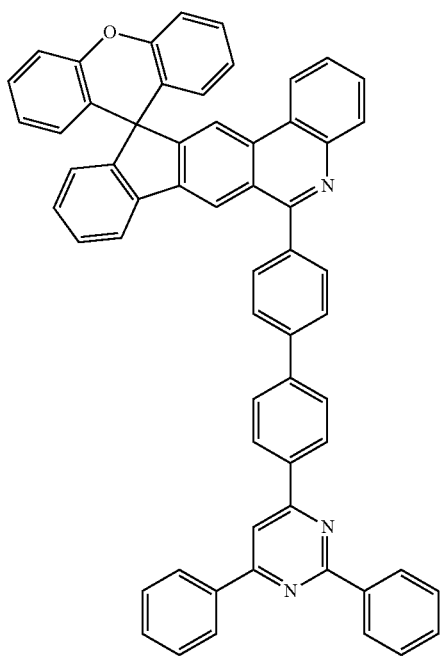

-continued
5
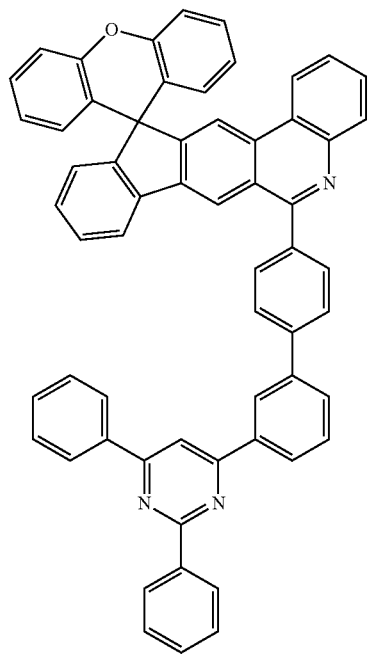
6
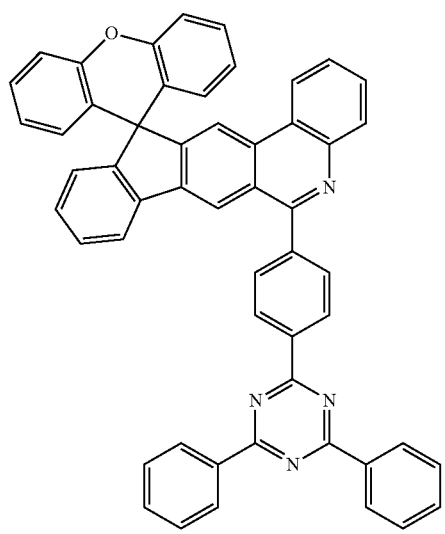
7
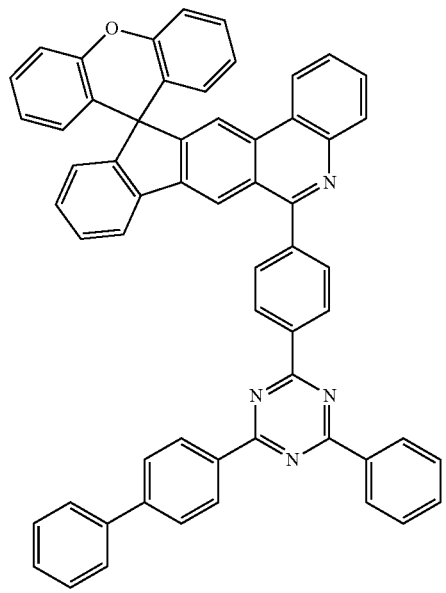
8
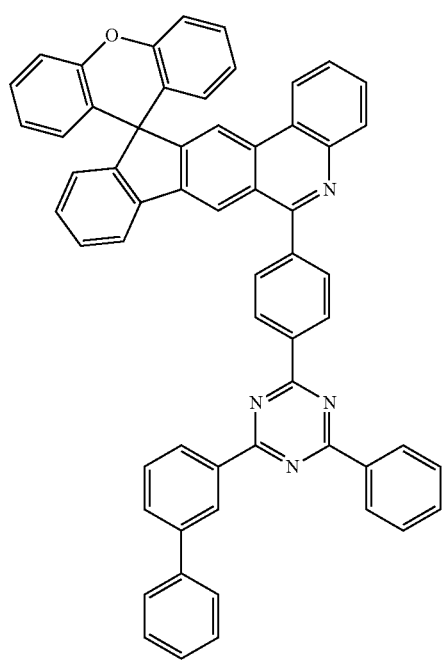

9
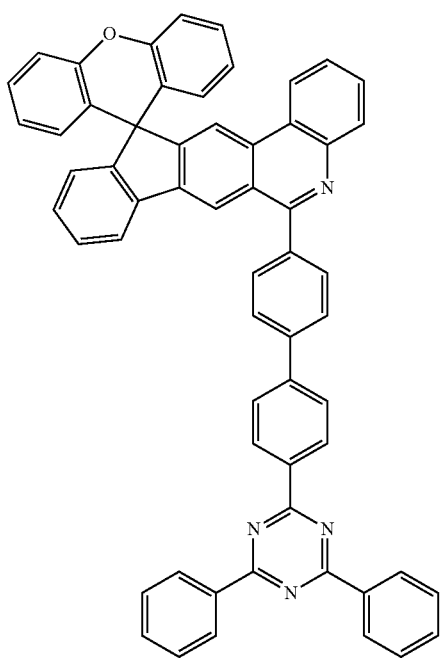
11
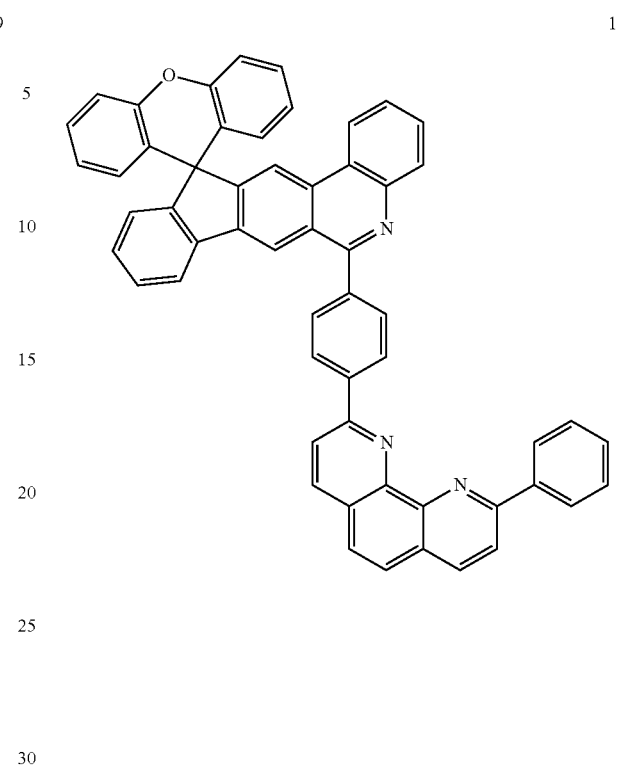
10
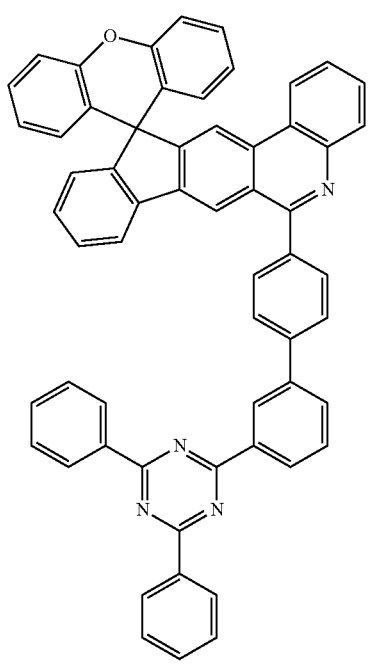
12
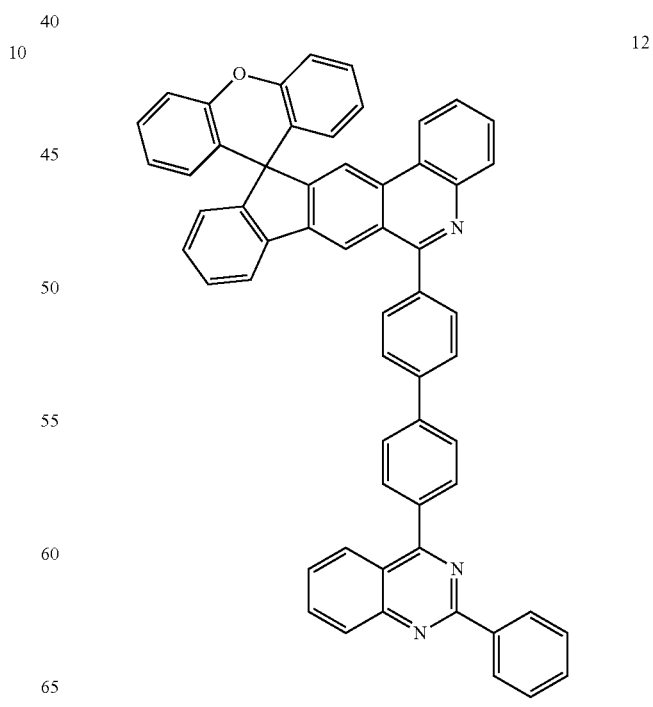

13
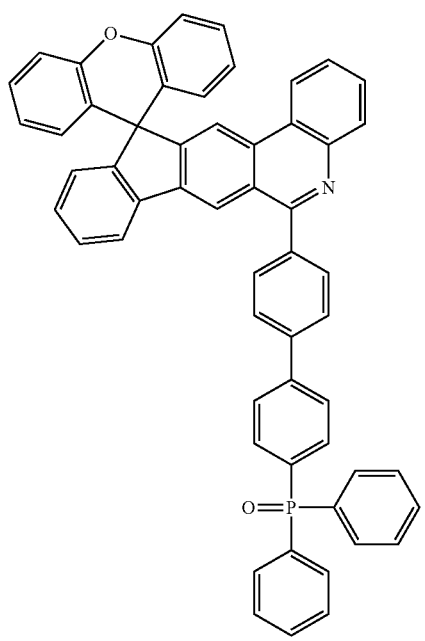
14
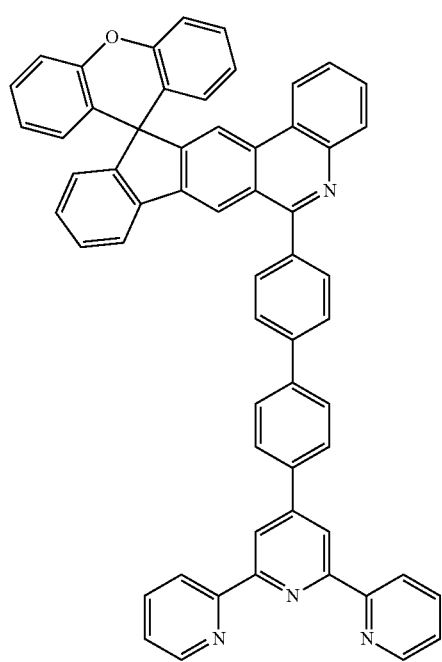
15
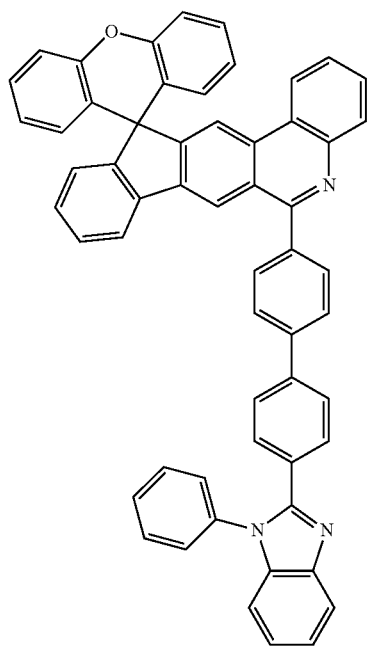
16
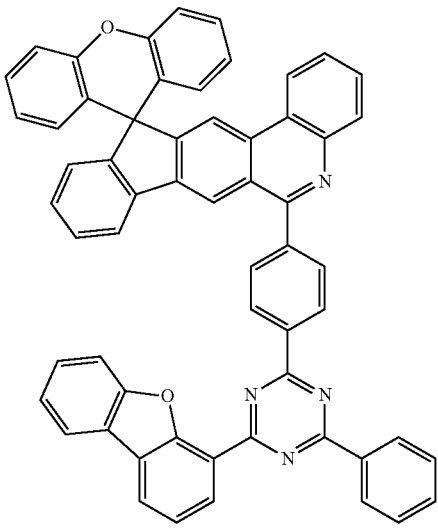

17
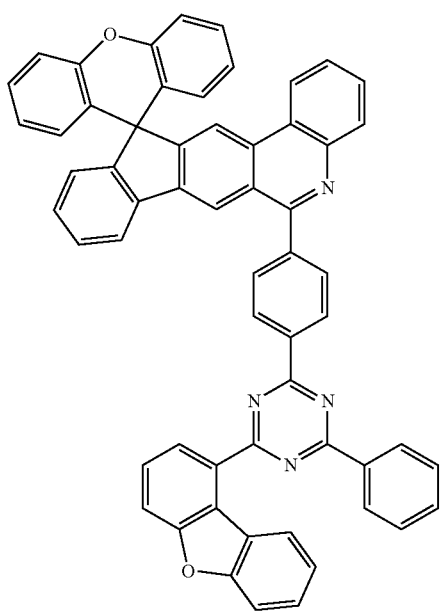
18
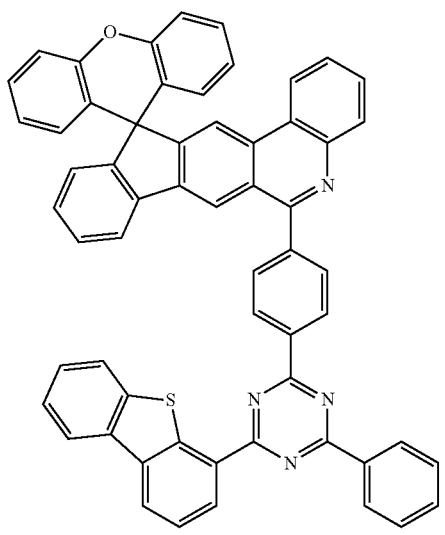
19
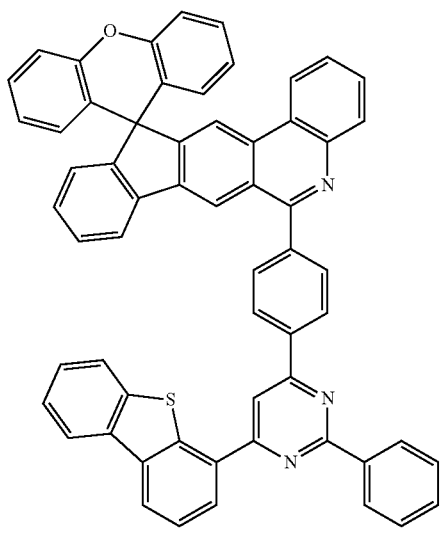
20
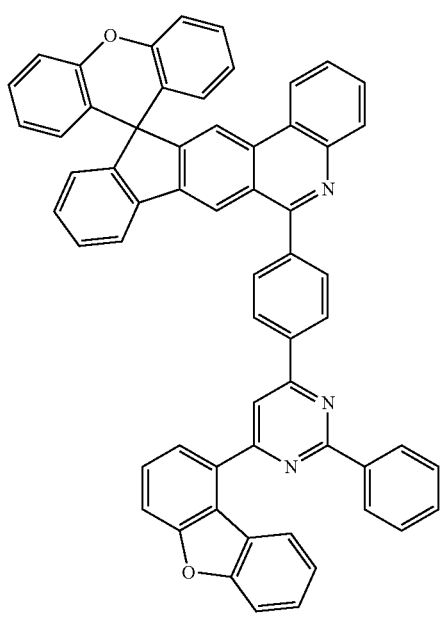
21
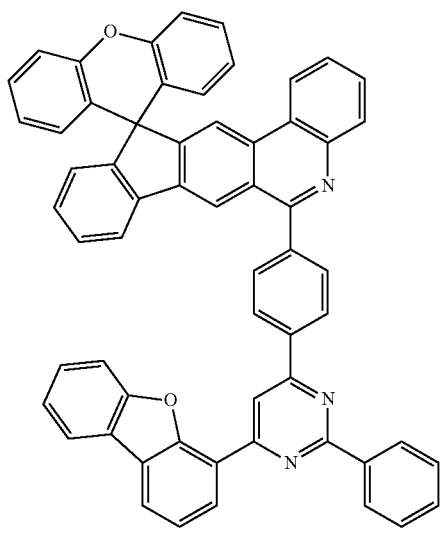
22
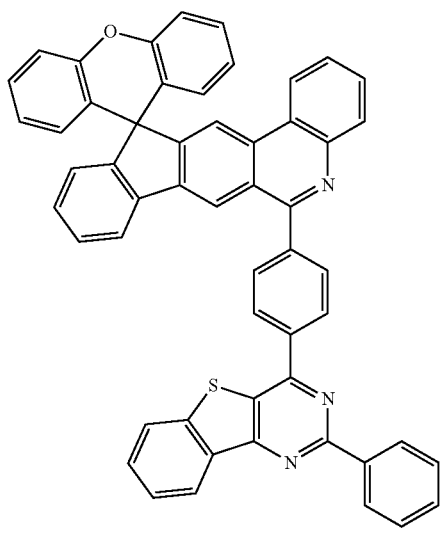

23
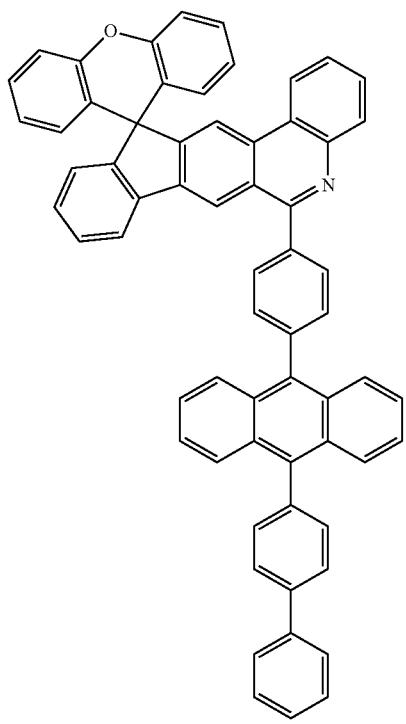
24
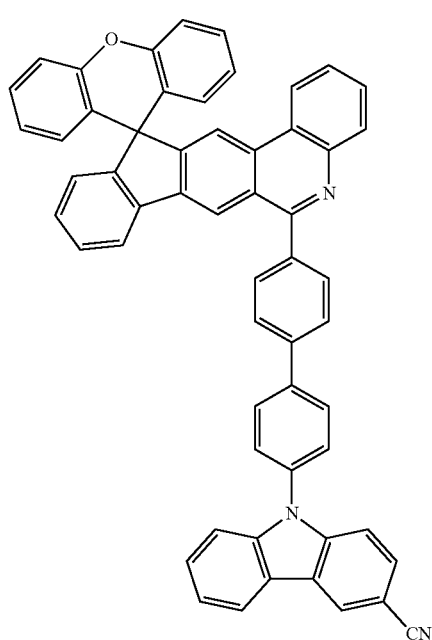
25
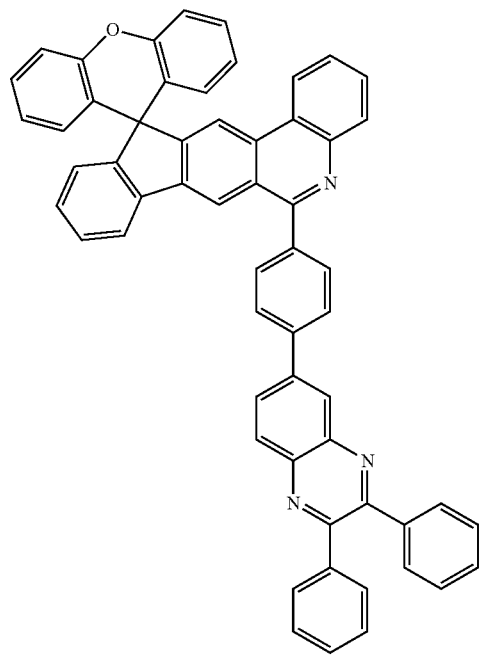
26
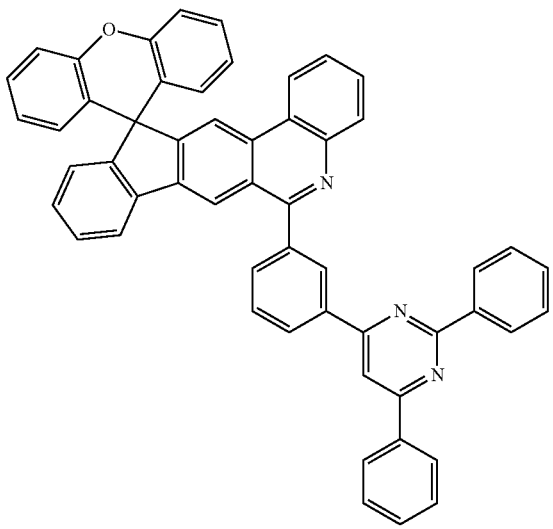

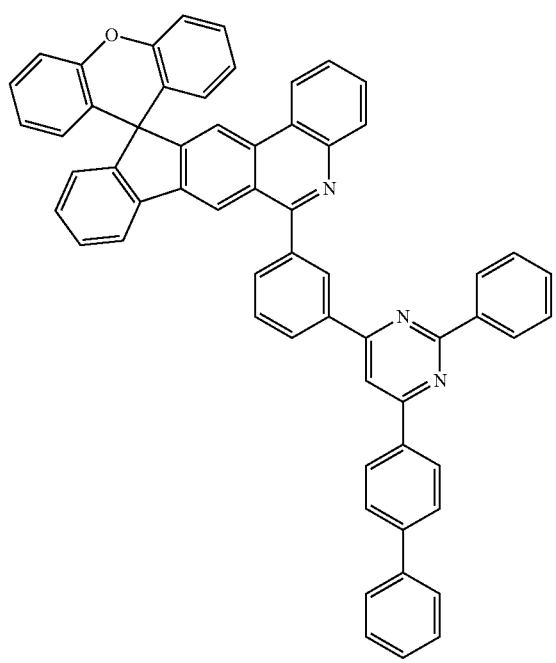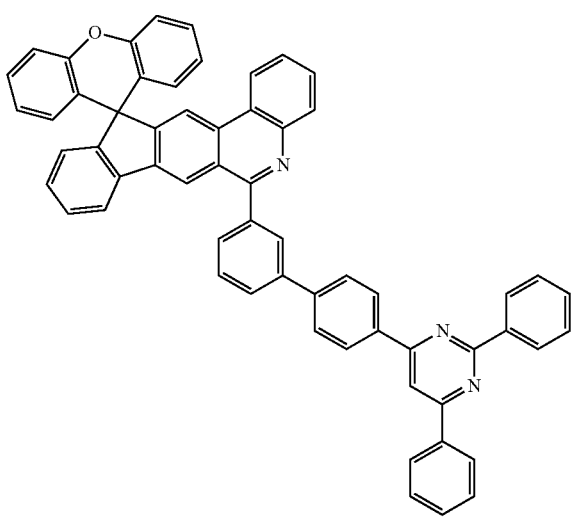

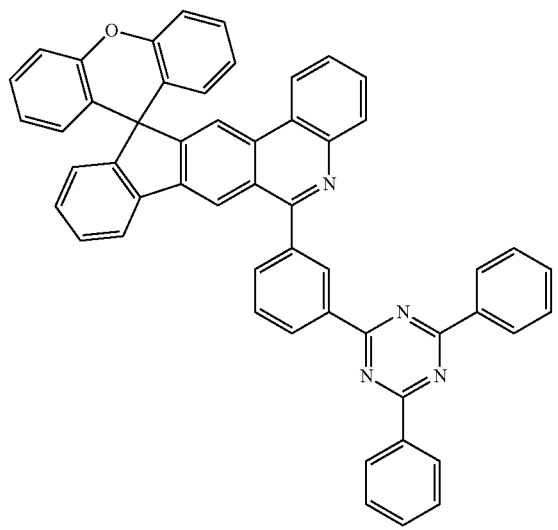
31
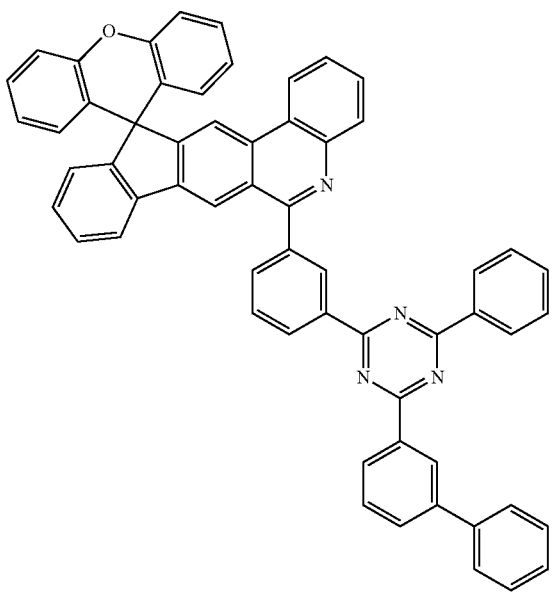
33
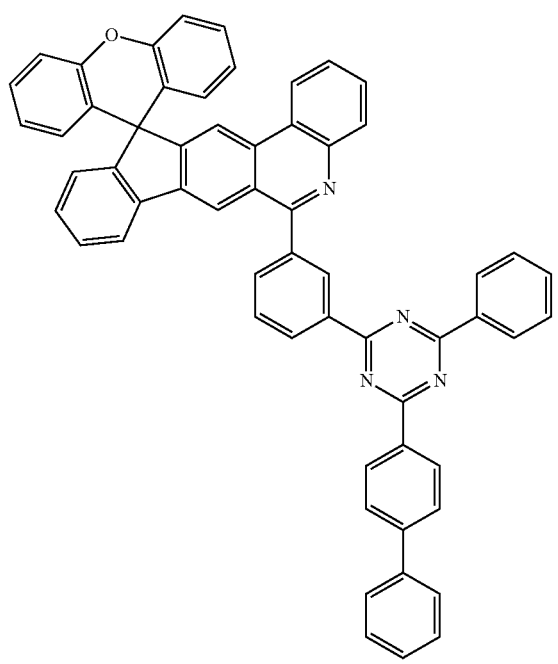
32
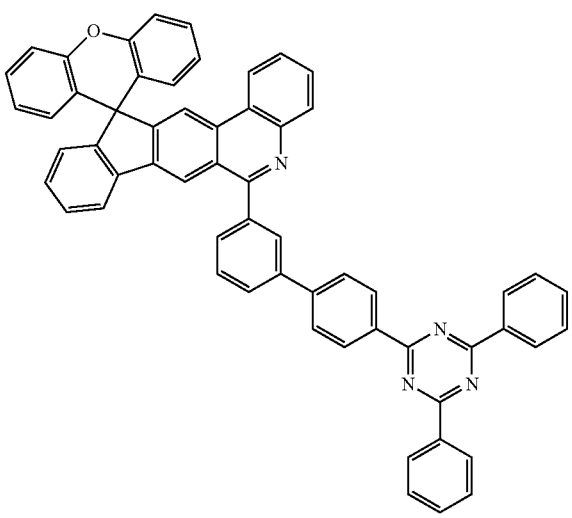
34

35
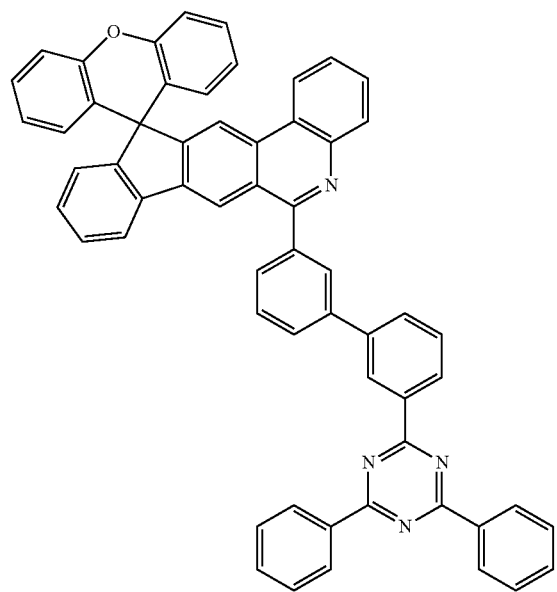
36
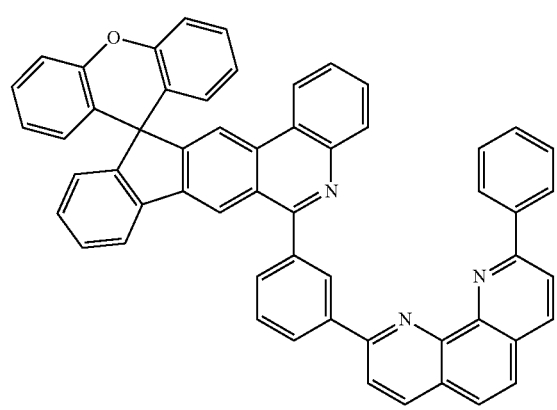
37
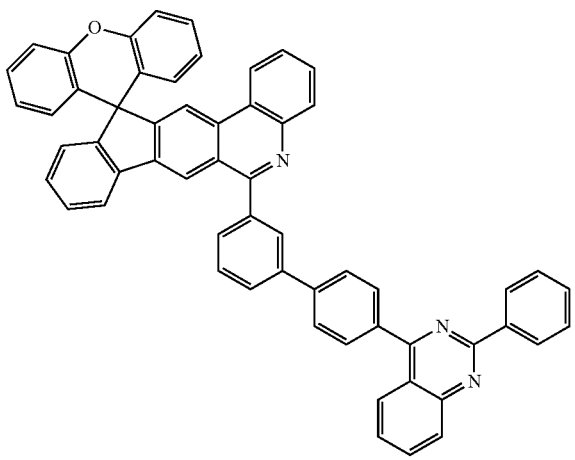
38
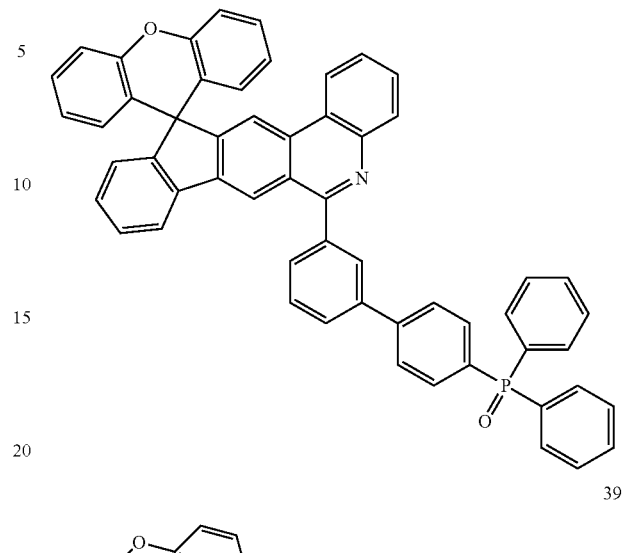
39
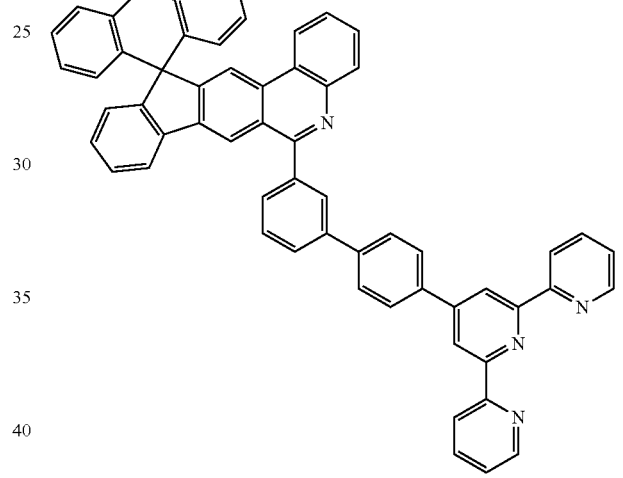
40
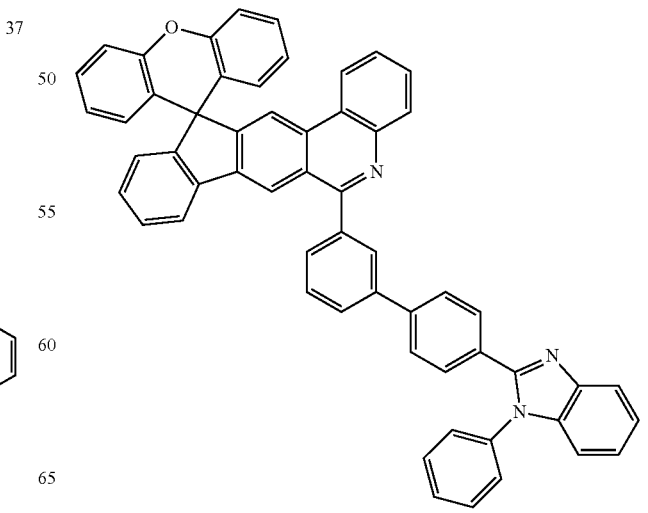

41
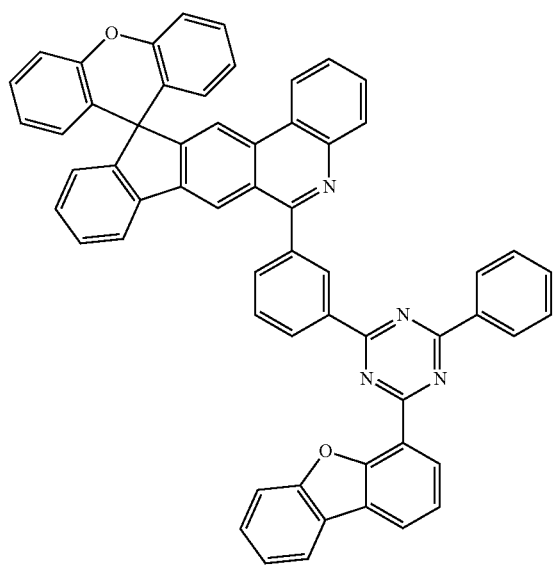
43
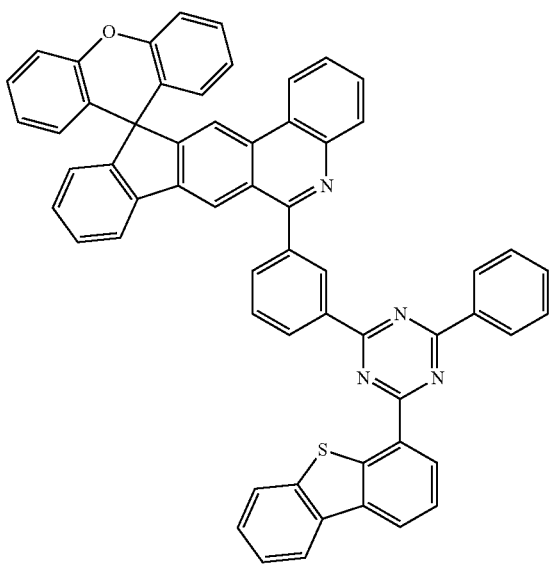
42
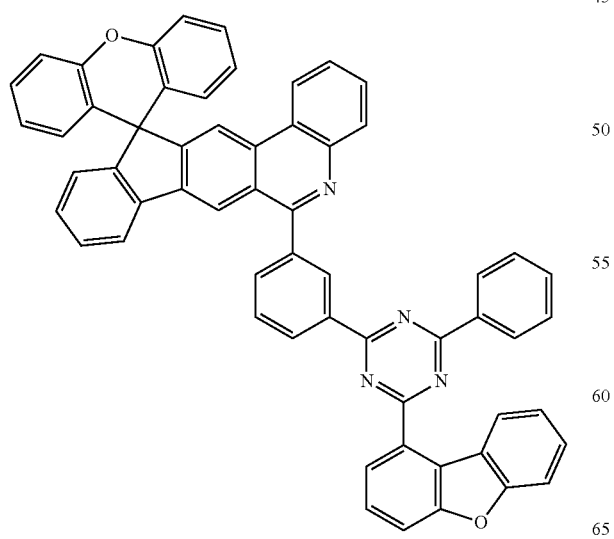
44
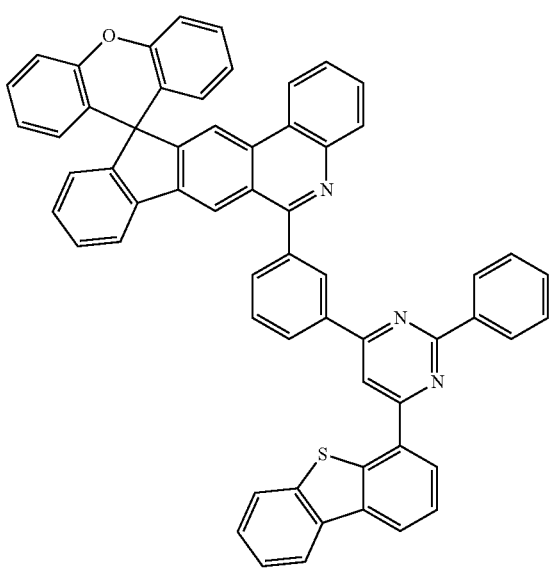

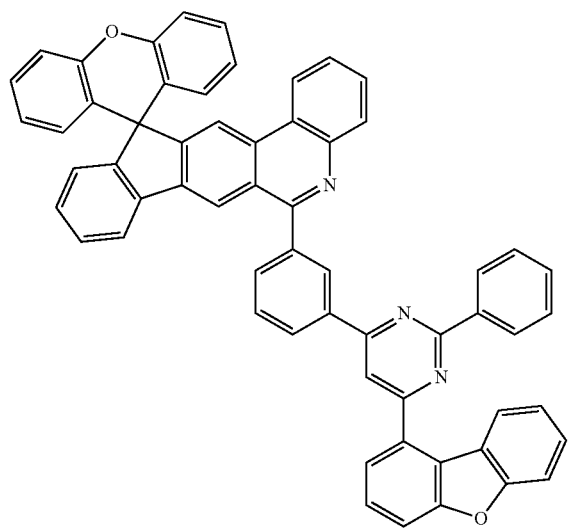
45
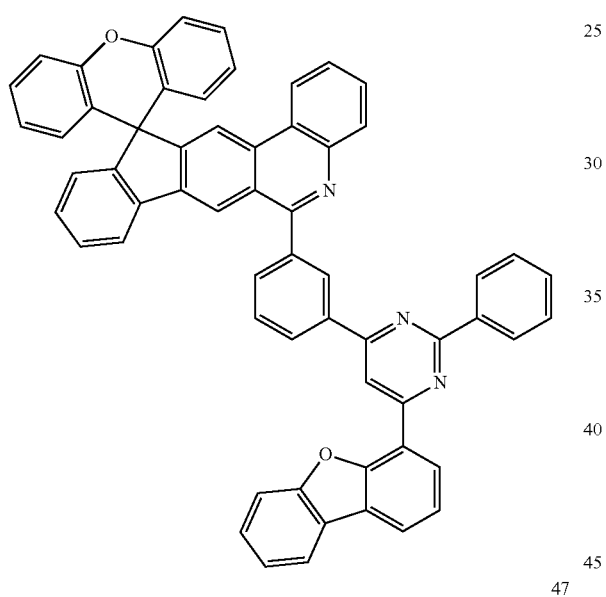
46
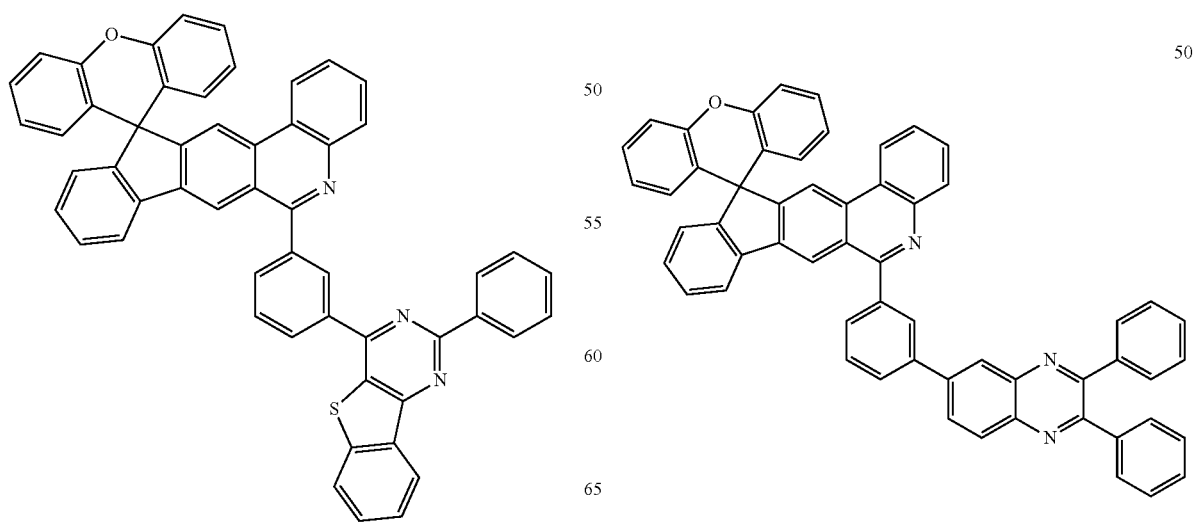
47
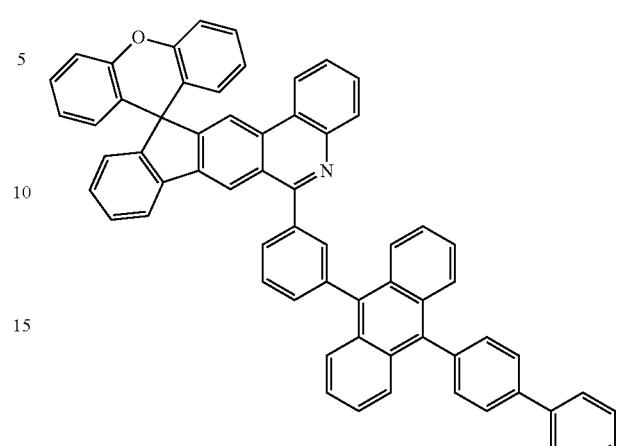
48
49
50

51
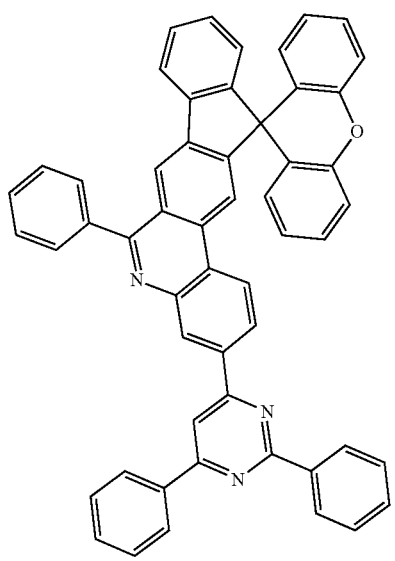
52
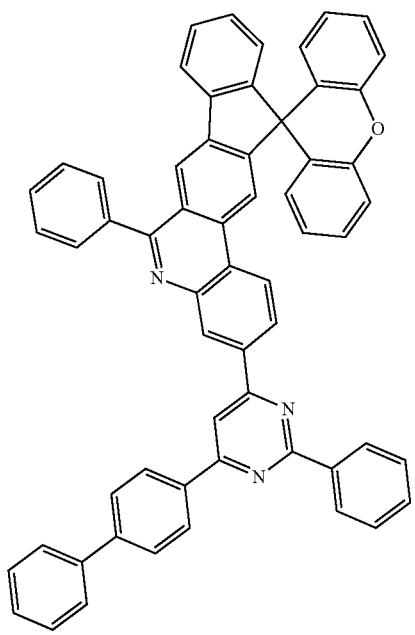
53
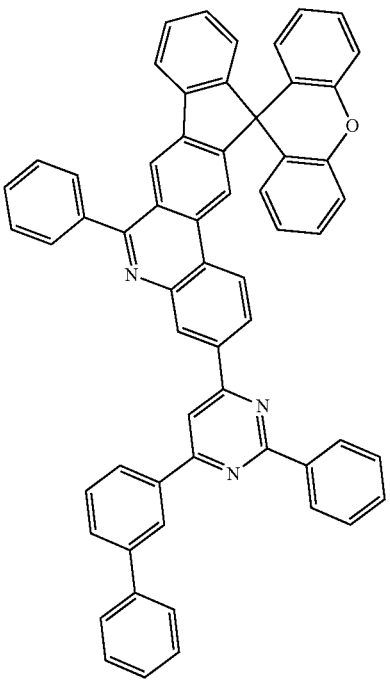
54
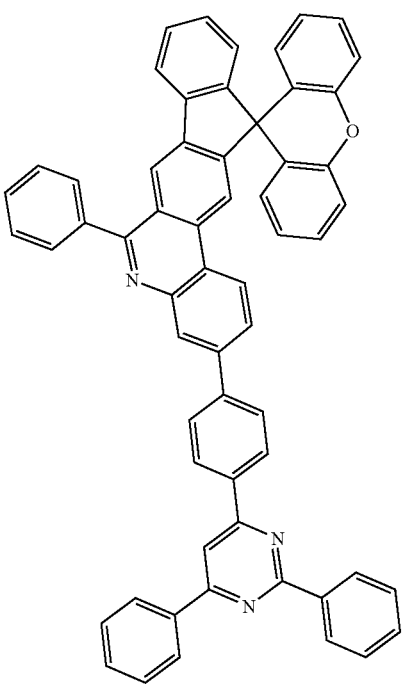

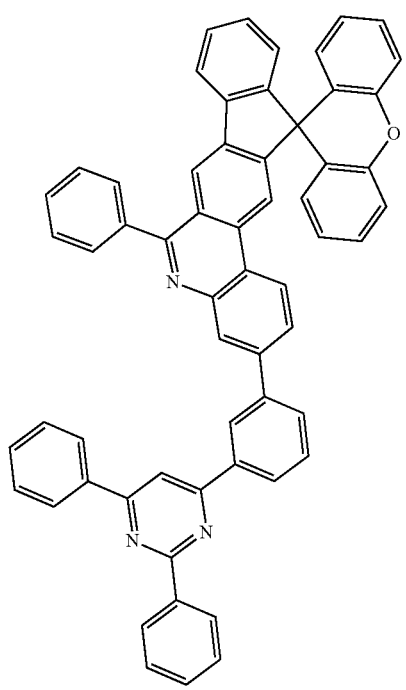
55
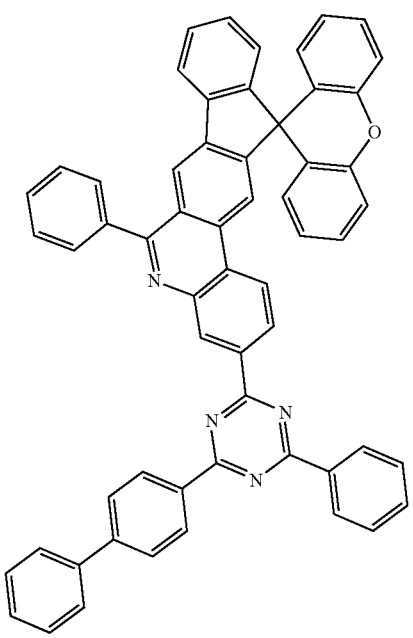
57
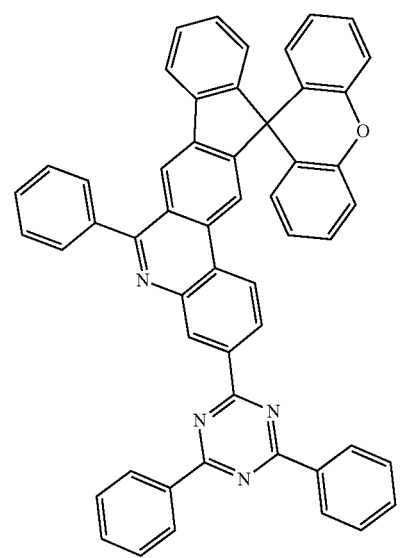
56
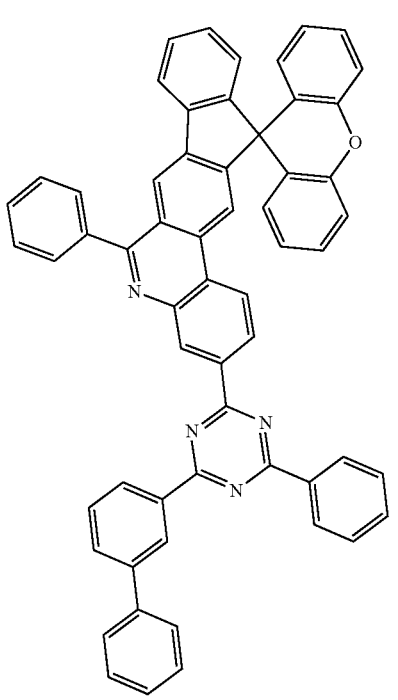
58

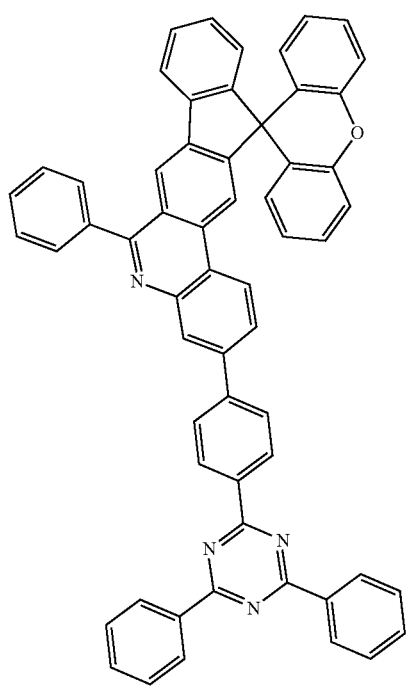
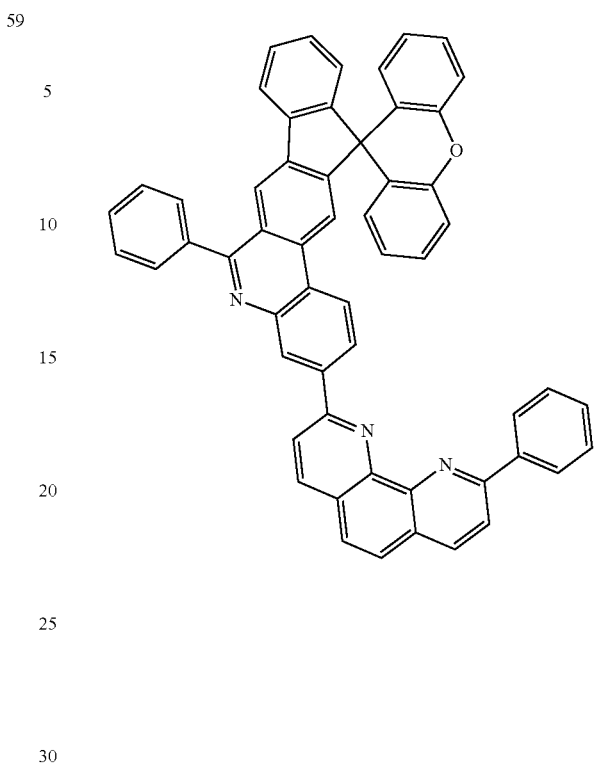
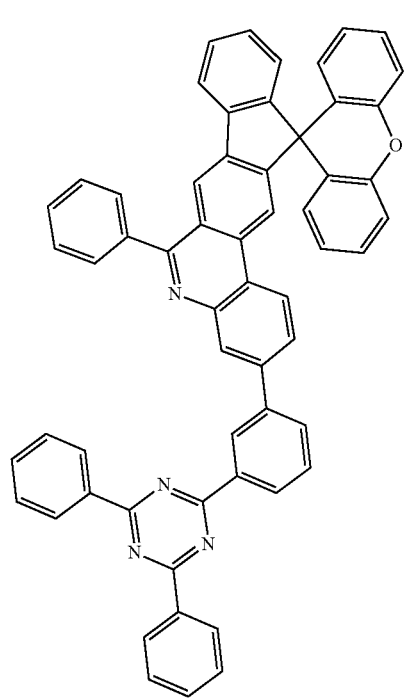
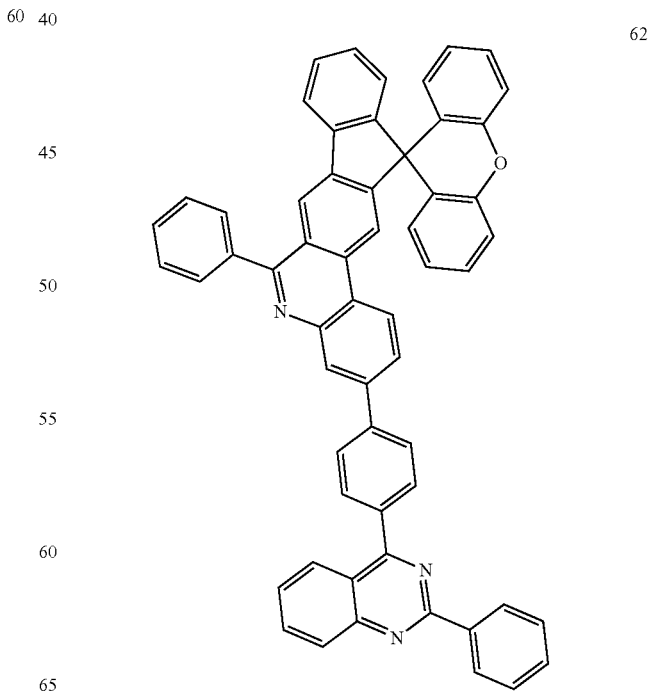

63
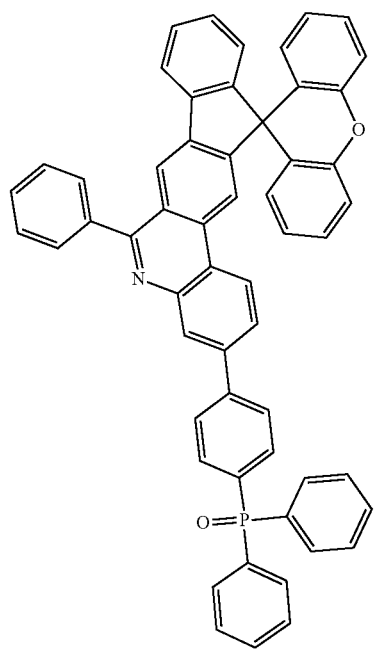
64
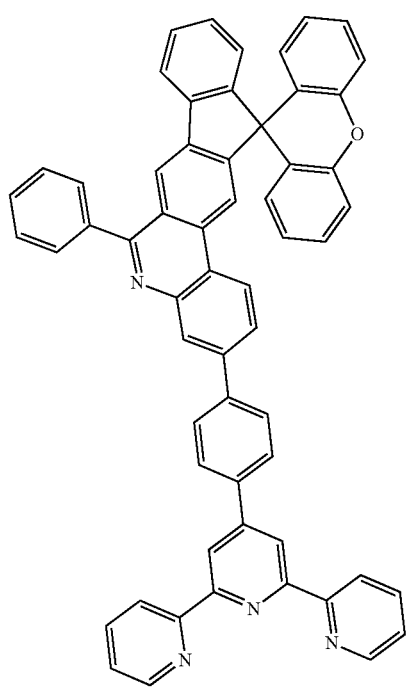
65
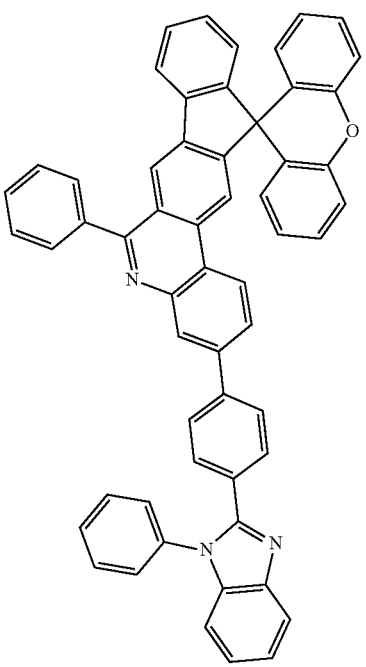
66
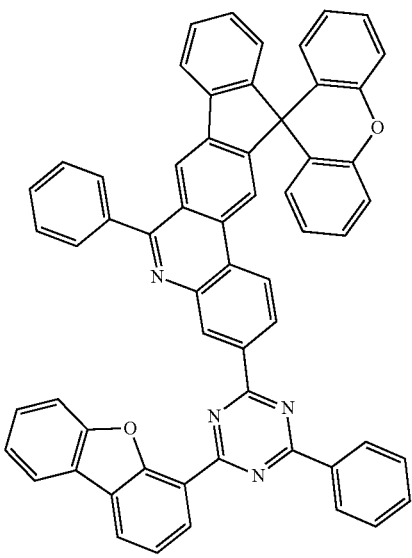

-continued
67
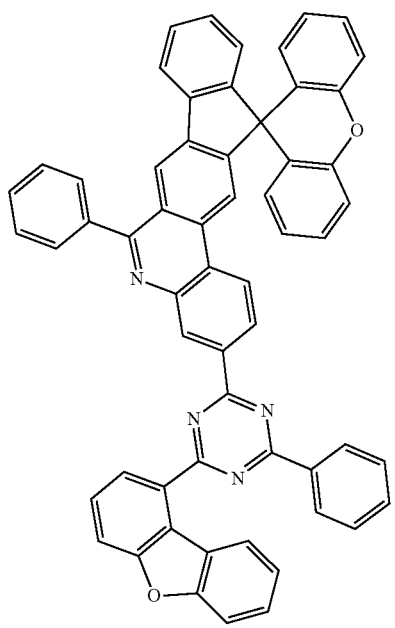
68
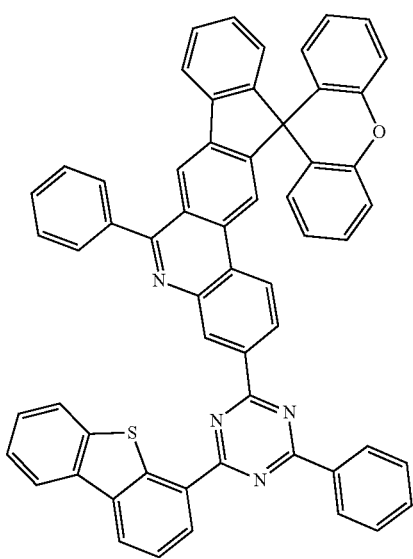
-continued
69
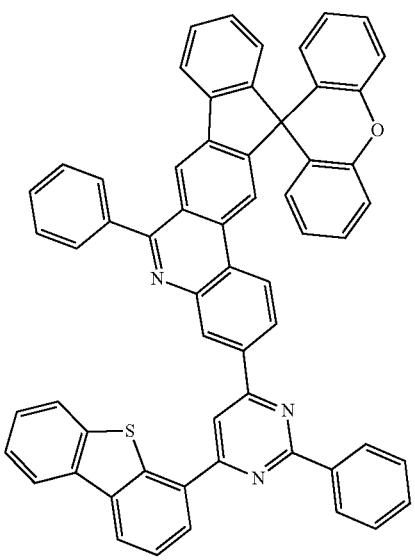
70
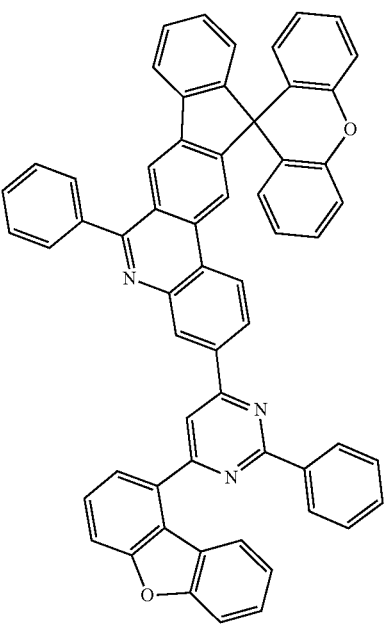

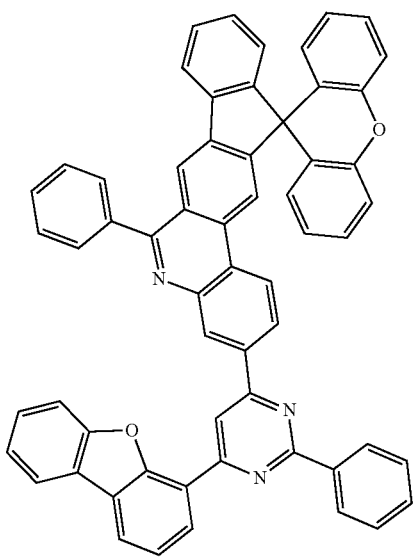
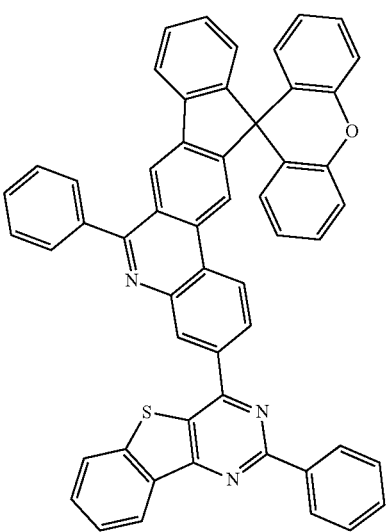
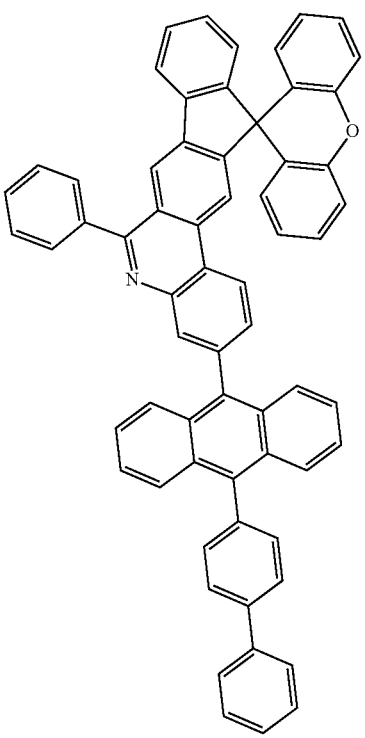
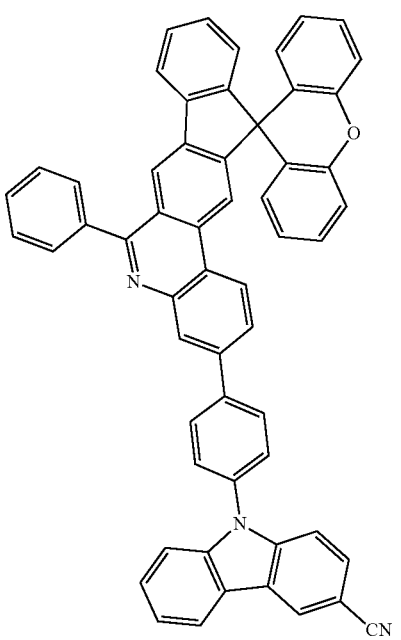

75
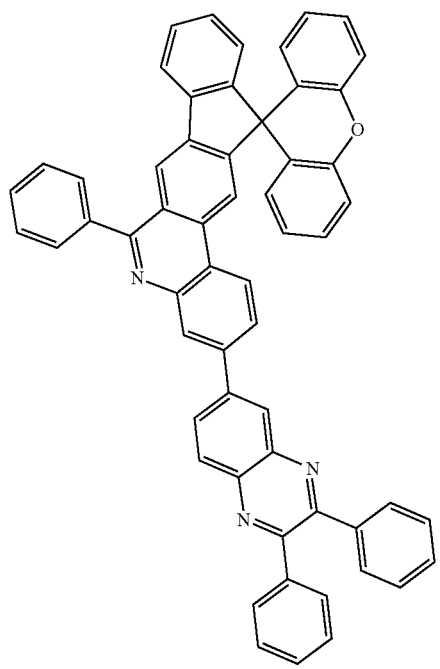
76
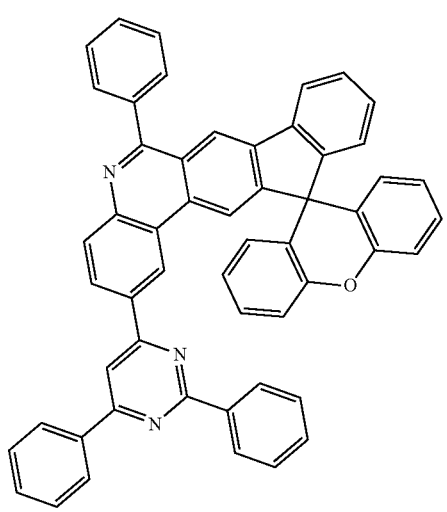
77
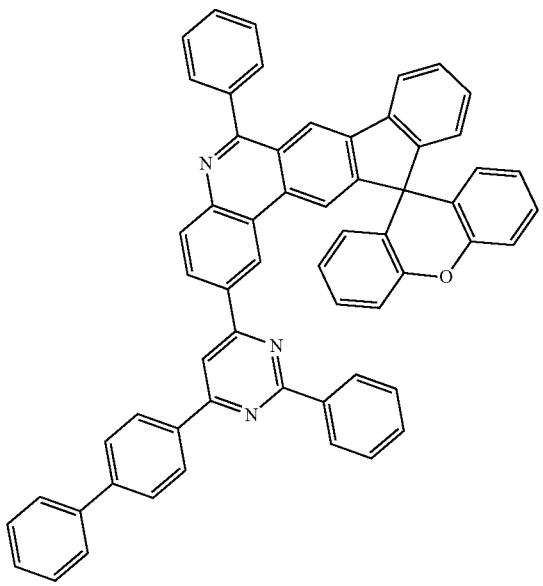
78
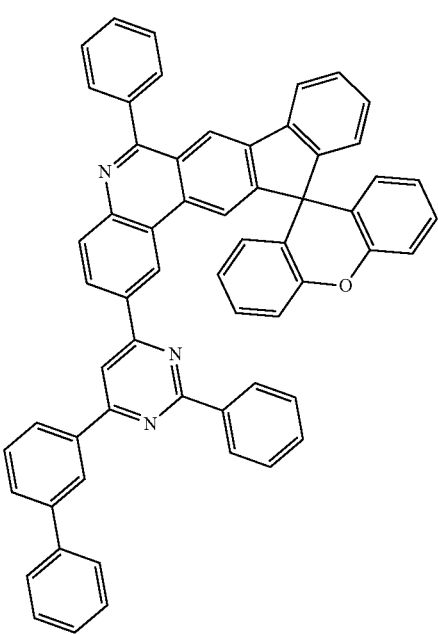

79
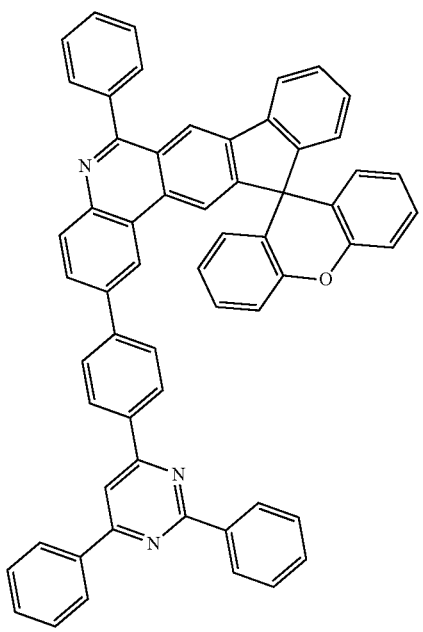
81
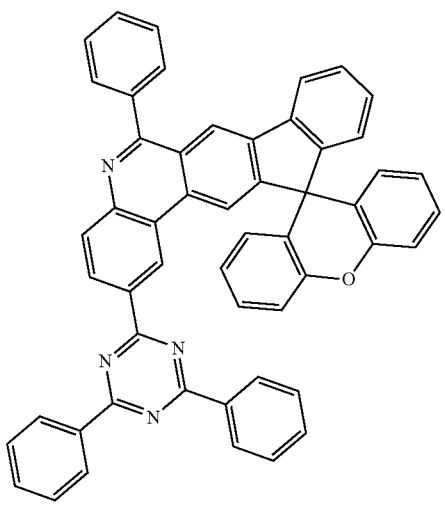
80
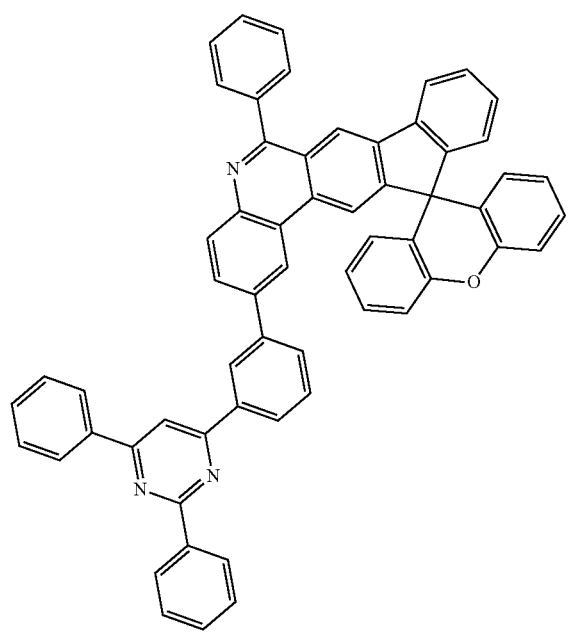
82
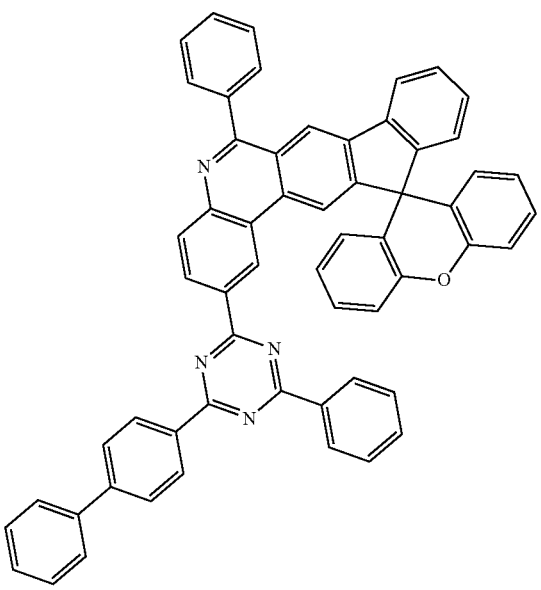

83
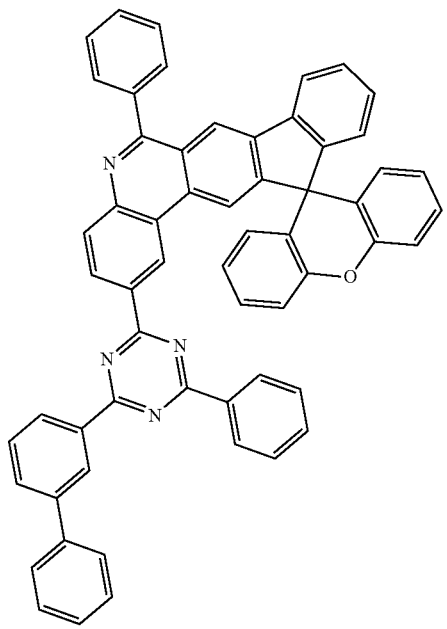
85
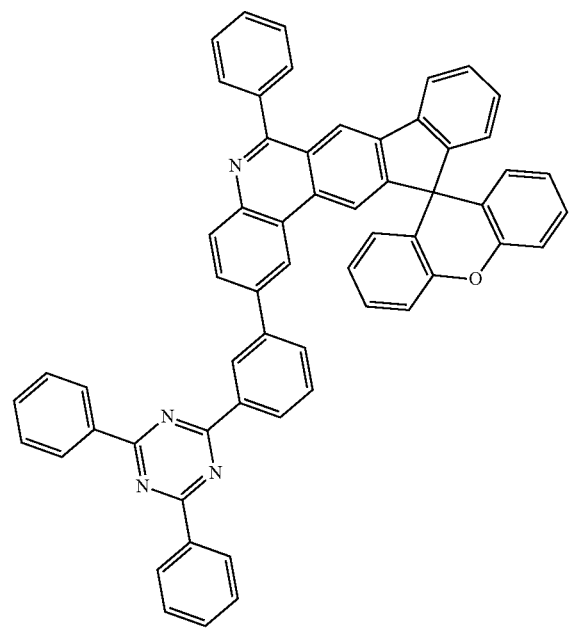
84
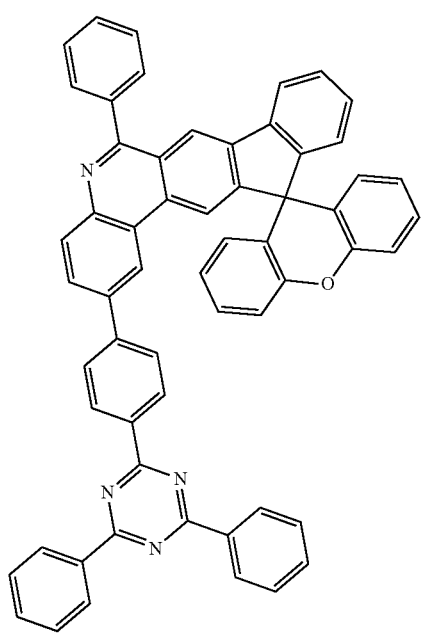
86
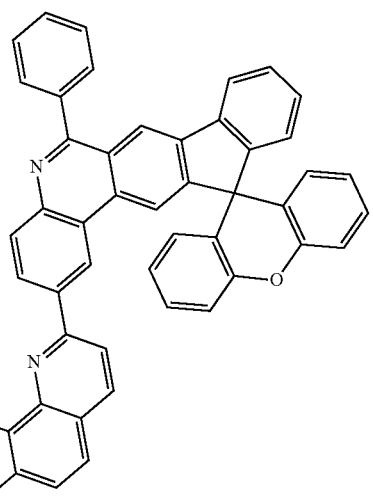

87
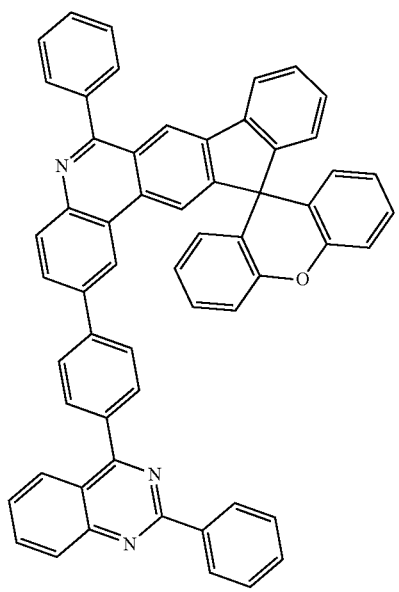
89
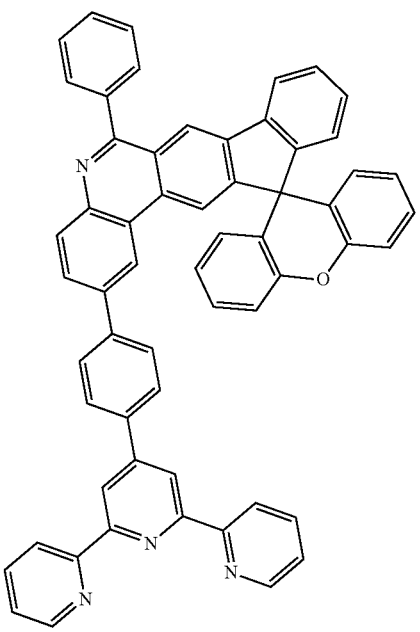
88
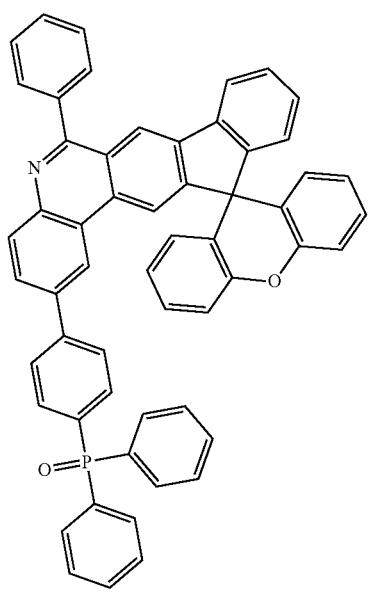
90
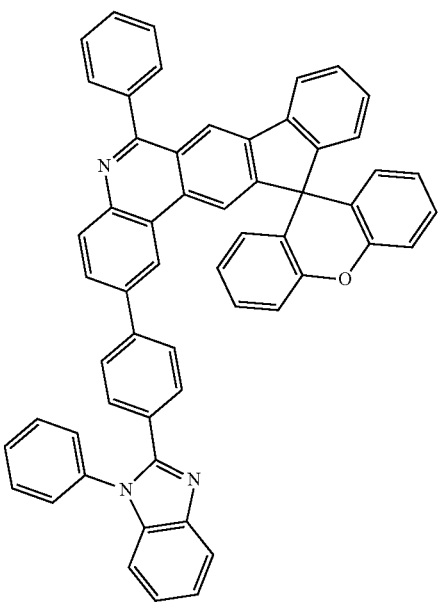

91
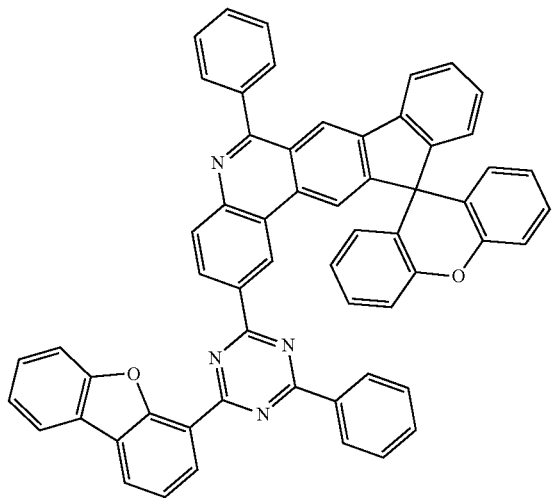
92
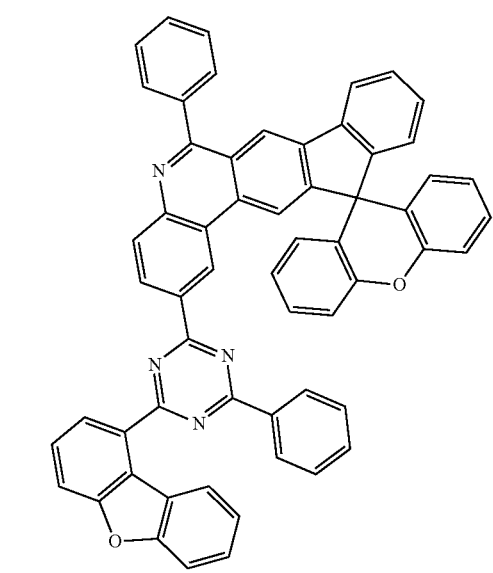
93
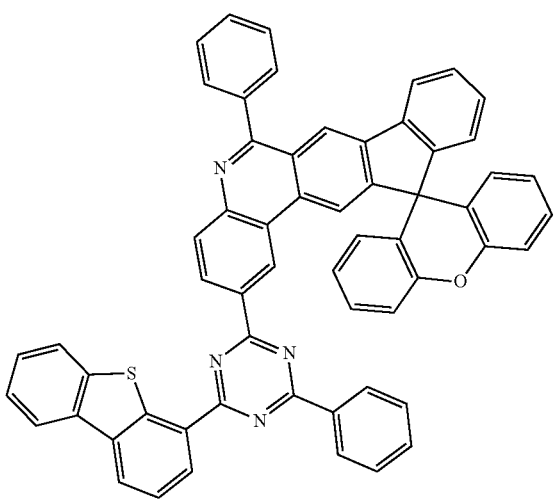
94
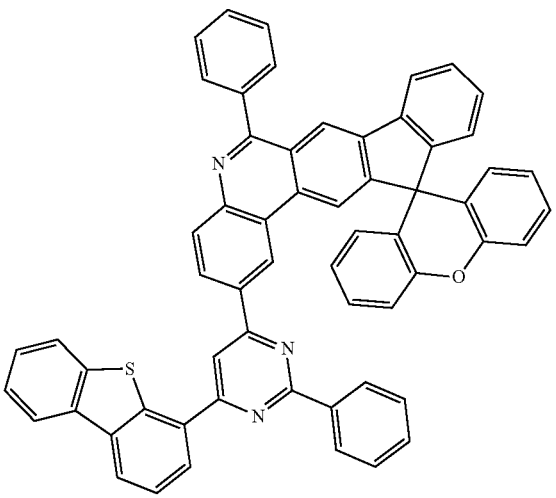
95
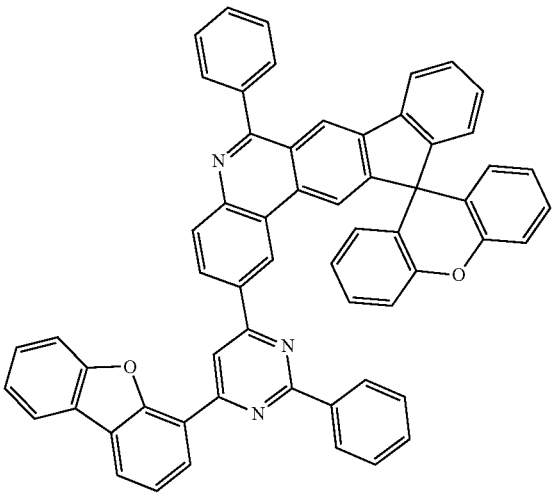
96

97
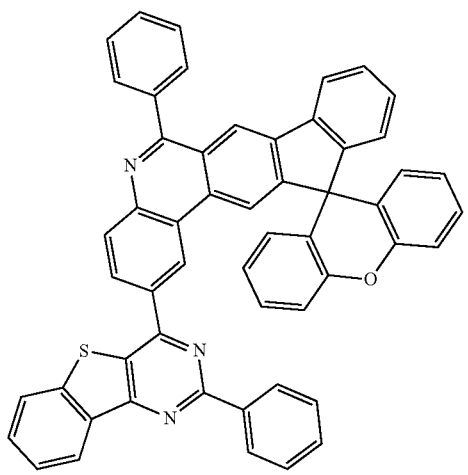
98
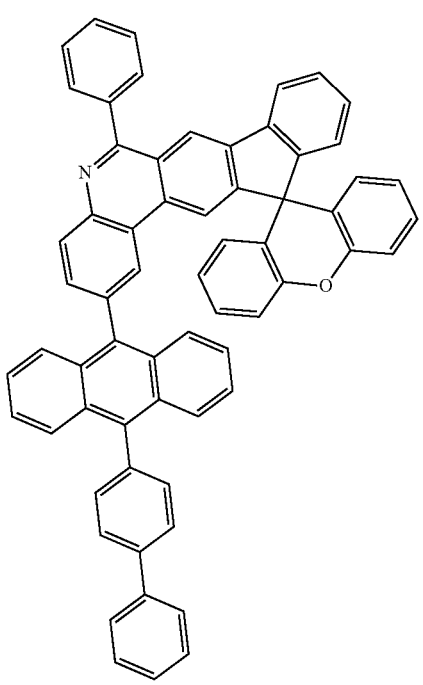
99
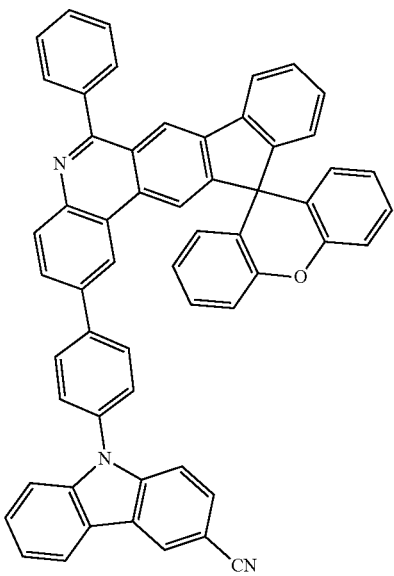
100
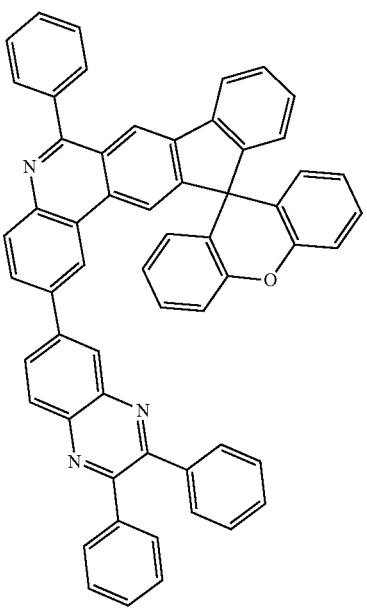

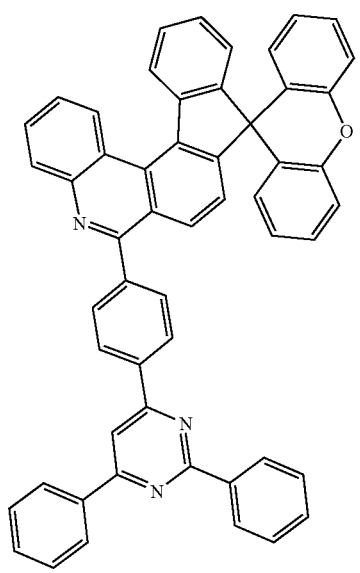
101
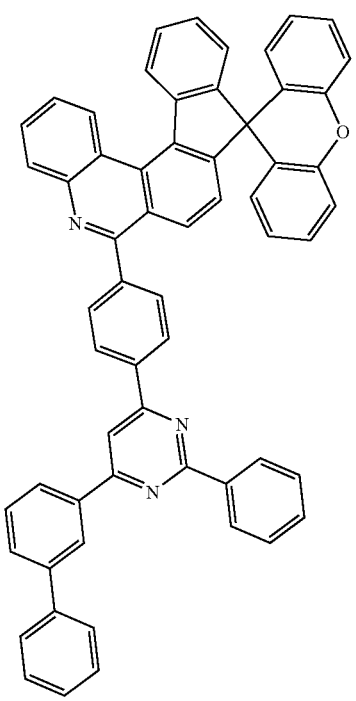
103
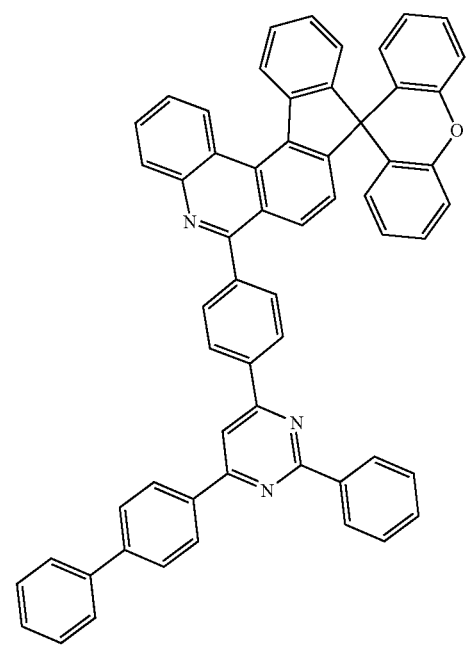
102
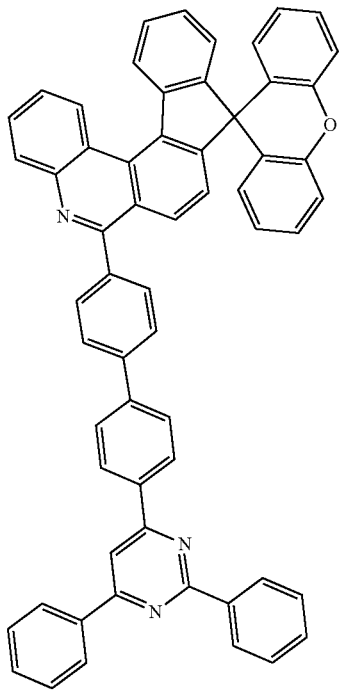
104

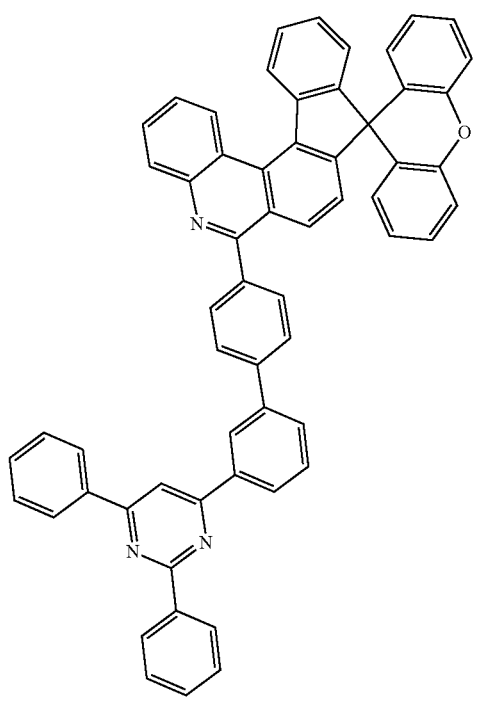
105
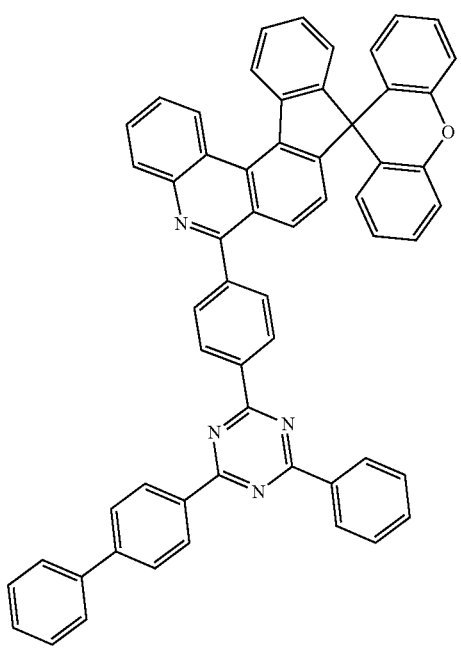
107
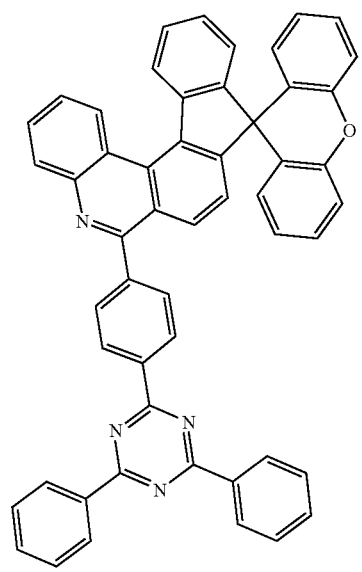
106
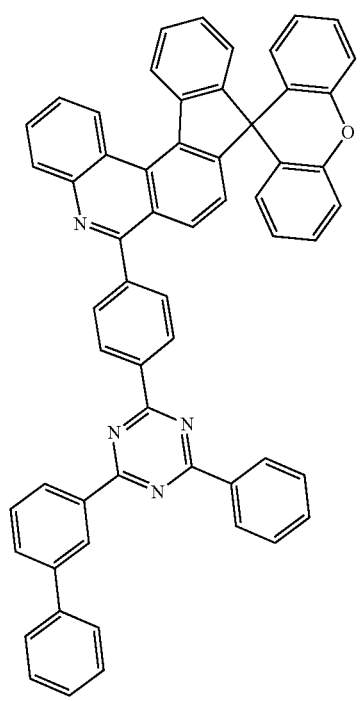
108

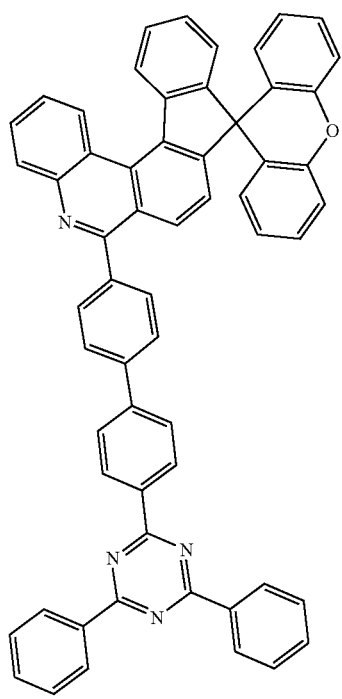
109
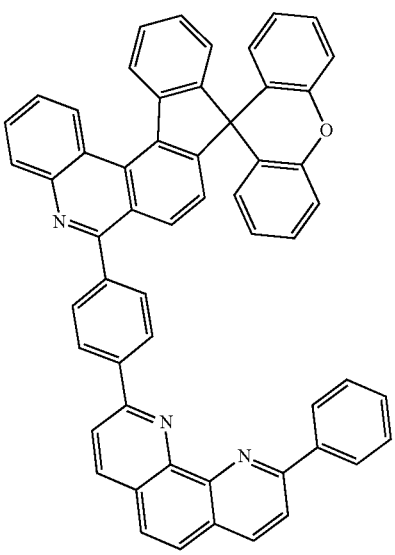
111
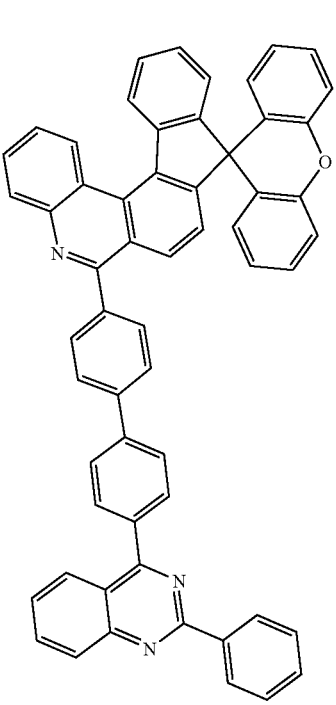
112

113
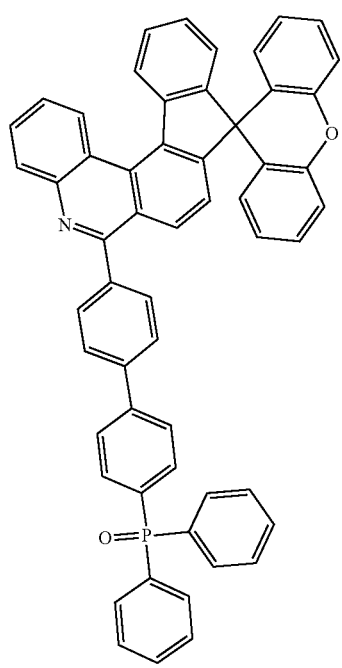
115
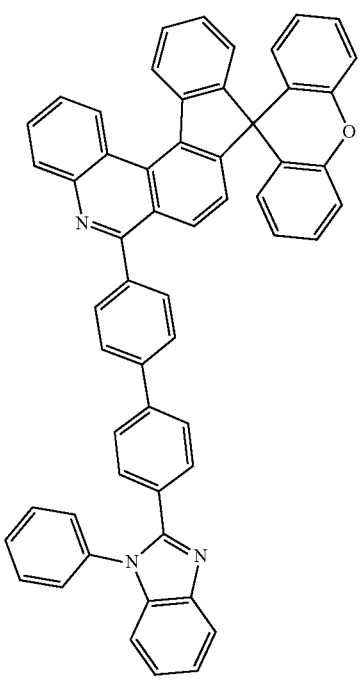
114
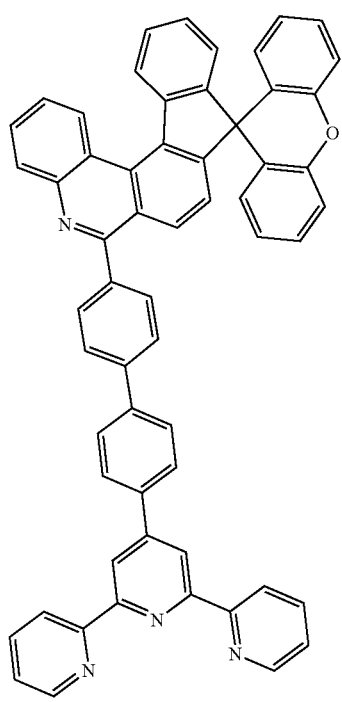
116
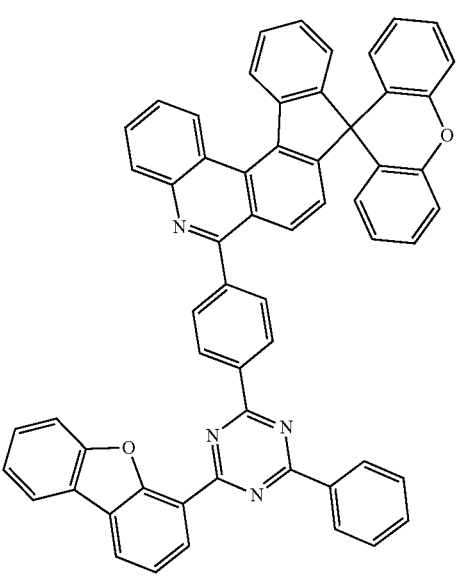

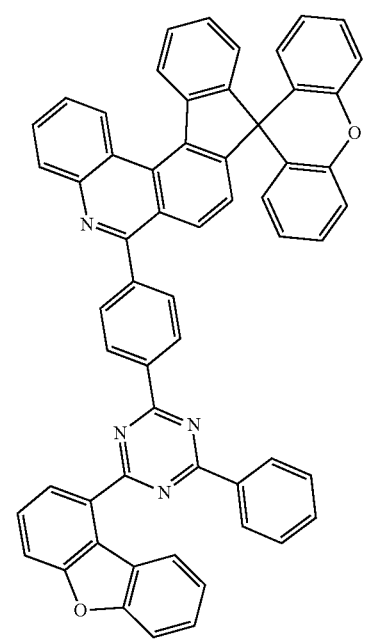
117
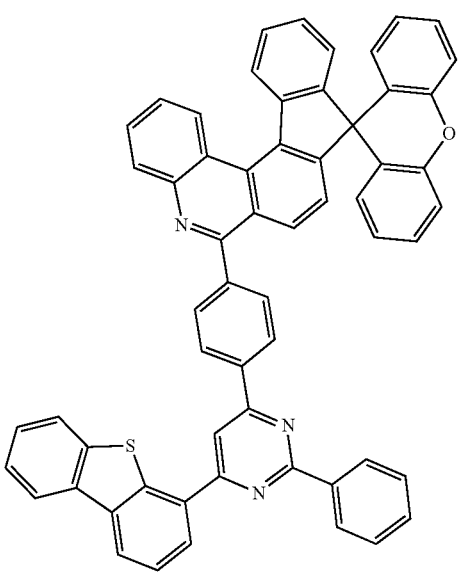
119
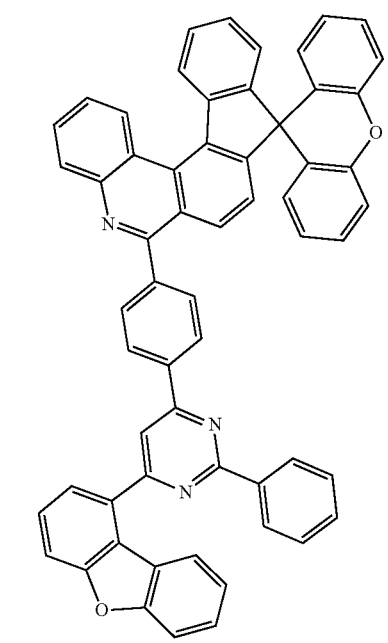
120

121
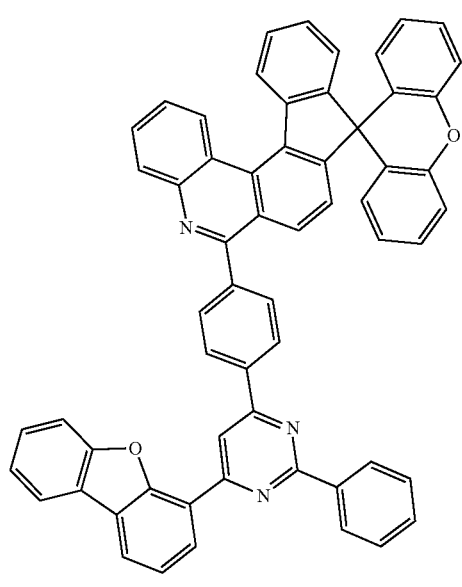
122
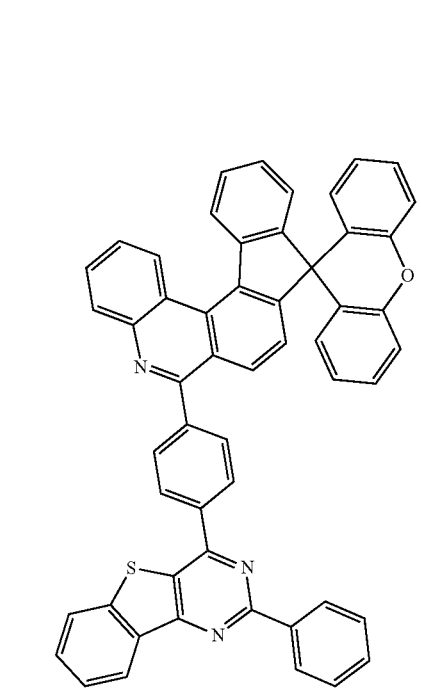
123
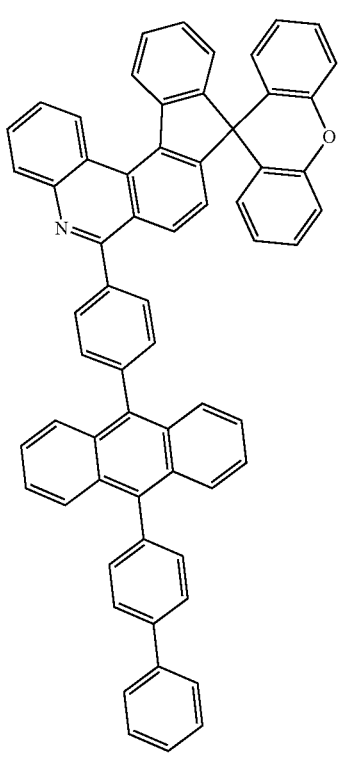
124
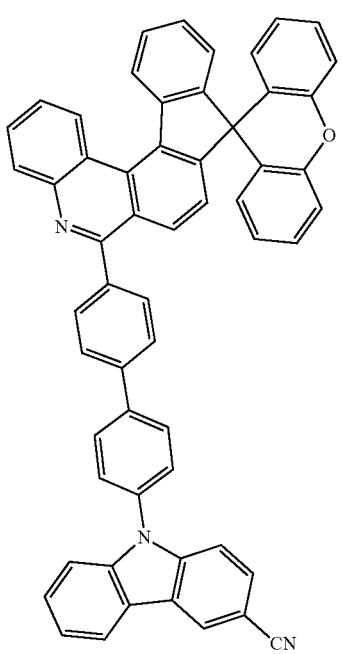

71
-continued
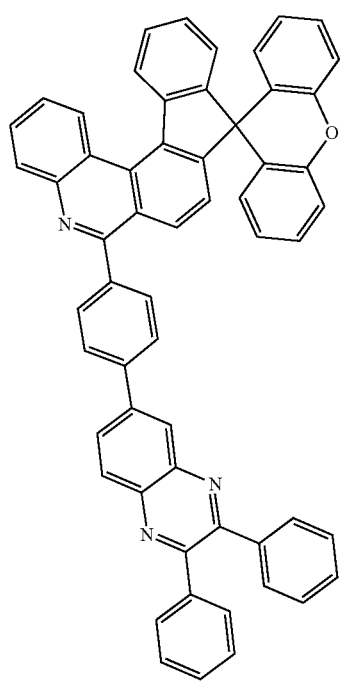
125
72
-continued
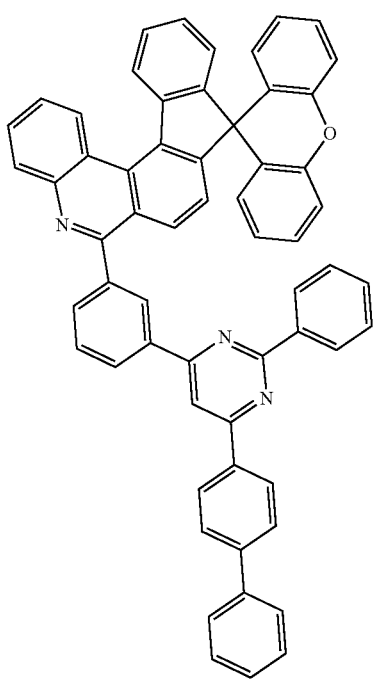
127
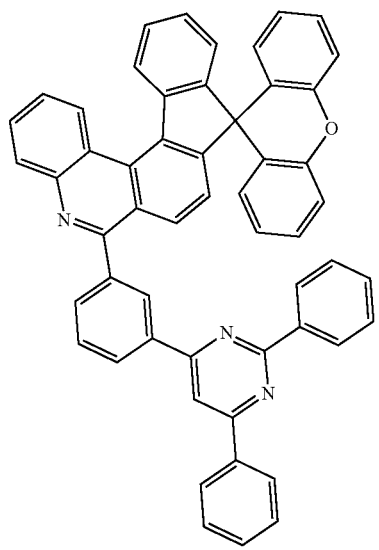
126
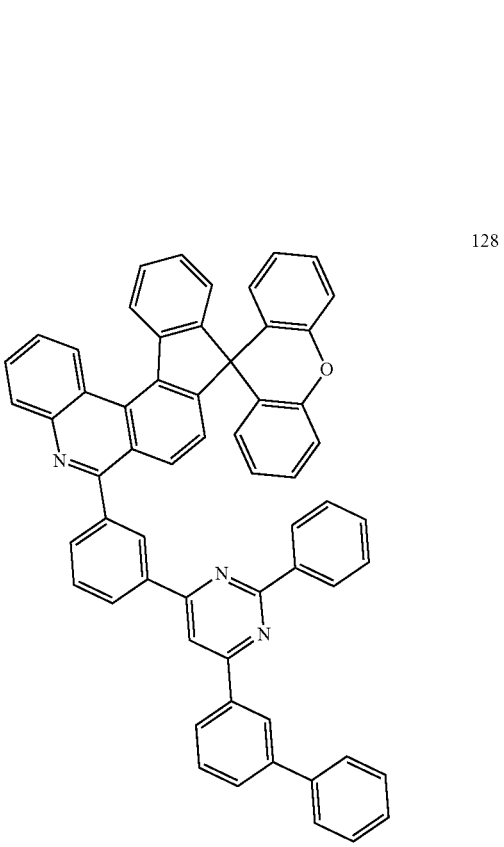
128

129
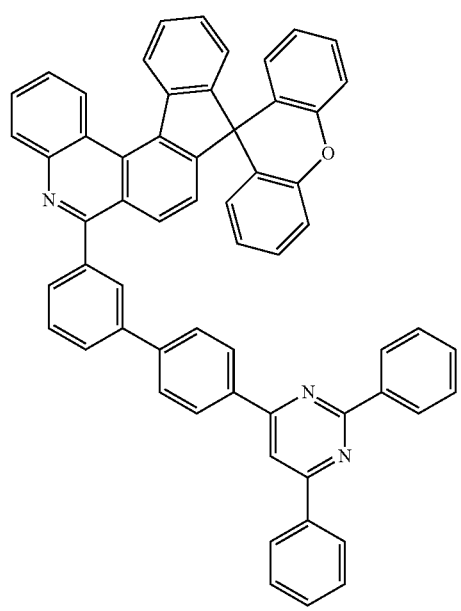
131
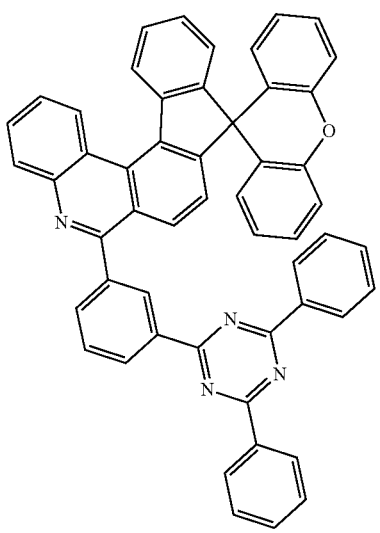
130
132

133
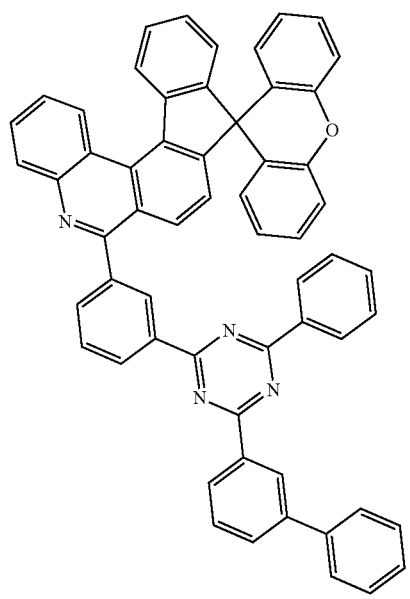
134
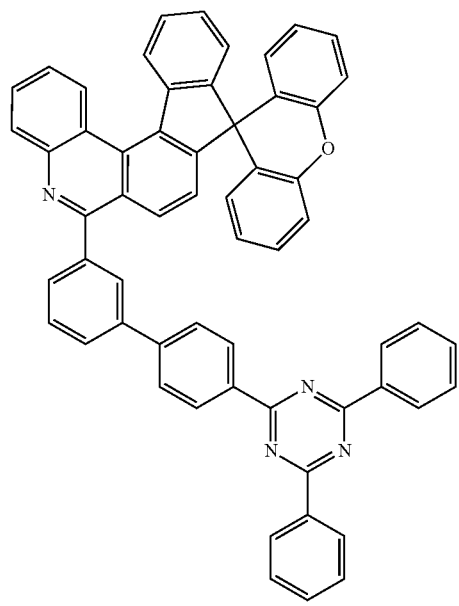
135
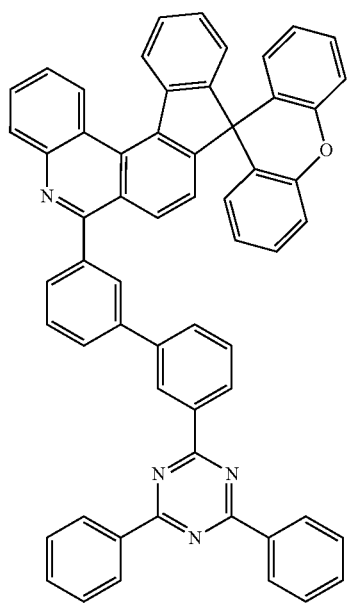
136
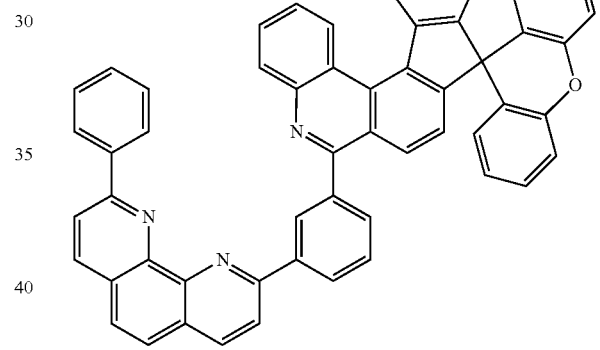
137
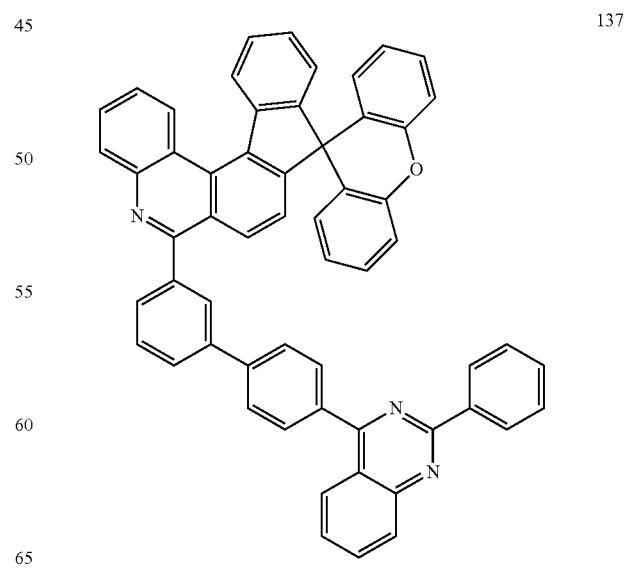

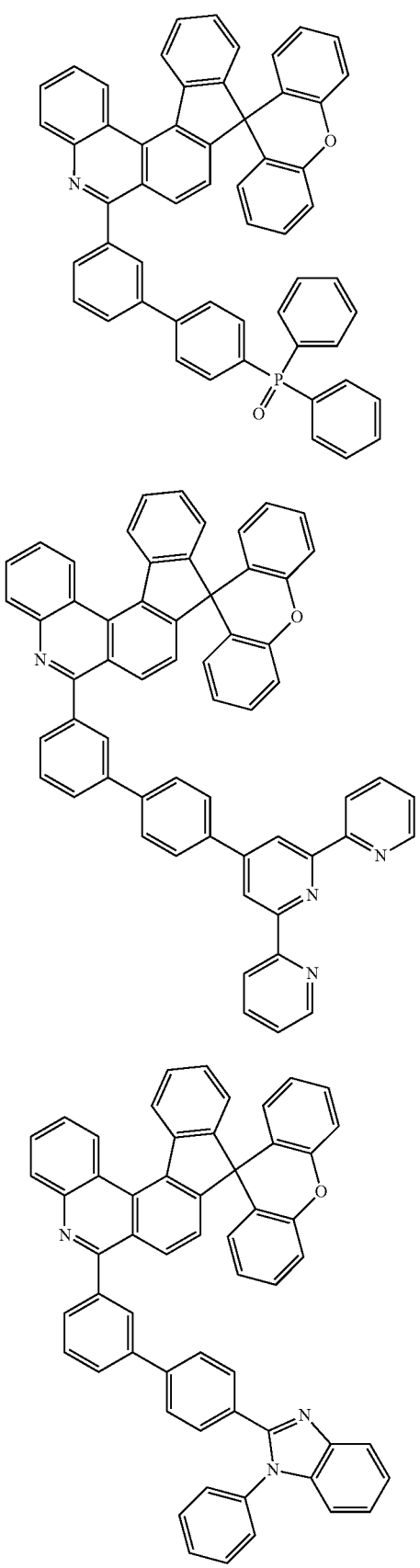

143
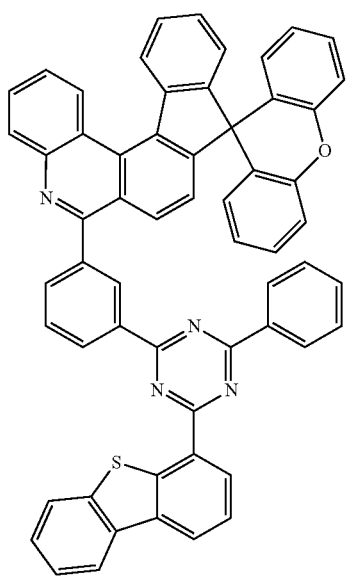
144
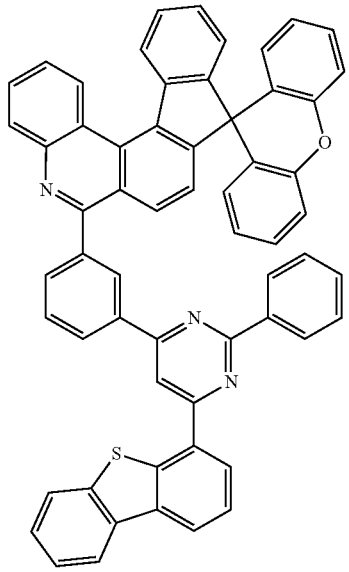
145
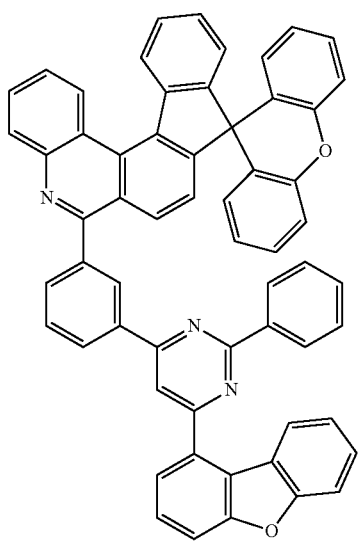
146
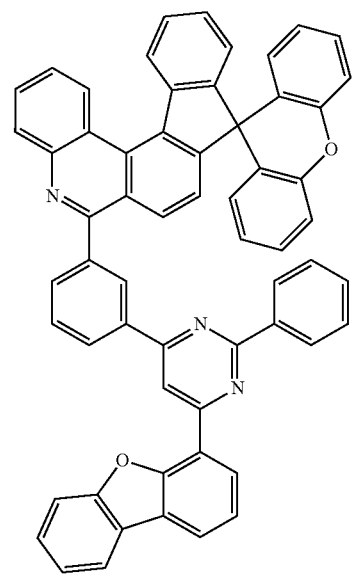

147
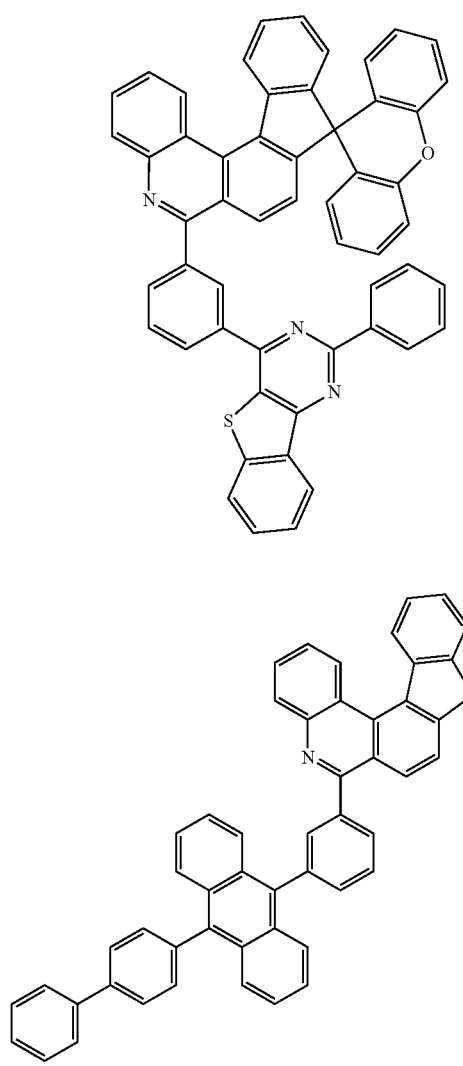
148
149
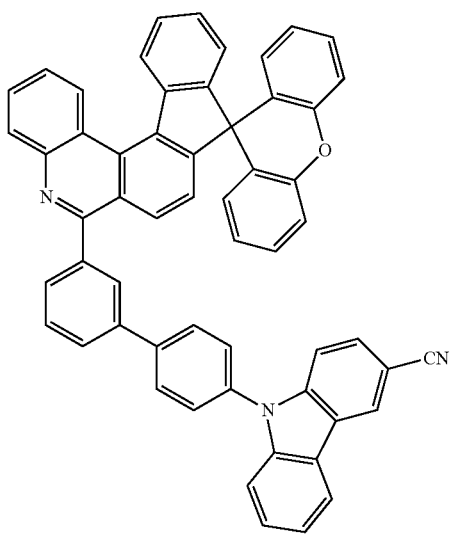
150
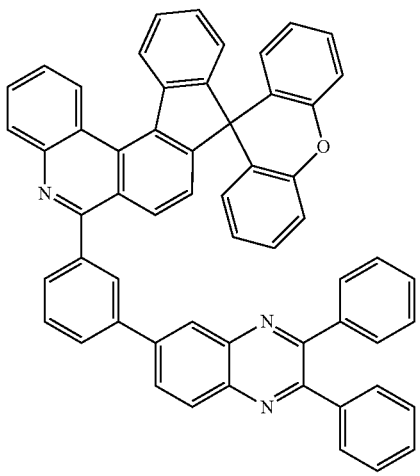
151
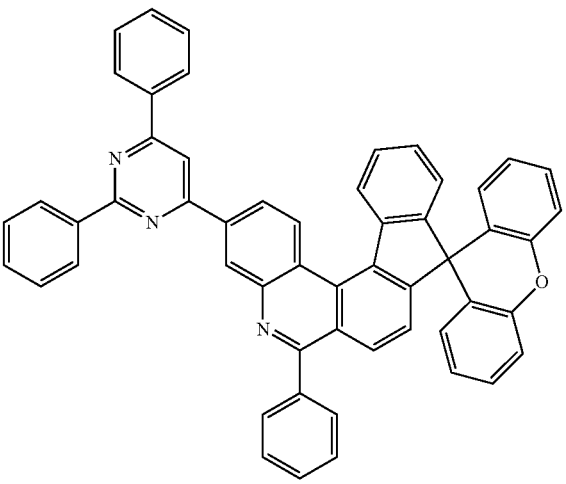
152
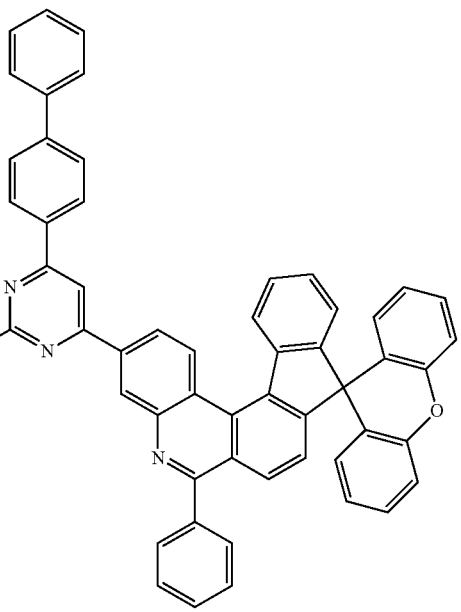

153
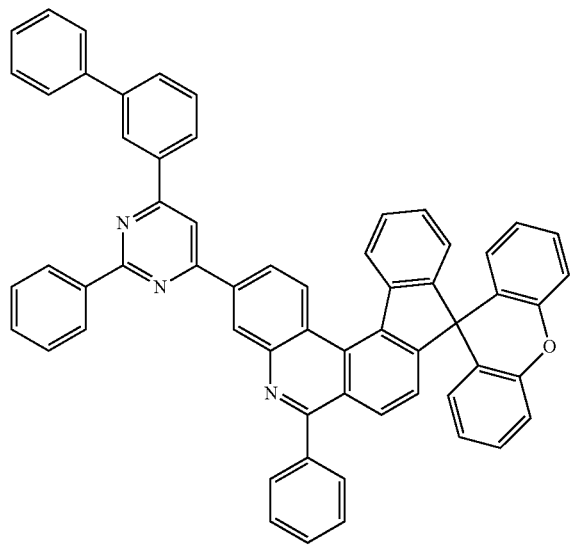
154
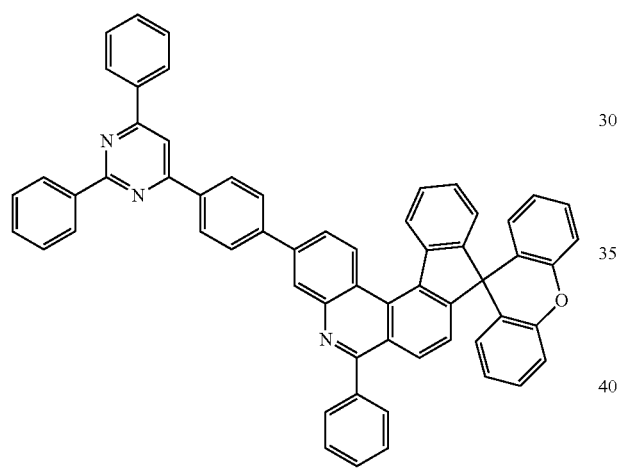
155
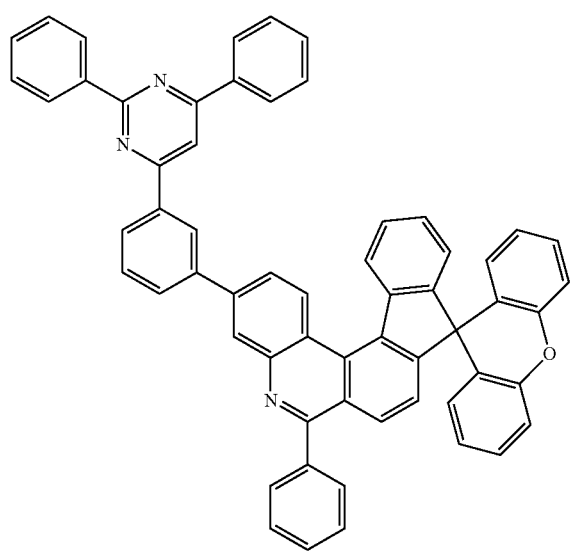
156
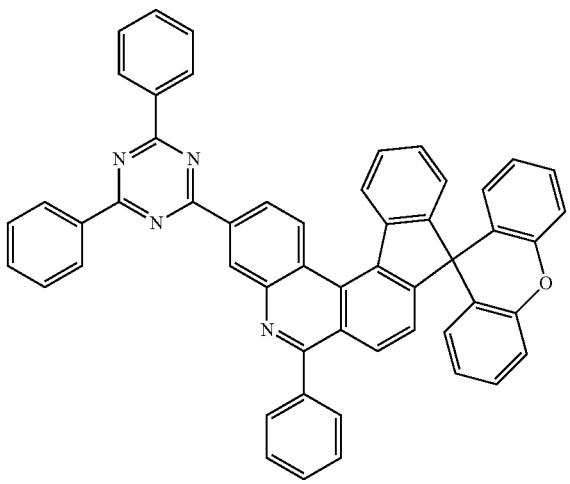
157
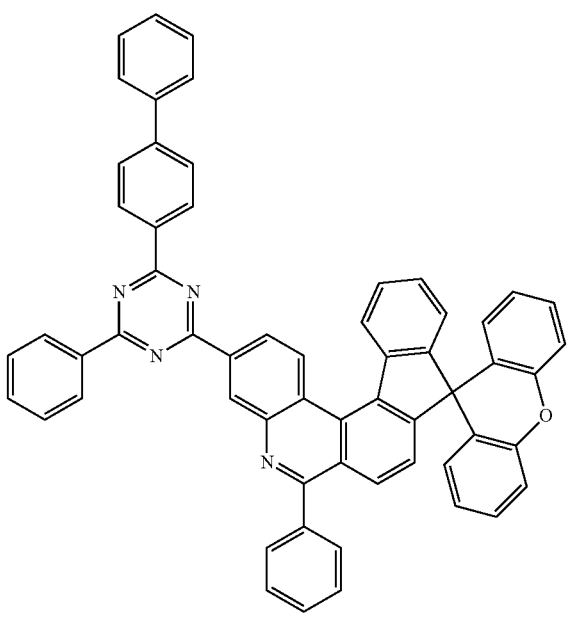

158
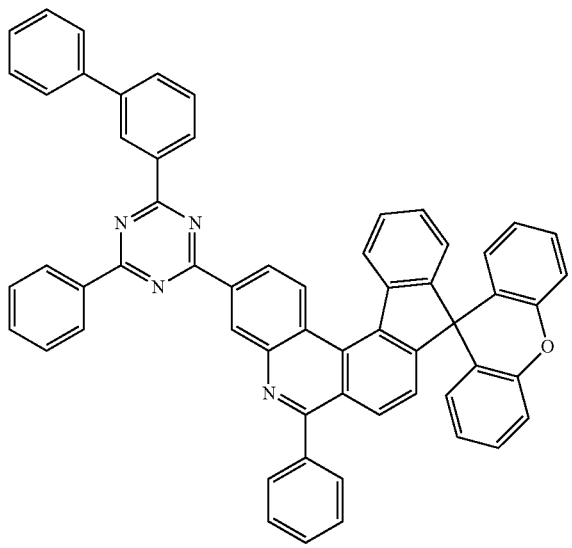
159
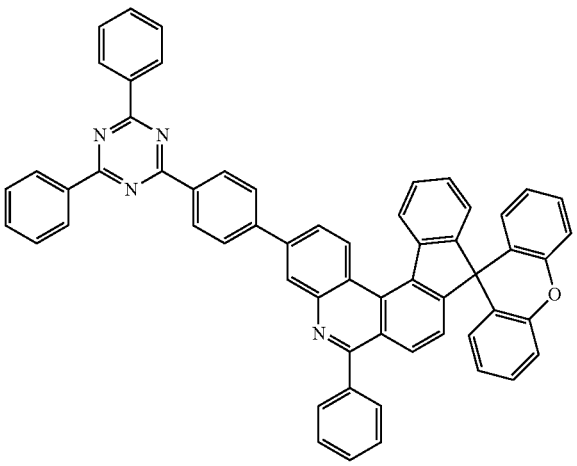
160
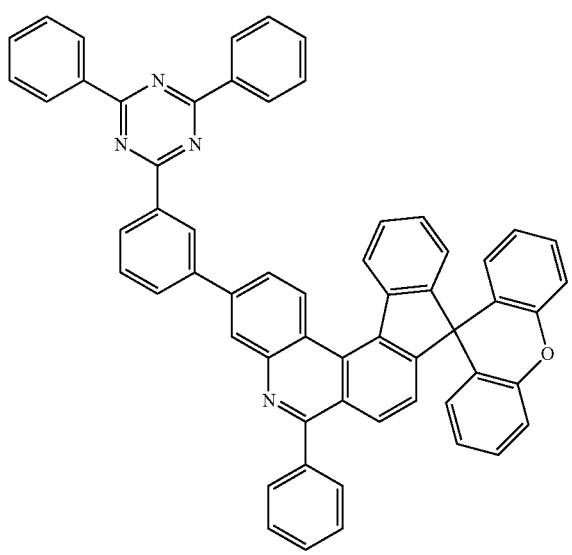
161
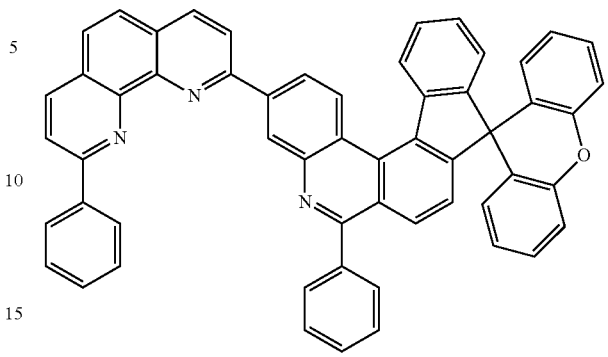
162
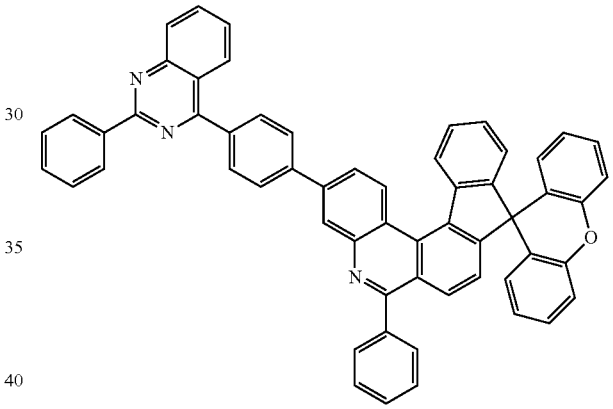
163
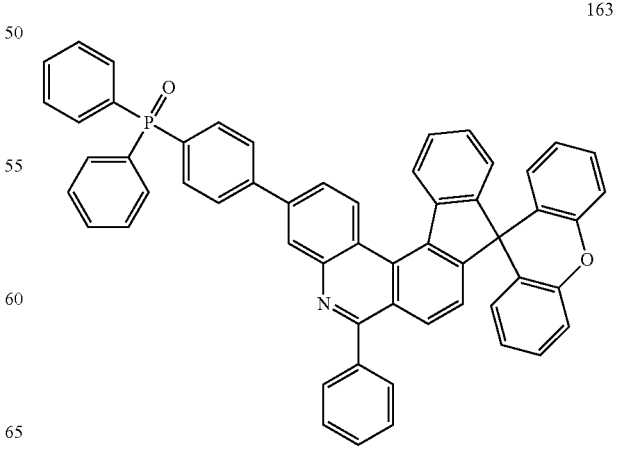

164
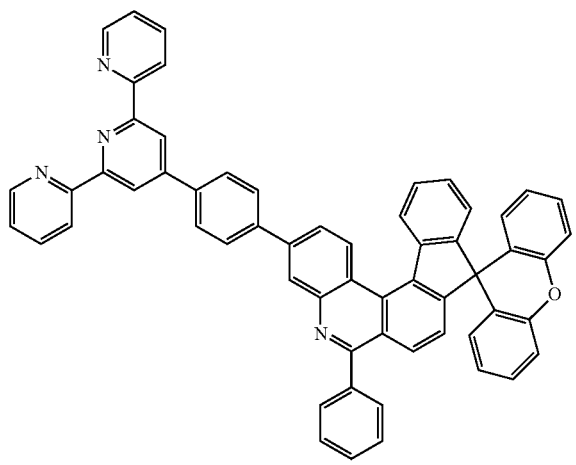
165
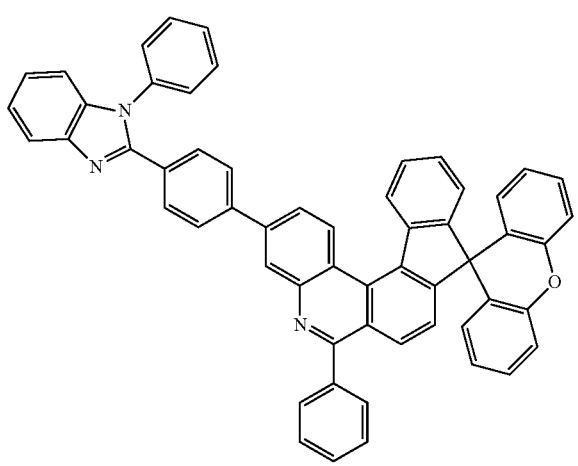
166
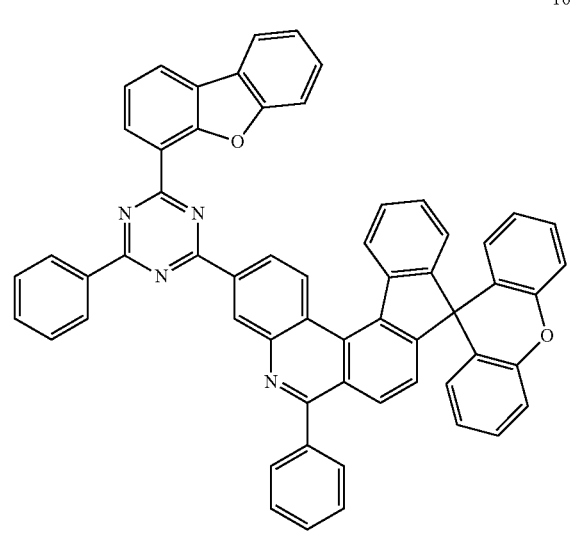
167
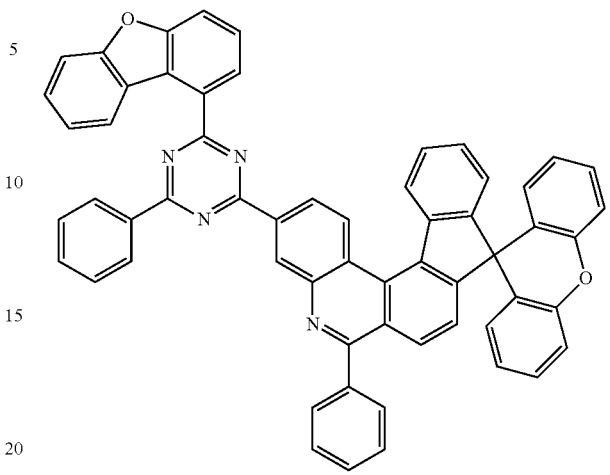
168
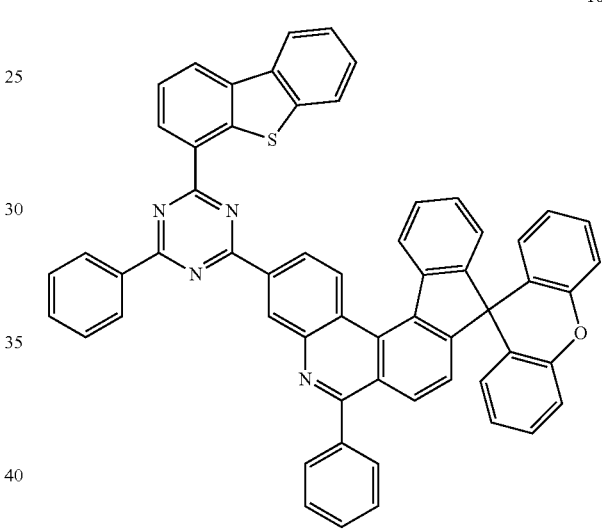
169
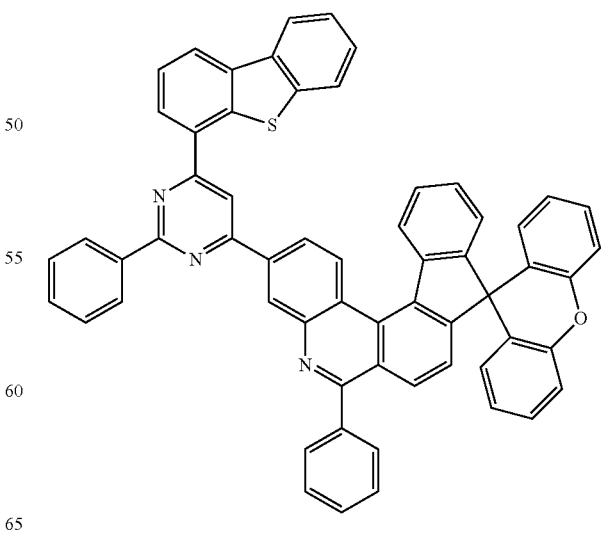

170
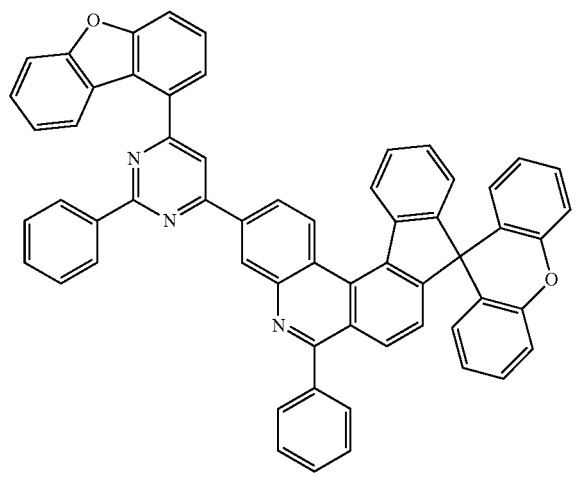
171
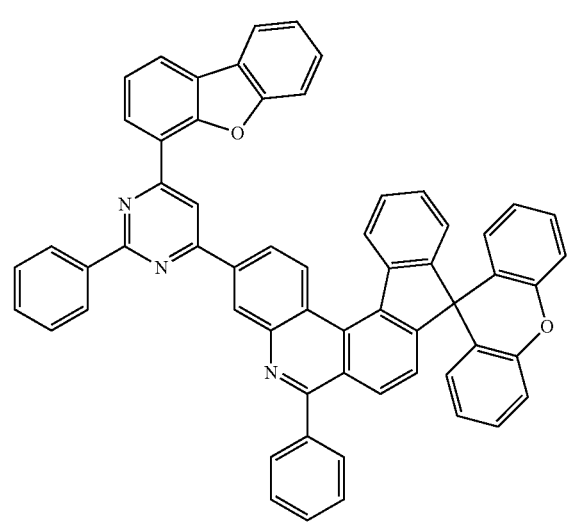
172
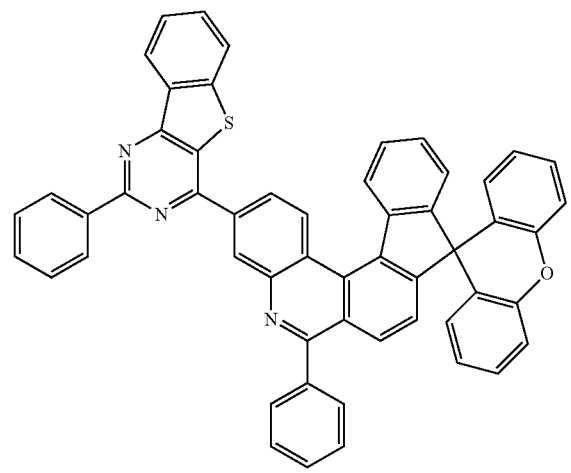
173
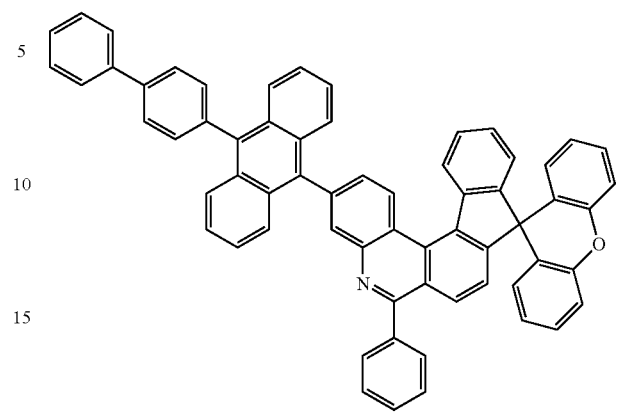
174
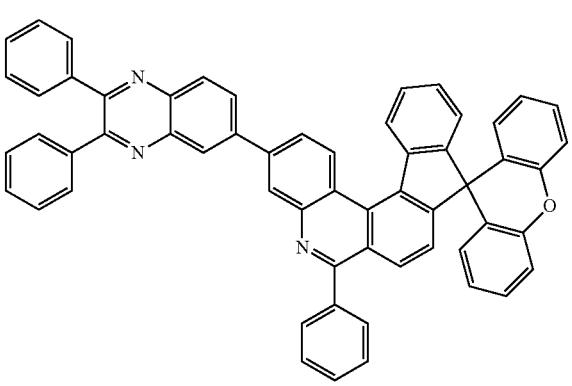
175

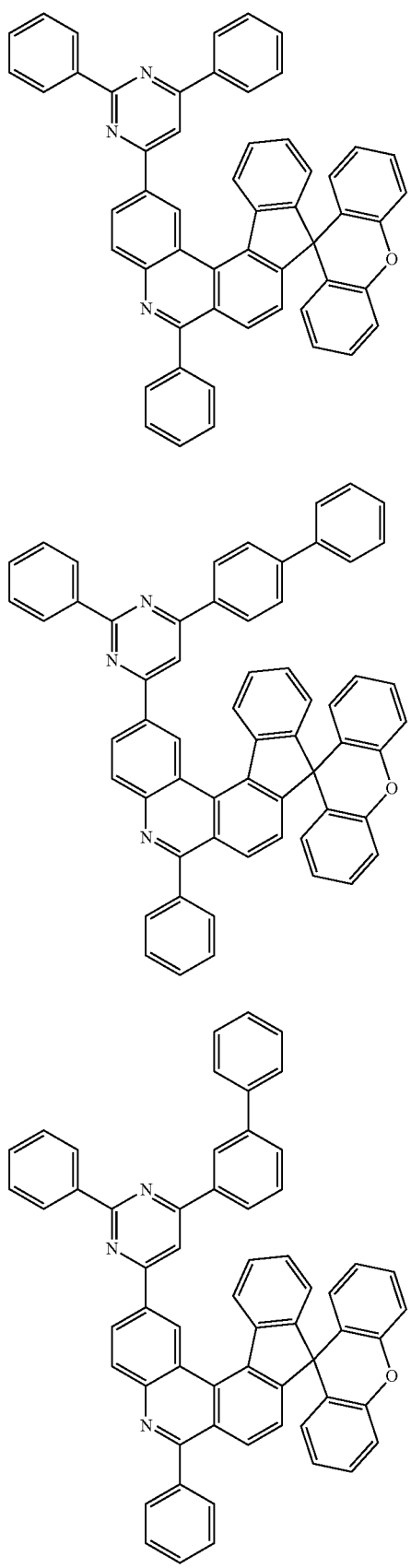
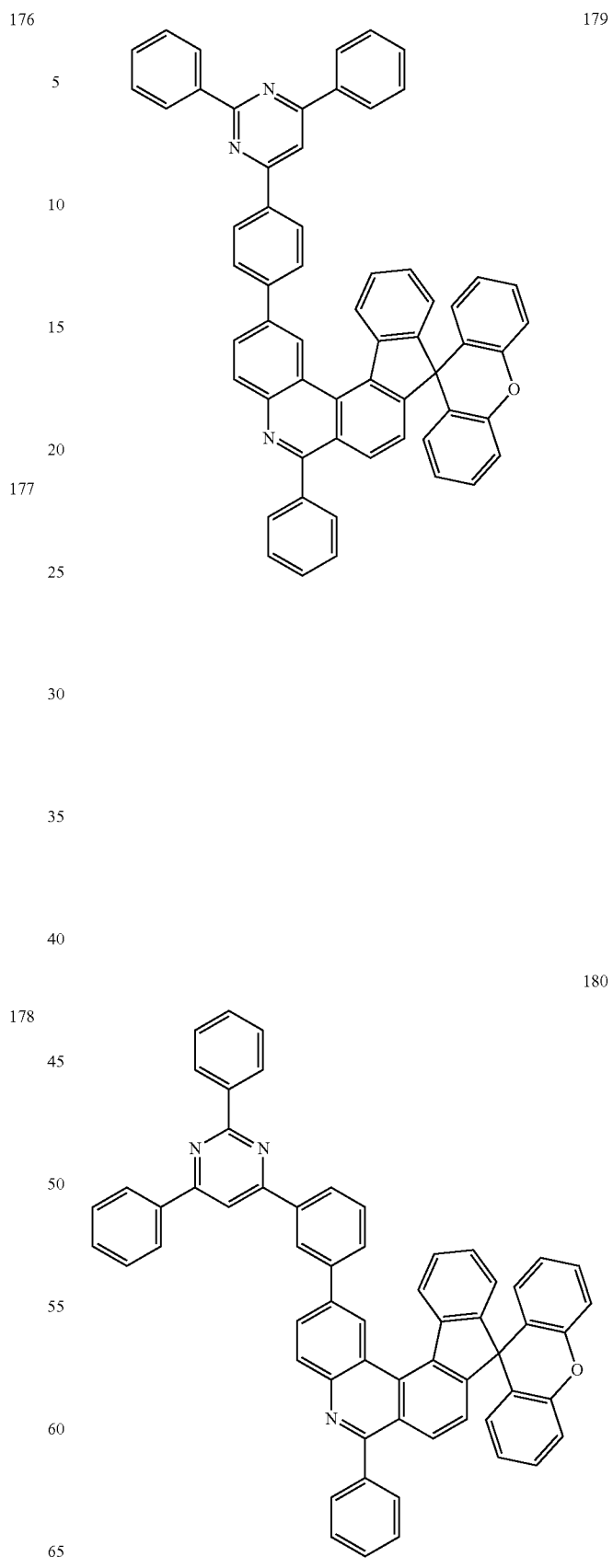

93
-continued
181
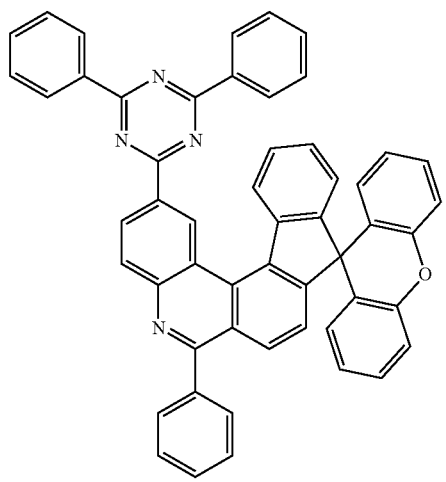
182
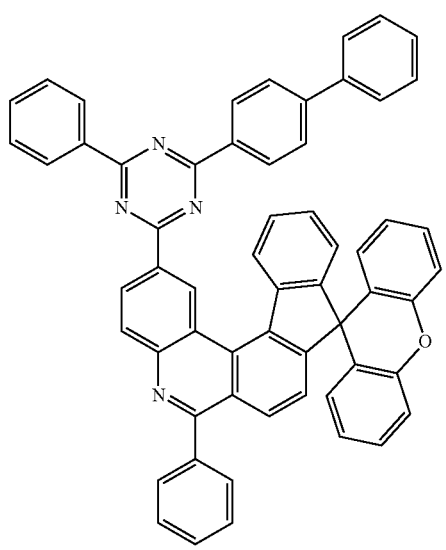
183
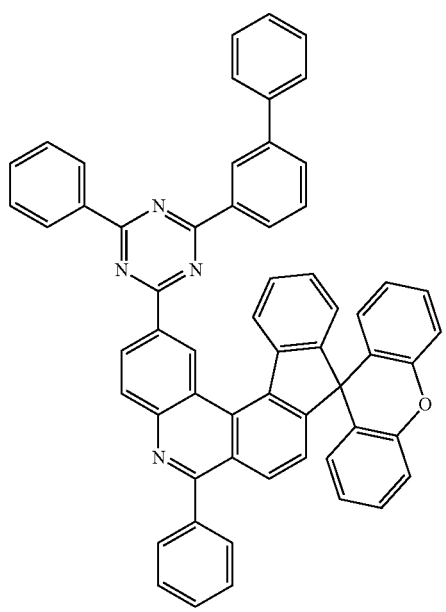
94
-continued
184
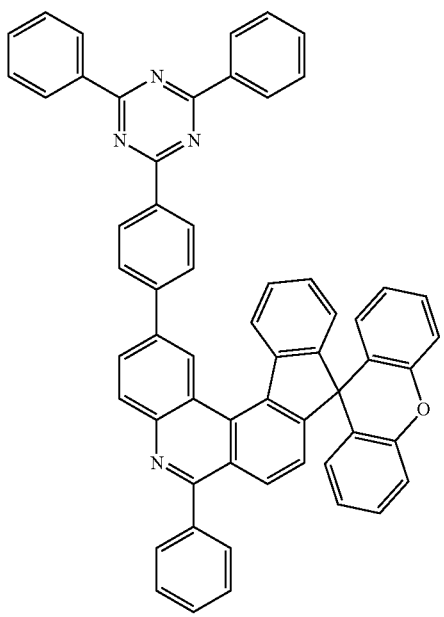
185
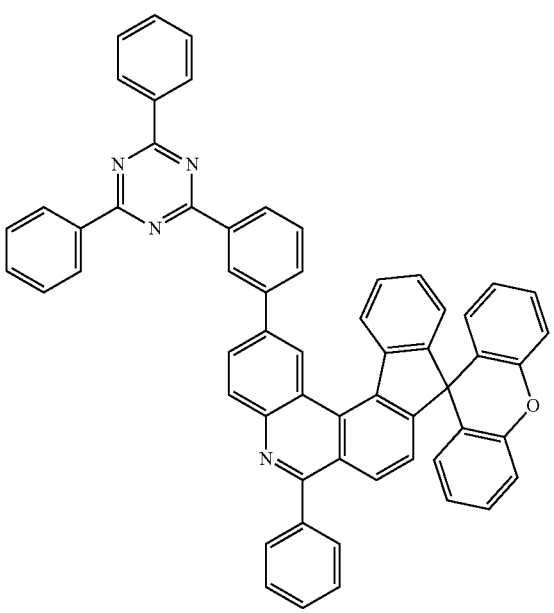

186
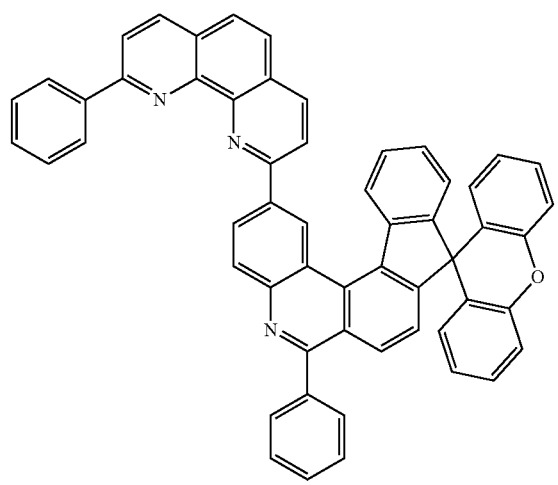
187
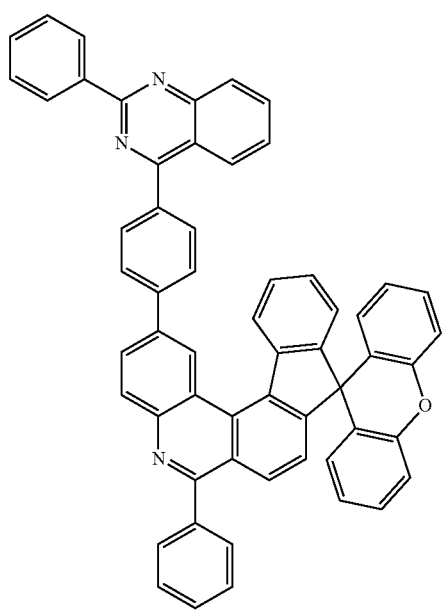
188
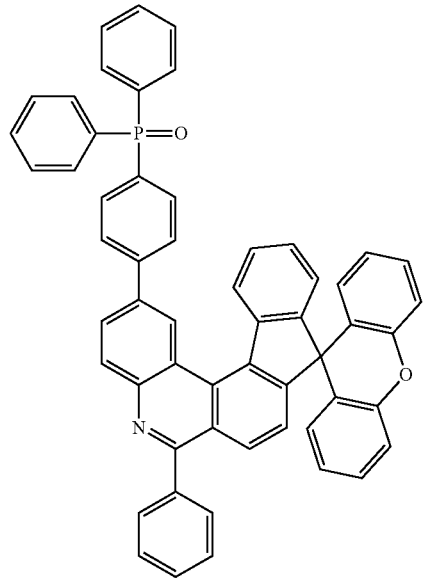
189
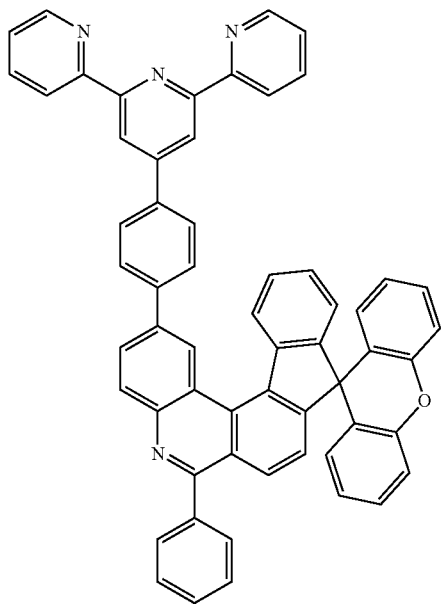

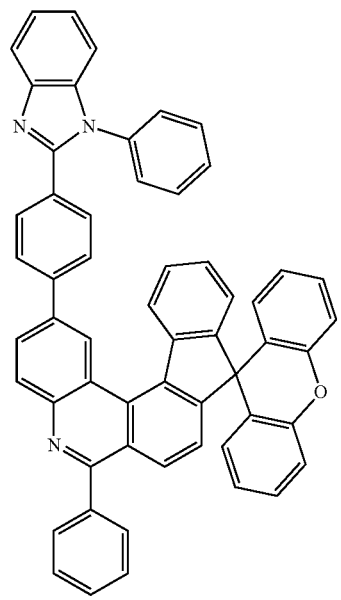
190
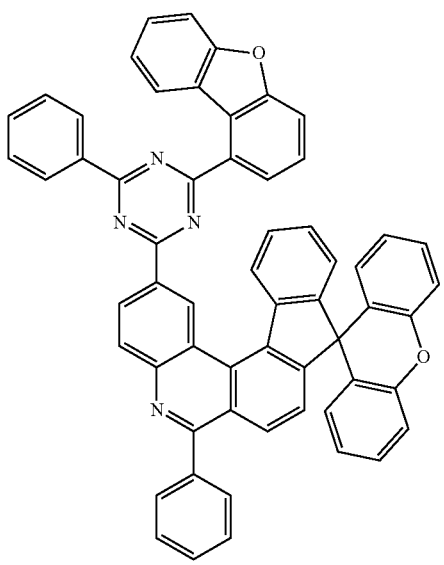
192
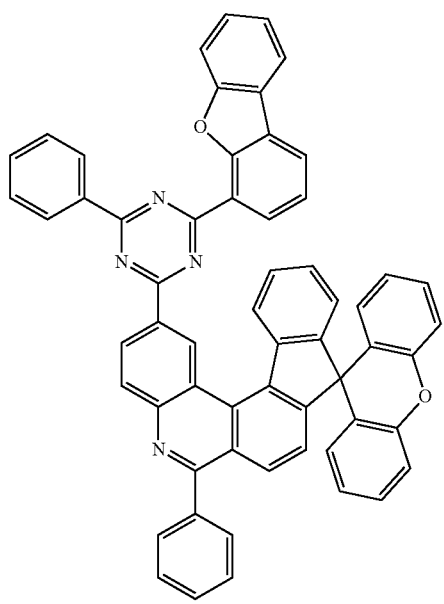
191

194
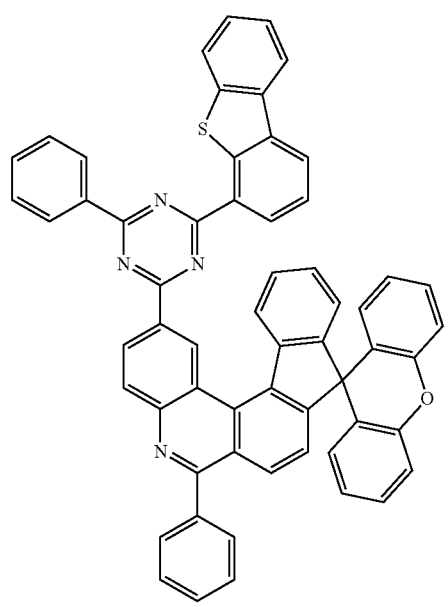
195
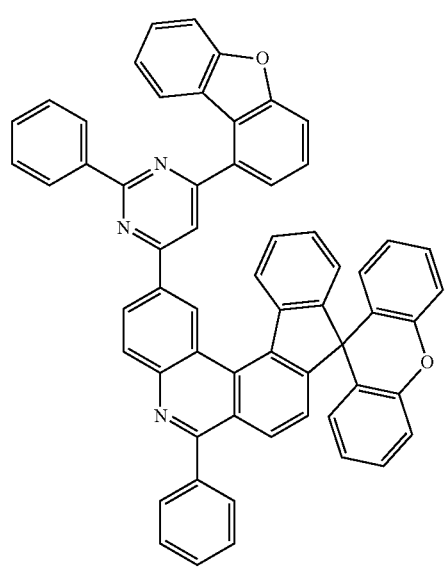
196
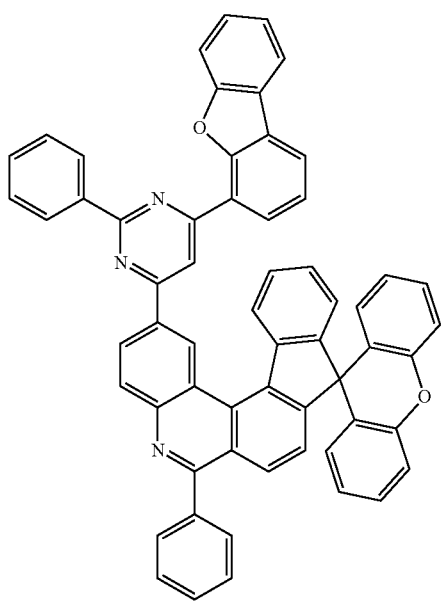
197
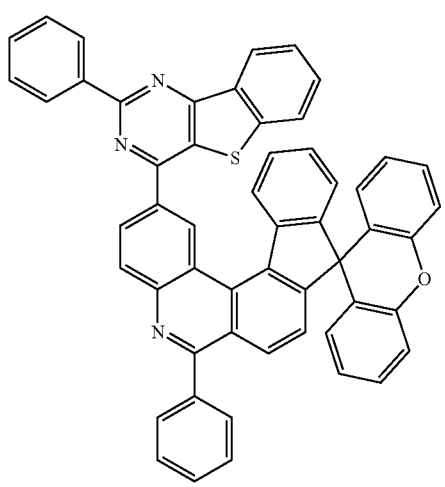

101
-continued
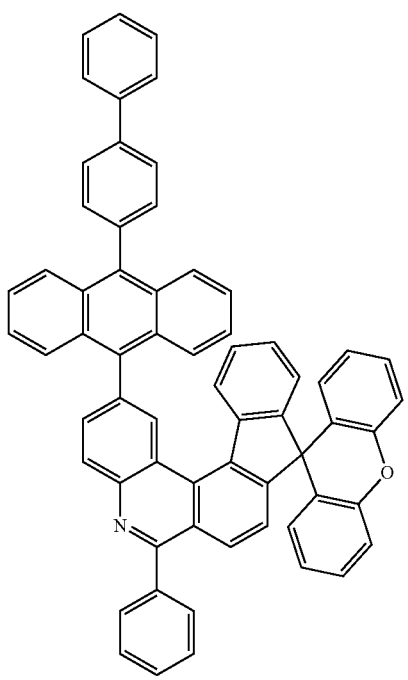
198
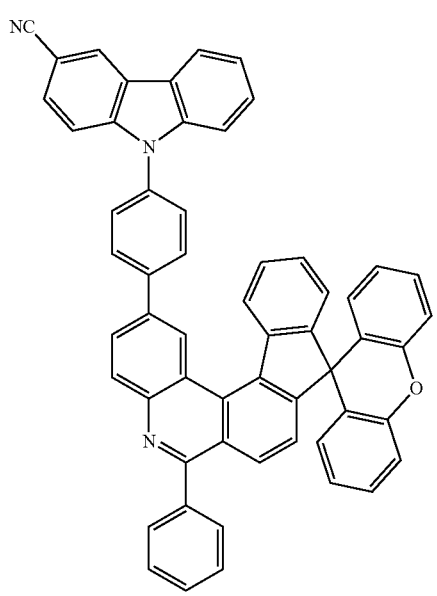
199
102
-continued
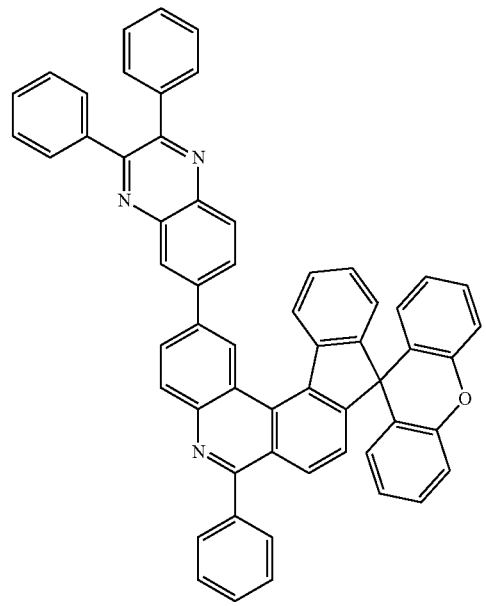
200
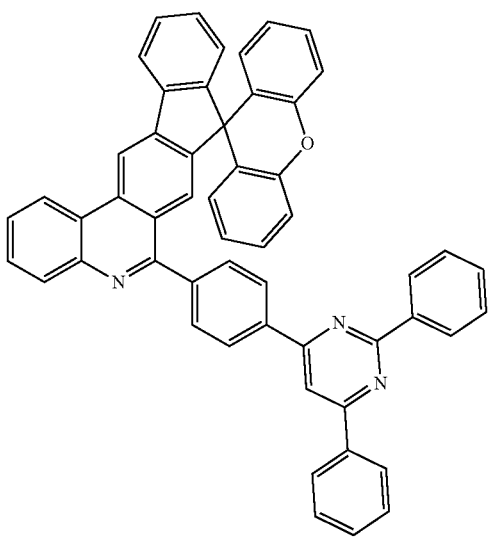
201

202
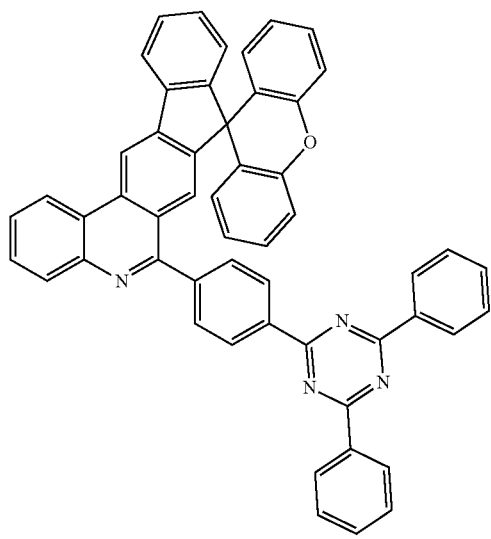
203
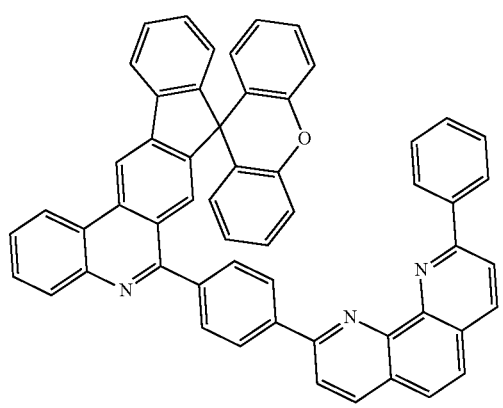
204
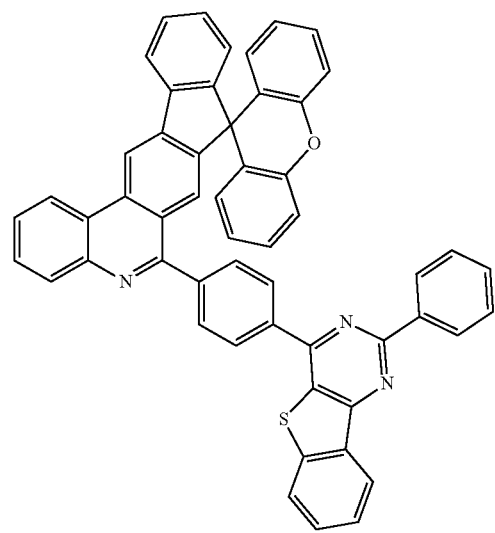
205
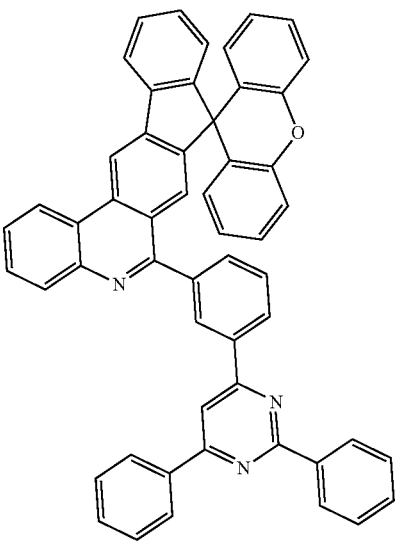
206
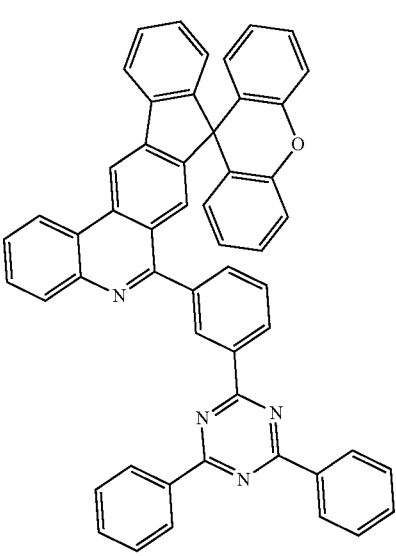
207
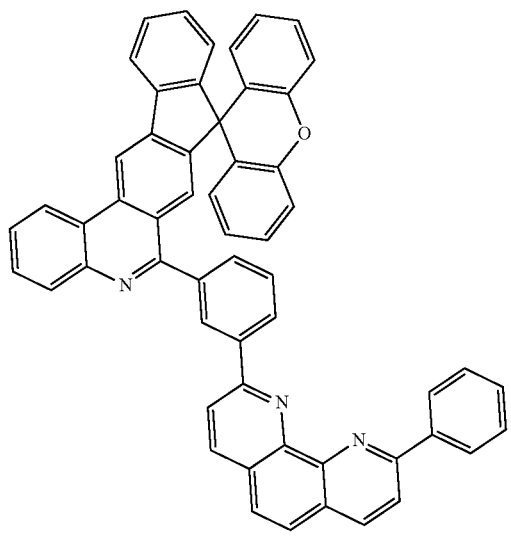

208
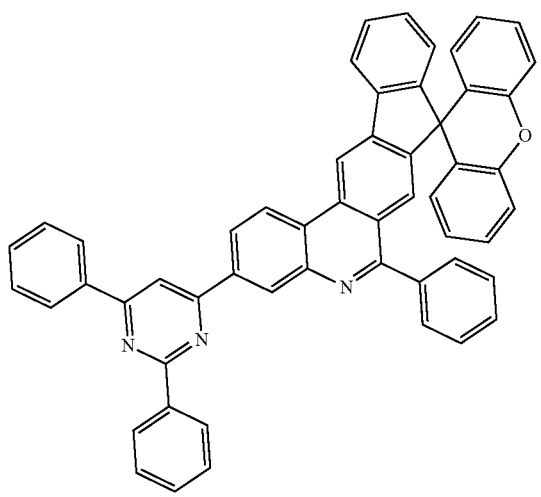
209
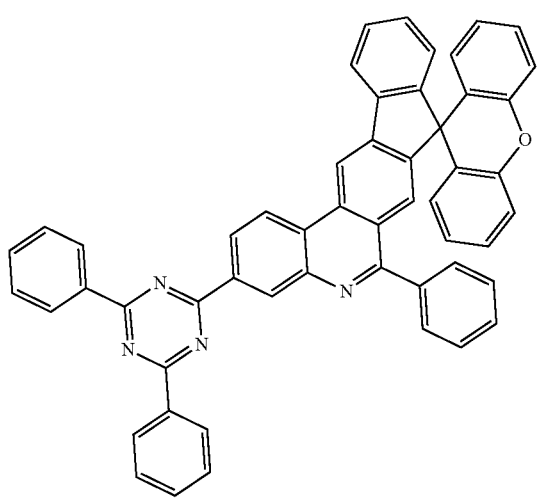
210
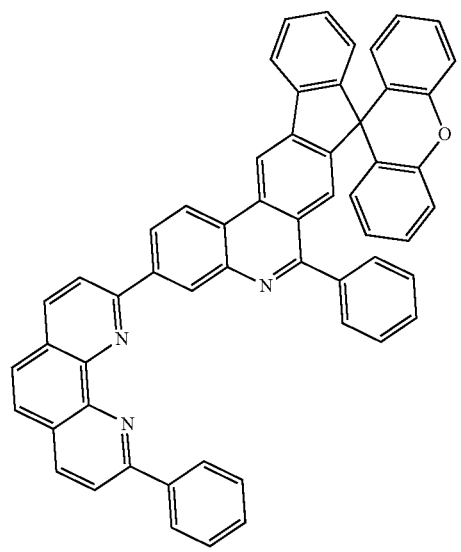
211
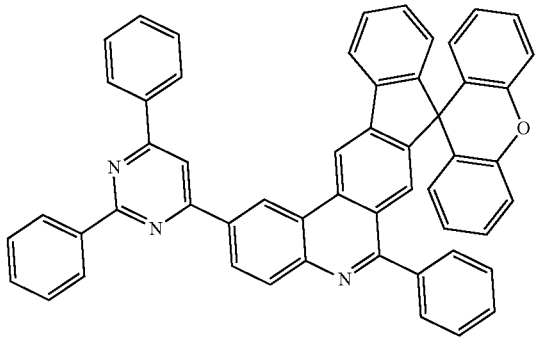
212
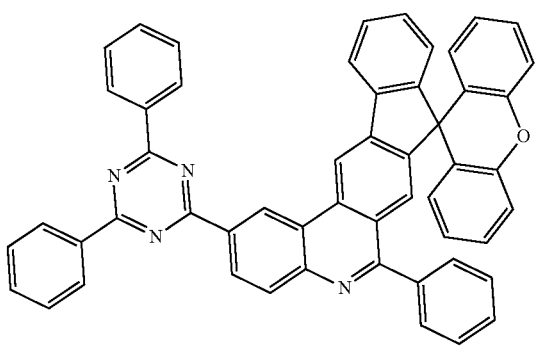
213

214
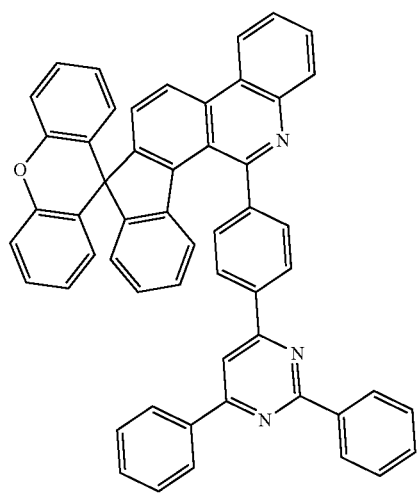
215
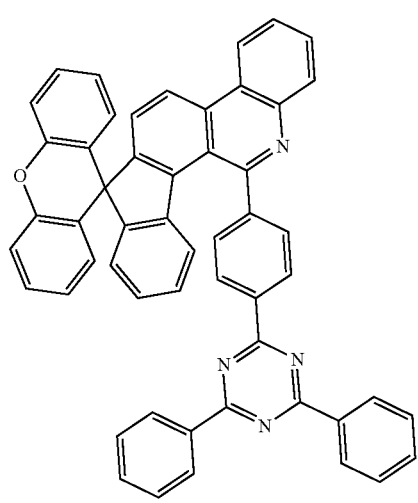
216
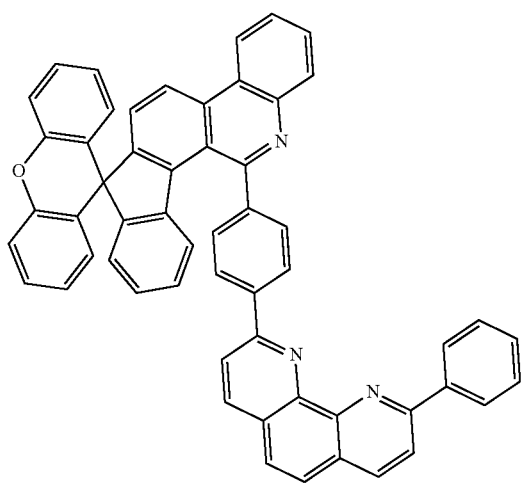
217
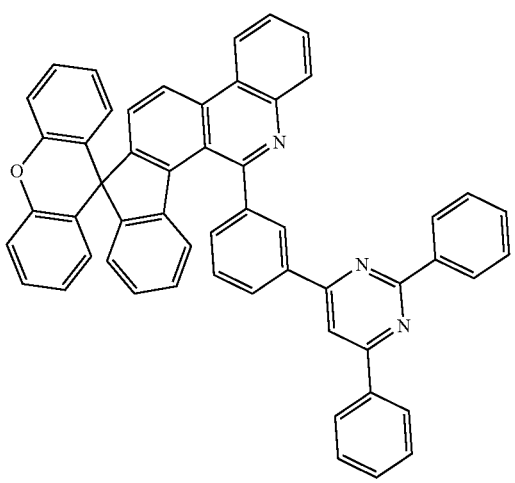
218
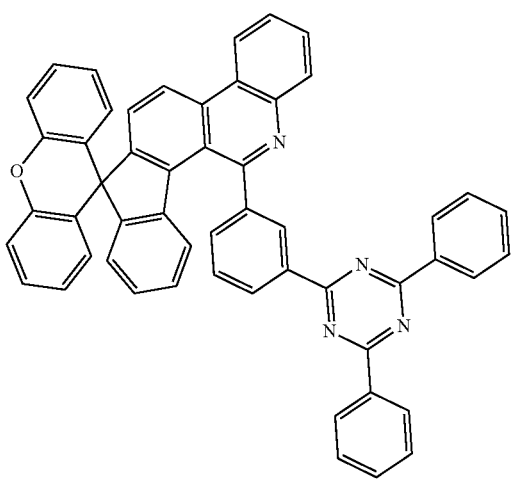
219
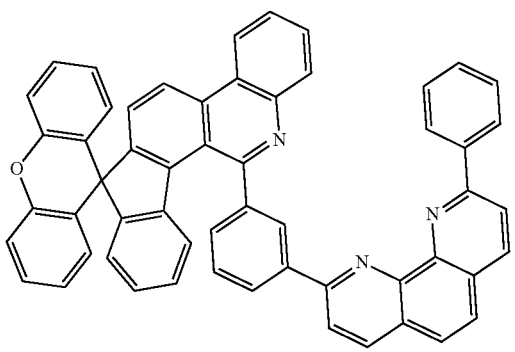

220
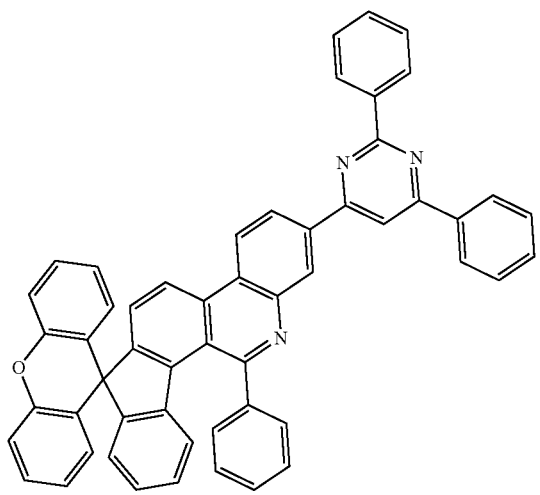
221
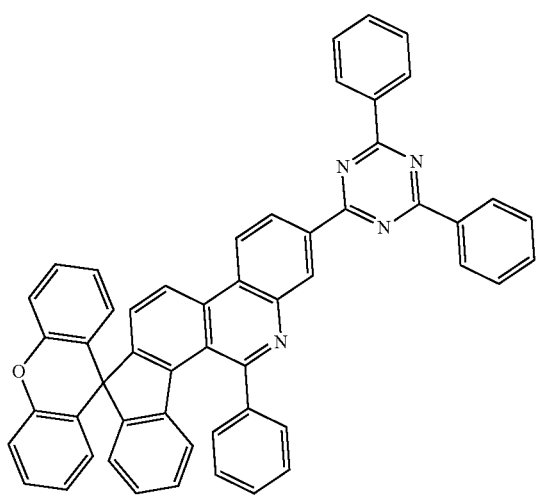
222
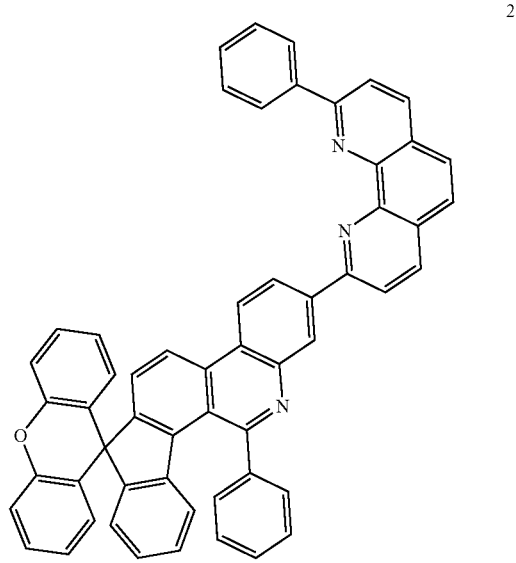
223
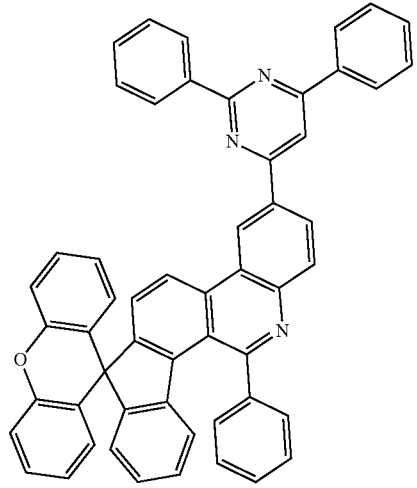
224
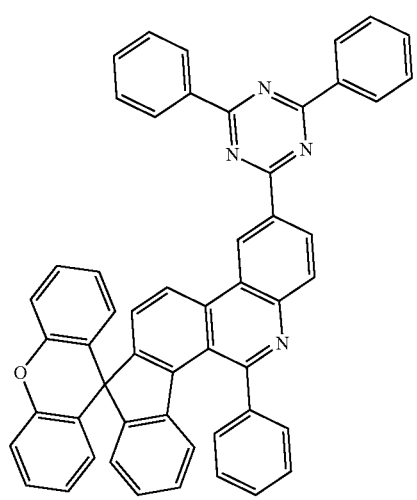
225
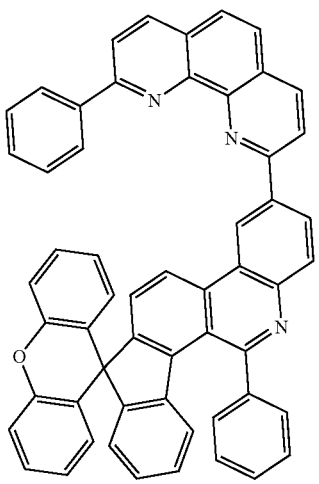

226
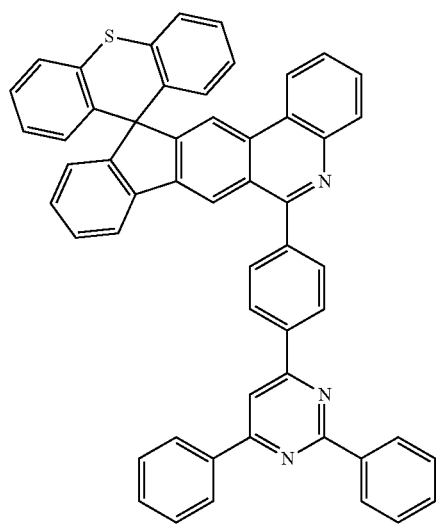
228
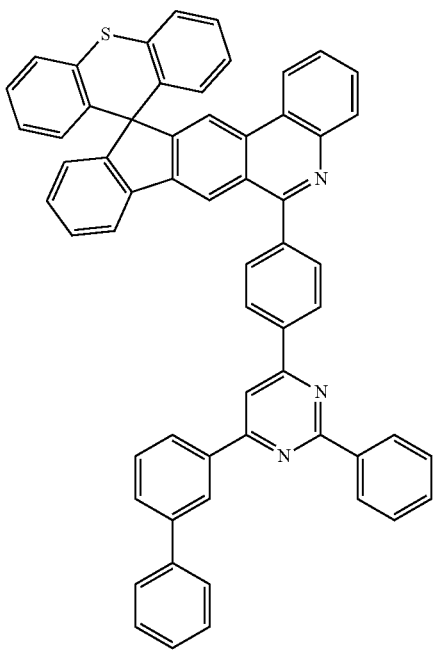
227
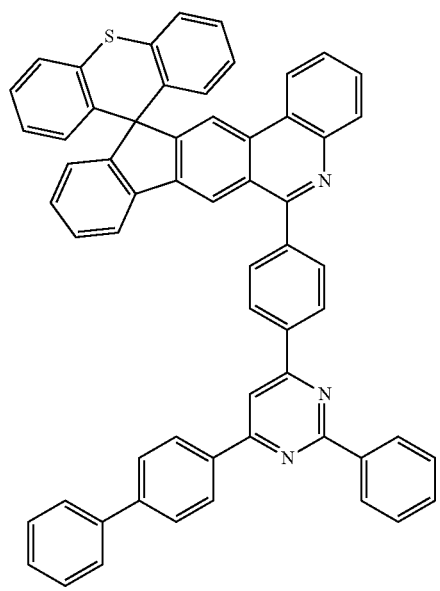
229
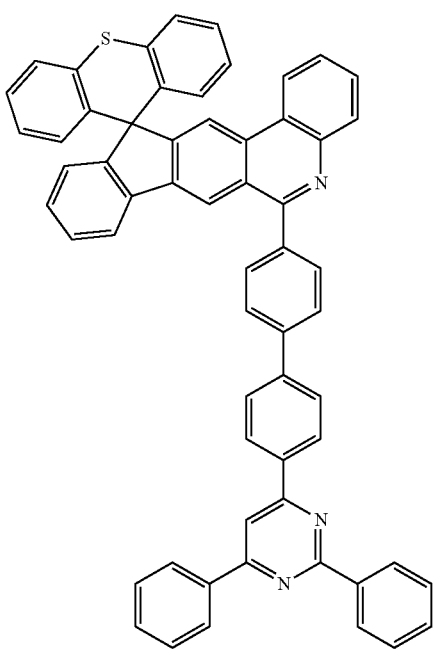

-continued
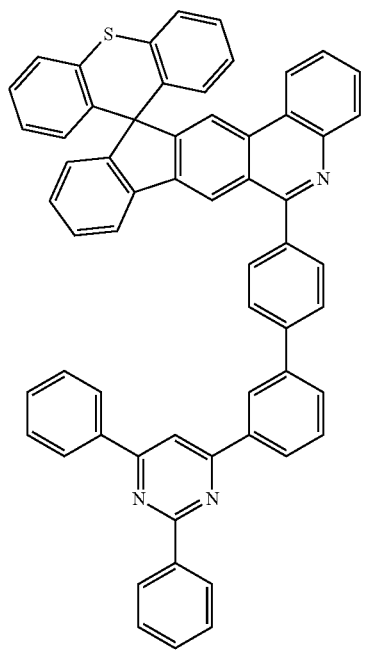
230
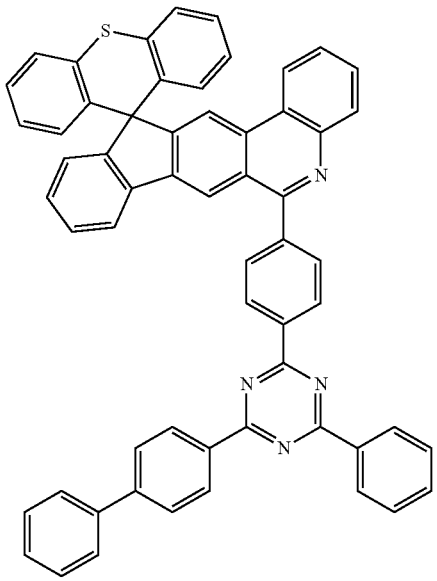
232
231
233

234
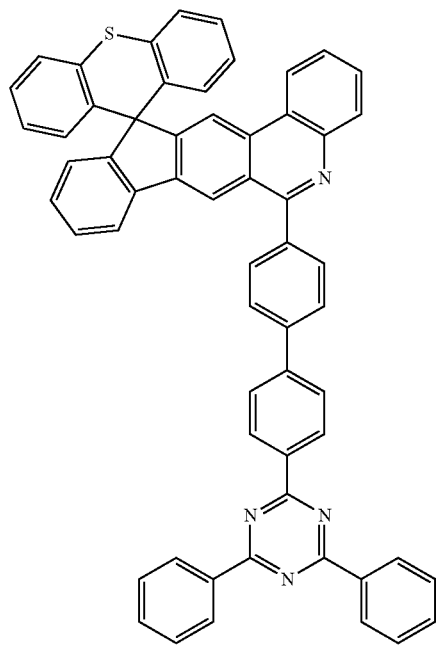
235
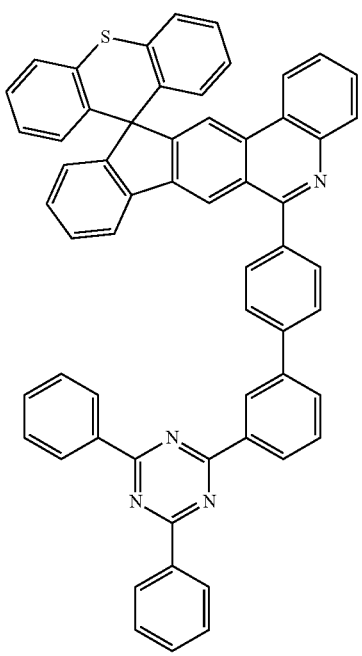
236
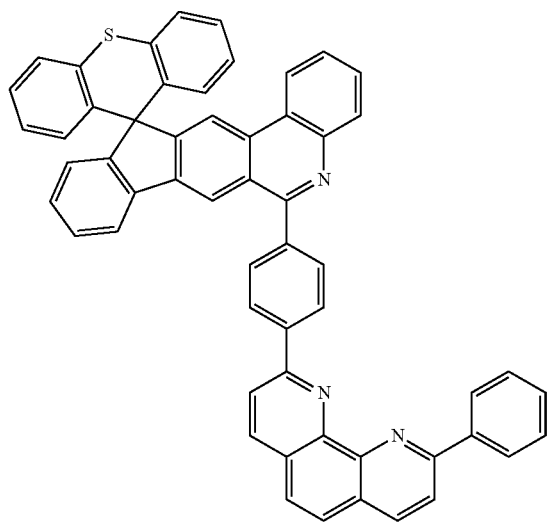
237
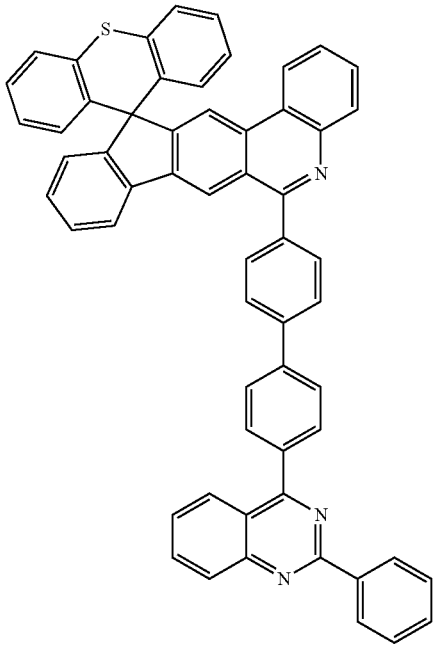

117
-continued
238
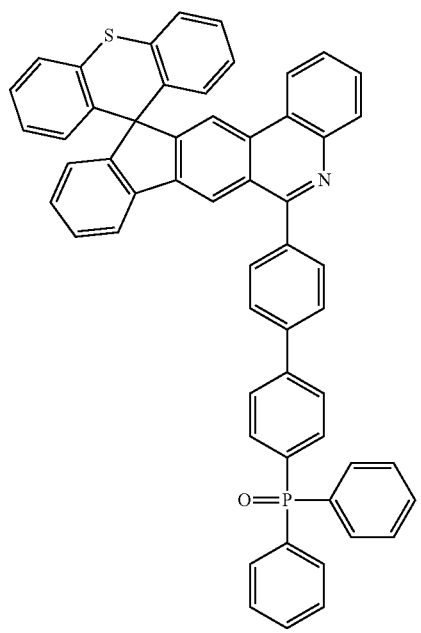
239
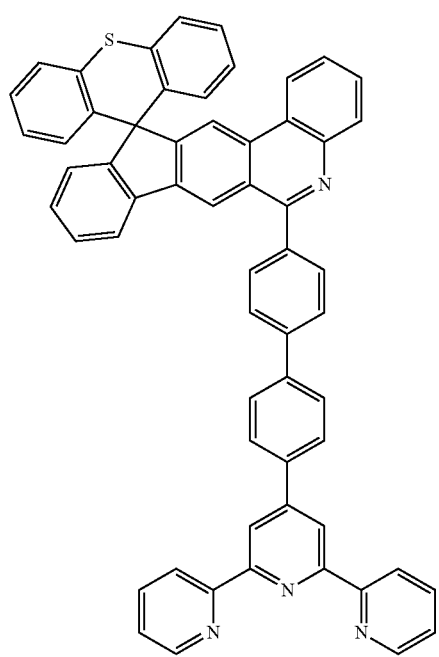
118
-continued
240
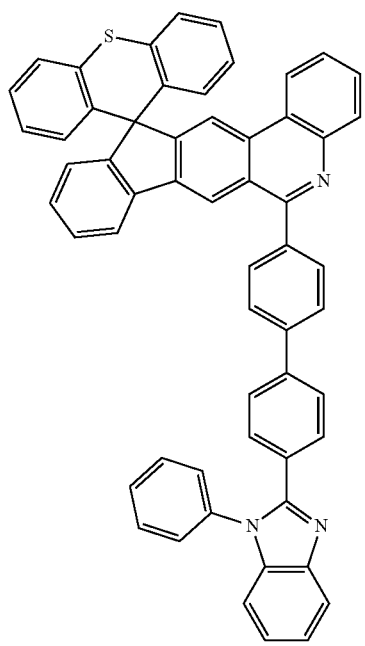
241
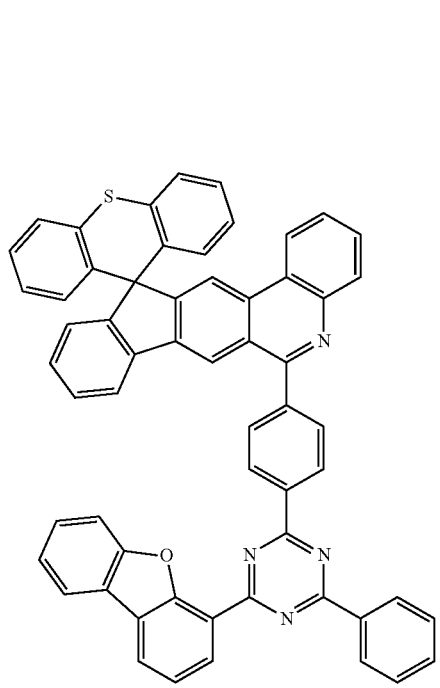

242
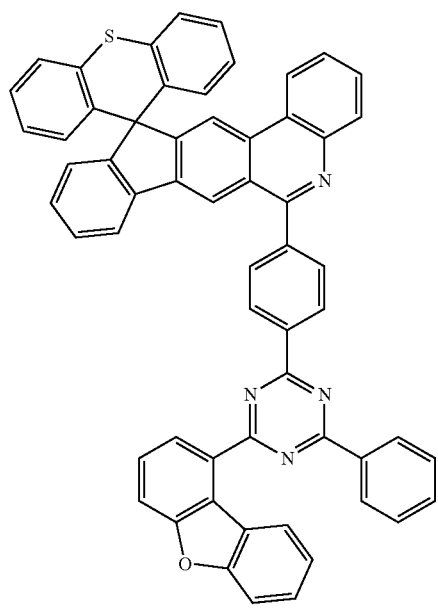
243
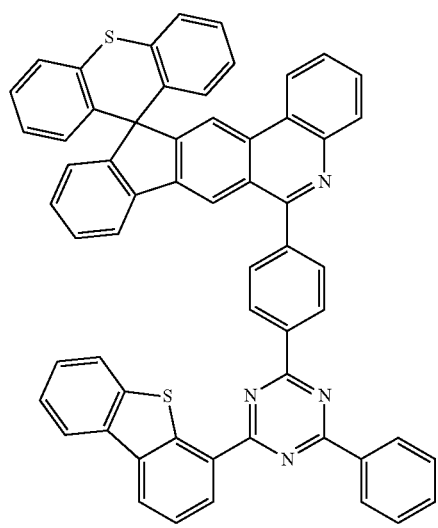
244
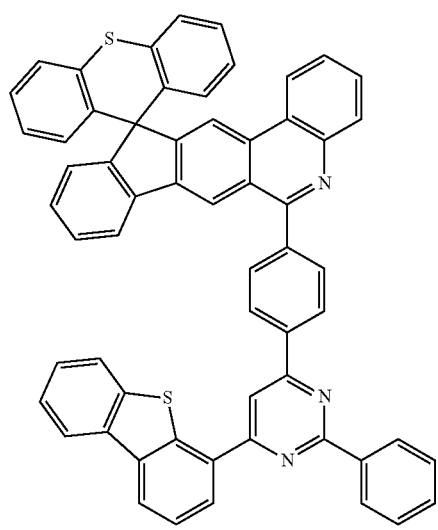
245
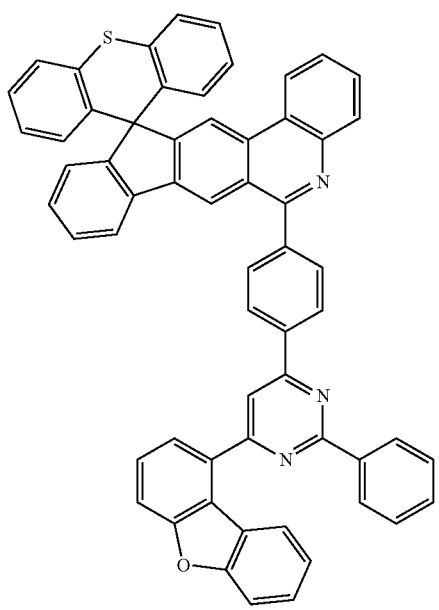
246
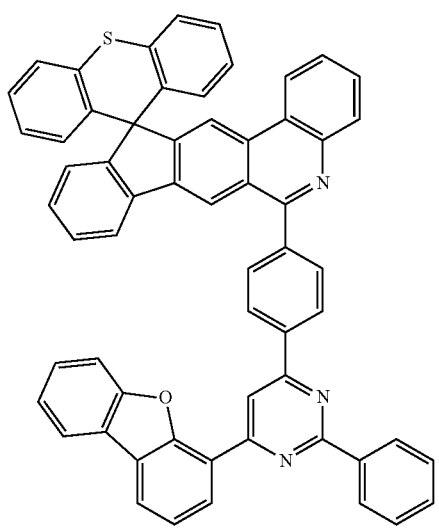
247
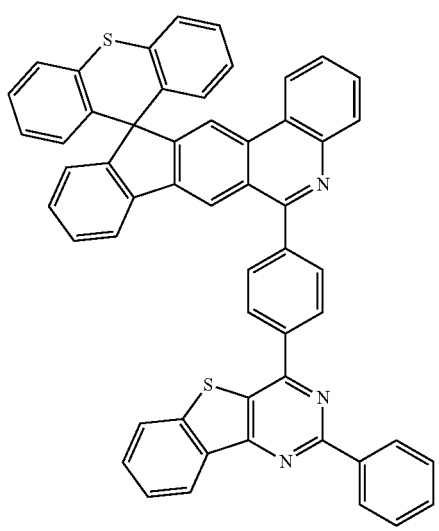

121
-continued
248
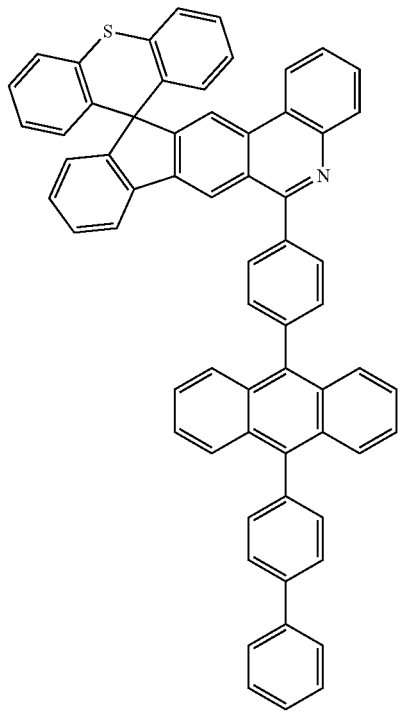
249
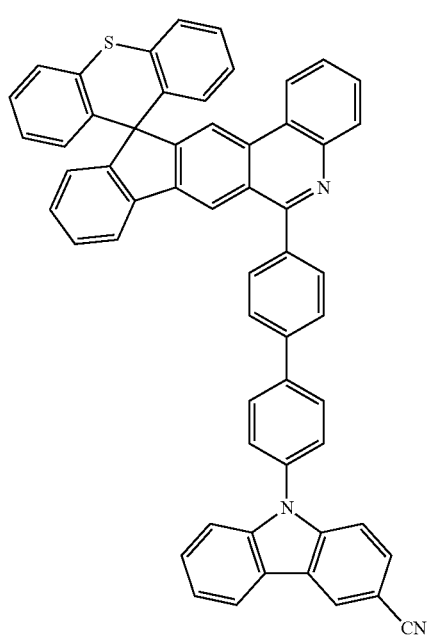
122
-continued
250
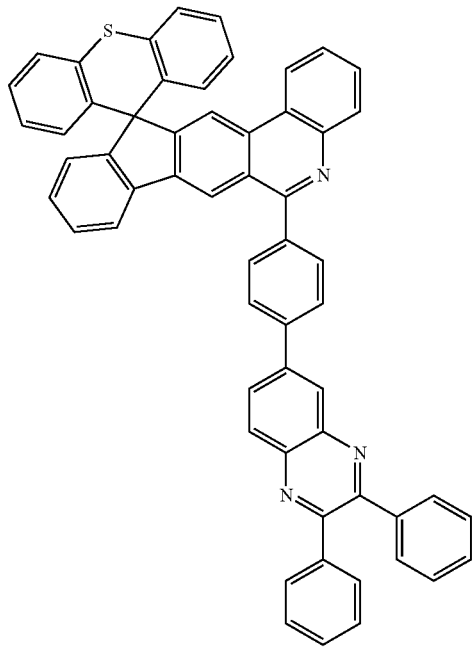
251
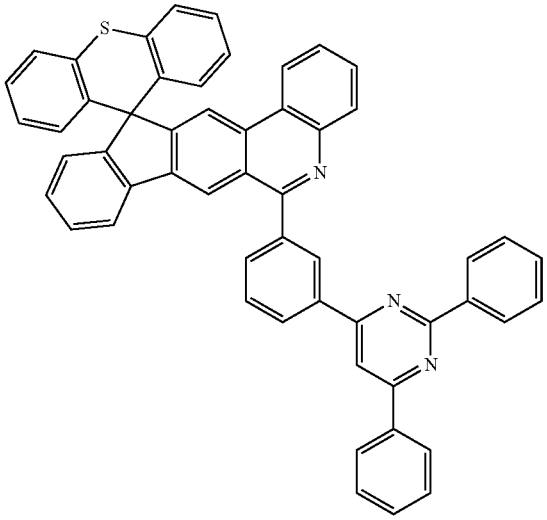

252
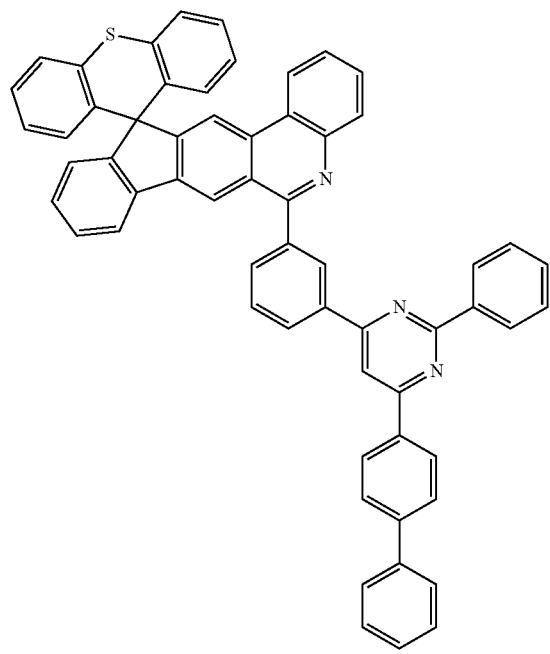
253
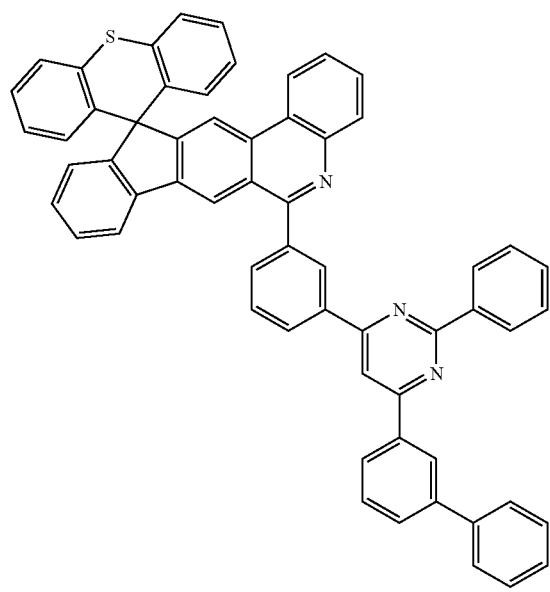
254
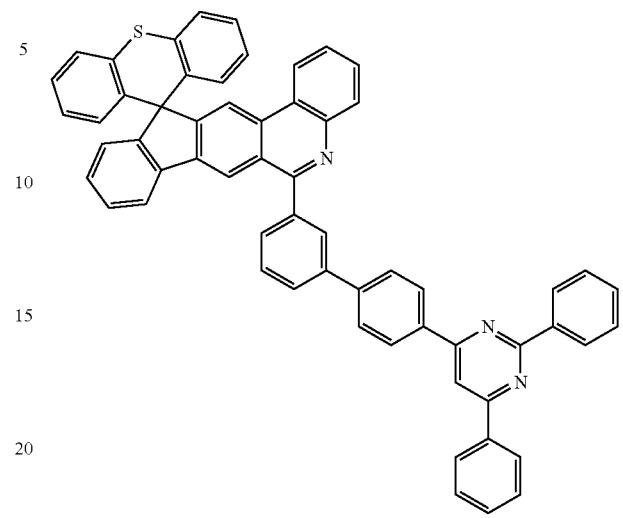
255
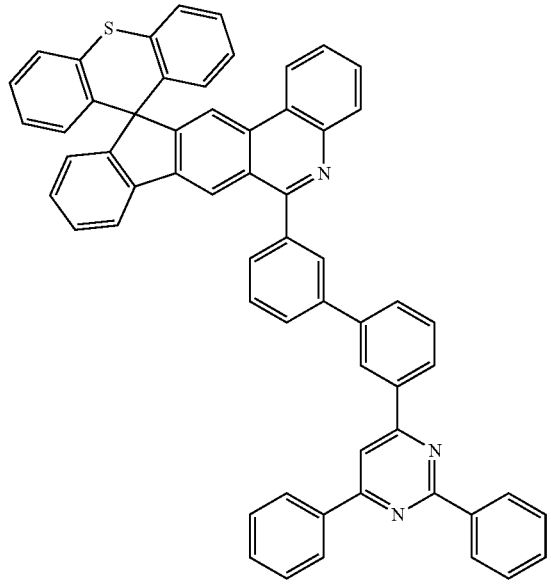

256
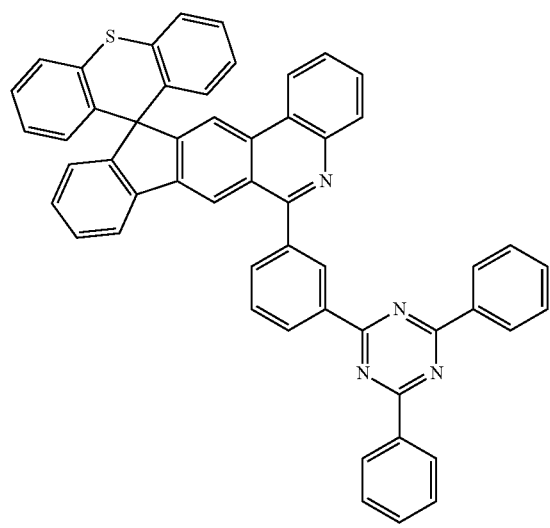
257
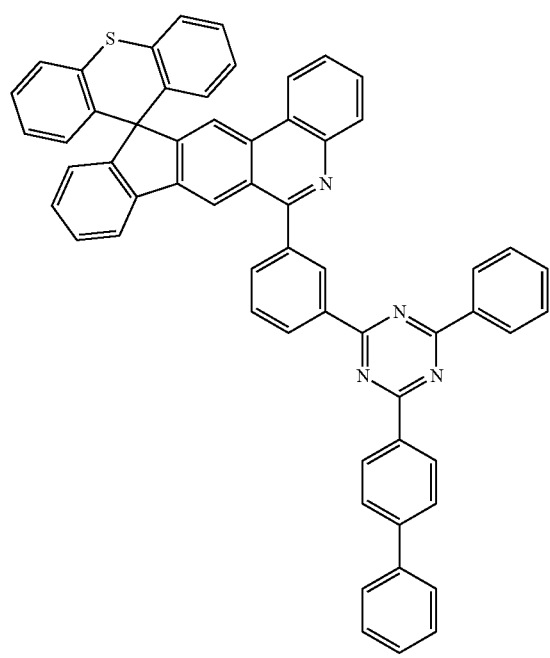
258
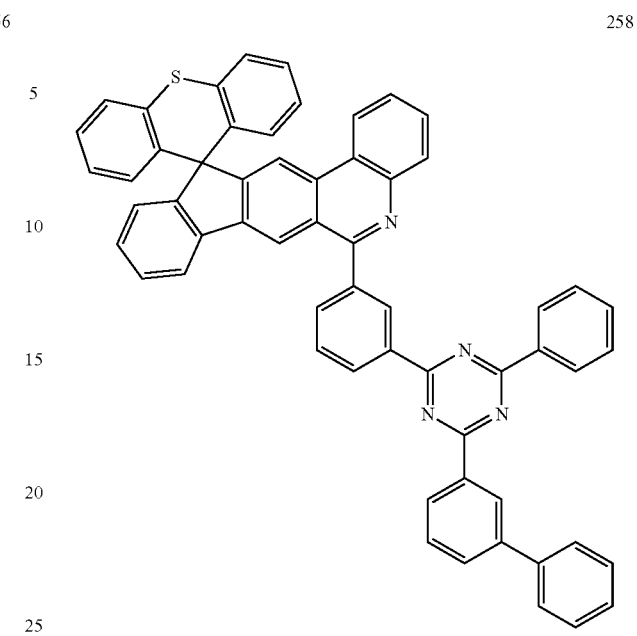
259
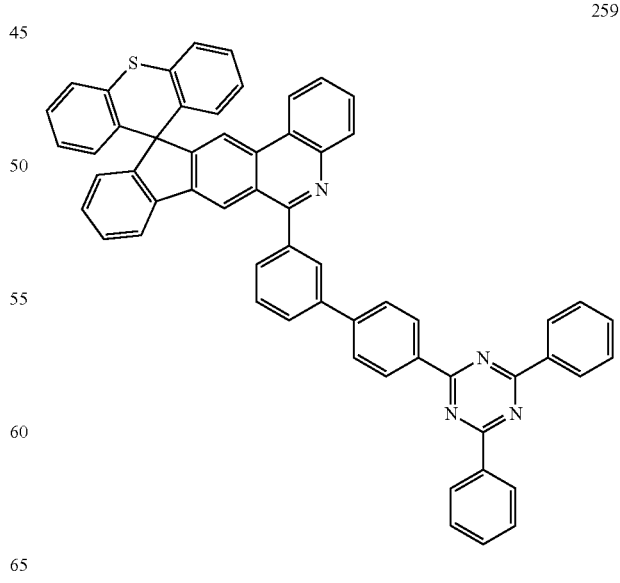

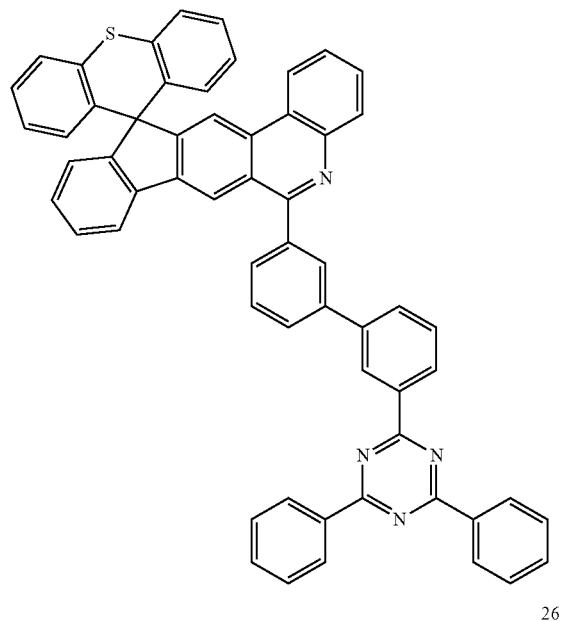
260
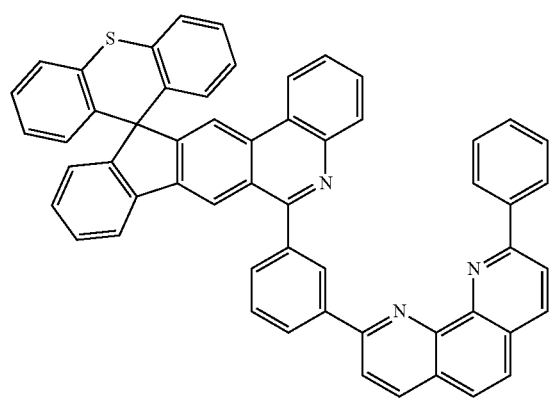
261
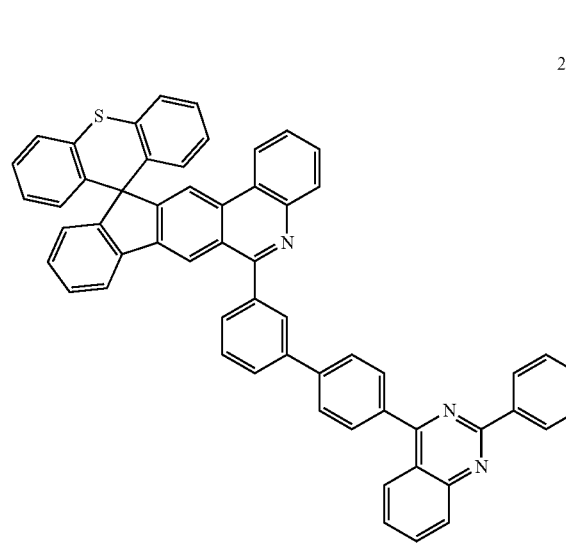
262
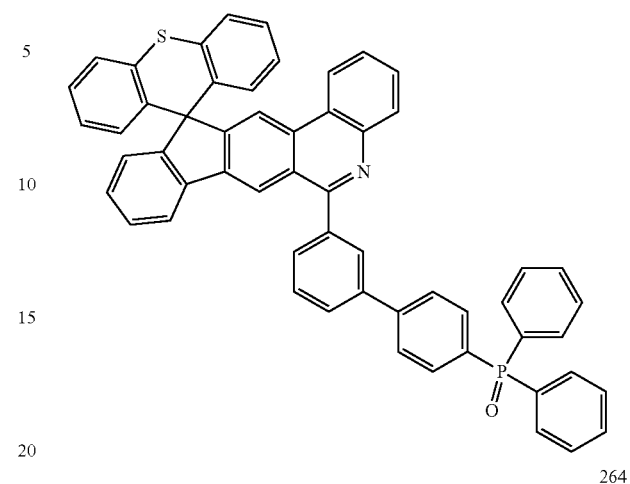
263
264
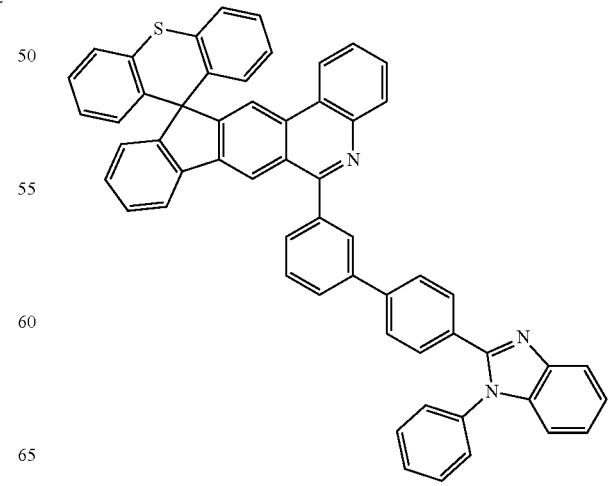
265

129
-continued
266
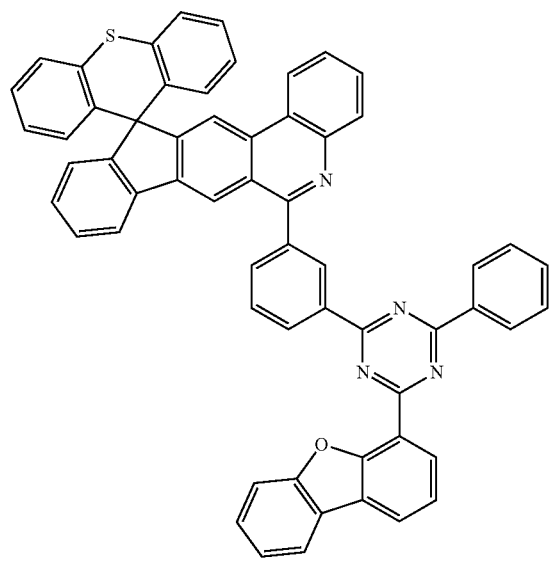
267
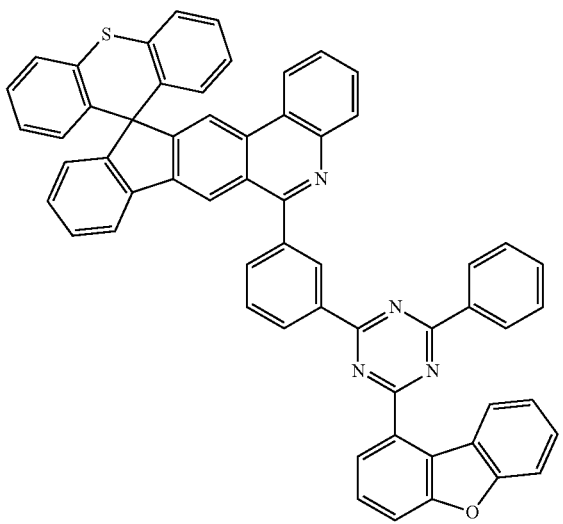
130
-continued
268
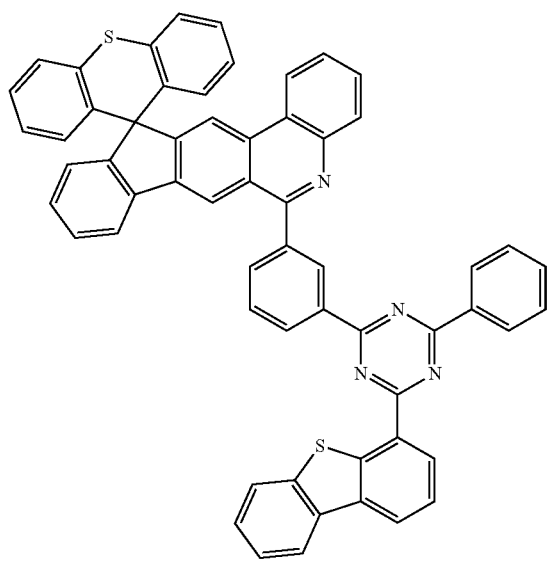
269
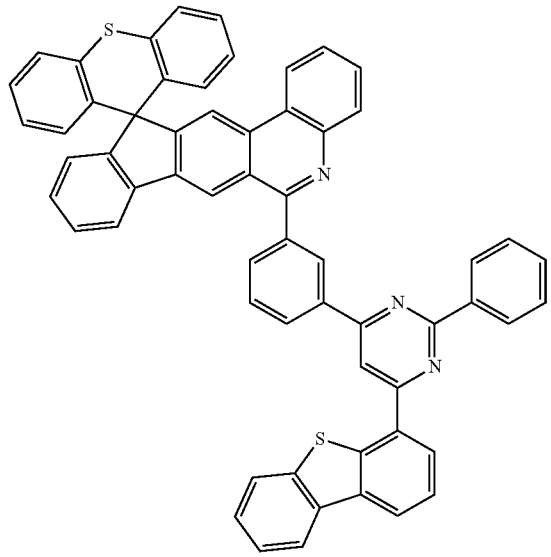

270
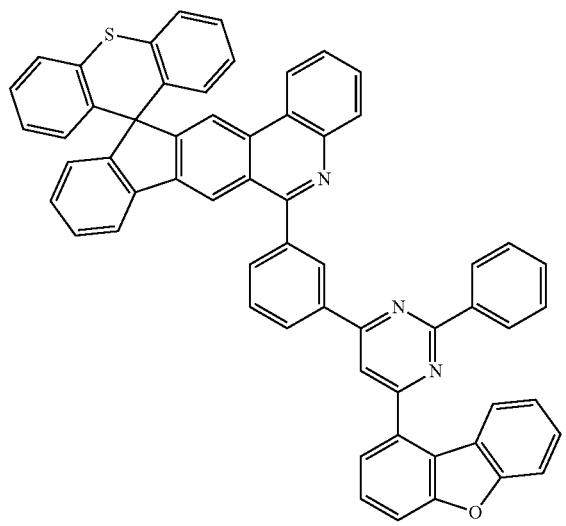
271
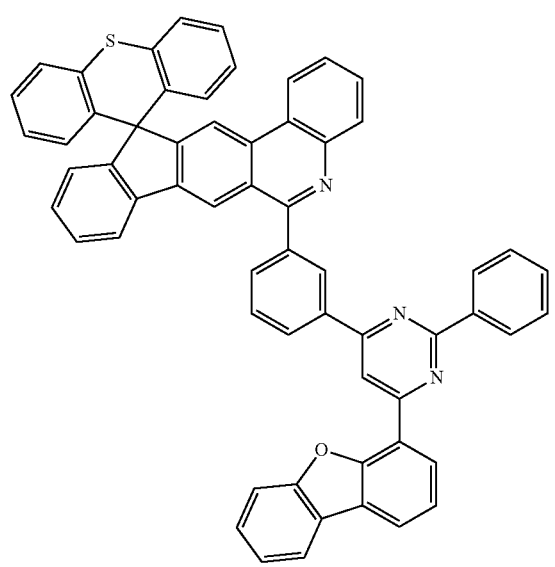
272
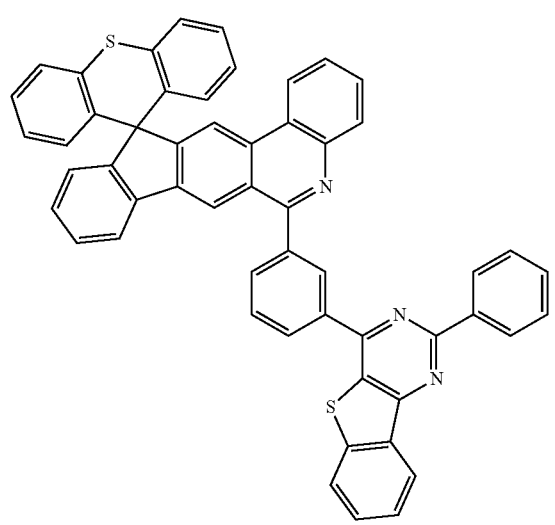
273
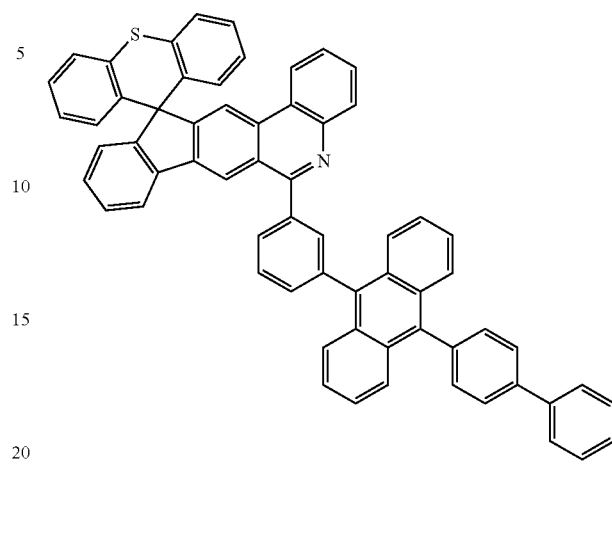
274
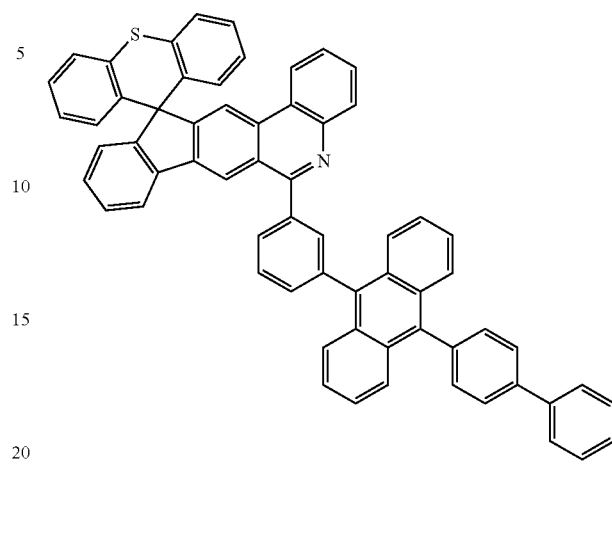
275
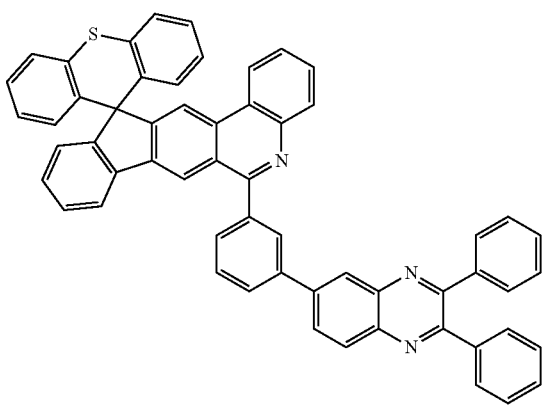

276
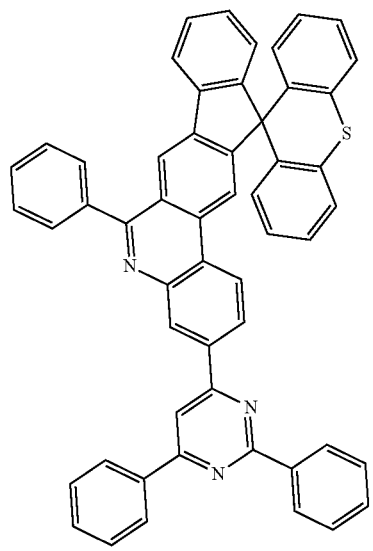
277
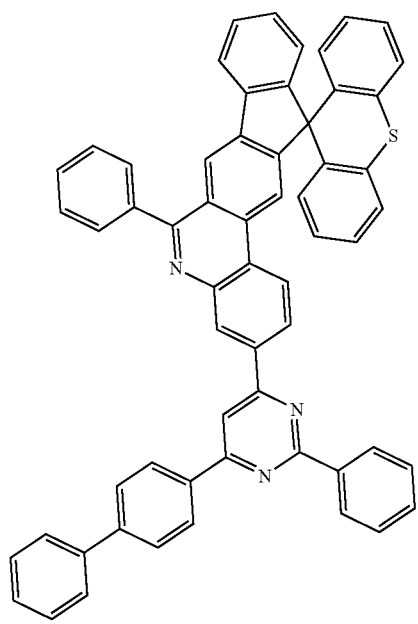
278
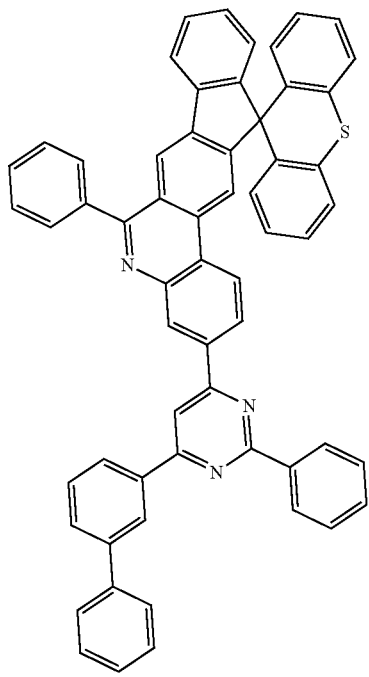
279
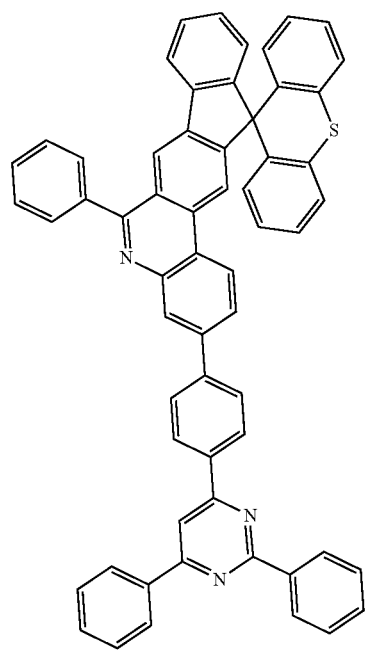

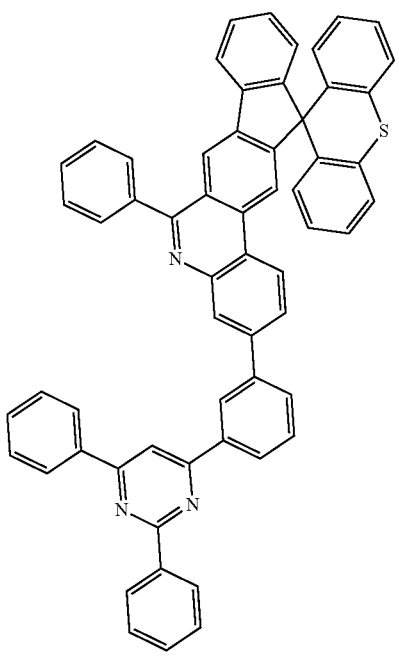
280
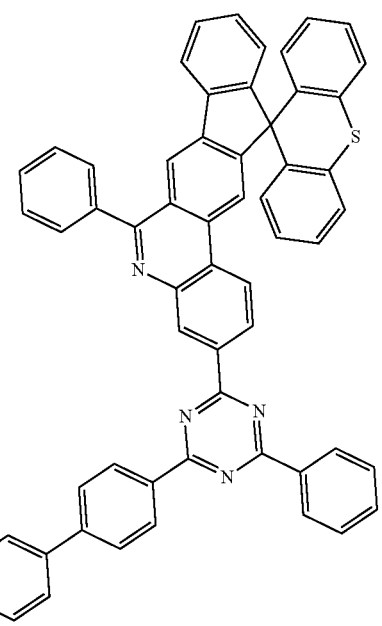
282
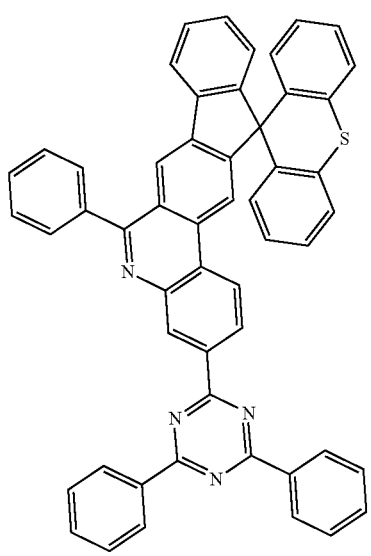
281

137
-continued
284
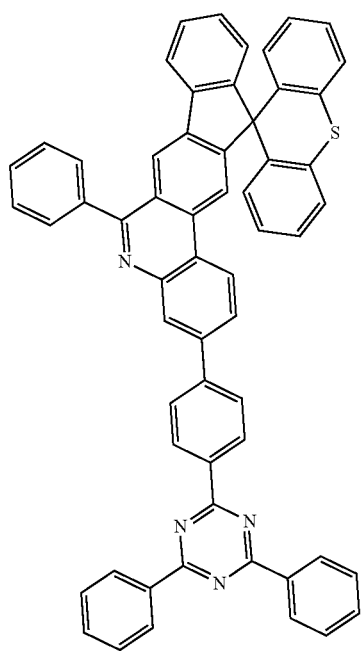
285
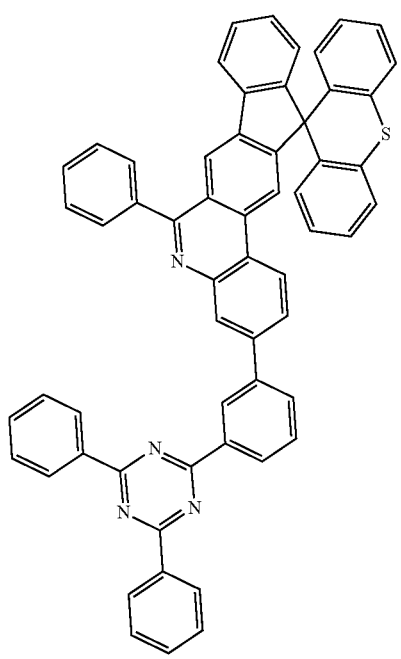
138
-continued
286
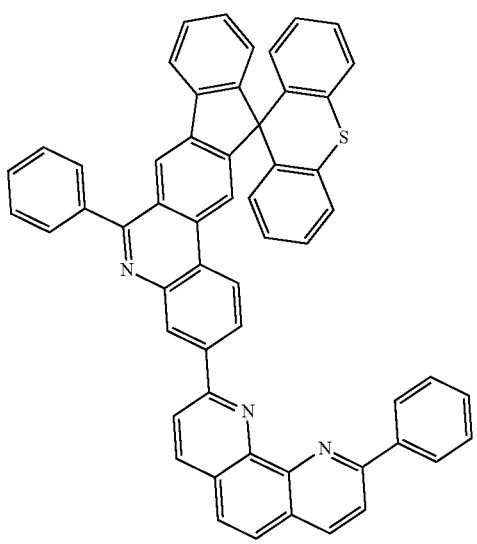
287
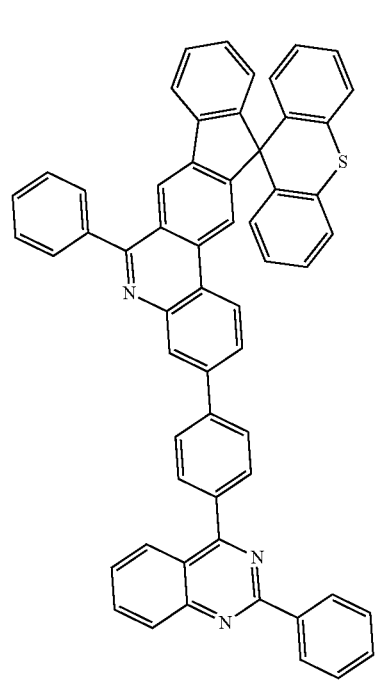

288
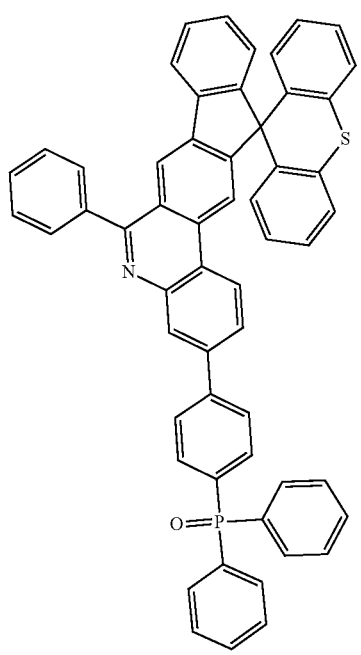
289
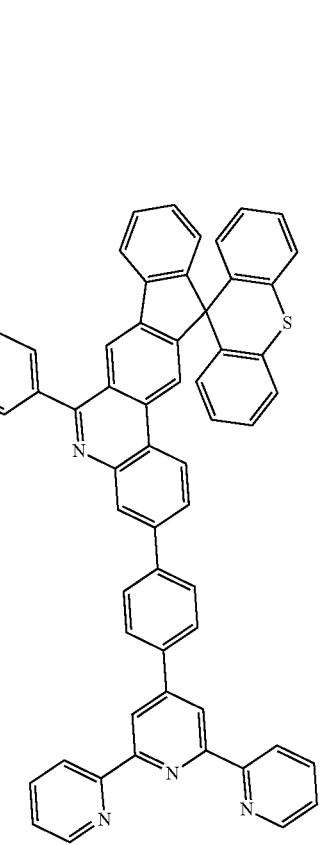
290
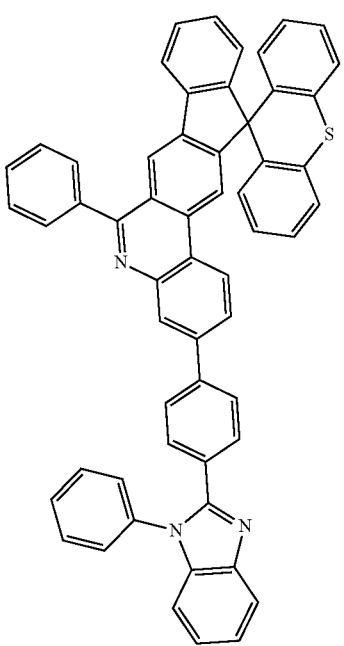
291
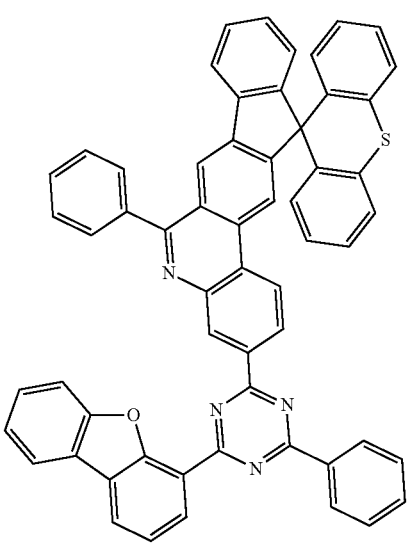

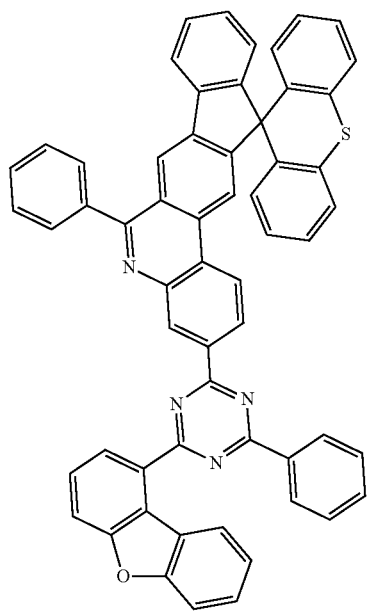
292
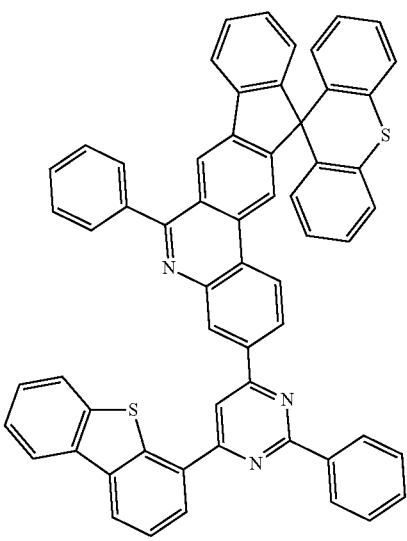
294
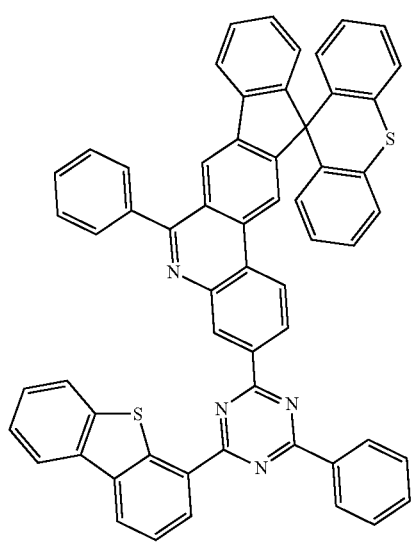
293
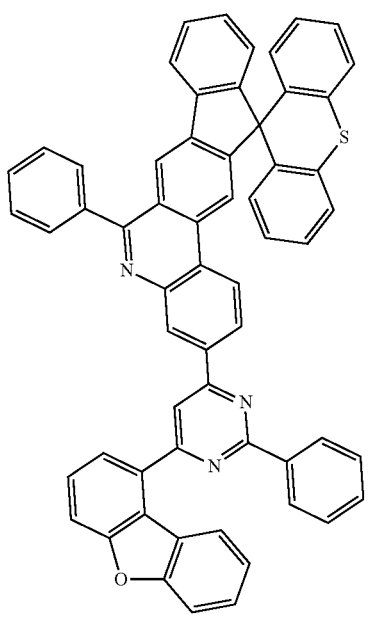
295

-continued
296
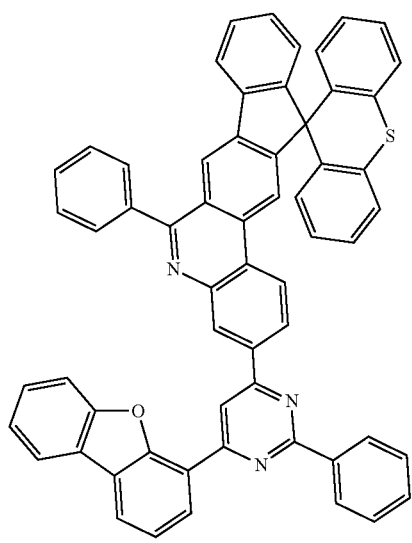
297
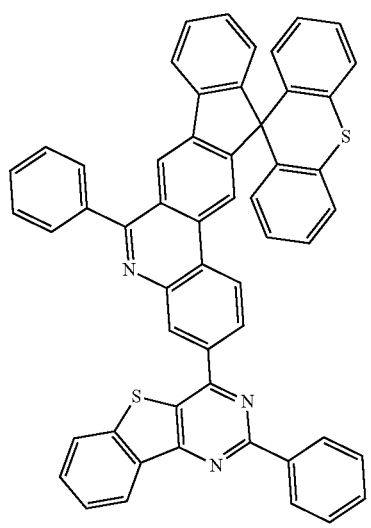
-continued
298
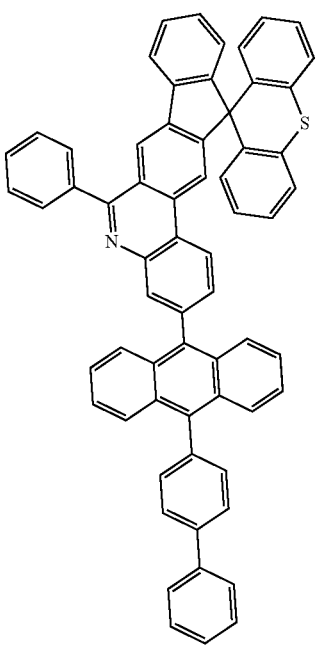
299
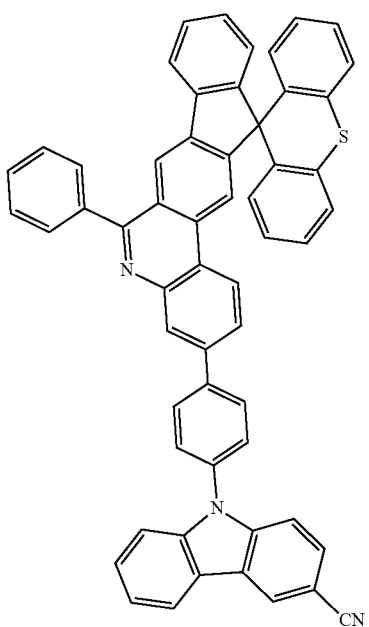

-continued
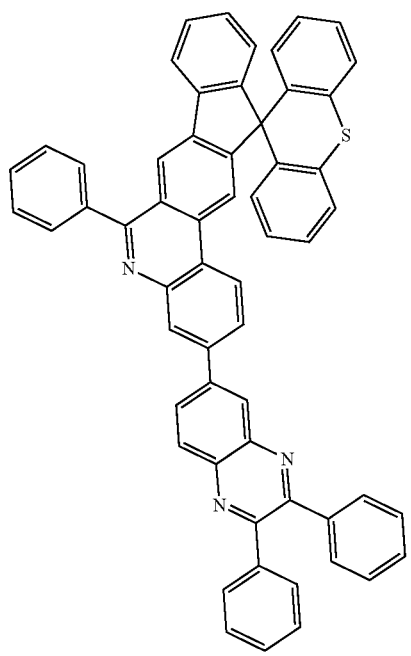
300
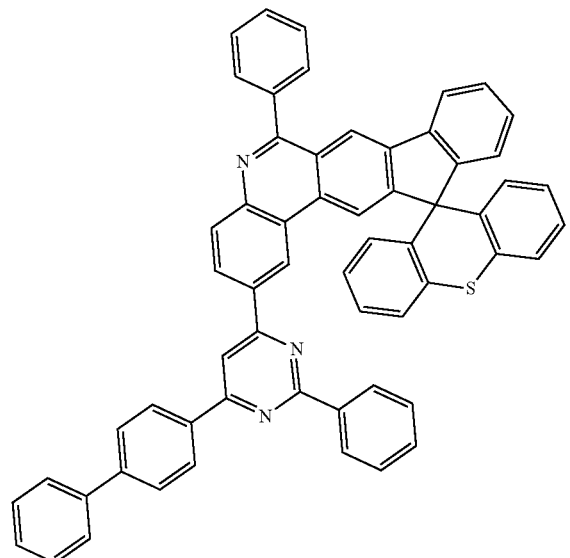
302
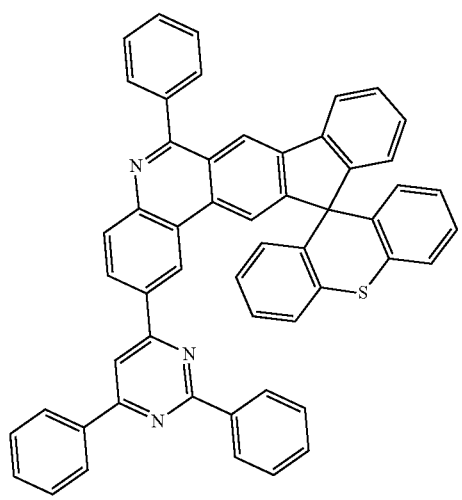
301
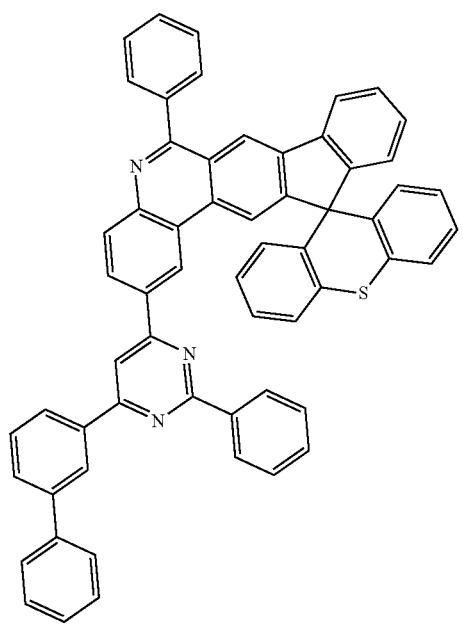
303

-continued
304
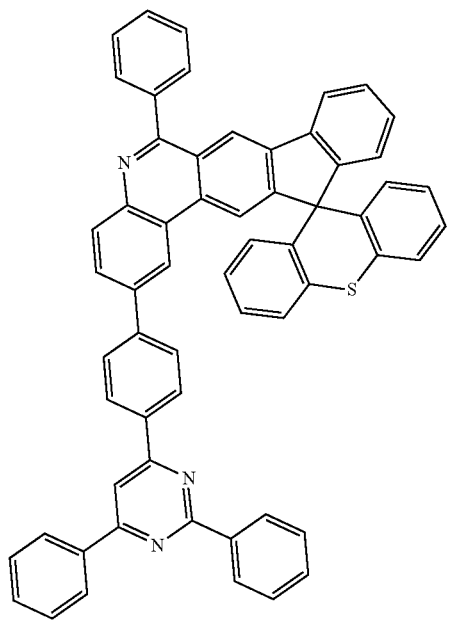
306
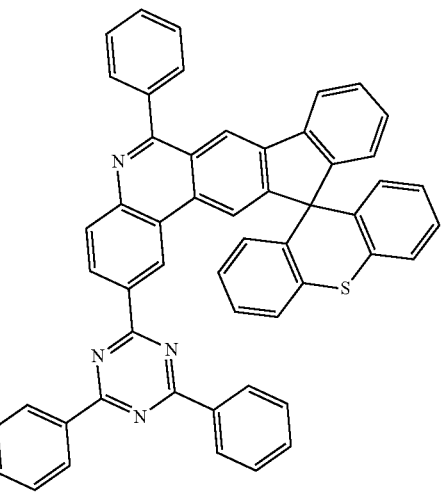
305
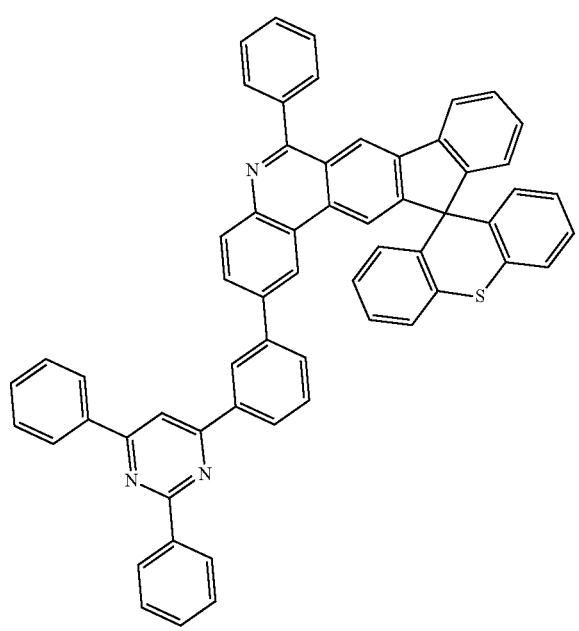
307
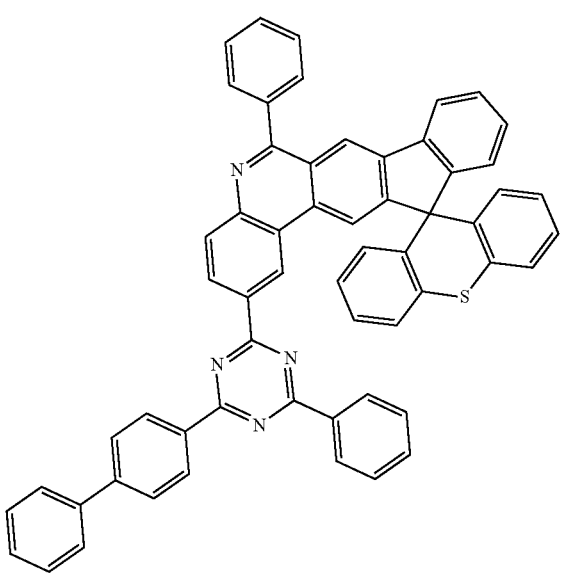

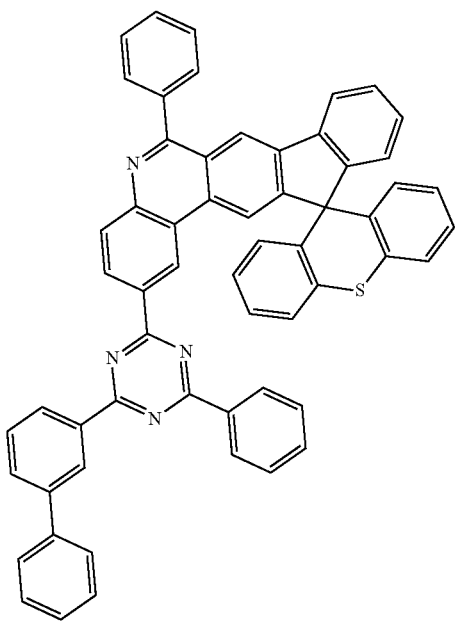
308
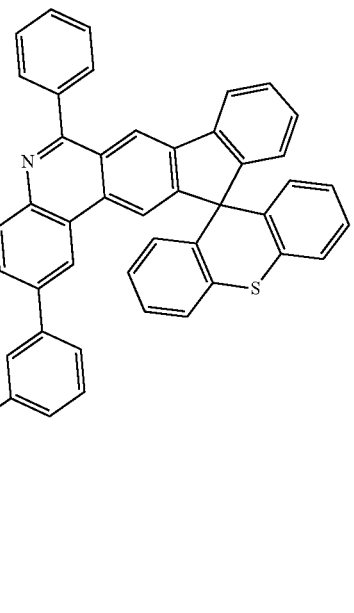
310
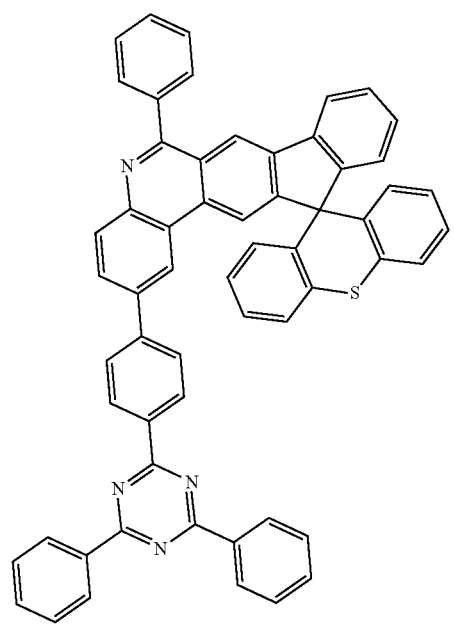
309
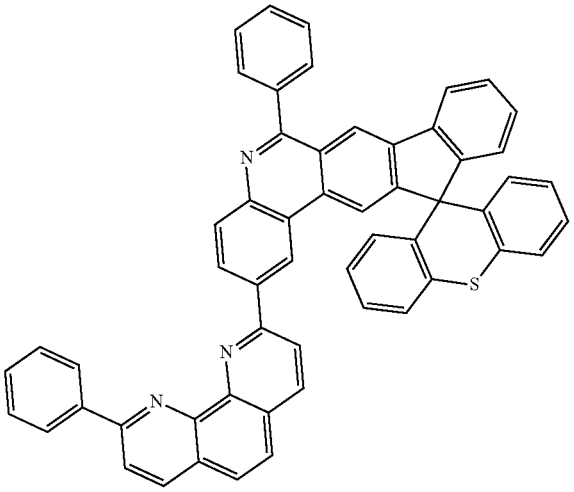
311

151
-continued
312
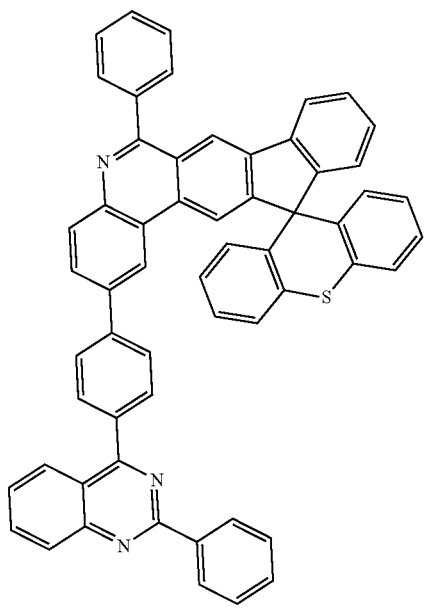
152
-continued
314
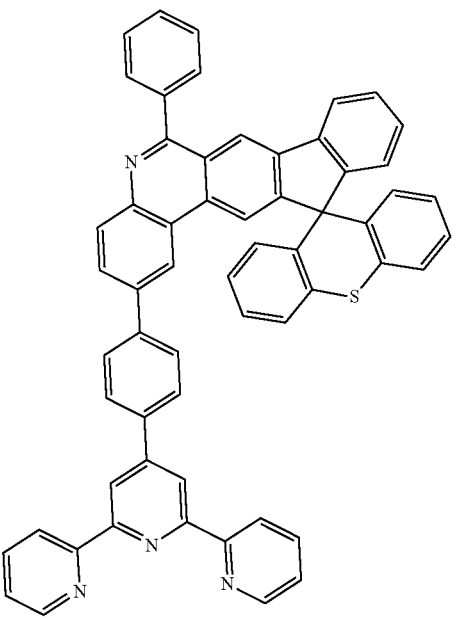
313
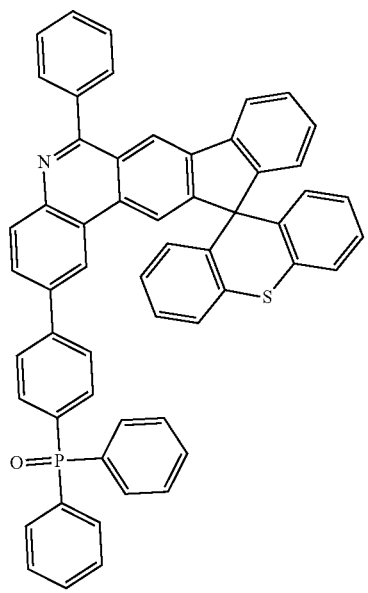
315
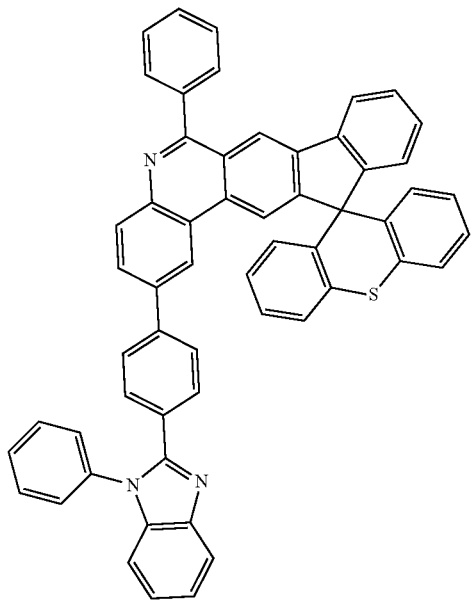

316
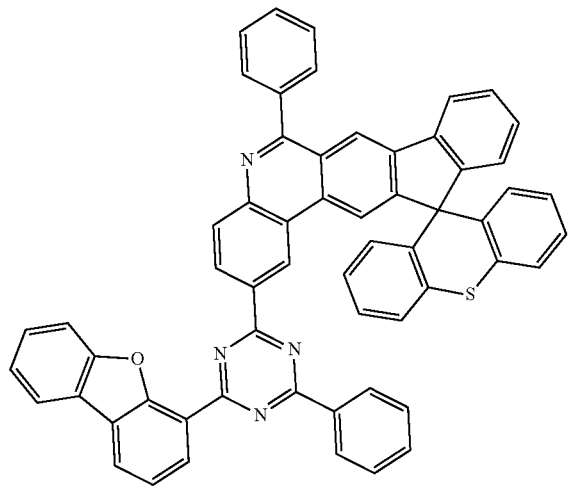
317
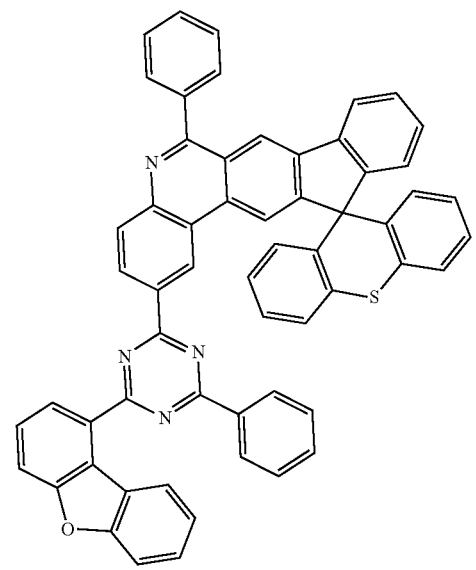
318
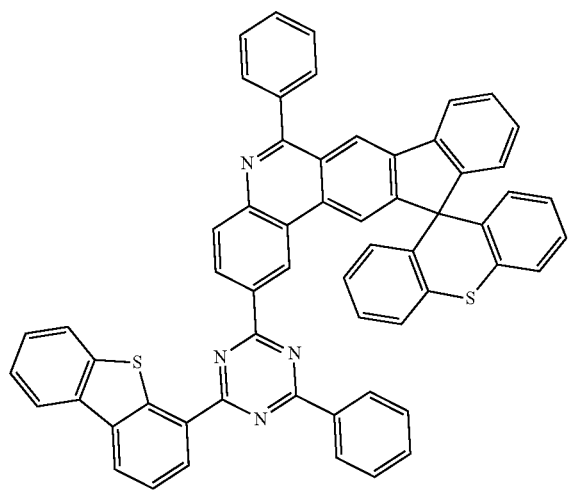
319
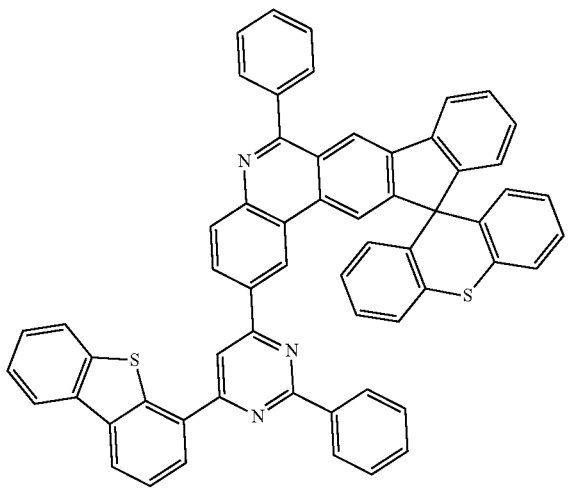
320
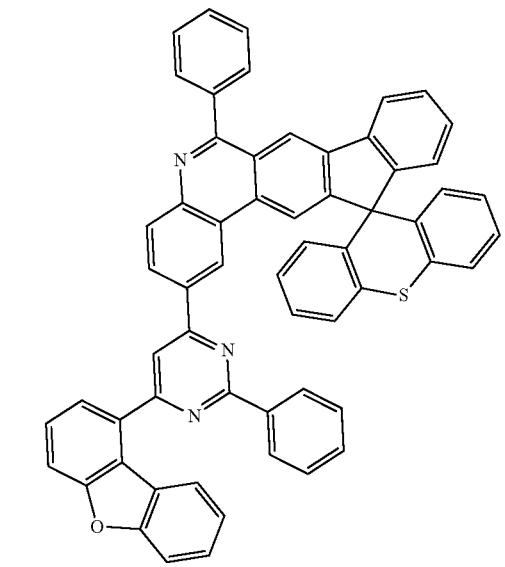
321
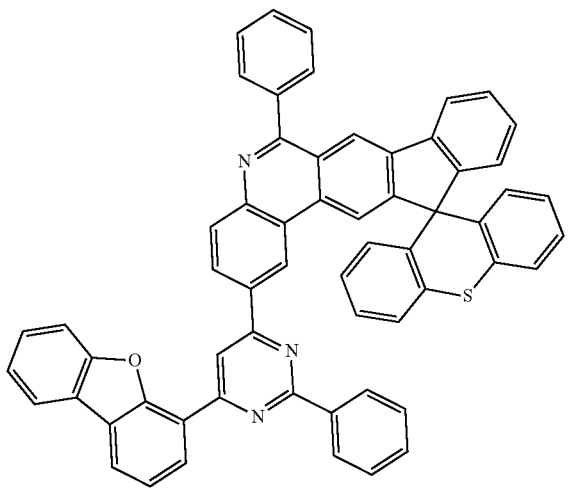

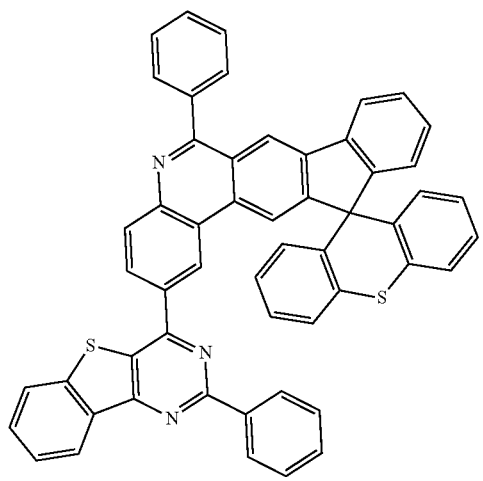
322
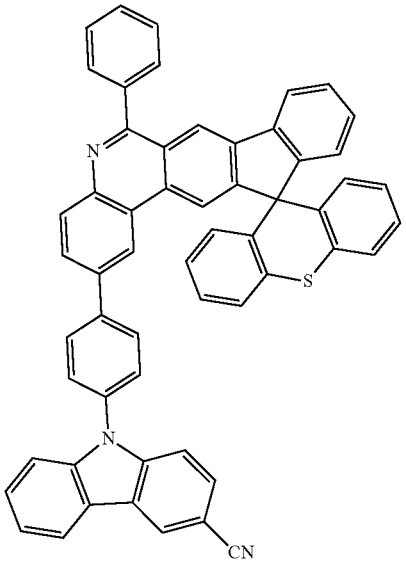
324
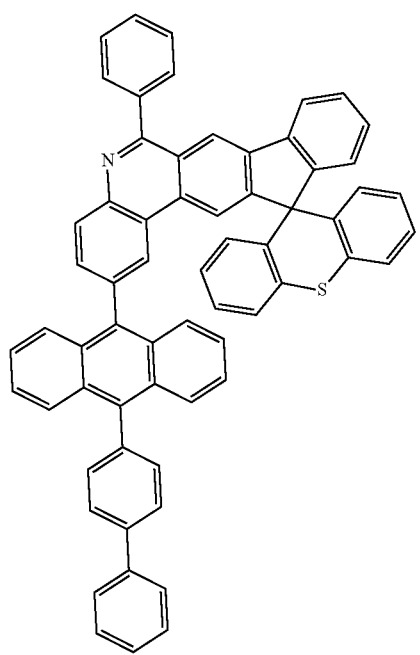
323
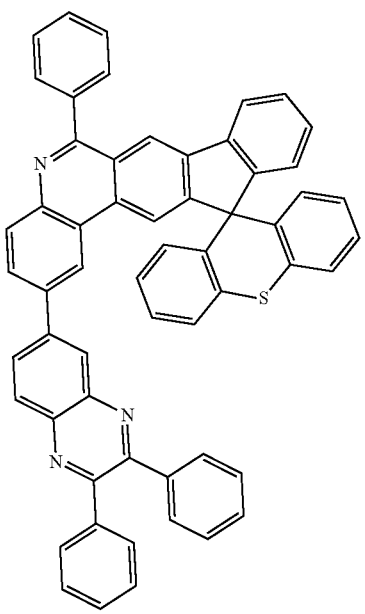
325

-continued
326
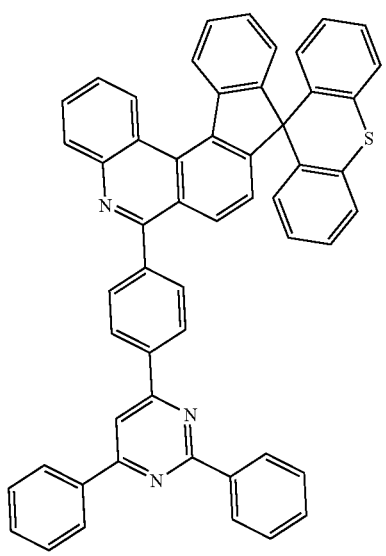
327
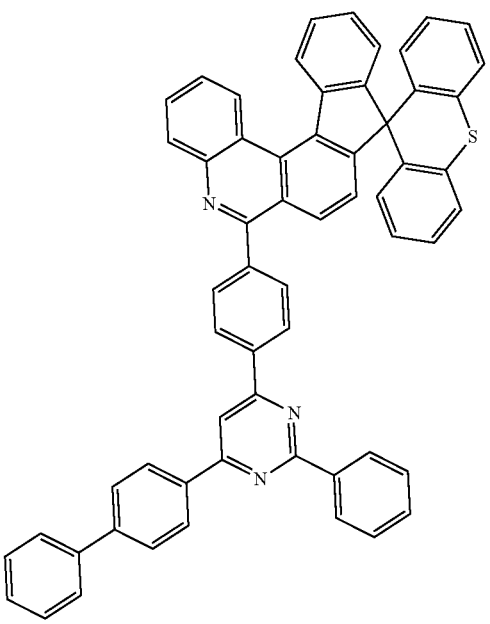
328
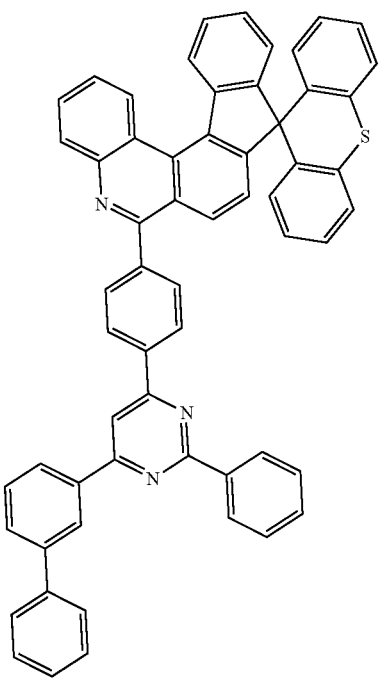
329
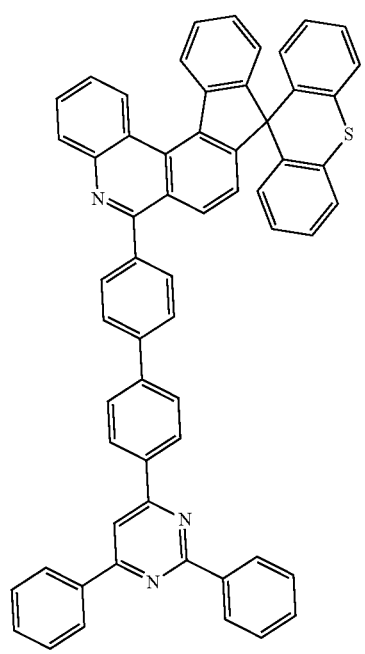

330
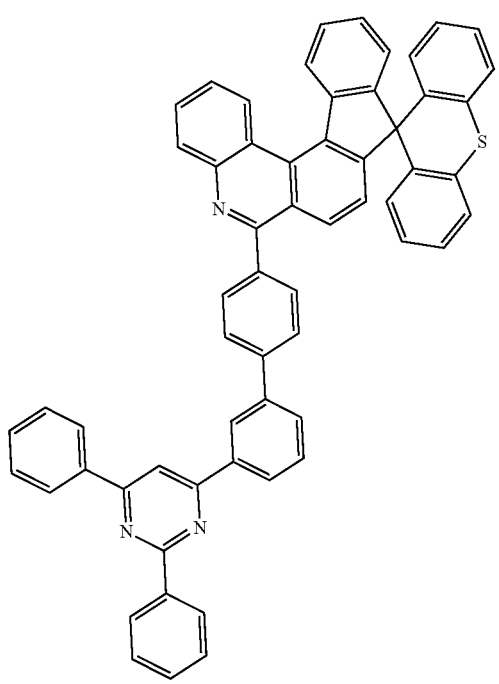
331
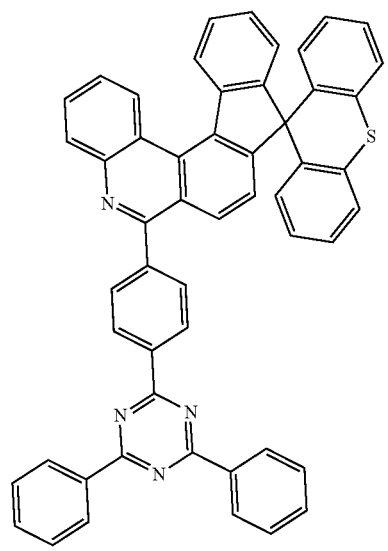
332
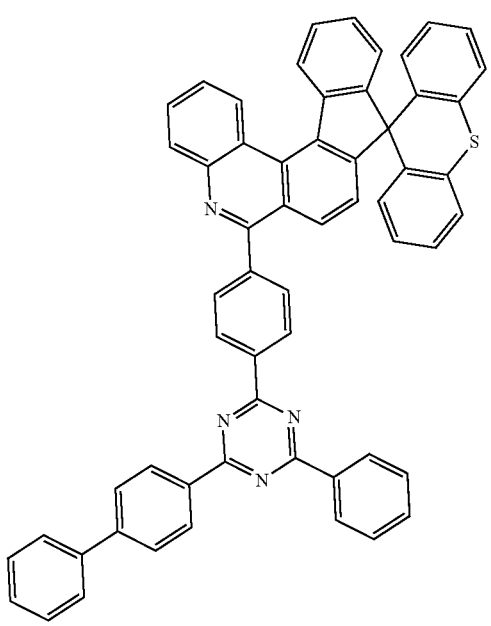
333
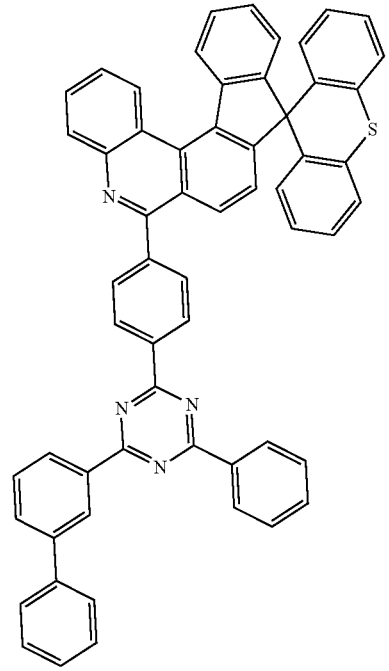

334
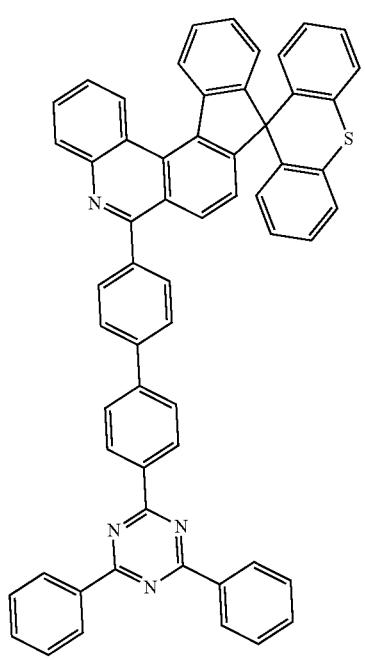
335
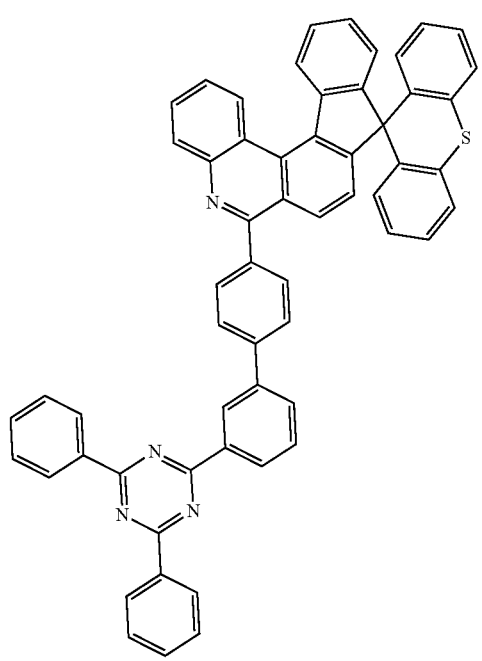
336
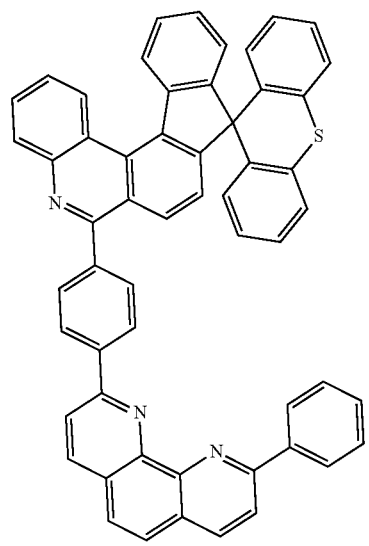
337
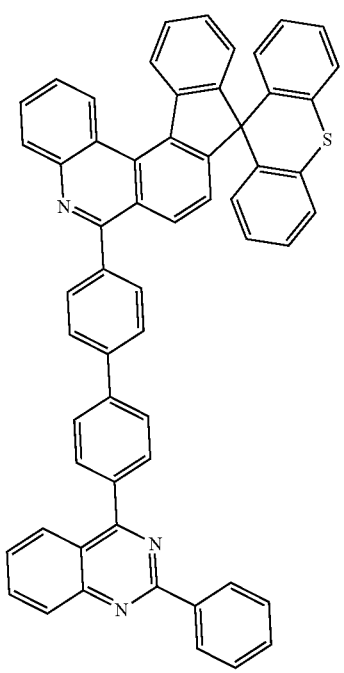

163
-continued
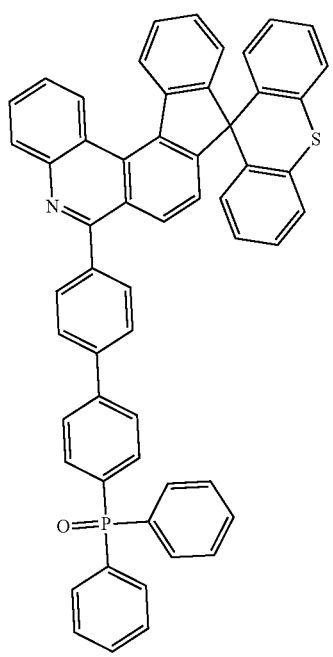
338
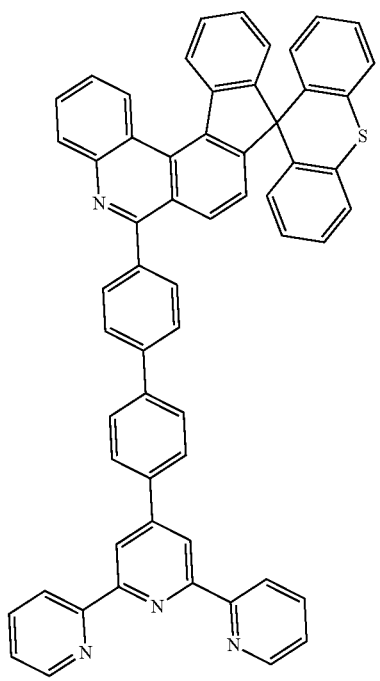
339
164
-continued
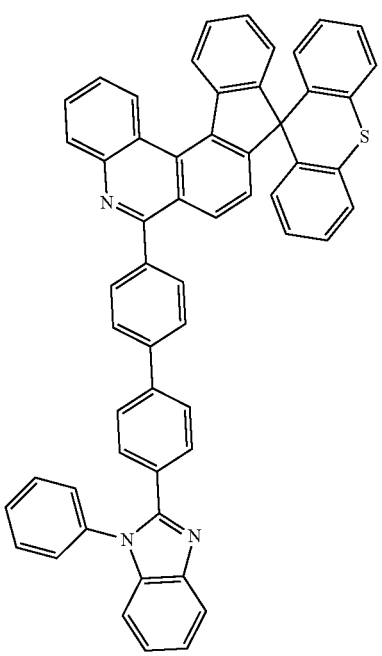
340
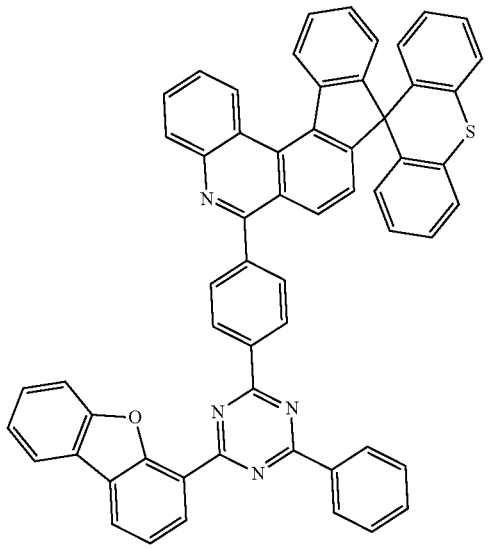
341

-continued
342
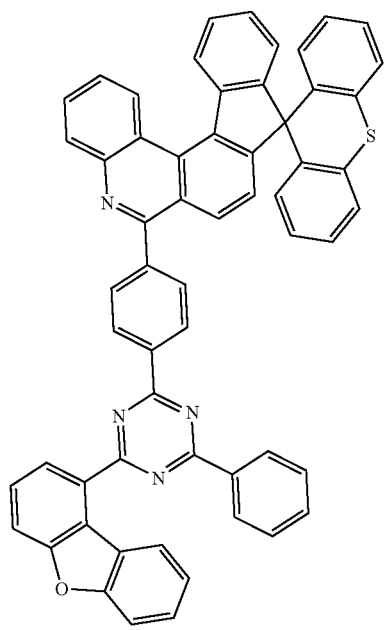
343
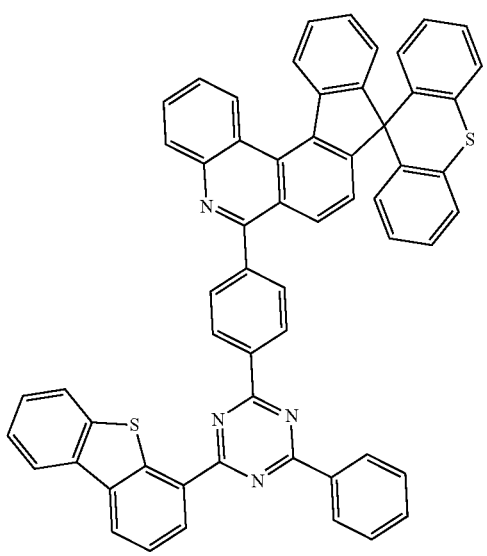
344
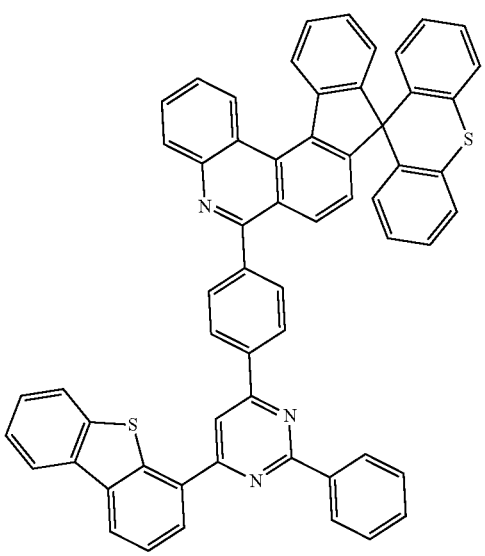
345
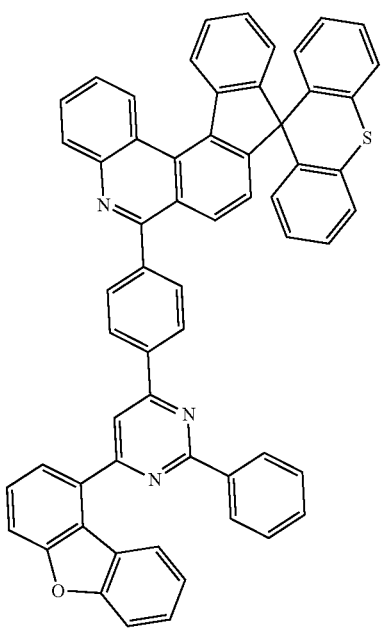

346
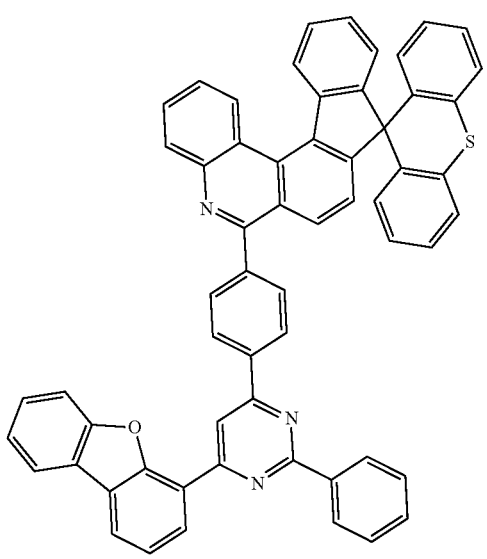
348
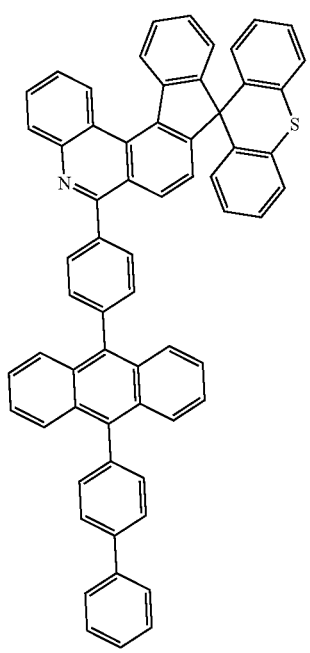
347
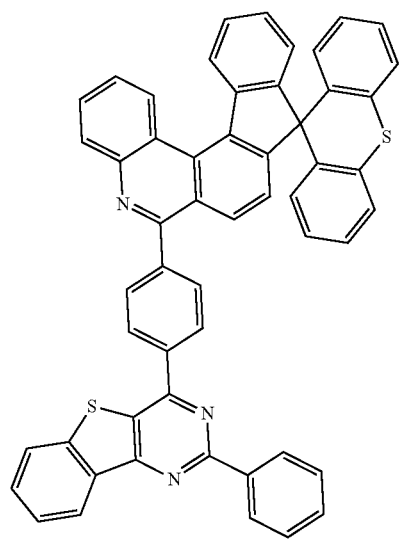
349
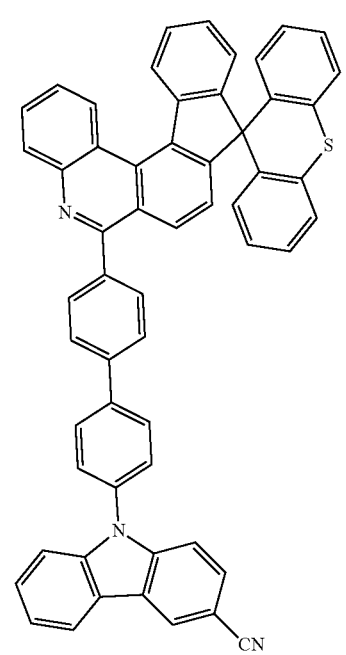

-continued
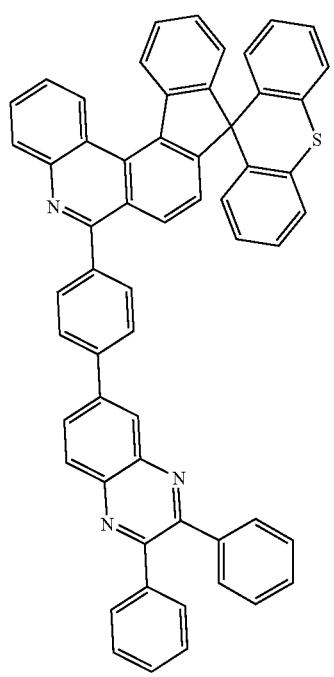
350
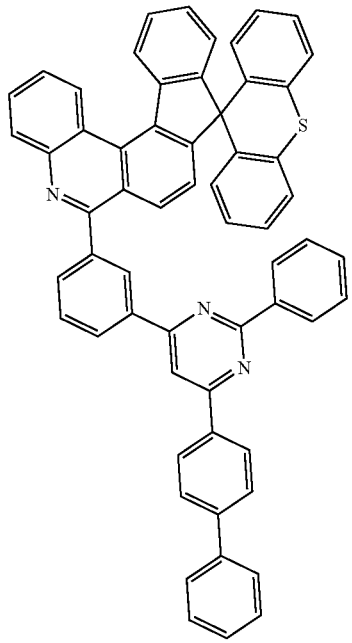
352
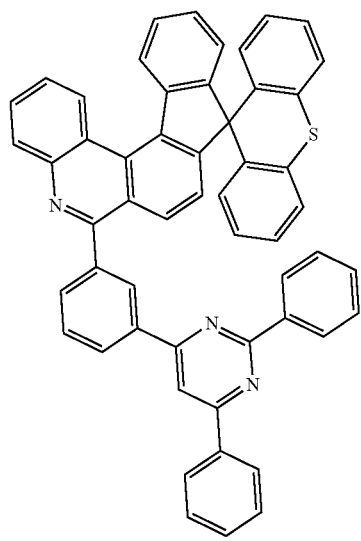
351
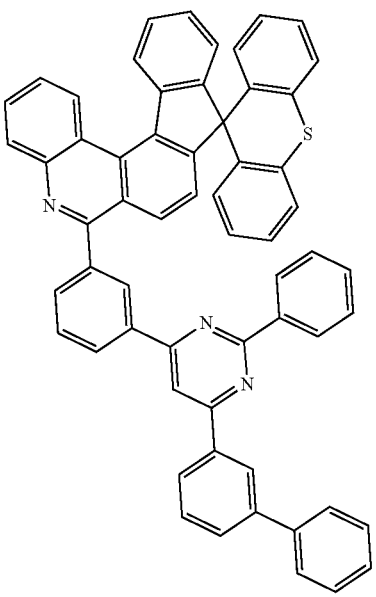
353

171
-continued
354
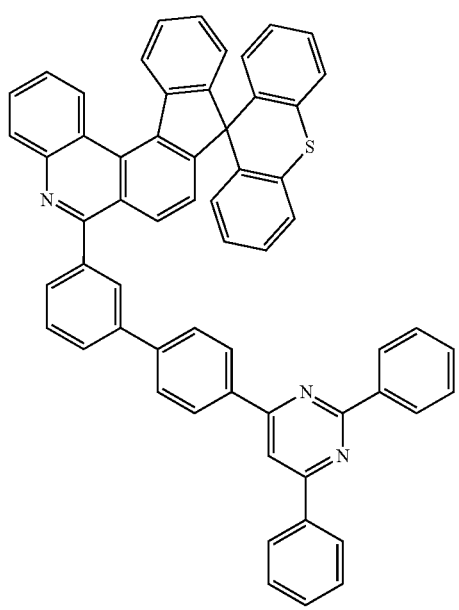
355
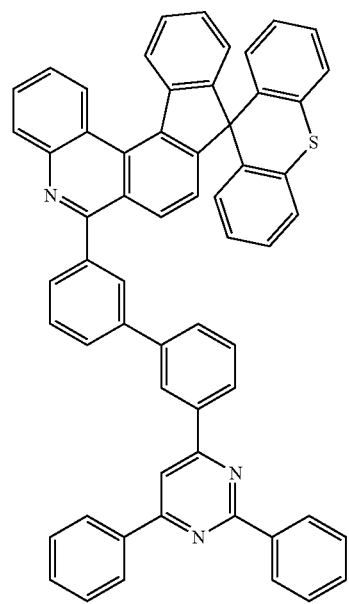
172
-continued
356
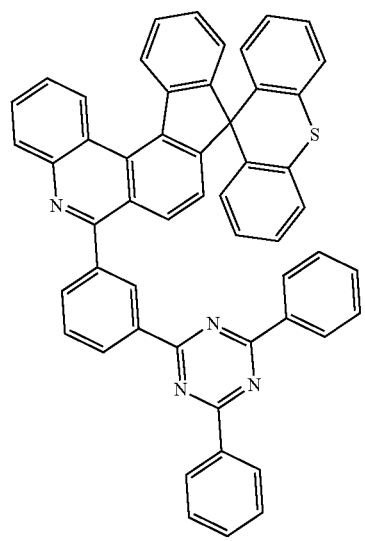
357
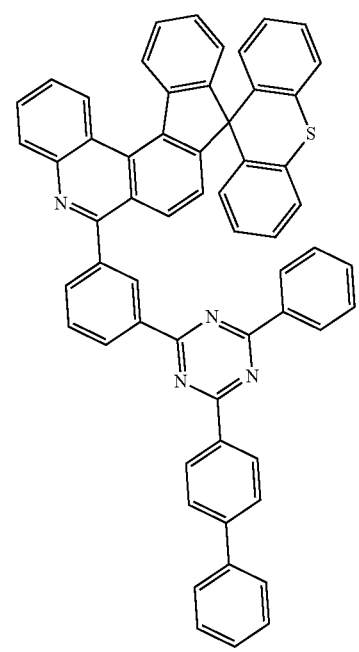

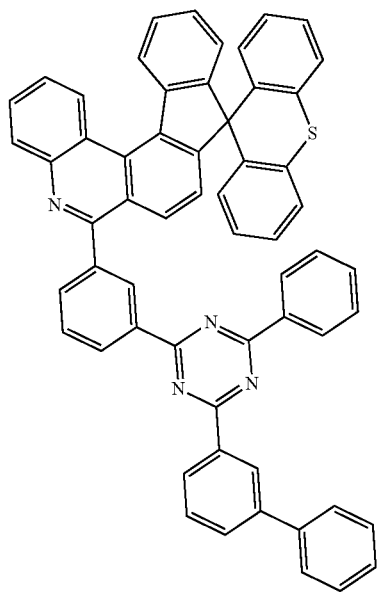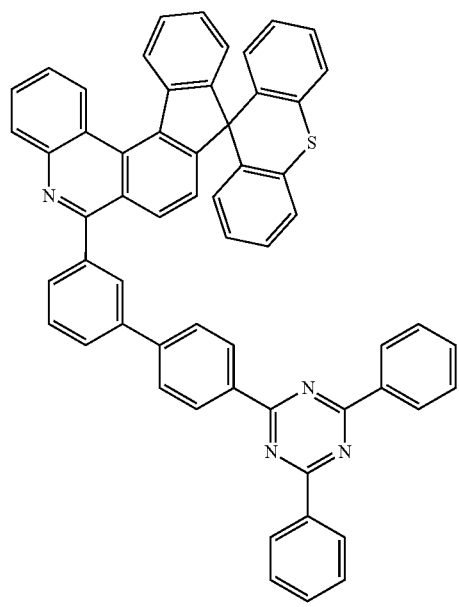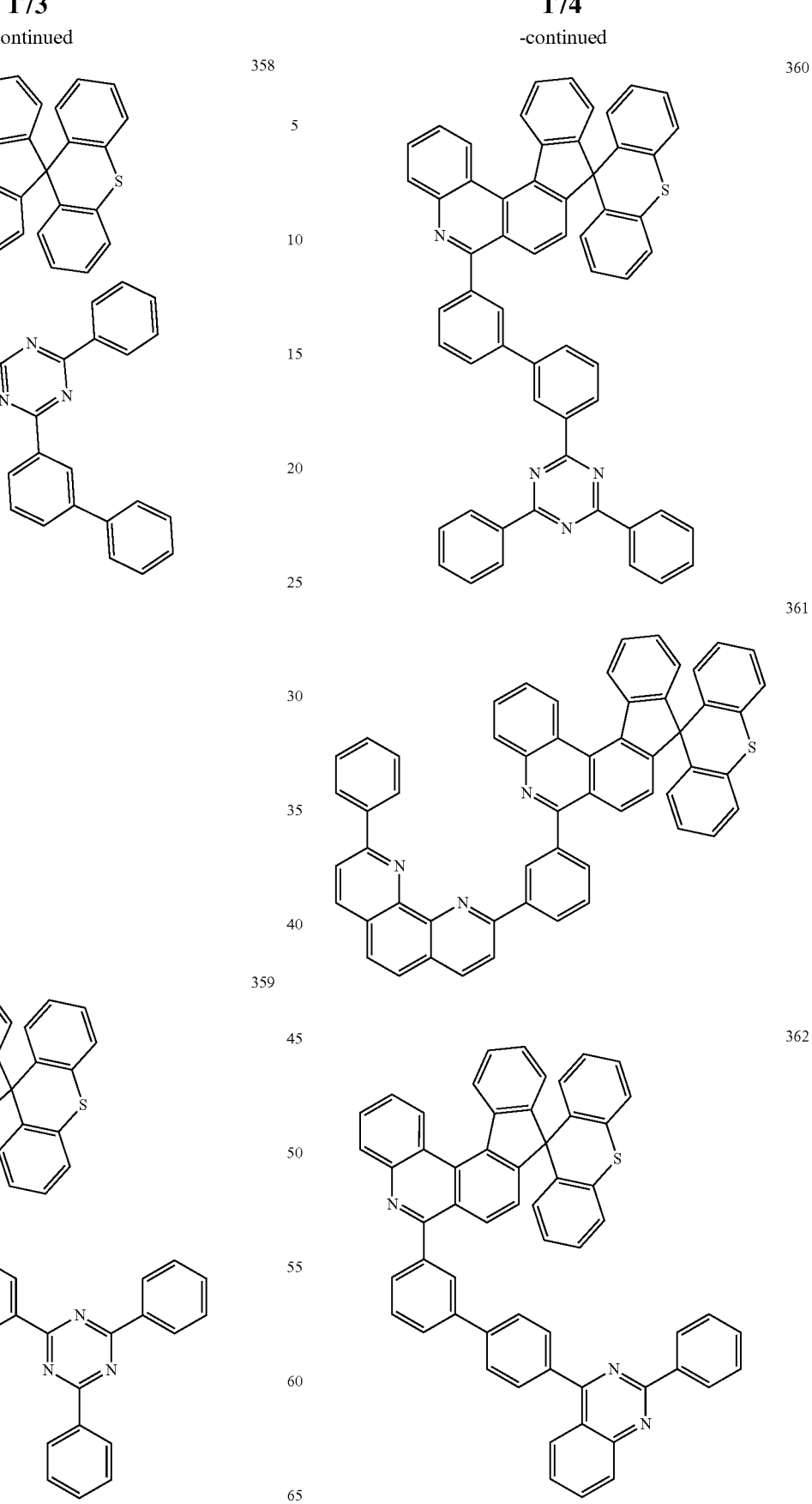

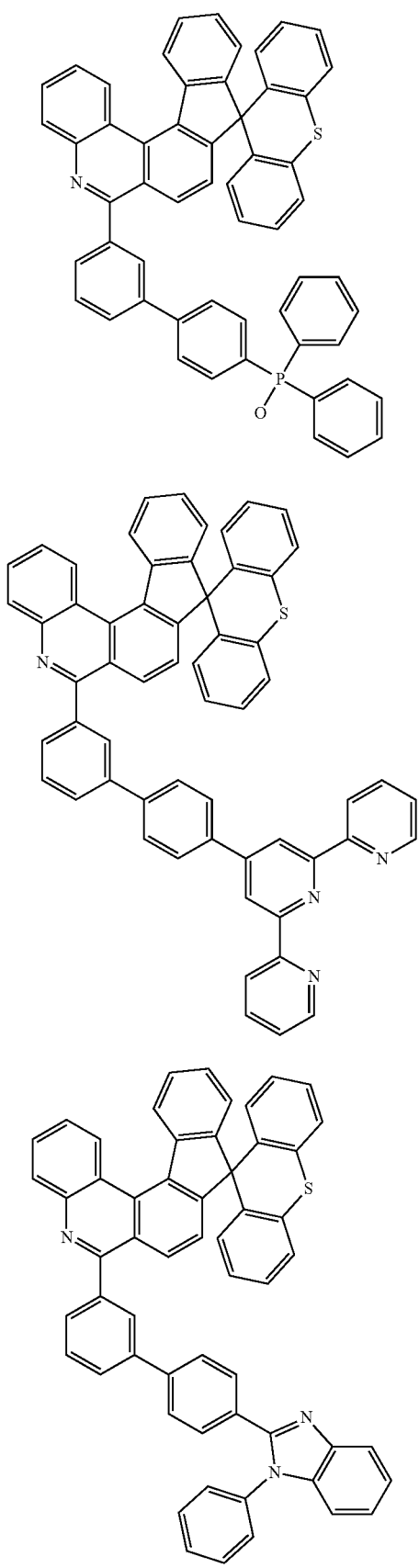

368
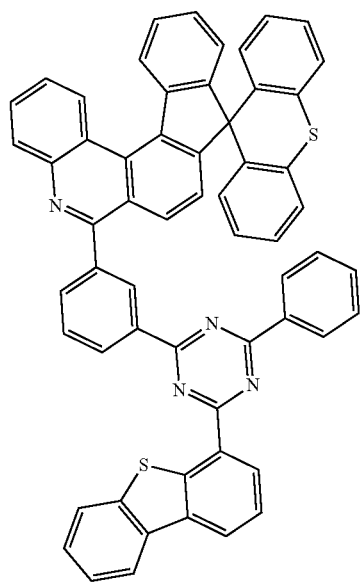
369
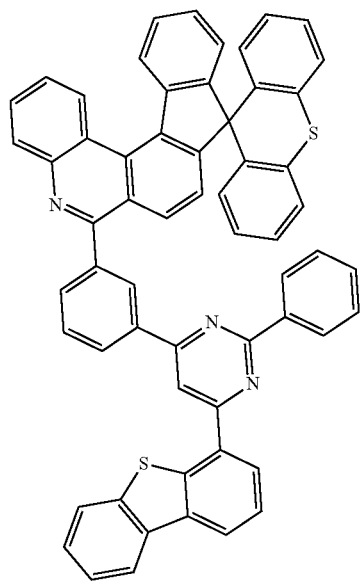
370
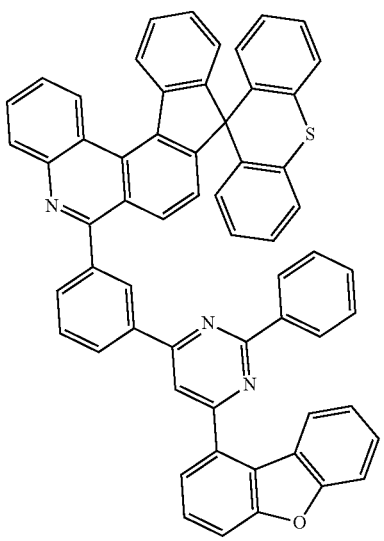
371
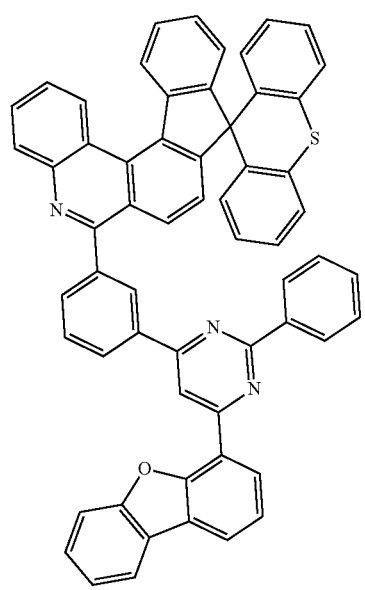
372
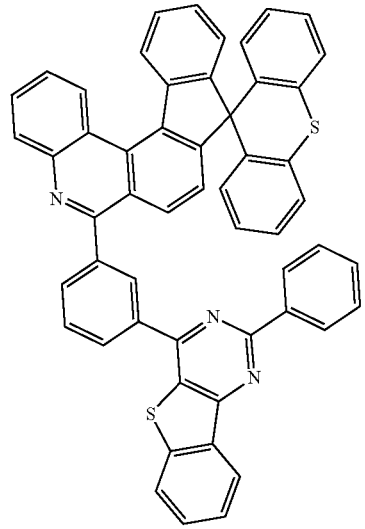

-continued
373
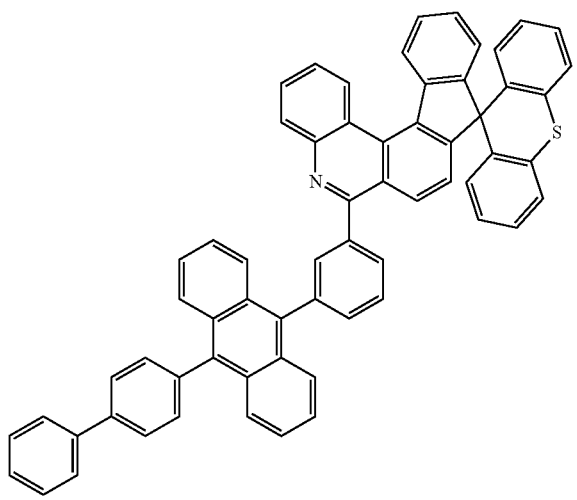
374
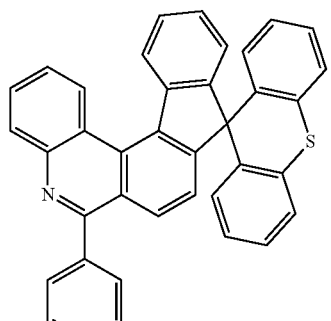
375
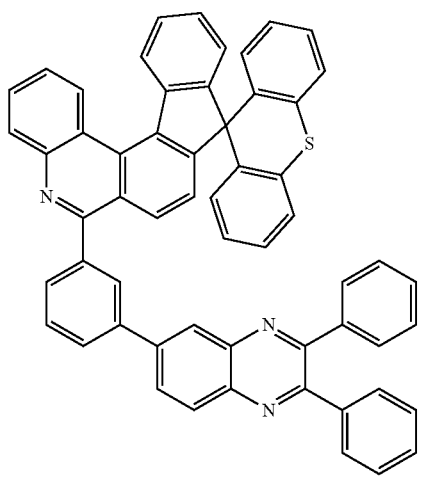
-continued
376
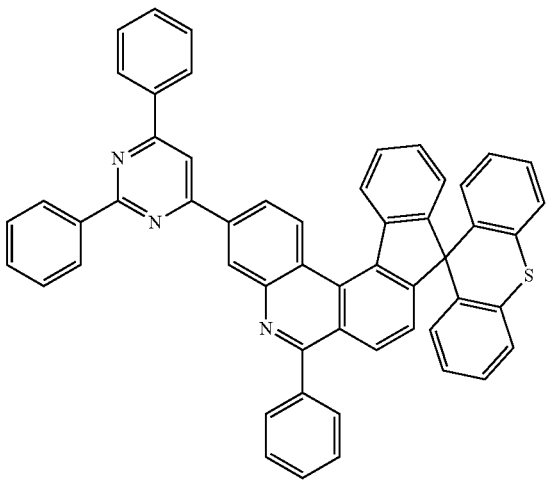
377
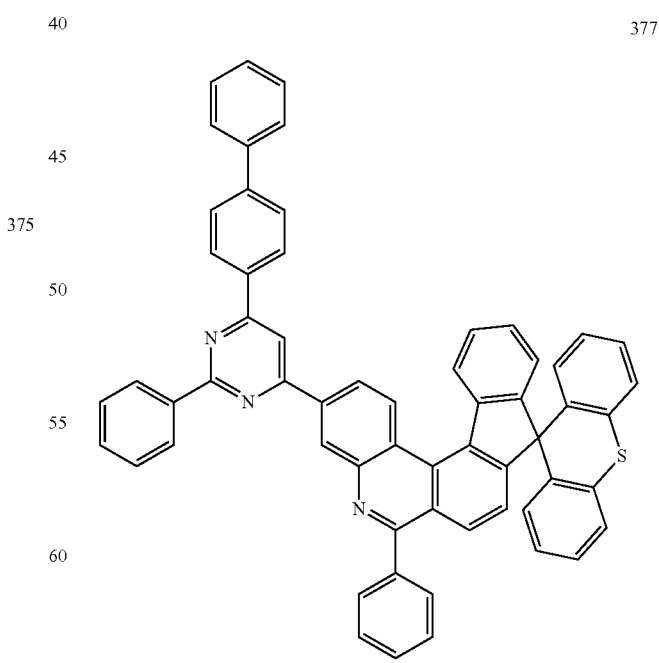

378
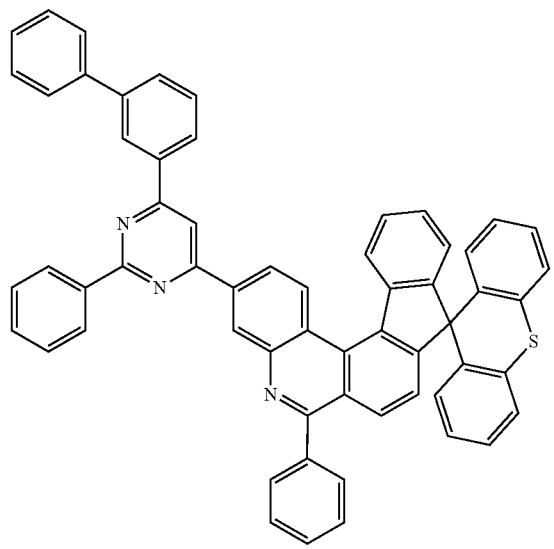
379
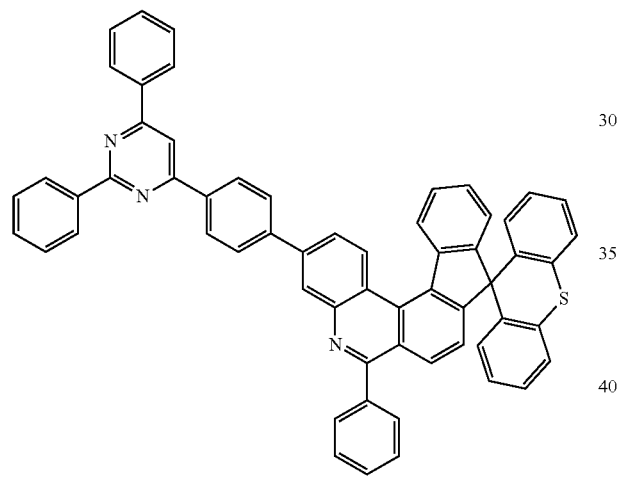
380
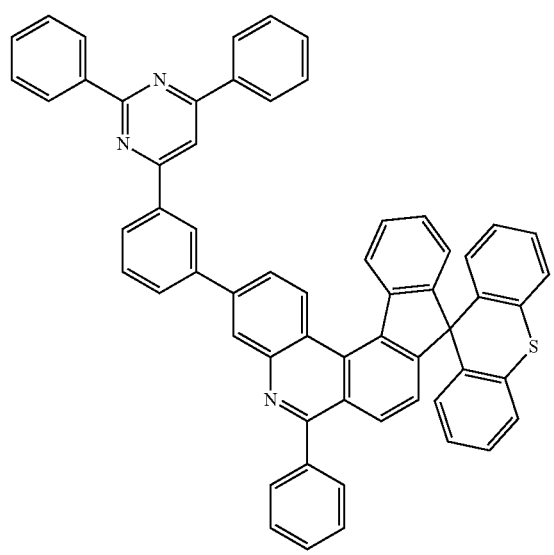
381
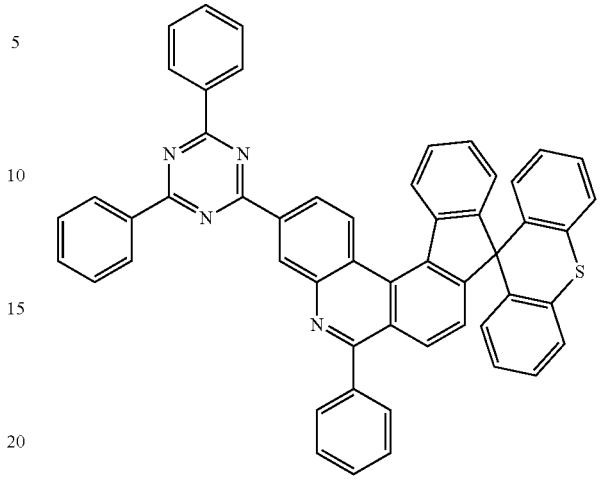
382
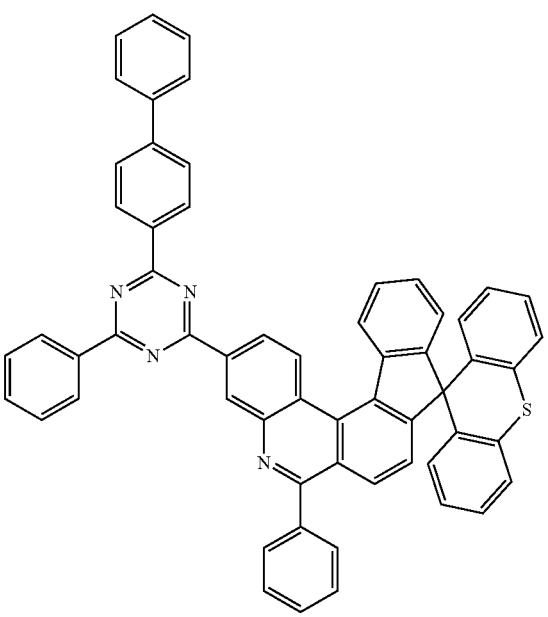

383
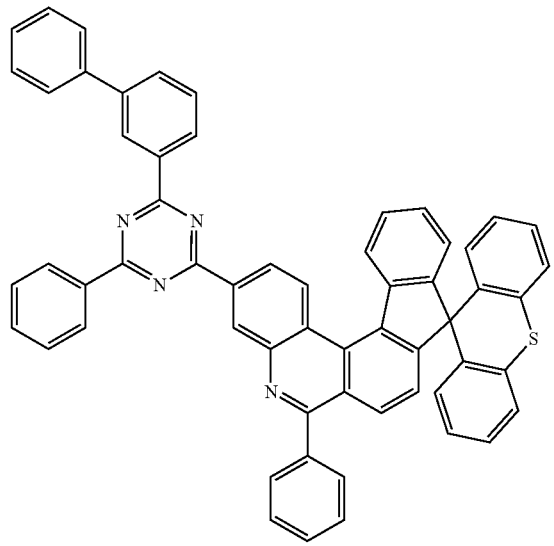
386
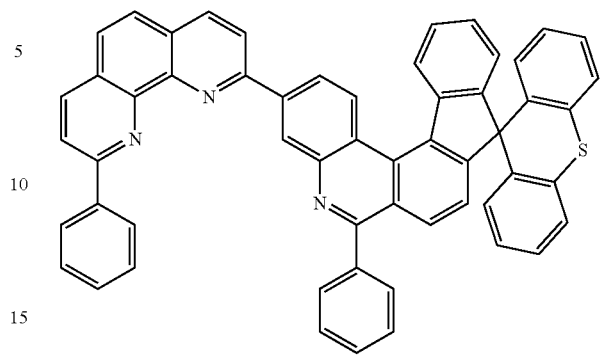
384
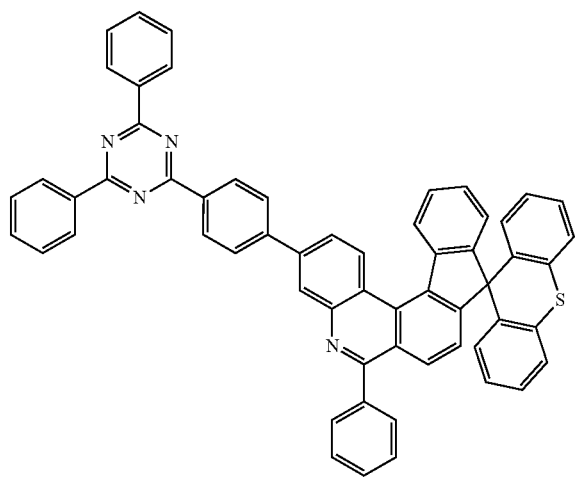
387
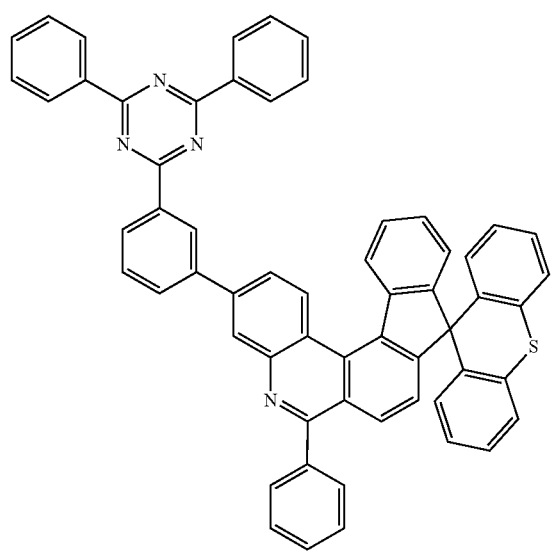
385
388
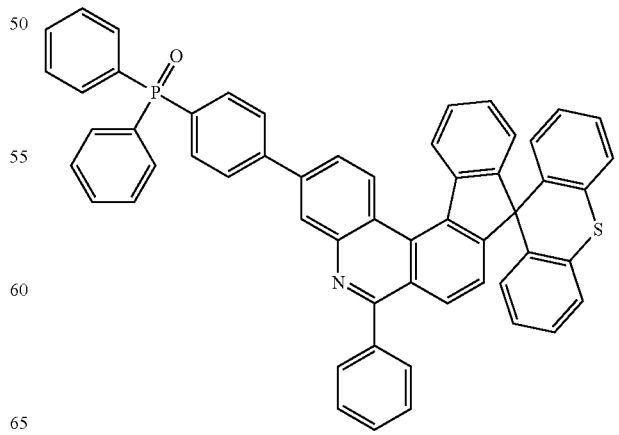

389
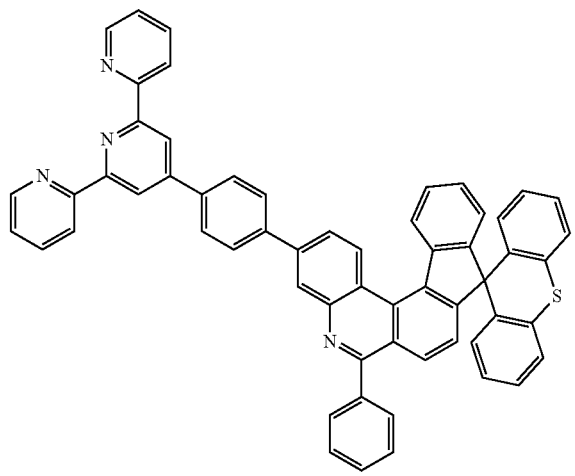
390
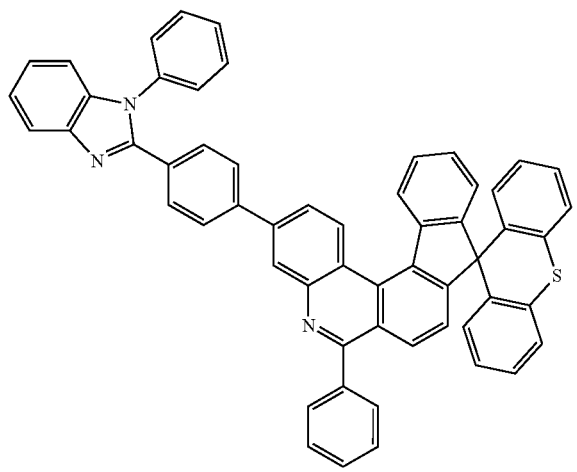
391
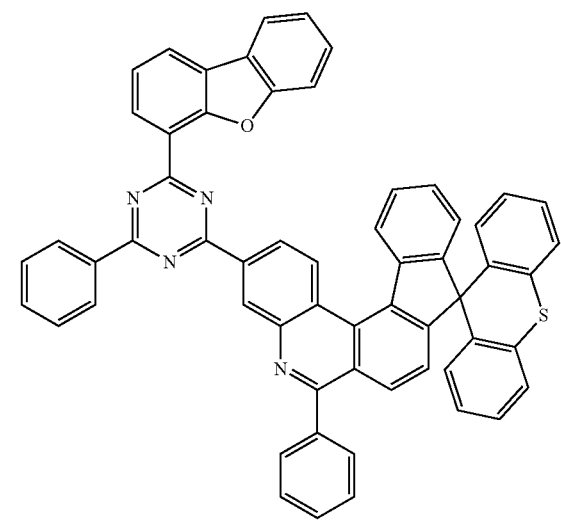
392
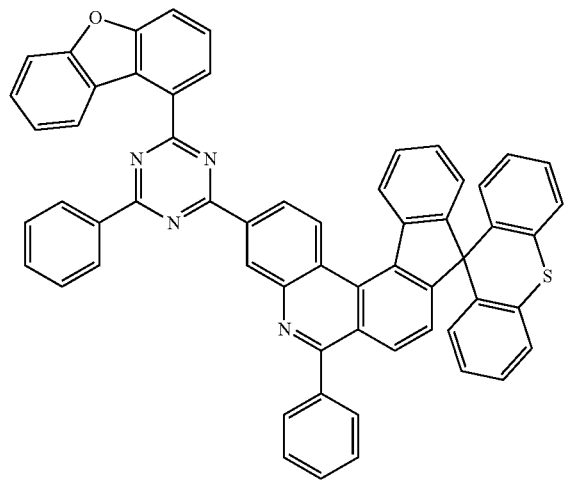
393
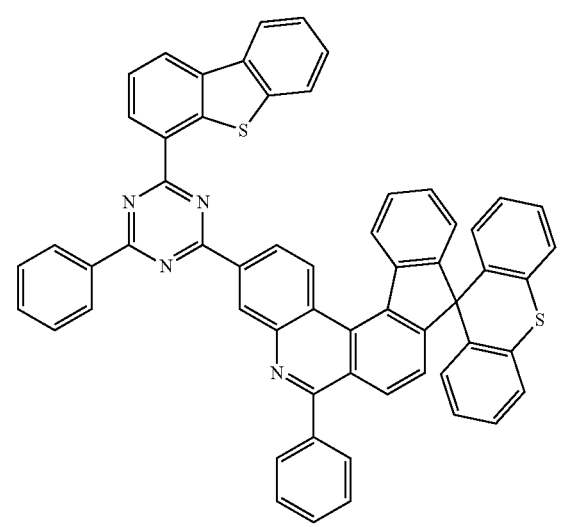
394
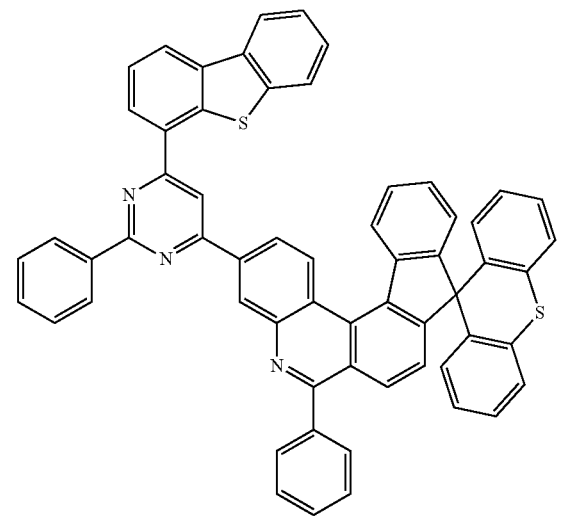

-continued
395
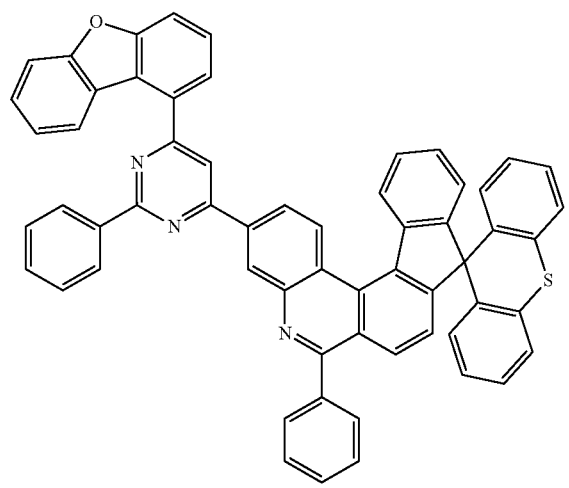
396
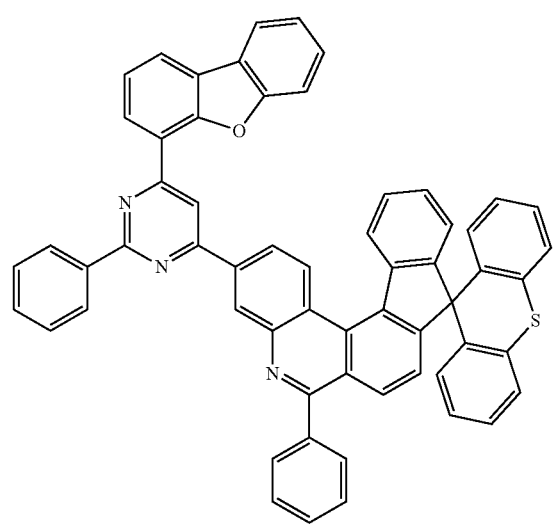
397
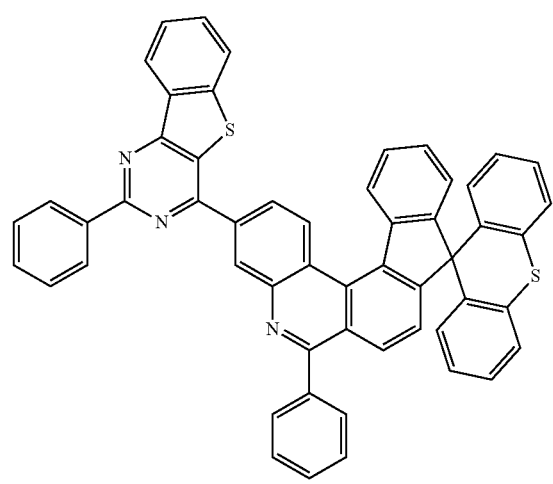
-continued
398
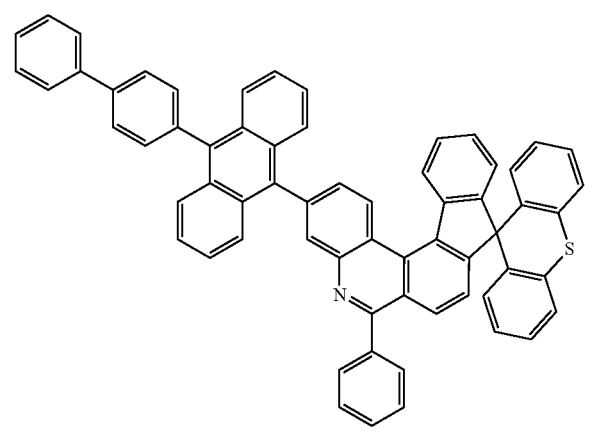
399
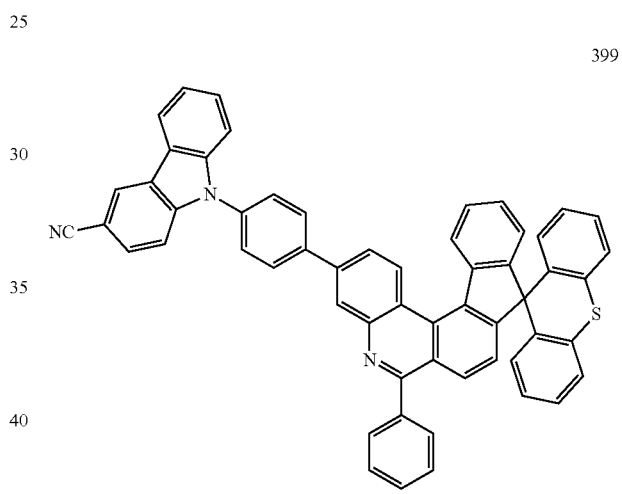
400
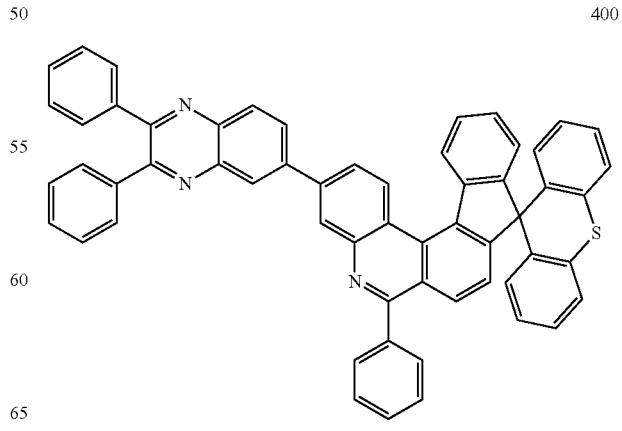

189
-continued
401
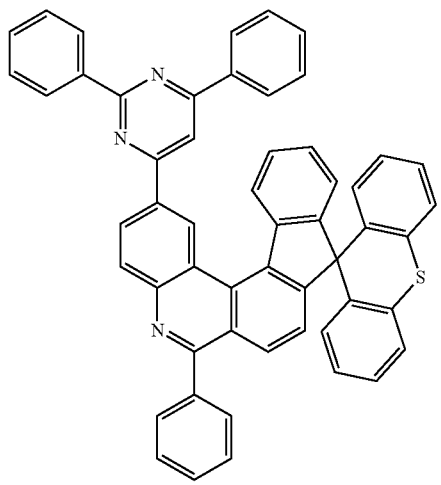
402
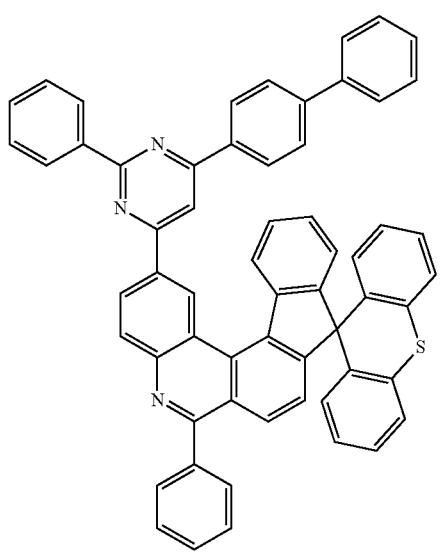
403
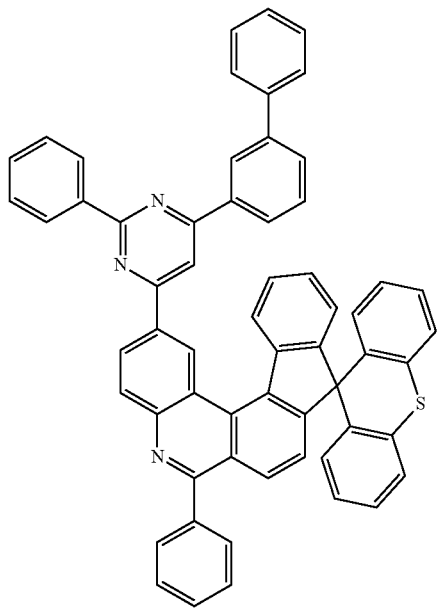
190
-continued
404
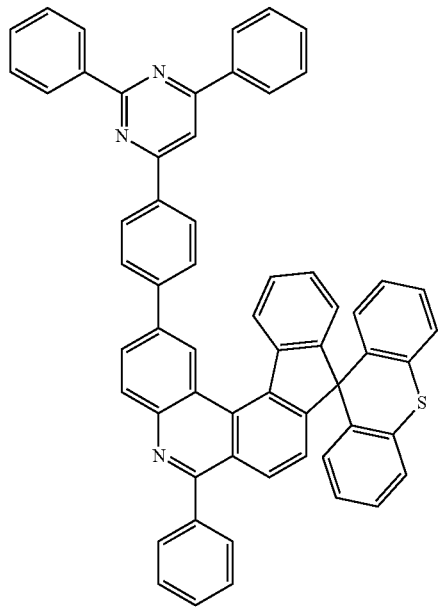
405
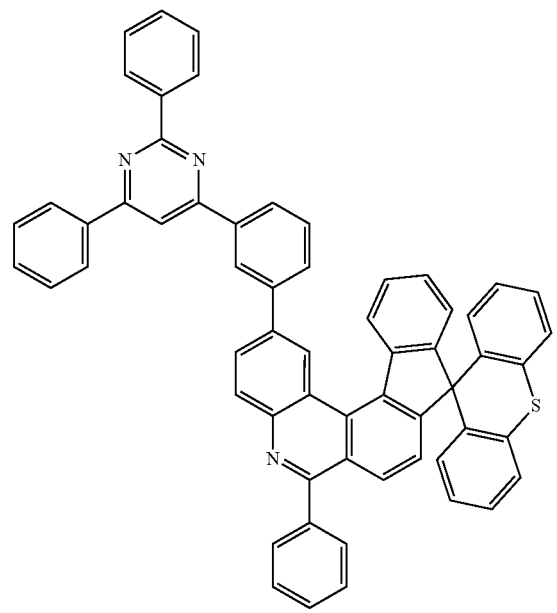

406
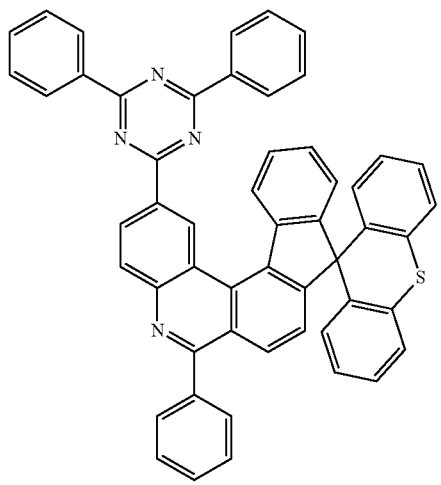
407
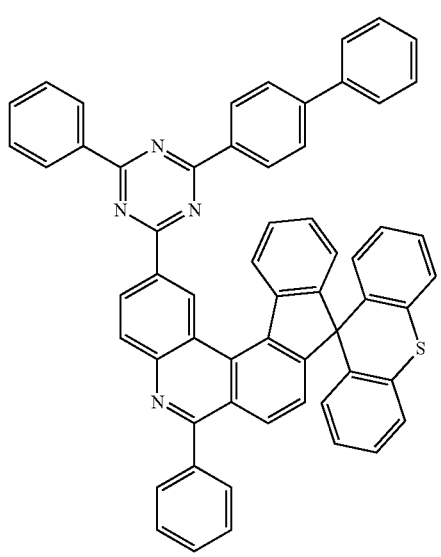
408
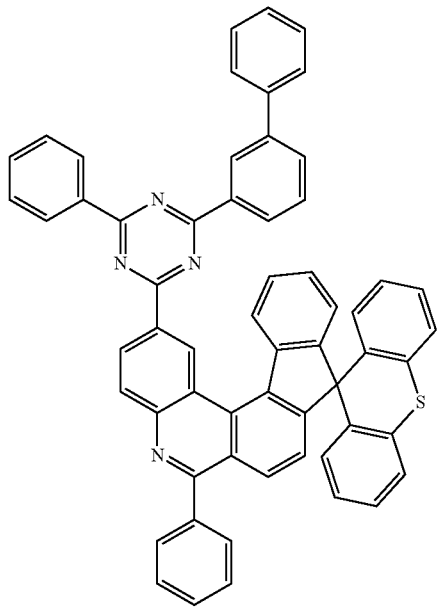
409
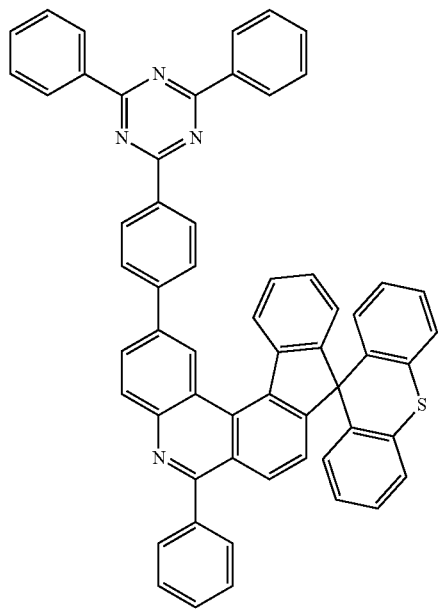
410
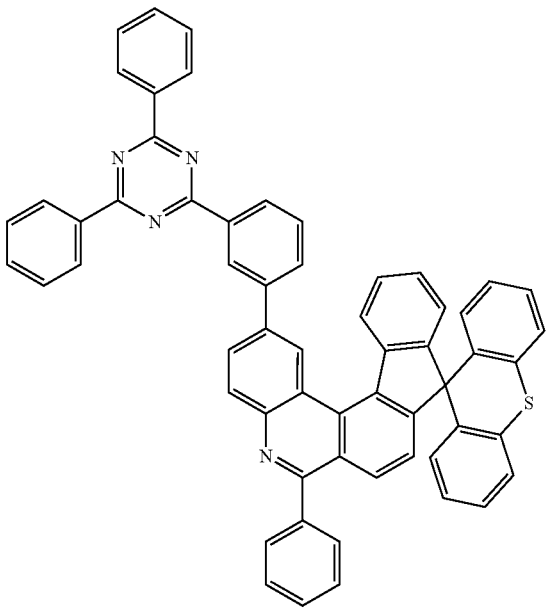

193
-continued
411
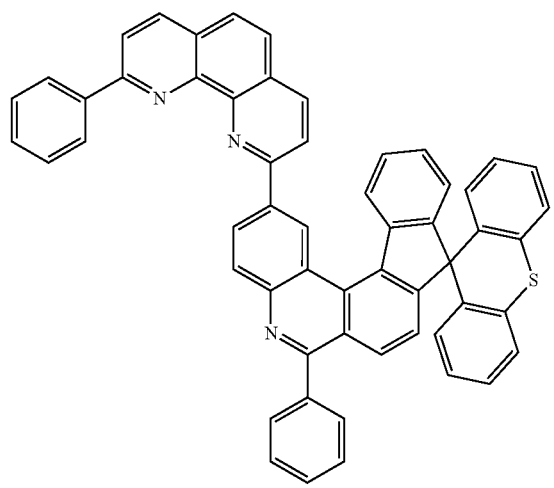
412
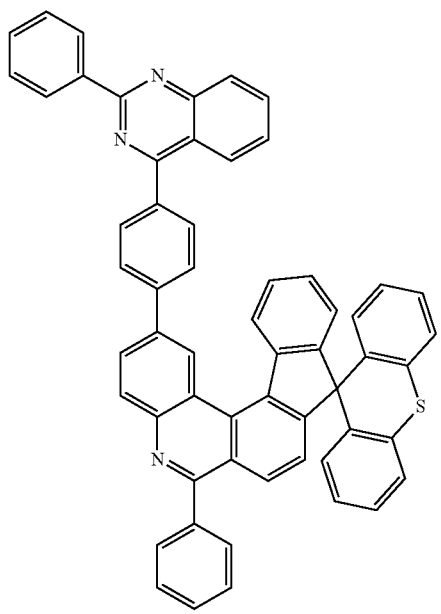
194
-continued
413
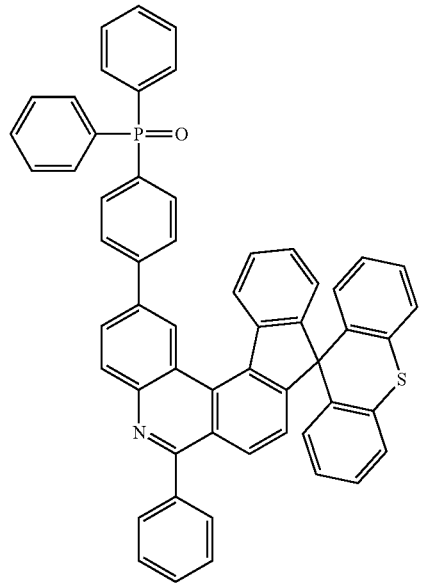
414
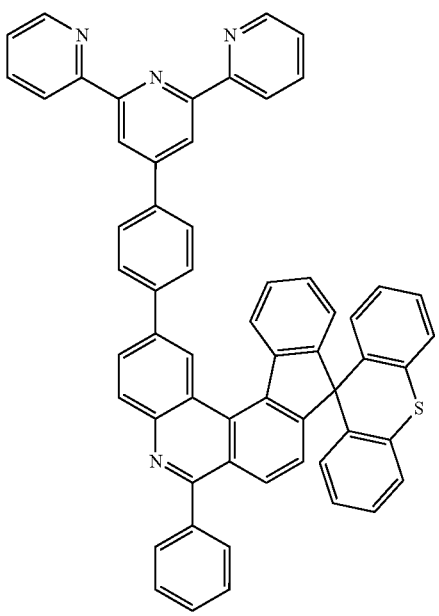

415

416

417

418

197
-continued
419
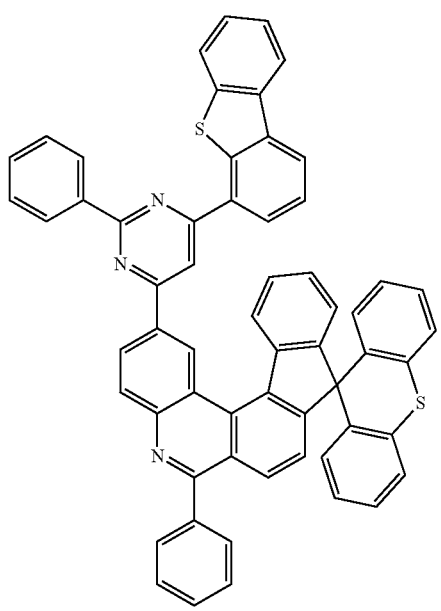
420
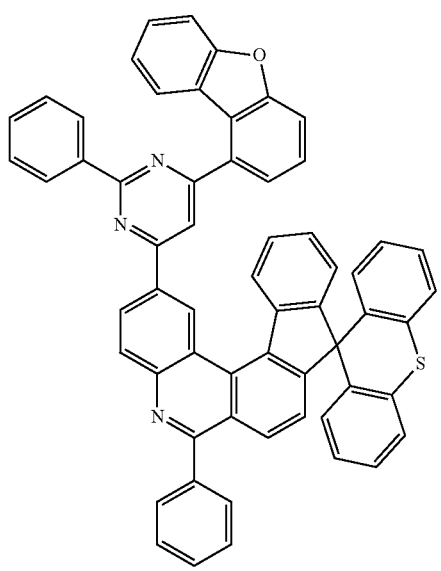
198
-continued
421
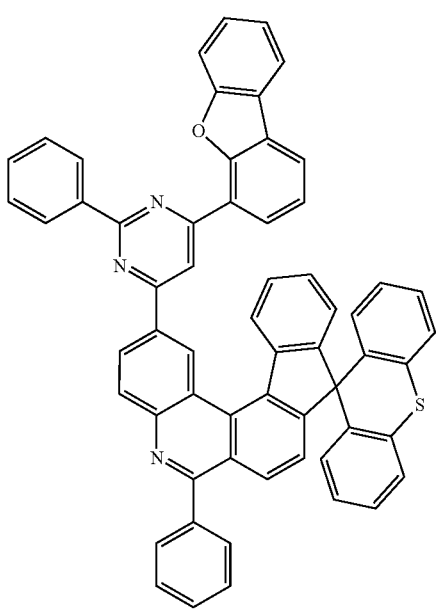
422

423
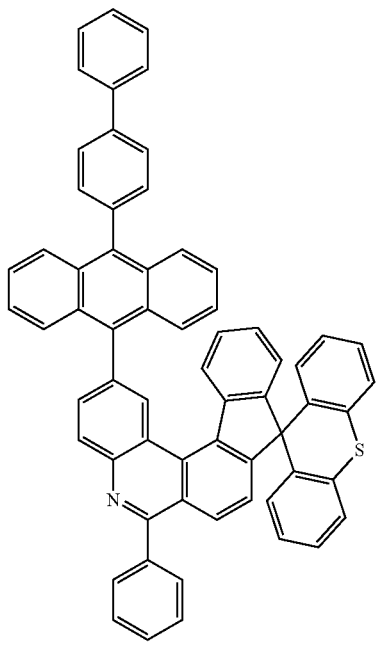
425
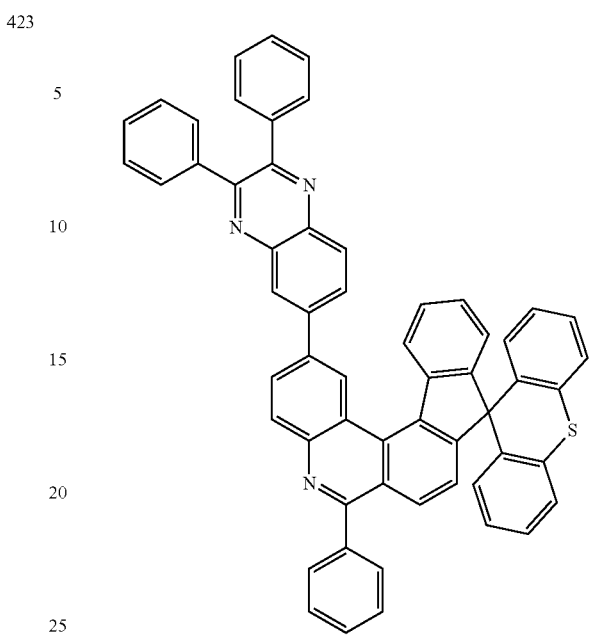
424
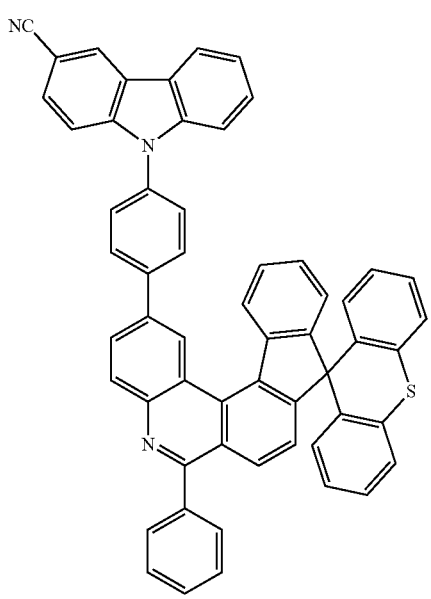
426
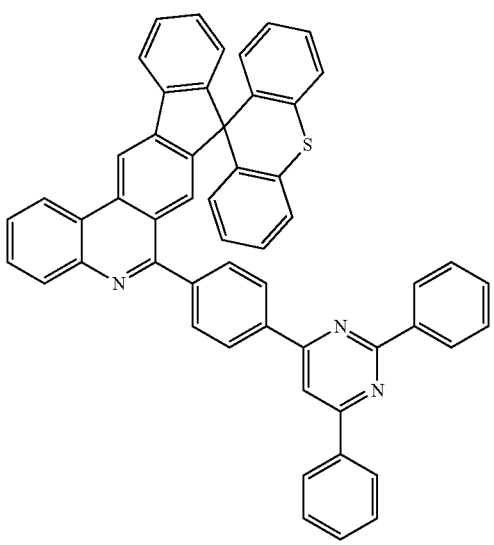

201
-continued
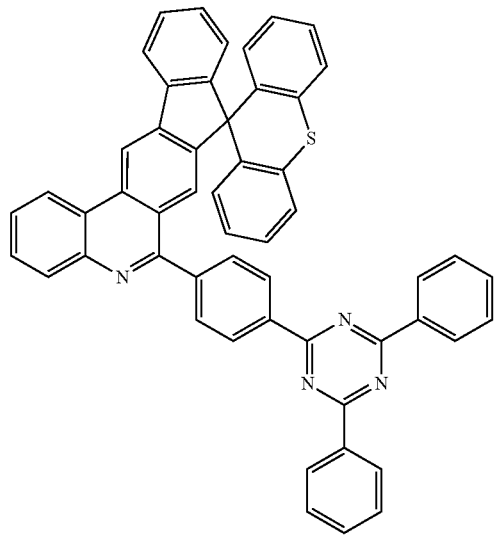
427
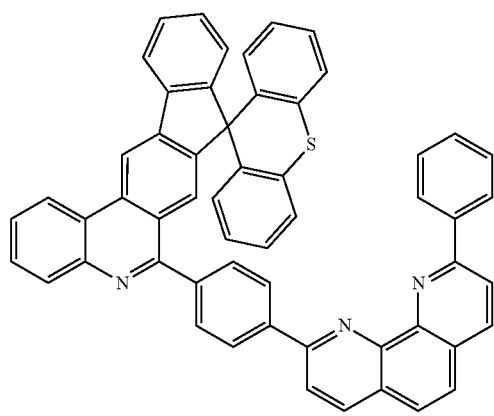
428
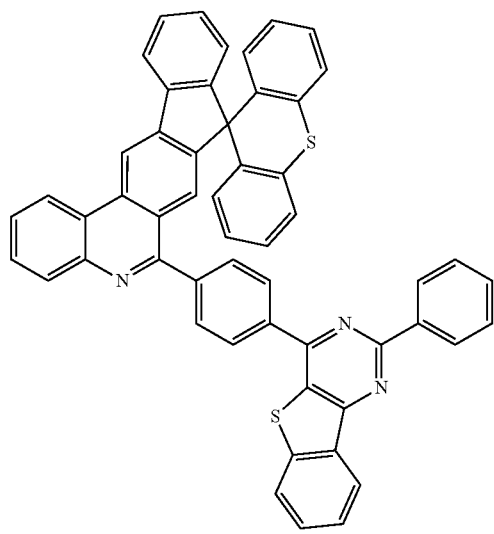
429
202
-continued
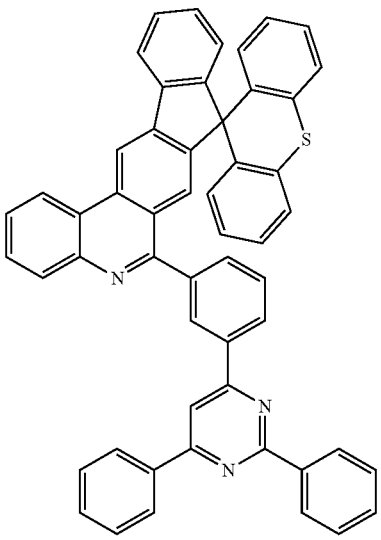
430
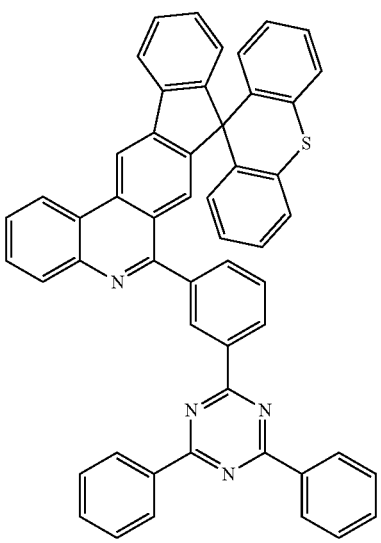
431
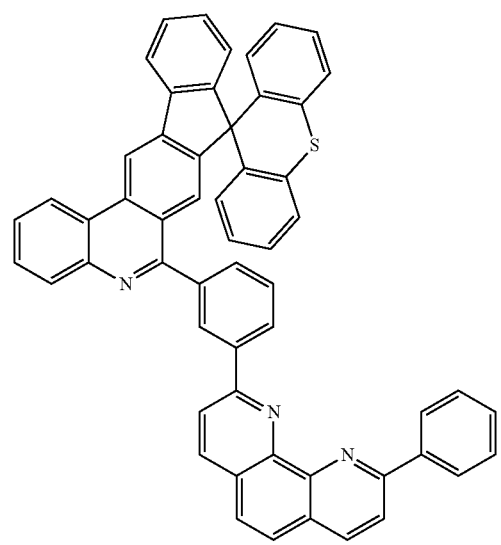
432

-continued
433
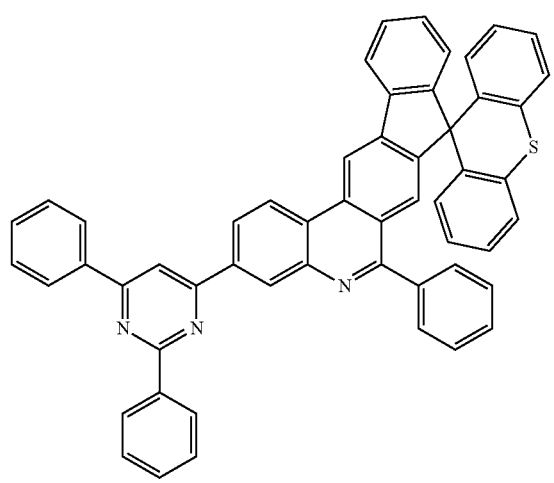
434
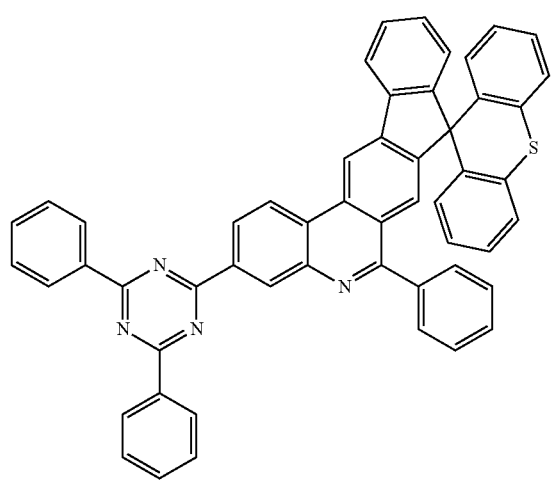
435
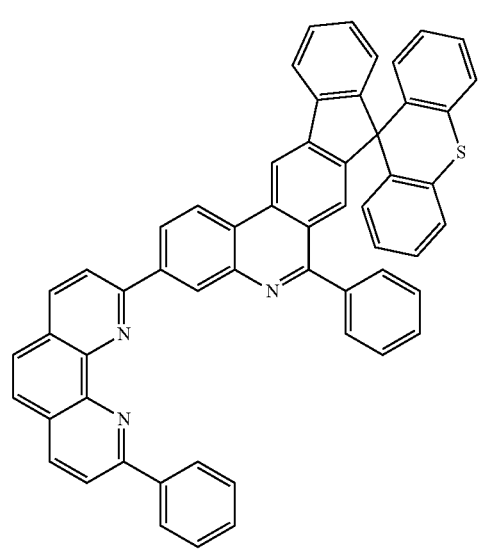
-continued
436
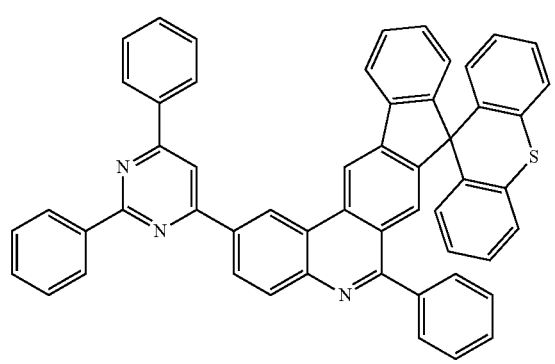
437
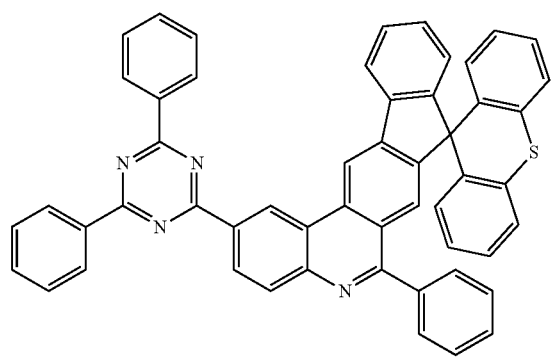
438
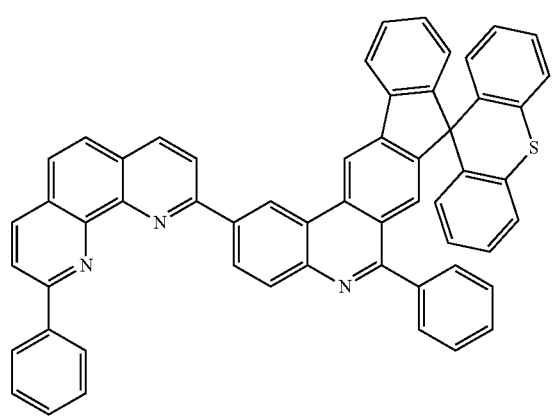

439
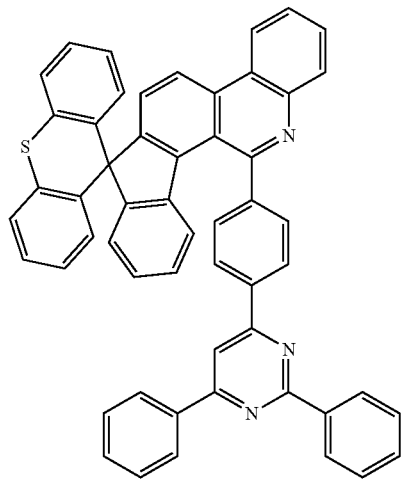
440
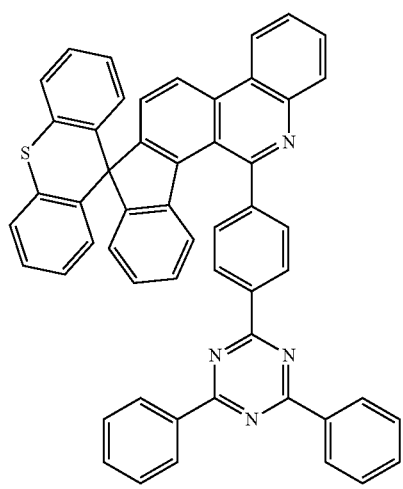
441
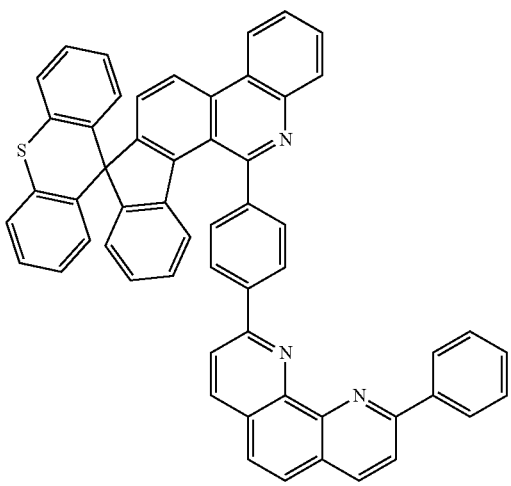
442
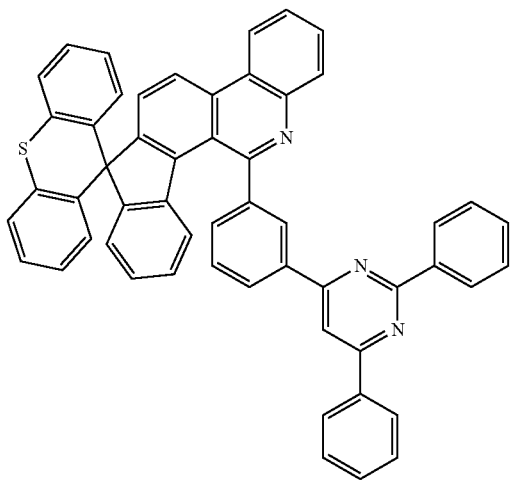
443
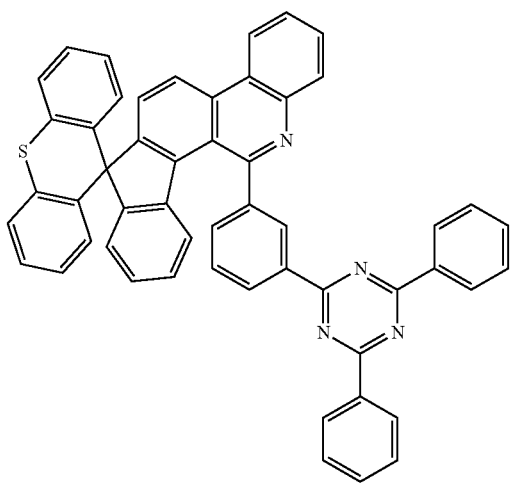
444
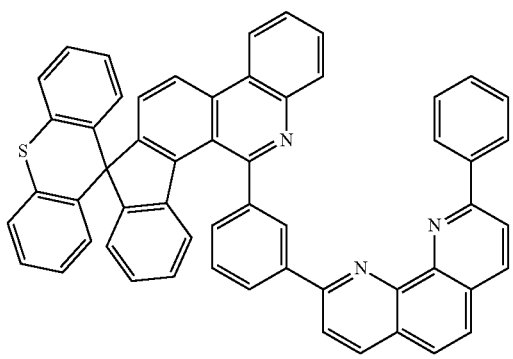

207
-continued
445
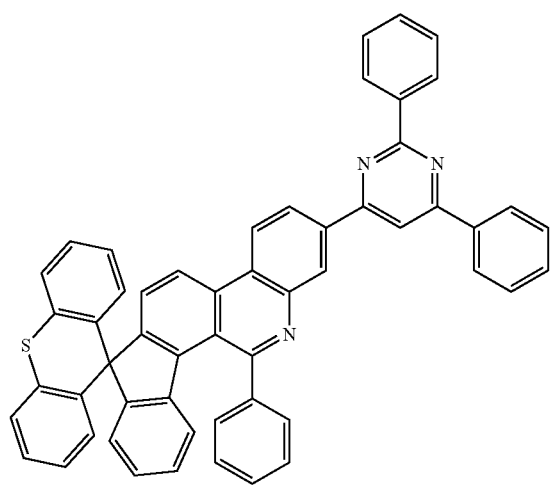
446
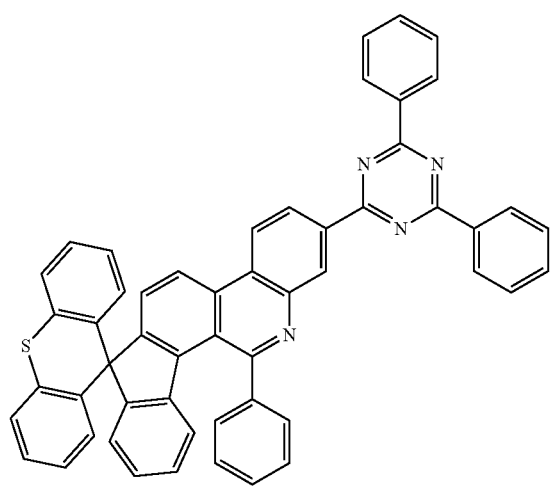
447
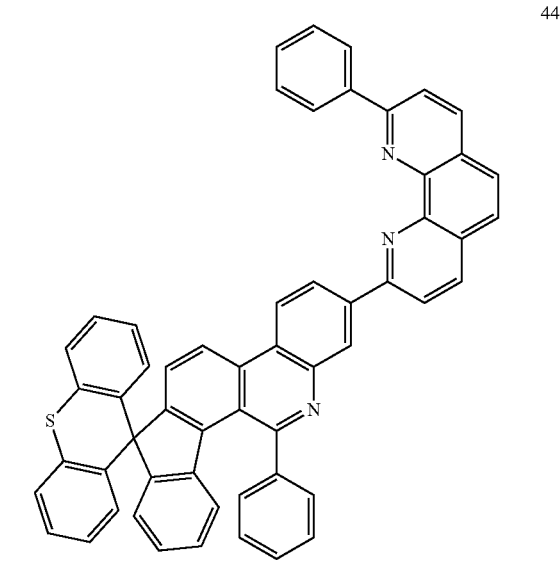
208
-continued
448
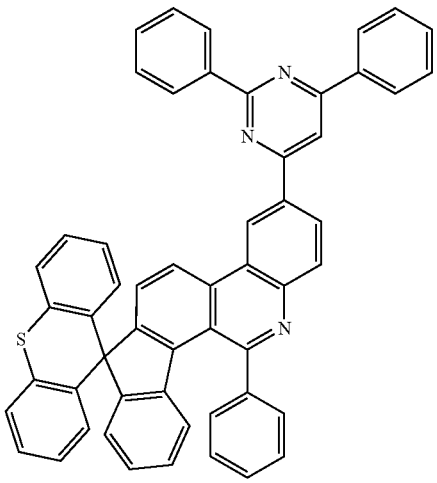
449
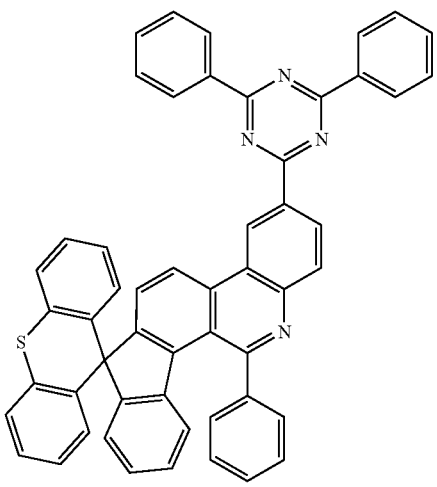
450
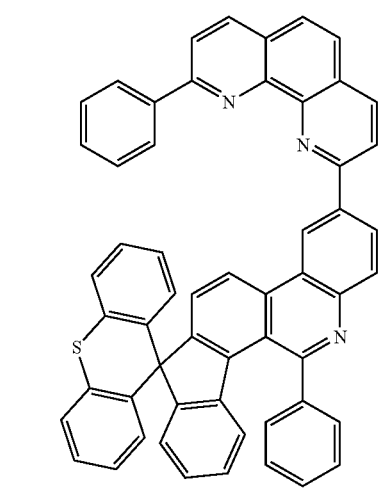

209
-continued
451
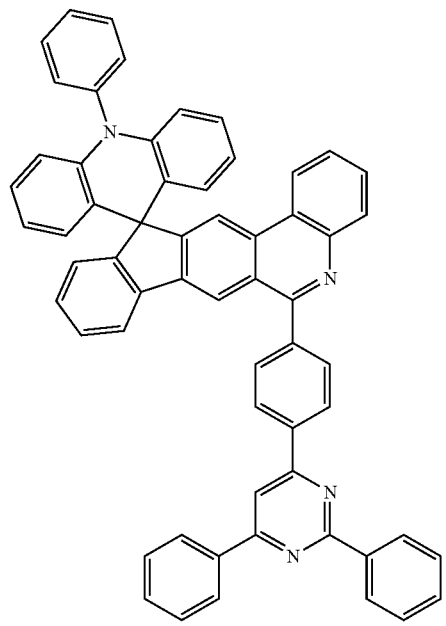
452
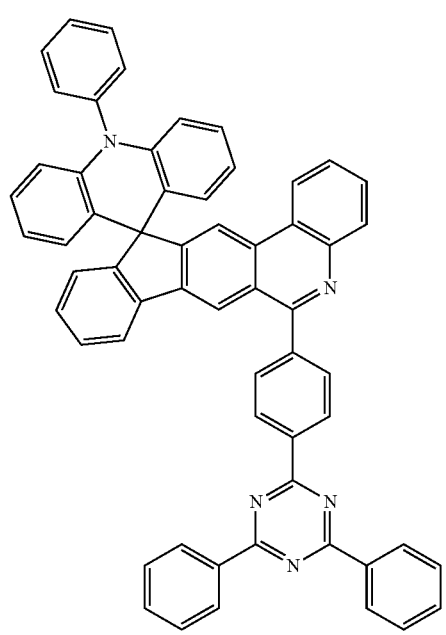
210
-continued
453
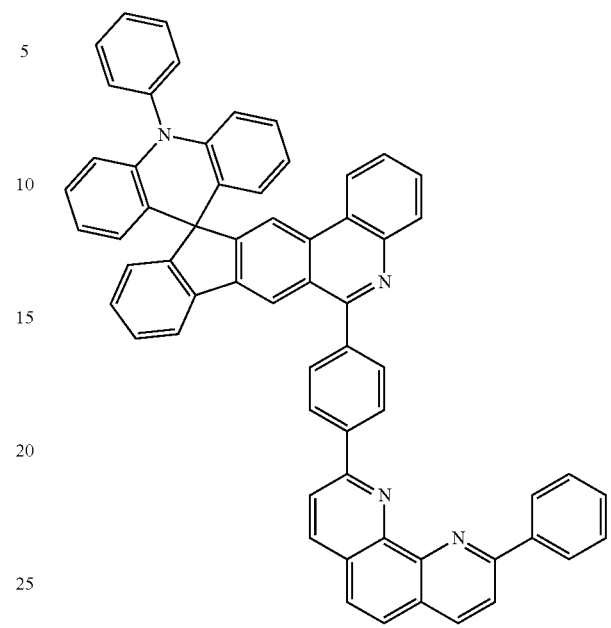
454
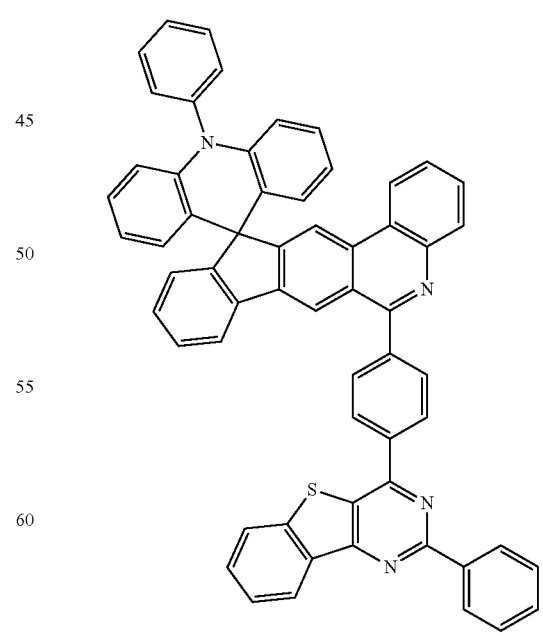

211
-continued
455
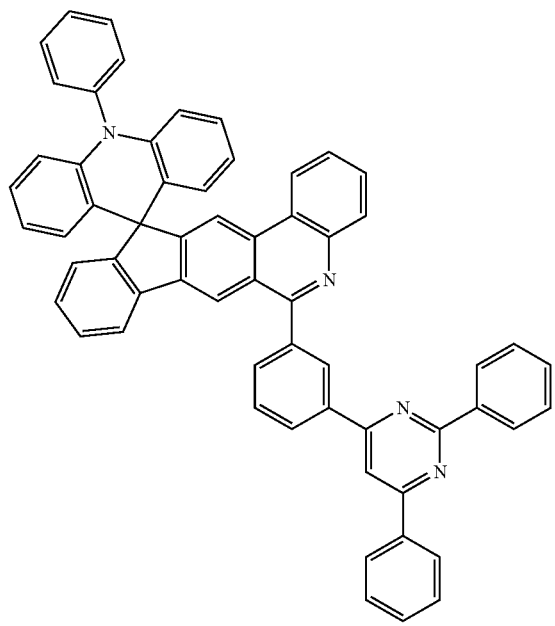
456
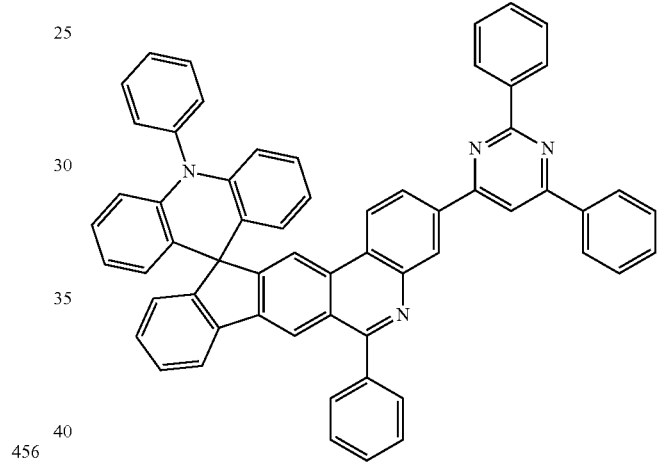
212
-continued
457
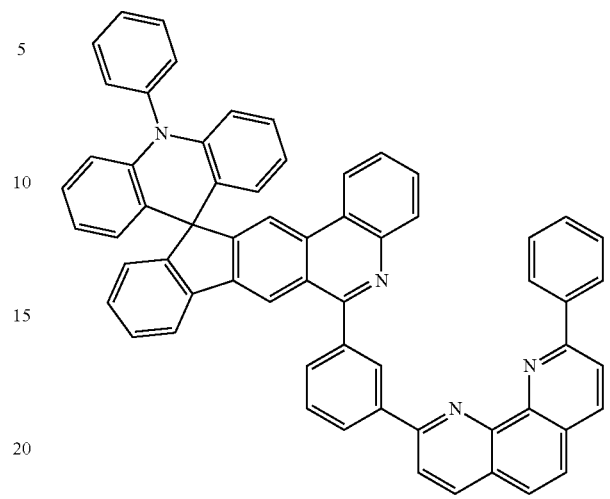
458
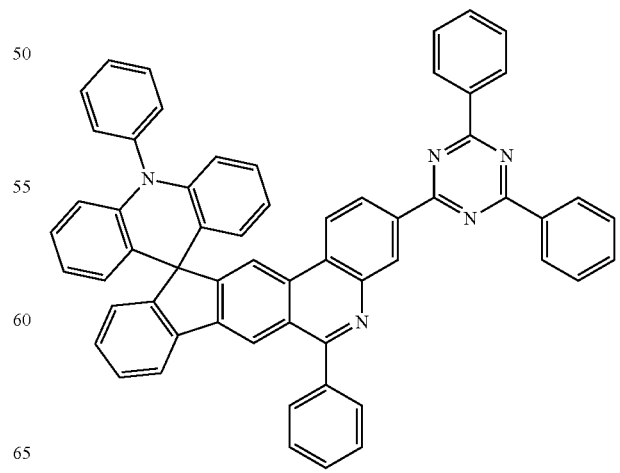
459

460
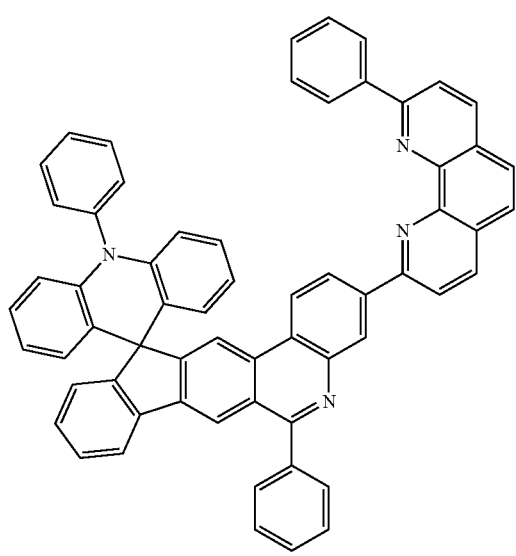
461
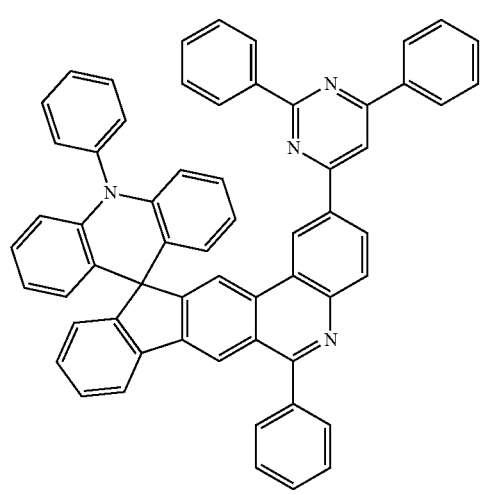
462
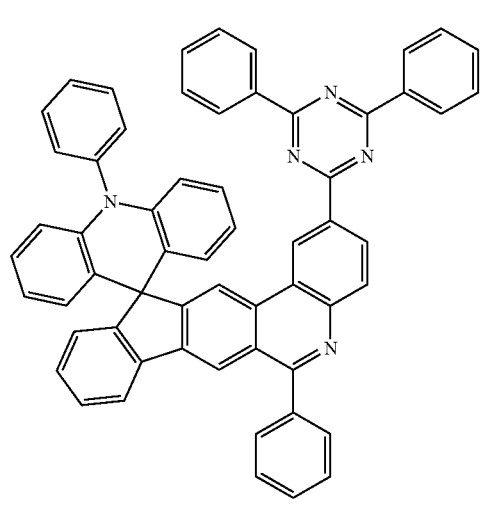
463
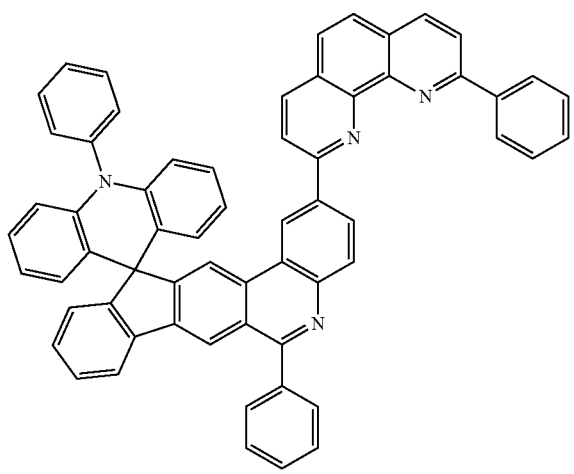
464
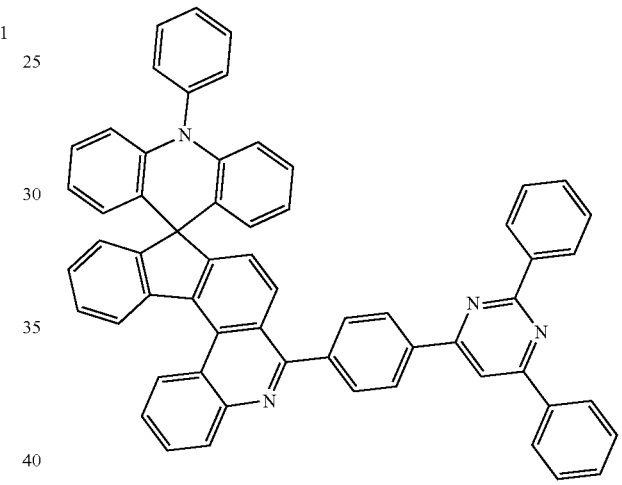
465
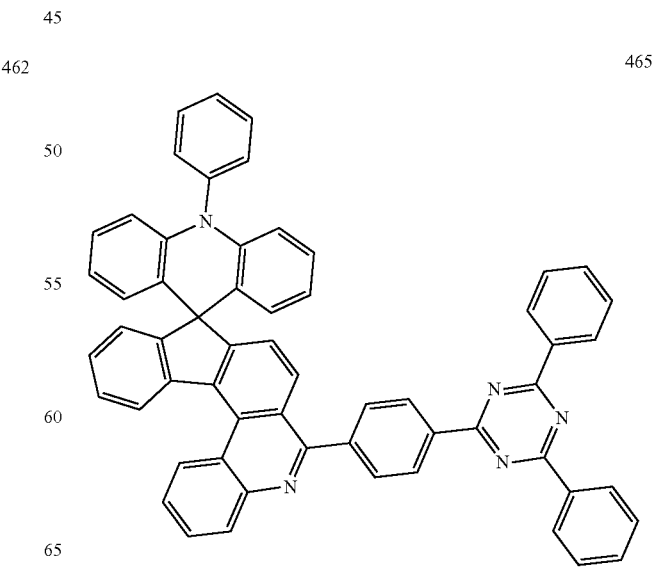

466
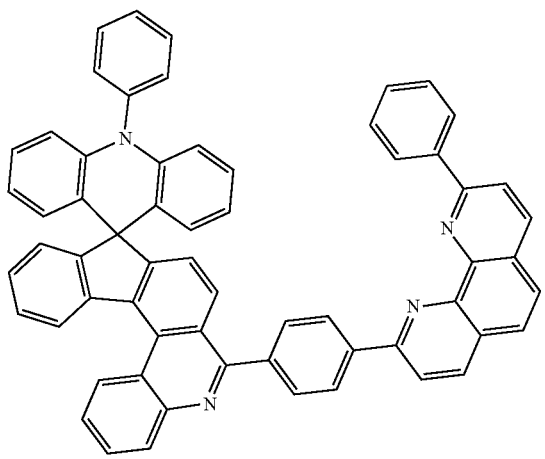
467
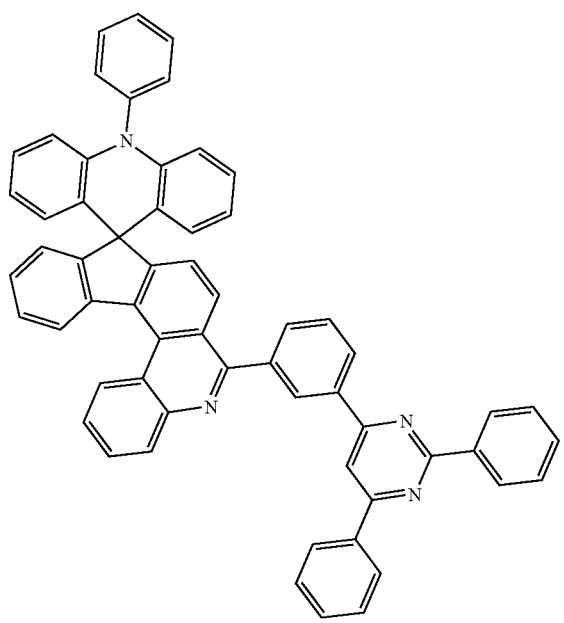
468
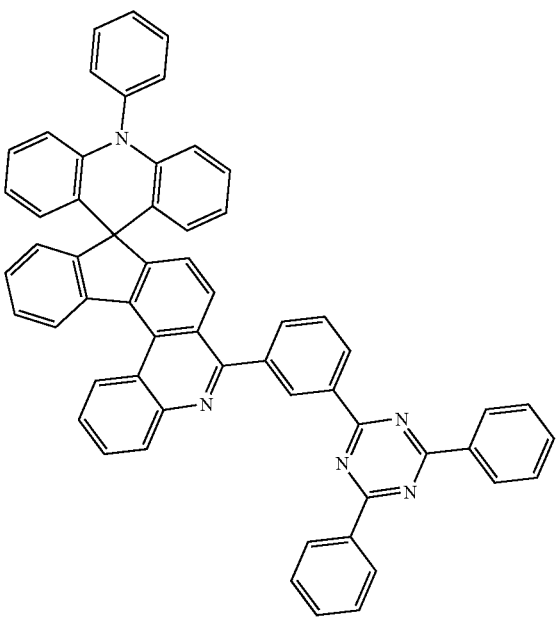
469
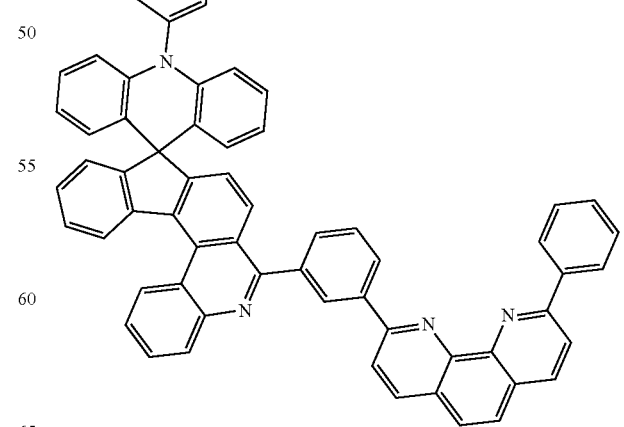

470
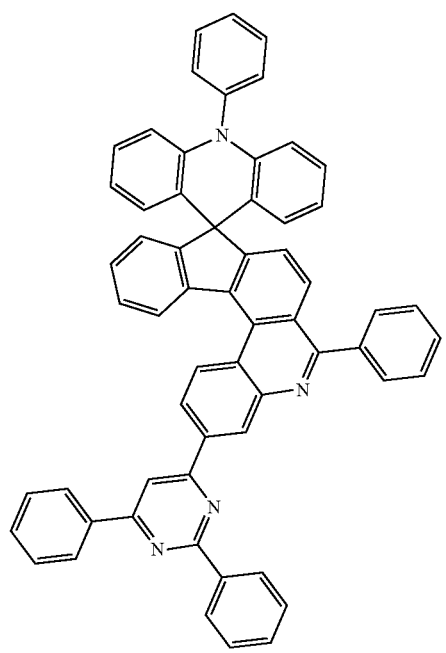
471
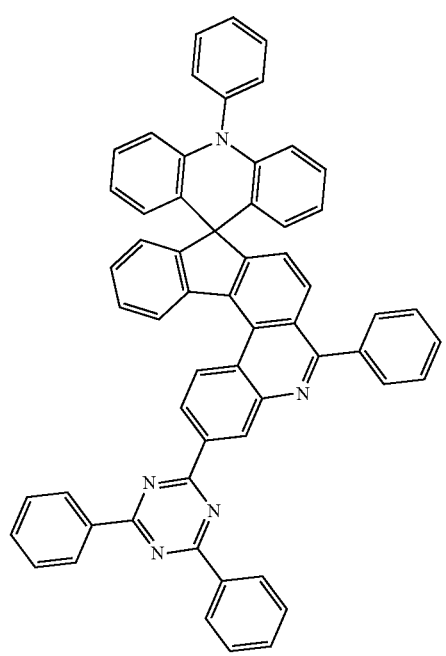
472
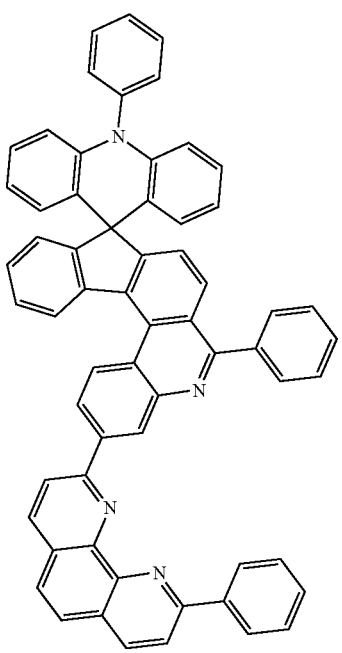
473
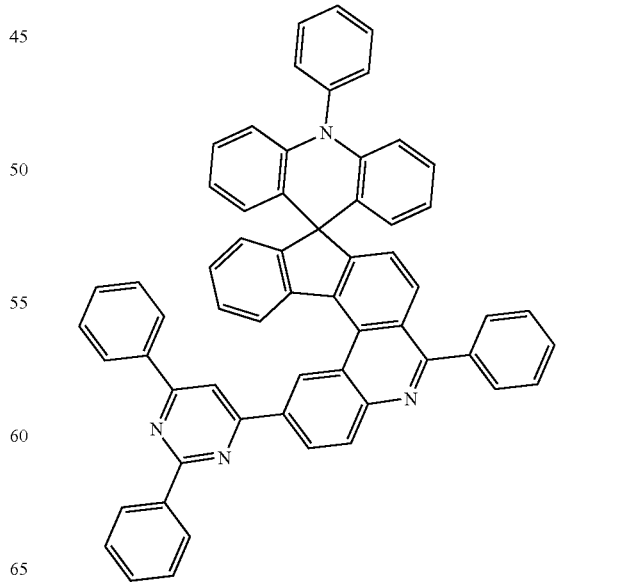

219
-continued
474
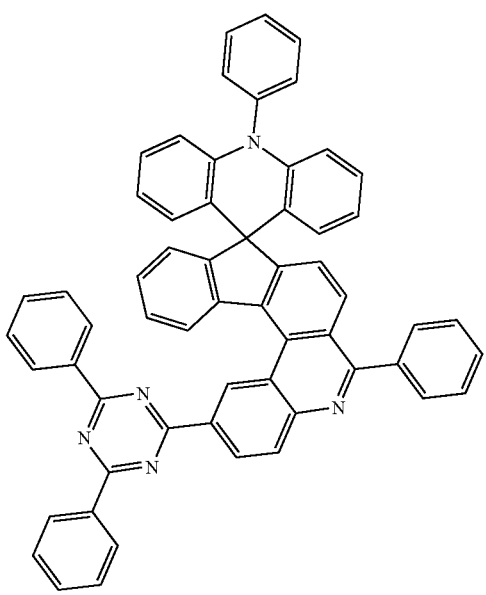
475
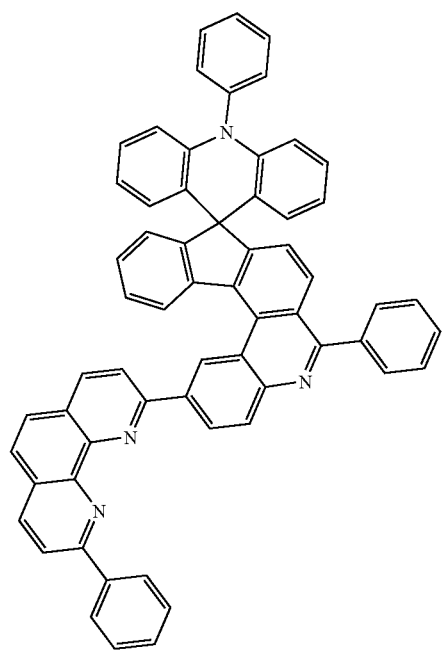
220
-continued
476
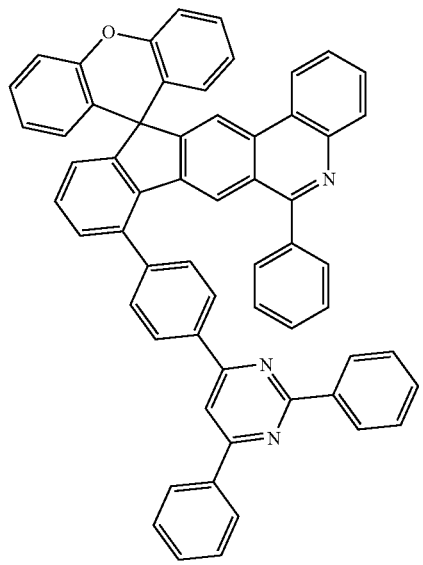
477
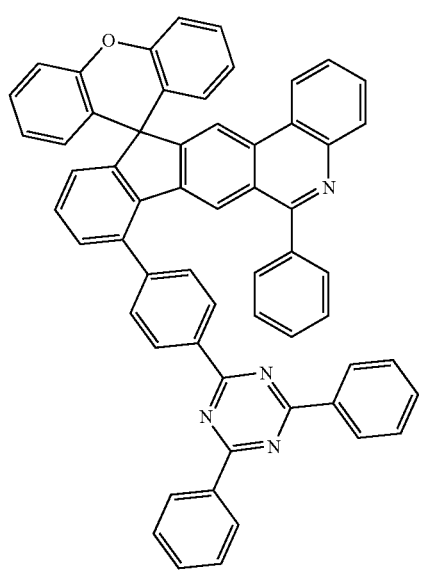
478
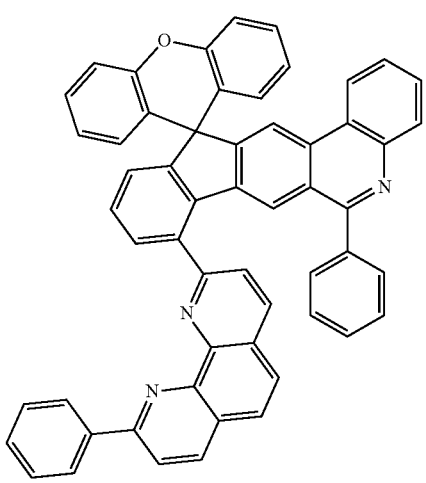

221
-continued
479
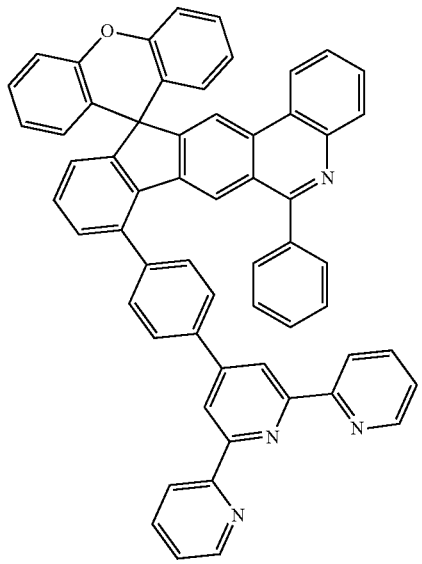
480
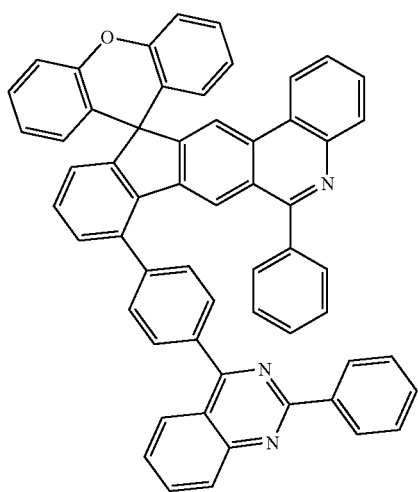
481
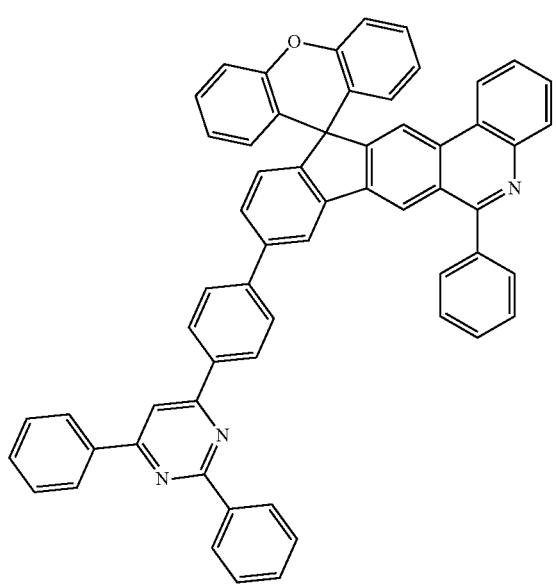
222
-continued
482
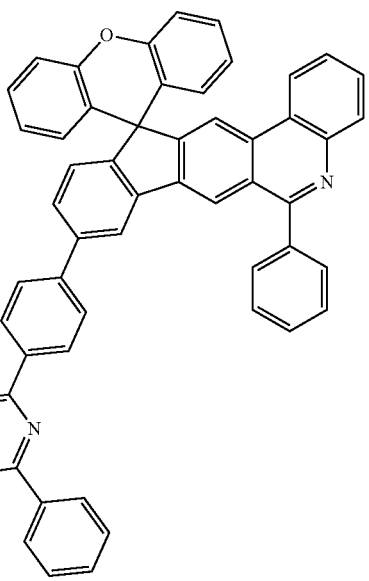
483
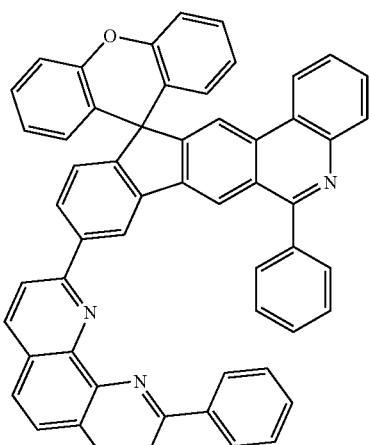
484
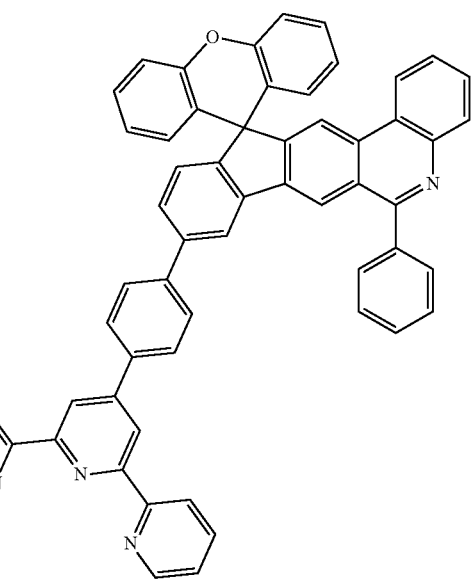

485
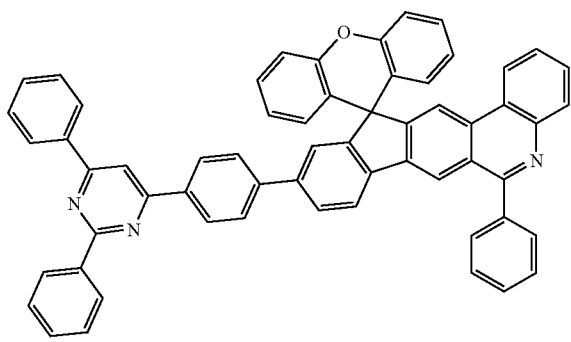
486
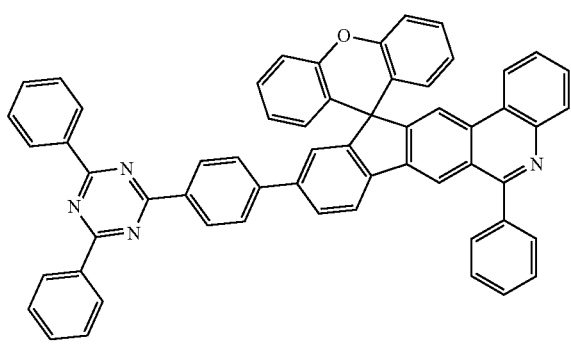
487
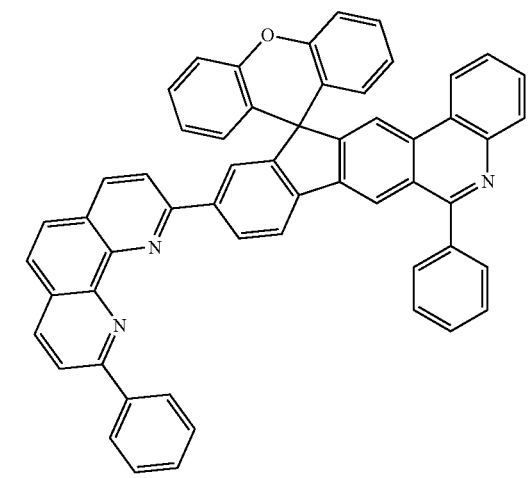
488
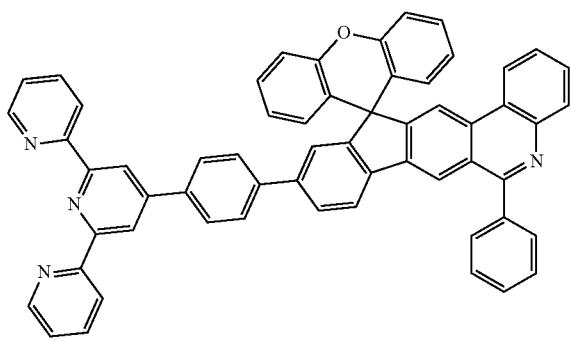
489
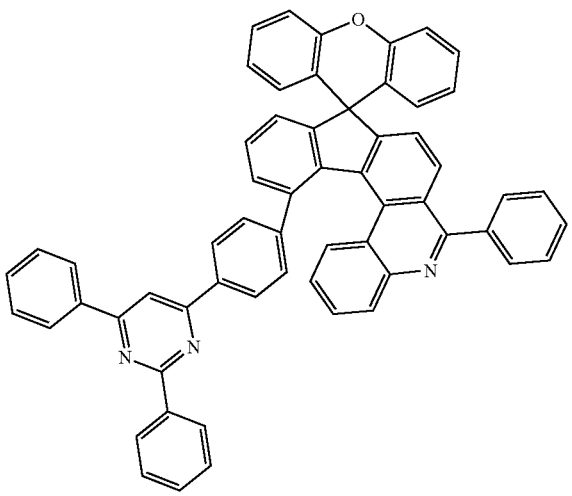
490
491
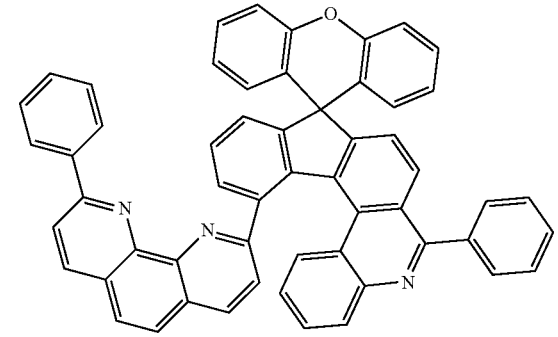

-continued
492
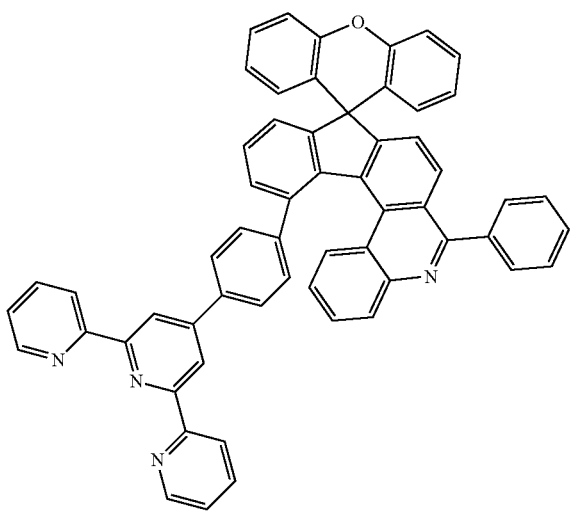
493
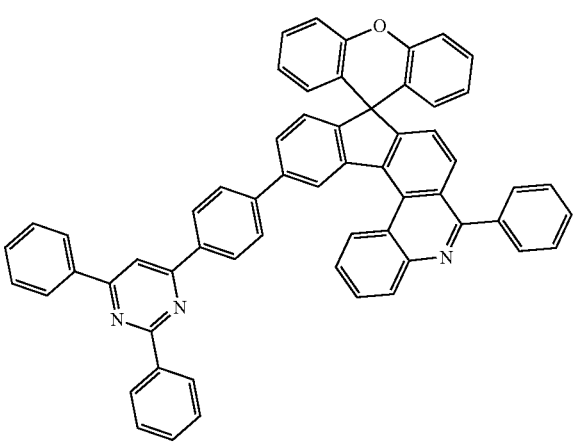
494
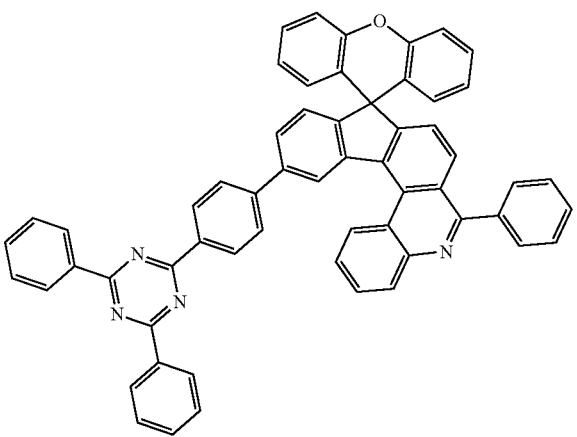
-continued
495
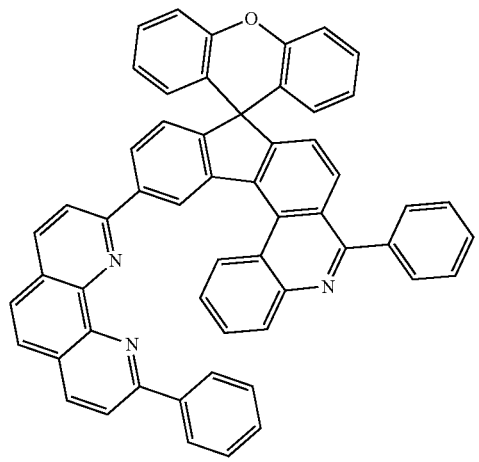
496
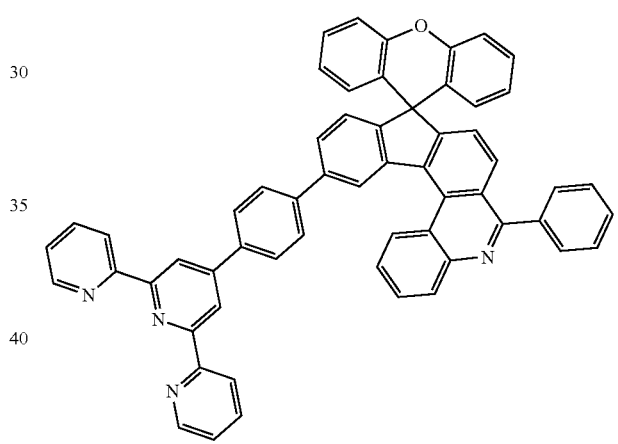
497
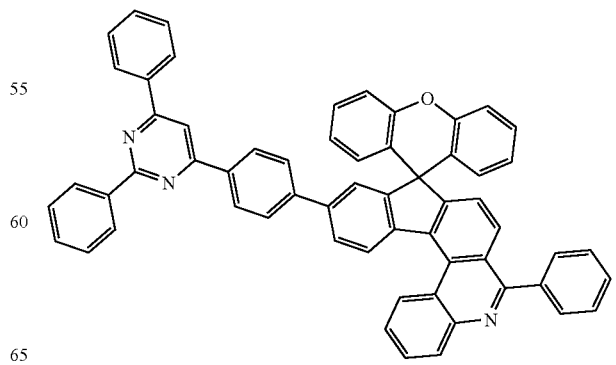

498
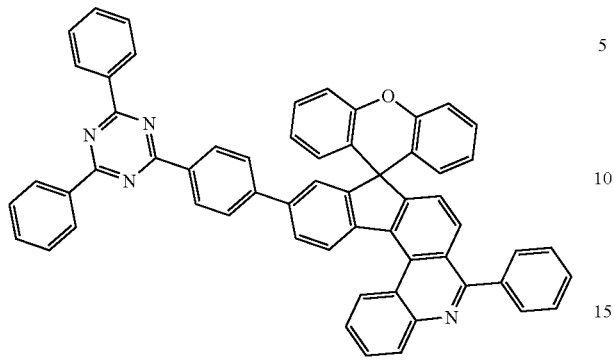
501
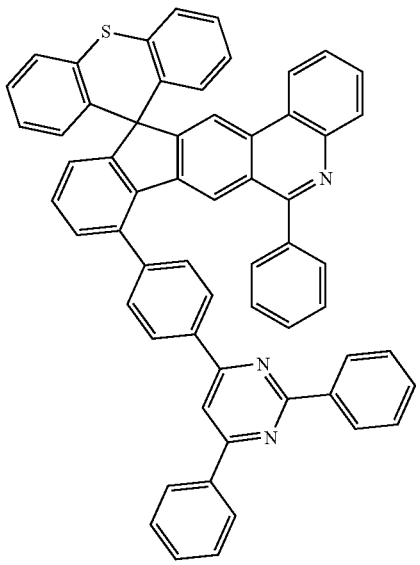
499
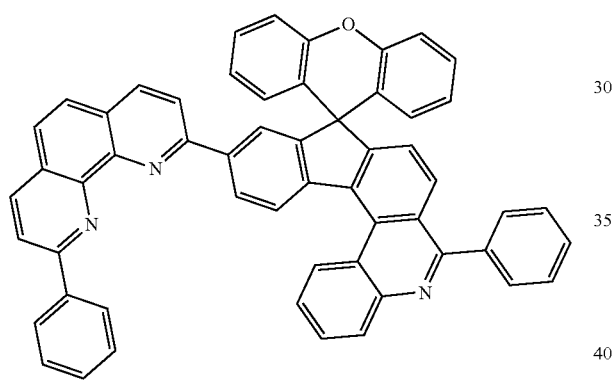
502
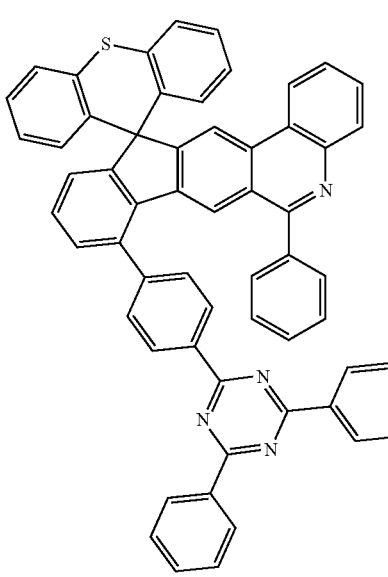
500
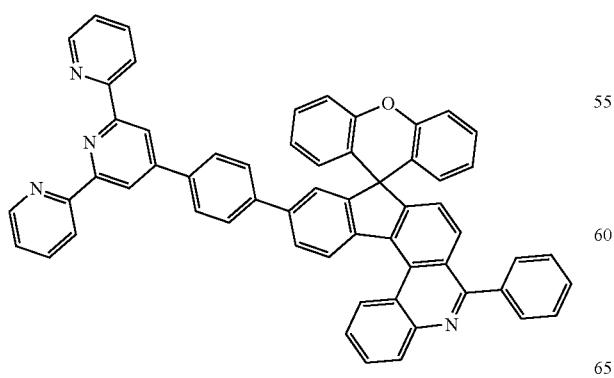
503
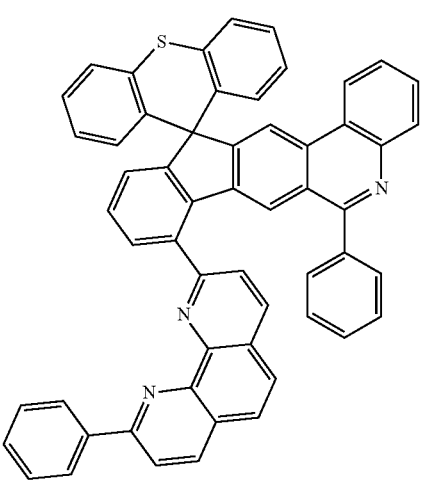

504
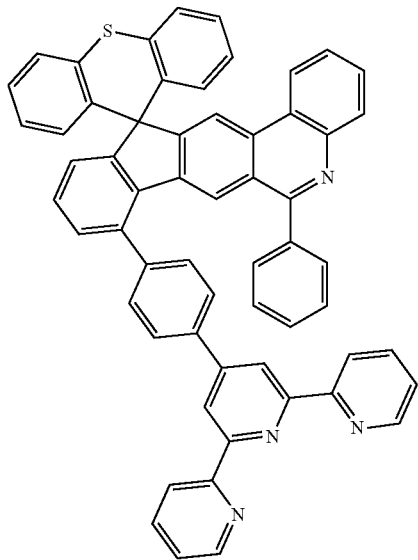
505
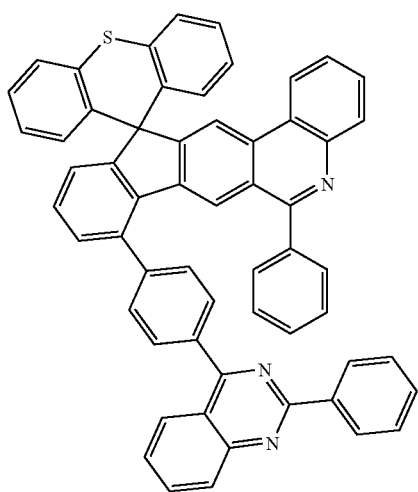
506
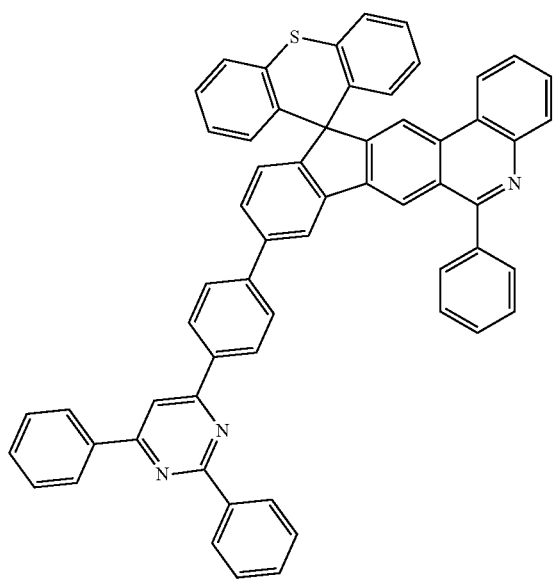
507
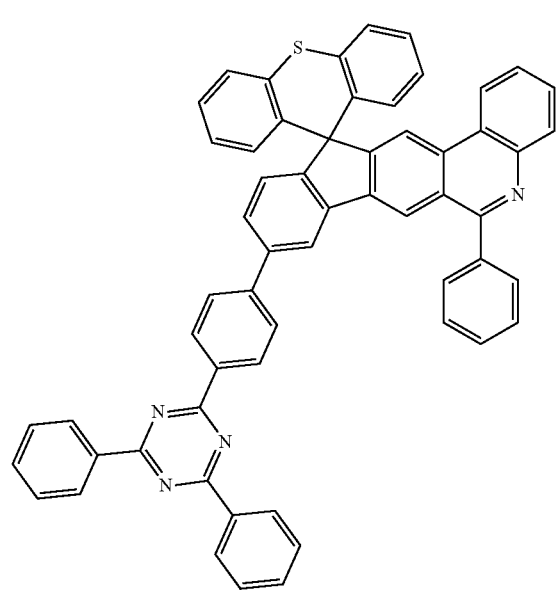
508
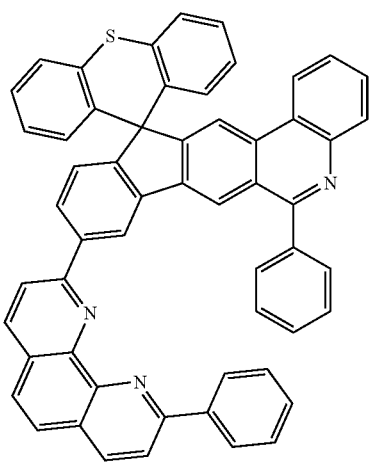
509
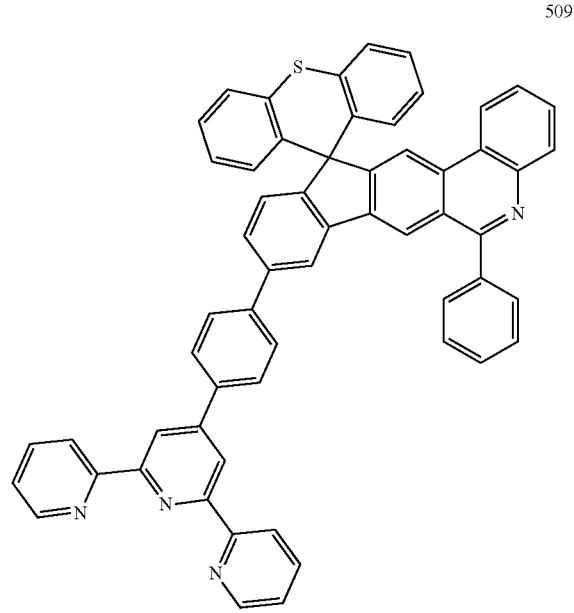

510
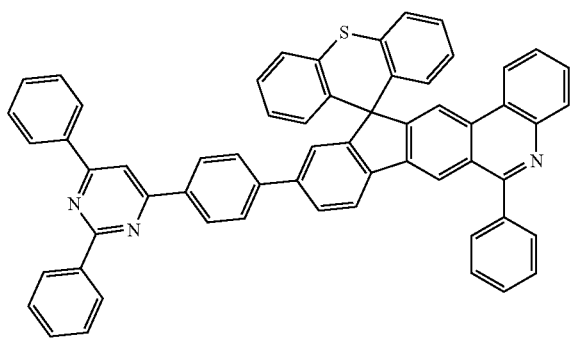
511
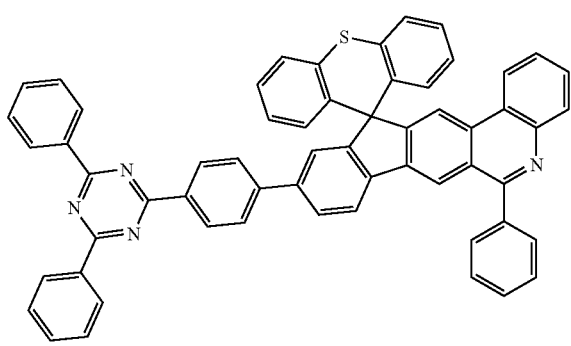
512
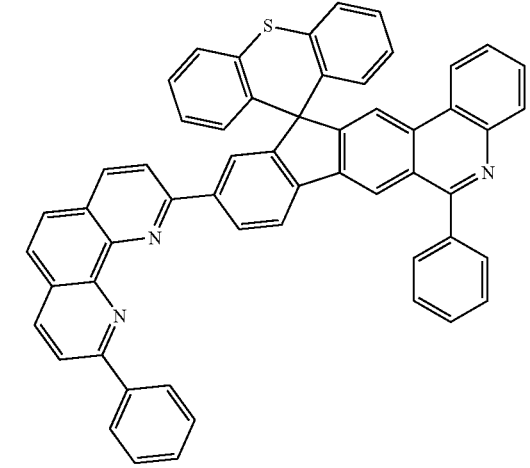
513
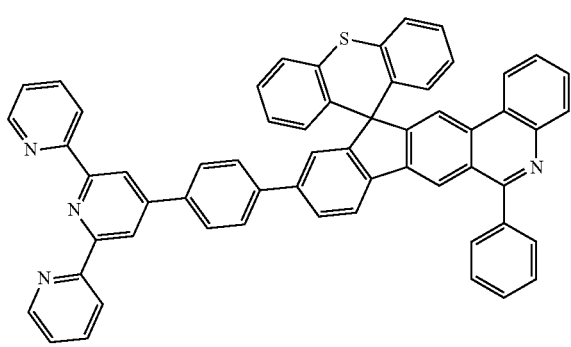
514
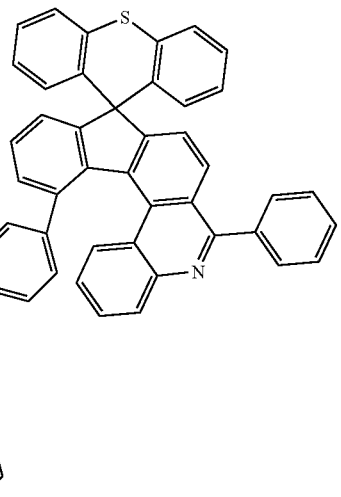
515
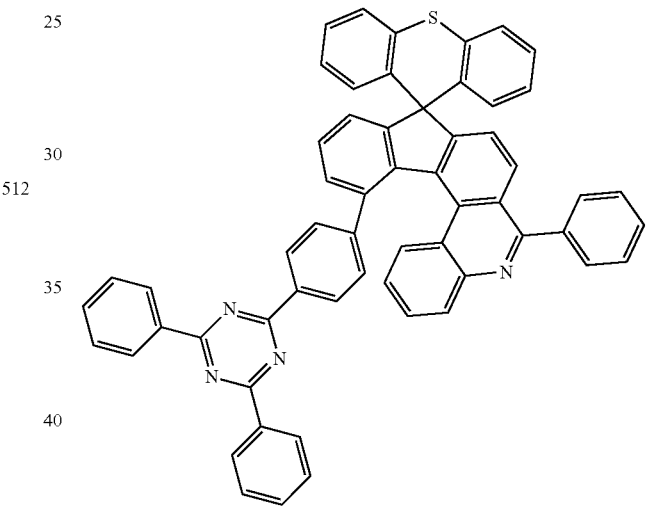
516
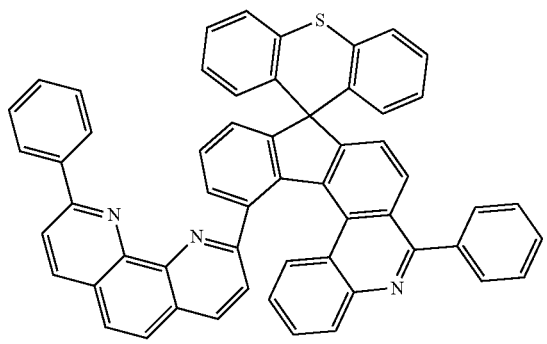

517
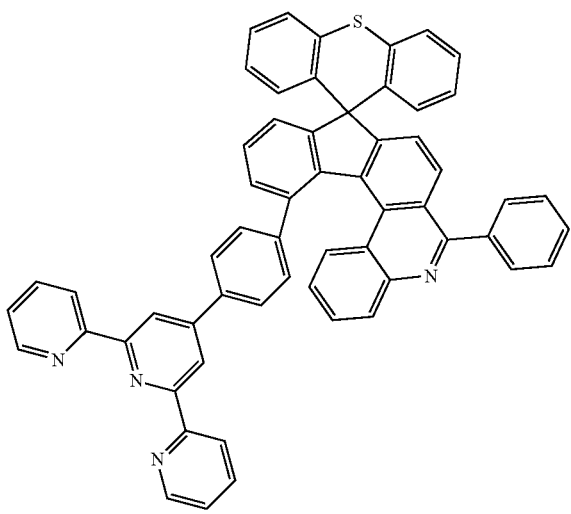
518
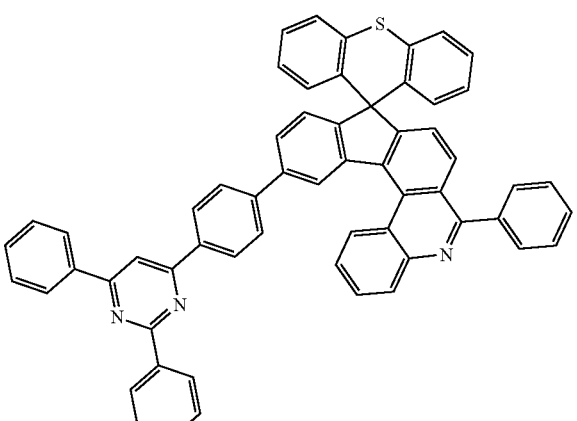
519
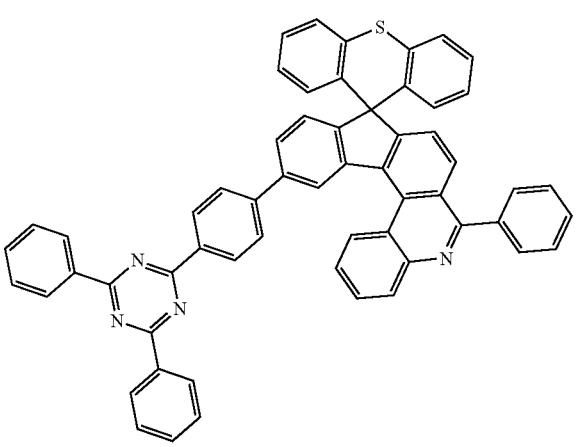
520
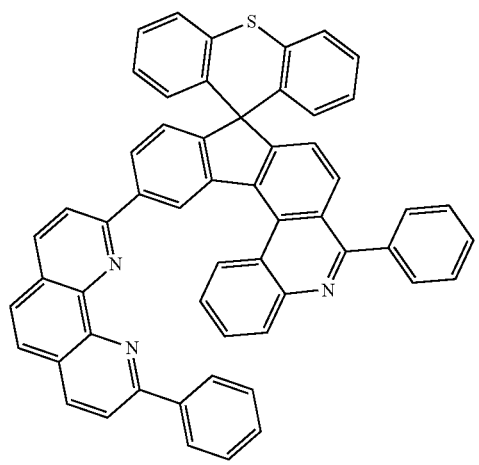
521
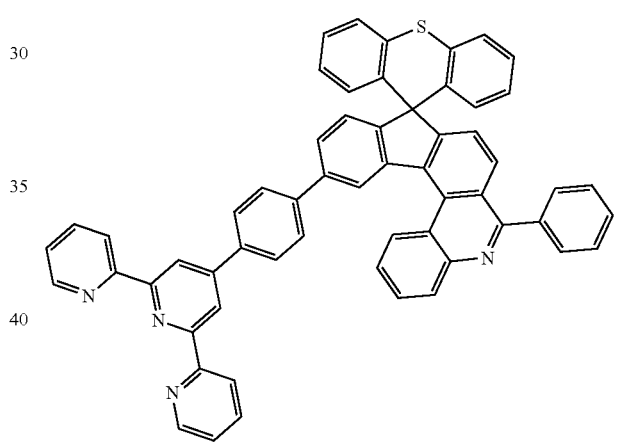
522
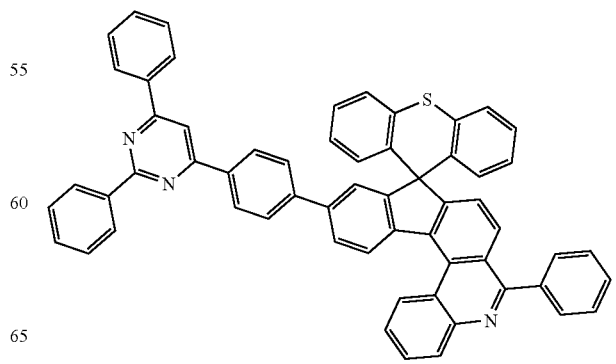

-continued
523
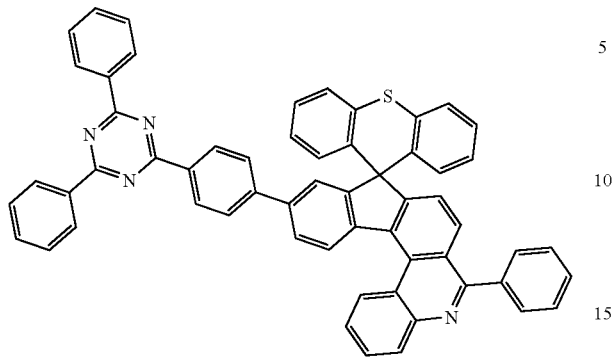
524
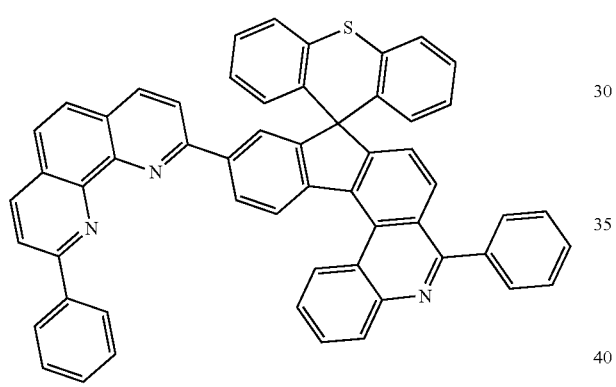
525
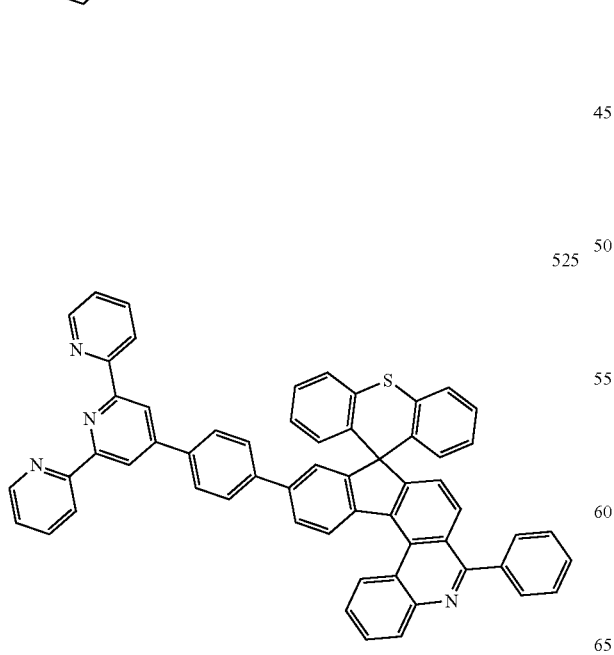
-continued
526
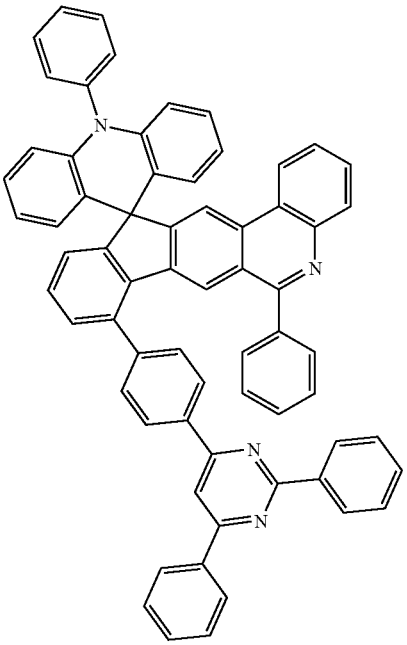
527
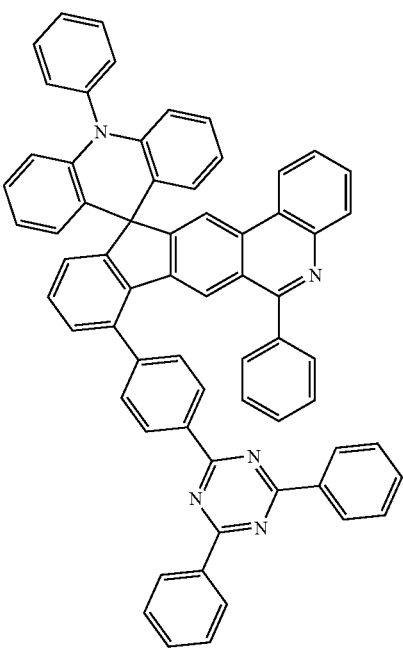

-continued
528
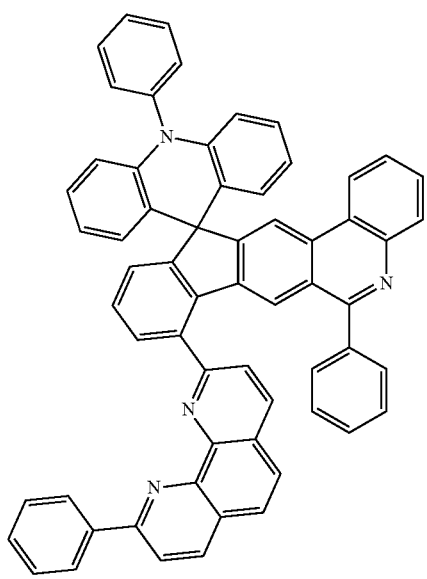
-continued
530
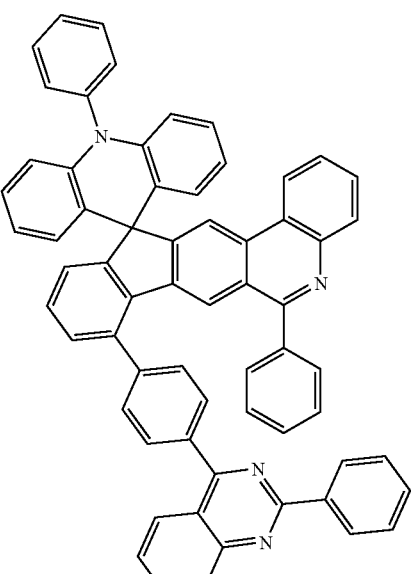
529
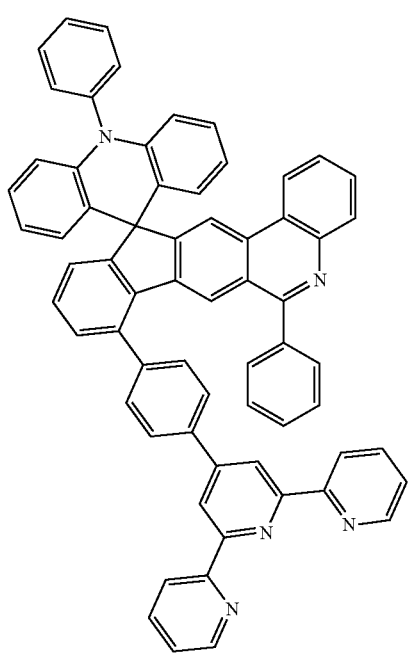
531
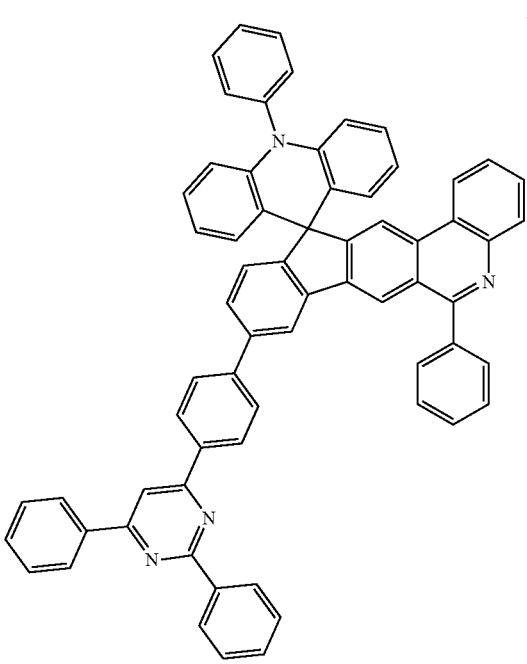

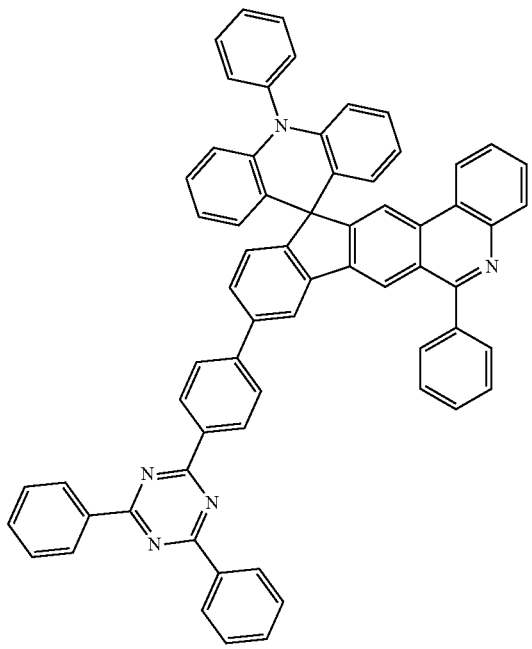
532
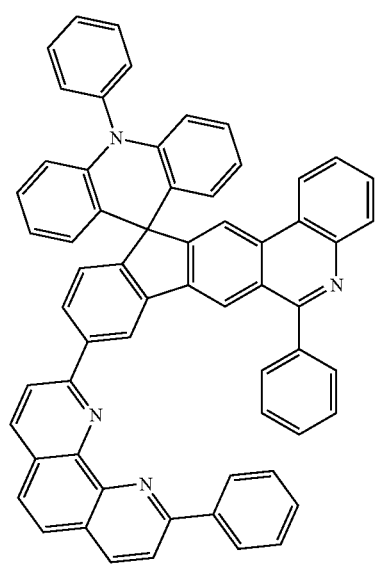
533
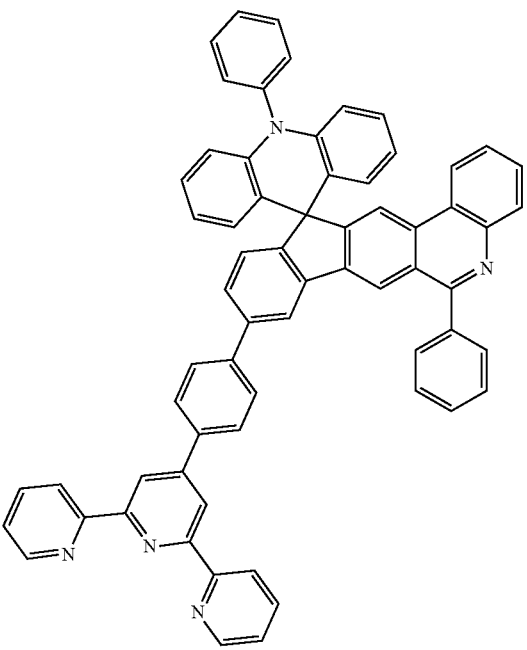
534
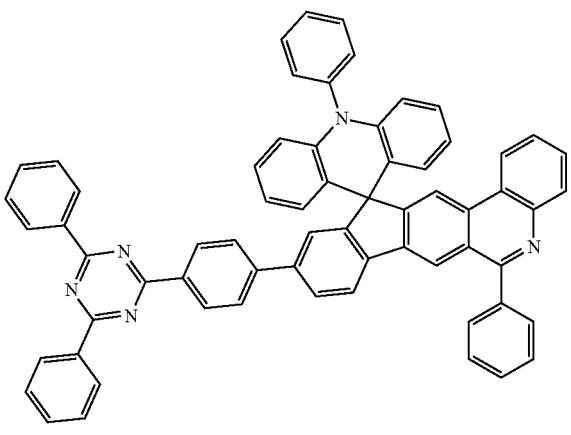
535
536

-continued
537
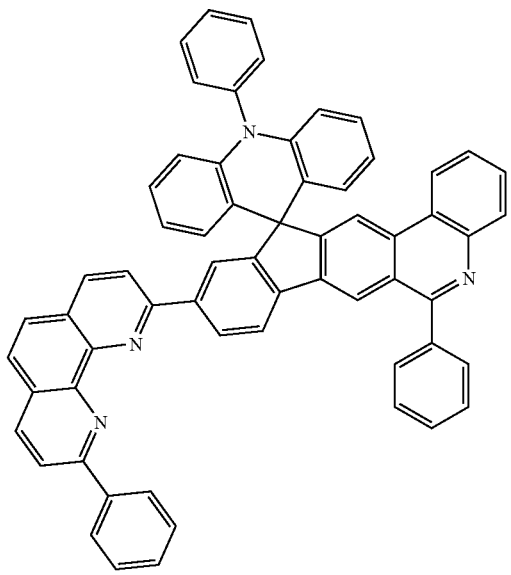
538
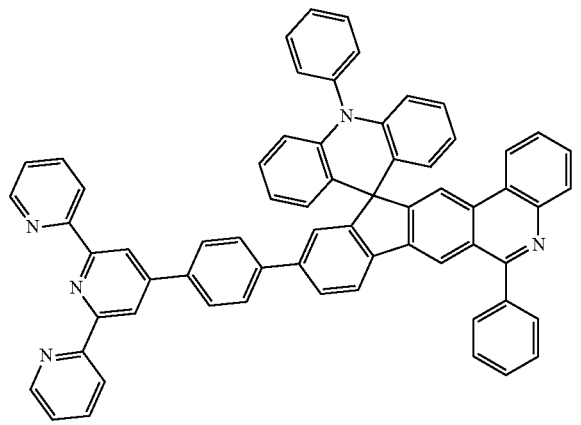
539
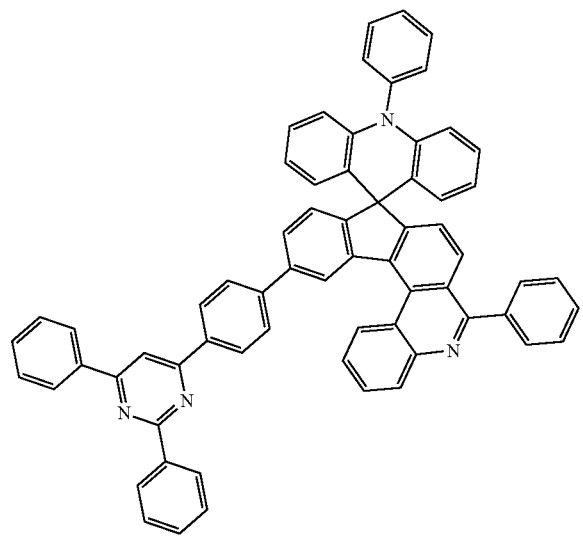
-continued
540
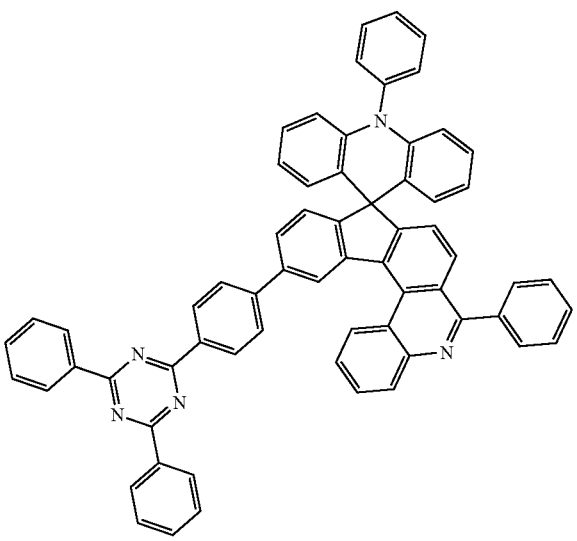
541
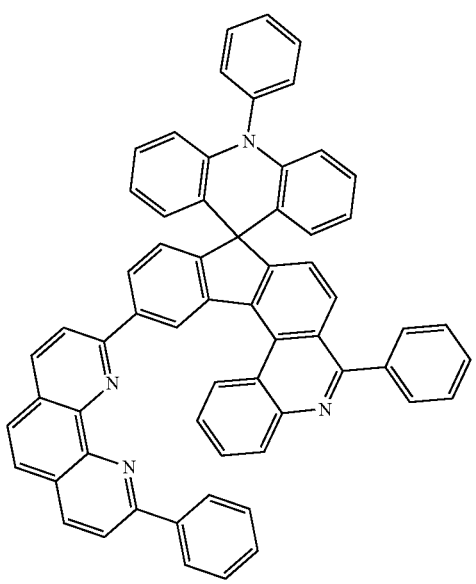

542
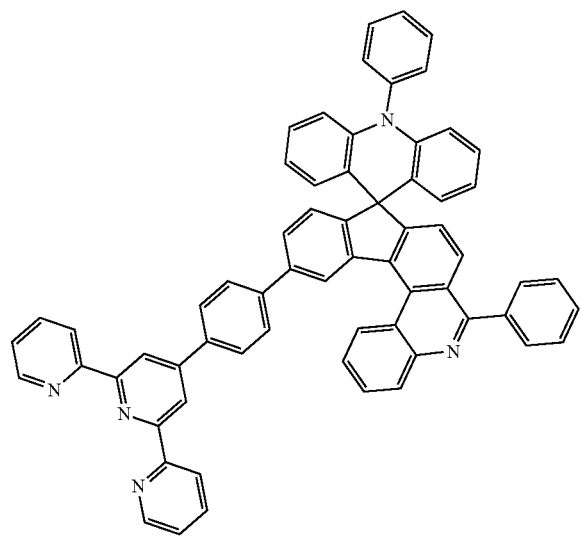
543
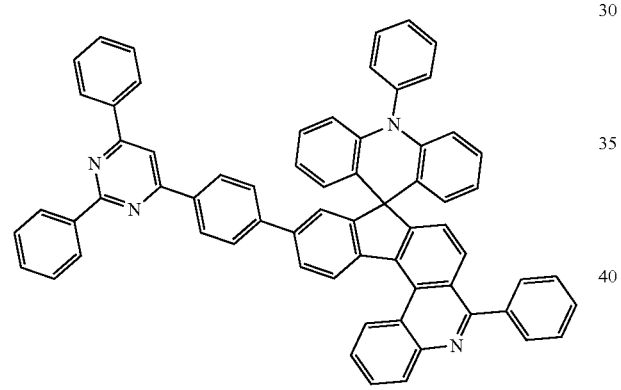
544
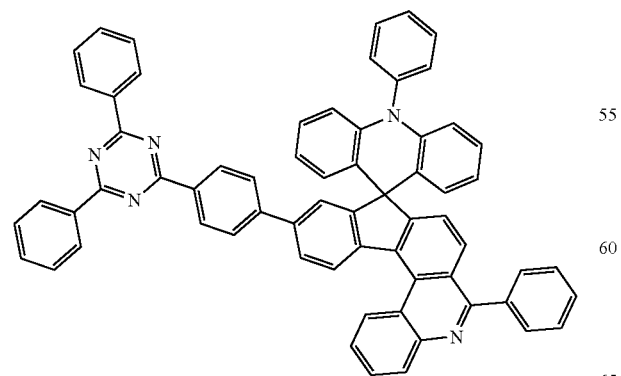
545
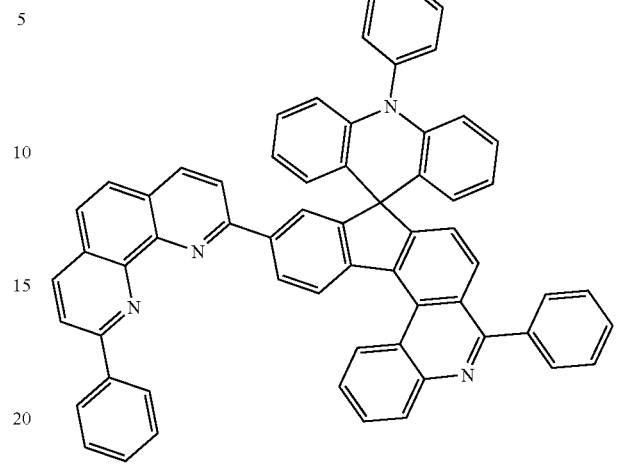
546
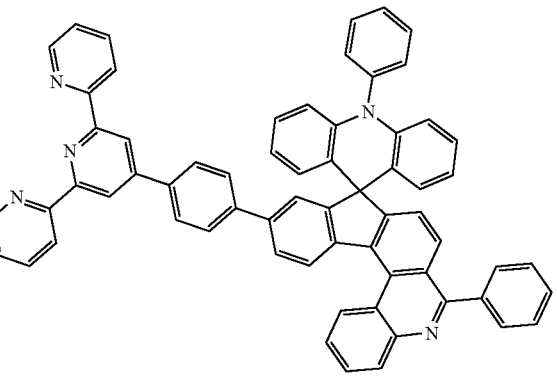
547
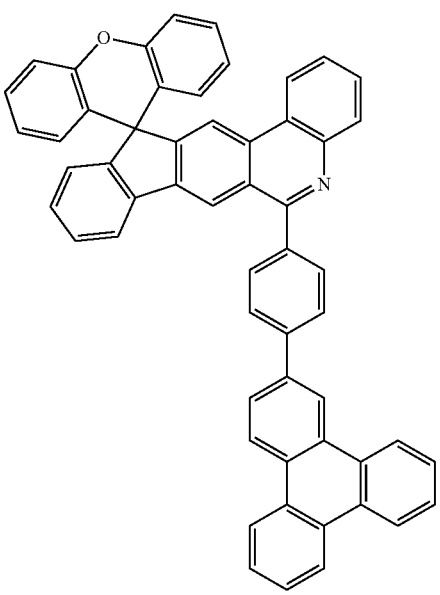

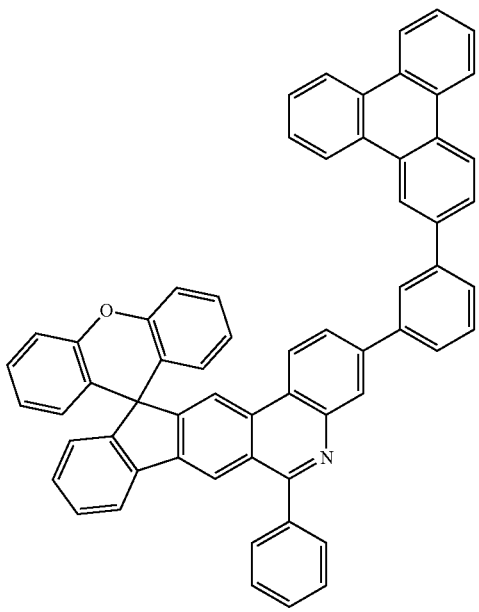

548

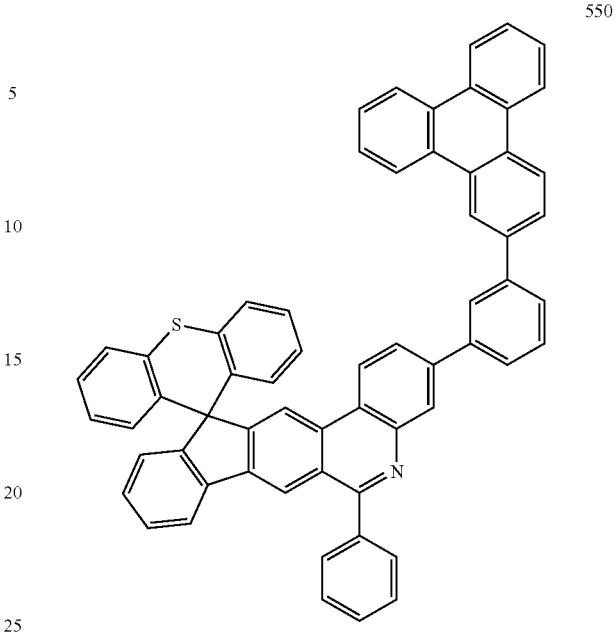

550

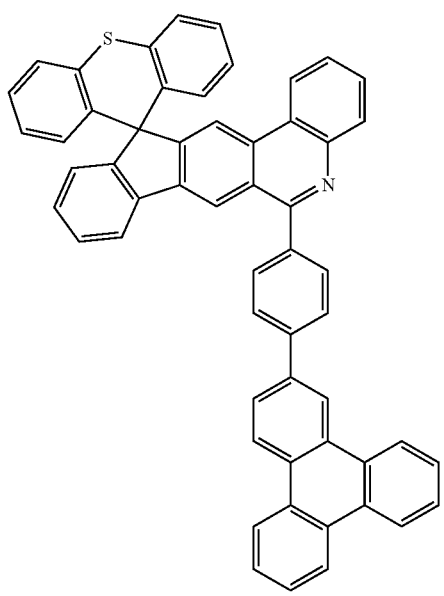

549

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Another embodiment of the present specification provides an organic light emitting device comprising a first electrode; a second electrode; and one or more organic material layers provided between the first electrode and the second electrode, wherein one or more layers of the organic material layers comprise the heterocyclic compound represented by Chemical Formula 1.

In one embodiment of the present specification, the first electrode may be an anode, and the second electrode may be a cathode.

In another embodiment of the present specification, the first electrode may be a cathode, and the second electrode may be an anode.

In one embodiment of the present specification, the organic light emitting device may be a blue organic light emitting device, and the heterocyclic compound according to Chemical Formula 1 may be used as a material of the blue organic light emitting device.

In another embodiment of the present specification, the organic light emitting device may be a green organic light emitting device, and the heterocyclic compound according to Chemical Formula 1 may be used as a material of the green organic light emitting device.

In another embodiment of the present specification, the organic light emitting device may be a red organic light emitting device, and the heterocyclic compound according to Chemical Formula 1 may be used as a material of the red organic light emitting device.

Specific details on the heterocyclic compound represented by Chemical Formula 1 are the same as the descriptions provided above.

The organic light emitting device of the present specification may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device of the present specification, the organic material layer comprises an electron transfer layer, and the electron transfer layer may comprise the heterocyclic compound.

In another organic light emitting device of the present specification, the organic material layer comprises a hole blocking layer, and the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present specification. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound represented by Chemical Formula 1 may further comprise other materials as necessary.

In addition, the organic light emitting device according to one embodiment of the present specification comprises a first electrode, a second electrode, and two or more stacks provided between the first electrode and the second electrode, and the two or more stacks each independently comprise a light emitting layer, a charge generation layer is included between the two or more stacks, and the charge generation layer comprises the heterocyclic compound represented by Chemical Formula 1.

In addition, the organic light emitting device according to one embodiment of the present specification comprises a first electrode, a first stack provided on the first electrode and comprising a first light emitting layer, a charge generation layer provided on the first stack, a second stack provided on the charge generation layer and comprising a second light emitting layer, and a second electrode provided on the second stack. Herein, the charge generation layer may comprise the heterocyclic compound represented by Chemical Formula 1. In addition, the first stack and the second stack may each independently further comprise one or more types of the hole injection layer, the hole transfer layer, the hole blocking layer, the electron transfer layer, the electron injection layer and the like described above.

In one embodiment of the present application, the charge generation layer is an N-type charge generation layer, and the charge generation layer comprises the heterocyclic compound represented by Chemical Formula 1.

The charge generation layer may be an N-type charge generation layer, and the charge generation layer may further comprise a dopant known in the art in addition to the heterocyclic compound represented by Chemical Formula 1.

As the organic light emitting device according to one embodiment of the present specification, an organic light emitting device having a 2-stack tandem structure is illustrated in FIG. 4.

Herein, the first electron blocking layer, the first hole blocking layer, the second hole blocking layer and the like described in FIG. 4 may not be included in some cases.

In the organic light emitting device according to one embodiment of the present specification, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present specification may be a top-emission type, a bottom-emission type or a dual-emission type depending on the materials used.

The heterocyclic compound according to one embodiment of the present specification may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

<Preparation Example 1> Preparation of Intermediates A and B

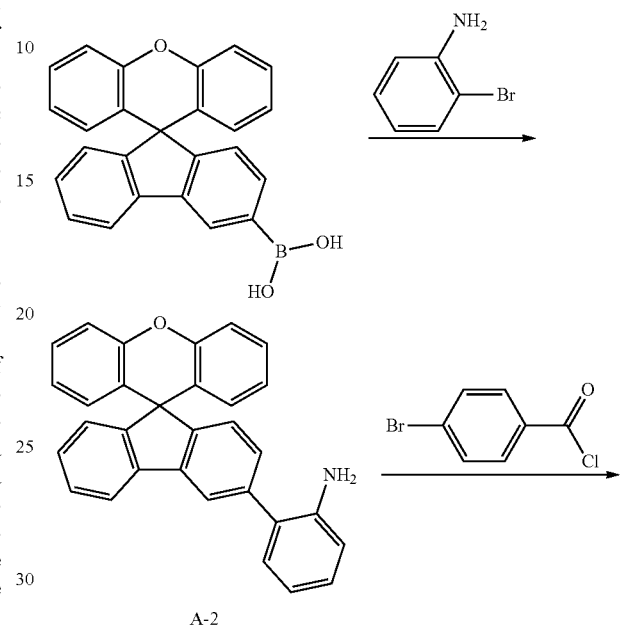

A-2

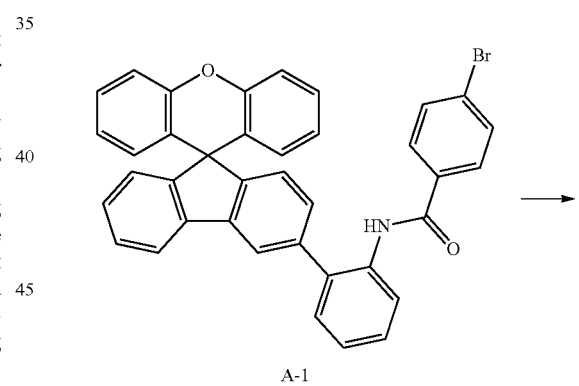

A-1

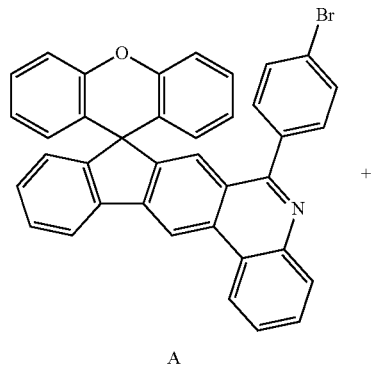

A

251

-continued

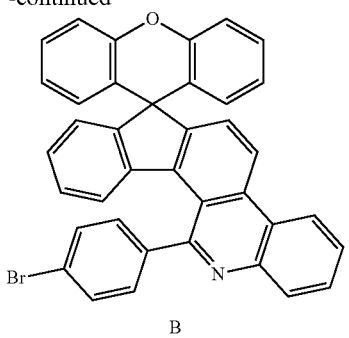

B

<Preparation Example 2> Preparation of Compound 1

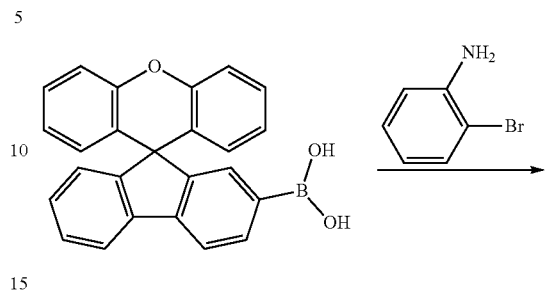

1) Preparation of Intermediate A-2

After dissolving spiro[fluorene-9,9'-xanthen]-3-ylboronic acid (50 g, 132.90 mmol) and 2-bromoaniline (25.15 g, 146.19 mmol) in dioxane/water (H$_2$O) (500 ml/100 ml), Pd(PPh$_3$)$_4$ (7.68 g, 6.65 mmol) and NaHCO$_3$ (33.50 g, 398.71 mmol) were introduced thereto, and the result was stirred for 15 hours under reflux. After the reaction was completed, methylene chloride (MC) was introduced to dissolve the reaction solution, and then the result was extracted with distilled water. The organic layer was dried with anhydrous MgSO$_4$, and, after removing the solvent using a rotary evaporator, purified with column chromatography using dichloromethane and hexane as a developing solvent to obtain Intermediate A-2 (41 g, yield: 72%).

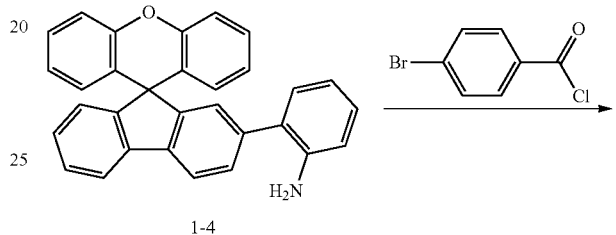

1-4

2) Preparation of Intermediate A-1

After dissolving Intermediate A-2 (41 g, 96.81 mmol) in methylene chloride (MC) (500 ml), TEA (29.39 g, 290.44 mmol) was introduced thereto. The temperature was lowered from room temperature to 0° C., and 4-bromobenzoyl chloride (23.37 g, 106.49 mmol) dissolved in methylene chloride (MC) was slowly added dropwise thereto. After the reaction was completed, the result was extracted with methylene chloride (MC) and distilled water. The organic layer was dried with anhydrous MgSO$_4$, and, after removing the solvent using a rotary evaporator, purified with column chromatography using dichloromethane and hexane as a developing solvent to obtain Intermediate A-1 (52 g, yield: 88%).

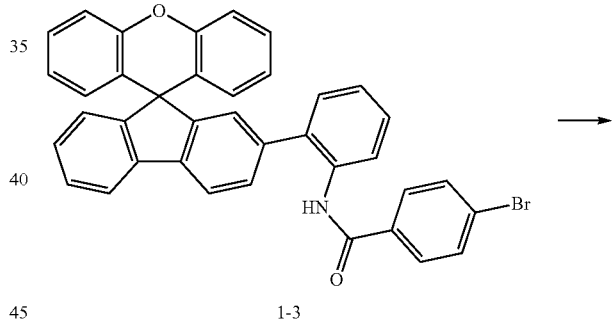

1-3

3) Preparation of Intermediates A and B

After dissolving Intermediate A-1 (52 g, 85.74 mmol) in nitrobenzene (500 ml), POCl$_3$ (14.46 g, 94.31 mmol) was slowly added dropwise thereto, and the result was stirred for 4 hours at 150° C. After the reaction was completed, the result was neutralized with an aqueous NaHCO$_3$ solution, and then extracted with methylene chloride (MC) and distilled water. The organic layer was dried with anhydrous MgSO$_4$, and, after removing the solvent using a rotary evaporator, purified with column chromatography using dichloromethane and hexane as a developing solvent to obtain Intermediate A (18 g, yield: 35%) and Intermediate B (20 g, yield: 39%).

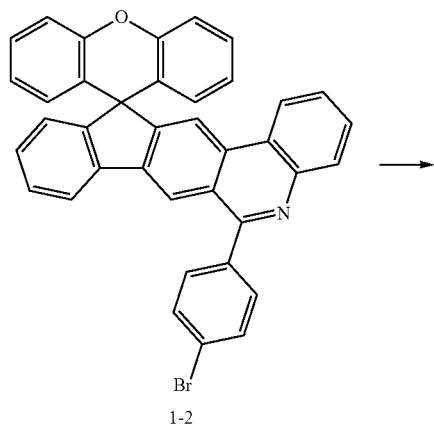

1-2

-continued

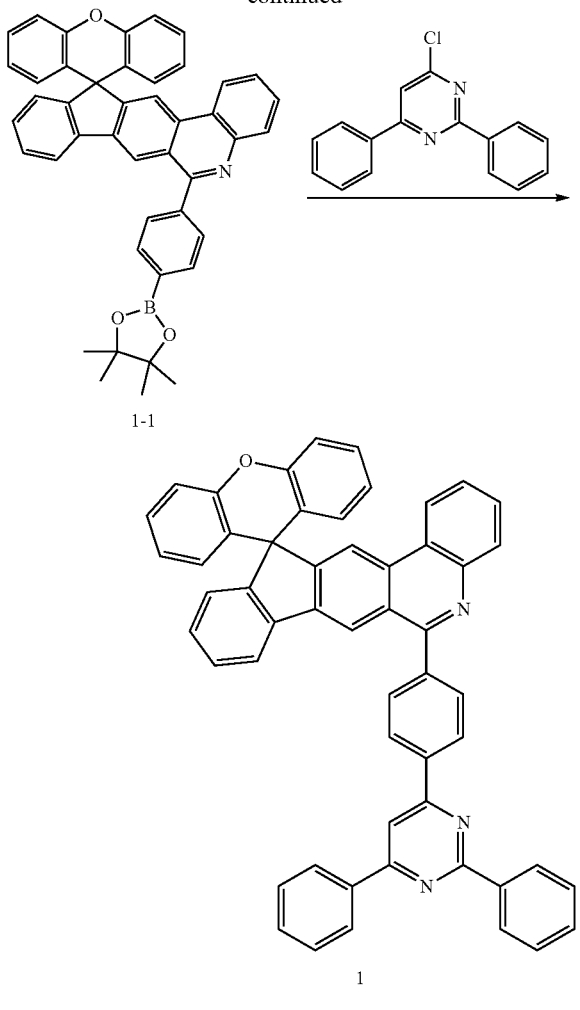

1) Preparation of Compound 1-4

After dissolving spiro[fluorene-9,9'-xanthen]-2-ylboronic acid (50 g, 132.90 mmol) and 2-bromoaniline (25.15 g, 146.19 mmol) in dioxane/water (H₂O) (500 ml/100 ml), Pd(PPh₃)₄ (7.68 g, 6.65 mmol) and NaHCO₃ (33.50 g, 398.71 mmol) were introduced thereto, and the result was stirred for 15 hours under reflux. After the reaction was completed, methylene chloride (MC) was introduced to dissolve the reaction solution, and then the result was extracted with distilled water. The organic layer was dried with anhydrous MgSO₄, and, after removing the solvent using a rotary evaporator, purified with column chromatography using dichloromethane and hexane as a developing solvent to obtain Compound 1-4 (41 g, yield: 72%).

2) Preparation of Compound 1-3

After dissolving Compound 1-4 (41 g, 96.81 mmol) in methylene chloride (MC) (500 ml), TEA (29.39 g, 290.44 mmol) was introduced thereto. The temperature was lowered from room temperature to 0° C., and 4-bromobenzoyl chloride (23.37 g, 106.49 mmol) dissolved in methylene chloride (MC) was slowly added dropwise thereto. After the reaction was completed, the result was extracted with methylene chloride (MC) and distilled water. The organic layer was dried with anhydrous MgSO₄, and, after removing the solvent using a rotary evaporator, purified with column chromatography using dichloromethane and hexane as a developing solvent to obtain Compound 1-3 (52 g, yield: 88%).

3) Preparation of Compound 1-2

After dissolving Compound 1-3 (52 g, 85.74 mmol) in nitrobenzene (500 ml), POCl₃ (14.46 g, 94.31 mmol) was slowly added dropwise thereto, and the result was stirred for 4 hours at 150° C. After the reaction was completed, the result was neutralized with an aqueous NaHCO₃ solution, and then extracted with methylene chloride (MC) and distilled water. The organic layer was dried with anhydrous MgSO₄, and, after removing the solvent using a rotary evaporator, purified with column chromatography using dichloromethane and hexane as a developing solvent to obtain Compound 1-2 (43 g, yield: 85%).

4) Preparation of Compound 1-1

After dissolving Compound 1-2 (43 g, 73.07 mmol) and bis(pinacolato)diboron (27.83 g, 109.60 mmol) in 1,4-dioxane (400 ml), Pd(dppf)Cl₂ (2.14 g, 2.92 mmol) and KOAc (21.51 g, 219.21 mmol) were introduced thereto, and the result was stirred for 5 hours under reflux. After the reaction was completed, the result was extracted with methylene chloride (MC) and water. The organic layer was dried with anhydrous MgSO₄, and then silica gel filtered. The result was precipitated using methylene chloride (MC)/methanol (MeOH), and then filtered to obtained Compound 1-1 (42 g, yield: 90%).

5) Preparation of Compound 1

After dissolving Compound 1-1 (10 g, 15.73 mmol) and 4-chloro-2,6-diphenylpyrimidine (4.41 g, 16.52 mmol) in toluene/ethanol/water (100 ml/20 ml/20 ml), Pd(PPh₃)₄ (0.91 g, 0.79 mmol) and K₃PO₄ (10.02 g, 47.20 mmol) were introduced thereto, and the result was stirred for 5 hours under reflux. After the reaction was completed, the result was cooled to room temperature, and produced solids were filtered and then washed with ethyl acetate (EA) and methanol (MeOH). After that, the solids were all dissolved in an excess amount of dichloromethane, and then silica gel filtered to obtain Compound 1 (9 g, yield: 77%).

<Preparation Example 3> Syntheses of Target Compounds

Target compounds were prepared in the same manner as in Preparation Example 1 except that Intermediate C of the following Table 1 was used instead of spiro[fluorene-9,9'-xanthen]-2-ylboronic acid, Intermediate D of the following Table 1 was used instead of 2-bromoaniline, Intermediate E of the following Table 1 was used instead of 4-bromobenzoyl chloride, and Intermediate F of the following Table 1 was used instead of 4-chloro-2,6-diphenylpyrimidine

TABLE 1

| Compound | Intermediate C | Intermediate D | Intermediate E | Intermediate F | Target Compound | Yield |
|---|---|---|---|---|---|---|
| 6 | | | | | | 74% |
| 11 | | | | | | 72% |

TABLE 1-continued

| Compound | Intermediate C | Intermediate D | Intermediate E | Intermediate F | Target Compound | Yield |
|---|---|---|---|---|---|---|
| 12 | | | | | | 81% |

TABLE 1-continued

| Compound | Intermediate C | Intermediate D | Intermediate E | Intermediate F | Target Compound | Yield |
|---|---|---|---|---|---|---|
| 15 | | | | | | 77% |

TABLE 1-continued
| Compound | Intermediate C | Intermediate D | Intermediate E | Intermediate F | Target Compound | Yield |
|---|---|---|---|---|---|---|
| 23 | 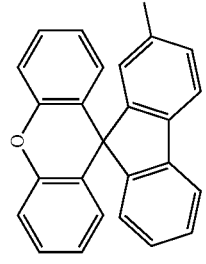 | 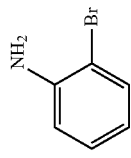 | 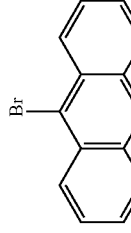 | 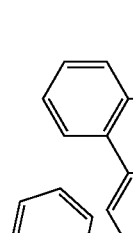 | 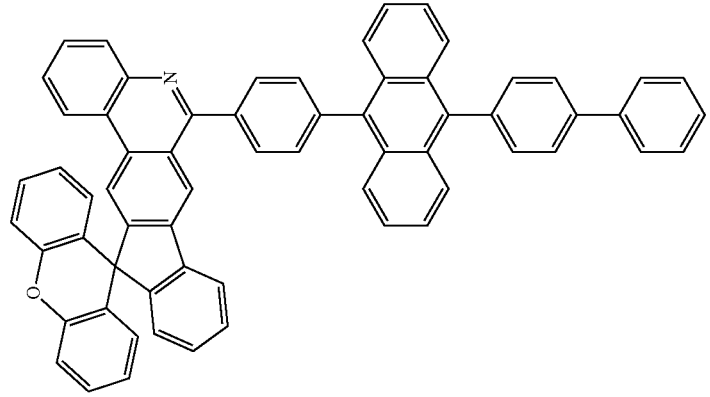 | 72% |

TABLE 1-continued

| Compound | Intermediate C | Intermediate D | Intermediate E | Intermediate F | Target Compound | Yield |
|---|---|---|---|---|---|---|
| 26 | | | | | | 67% |
| 31 | | | | | | 64% |

TABLE 1-continued

| Compound | Intermediate C | Intermediate D | Intermediate E | Intermediate F | Target Compound | Yield |
|---|---|---|---|---|---|---|
| 36 | | | | | | 69% |
| 42 | | | | | | 75% |

TABLE 1-continued
| Compound | Intermediate C | Intermediate D | Intermediate E | Intermediate F | Target Compound | Yield |
|---|---|---|---|---|---|---|
| 56 | 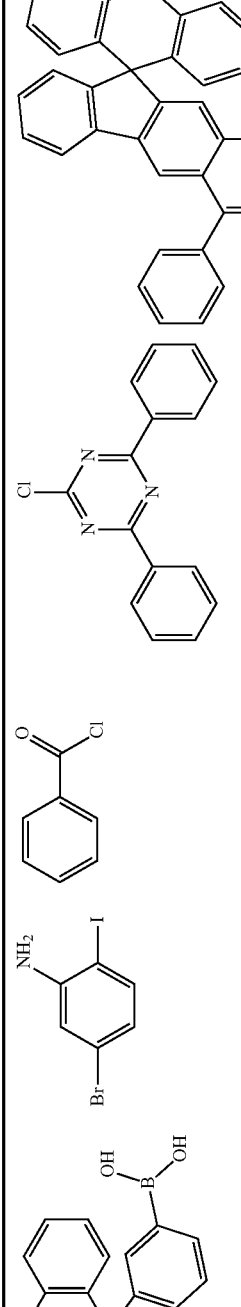 | 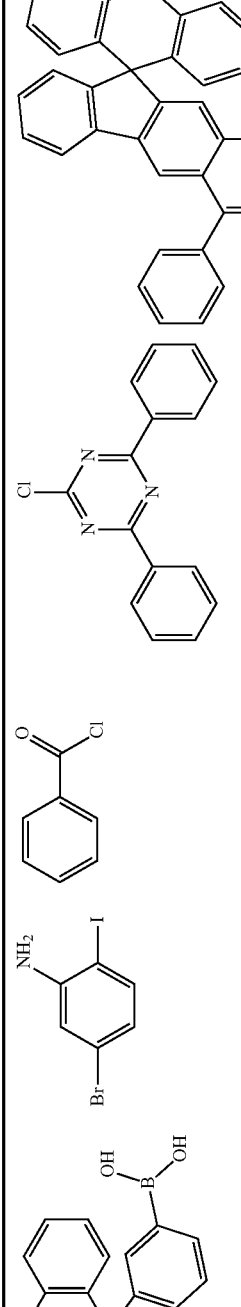 | 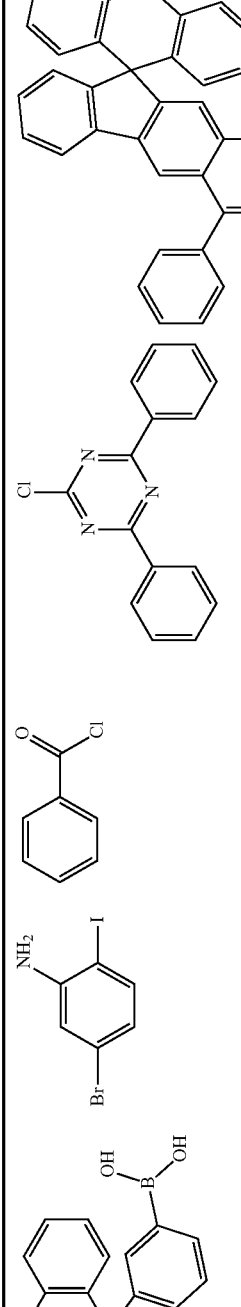 | 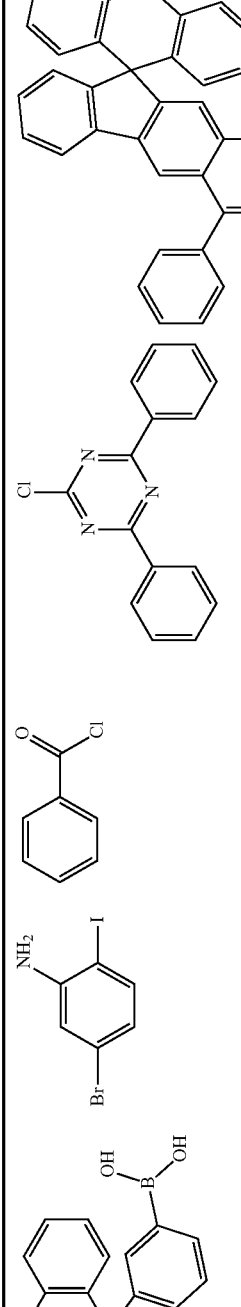 | 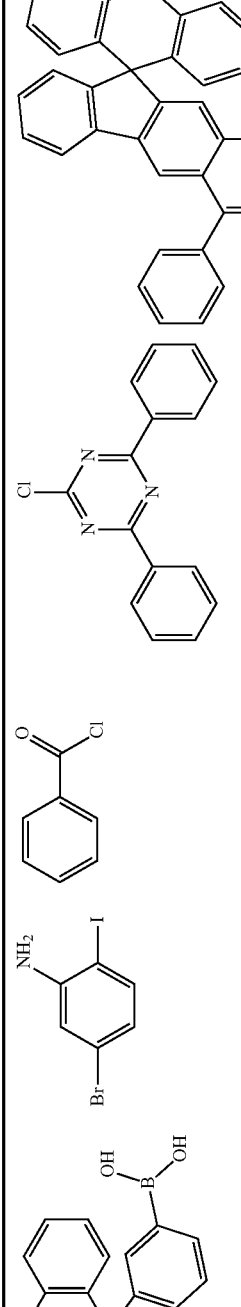 | 77% |

TABLE 1-continued
| Compound | Intermediate C | Intermediate D | Intermediate E | Intermediate F | Target Compound | Yield |
|---|---|---|---|---|---|---|
| 62 | 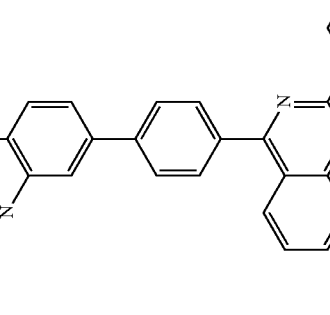 | 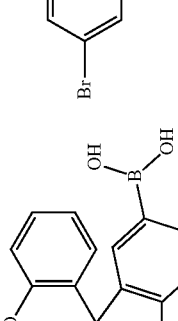 | 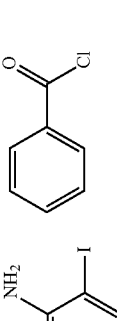 | 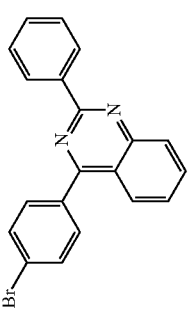 | 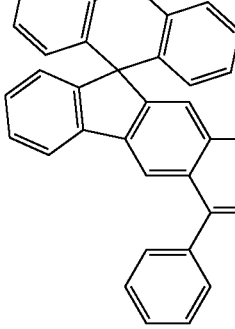 | 70% |

TABLE 1-continued

| Compound | Intermediate C | Intermediate D | Intermediate E | Intermediate F | Target Compound | Yield |
|---|---|---|---|---|---|---|
| 71 | [structure] | [structure] | [structure] | [structure] | [structure] | 68% |
| 77 | [structure] | [structure] | [structure] | [structure] | [structure] | 82% |

TABLE 1-continued

| Compound | Intermediate C | Intermediate D | Intermediate E | Intermediate F | Target Compound | Yield |
|---|---|---|---|---|---|---|
| 91 | | | | | | 77% |
| 93 | | | | | | 62% |

TABLE 1-continued
| Compound | Intermediate C | Intermediate D | Intermediate E | Intermediate F | Target Compound | Yield |
|---|---|---|---|---|---|---|
| 104 | 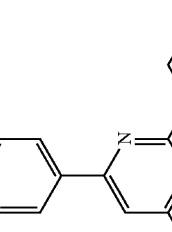 |  |  | 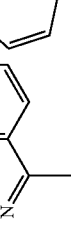 | 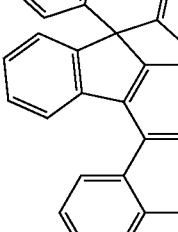 | 66% |

TABLE 1-continued
| Compound | Intermediate C | Intermediate D | Intermediate E | Intermediate F | Target Compound | Yield |
|---|---|---|---|---|---|---|
| 105 | 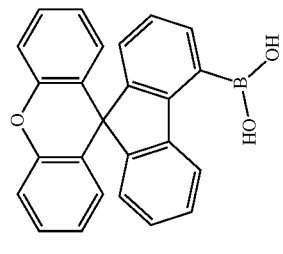 | 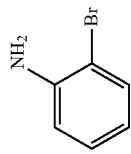 | 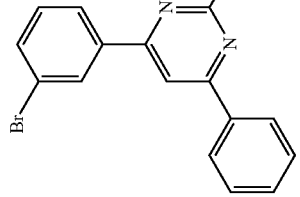 | 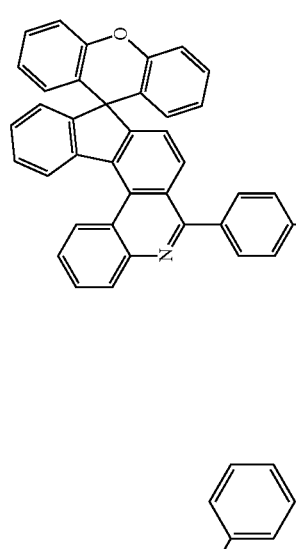 | 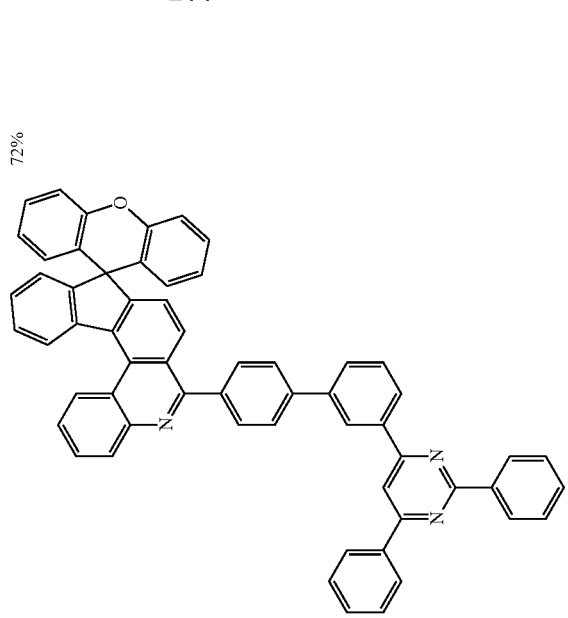 | 72% |

TABLE 1-continued

| Compound | Intermediate C | Intermediate D | Intermediate E | Intermediate F | Target Compound | Yield |
|---|---|---|---|---|---|---|
| 111 | (spiro xanthene-fluorene boronic acid) | 2-bromoaniline | 4-bromobenzoyl chloride | 2-bromo-9-phenyl-1,10-phenanthroline | (target structure) | 66% |

TABLE 1-continued
| Compound | Intermediate C | Intermediate D | Intermediate E | Intermediate F | Target Compound | Yield |
|---|---|---|---|---|---|---|
| 124 | 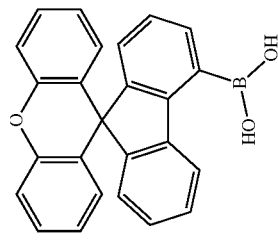 | 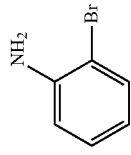 | 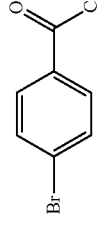 | 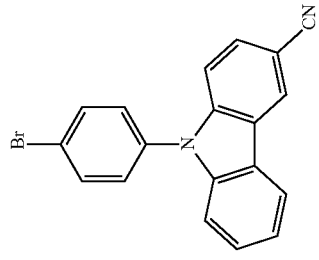 | 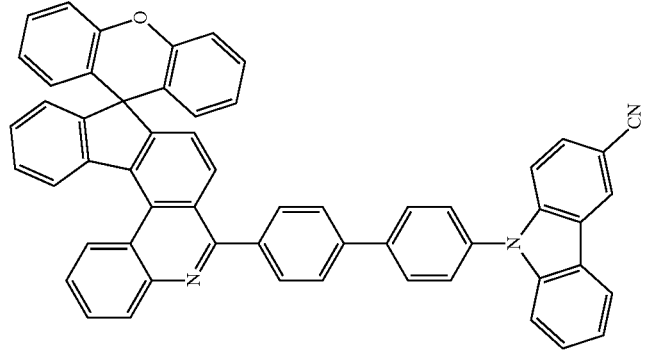 | 70% |

TABLE 1-continued

| Compound | Intermediate C | Intermediate D | Intermediate E | Intermediate F | Target Compound | Yield |
|---|---|---|---|---|---|---|
| 134 | (structure) | (structure) | (structure) | (structure) | (structure) | 59% |

TABLE 1-continued

| Compound | Intermediate C | Intermediate D | Intermediate E | Intermediate F | Target Compound | Yield |
|---|---|---|---|---|---|---|
| 146 | | | | | | 62% |
| 151 | | | | | | 64% |

TABLE 1-continued

| Compound | Intermediate C | Intermediate D | Intermediate E | Intermediate F | Target Compound | Yield |
|---|---|---|---|---|---|---|
| 156 | | | | | | 64% |
| 161 | | | | | | 71% |

TABLE 1-continued

| Compound | Intermediate C | Intermediate D | Intermediate E | Intermediate F | Target Compound | Yield |
|---|---|---|---|---|---|---|
| 168 | | | | | | 73% |
| 179 | | | | | | 77% |

TABLE 1-continued

| Compound | Intermediate C | Intermediate D | Intermediate E | Intermediate F | Target Compound | Yield |
|---|---|---|---|---|---|---|
| 183 | [spiro[fluorene-xanthene] boronic acid structure] | 4-bromo-2-iodoaniline | benzoyl chloride | 2-chloro-4-(biphenyl-3-yl)-6-phenyl-1,3,5-triazine | [target compound structure] | 75% |

TABLE 1-continued
| Compound | Intermediate C | Intermediate D | Intermediate E | Intermediate F | Target Compound | Yield |
|---|---|---|---|---|---|---|
| 215 | 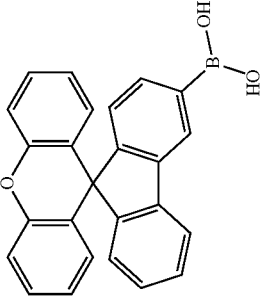 | 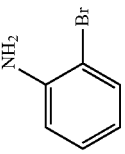 | 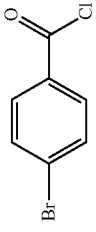 |  | 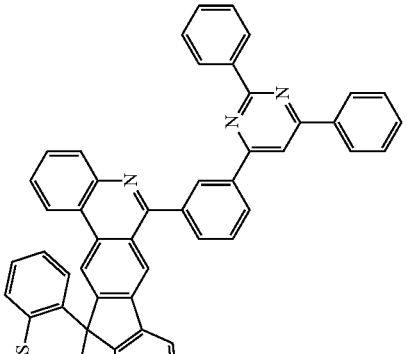 | 72% |
| 251 | 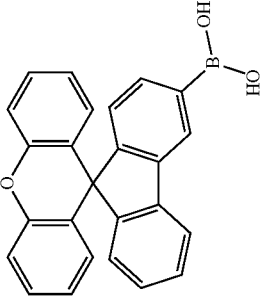 | 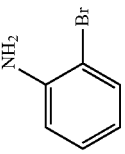 | 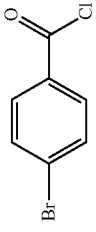 |  | 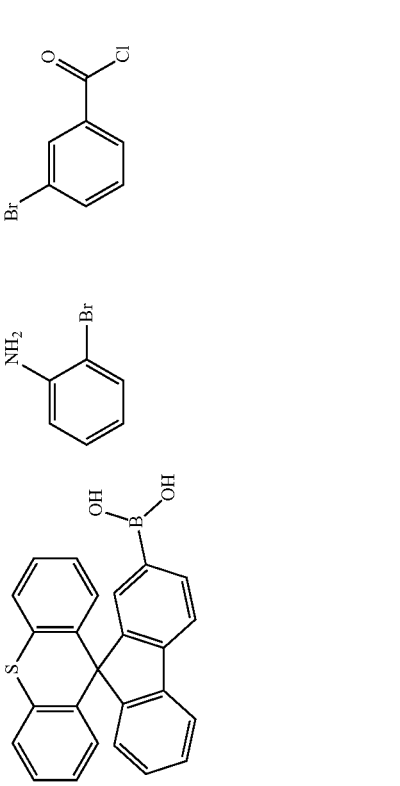 | 78% |

TABLE 1-continued

| Compound | Intermediate C | Intermediate D | Intermediate E | Intermediate F | Target Compound | Yield |
|---|---|---|---|---|---|---|
| 256 | | | | | | 66% |
| 266 | | | | | | 72% |

TABLE 1-continued

| Compound | Intermediate C | Intermediate D | Intermediate E | Intermediate F | Target Compound | Yield |
|---|---|---|---|---|---|---|
| 268 | (structure) | (structure) | (structure) | (structure) | (structure) | 66% |

TABLE 1-continued

| Compound | Intermediate C | Intermediate D | Intermediate E | Intermediate F | Target Compound | Yield |
|---|---|---|---|---|---|---|
| 279 | (structure) | (structure) | (structure) | (structure) | (structure) | 70% |

TABLE 1-continued

| Com-pound | Intermediate C | Intermediate D | Intermediate E | Intermediate F | Target Compound | Yield |
|---|---|---|---|---|---|---|
| 284 | (spiro thioxanthene-fluorene boronic acid) | 5-bromo-2-iodoaniline | benzoyl chloride | 2-(4-bromophenyl)-4,6-diphenyl-1,3,5-triazine | (target structure) | 69% |

TABLE 1-continued

| Compound | Intermediate C | Intermediate D | Intermediate E | Intermediate F | Target Compound | Yield |
|---|---|---|---|---|---|---|
| 288 | (spiro-thioxanthene-fluorene boronic acid) | 2-iodo-5-bromoaniline | benzoyl chloride | (4-bromophenyl)diphenylphosphine oxide | (target structure) | 82% |
| 307 | (spiro-thioxanthene-fluorene boronic acid) | 2-iodo-4-bromoaniline | benzoyl chloride | 2-chloro-4-(4-biphenyl)-6-phenyl-1,3,5-triazine | (target structure) | 77% |

TABLE 1-continued

| Compound | Intermediate C | Intermediate D | Intermediate E | Intermediate F | Target Compound | Yield |
|---|---|---|---|---|---|---|
| 324 | | | | | | 62% |

TABLE 1-continued

| Compound | Intermediate C | Intermediate D | Intermediate E | Intermediate F | Target Compound | Yield |
|---|---|---|---|---|---|---|
| 336 | | | | | | 66% |

TABLE 1-continued
| Compound | Intermediate C | Intermediate D | Intermediate E | Intermediate F | Target Compound | Yield |
|---|---|---|---|---|---|---|
| 337 | 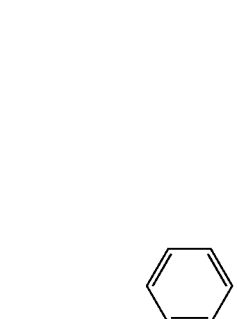 |  | 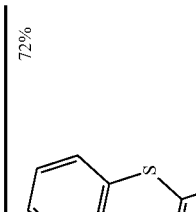 | 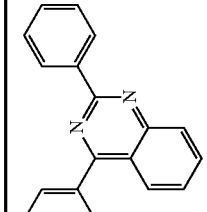 | 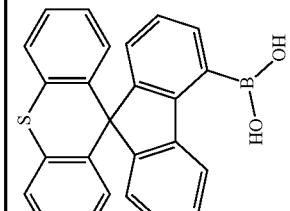 | 72% |

TABLE 1-continued
| Compound | Intermediate C | Intermediate D | Intermediate E | Intermediate F | Target Compound | Yield |
|---|---|---|---|---|---|---|
| 351 | 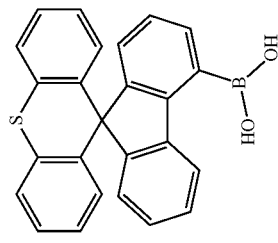 | 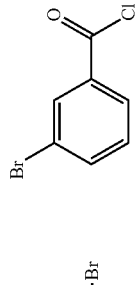 | 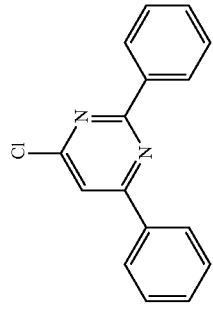 | 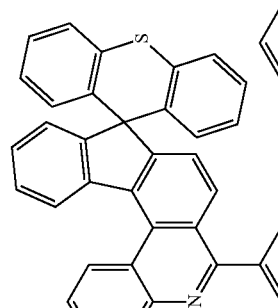 | 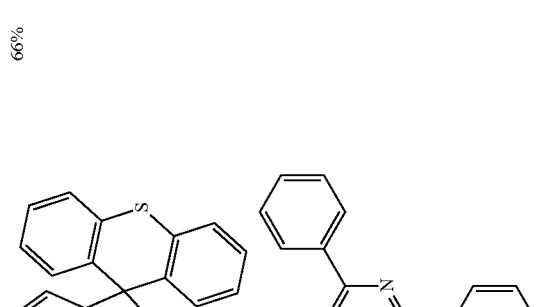 | 66% |

TABLE 1-continued

| Compound | Intermediate C | Intermediate D | Intermediate E | Intermediate F | Target Compound | Yield |
|---|---|---|---|---|---|---|
| 356 | | | | | | 70% |

TABLE 1-continued

| Compound | Intermediate C | Intermediate D | Intermediate E | Intermediate F | Target Compound | Yield |
|---|---|---|---|---|---|---|
| 366 | | | | | | 59% |
| 389 | | | | | | 69% |

TABLE 1-continued

| Compound | Intermediate C | Intermediate D | Intermediate E | Intermediate F | Target Compound | Yield |
|---|---|---|---|---|---|---|
| 423 | (structure) | (structure) | (structure) | (structure) | (structure) | 82% |

TABLE 1-continued

| Compound | Intermediate C | Intermediate D | Intermediate E | Intermediate F | Target Compound | Yield |
|---|---|---|---|---|---|---|
| 461 | [structure] | [structure] | [structure] | [structure] | [structure] | 77% |
| 547 | [structure] | [structure] | [structure] | [structure] | [structure] | 62% |

TABLE 1-continued

| Compound | Intermediate C | Intermediate D | Intermediate E | Intermediate F | Target Compound | Yield |
|---|---|---|---|---|---|---|
| 548 | (structure) | (structure) | (structure) | (structure) | (structure) | 66% |

The following Table 2 and Table 3 present 1H NMR data and FD-MS data of the synthesized compounds, and through the following data, syntheses of target compounds may be identified.

TABLE 2

| NO | $^1$H NMR (CDCl$_3$, 300 Mz) |
|---|---|
| 1 | 8.69 (2H, dd), 8.37-8.22 (6H, m), 8.14 (1H, dd), 7.97-7.83 (4H, m), 7.77-7.0 (3H, m), 7.60-7.46 (8H, m), 7.40-7.28 (3H, m), 7.19-7.08 (4H, m), 6.95 (1H, ddd) |
| 6 | 8.69 (2H, dd), 8.39-8.33 (4H, m), 8.27-8.23 (3H, m), 8.14 (1H, dd), 7.92-7.83 (2H, m), 7.78-7.69 (3H, m), 7.61-7.47 (8H, m), 7.41-7.28 (3H, m), 7.19-7.08 (4H, m), 6. 95 (2H, ddd) |
| 11 | 8.69 (4H, s), 8.39-8.31 (4H, m), 8.24 (1H, dd), 8.14 (1H, dd), 7.92-7.83 (3H, m), 7.77-7.69 (3H, m), 7.61-7.47 (6H, m), 7.41-7.28 (5H, m), 7.20-7.08 (4H, m), 6.95 (2H, ddd) |
| 12 | 8.69 (2H, dd), 8.37-8.22 (5H, m), 8.17-8.11 (2H, m), 7.92-7.70 (11H, m), 7.60-7.47 (5H, m), 7.41-7.28 (3H, m), 7.20-7.08 (4H, m), 6.95 (2H, ddd) |
| 15 | 8.69 (2H, dd), 8.56 (1H, dd), 8.28-8.22 (3H, m), 8.14 (1H, dd), 7.92-7.69 (8H, m), 7.65-7.08 (18H, m), 6.95 (2H, ddd) |
| 23 | 8.69 (2H, dd), 8.27-8.18 (6H, m), 7.92-7.84 (2H, m), 7.77-7.69 (5H, m), 7.61-7.08 (20H, m), 6.95 (2H, ddd) |
| 26 | 8.38-8.30 (4H, m), 8.27-8.21 (2H, m), 8.14 (1H, dd), 7.97-7.83 (5H, m), 7.77-7.68 (3H, m), 7.61-7.47 (8H, m), 7.41-7.28 (3H, m), 7.20-7.08 (4H, m), 6.95 (2H, ddd) |
| 31 | 8.41-8.33 (7H, m), 8.24 (1H, dd), 8.14 (1H, dd), 7.92-7.84 (2H, m), 7.78-7.69 (4H, m), 7.61-7.47 (8H, m), 7.41-7.28 (3H, m), 7.20-7.08 (4H, m), 6.95 (2H, ddd) |
| 36 | 8.72 (1H, dd), 8.40-8.21 (7H, m), 8.14 (1H, dd), 7.92-7.83 (3H, m), 7.77-7.69 (4H, m), 7.61-7.46 (6H, m), 7.41-7.28 (5H, m), 7.20-7.08 (4H, m), 6.95 (2H, ddd) |
| 42 | 8.39-8.30 (5H, m), 8.24 (1H, dd), 8.14 (1H, dd), 7.98 (1H, dd), 7.92-7.84 (2H, m), 7.78-7.69 (4H, m), 7.63-7.28 (14H, m), 7.20-7.08 (4H, m), 6.95 (2H, ddd) |
| 56 | 8.40-8.33 (5H, m), 8.28-8.15 (3H, m), 8.05 (1H, d), 7.92-7.86 (2H, m), 7.76-7.46 (12H, m), 7.41-7.28 (3H, m), 7.20-7.09 (4H, m), 6.95 (2H, ddd) |
| 62 | 8.38-8.07 (10H, m), 7.91-7.82 (5H, m), 7.76-7.47 (11H, m), 7.41-7.28 (3H, m), 7.20-7.09 (4H, m), 6.95 (2H, ddd) |
| 71 | 8.40-8.32 (3H, m), 8.27-8.17 (4H, m), 8.10-7.95 (3H, m), 7.93-7.86 (2H, m), 7.78-7.08 (17H, m), 7.19-7.08 (4H, m), 6.95 (2H, ddd) |
| 77 | 8.38-8.16 (9H, m), 8.11-8.05 (2H, m), 7.92-7.82 (3H, m), 7.78-7.28 (17H, m), 7.19-7.08 (4H, m), 6.95 (2H, ddd) |
| 91 | 8.39-8.32 (3H, m), 8.27-8.16 (3H, m), 8.12-8.05 (3H, m), 7.98 (1H, dd), 7.89 (1H, s), 7.76-7.08 (17H, m), 7.19-7.08 (4H, m), 6.95 (2H, ddd) |
| 93 | 8.55 (1H, dd), 8.45 (1H, dd), 8.38-8.32 (3H, m), 8.27-8.16 (3H, m), 8.13-8.05 (2H, m), 7.92-7.84 (2H, m), 7.76-7.46 (12H, m), 7.41-7.27 (4H, m), 7.20-7.08 (4H, m), 6.95 (2H, ddd) |
| 104 | 8.69 (2H, dd), 8.38-8.20 (6H, m), 8.14 (1H, dd), 7.97-7.83 (7H, m), 7.78-7.67 (3H, m), 7.57-7.28 (12H, m), 7.20-7.08 (4H, m), 6.95 (2H, ddd) |
| 105 | 8.69 (2H, dd), 8.35 (2H, ddd), 8.27-8.22 (2H, m), 8.14 (1H, dd), 7.97-7.82 (7H, m), 7.77-7.67 (4H, m), 7.60-7.27 (13H, m), 7.20-7.09 (4H, m), 6.95 (2H, ddd) |
| 111 | 8.69 (4H, s), 8.40-8.31 (4H, m), 8.24 (1H, dd), 8.14 (1H, dd), 7.88-7.84 (2H, m), 7.76-7.66 (3H, m), 7.60-7.27 (12H, m), 7.20-7.08 (4H, m), 6.95 (2H, ddd) |
| 124 | 8.69 (2H, dd), 8.55 (1H, dd), 8.27-8.11 (4H, m), 7.94-7.68 (9H, m), 7.61-7.27 (9H, m), 7.20-7.08 (6H, m), 6.95 (2H, ddd) |
| 134 | 8.39-8.22 (9H, m), 8.14 (1H, dd), 7.86 (1H, dd), 7.78-7.68 (4H, m), 7.64-7.28 (15H, m), 7.20-7.08 (4H, m), 6.95 (2H, ddd) |
| 146 | 8.39-8.31 (4H, m), 8.27-8.21 (2H, m), 8.17-8.05 (2H, m), 8.01-7.91 (2H, m), 7.86 (1H, dd), 7.78-7.68 (5H, m), 7.61-7.27 (13H, m), 7.20-7.08 (4H, m), 6.95 (2H, ddd) |
| 151 | 8.41-8.31 (3H, m), 8.27-8.16 (4H, m), 8.05 (1H, d), 7.96-7.87 (3H, m), 7.76-7.27 (16H, m), 7.19-7.10 (4H, m), 6.95 (2H, ddd) |
| 156 | 8.40-8.33 (5H, m), 8.27-8.16 (3H, m), 8.05 (1H, d) 7.90 (1H, dd), 7.76-7.27 (16H, m), 7.20-7.08 (4H, m), 6.95 (2H, ddd) |
| 161 | 8.76 (1H, dd), 8.40-8.16 (8H, m), 8.05 (1H, d), 7.86 (1H, dd), 7.77-7.28 (16H, m), 7.19-7.08 (4H, m), 6.95 (2H, ddd) |
| 168 | 8.55 (1H, dd), 8.45 (1H, dd), 8.41-8.33 (3H, m), 8.27-8.16 (3H, m), 8.05 (1H, d), 7.92-7.83 (2H, m), 7.76-7.28 (17H, m), 7.19-7.08 (4H, m), 6.95 (2H, ddd) |
| 179 | 8.38-8.15 (9H, m), 7.97-7.91 (3H, m), 7.85 (2H, dd), 7.78-7.28 (17H, m), 7.20-7.08 (4H, m), 6.95 (2H, ddd) |
| 183 | 8.41-8.33 (3H, m), 8.27-8.16 (3H, m), 8.12-8.05 (2H, m), 7.94 (1H, dd), 7.78-7.27 (20H, m), 7.20-7.09 (4H, m), 6.95 (2H, ddd) |
| 215 | 8.69 (2H, dd), 8.39-8.33 (4H, m), 8.28-8.22 (3H, m), 8.14 (1H, dd), 7.86 (1H, dd), 7.78-7.71 (2H, m), 7.61-7.47 (10H, m), 7.41-7.29 (3H, m), 7.19-7.10 (4H, m), 6.95 (2H, ddd) |
| 251 | 8.38-8.30 (4H, m), 8.27-8.20 (2H, m), 8.14 (1H, dd), 7.97-7.83 (5H, m), 7.78-7.66 (6H, m), 7.61-7.46 (8H, m), 7.41-7.30 (3H, m), 6.99-6.92 (4H, m) |
| 256 | 8.39-8.30 (7H, m), 8.24 (1H, dd), 8.14 (1H, dd), 7.92-7.83 (2H, m), 7.78-7.66 (6H, m), 7.60-7.47 (8H, m), 7.41-7.30 (3H, m), 6.99-6.93 (4H, m) |
| 266 | 8.39-8.30 (5H, m), 8.24 (1H, dd), 8.17-8.06 (2H, m), 7.98 (1H, dd), 7.92-7.84 (2H, m), 7.78-7.28 (19H, m), 6.99-6.93 (4H, m) |
| 268 | 8.55 (1H, dd), 8.48-8.30 (6H, m), 8.24 (1H, dd), 8.14 (1H, dd), 7.92-7.83 (3H, m), 7.78-7.47 (14H, m), 7.41-7.28 (4H, m), 6.99-6.93 (4H, m) |
| 279 | 8.38-8.16 (9H, m), 8.11 (1H, d), 7.98-7.82 (5H, m), 7.78-7.46 (15H, m), 7.41-7.30 (3H, m), 6.99-6.92 (4H, m) |
| 284 | 8.39-8.33 (4H, m), 8.28-8.16 (6H, m), 8.11 (1H, d), 7.89 (1H, s), 7.78-7.46 (15H, m), 7.40-7.22 (5H, m), 7.00-6.92 (4H, m) |
| 288 | 8.29-8.15 (8H, m), 8.14-8.05 (5H, m), 7.89 (1H, s), 7.78-7.46 (15H, m), 7.41-7.30 (3H, m), 6.99-6.92 (4H, m) |
| 307 | 8.39-8.32 (3H, m), 8.28-8.15 (5H, m), 8.11-8.05 (2H, m), 7.89 (1H, s), 7.77-7.22 (21H, m), 7.01-6.93 (4H, m) |
| 324 | 8.55 (1H, dd), 8.41 (1H, d), 8.27-16 (5H, m), 7.98-7.85 (5H, m), 7.75-7.30 (15H, m), 7.18-7.08 (2H, m), 6.99-6.92 (4H, m) |
| 336 | 8.69 (1H, s), 8.39-8.31 (4H, m), 8.24 (1H, dd), 8.14 (1H, dd), 7.89-7.83 (2H, m), 7.65 (5H, m), 7.61-7.30 (12H, m), 7.00-6.92 (4H, m) |
| 337 | 8.69 (2H, dd), 8.38-8.21 (5H, m), 8.17-8.10 (2H, m), 7.89-7.65 (12H, m), 7.61-7.31 (10H, m), 7.00-6.92 (4H, m) |
| 351 | 8.38-8.30 (4H, m), 8.27-8.21 (2H, m), 8.27-8.20 (2H, m), 8.14 (1H, dd), 7.97-7.83 (4H, m), 7.78-7.65 (6H, m), 7.61-7.31 (12H, m), 7.01-6.94 (4H, m) |
| 356 | 8.39-8.29 (7H, m), 8.24 (1H, dd), 8.14 (1H, dd), 7.86 (1H, dd), 7.78-7.67 (5H, m), 7.61-7.30 (12H, m), 6.99-6.92 (4H, m) |
| 366 | 8.41-8.30 (5H, m), 8.24 (1H, dd), 8.16-8.05 (2H, m), 7.98 (1H, dd), 7.86 (1H, dd), 7.79-7.28 (20H, m), 7.01-6.93 (4H, m) |
| 423 | 8.41 (1H, d), 8.27-8.16 (7H, m), 7.94 (1H, d), 7.78-7.22 (26H, m), 6.99-6.92 (4H, m) |
| 461 | 8.39-8.32 (3H, m), 8.27-8.16 (4H, m), 8. 11-8.05 (2H, m), 7.97-7.86 (3H, m), 7.76-7.46 (12H, m), 7.38 (1H, ddd), 7.27-6.97 (11H, m), 6.89 (2H, ddd) |
| 547 | 9.27 (1H, d), 8.79 (1H, dd), 8.69 (2H, dd), 8.40-8.22 (5H, m), 8.14 (1H, dd), 7.91-7.49 (14H, m), 7.41-7.28 (3H, m), 7.20-7.08 (4H, m), 6.95 (2H, ddd) |
| 548 | 9.27 (1H, d), 8.79 (1H, dd), 8.39-8.08 (9H, m), 7.97-7.86 (2H, m), 7.78-7.47 (15H, m), 7.41-7.27 (3H, m), 7.19-7.08 (4H, m), 6.95 (2H, ddd) |

TABLE 3

| Compound | FD-MS | Compound | FD-MS |
| --- | --- | --- | --- |
| 1 | m/z = 739.88 (C54H33N3O = 739.26) | 6 | m/z = 740.87 (C53H32N4O = 740.26) |
| 11 | m/z = 763.90 (C56H33N3O = 763.26) | 12 | m/z = 789.94 (C58H35N3O = 789.28) |
| 15 | m/z = 777.93 (C57H35N3O = 777.28) | 23 | m/z = 838.02 (C64H39NO = 837.30) |
| 26 | m/z = 739.88 (C54H33N3O = 739.26) | 31 | m/z = 740.87 (C53H32N4O = 740.26) |
| 36 | m/z = 763.90 (C56H33N3O = 763.26) | 42 | m/z = 830.95 (C59H34N4O2 = 830.27) |
| 56 | m/z = 740.87 (C53H32N4O = 740.87) | 62 | m/z = 789.94 (C58H35N3O = 789.28) |
| 71 | m/z = 829.96 (C60H35N3O2 = 829.27) | 77 | m/z = 815.98 (C60H37N3O = 815.29) |
| 91 | m/z = 830.95 (C59H34N4O2 = 830.27) | 93 | m/z = 847.01 (C59H34N4OS = 846.25) |
| 104 | m/z = 815.98 (C60H37N3O = 815.29) | 105 | m/z = 815.98 (C60H37N3O = 815.29) |
| 111 | m/z = 763.90 (C56H33N3O = 763.26) | 124 | m/z = 775.91 (C60H37N3O = 775.26) |
| 134 | m/z = 816.96 (C59H36N4O = 816.29) | 146 | m/z = 829.96 (C60H35N3O2 = 829.27) |
| 151 | m/z = 739.88 (C54H33N3O = 739.26) | 156 | m/z = 740.87 (C53H32N4O = 740.26) |
| 161 | m/z = 763.90 (C56H33N3O = 763.26) | 168 | m/z = 847.01 (C59H34N4OS = 846.25) |
| 179 | m/z = 815.98 (C60H37N3O = 815.29) | 183 | m/z = 816.96 (C59H36N4O = 816.29) |
| 215 | m/z = 740.87 (C53H32NO = 740.26) | 251 | m/z = 755.94 (C54H33N3S = 755.24) |
| 256 | m/z = 756.93 (C53H32N4S = 756.23) | 266 | m/z = 847.01 (C59H34N4OS = 846.25) |
| 268 | m/z = 863.07 (C59H34N4S2 = 862.22) | 279 | m/z = 832.04 (C60H37N3S = 831.27) |
| 284 | m/z = 833.03 (C59H36N4S = 833.27) | 288 | m/z = 801.94 (C56H36NOPS = 801.23) |
| 307 | m/z = 833.03 (C59H36N4S = 832.27) | 324 | m/z = 791.97 (C57H33N3S = 791.24) |
| 336 | m/z = 779.96 (C56H33N3S = 779.24) | 337 | m/z = 806.00 (C58H35N3S = 805.26) |
| 351 | m/z = 755.24 (C54H33N3S = 755.94) | 356 | m/z = 756.93 (C53H32N4S = 756.23) |
| 366 | m/z = 847.01 (C59H34N4OS = 846.25) | 389 | m/z = 833.03 (C59H36N4S = 832.27) |
| 423 | m/z = 854.08 (C64H39NS = 853.28) | 461 | m/z = 814.99 (C60H38N4 = 814.31) |
| 547 | m/z = 735.89 (C56H33NO = 735.26) | 548 | m/z = 811.98 (C62H37NO = 811.29) |

<Experimental Example 1> Manufacture of Organic Light Emitting Device

1) Manufacture of Organic Light Emitting Device

Comparative Examples 1-1, 1-2 and Examples 1 to 41

A transparent indium tin oxide (ITO) electrode thin film obtained from glass for an organic light emitting device (OLED) (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4',4''-tris(N,N-(2-naphthyl)-phenylamino)triphenylamine (2-TNATA) was introduced to a cell in the vacuum deposition apparatus.

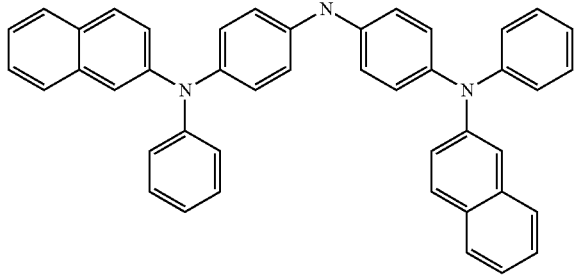

2-TNATA

Subsequently, the chamber was evacuated until the degree of vacuum therein reached 10⁻⁶ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

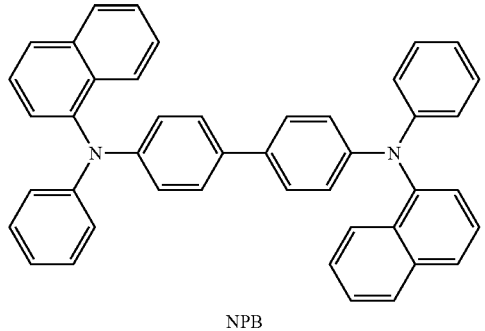

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

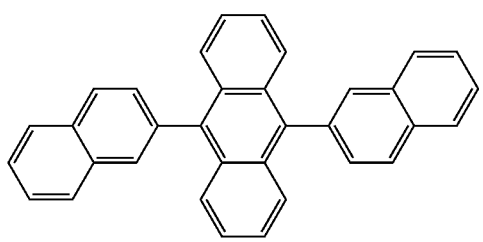

H1

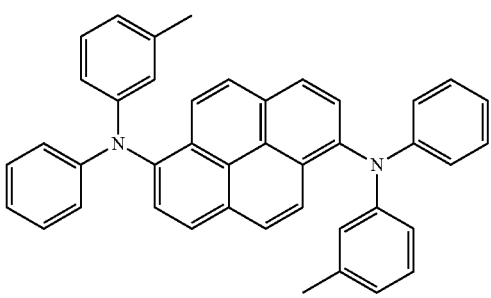

D1

Subsequently, a compound presented in the following Table and LiQ were deposited in a weight ratio of 2:1 to a thickness of 300 Å to form an electron transfer layer.

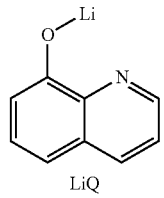

LiQ

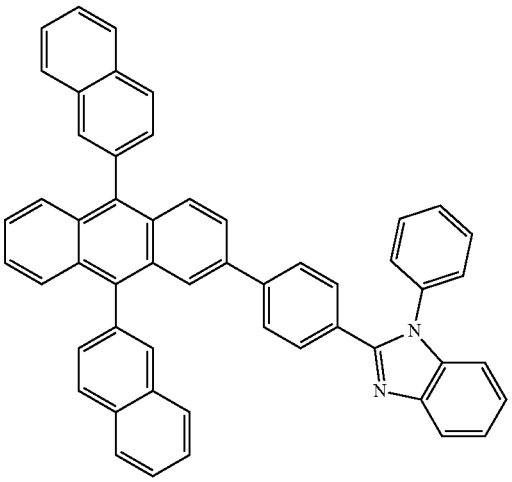

E1

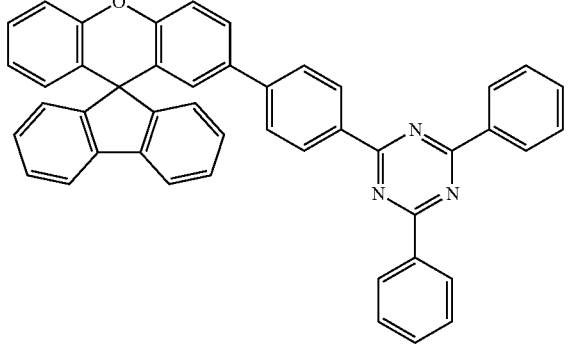

E2

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under 10⁻⁶ torr to 10⁻⁸ torr by each material to be used in the OLED manufacture.

2) Driving Voltage and Light Emission Efficiency of Organic Light Emitting Device For the organic light emitting devices manufactured as above, electroluminescent (EL) properties were measured using M7000 manufactured by McScience Inc., and with the measurement results, $T_{95}$ when standard luminance was 700 cd/m² was measured using a lifetime measurement system (M6000) manufactured by McScience Inc. Results of measuring driving voltage, light emission efficiency, color coordinate (CIE) and lifetime of the blue organic light emitting devices manufactured according to the present disclosure are as shown in the following Table 4.

TABLE 4

| | Compound | Driving Voltage (V) | Light Emission Efficiency (cd/A) | CIE (x, y) | Lifetime ($T_{95}$) |
|---|---|---|---|---|---|
| Example 1 | 1 | 5.11 | 7.11 | (0.134, 0.101) | 87 |
| Example 2 | 6 | 4.96 | 6.84 | (0.134, 0.102) | 91 |
| Example 3 | 12 | 5.14 | 6.79 | (0.134, 0.101) | 61 |
| Example 4 | 15 | 4.99 | 6.88 | (0.134, 0.103) | 62 |
| Example 5 | 23 | 5.45 | 6.12 | (0.134, 0.102) | 65 |
| Example 6 | 26 | 5.43 | 6.49 | (0.134, 0.101) | 61 |
| Example 7 | 31 | 5.72 | 6.92 | (0.134, 0.102) | 59 |
| Example 8 | 42 | 5.32 | 6.33 | (0.134, 0.101) | 59 |
| Example 9 | 56 | 5.40 | 6.13 | (0.134, 0.101) | 62 |
| Example 10 | 62 | 5.30 | 6.72 | (0.134, 0.100) | 67 |
| Example 11 | 71 | 5.37 | 6.35 | (0.134, 0.101) | 54 |
| Example 12 | 77 | 5.38 | 6.41 | (0.134, 0.100) | 55 |
| Example 13 | 91 | 5.27 | 6.42 | (0.134, 0.100) | 60 |
| Example 14 | 93 | 5.48 | 6.21 | (0.134, 0.100) | 59 |
| Example 15 | 104 | 4.72 | 7.39 | (0.134, 0.100) | 59 |
| Example 16 | 105 | 5.45 | 6.68 | (0.134, 0.100) | 61 |
| Example 17 | 124 | 5.22 | 6.28 | (0.134, 0.102) | 44 |
| Example 18 | 134 | 5.12 | 6.20 | (0.134, 0.101) | 58 |
| Example 19 | 146 | 5.09 | 6.77 | (0.134, 0.102) | 61 |
| Example 20 | 151 | 5.42 | 6.88 | (0.134, 0.100) | 63 |
| Example 21 | 156 | 5.21 | 5.45 | (0.134, 0.103) | 59 |
| Example 22 | 168 | 5.38 | 6.66 | (0.134, 0.100) | 62 |
| Example 23 | 179 | 5.40 | 6.36 | (0.134, 0.100) | 63 |
| Example 24 | 183 | 5.56 | 5.91 | (0.134, 0.100) | 58 |
| Example 25 | 215 | 5.19 | 7.15 | (0.134, 0.100) | 82 |
| Example 26 | 251 | 5.42 | 6.88 | (0.134, 0.100) | 62 |
| Example 27 | 256 | 5.42 | 6.56 | (0.134, 0.102) | 65 |
| Example 28 | 266 | 5.46 | 6.81 | (0.134, 0.101) | 62 |
| Example 29 | 268 | 5.30 | 6.72 | (0.134, 0.102) | 63 |
| Example 30 | 279 | 5.37 | 6.35 | (0.134, 0.100) | 58 |
| Example 31 | 284 | 5.42 | 6.34 | (0.134, 0.100) | 59 |
| Example 32 | 288 | 5.49 | 6.68 | (0.134, 0.100) | 63 |
| Example 33 | 307 | 5.42 | 6.77 | (0.134, 0.100) | 62 |
| Example 34 | 324 | 5.56 | 6.18 | (0.134, 0.100) | 45 |
| Example 35 | 337 | 5.12 | 6.20 | (0.134, 0.100) | 59 |
| Example 36 | 351 | 5.09 | 6.97 | (0.134, 0.100) | 64 |
| Example 37 | 356 | 5.41 | 6.76 | (0.134, 0.100) | 60 |
| Example 38 | 366 | 5.21 | 5.45 | (0.134, 0.100) | 56 |
| Example 39 | 389 | 5.42 | 6.88 | (0.134, 0.102) | 56 |
| Example 40 | 423 | 4.96 | 6.84 | (0.134, 0.101) | 57 |
| Example 41 | 461 | 5.14 | 6.79 | (0.134, 0.102) | 57 |
| Comparative Example 1-1 | E1 | 5.69 | 6.11 | (0.134, 0.100) | 52 |
| Comparative Example 1-2 | E2 | 5.62 | 6.07 | (0.134, 0.101) | 55 |

As seen from the results of Table 4, the organic light emitting device using the electron transfer layer material of the blue organic light emitting device of the present disclosure had lower driving voltage and significantly improved light emission efficiency and lifetime compared to the Comparative Examples 1-1 and 1-2. Particularly, it was identified that Compounds 1, 6, 215 and 284 were superior in all aspects of driving voltage, light emission efficiency and lifetime. It was identified that the organic light emitting device had a lowered driving voltage, and enhanced light emission efficiency and lifetime compared to Comparative Example 1-2 by, due to the heteroring formed in the spirofluorene structure, having an enhanced electron transfer ability and thereby having an improved balance between electrons and holes in the light emitting layer.

Such a result is considered to be due to the fact that, when using the disclosed compound having proper length and strength, and flatness as an electron transfer layer, a compound in an excited state is made by receiving electrons under a specific condition, and particularly when a hetero-skeleton site of the compound is formed in an excited state, excited energy moves to a stable state before the excited hetero-skeleton site goes through other reactions, and a relatively stabilized compound is capable of efficiently transferring electrons without the compound being decomposed or destroyed. For reference, compounds that are stable when excited are considered to be aryl or acene-based compounds or polycyclic hetero-compounds. Accordingly, it is considered that excellent results in all aspects of driving, efficiency and lifetime were obtained by the compound of the present disclosure enhancing enhanced electron-transfer properties or improved stability.

<Experimental Example 2> Manufacture of Organic Light Emitting Device

1) Manufacture of Organic Light Emitting Device

Comparative Example 2

A transparent indium tin oxide (ITO) electrode thin film obtained from glass for an organic light emitting device (OLED) (manufactured by Samsung-Corning Co., Ltd.) was ultrasonic cleaned using trichloroethylene, acetone, ethanol and distilled water consecutively for 5 minutes each, stored in isopropanol, and used.

Next, an ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

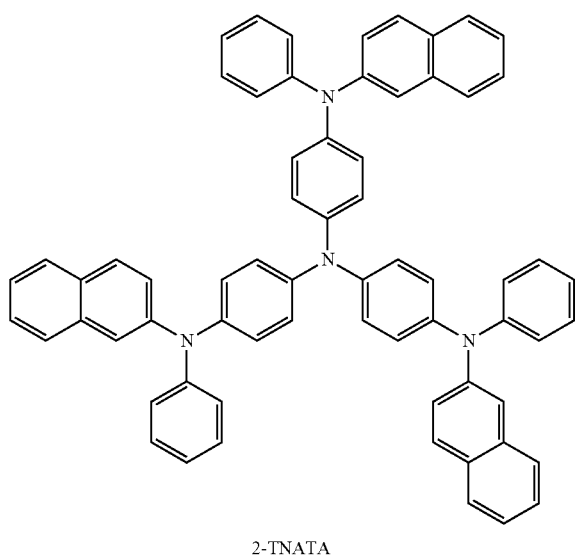

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell of the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

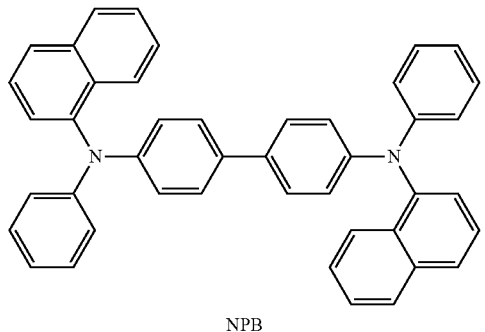

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

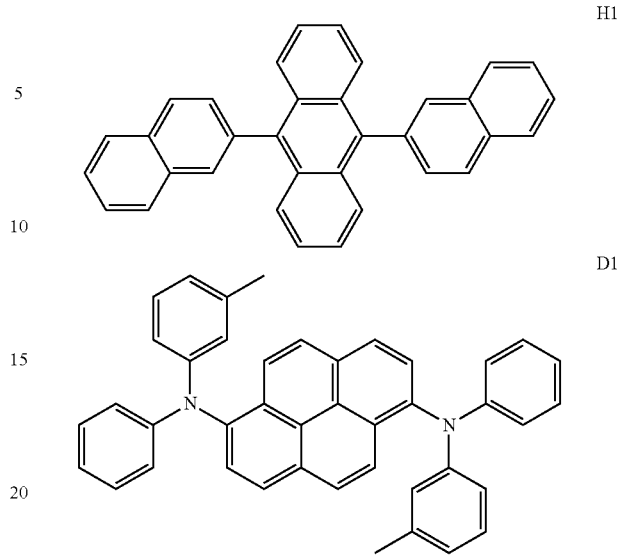

Subsequently, the following structural formula E1 and LiQ were deposited in a weight ratio of 2:1 to a thickness of 300 Å to form an electron transfer layer.

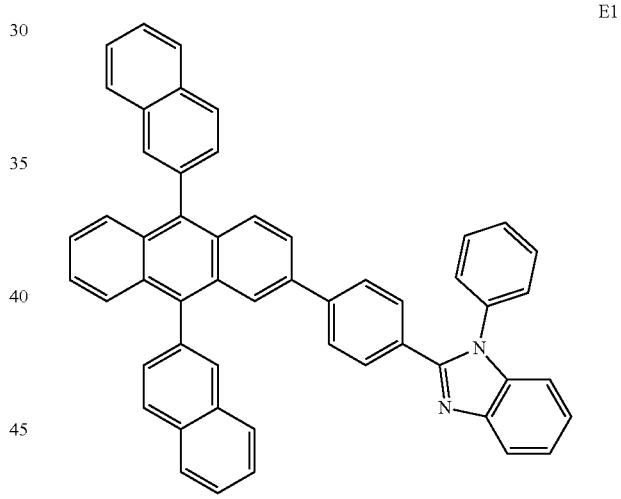

As an electron injection layer, lithium fluoride (LiF) was deposited to a thickness of 10 Å, and an Al cathode was employed to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Examples 42 to 45

Organic light emitting devices were manufactured in the same manner as in Comparative Example 2 except that the electron transfer layer E1 was formed to a thickness of 250 Å, and then a hole blocking layer was formed on the electron transfer layer using a compound presented in the following Table 5 to a thickness of 50 Å.

Results of measuring driving voltage, light emission efficiency, color coordinate (CIE) and lifetime of the blue organic light emitting devices manufactured according to the present disclosure are as shown in the following Table 5.

TABLE 5

| Compound | Driving Voltage (V) | Light Emission Efficiency (cd/A) | CIE (x, y) | Lifetime ($T_{95}$) |
|---|---|---|---|---|
| Example 42 | 23 | 4.87 | 6.27 | (0.134, 0.101) | 90 |
| Example 43 | 423 | 4.73 | 6.57 | (0.134, 0.102) | 92 |
| Example 44 | 547 | 5.11 | 6.55 | (0.134, 0.101) | 95 |
| Example 45 | 548 | 4.87 | 6.53 | (0.134, 0.103) | 89 |
| Comparative Example 2 | — | 5.50 | 5.57 | (0.134, 0.100) | 50 |

As seen from the results of Table 5, the organic light emitting device using the hole blocking layer material of the blue organic light emitting device of the present disclosure had lower driving voltage and significantly improved light emission efficiency and lifetime compared to Comparative Example 2.

<Experimental Example 3> Manufacture of Organic Light Emitting Device

1) Manufacture of Organic Light Emitting Device

Comparative Example 3 and Examples 46 to 51

A transparent indium tin oxide (ITO) electrode thin film obtained from glass for an organic light emitting device (OLED) (manufactured by Samsung-Corning Co., Ltd.) was ultrasonic cleaned using trichloroethylene, acetone, ethanol and distilled water consecutively for 5 minutes each, stored in isopropanol, and used.

On the transparent ITO electrode (anode), organic materials were formed in a 2-stack white organic light emitting device (WOLED) structure. As for the first stack, TAPC was thermal vacuum deposited first to a thickness of 300 Å to form a hole transfer layer. After forming the hole transfer layer, a light emitting layer was thermal vacuum deposited thereon as follows. As the light emitting layer, TCz1, a host, was 8% doped with FIrpic, a blue phosphorescent dopant, and deposited to 300 Å. After forming an electron transfer layer to 400 Å using TmPyPB, the compound described in the following Table 6 was 20% doped with $Cs_2CO_3$ to form a charge generation layer to 100 Å.

As for the second stack, $MoO_3$ was thermal vacuum deposited first to a thickness of 50 Å to form a hole injection layer. A hole transfer layer, a common layer, was formed to 100 Å by 20% doping $MoO_3$ to TAPC and then depositing TAPC to 300 Å. A light emitting layer was formed by 8% doping Ir(ppy)$_3$, a green phosphorescent dopant, to TCz1, a host, and depositing the result to 300 Å, and then an electron transfer layer was formed to 600 Å using TmPyPB. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic light emitting device was manufactured.

Meanwhile, all the organic compounds required to manufacture the OLED were vacuum sublimation purified under $10^{-6}$ torr to $10^{-8}$ torr for each material to be used in the OLED manufacture.

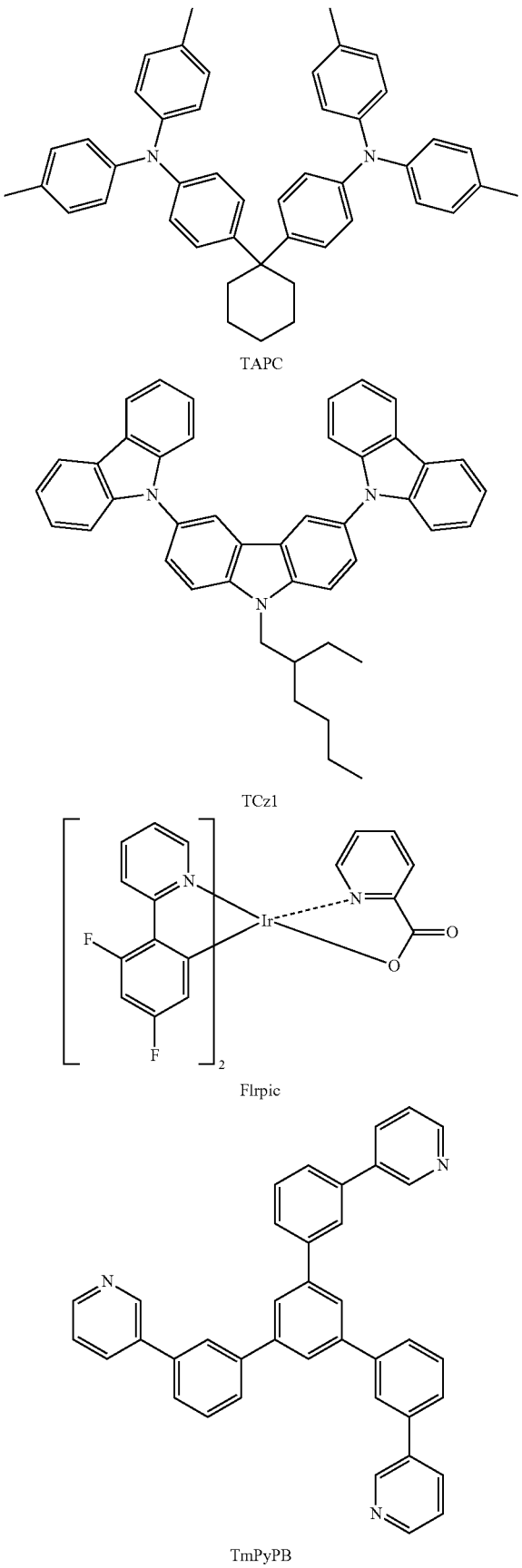

TAPC

TCz1

FIrpic

TmPyPB

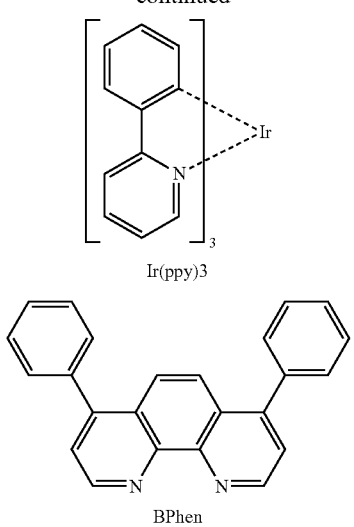

Ir(ppy)3

BPhen

Results of measuring driving voltage, light emission efficiency, color coordinate (CIE) and lifetime of the white organic light emitting devices manufactured according to the present disclosure are as shown in the following Table 6.

TABLE 6

| Compound | Driving Voltage (V) | Light Emission Efficiency (cd/A) | CIE (x, y) | Lifetime ($T_{95}$) |
|---|---|---|---|---|
| Example 46 | 11 | 6.78 | 58.24 | (0.213, 0.430) | 48 |
| Example 47 | 36 | 6.84 | 60.44 | (0.212, 0.421) | 42 |
| Example 48 | 111 | 6.44 | 66.32 | (0.211, 0.433) | 49 |
| Example 49 | 161 | 6.92 | 59.68 | (0.214, 0.439) | 52 |
| Example 50 | 336 | 6.27 | 67.99 | (0.212, 0.424) | 53 |
| Example 51 | 389 | 6.82 | 59.18 | (0.214, 0.437) | 48 |

As seen from the results of Table 6, the organic light emitting device using the charge generation layer material of the 2-stack white organic light emitting device of the present disclosure had lower driving voltage and improved light emission efficiency compared to Comparative Example 3. Such a result is considered to be due to the fact that the compound of the present disclosure used as an N-type charge generation layer formed with the disclosed skeleton having proper length and strength, and flatness and a proper hetero-compound capable of binding to metals forms a gap state in the N-type charge generation layer by doping an alkali metal or an alkaline earth metal, and electrons produced from a P-type charge generation layer are readily injected into an electron transfer layer through the gap state produced in the N-type charge generation layer. Accordingly, the P-type charge generation layer may favorably inject and transfer electrons to the N-type charge generation layer, and as a result, driving voltage was lowered, and light emission efficiency and lifetime were improved in the organic light emitting device.

The invention claimed is:
1. A heterocyclic compound represented by the following Chemical Formula 1:

[Chemical Formula 1]

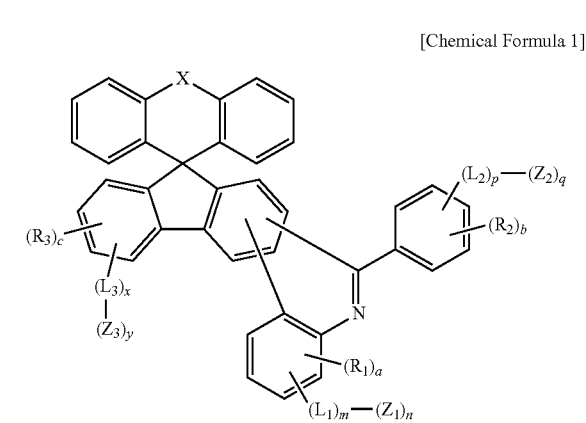

wherein, in Chemical Formula 1,
X is O; S; or $NR_{21}$;
$L_1$ to $L_3$ are the same as or different from each other, and each independently a direct bond; a substituted or unsubstituted arylene group; or a substituted or unsubstituted heteroarylene group;
$Z_1$ to $Z_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group;
$R_1$ to $R_3$ are the same as or different from each other, and each independently selected from the group consisting of hydrogen; deuterium; a halogen group; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring;
$R_{21}$ is hydrogen; or a substituted or unsubstituted aryl group,
m, p, x, n, q and y are each an integer of 1 to 5;
a is an integer of 1 to 3;
b is an integer of 1 to 4;
c is an integer of 1 to 3; and
when m, p, x, n, q, y, a, b and c are an integer of 2 or greater, substituents in the parentheses are the same as or different from each other,
a substituted group is a group having a substitution in which a hydrogen atom bonded to a carbon atom of a compound is changed to at least one substituent, a position of substitution of the at least one substituent is a position at which the hydrogen atom is substituted, and, when two or more substituents substitute, the two or more substituents are the same as or different from each other, an unsubstituted group is a group having no substitution, the at least one substituent being one or more selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R''; —P(=O)RR'; C1 to C20 alkylamine; C6 to C60 monocyclic or polycyclic arylamine; and C2 to C60 monocyclic or polycyclic heteroarylamine, or a substituent linking two or more substituents among the at least one substituent, and R, R' and R'' are the same as or different from each other, and each independently hydrogen; deuterium; a cyano group; a substituted or unsubstituted alkyl group; a substituted or unsubstituted cycloalkyl group; a substituted or unsubstituted aryl group; or a substituted or unsubstituted heteroaryl group.

2. The heterocyclic compound of claim 1, wherein Chemical Formula 1 is represented by one of the following Chemical Formulae 2 to 5:

[Chemical Formula 2]

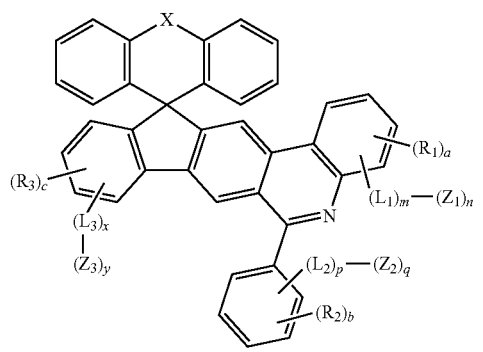

[Chemical Formula 3]

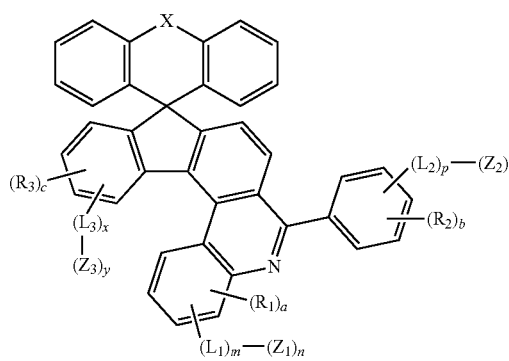

[Chemical Formula 4]

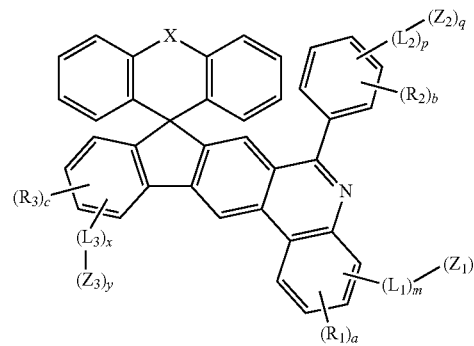

[Chemical Formula 5]

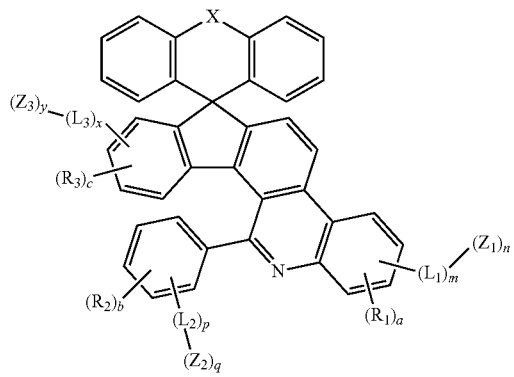

in Chemical Formula 2 to Chemical Formula 5, each substituent has the same definition as in Chemical Formula 1.

3. The heterocyclic compound of claim 1, wherein Chemical Formula 1 is represented by one of the following Chemical Formulae 6 to 8:

[Chemical Formula 6]

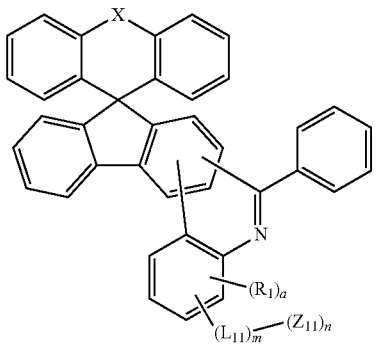

[Chemical Formula 7]

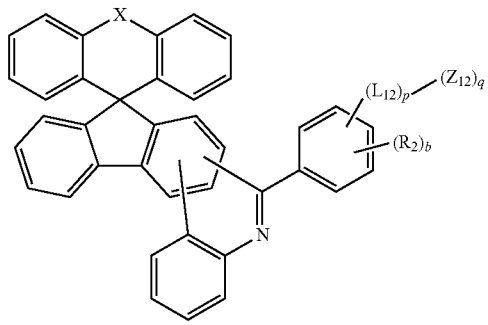

[Chemical Formula 8]

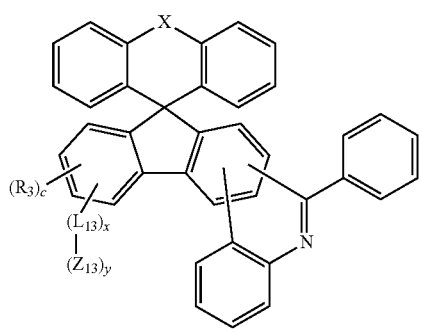

in Chemical Formulae 6 to 8,

X, $R_1$ to $R_3$, m, p, x, n, q, y, a, b and c have the same definitions as in Chemical Formula 1;

$L_{11}$ to $L_{13}$ are the same as or different from each other, and each independently a direct bond; a substituted or unsubstituted arylene group; or a substituted or unsubstituted heteroarylene group; and $Z_{11}$ to $Z_{13}$ are the same as or different from each other, and each independently selected from the group consisting of a cyano group; a substituted or unsubstituted aryl group; a substituted or unsubstituted heteroaryl group; and a substituted or unsubstituted phosphine oxide group.

4. The heterocyclic compound of claim 1, wherein $R_1$ to $R_3$ are hydrogen.

5. The heterocyclic compound of claim 1, wherein $Z_1$ to $Z_3$ are the same as or different from each other, and each independently hydrogen; deuterium; a cyano group; a substituted or unsubstituted C6 to C40 aryl group; a substituted or unsubstituted C2 to C40 heteroaryl group; or a substituted or unsubstituted phosphine oxide group.

6. The heterocyclic compound of claim 1, wherein Chemical Formula 1 is represented by any one of the following compounds:

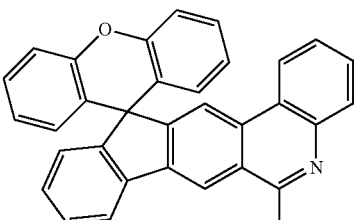
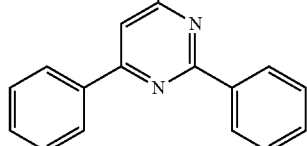

1

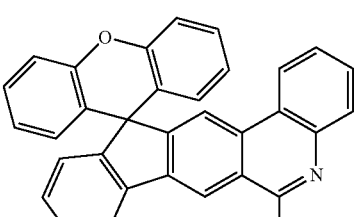
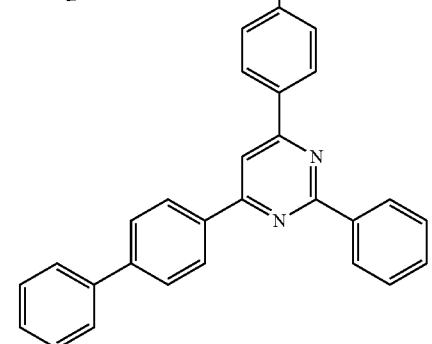

2

341
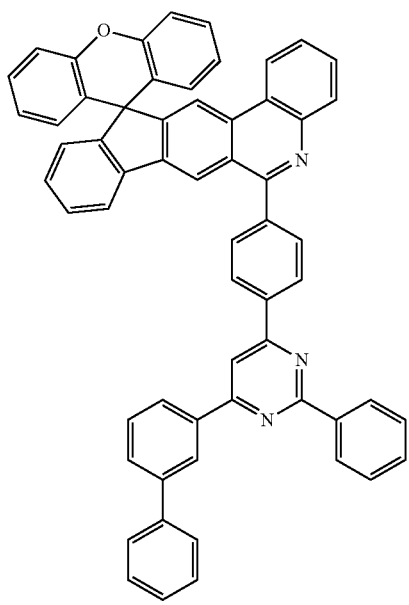
342
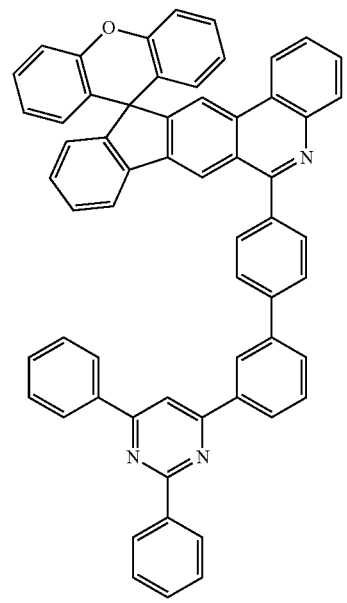

343
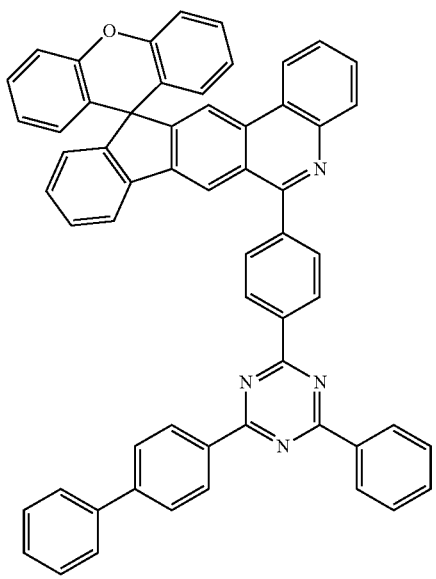
344
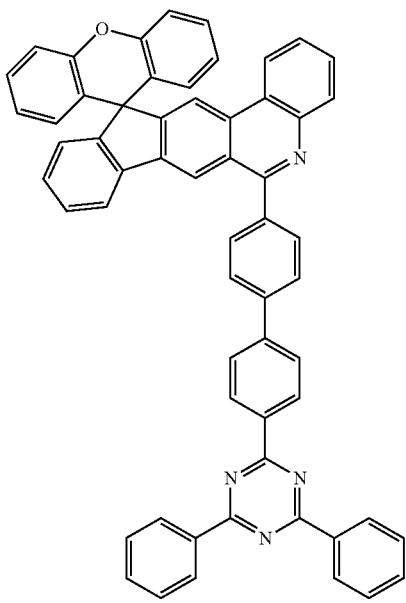
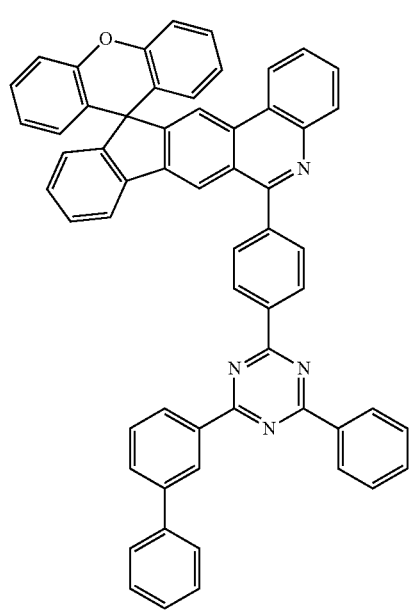
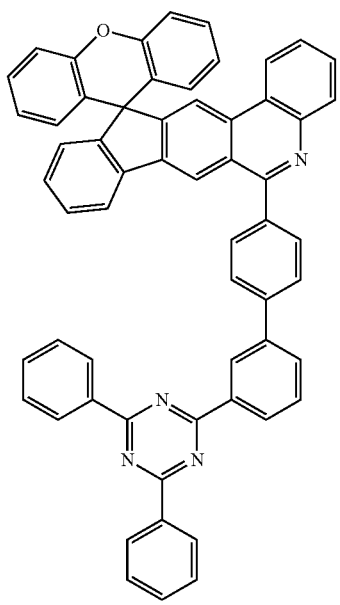

345
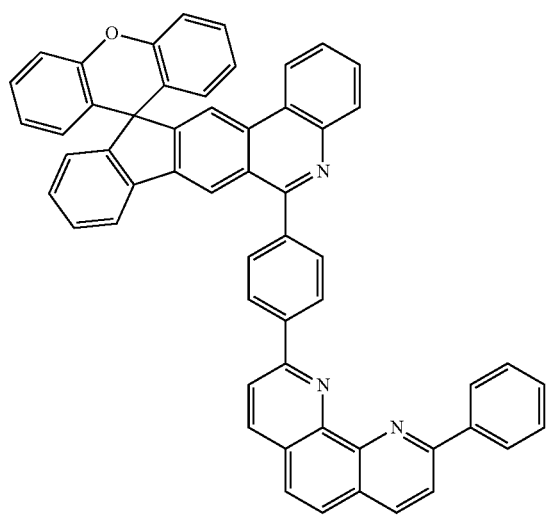 [SMILES: c1ccc(-c2ccc3ccc4ccc(-c5ccc(-c6nc7ccccc7c7cc8c(cc67)-c6ccccc6C86c7ccccc7Oc7ccccc76)cc5)nc4c3n2)cc1]
346
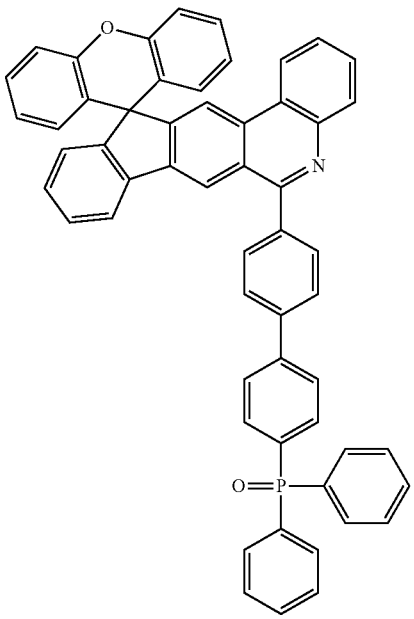
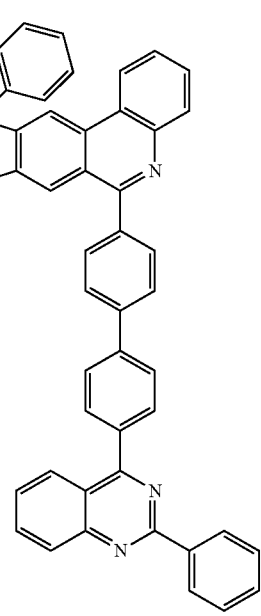
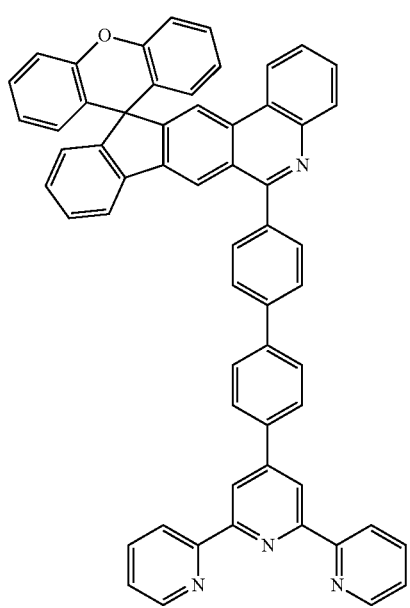 [SMILES: c1ccc(-c2nc(-c3ccc(-c4ccc(-c5nc6ccccc6c6cc7c(cc56)-c5ccccc5C75c6ccccc6Oc6ccccc65)cc4)cc3)c3ccccc3n2)cc1]

347
-continued
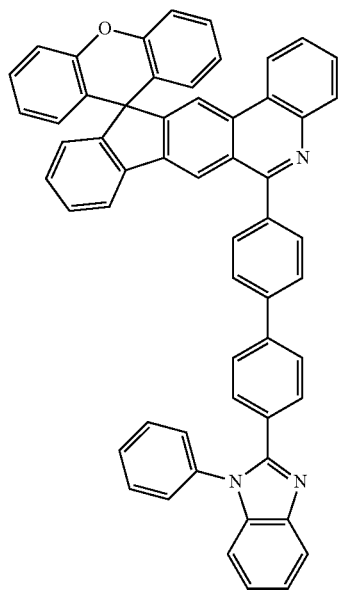 [SMILES: c1ccc(-n2c(-c3ccc(-c4ccc(-c5nc6ccccc6c6cc7c(cc56)-c5ccccc5C75c6ccccc6Oc6ccccc65)cc4)cc3)nc3ccccc32)cc1]
15
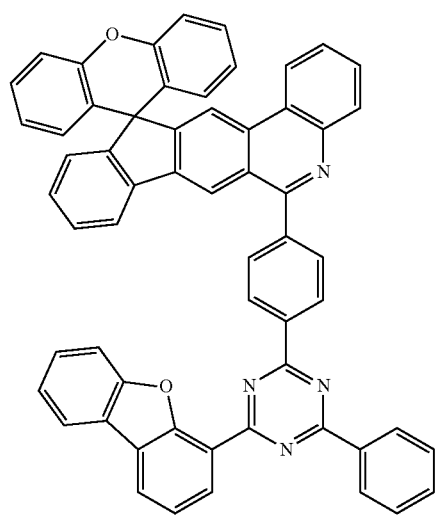
16
348
-continued
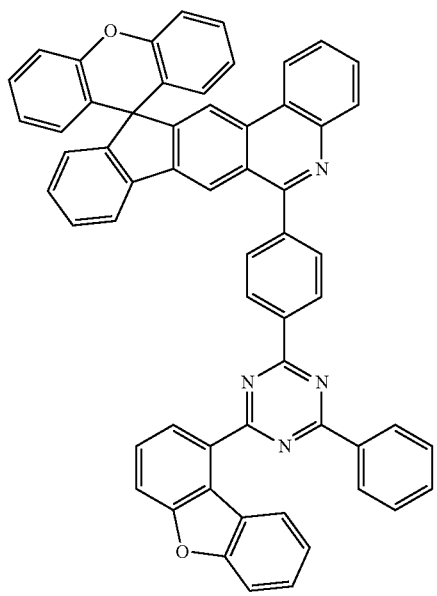
17
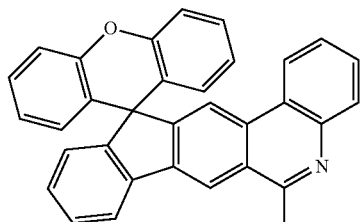
18
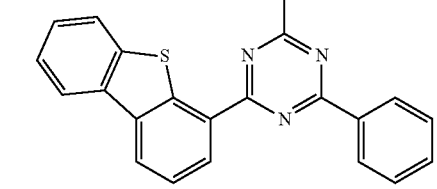
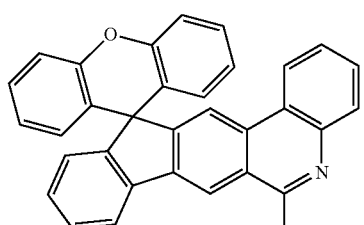
19
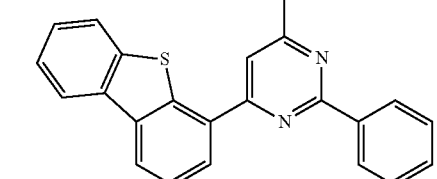

349
-continued
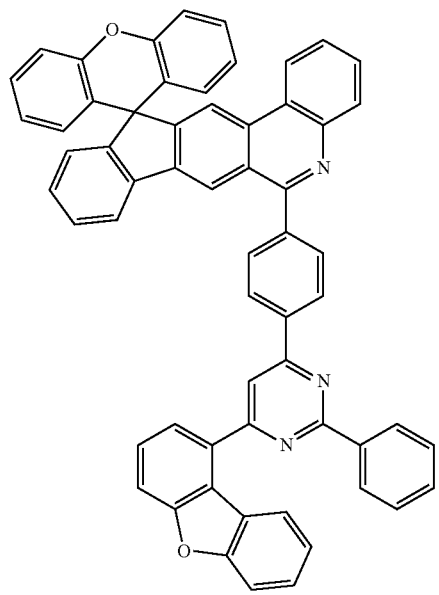
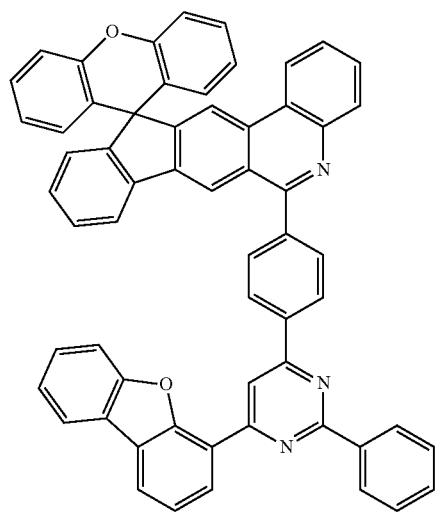
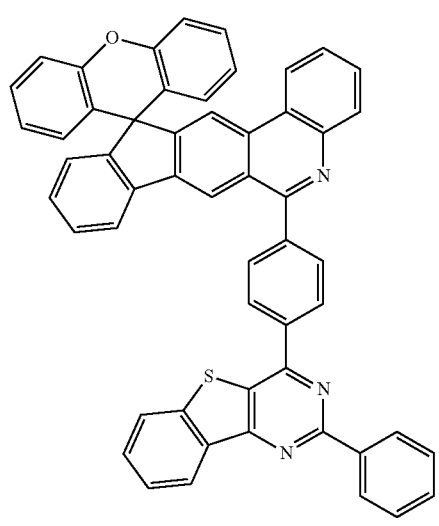
350
-continued
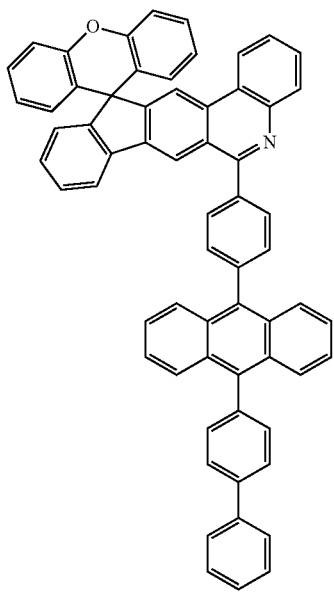 [SMILES: c1ccc(-c2ccc(-c3c4ccccc4c(-c4ccc(-c5nc6ccccc6c6cc7c(cc56)-c5ccccc5C75c6ccccc6Oc6ccccc65)cc4)c4ccccc34)cc2)cc1]
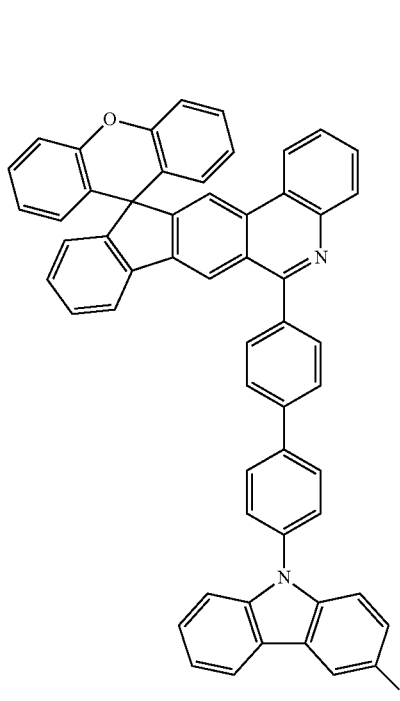

351
-continued
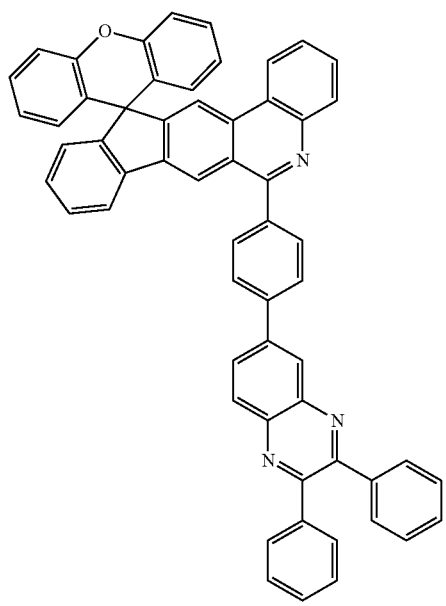
25
352
-continued
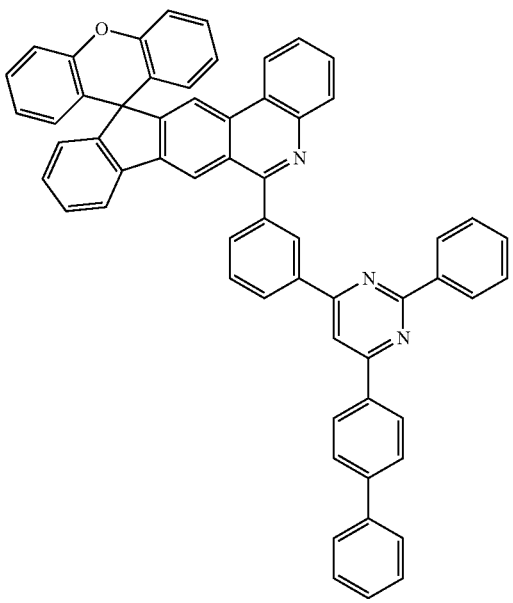
27
26
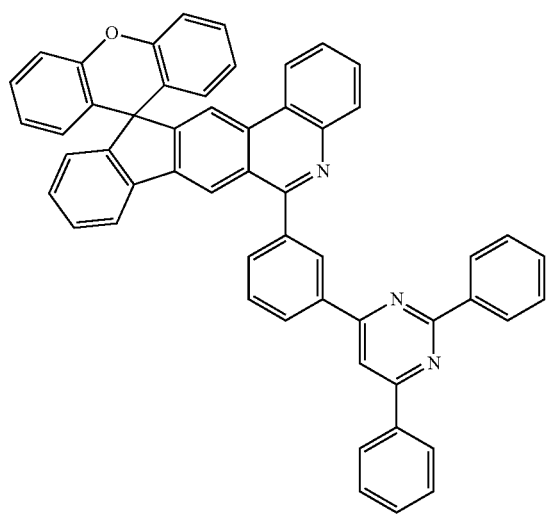 [SMILES: c1ccc(-c2cc(-c3cccc(-c4nc5ccccc5c5cc6c(cc45)-c4ccccc4C64c5ccccc5Oc5ccccc54)c3)nc(-c3ccccc3)n2)cc1]
28
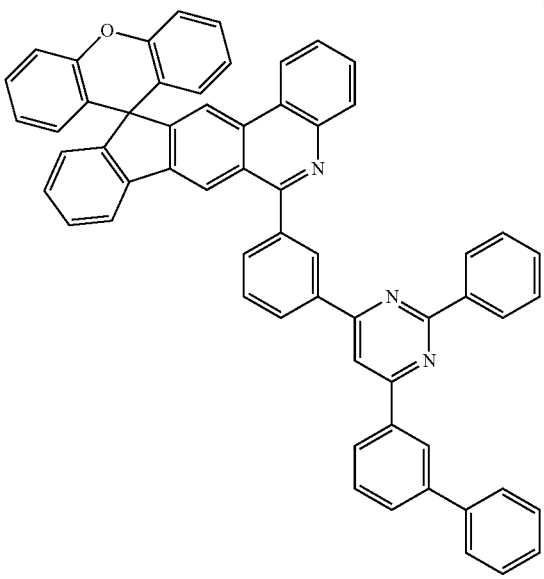

29
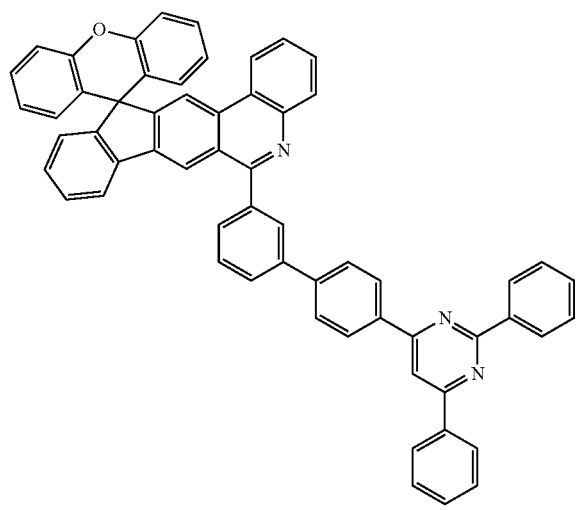
30
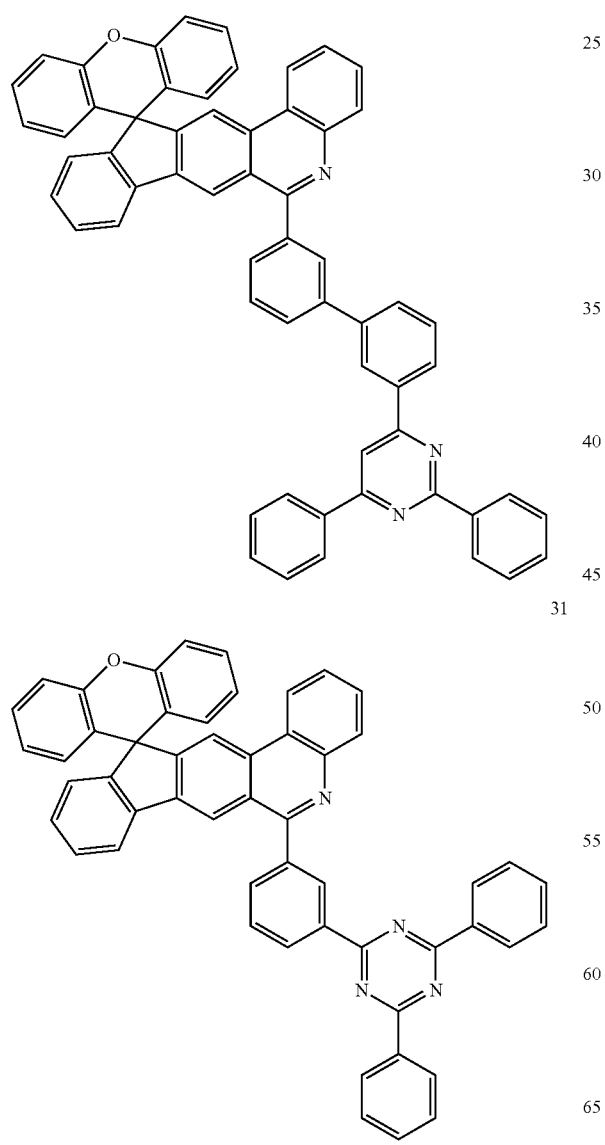
32
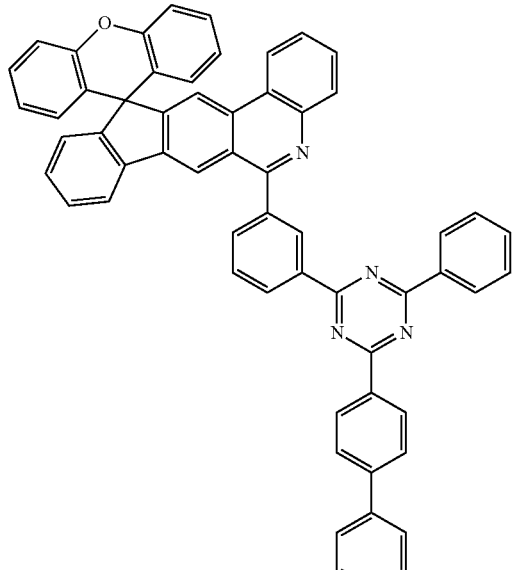
33
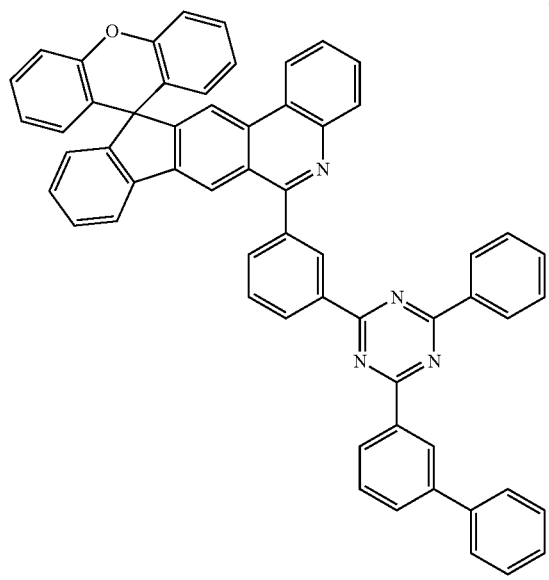

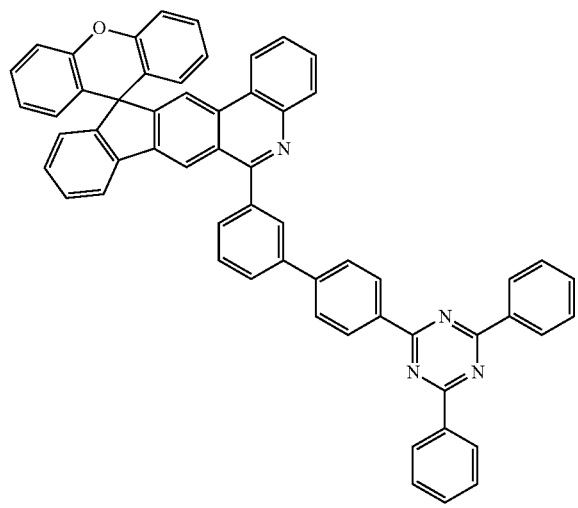
34
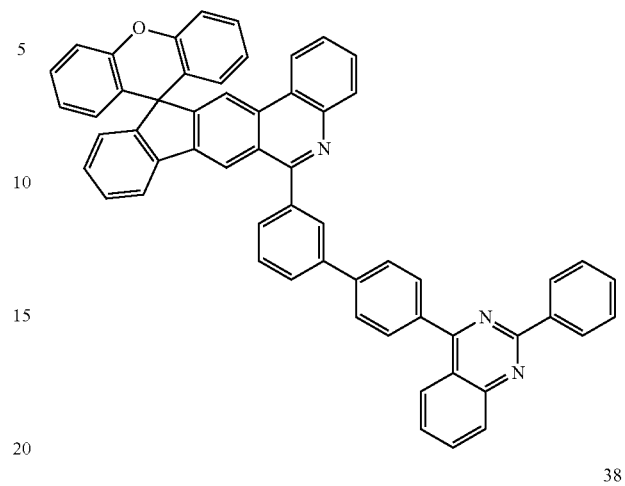
37
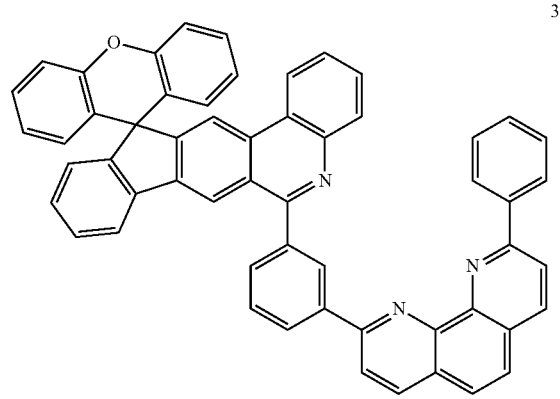
35
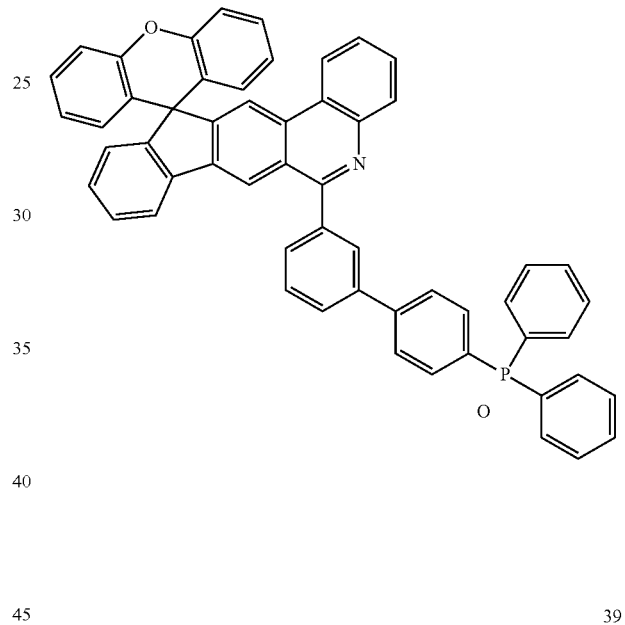
38
36
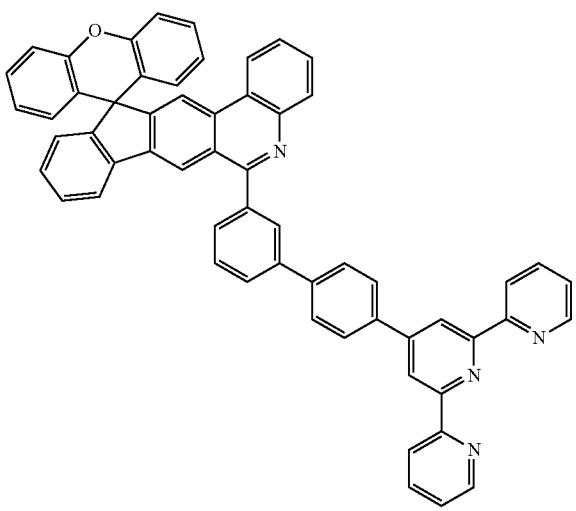
39

357
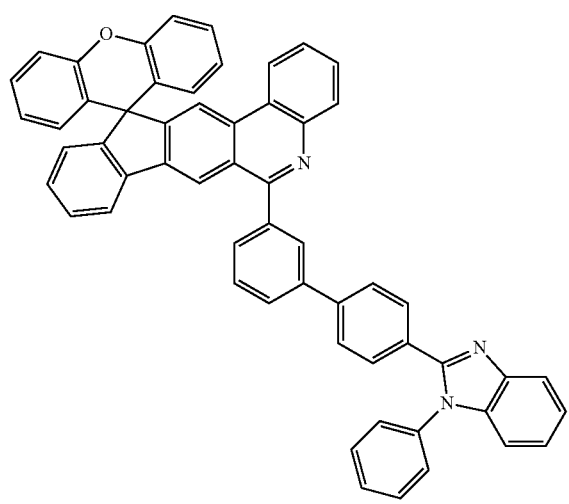
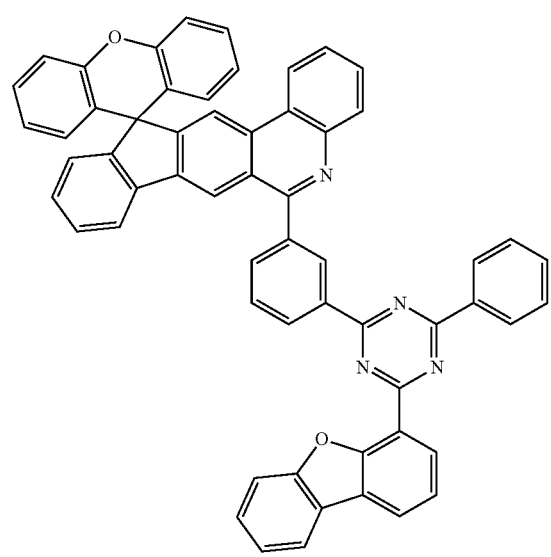
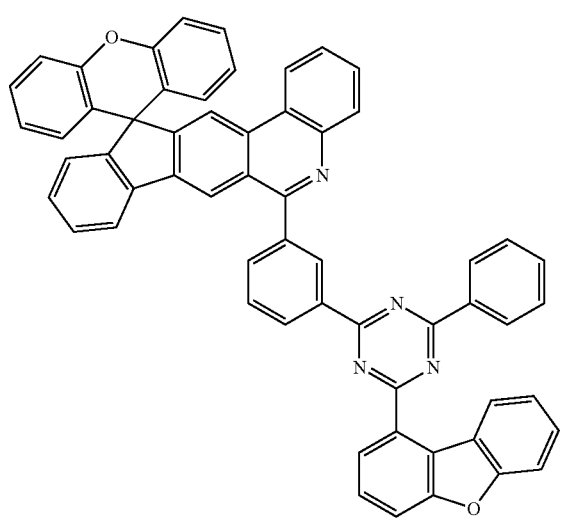 [SMILES: c1ccc(-c2nc(-c3cccc(-c4nc5ccccc5c5cc6c(cc45)-c4ccccc4C64c5ccccc5Oc5ccccc54)c3)nc(-c3cccc4oc5ccccc5c34)n2)cc1]
358
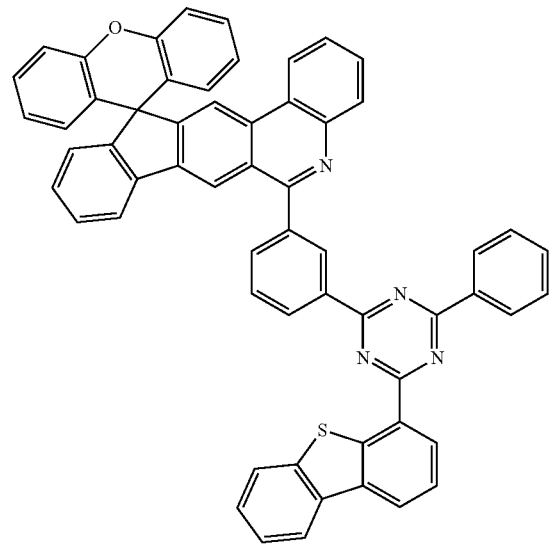
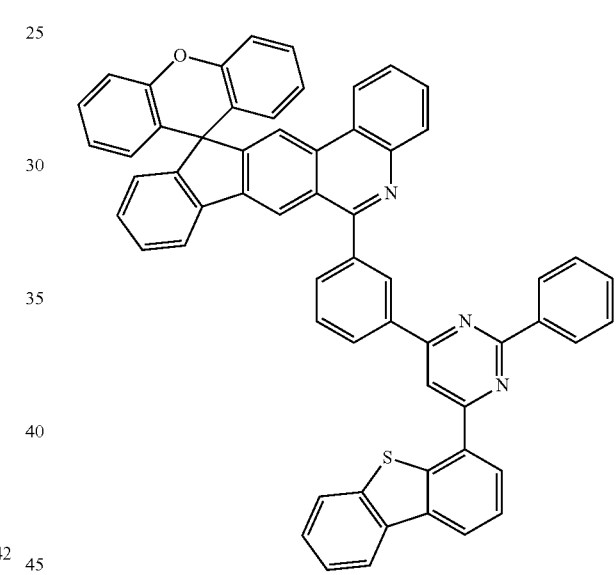
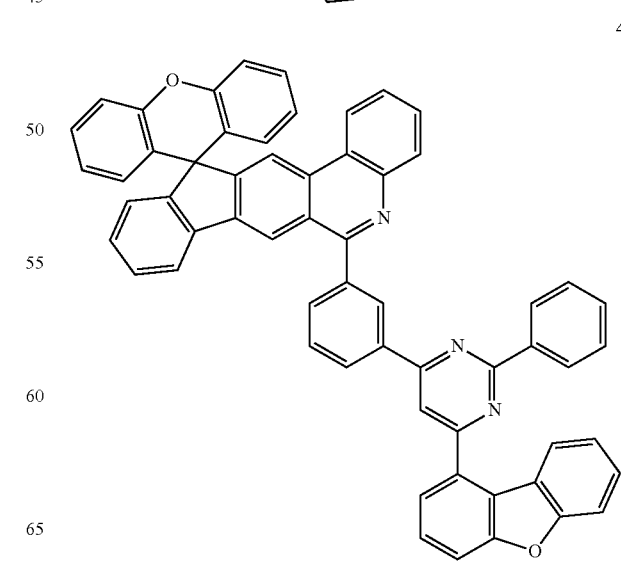

-continued
46
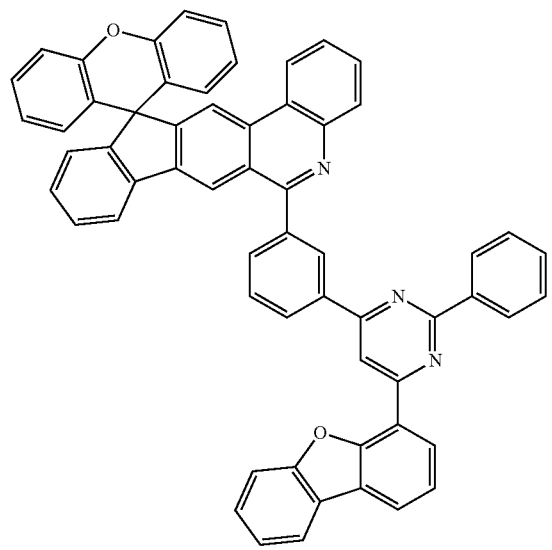
47
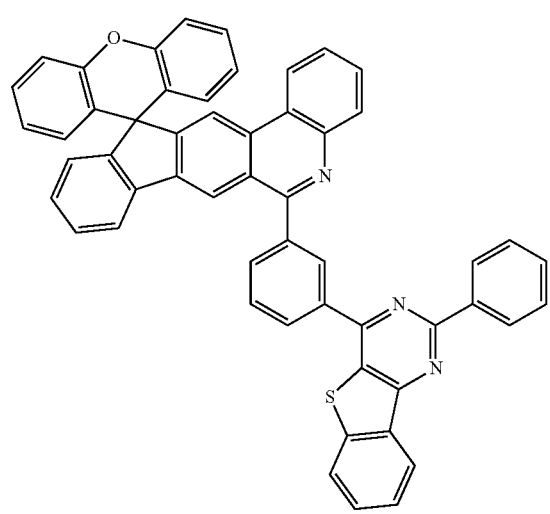
48
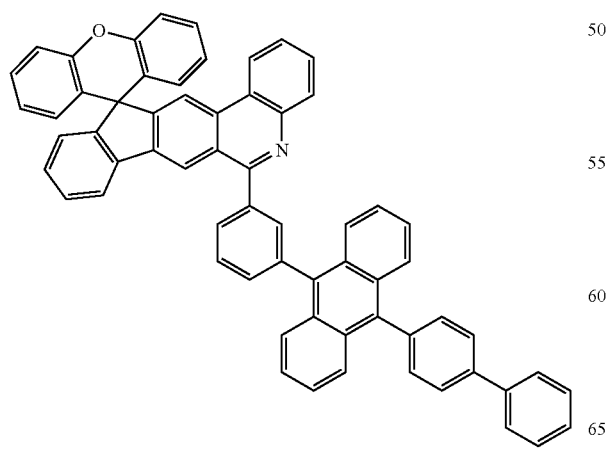
-continued
49
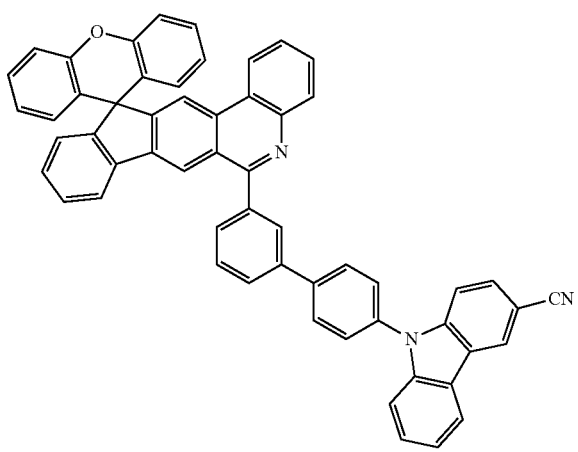
50
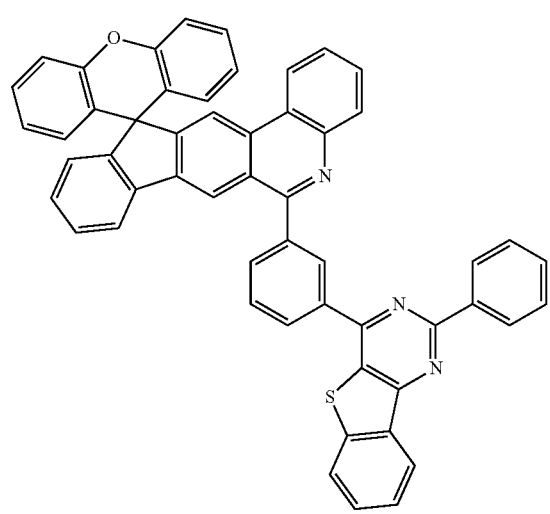
51
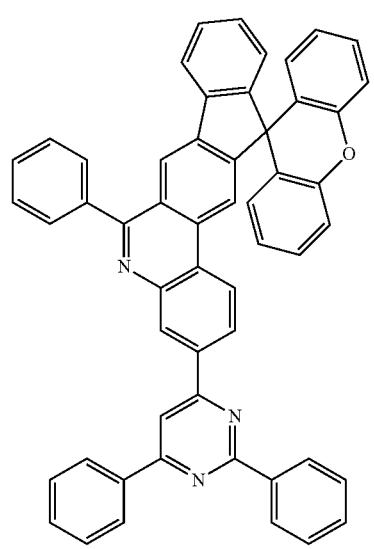

52
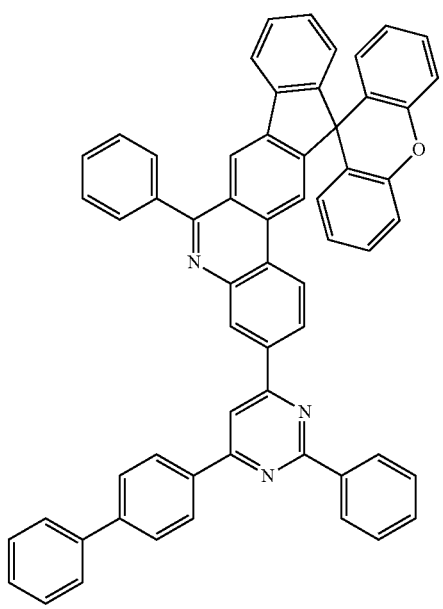
54
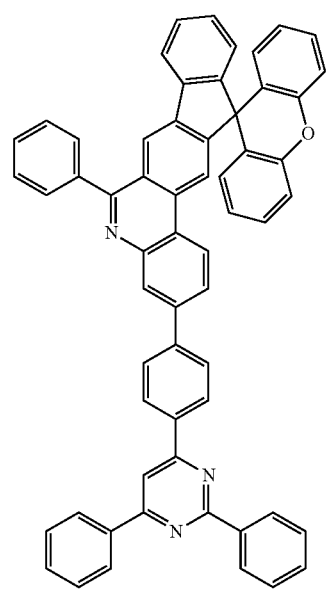
53
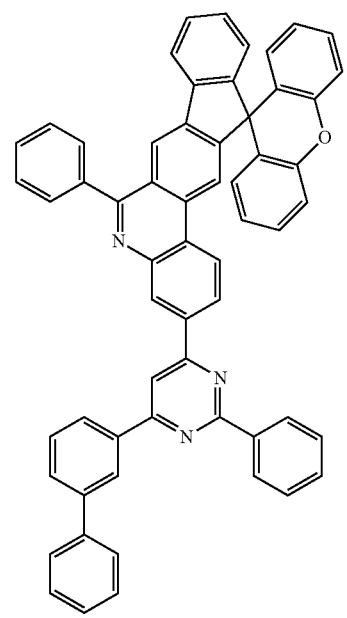
55
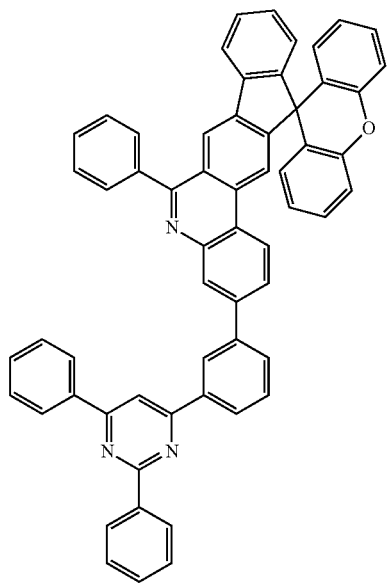

363
-continued
56
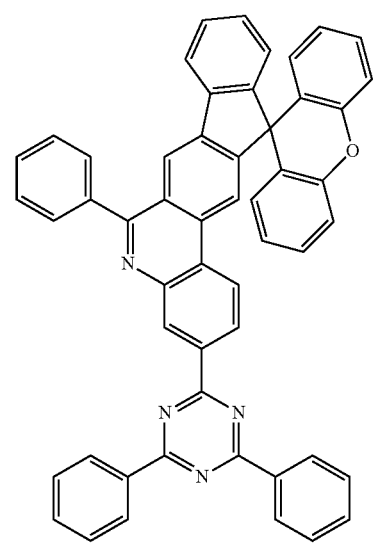 [SMILES: c1ccc(-c2nc(-c3ccccc3)nc(-c3ccc4c(c3)nc(-c3ccccc3)c3cc5c(cc34)C3(c4ccccc4Oc4ccccc43)c3ccccc3-5)n2)cc1]
57
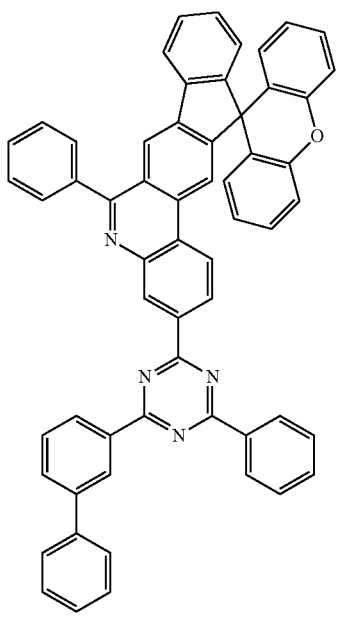
364
-continued
58
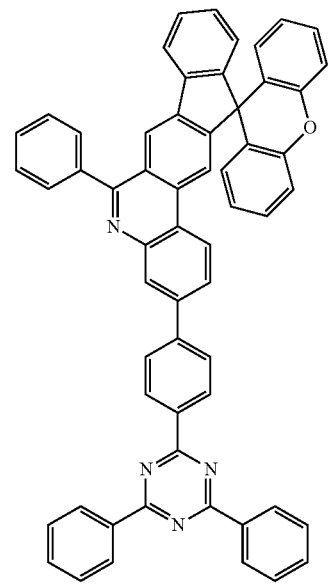
59

365
-continued
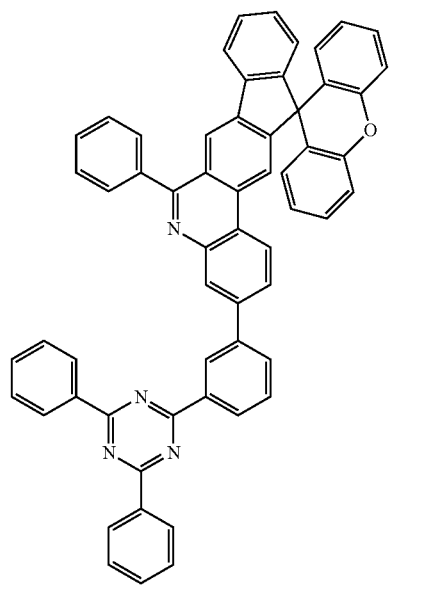
60
366
-continued
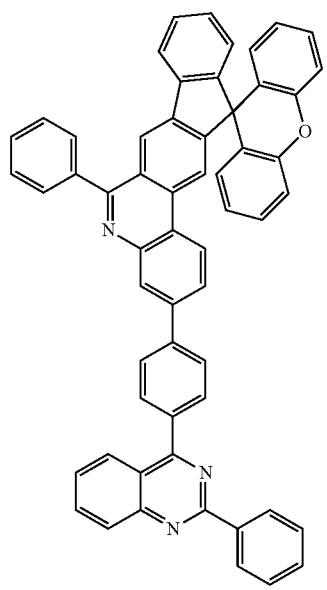
62
61
63
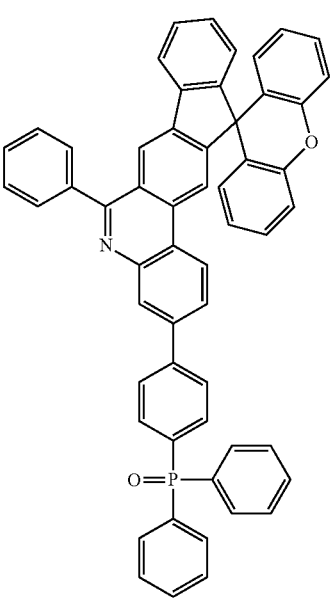

-continued
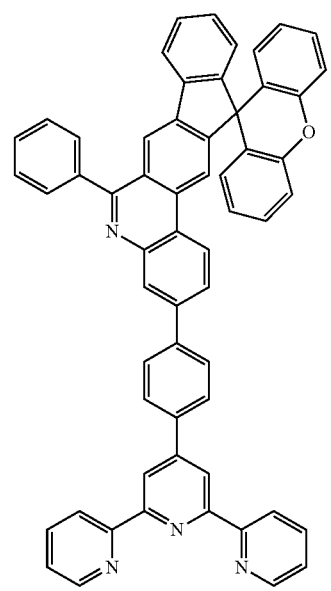
64
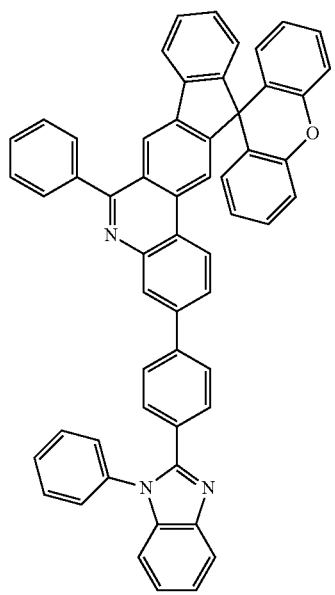
-continued
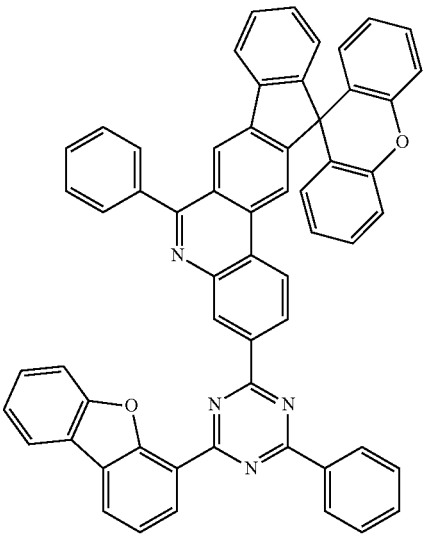
66
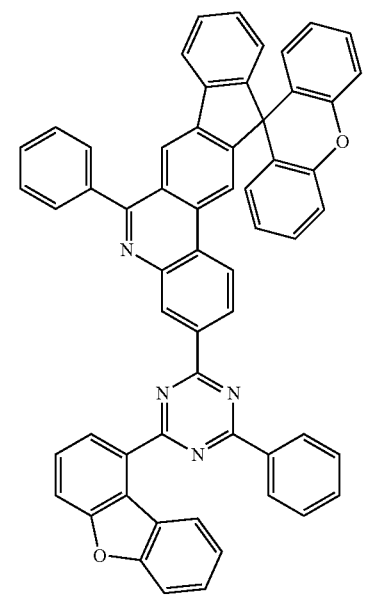
67
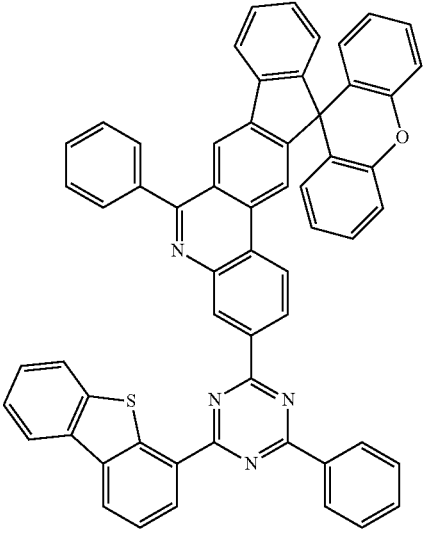
68

-continued
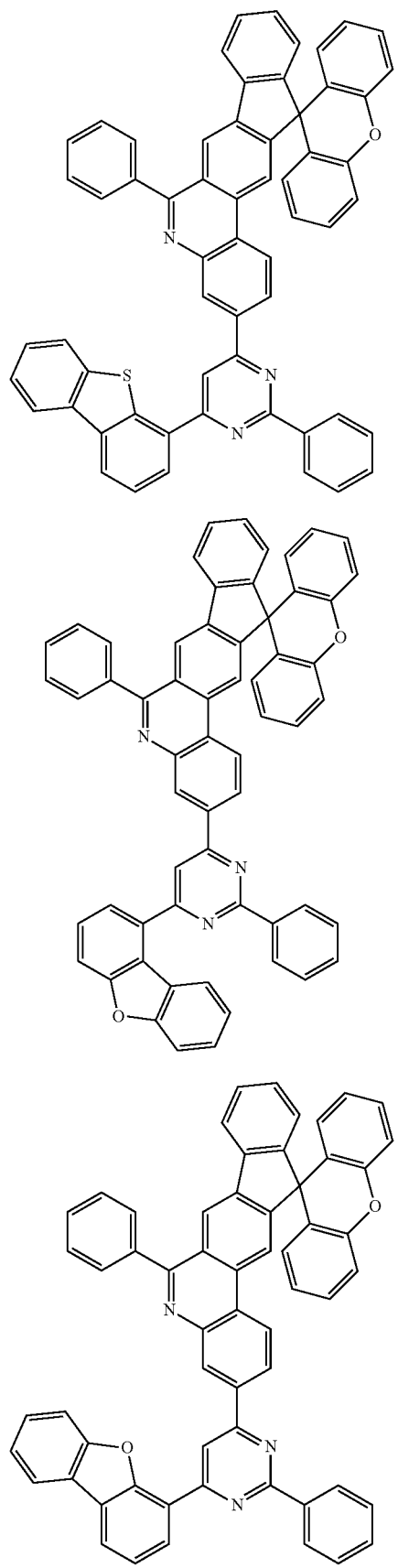
-continued

371
-continued
372
-continued
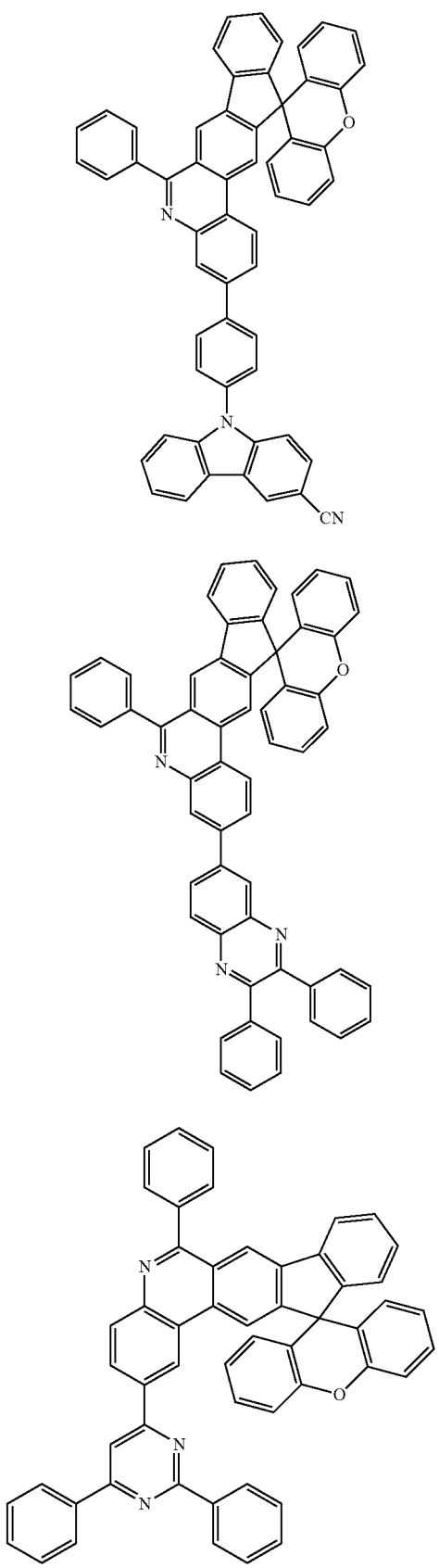
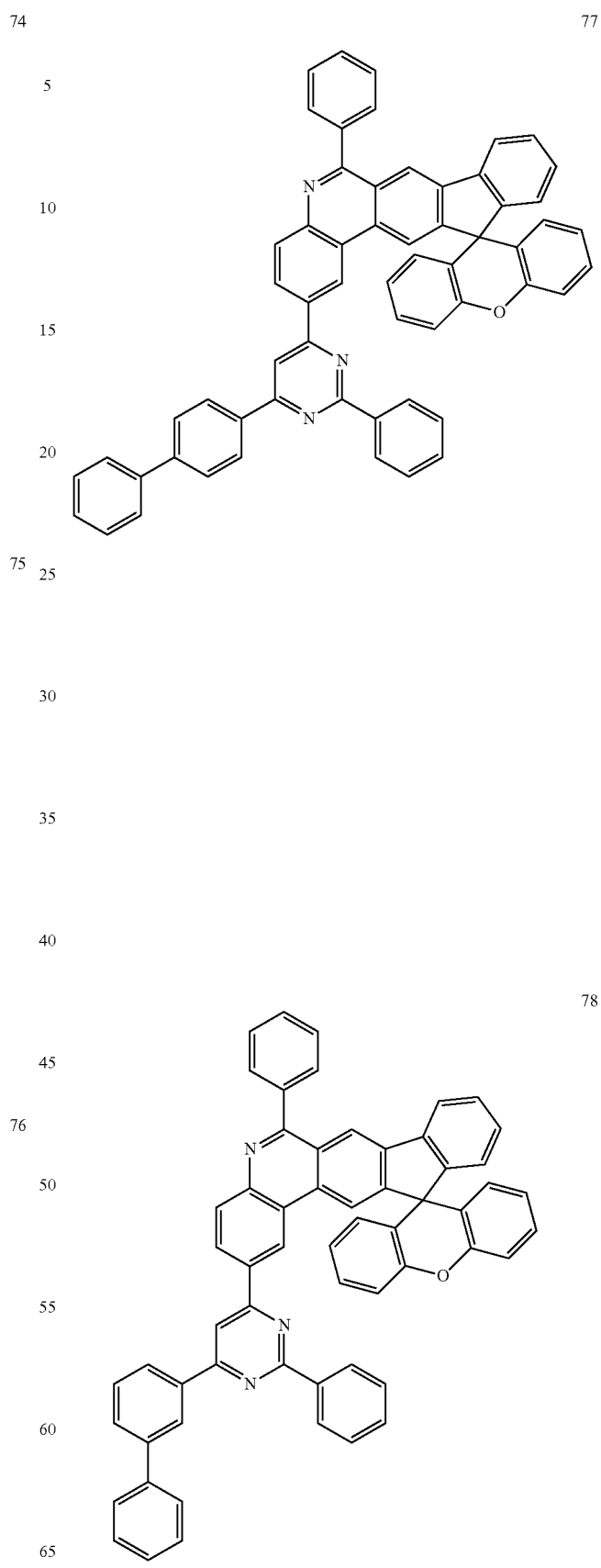

373
-continued
79
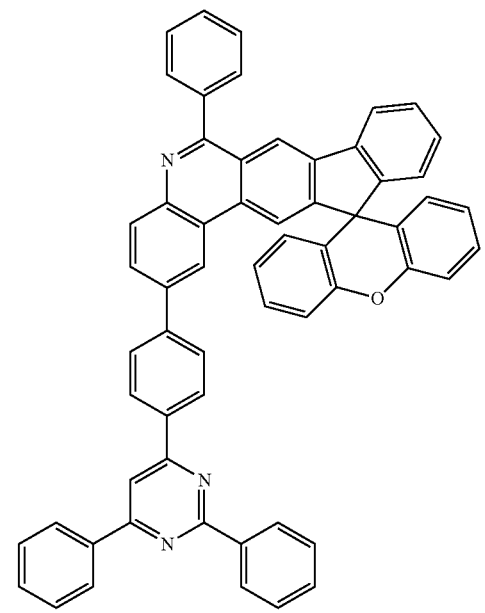
80
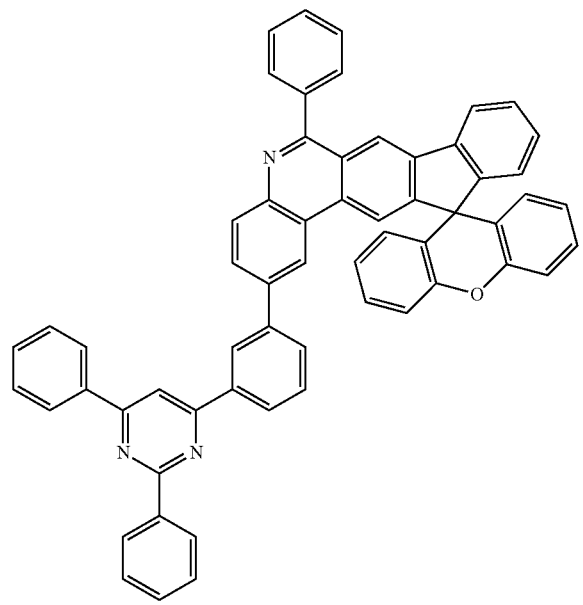
374
-continued
81
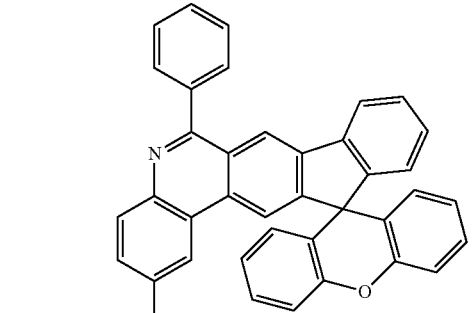
82
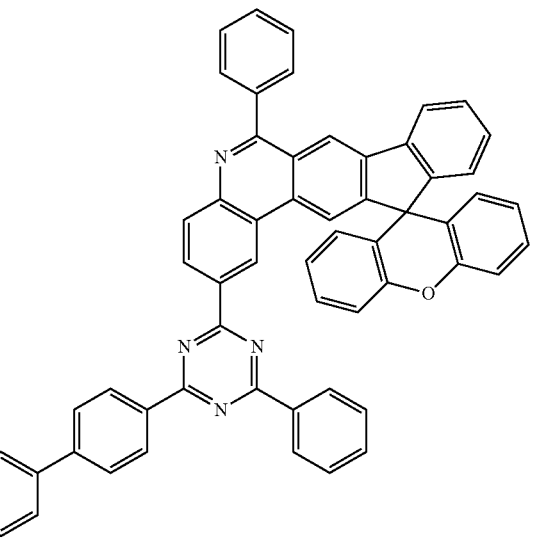
83
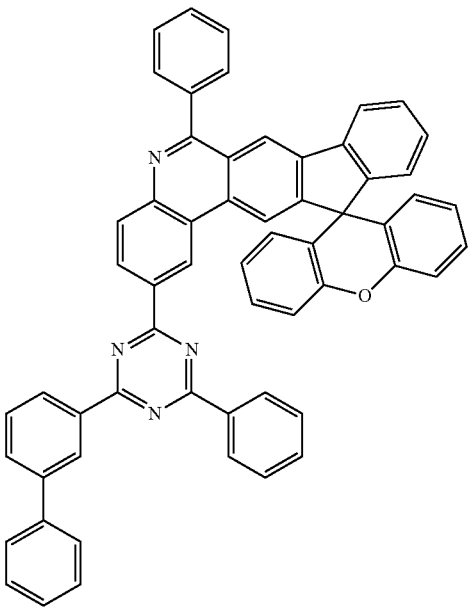

375
-continued
84
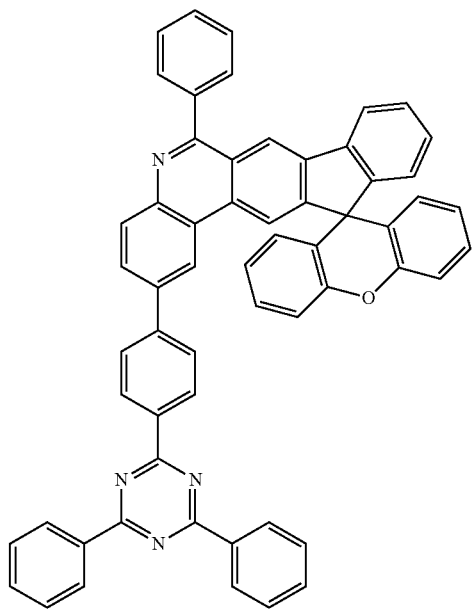
376
-continued
86
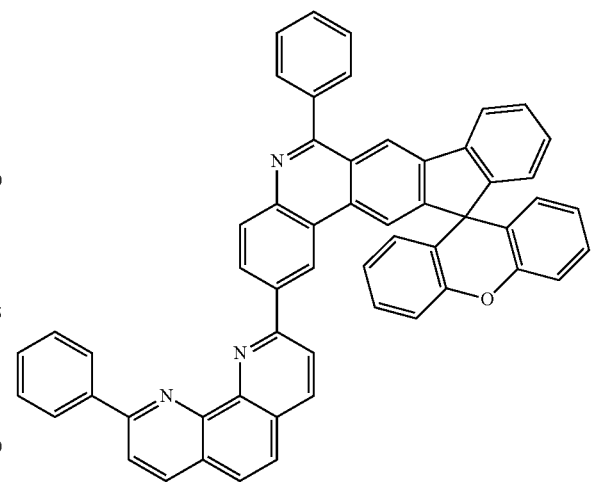
85
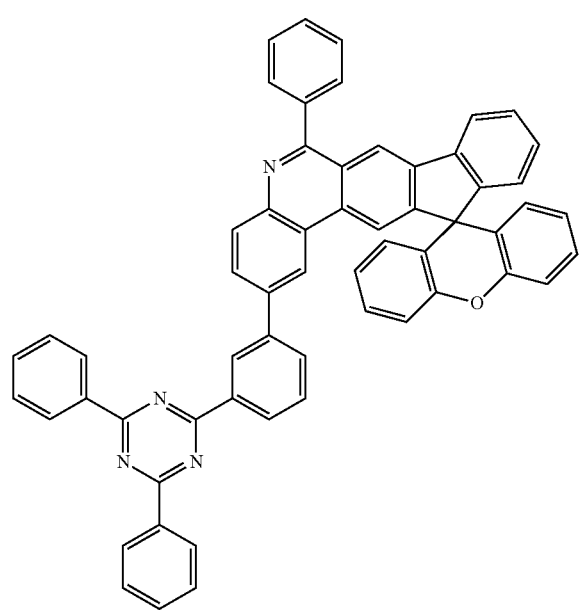
87
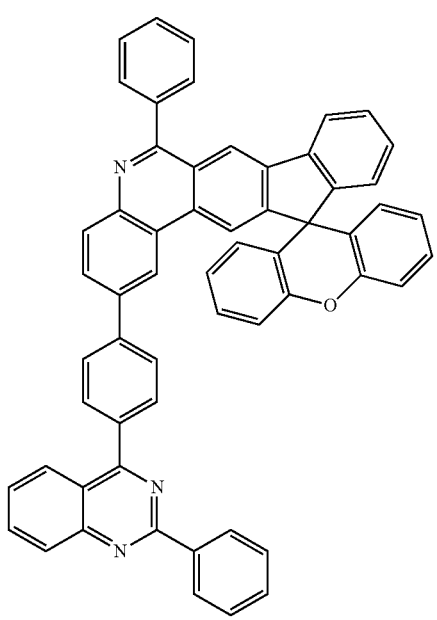

377
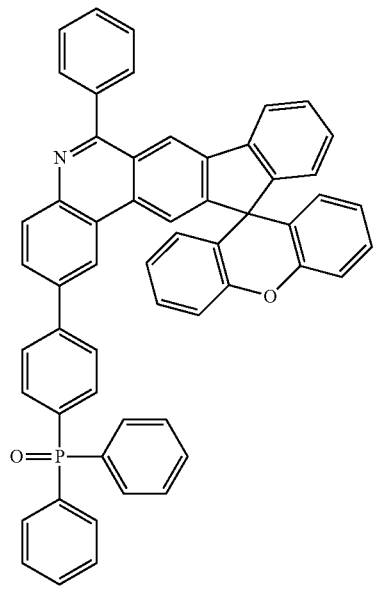
88
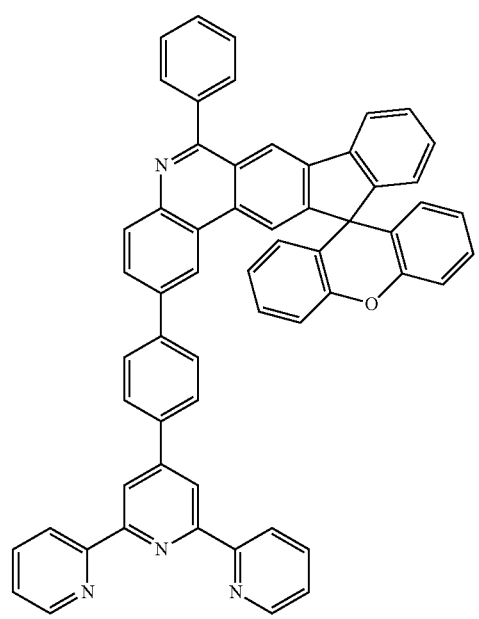
89
378
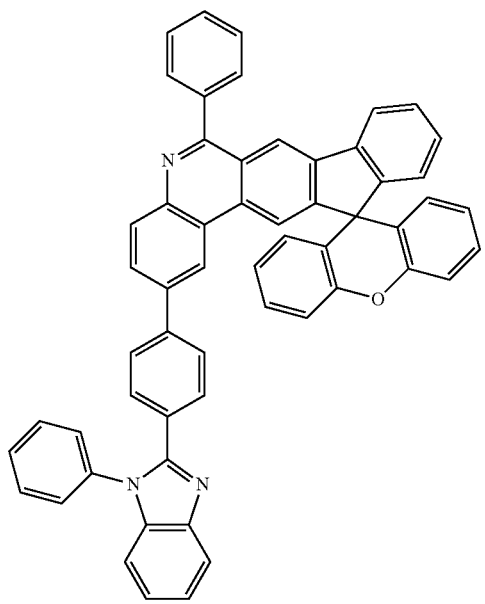
90
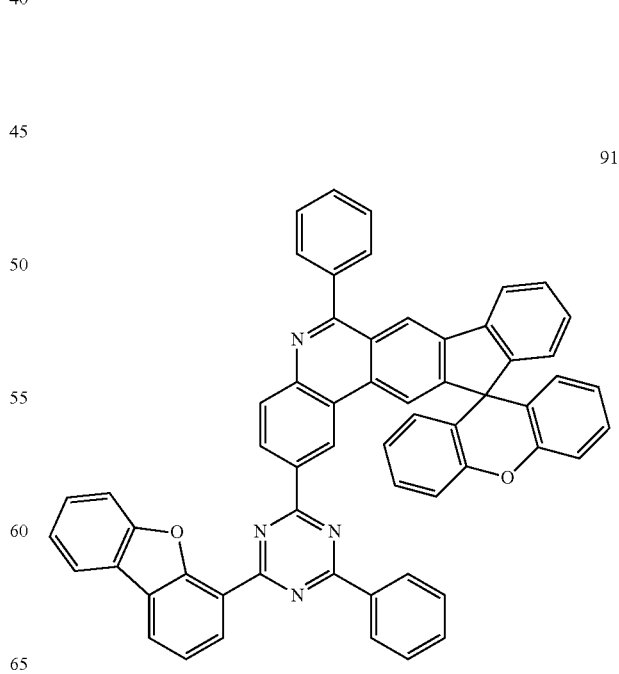
91

92
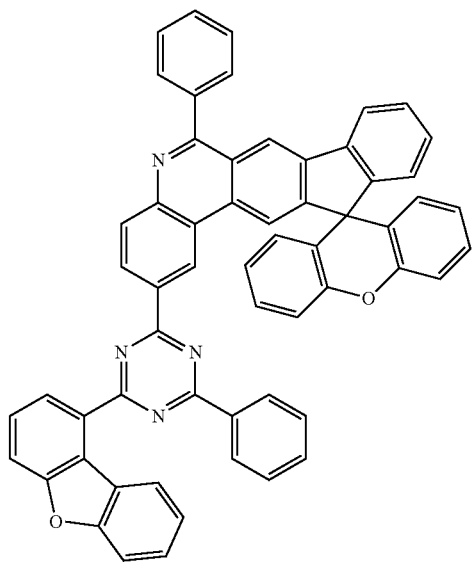
95
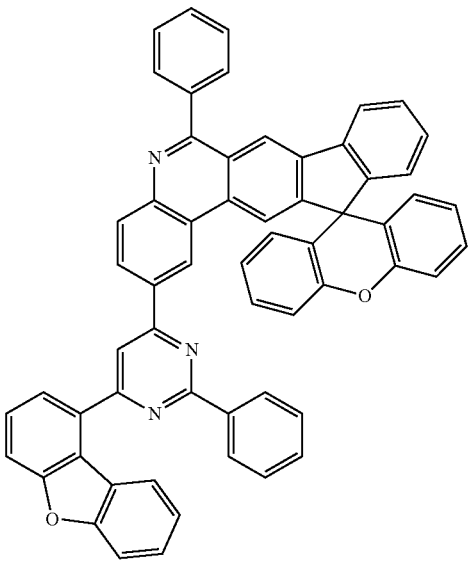
93
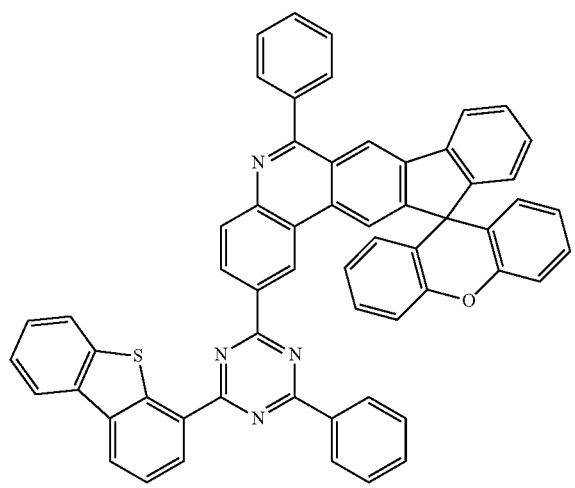
96
94
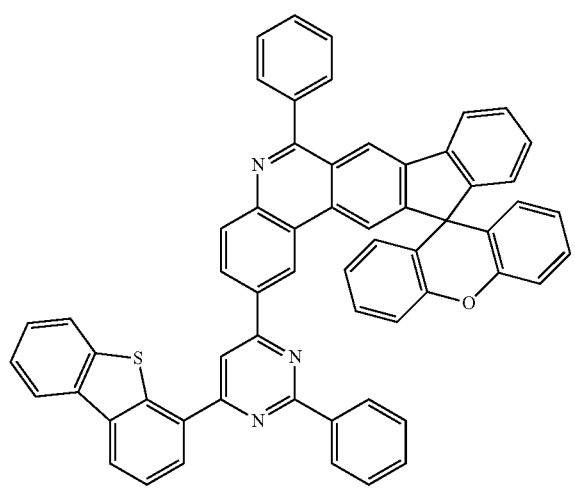 [SMILES: c1ccc(-c2nc(-c3ccc4nc(-c5ccccc5)c5cc6c(cc5c4c3)C3(c4ccccc4Oc4ccccc43)c3ccccc3-6)nc(-c3cccc4c3oc3ccccc34)n2)cc1]
97
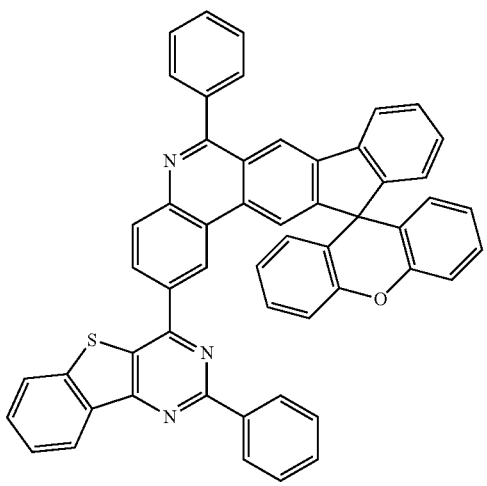

381
-continued
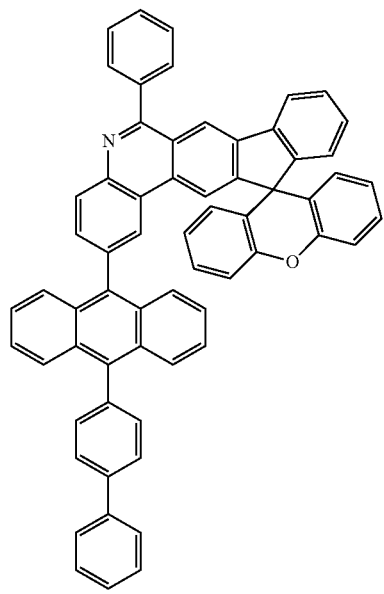
98
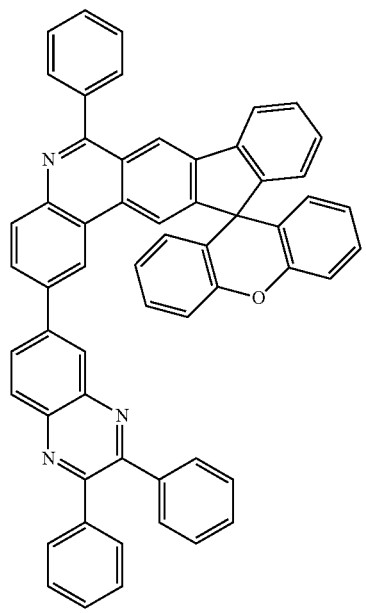
100
382
-continued
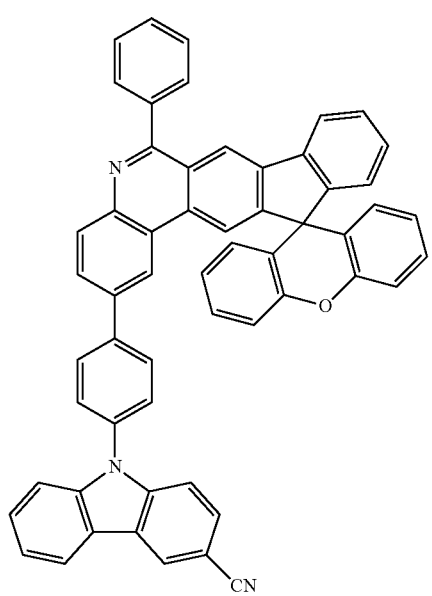
99
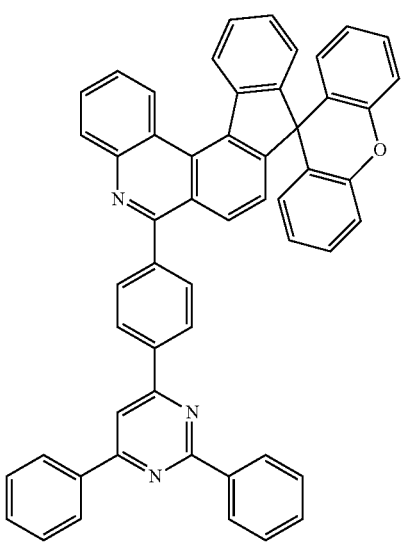
101

383
-continued
102
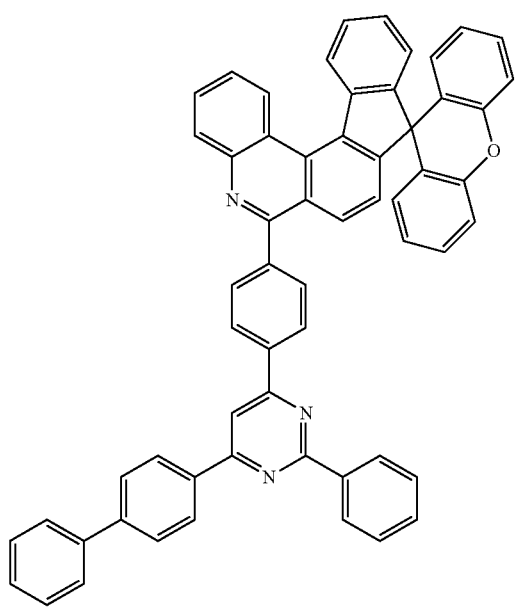
103
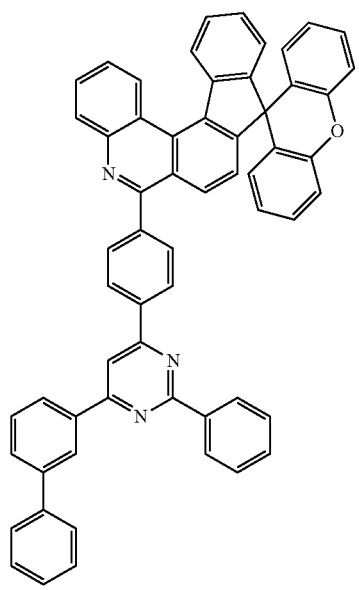
384
-continued
104
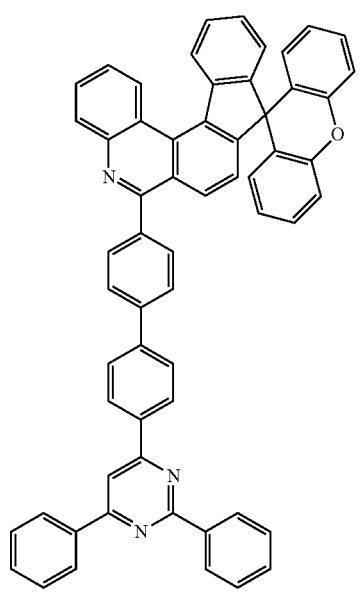 [SMILES: c1ccc(-c2cc(-c3ccc(-c4ccc(-c5nc6ccccc6c6c7c(ccc56)C5(c6ccccc6Oc6ccccc65)c5ccccc5-7)cc4)cc3)nc(-c3ccccc3)n2)cc1]
105
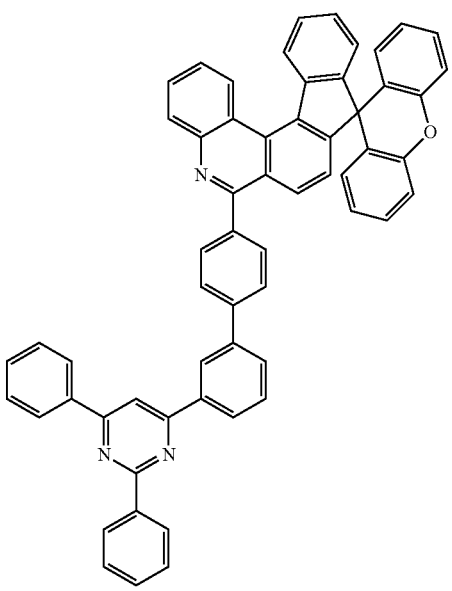 [SMILES: c1ccc(-c2cc(-c3cccc(-c4ccc(-c5nc6ccccc6c6c7c(ccc56)C5(c6ccccc6Oc6ccccc65)c5ccccc5-7)cc4)c3)nc(-c3ccccc3)n2)cc1]

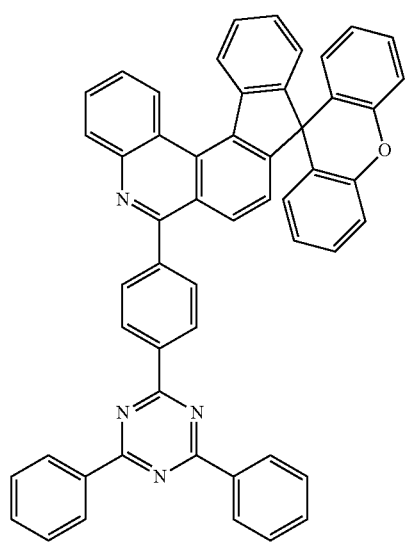
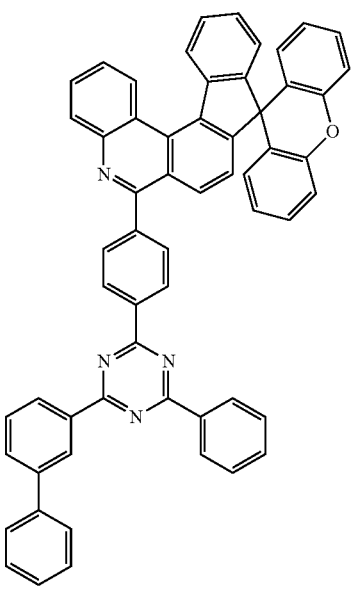

387
-continued
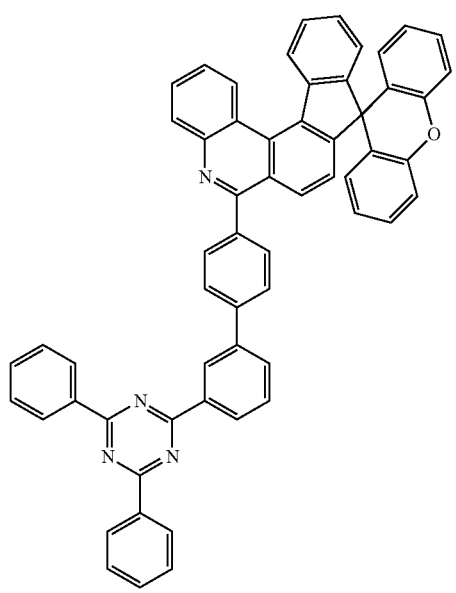
110
388
-continued
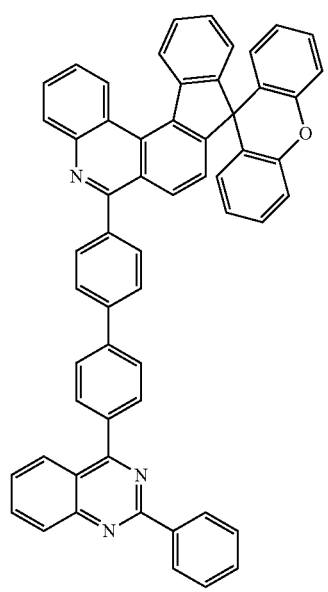
112
111
113

389
-continued
114
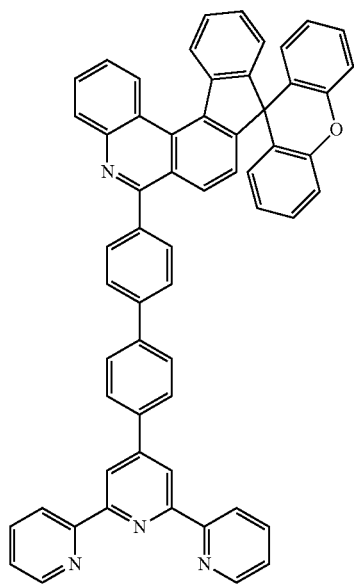
115
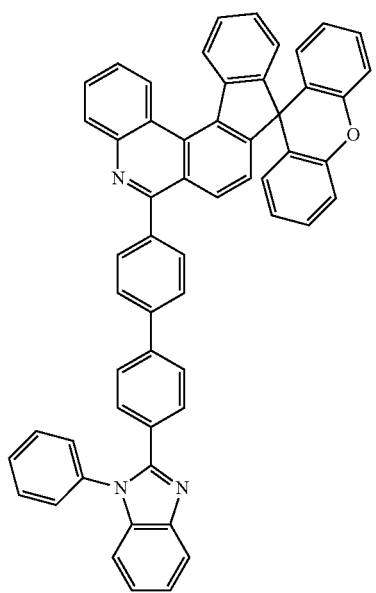
390
-continued
116
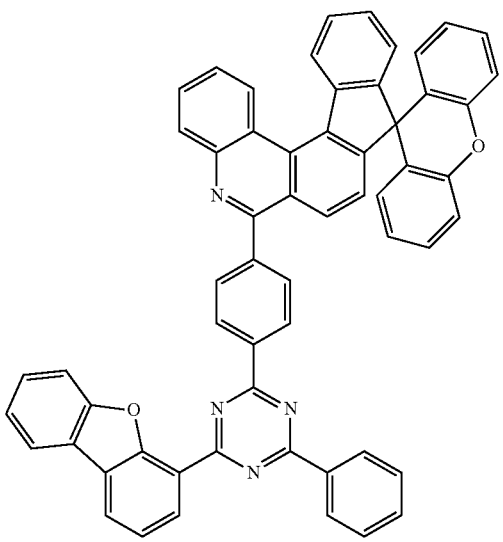
117
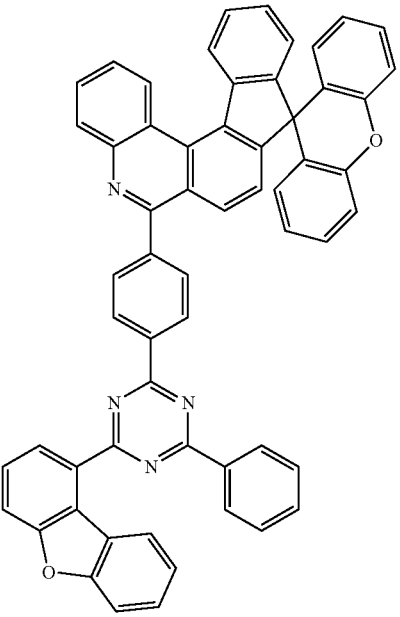

391
-continued
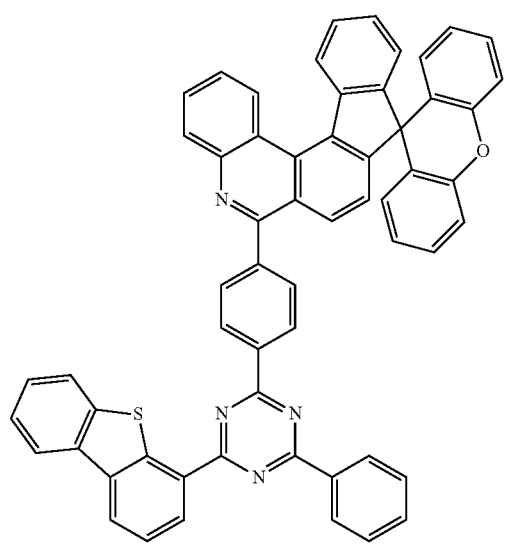
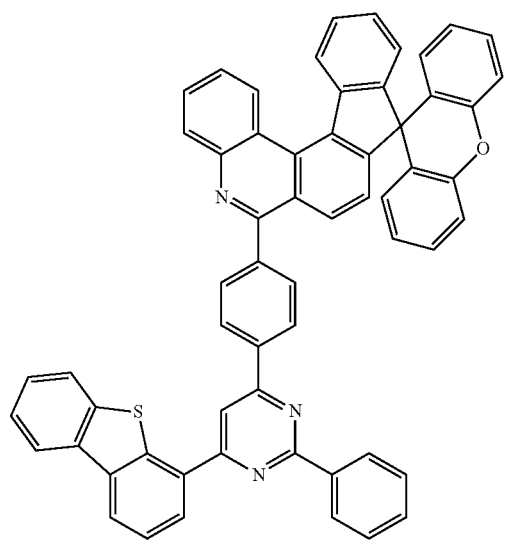
392
-continued
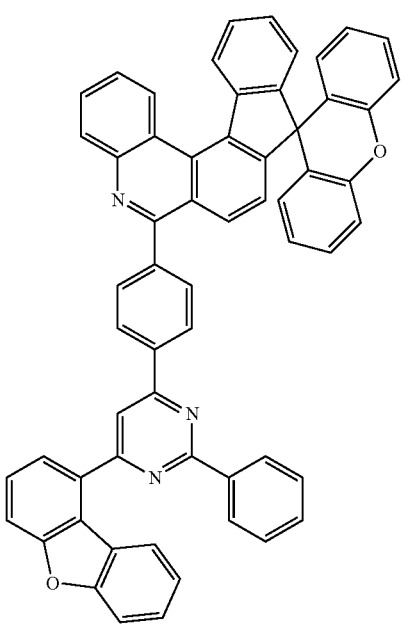
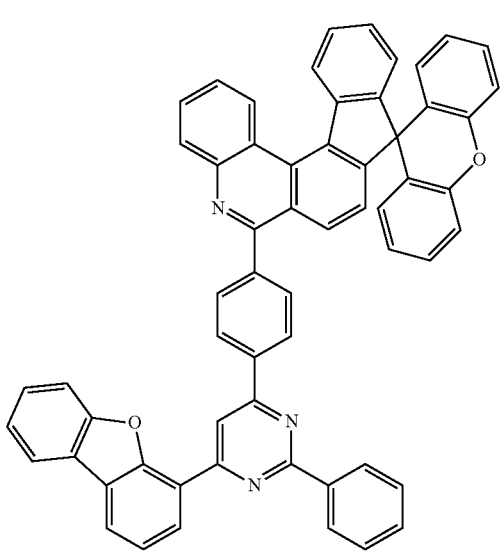

393
-continued
122
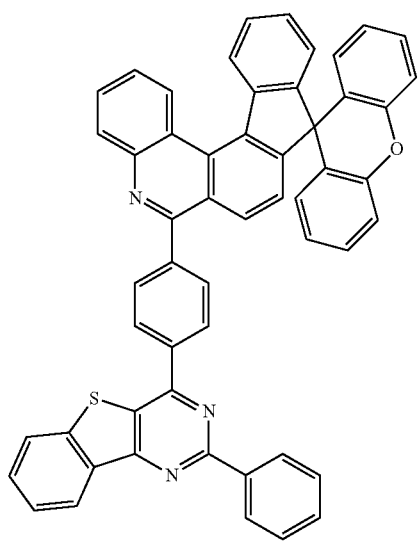
123
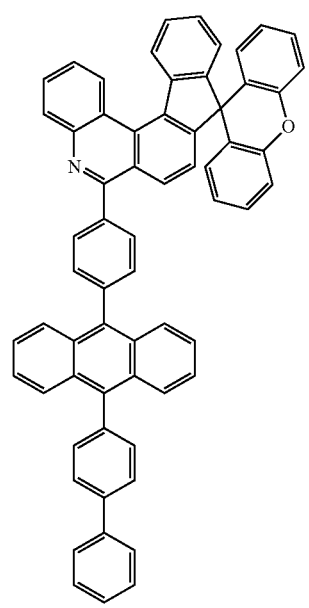
394
-continued
124
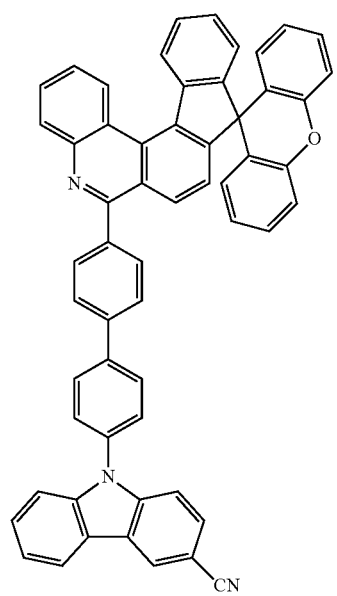 [SMILES: N#Cc1ccc2c(c1)c1ccccc1n2-c1ccc(-c2ccc(-c3nc4ccccc4c4c5c(ccc34)C3(c4ccccc4Oc4ccccc43)c3ccccc3-5)cc2)cc1]
125
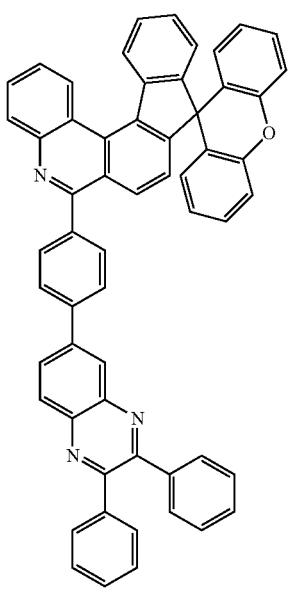

395
-continued
126
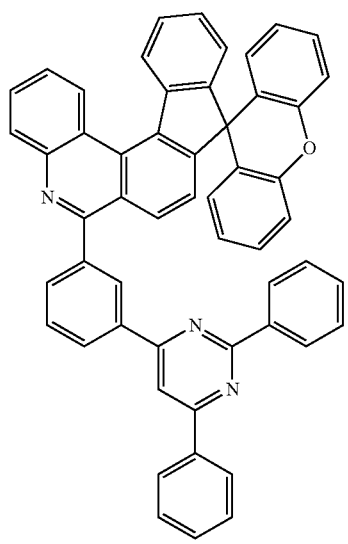
396
-continued
128
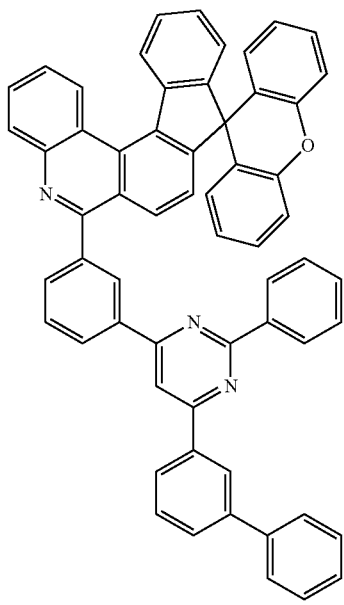
127
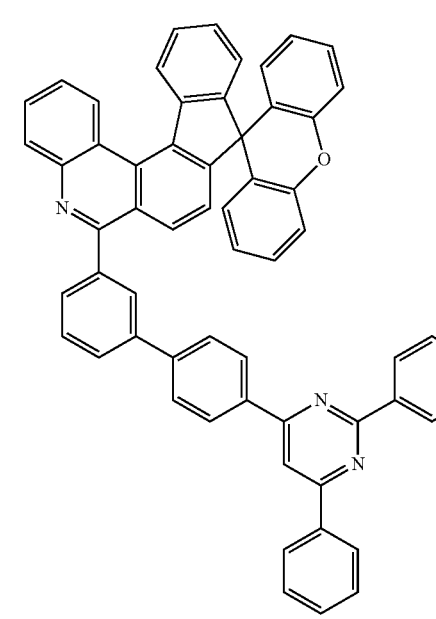
129

397
-continued
130
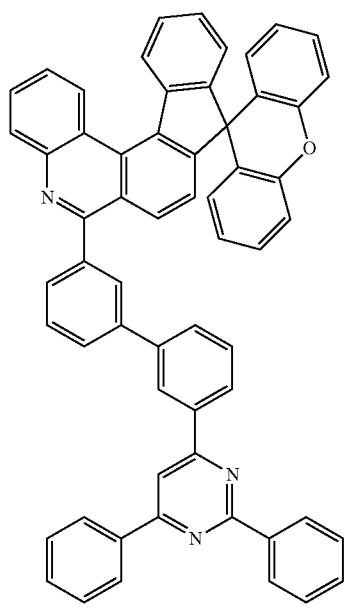
131
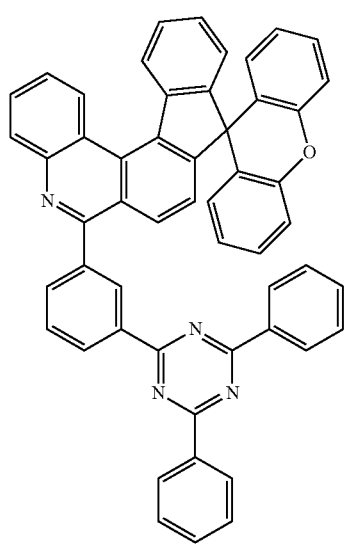
398
-continued
132
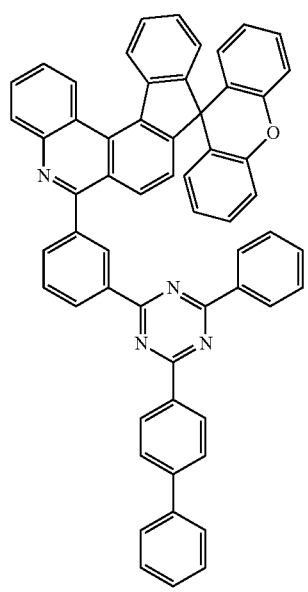
133
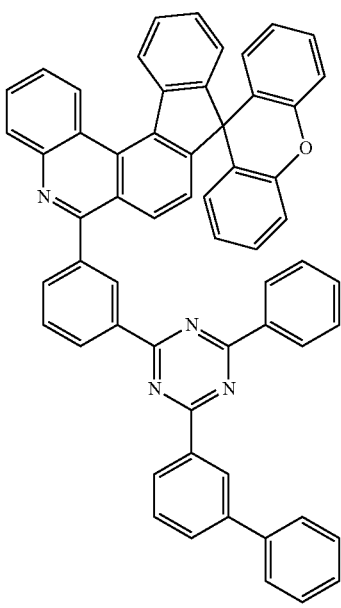

-continued
134
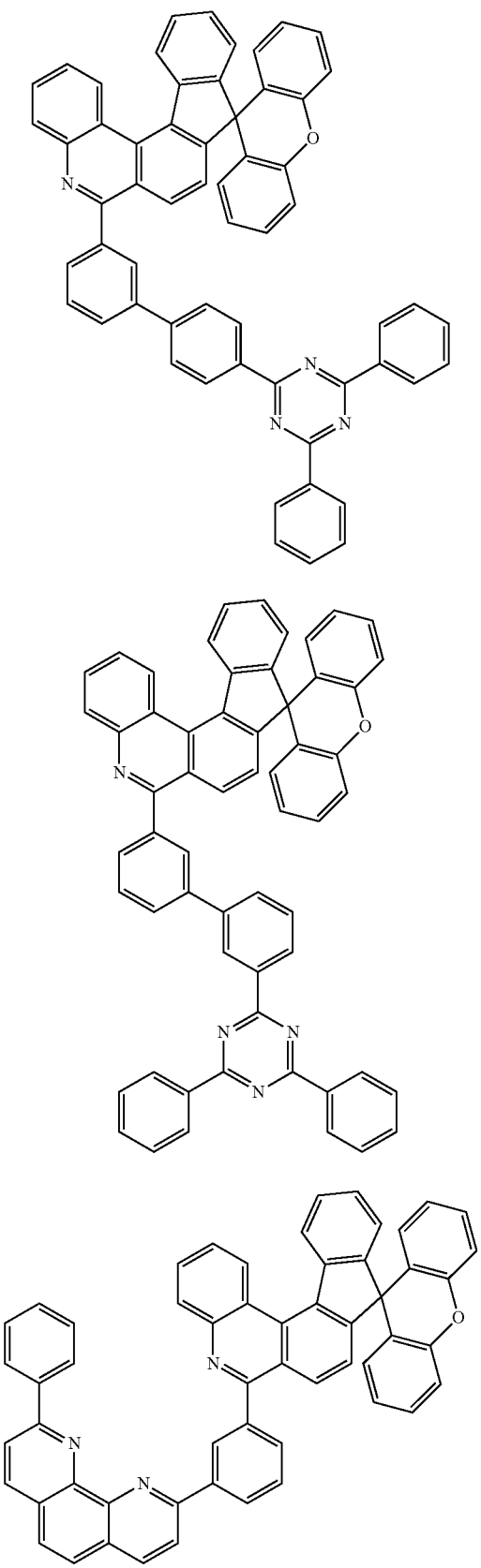
135
136
-continued
137
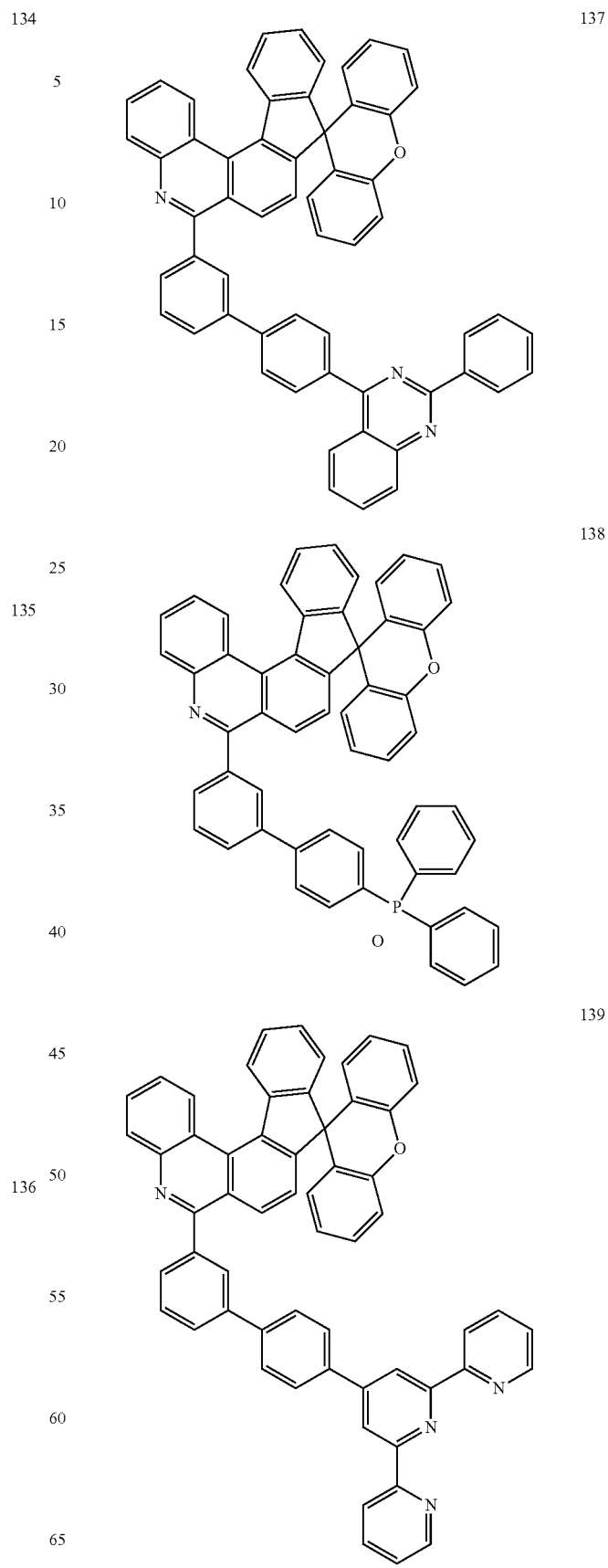
138
139

401
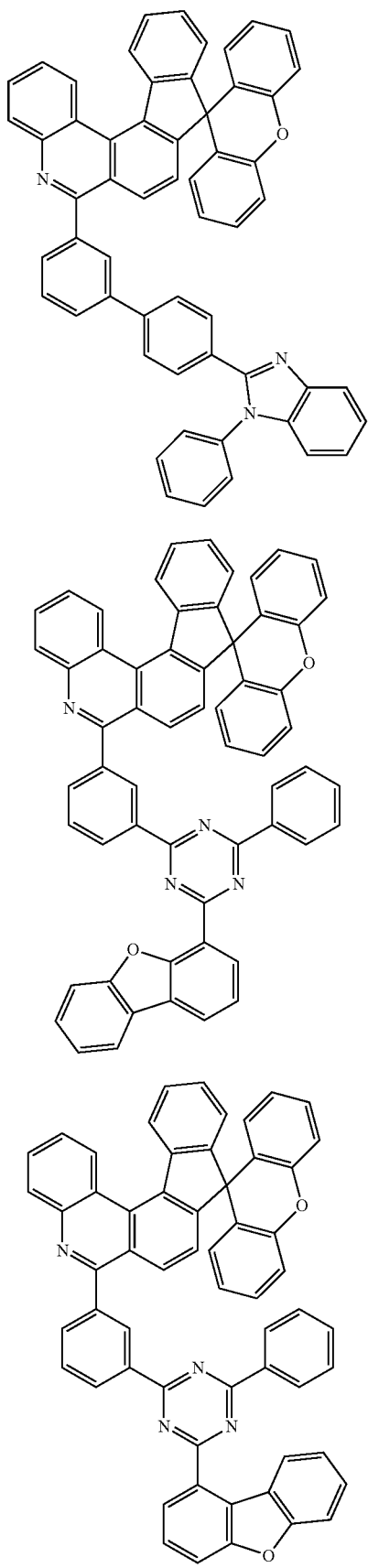
140
141
142
402
143
144

145
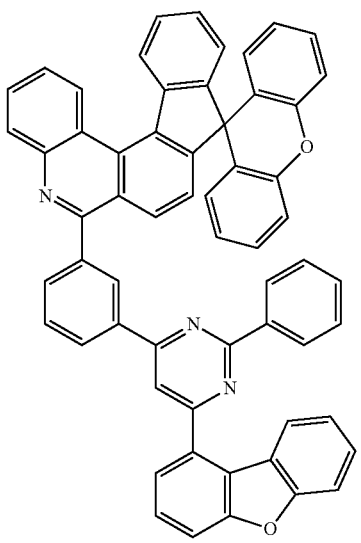
148
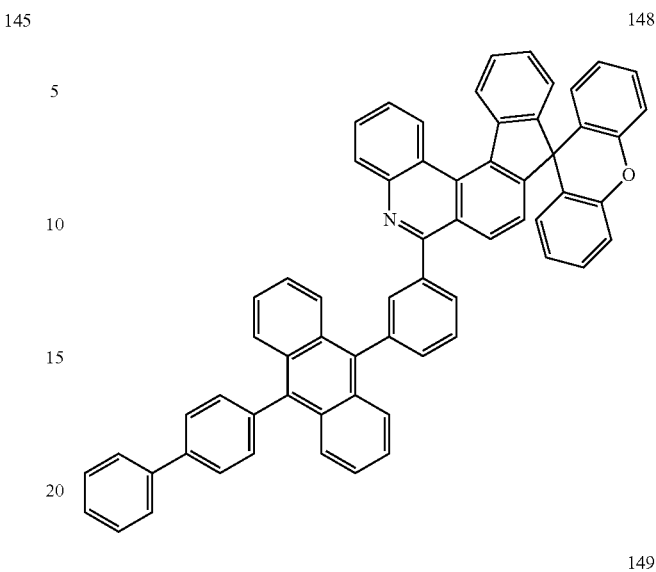
146
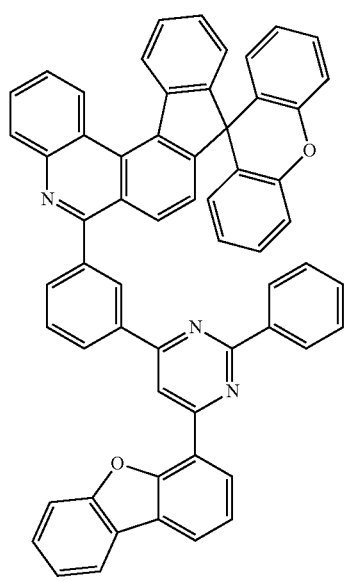 [SMILES: c1ccc(-c2nc(-c3cccc(-c4nc5ccccc5c5c6c(ccc45)C4(c5ccccc5Oc5ccccc54)c4ccccc4-6)c3)cc(-c3cccc4c3oc3ccccc34)n2)cc1]
149
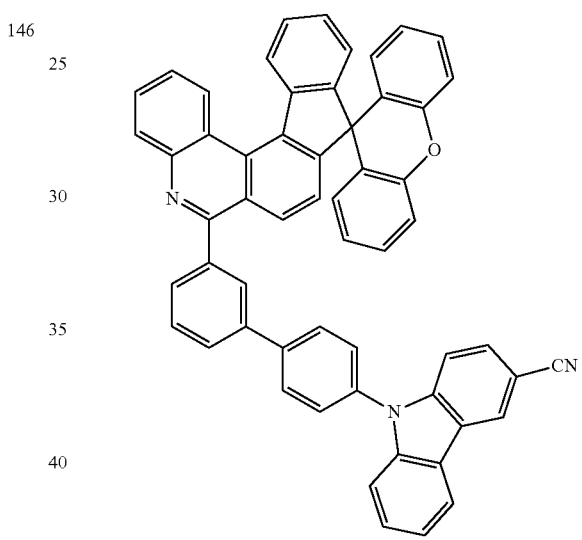
147
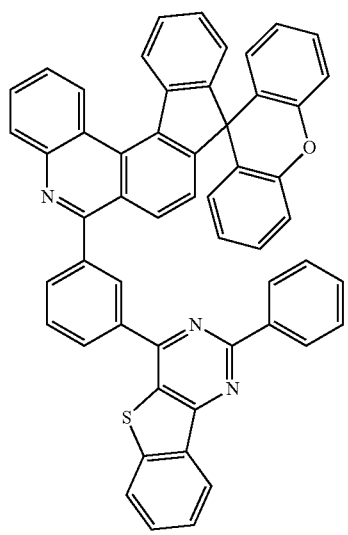
150
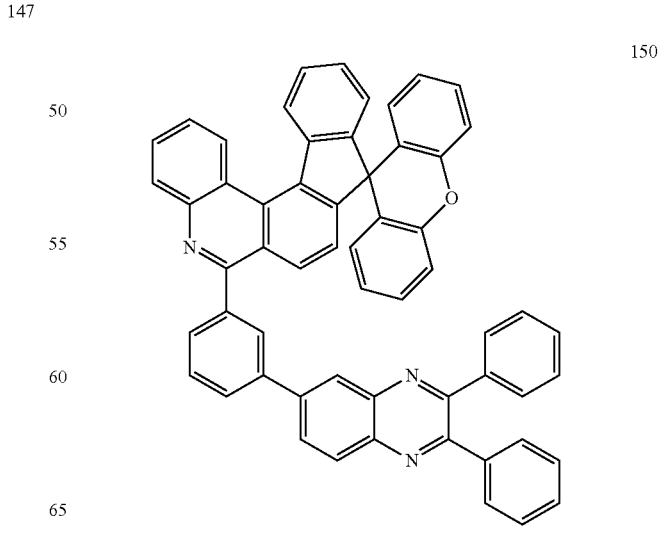

151
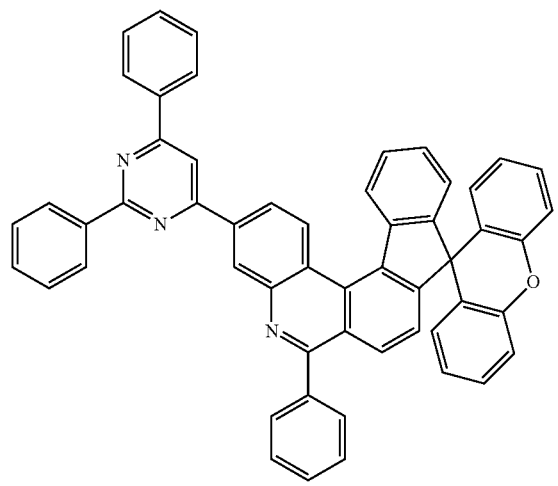
152
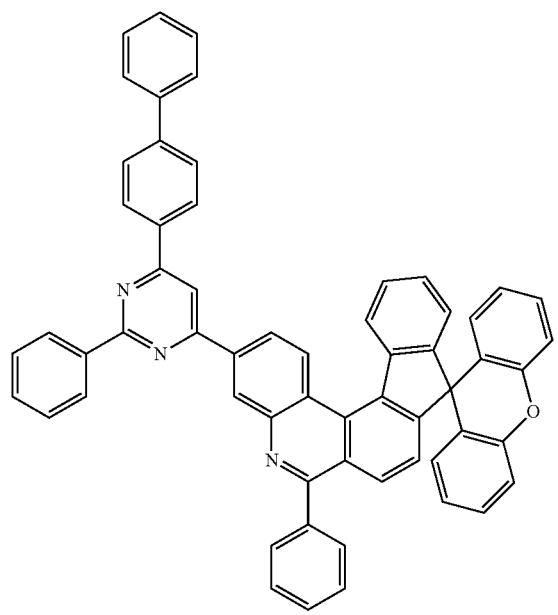
153
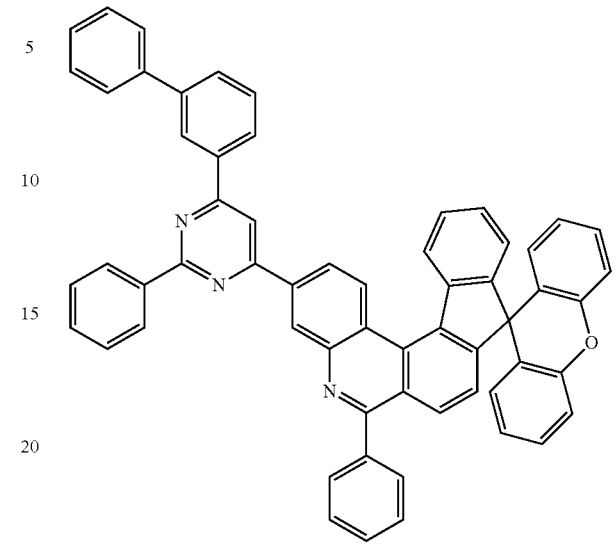
154
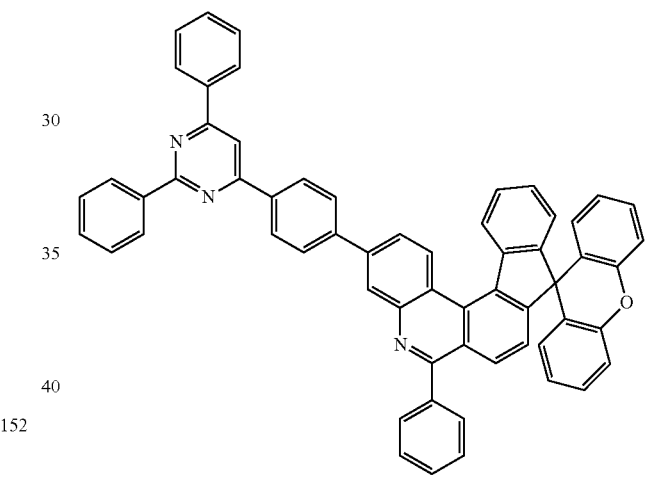
155
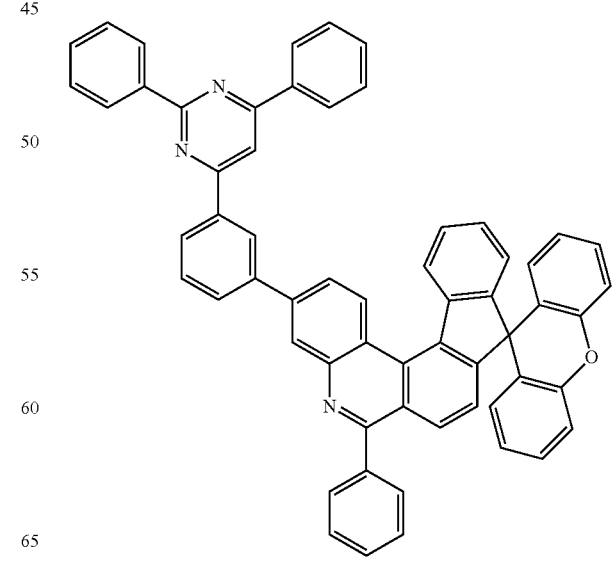

156
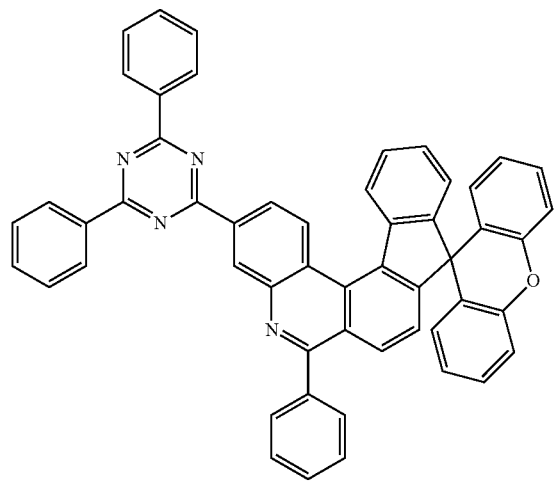
157
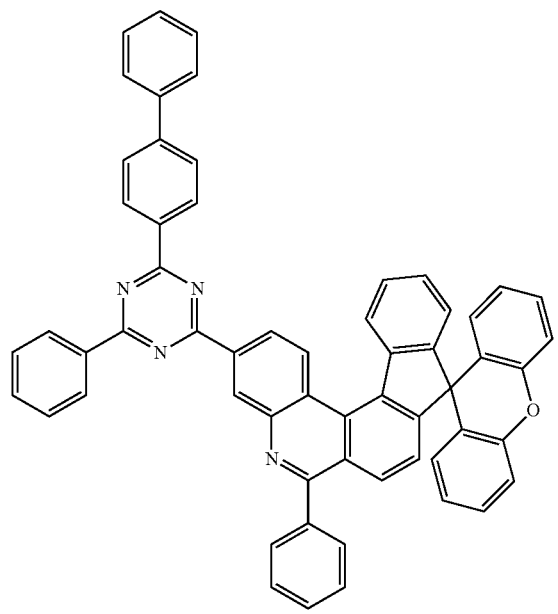
158
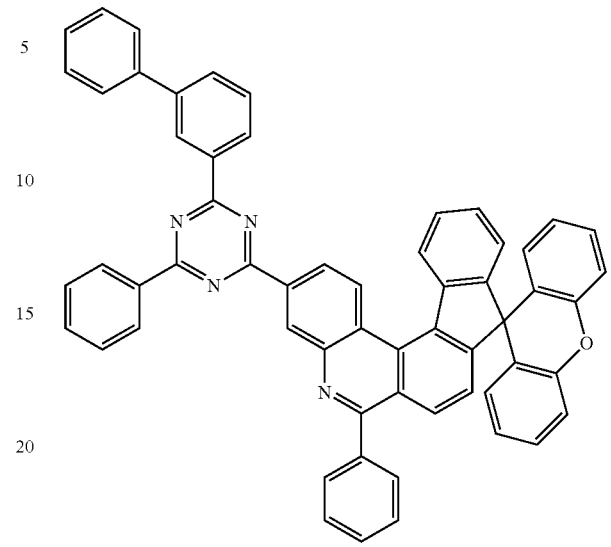
159
160
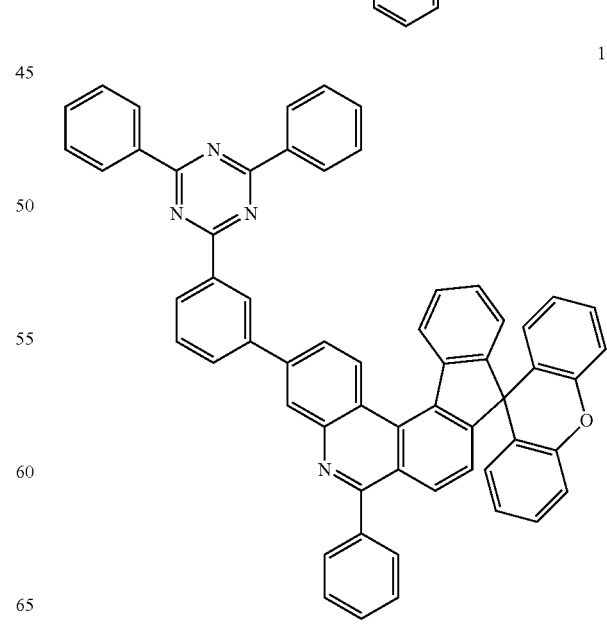

161
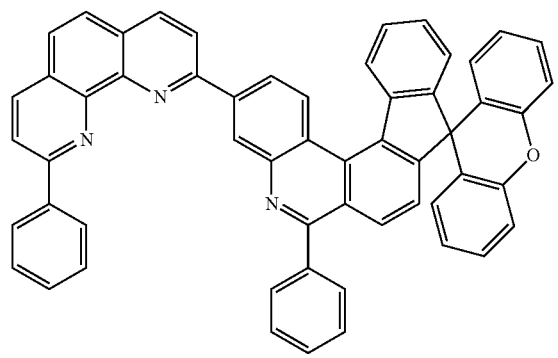 [SMILES: c1ccc(-c2ccc3ccc4ccc(-c5ccc6c(c5)nc(-c5ccccc5)c5ccc7c(c56)-c5ccccc5C75c6ccccc6Oc6ccccc65)nc4c3n2)cc1]
162
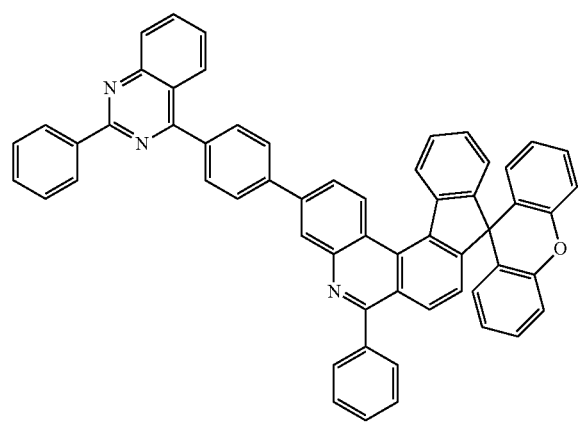
163
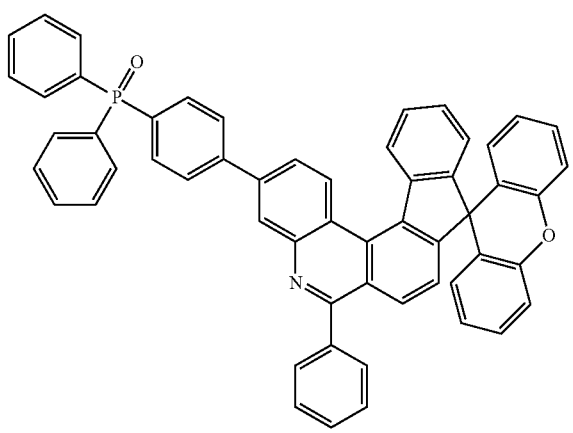
164
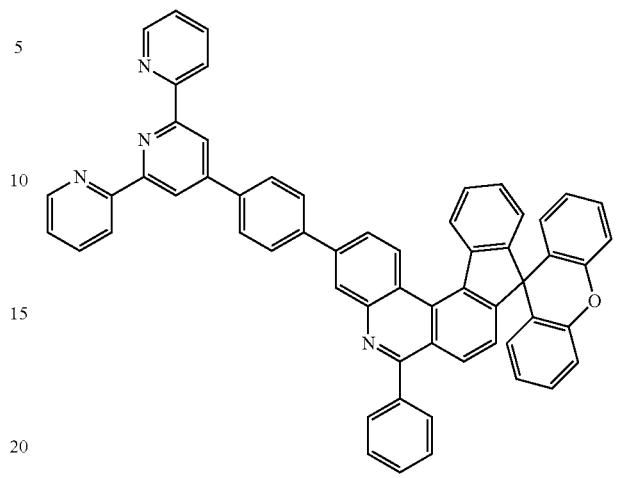
165
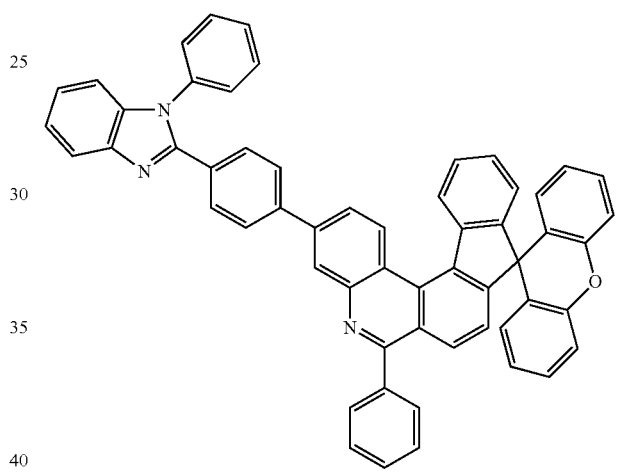
166
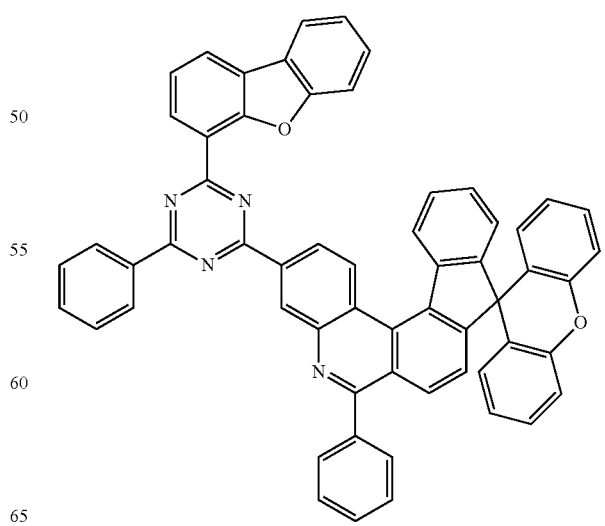

411
-continued
167
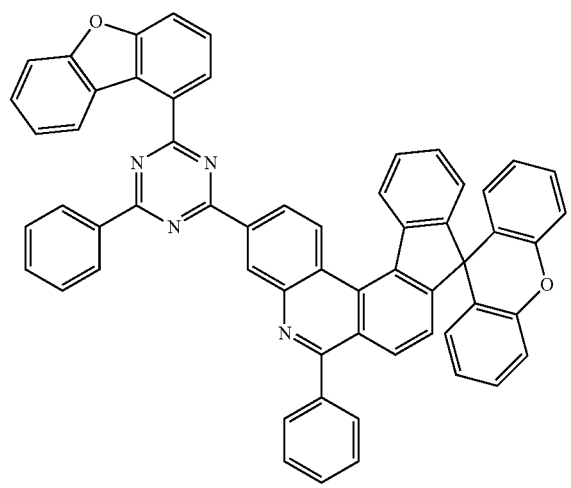
168
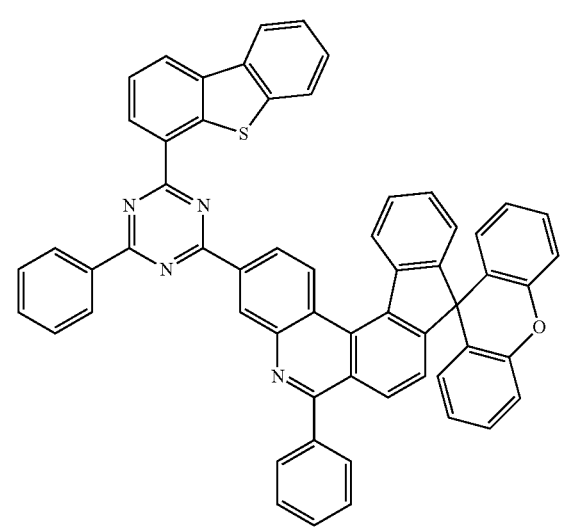
169
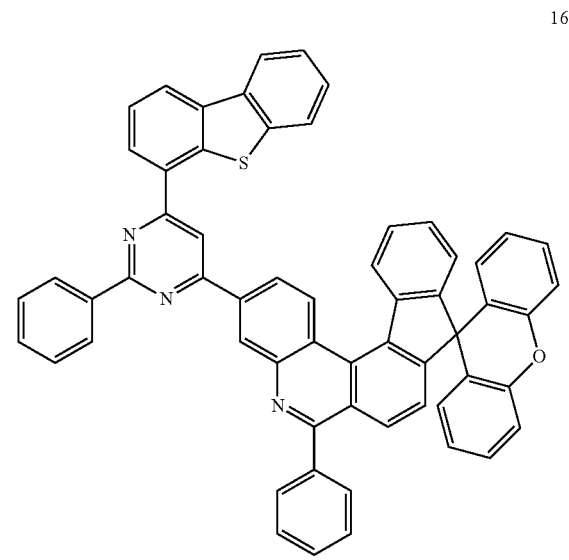
412
-continued
170
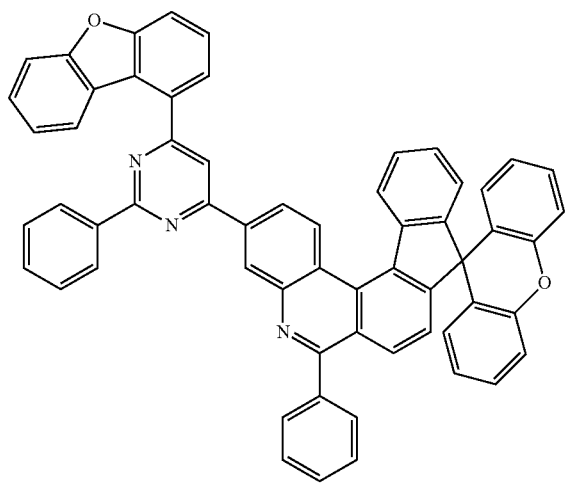
171
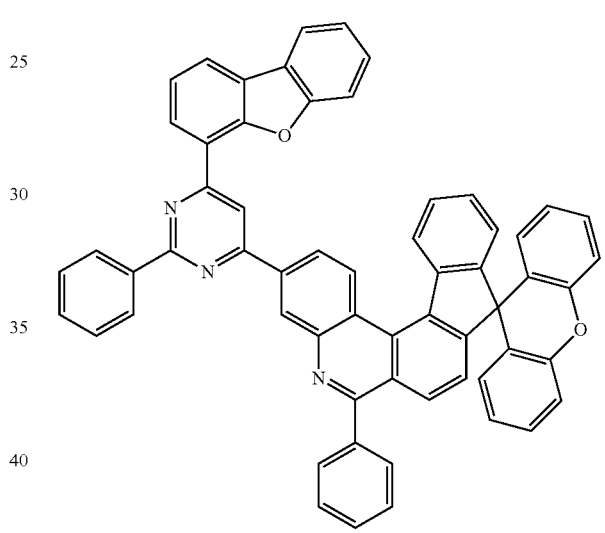
172
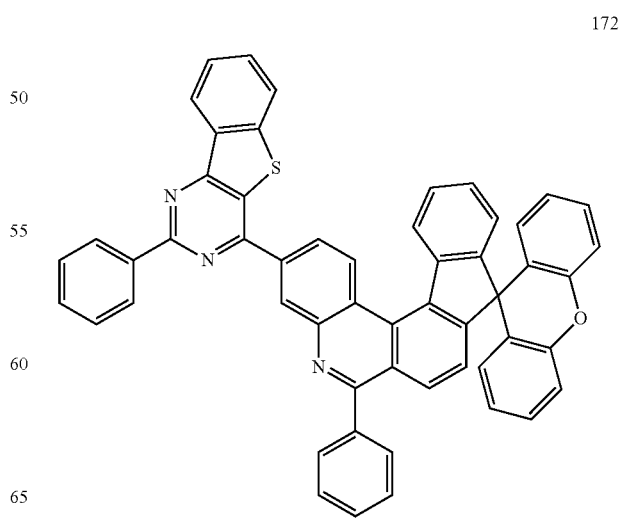

173
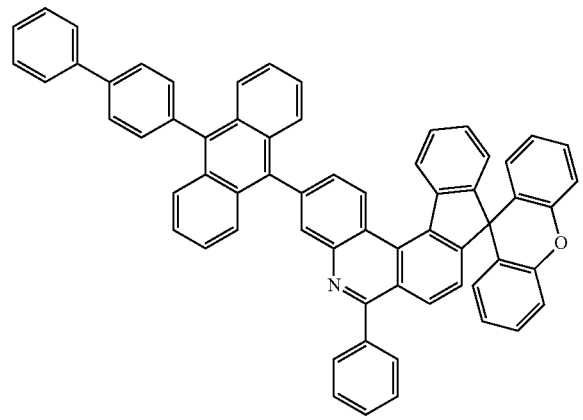
174
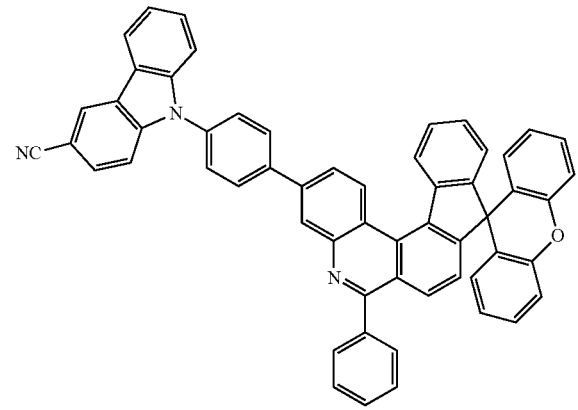
175
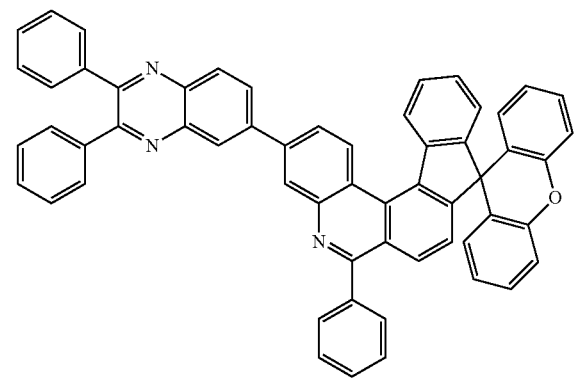
176
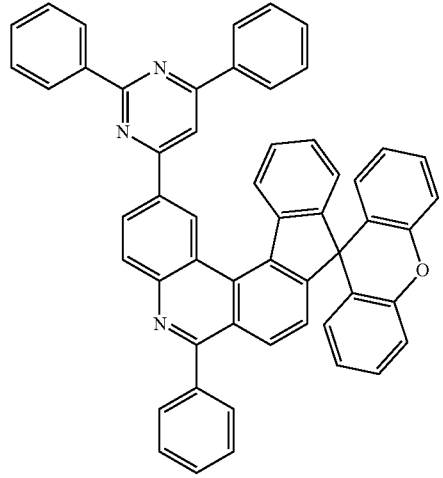
177
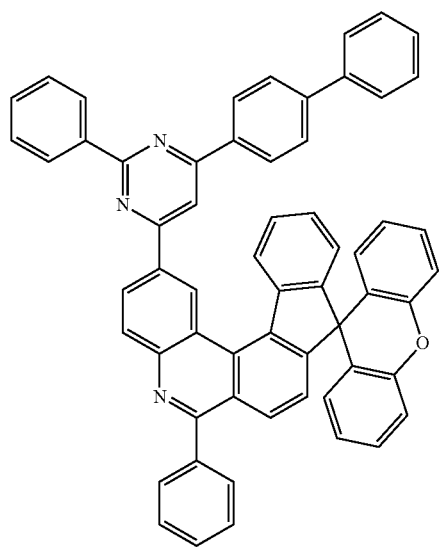
178
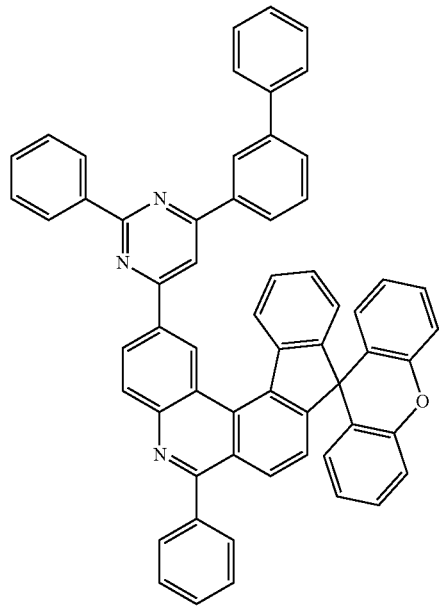

179
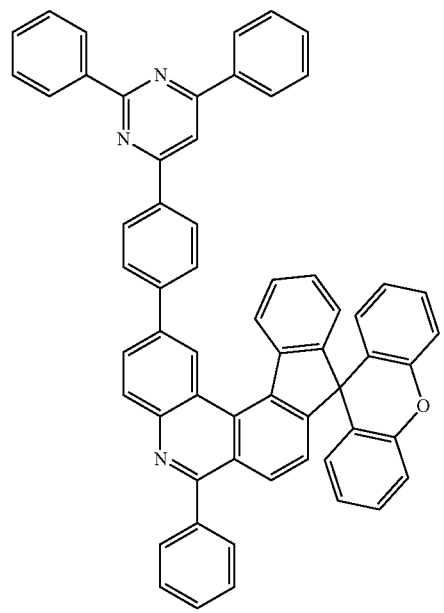 [SMILES: c1ccc(-c2cc(-c3ccc(-c4ccc5nc(-c6ccccc6)c6ccc7c(c6c5c4)-c4ccccc4C74c5ccccc5Oc5ccccc54)cc3)nc(-c3ccccc3)n2)cc1]
180
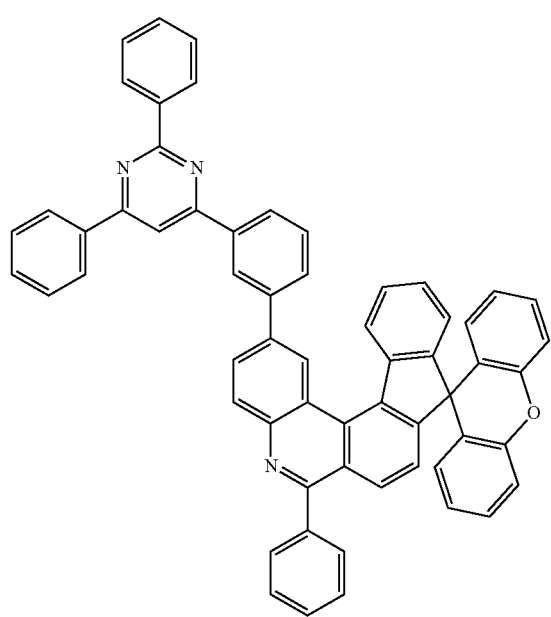
181
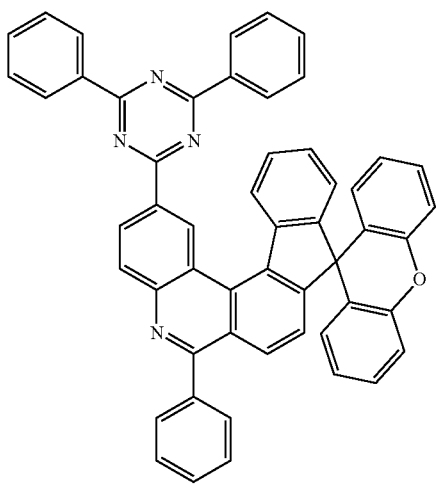
182
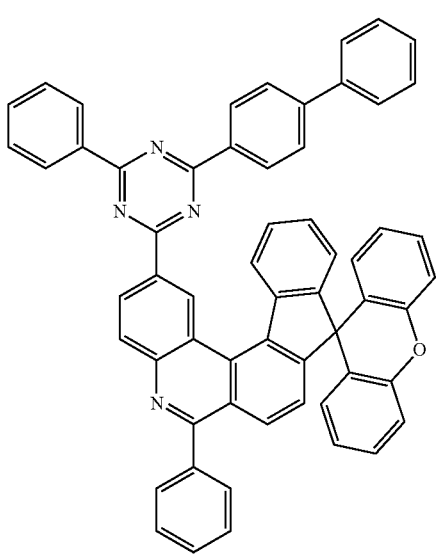
183
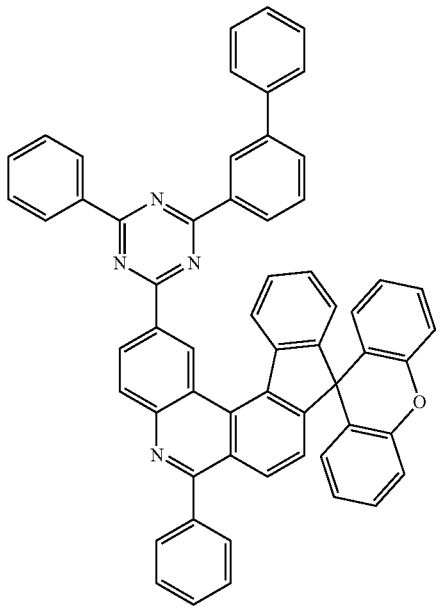 [SMILES: c1ccc(-c2cccc(-c3nc(-c4ccccc4)nc(-c4ccc5nc(-c6ccccc6)c6ccc7c(c6c5c4)-c4ccccc4C74c5ccccc5Oc5ccccc54)n3)c2)cc1]

417
-continued
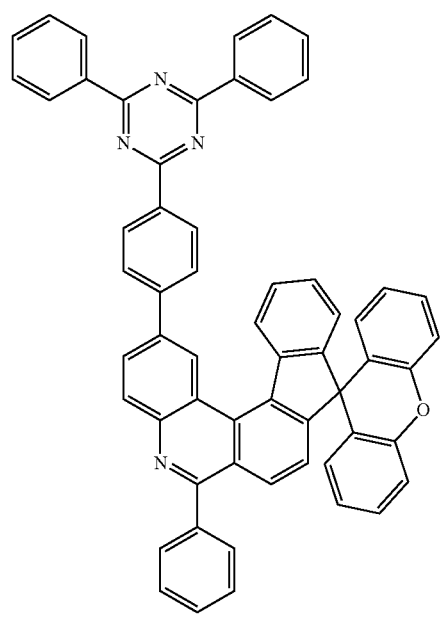
184
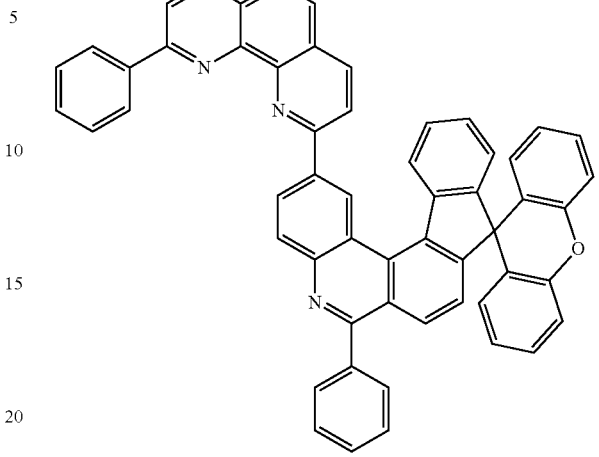
186
185
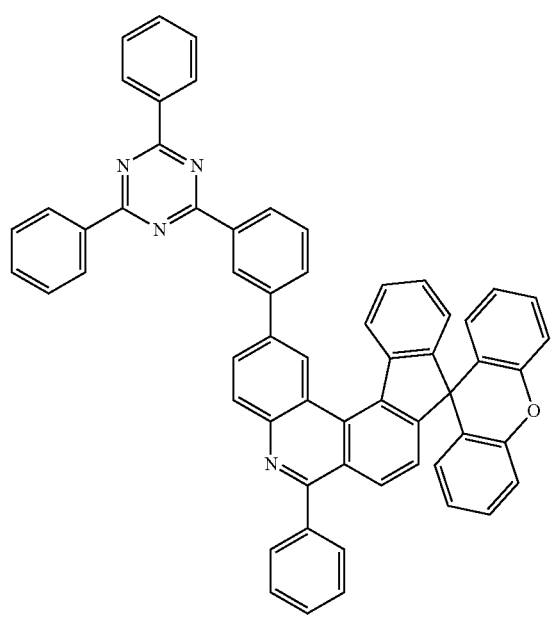
418
-continued
187
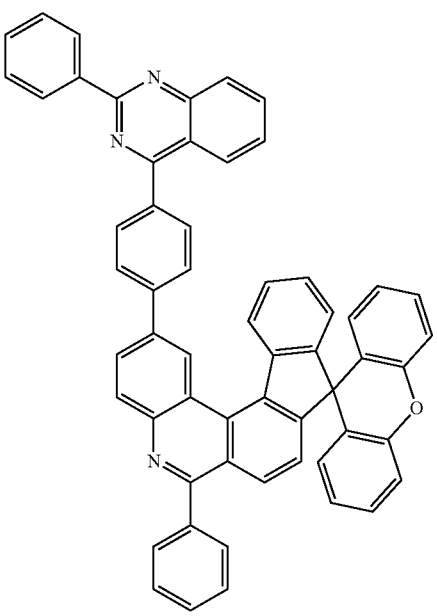

419
-continued
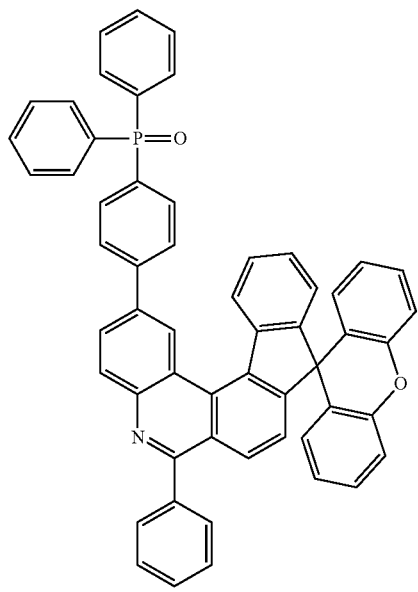
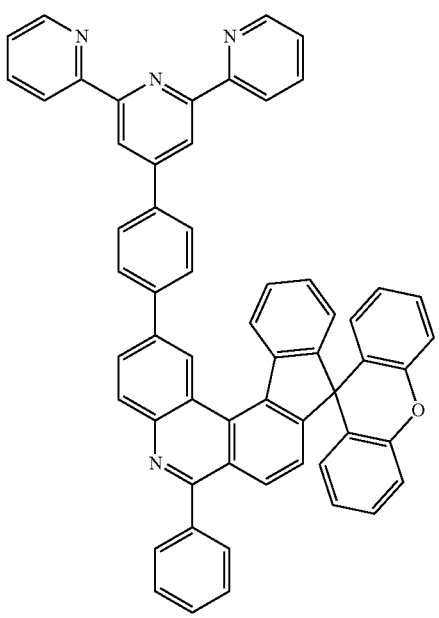
420
-continued
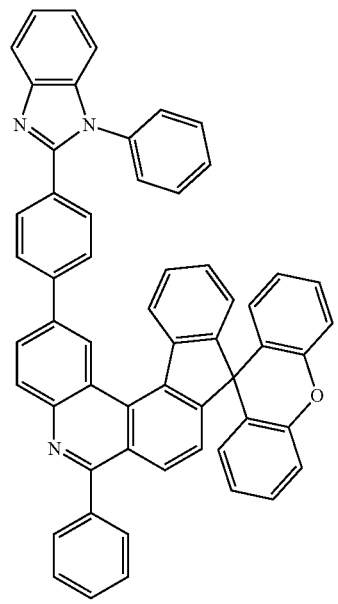
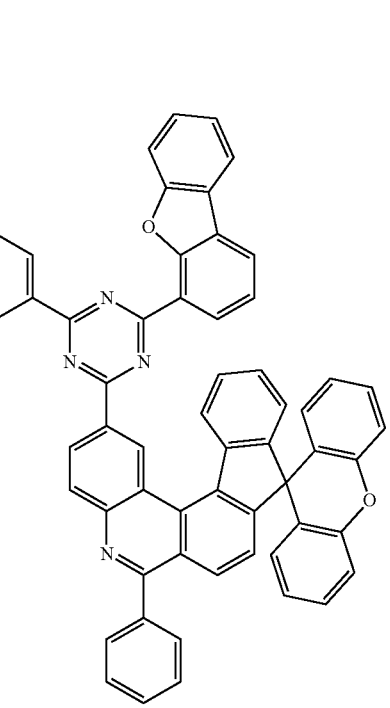

421
-continued
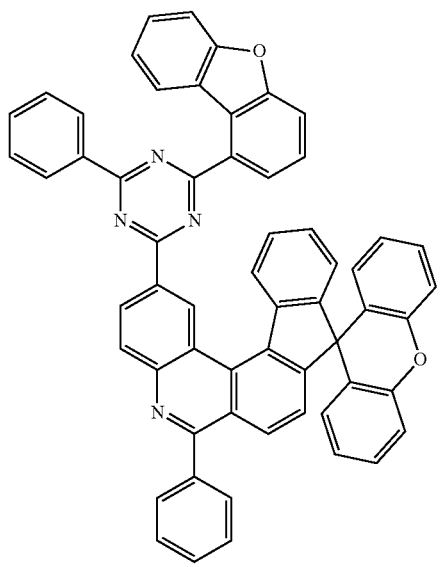
192
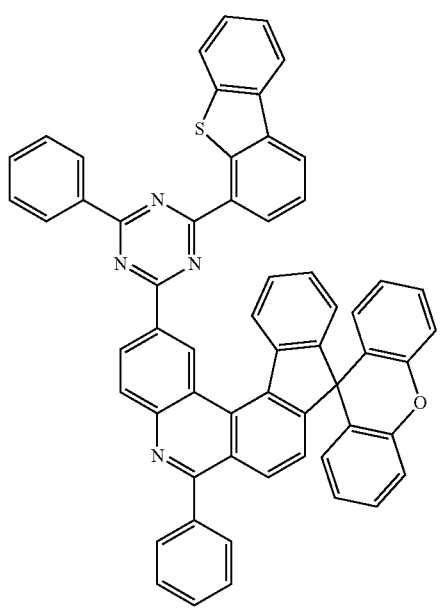
193
422
-continued
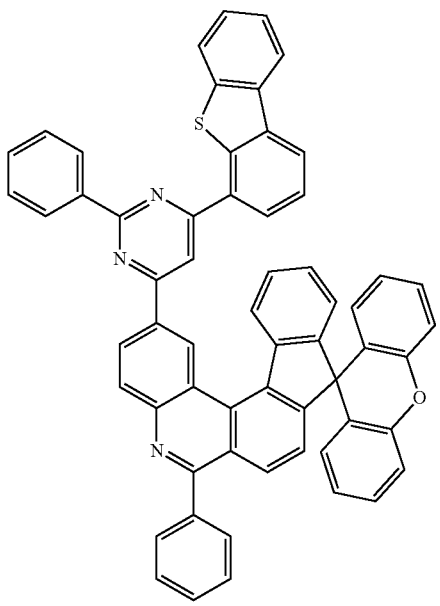
194
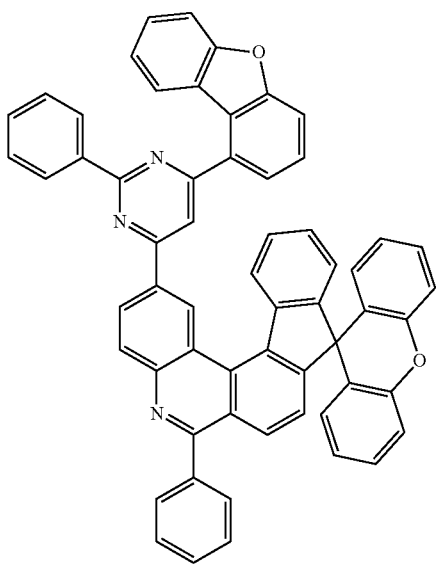
195

423
-continued
196
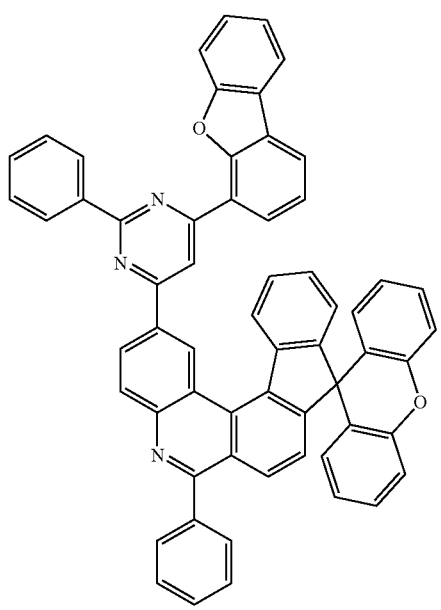
197
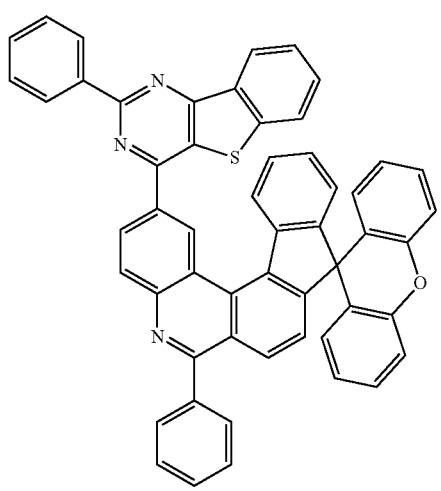
424
-continued
198
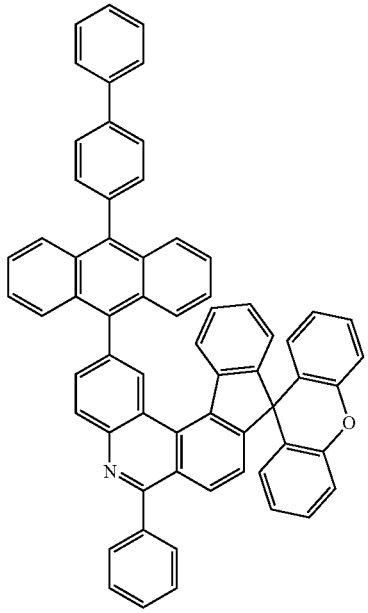 [SMILES: c1ccc(-c2ccc(-c3c4ccccc4c(-c4ccc5nc(-c6ccccc6)c6ccc7c(c6c5c4)-c4ccccc4C74c5ccccc5Sc5ccccc54)c4ccccc34)cc2)cc1]
199
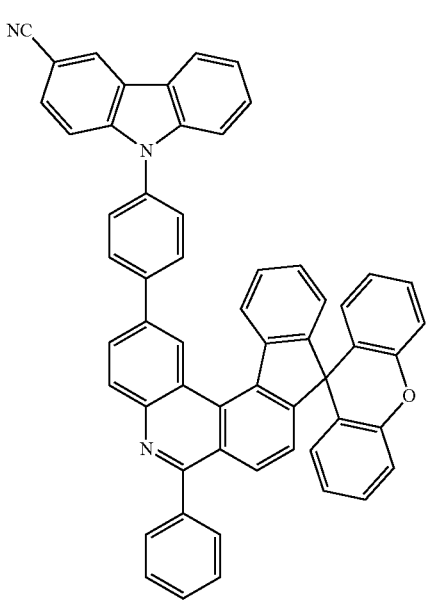

200
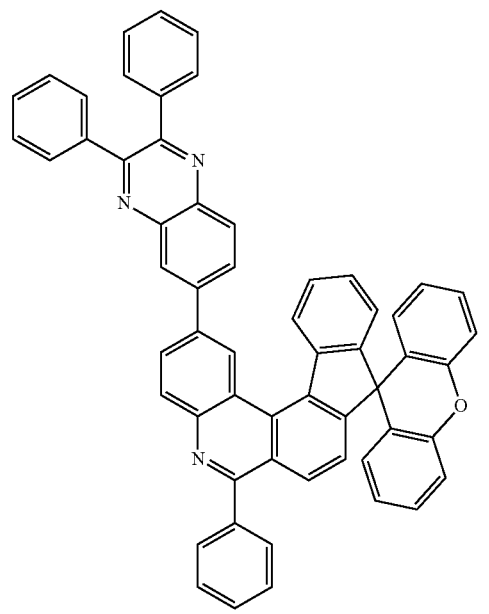
201
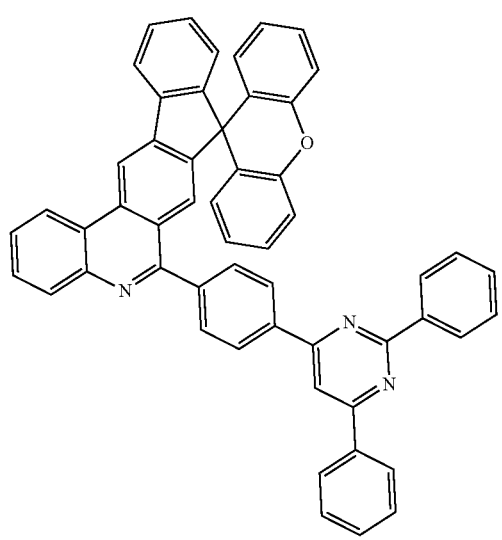
202
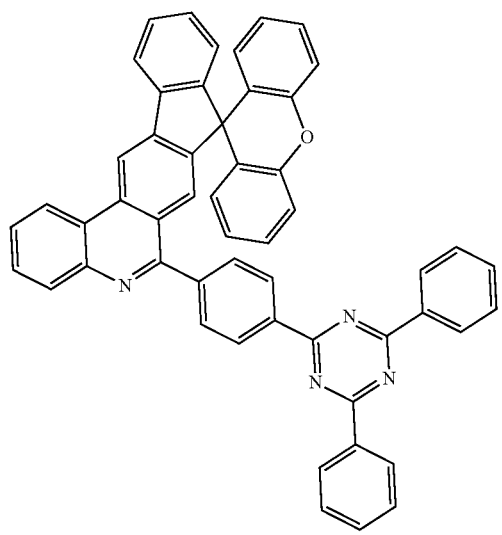
203
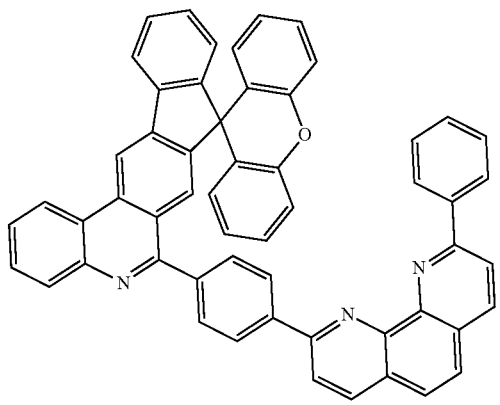
204
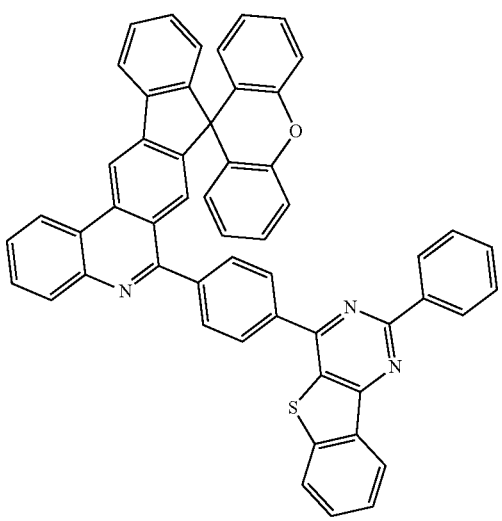
205
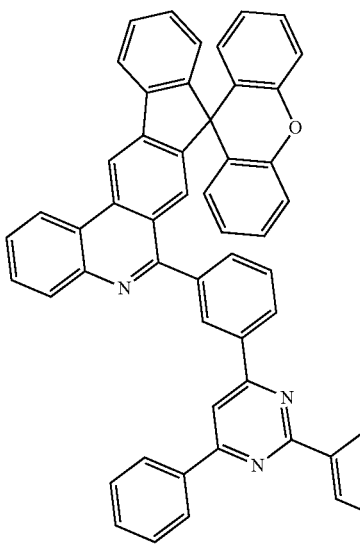

427
-continued
206
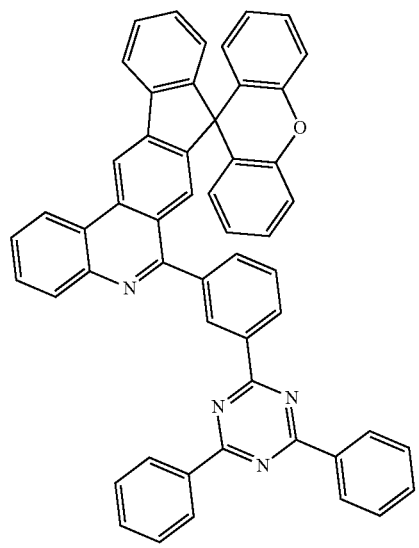
207
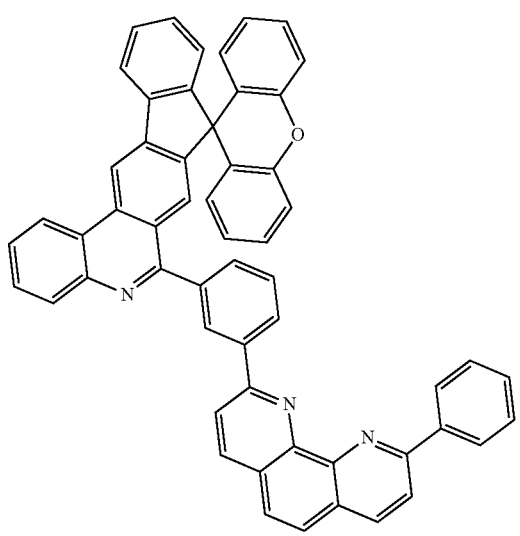
208
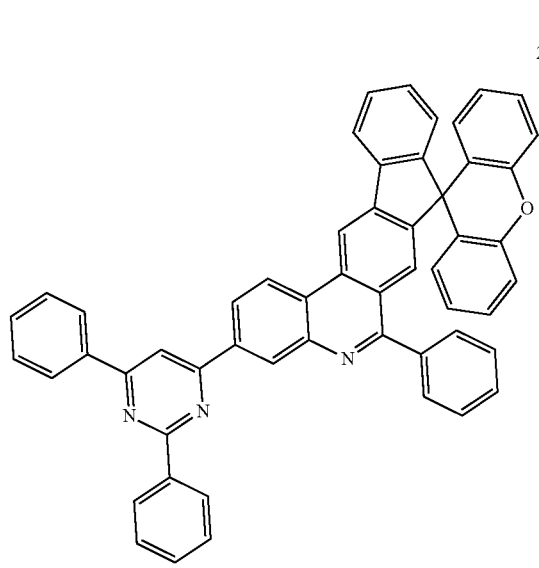
428
-continued
209
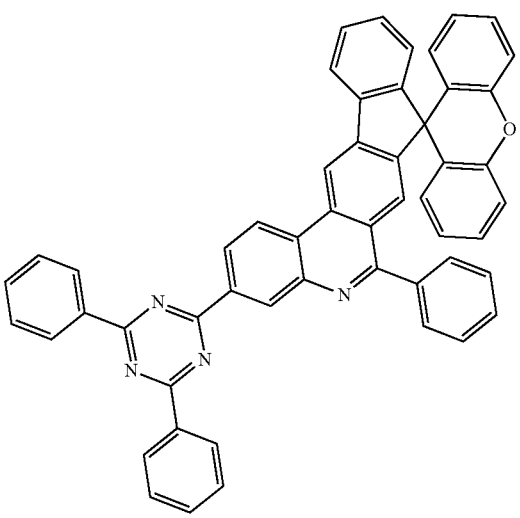
210
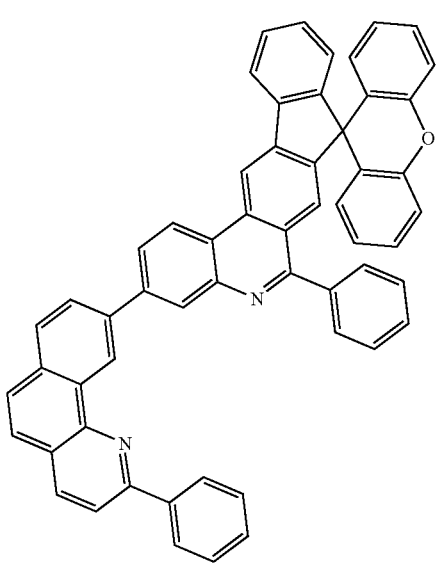
211
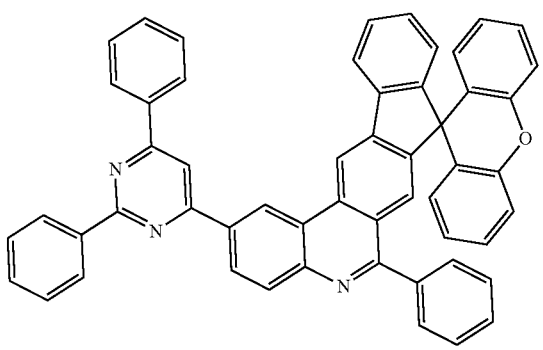

212
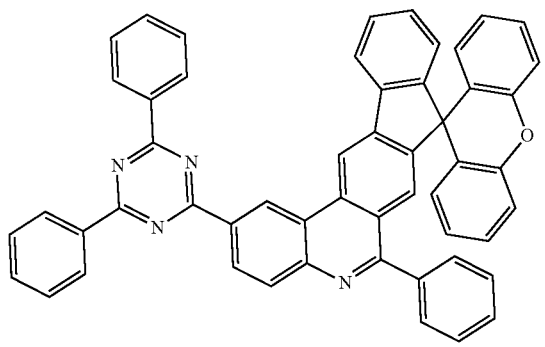
213
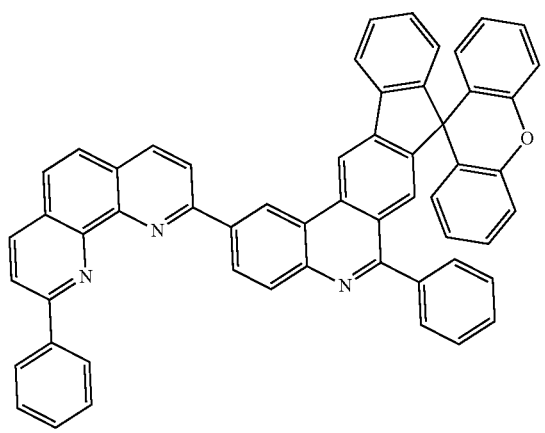
214
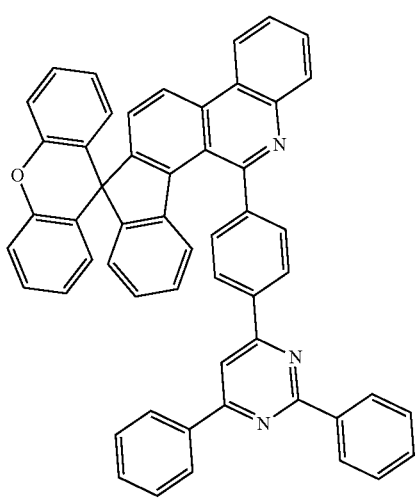
215
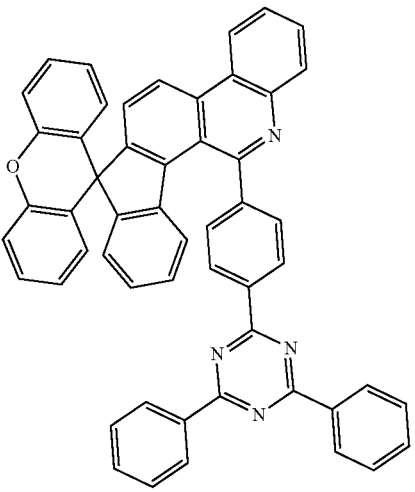
216
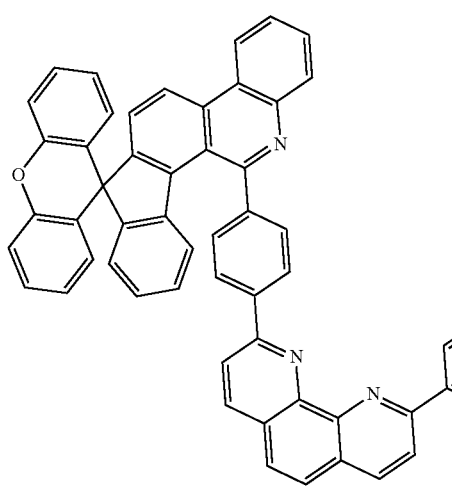
217
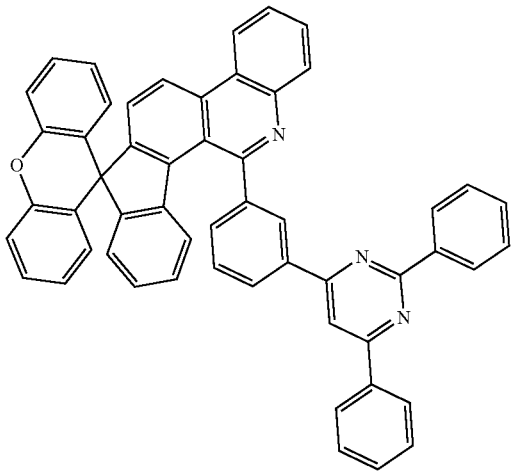

218
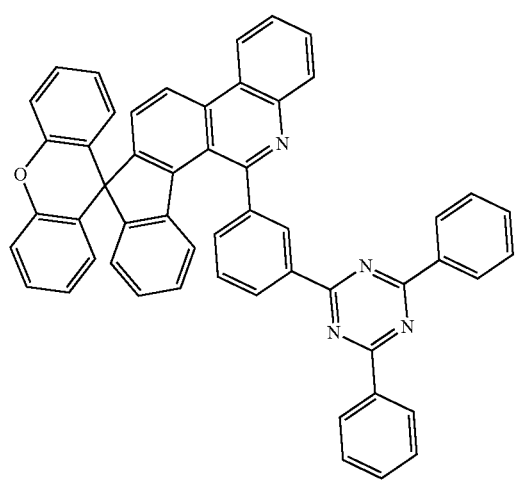
219
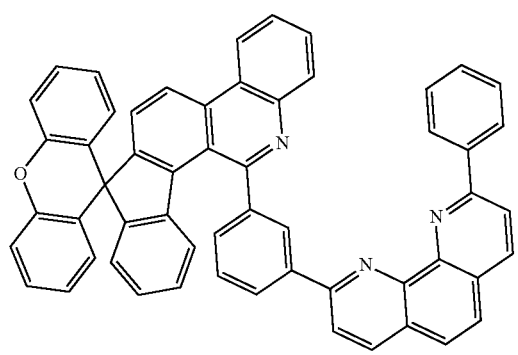
220
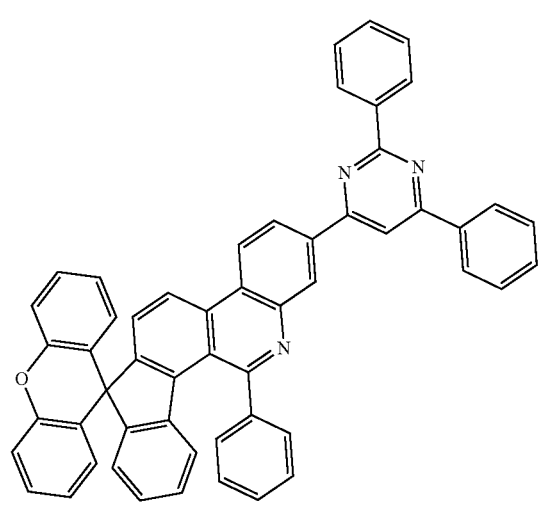
221
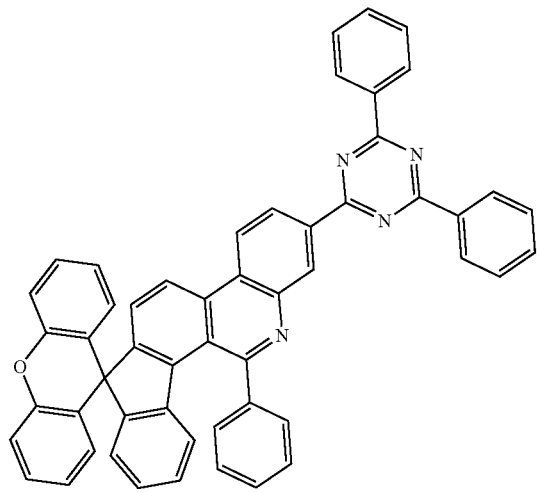
222
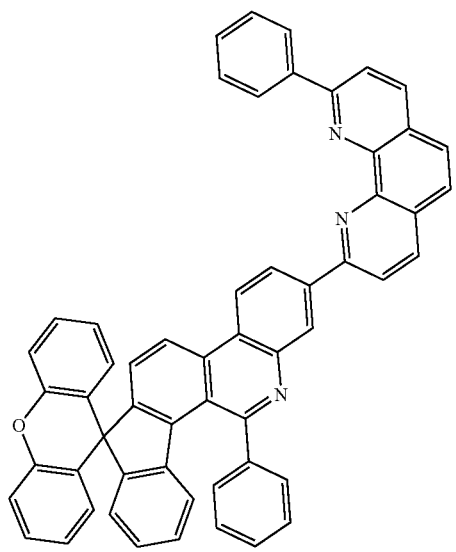
223
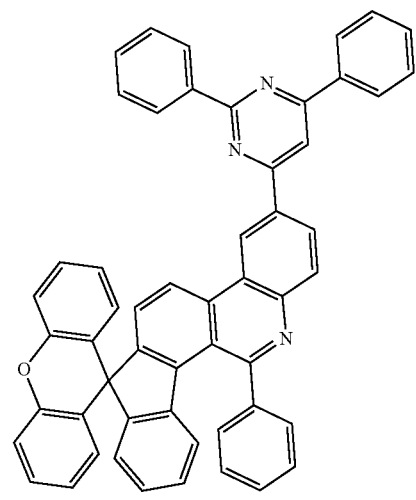

224
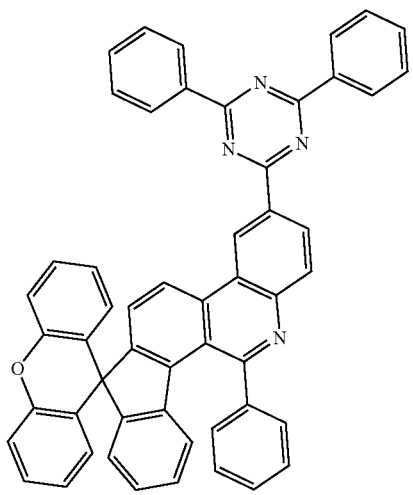
225
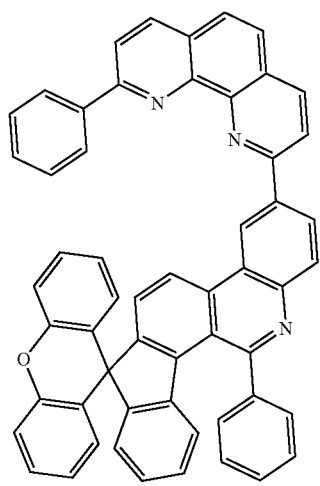
226
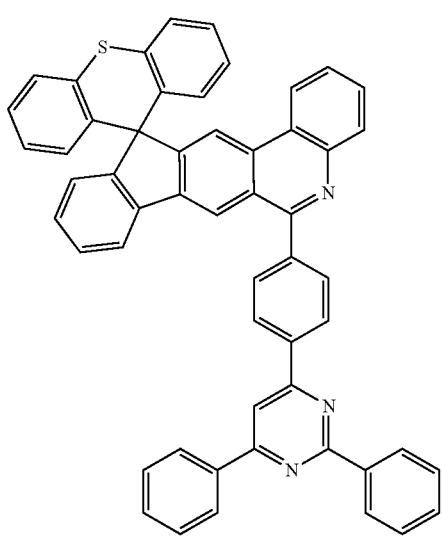
227
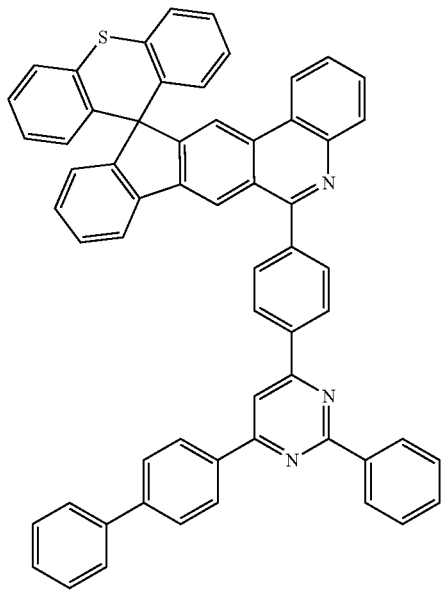
228
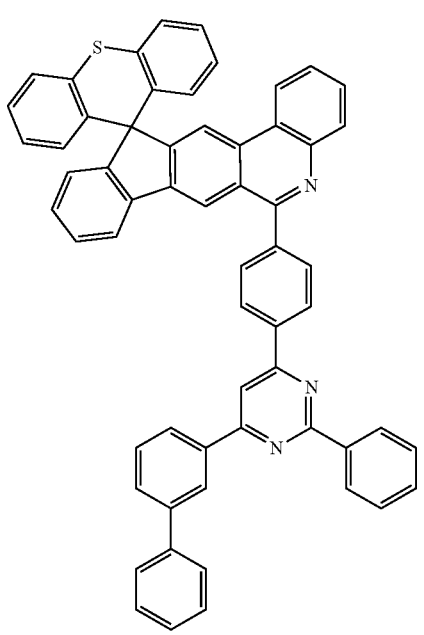

435
-continued
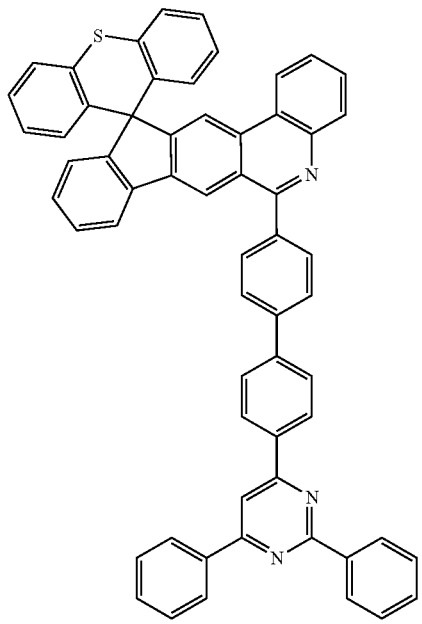
229
436
-continued
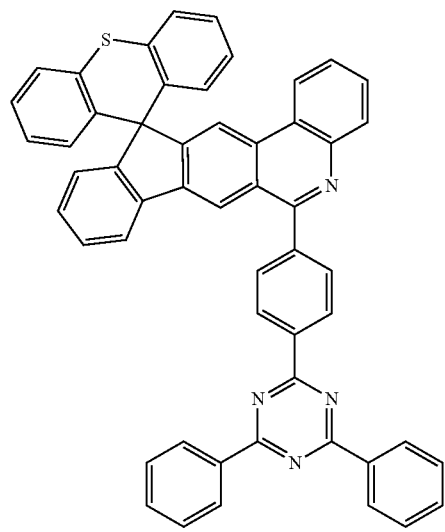
231
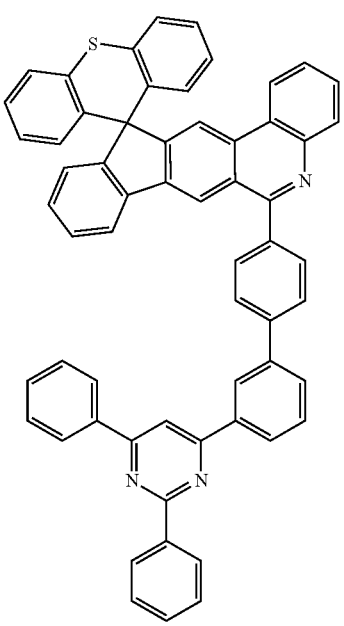
230
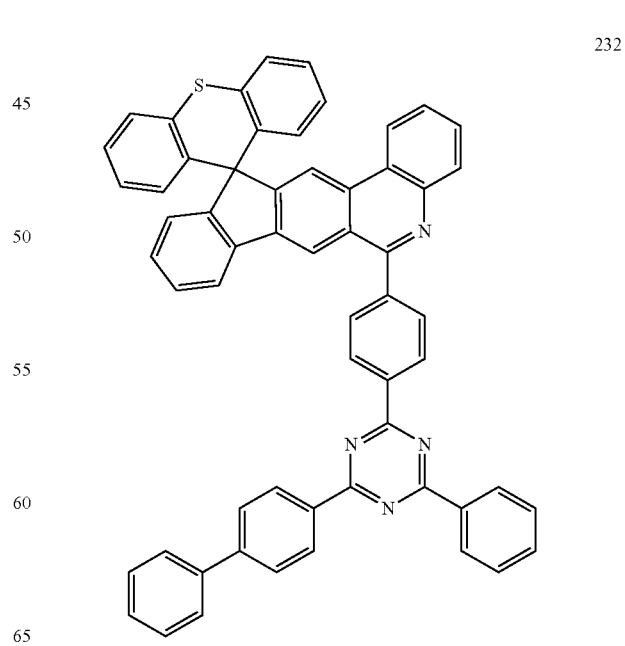
232

437
-continued
233
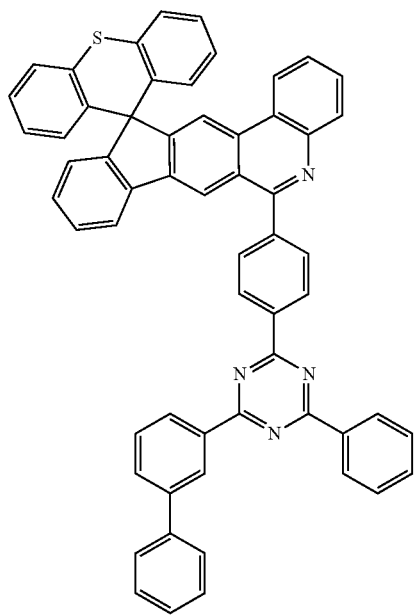
234
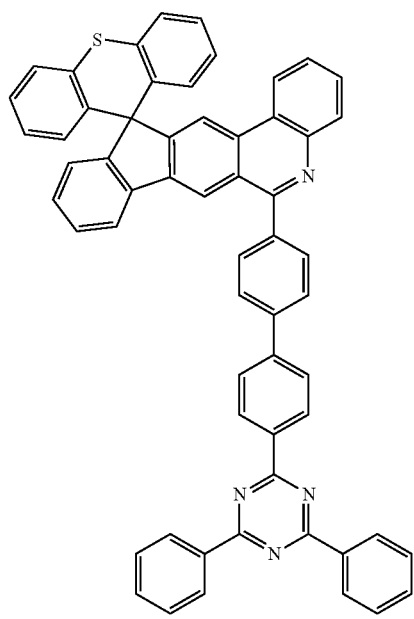
438
-continued
235
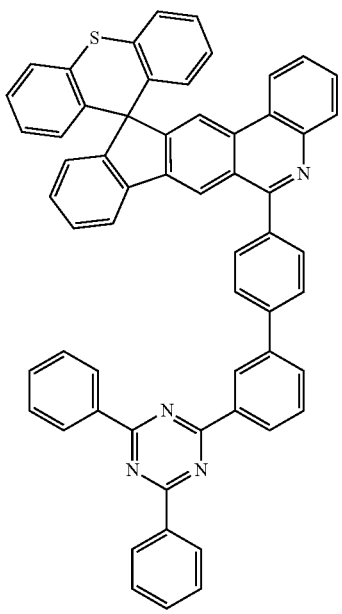
236
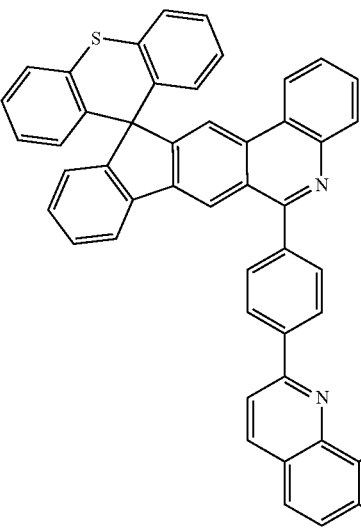

439
-continued
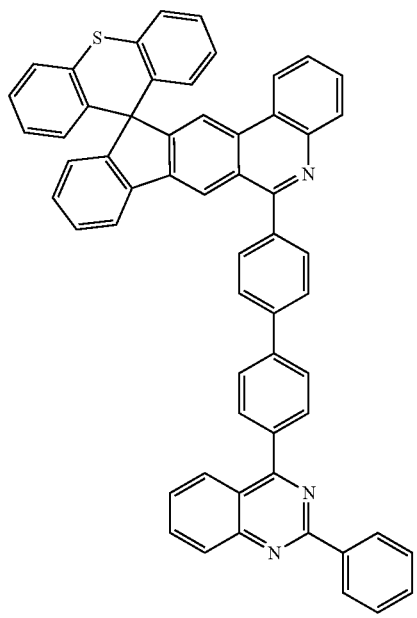
237
438
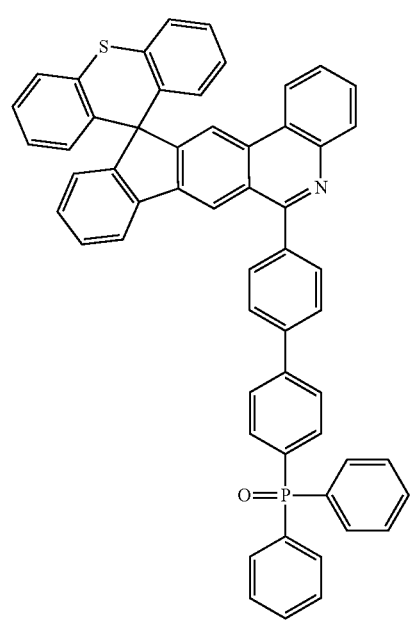
440
-continued
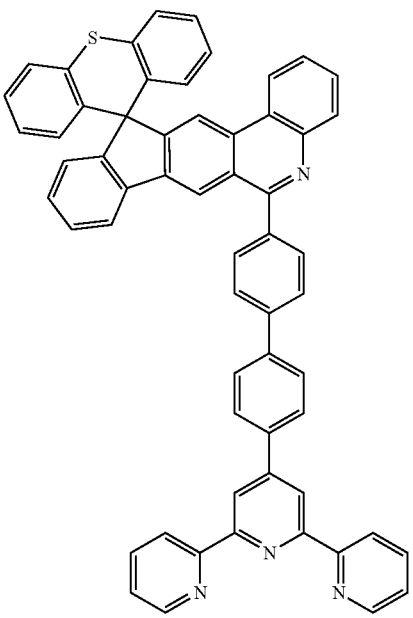
239
240
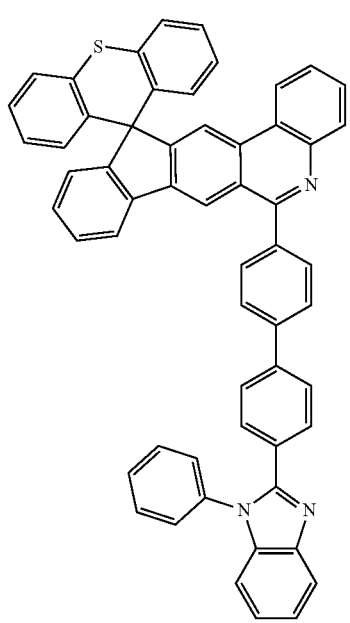

441
-continued
442
-continued
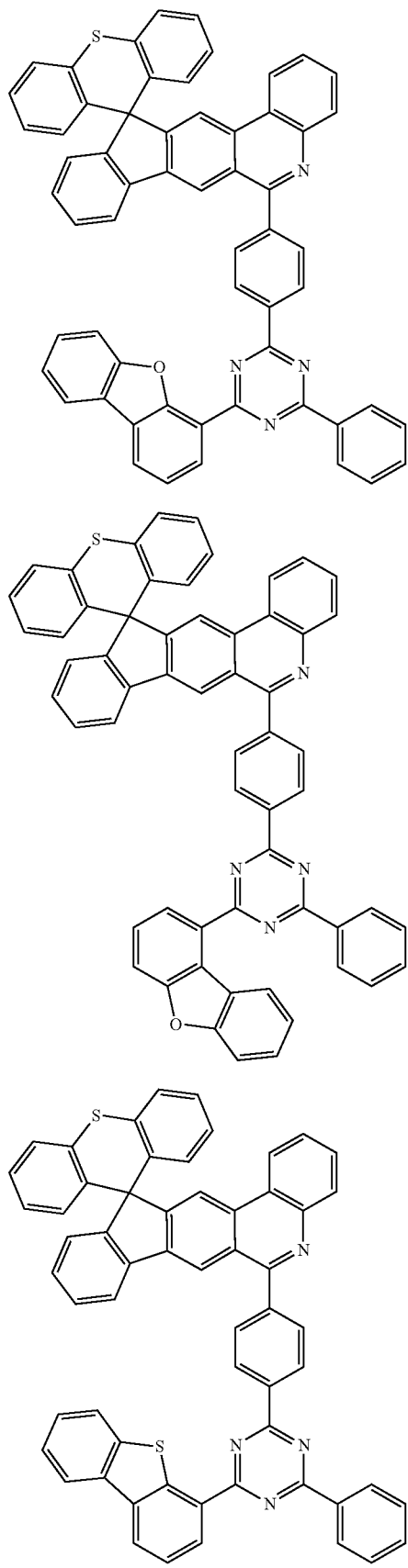
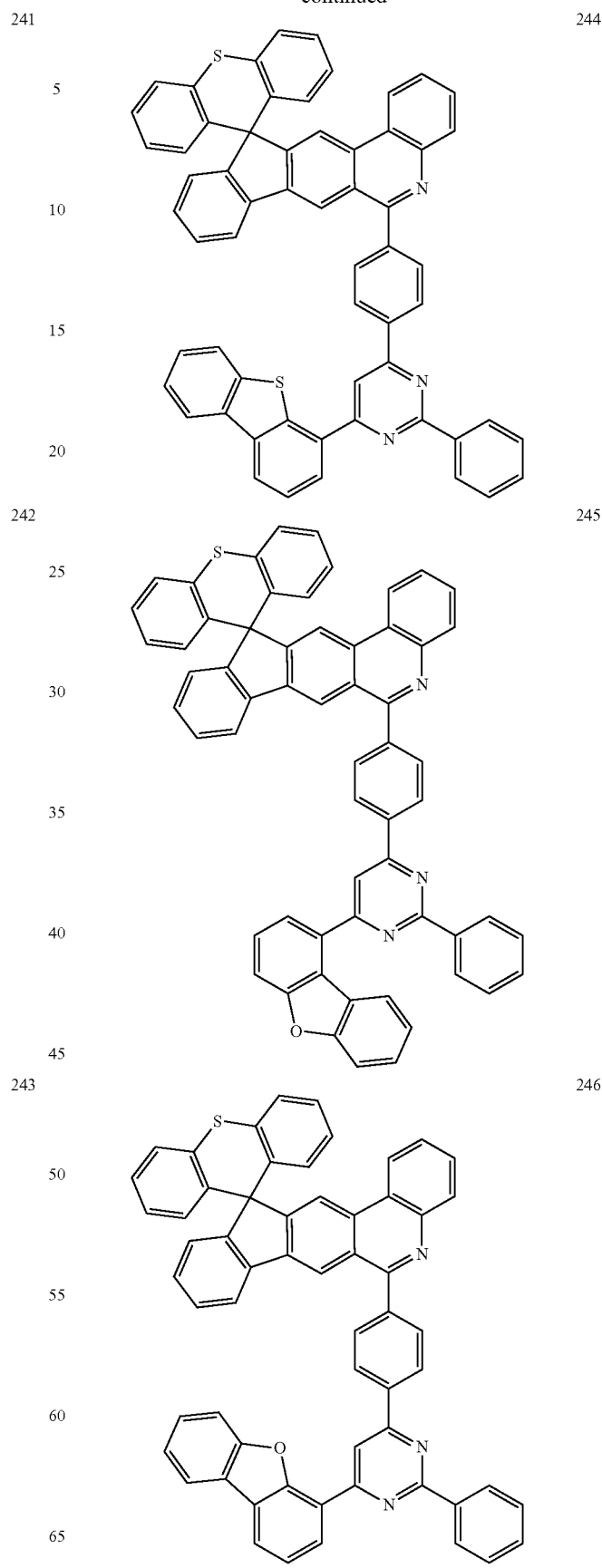

-continued
247
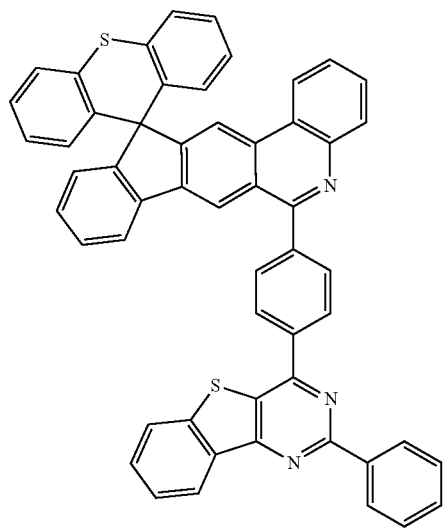
248
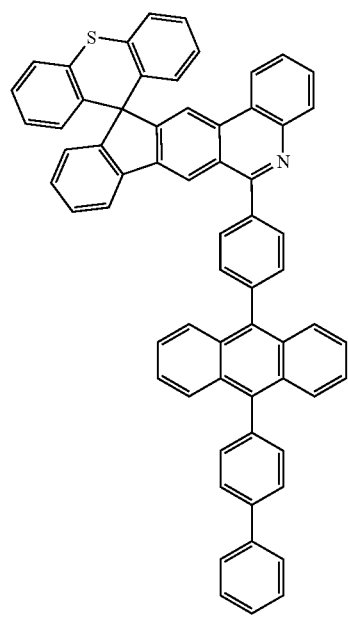
-continued
249
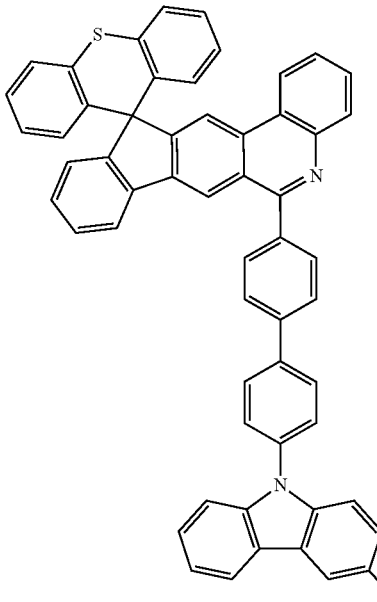
250
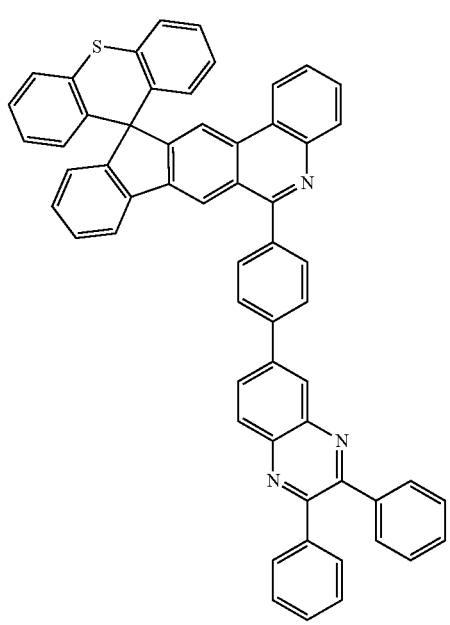

251
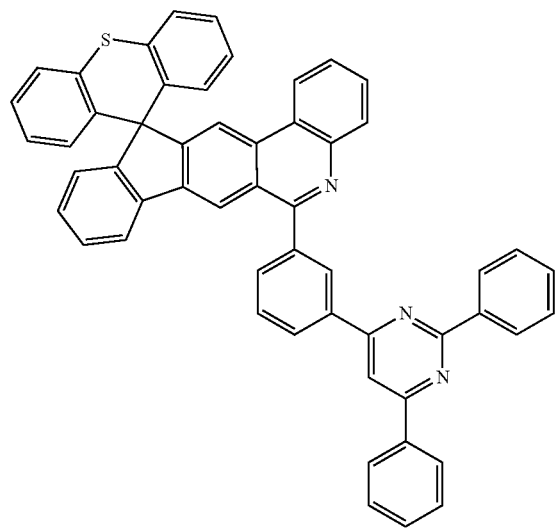
253
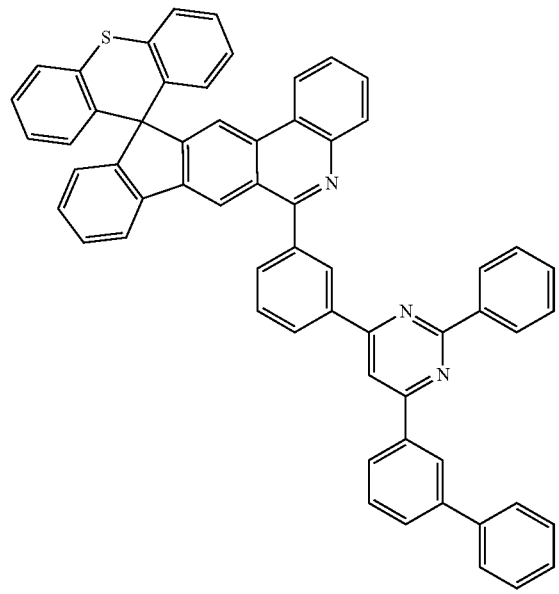
252
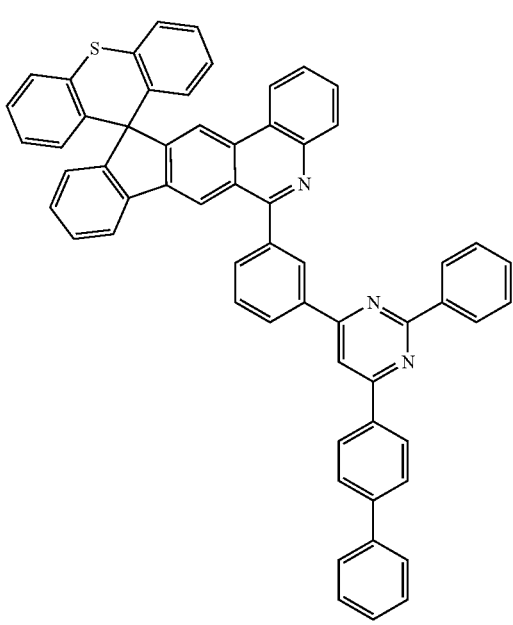
254
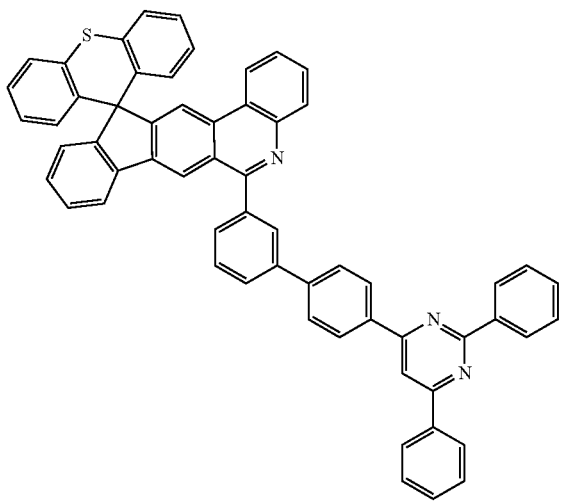

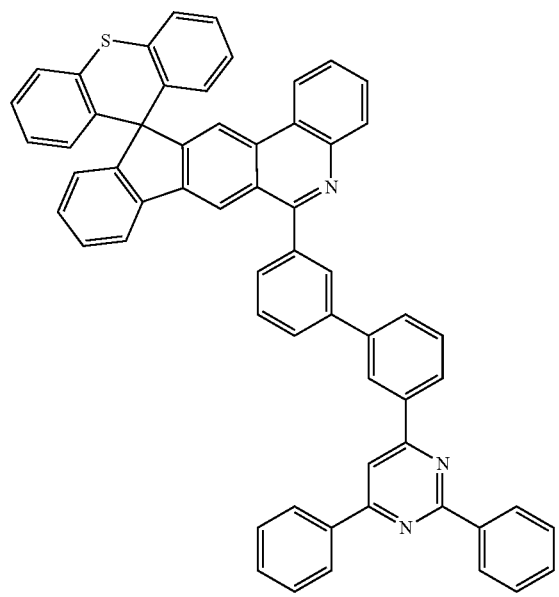
255
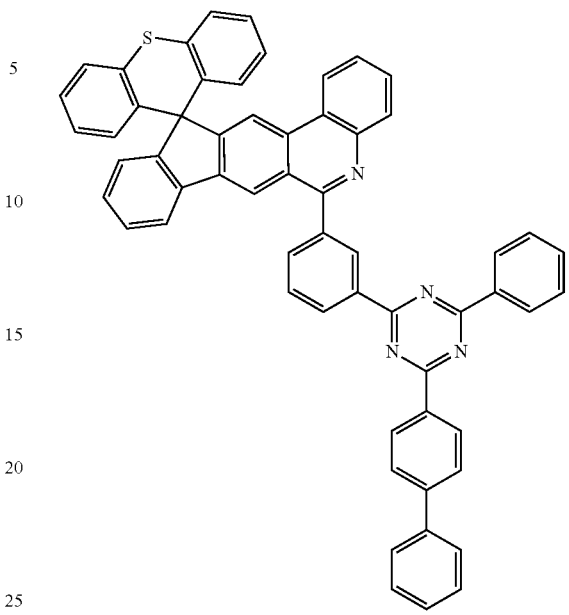
257
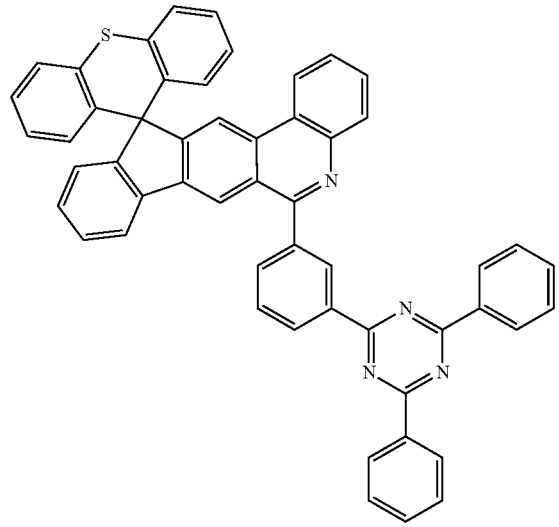
256
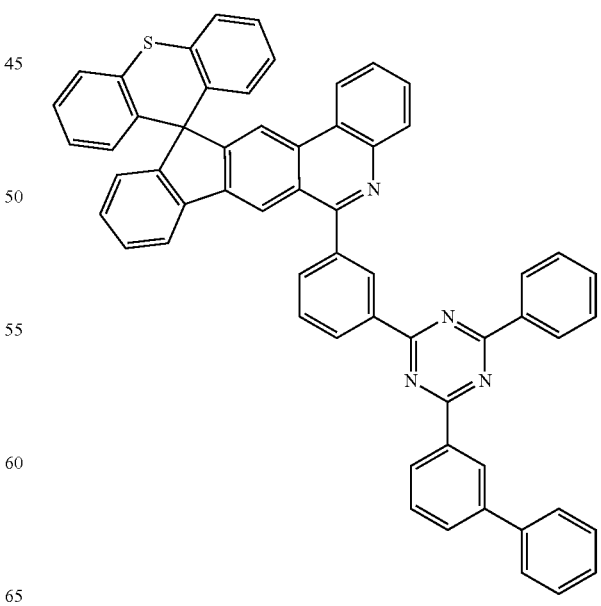
258

259
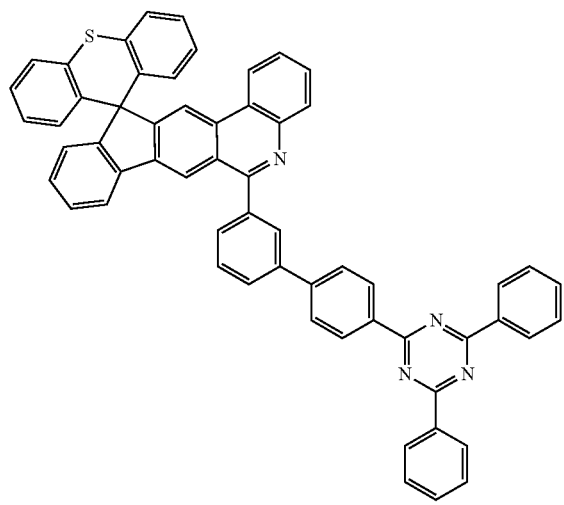
260
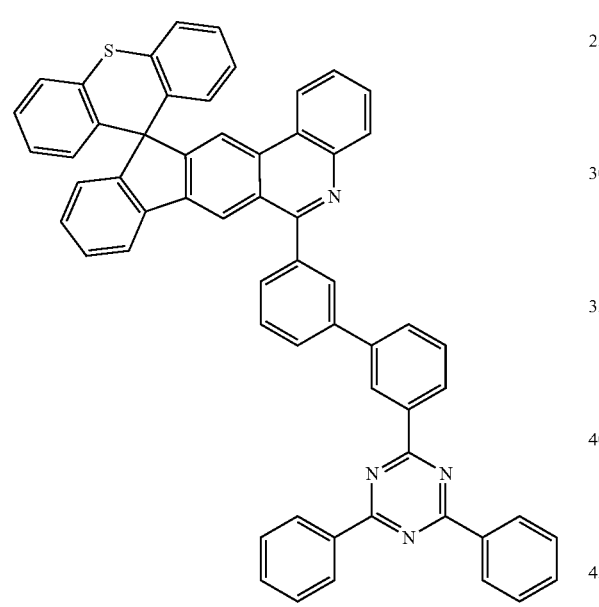
261
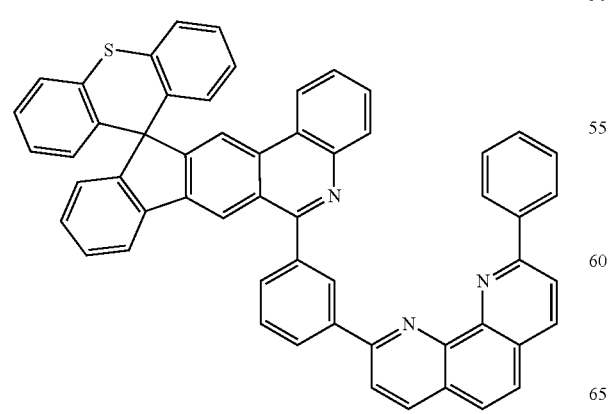
262
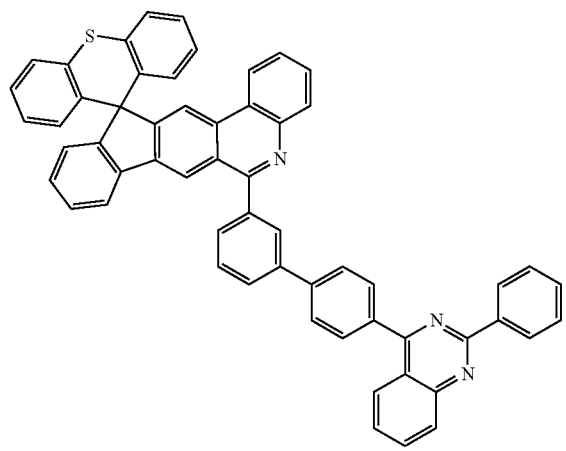
263
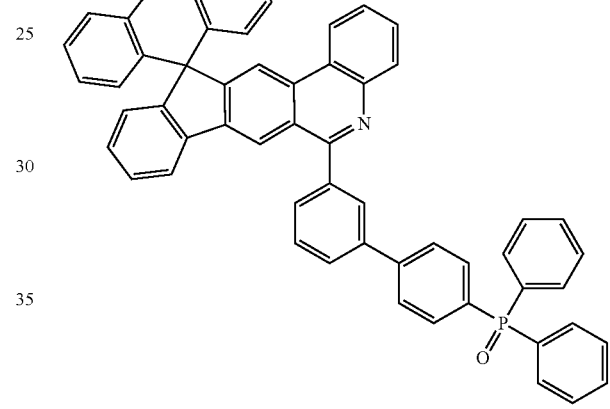
264
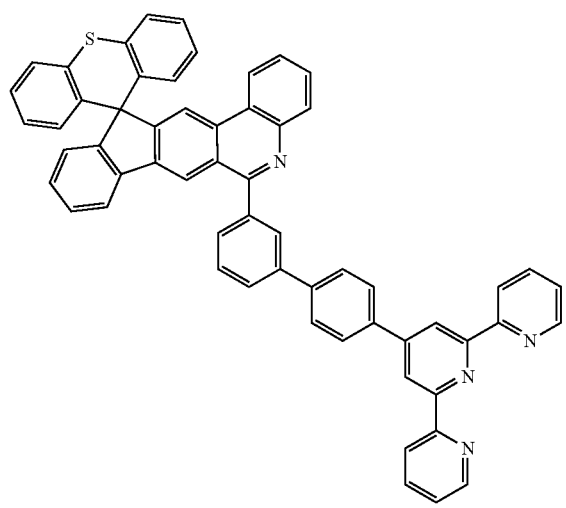

451
-continued
265
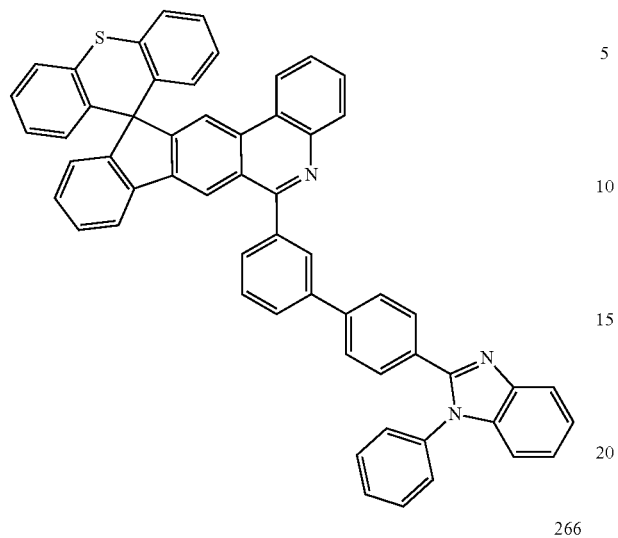
266
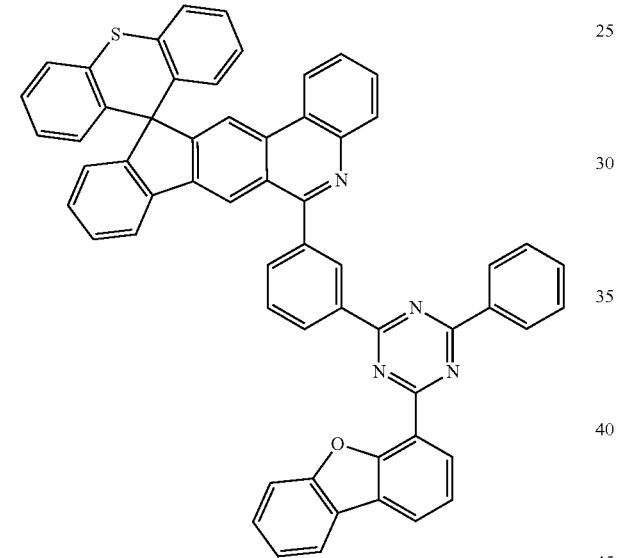
267
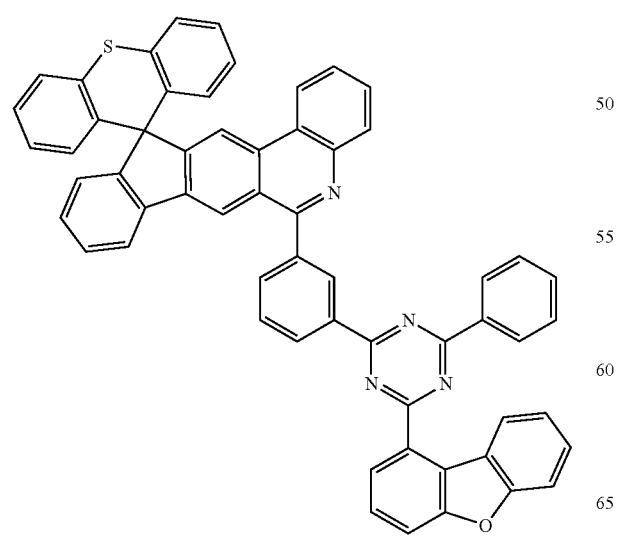
452
-continued
268
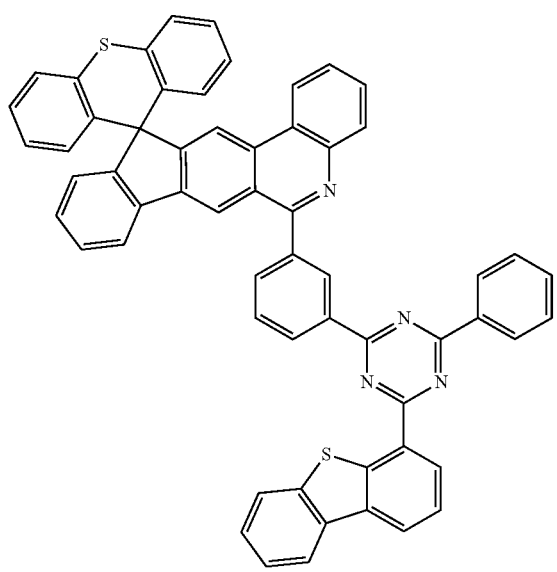
269
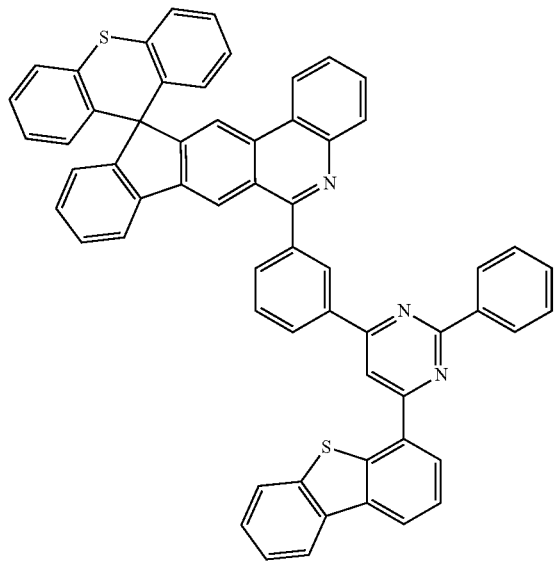

453
-continued
270
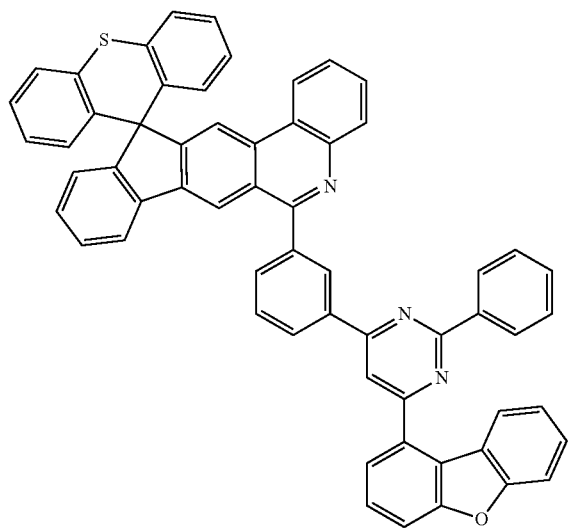
271
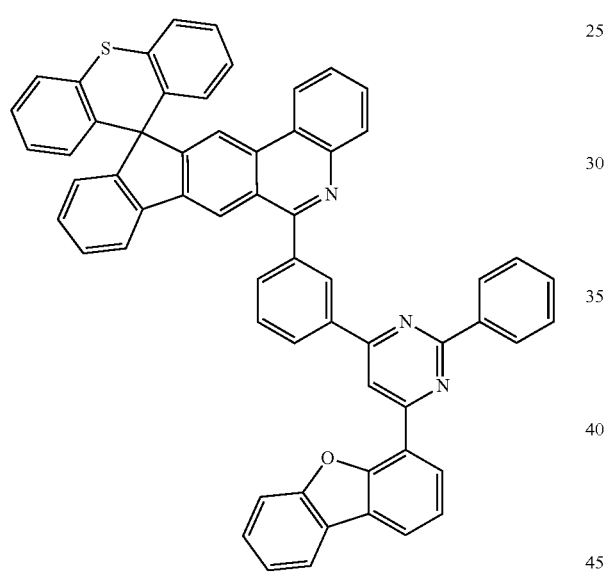
272
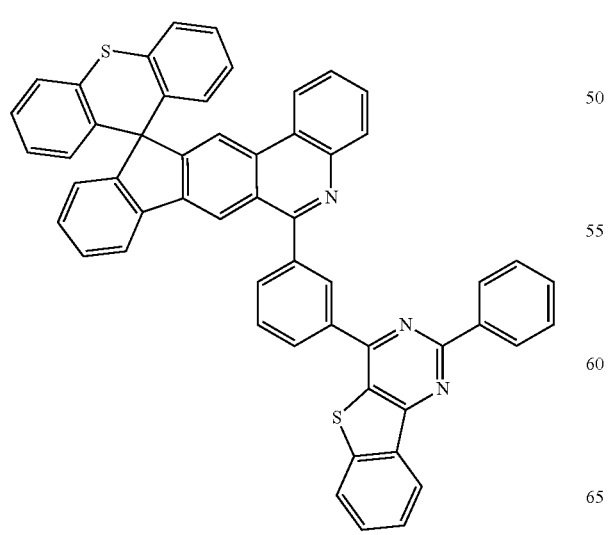
454
-continued
273
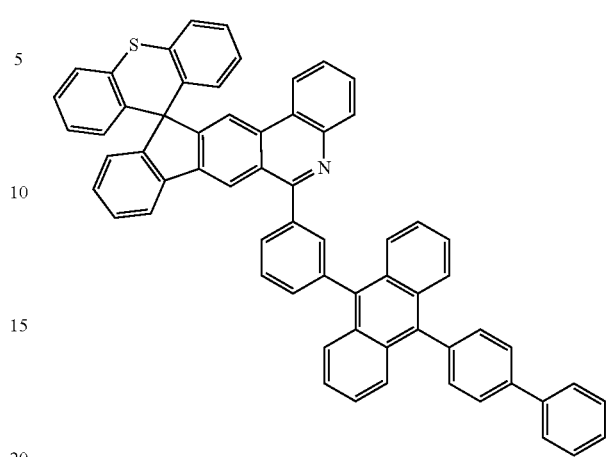
274
275
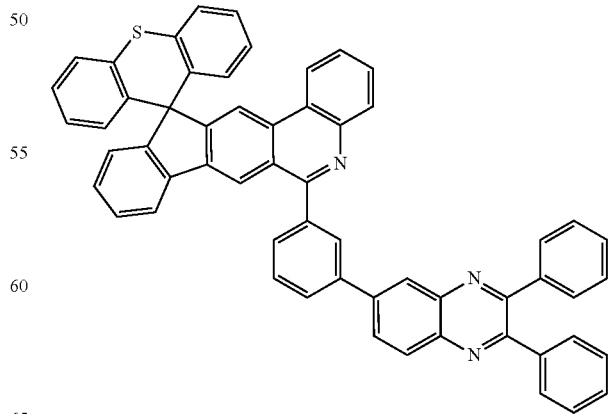

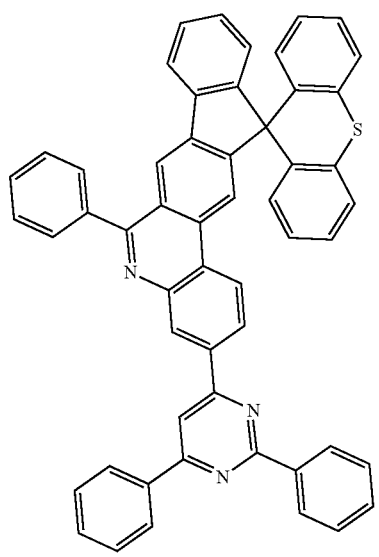
276
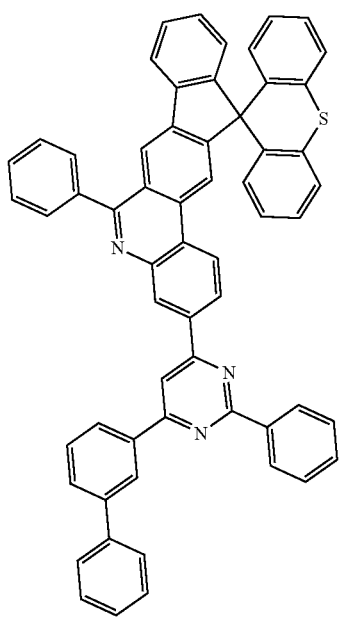
278
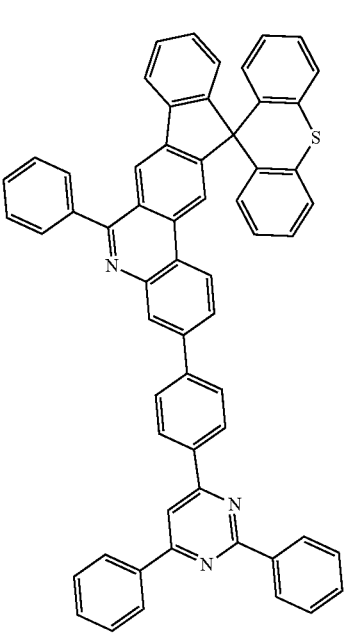
279

457
-continued
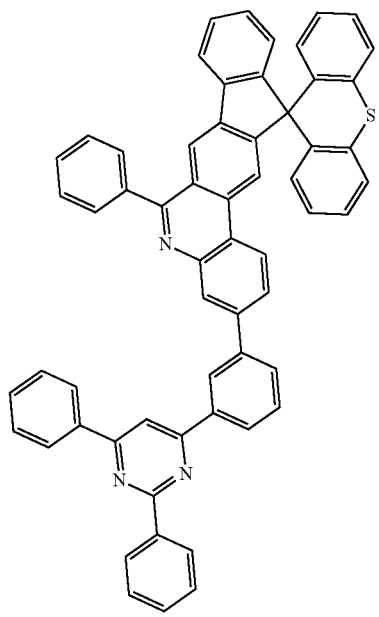
280
281
458
-continued
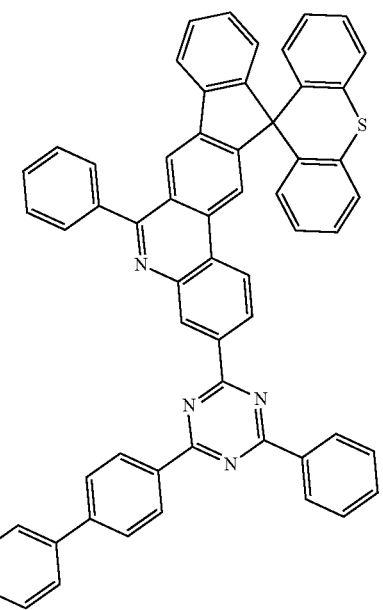
282
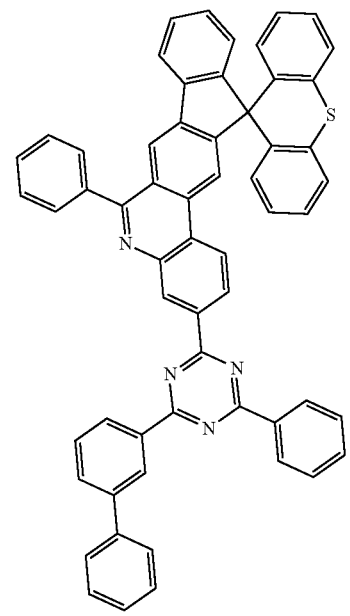
283

459
-continued
284
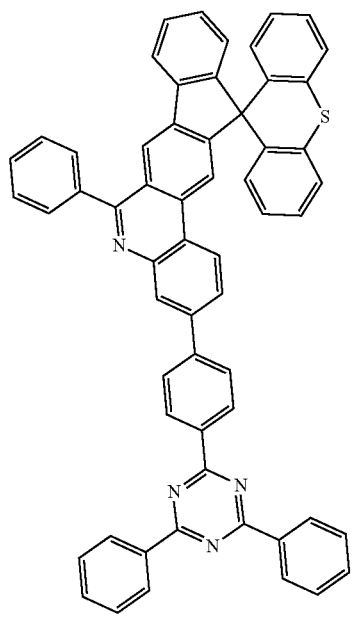
285
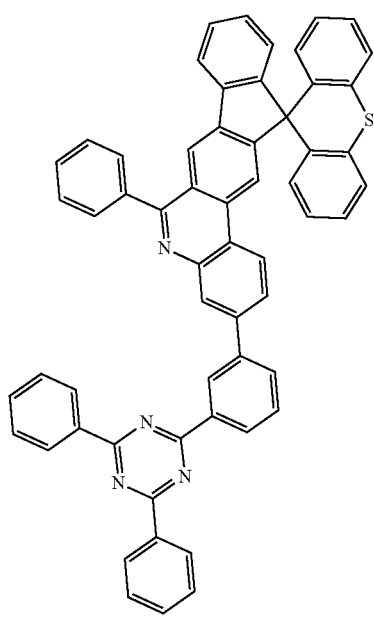
460
-continued
286
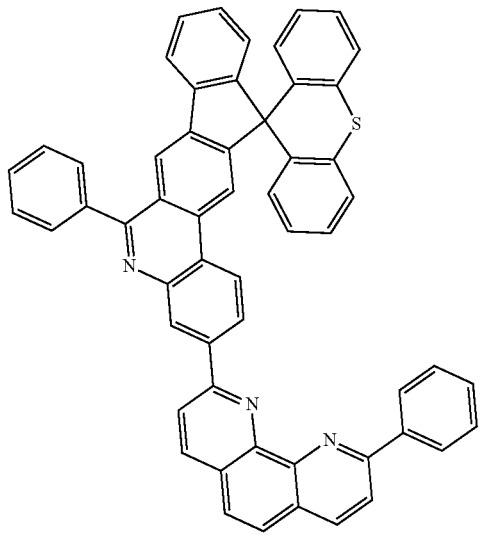
287
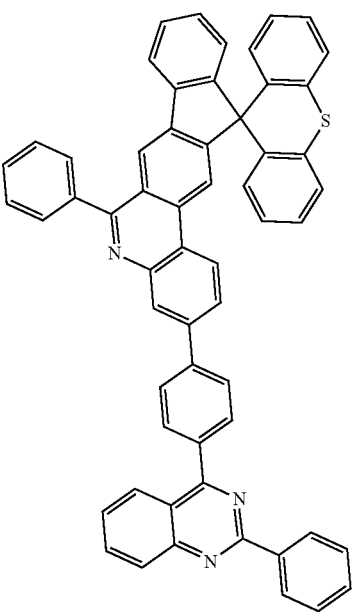

-continued
288
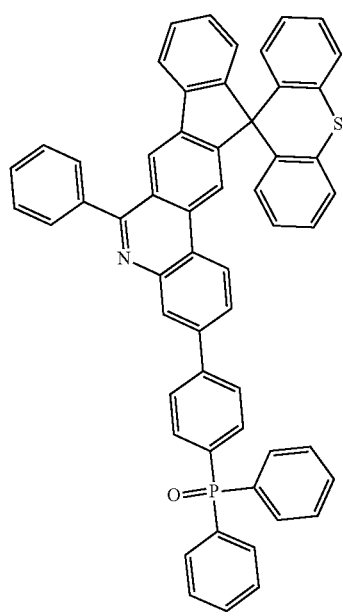
-continued
290
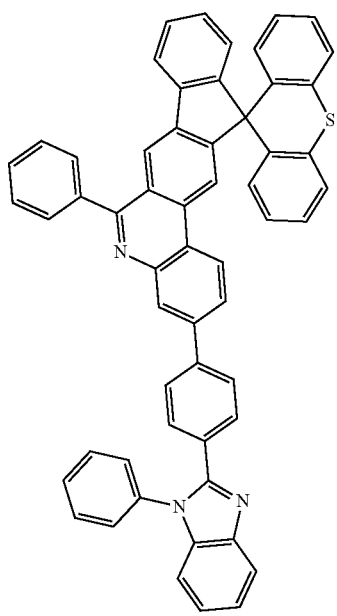
289
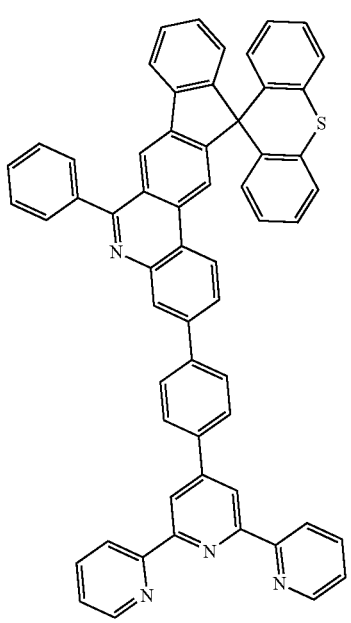
291
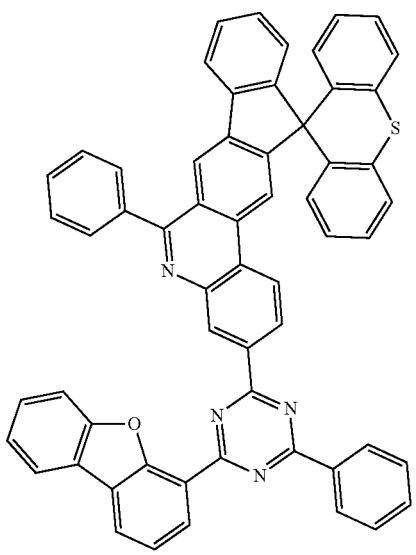

-continued
292
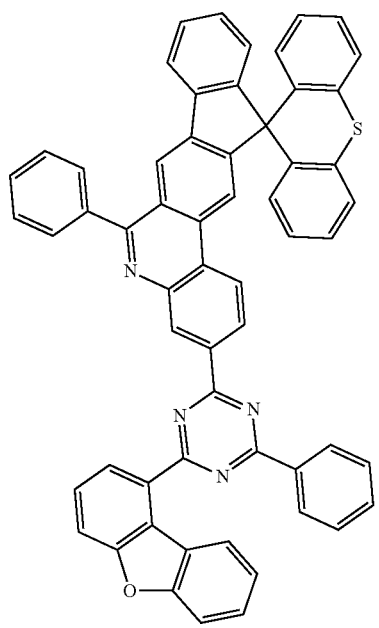
293
-continued
294
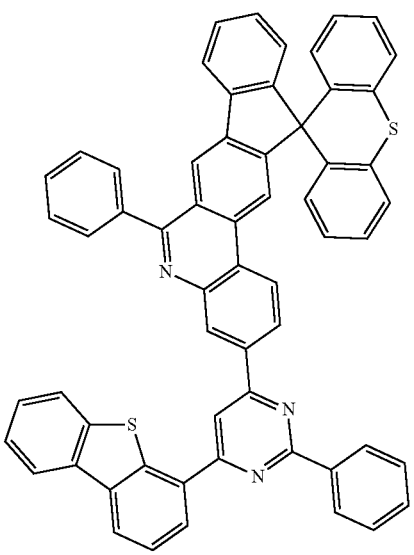
295

296
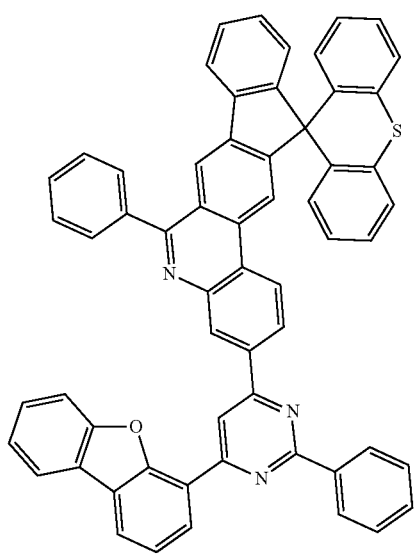
297
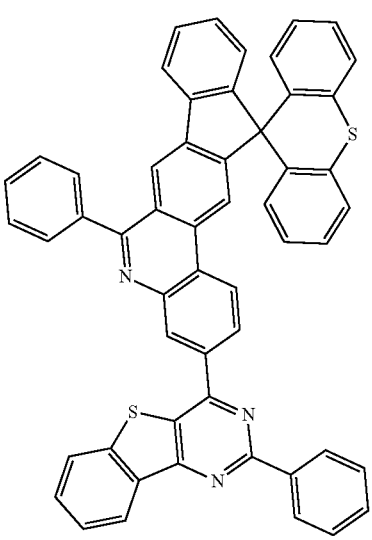
298
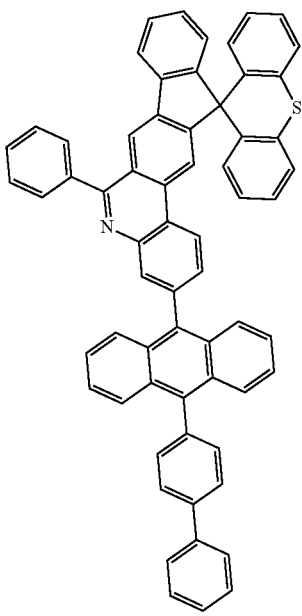
299
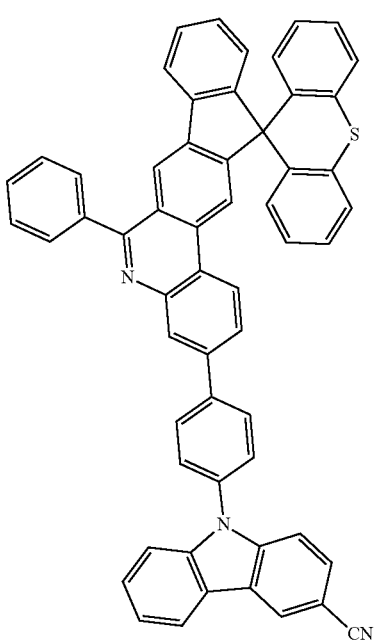

467
-continued
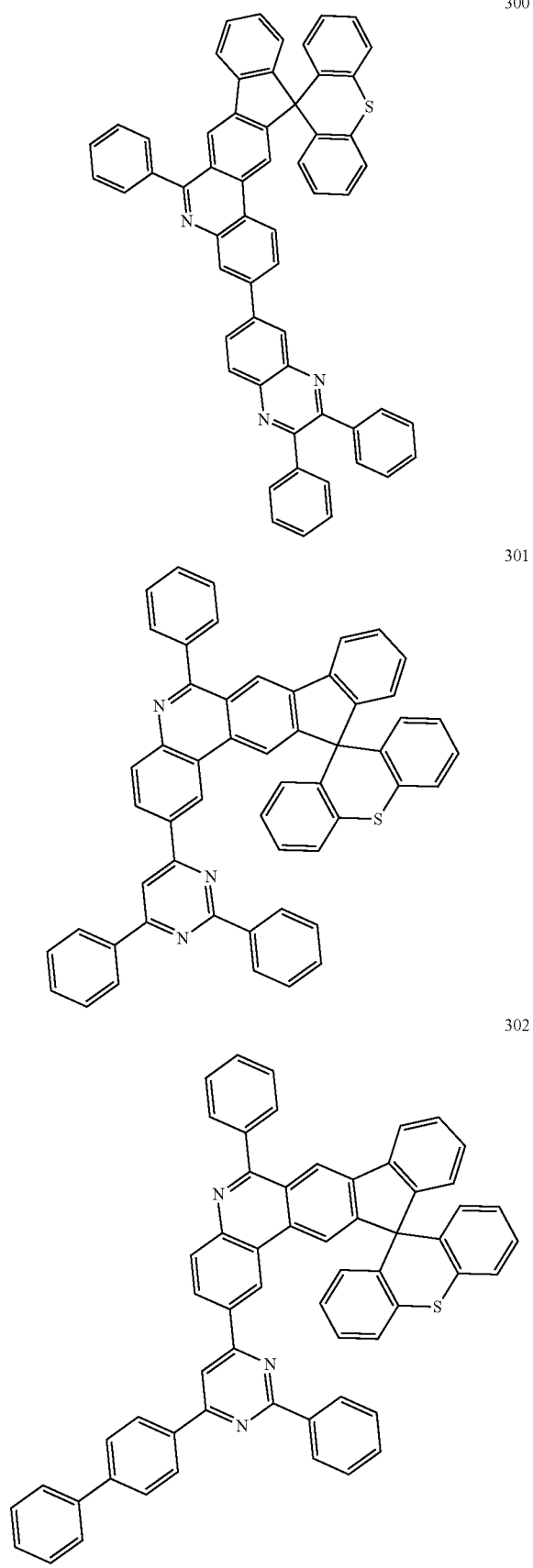
468
-continued
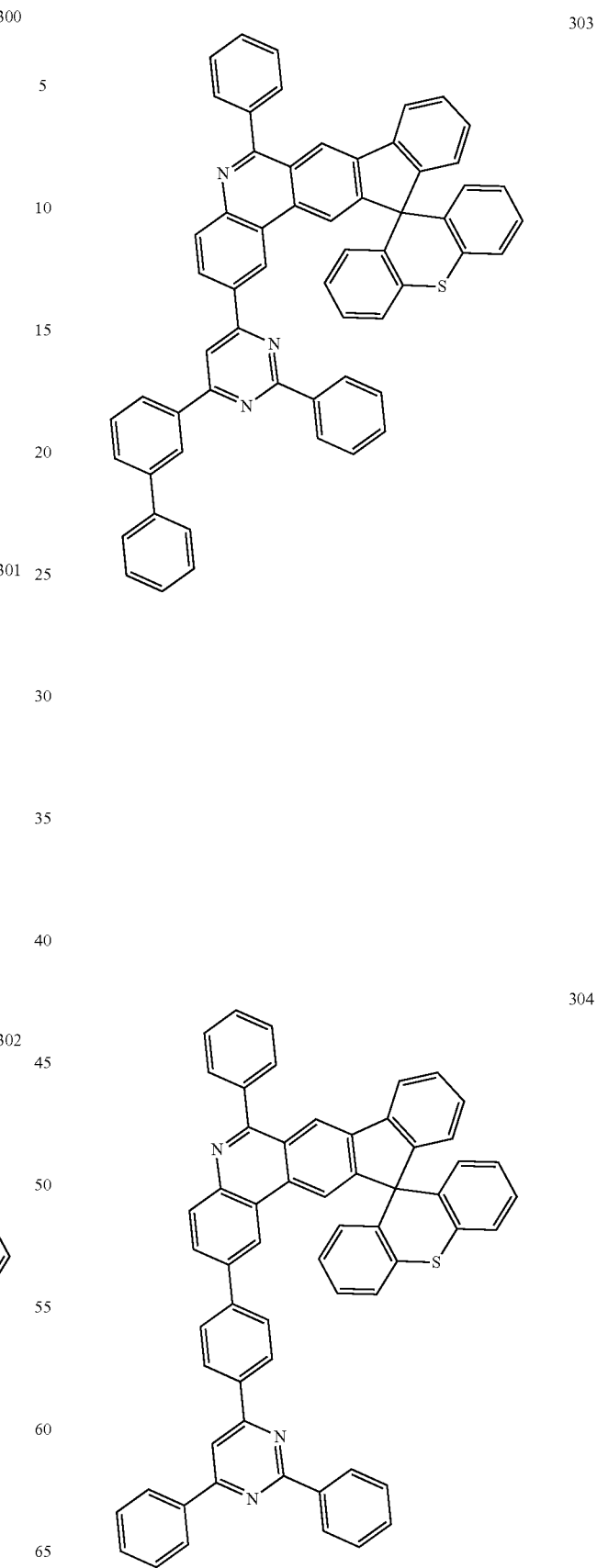

-continued
305
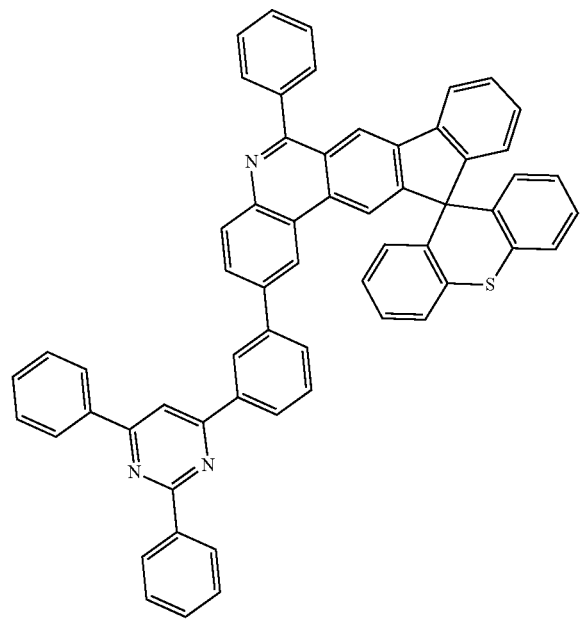
306
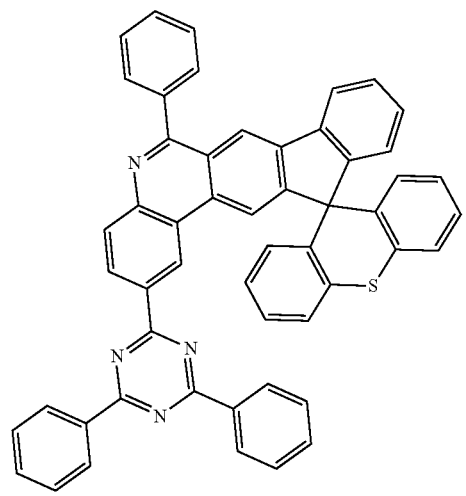
-continued
307
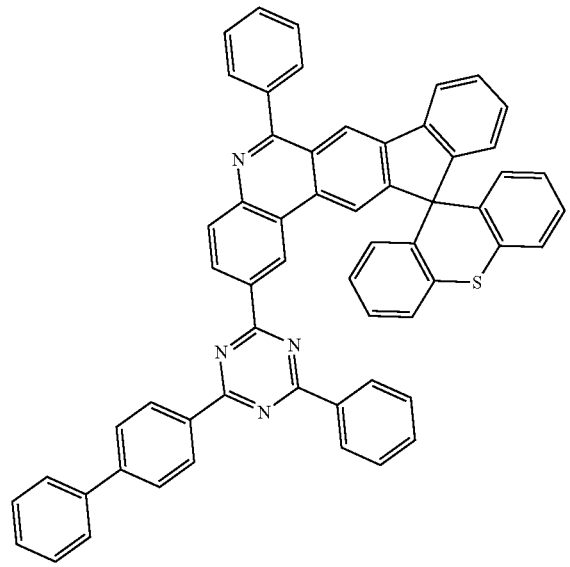
308
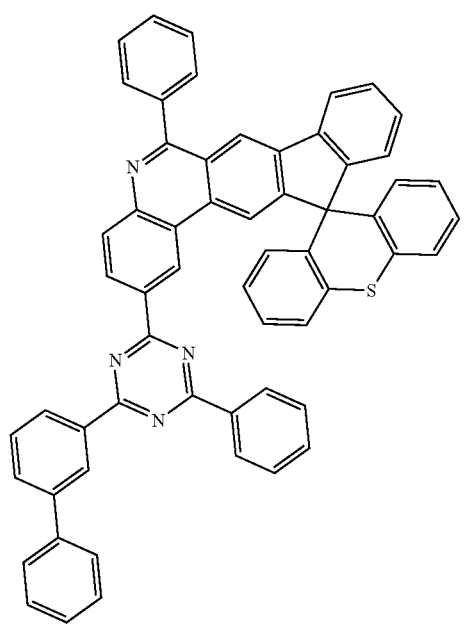

471
-continued
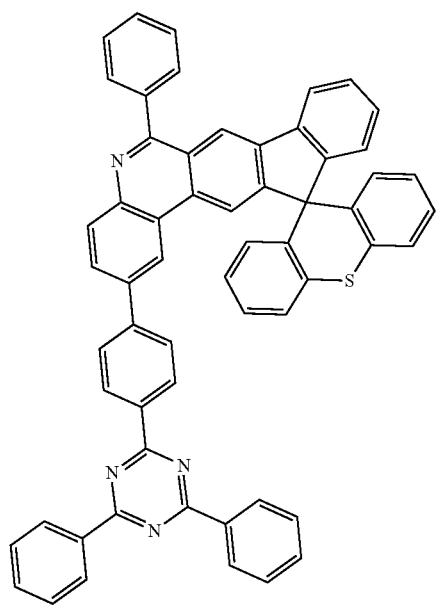
309
472
-continued
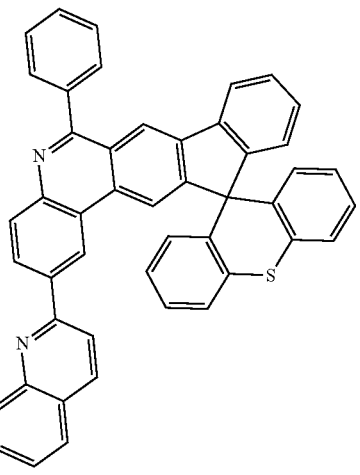
311
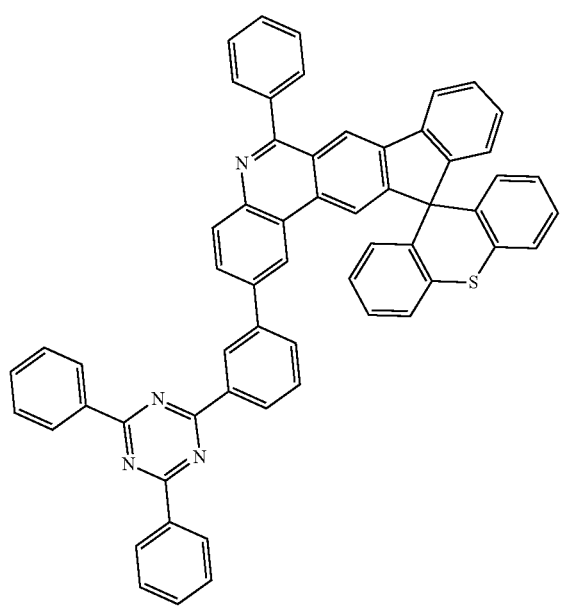
310
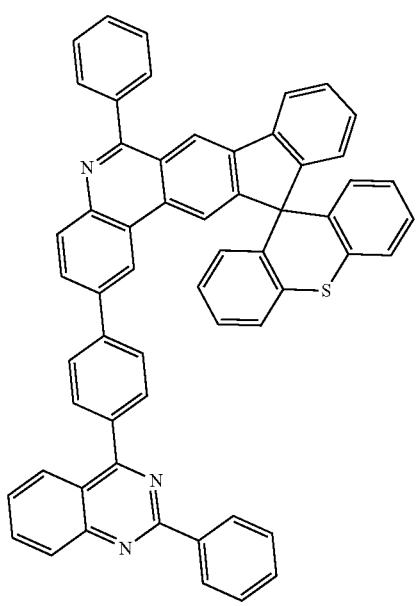
312

473
-continued
313
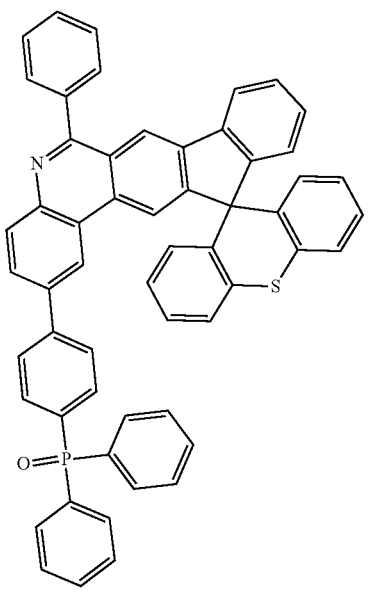
314
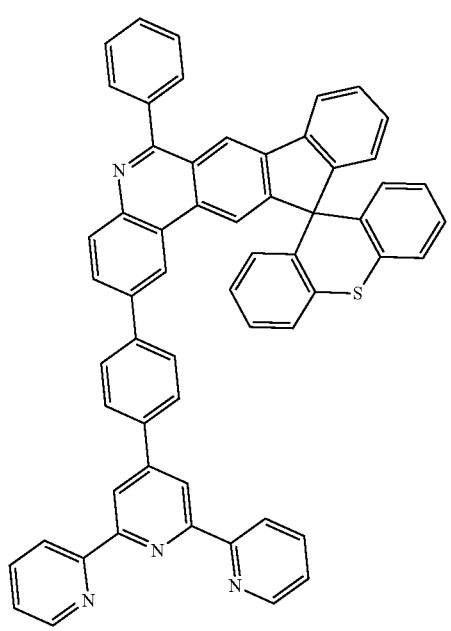
474
-continued
315
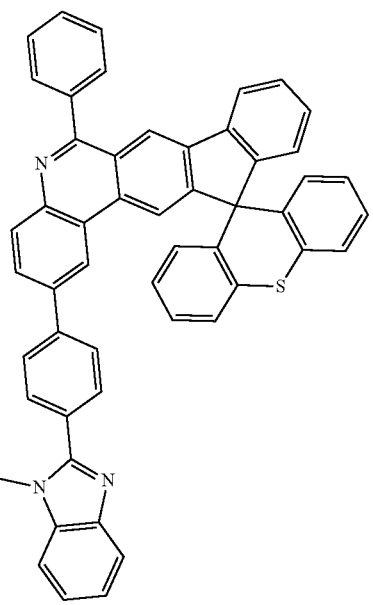
316
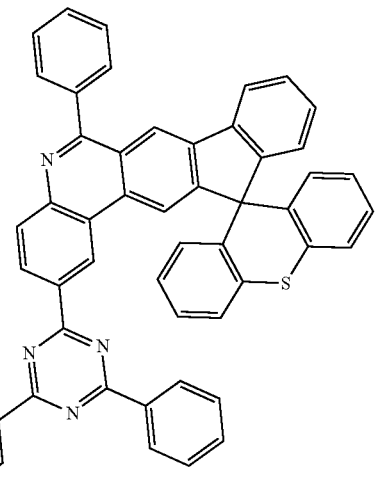

475
-continued
317
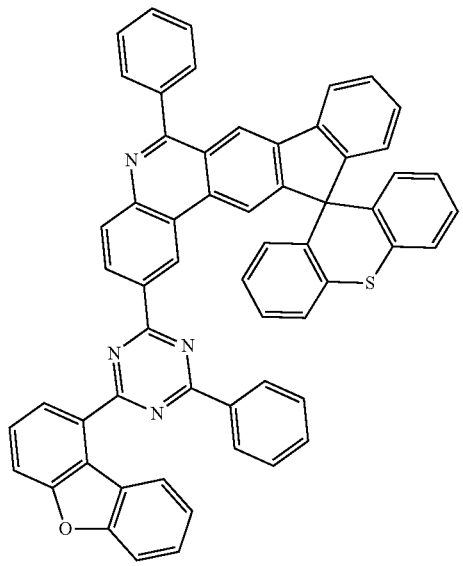
318
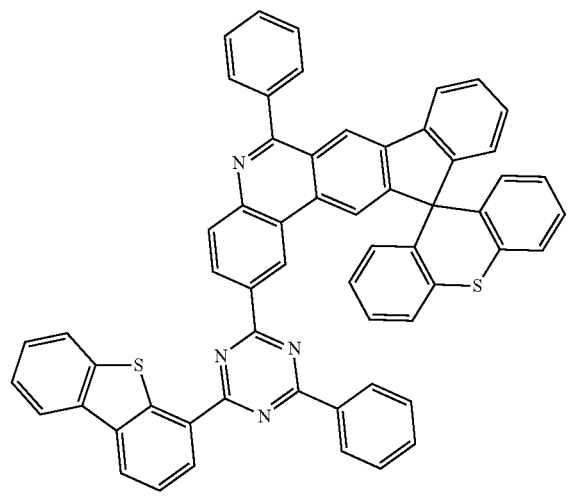
319
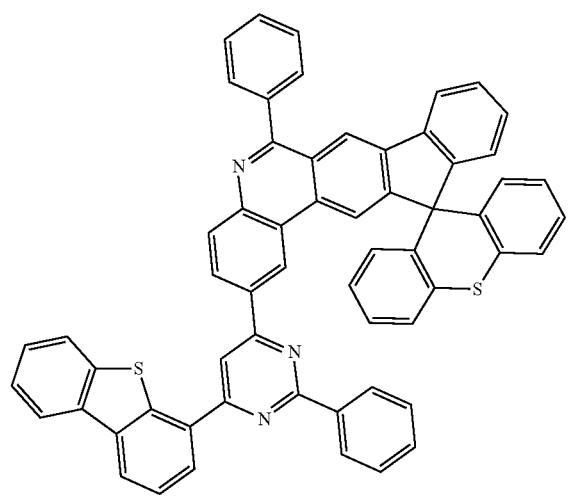
476
-continued
320
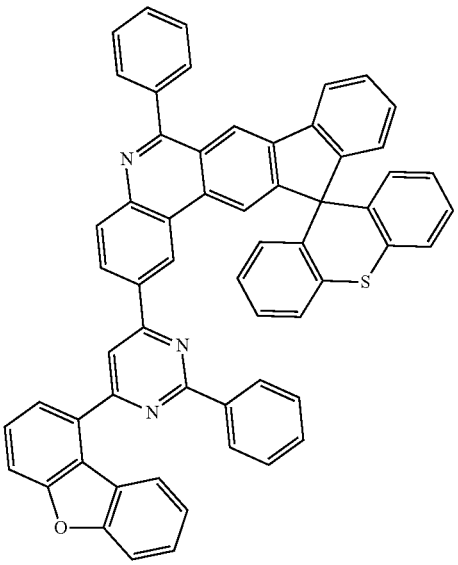
321
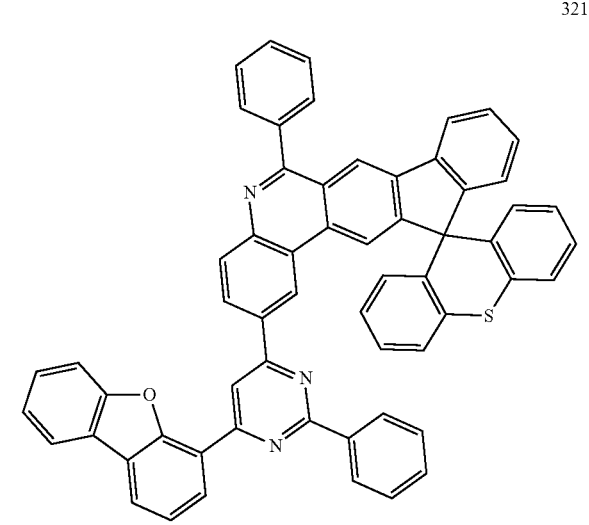
322
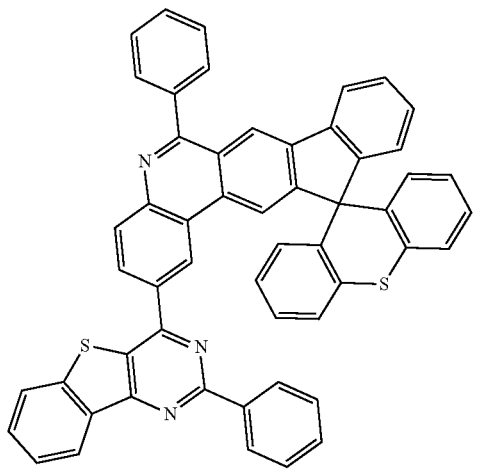

477
-continued
323
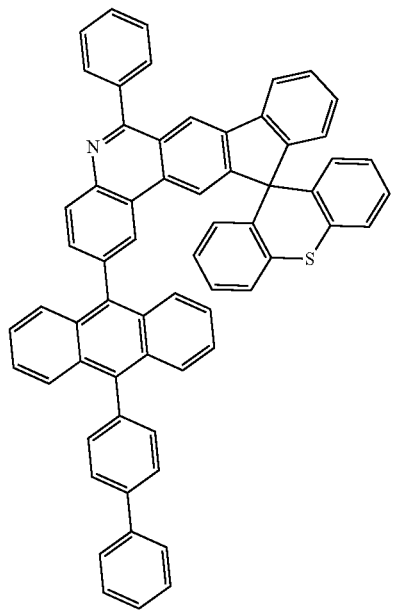
324
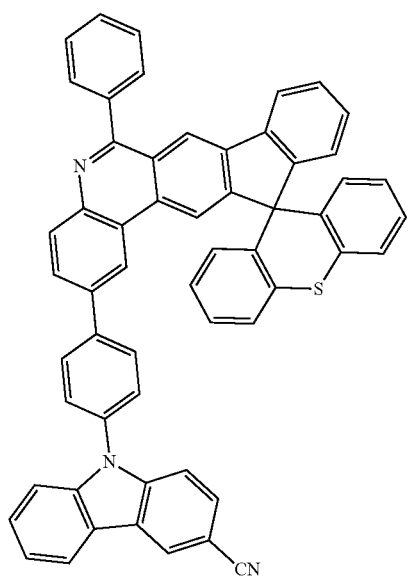
478
-continued
325
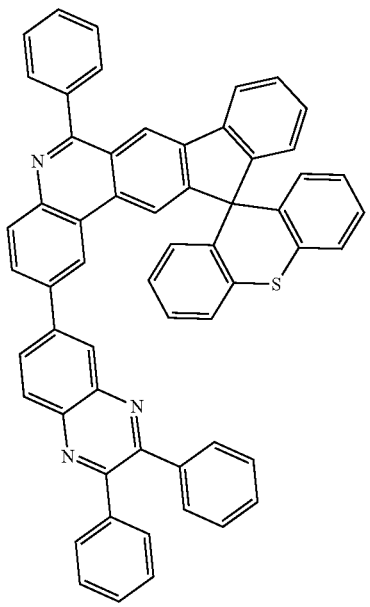
326
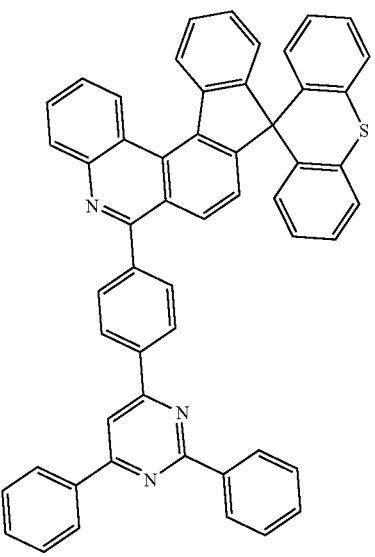

327
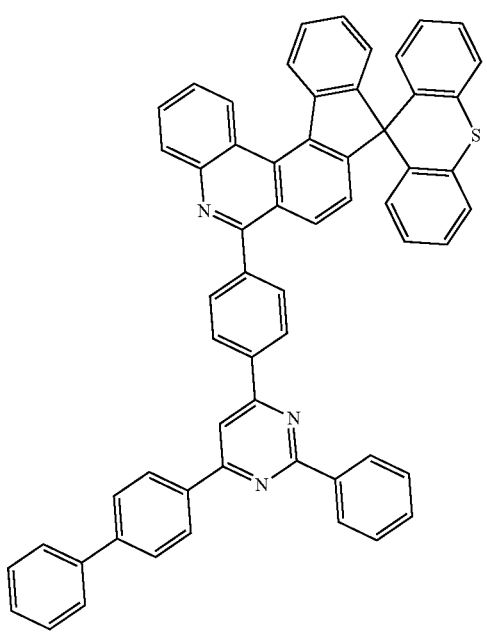
329
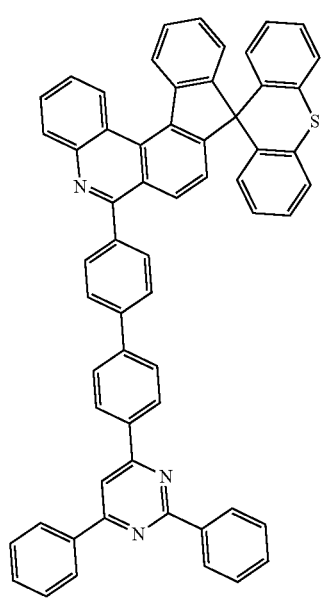
328
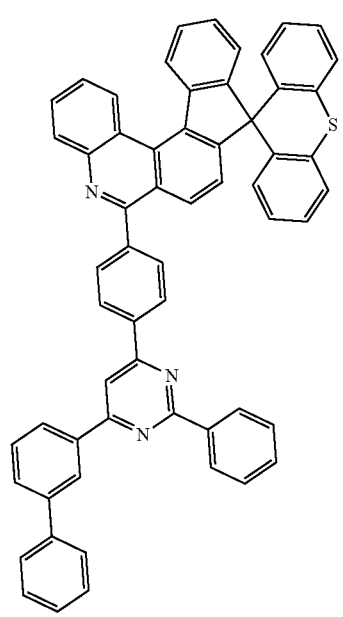
330
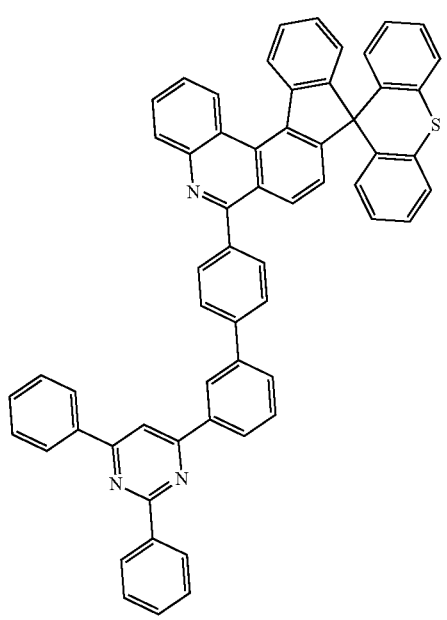

481
-continued
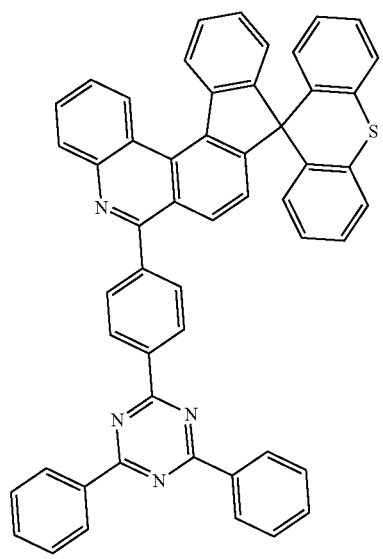
331
332
482
-continued
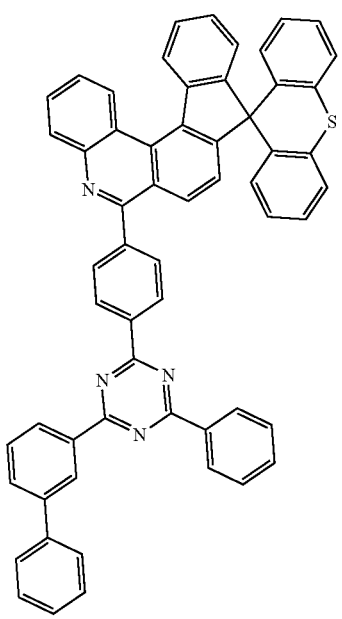
333
334

483
-continued
335
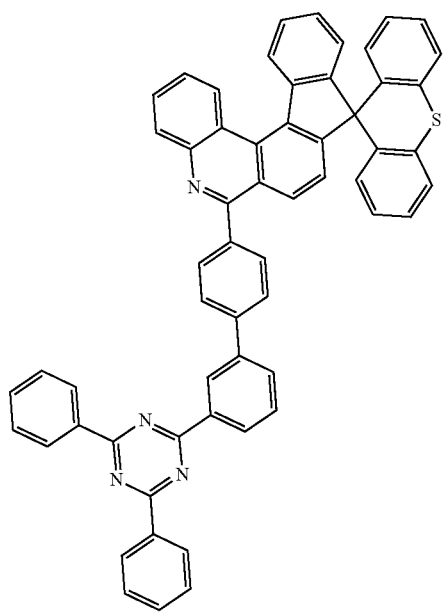
336
484
-continued
337
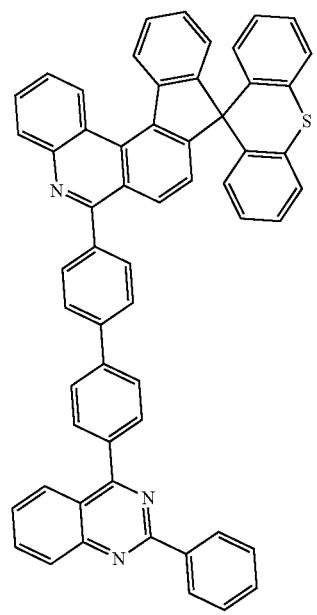
338
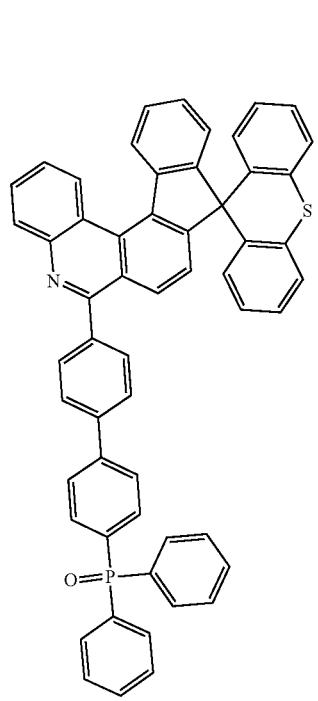

339
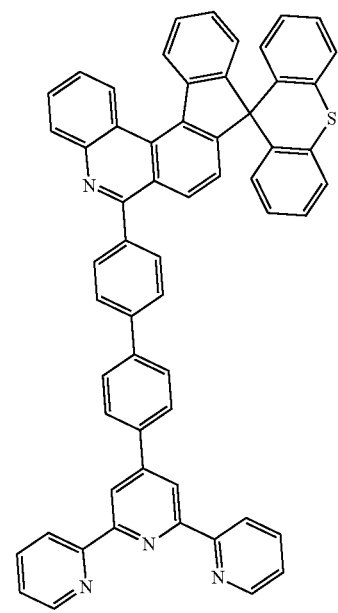
340
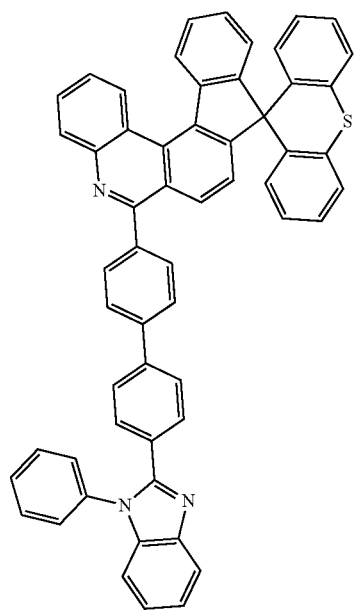
341
342
343
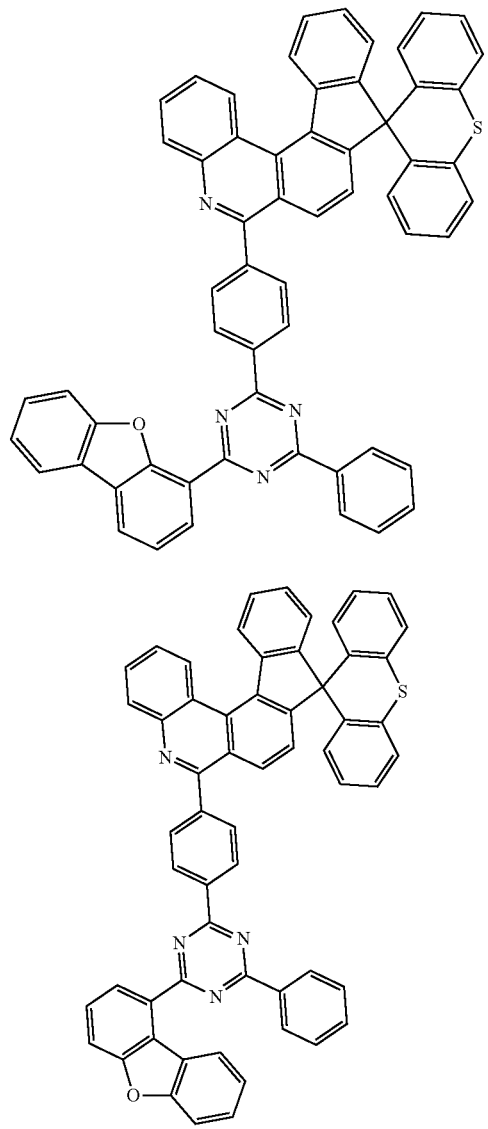

487
-continued
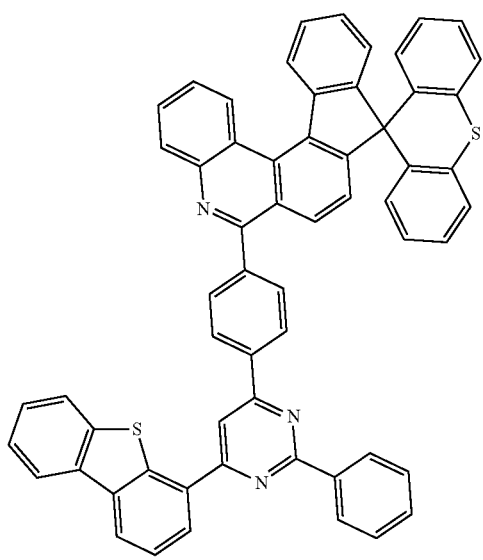
344
488
-continued
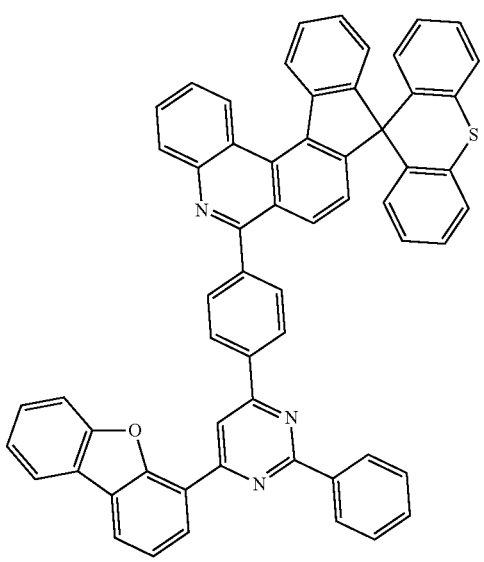
346
345
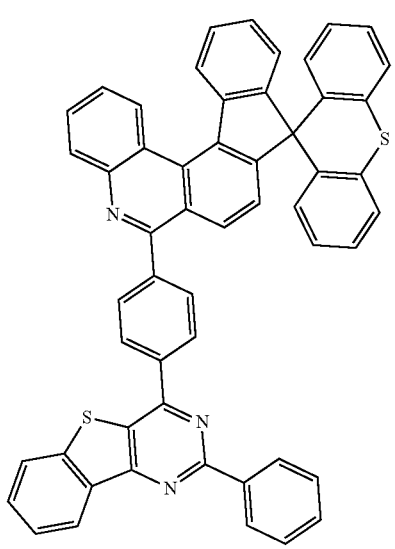
347

489
-continued
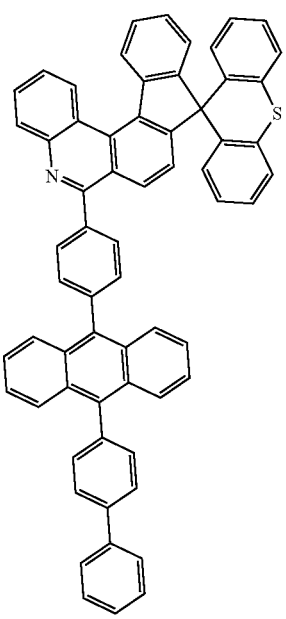
348
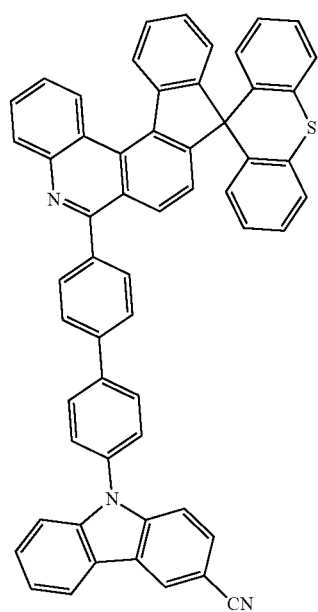
349
490
-continued
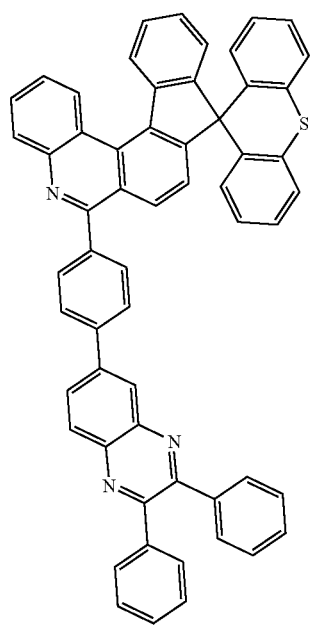
350
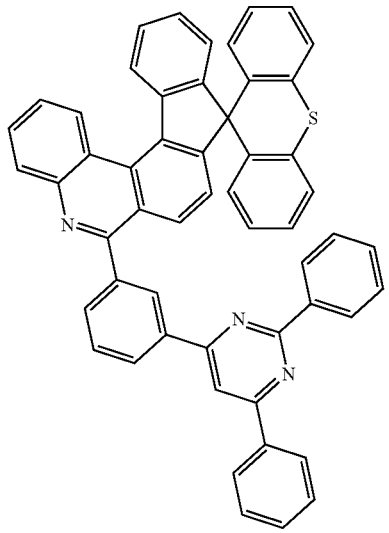
351

352
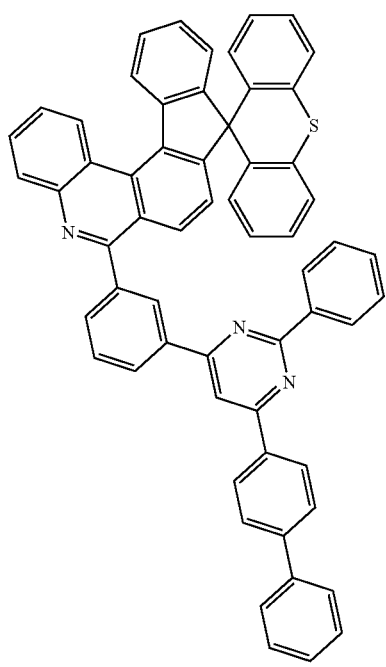
354
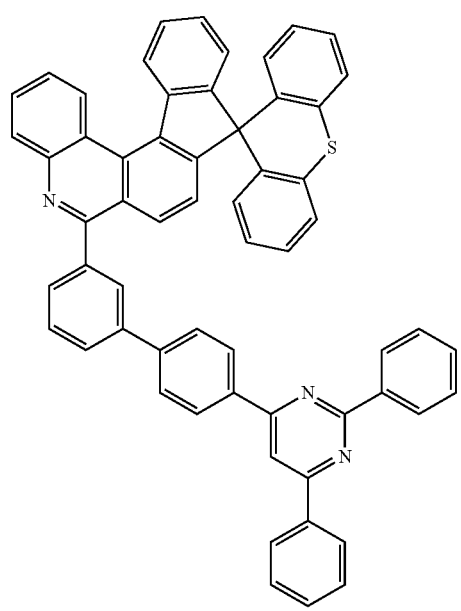
353
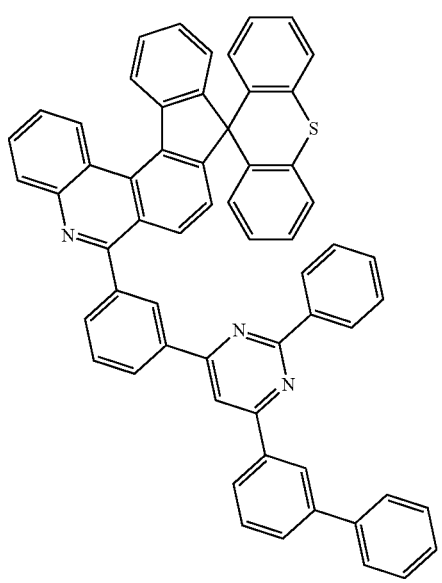
355
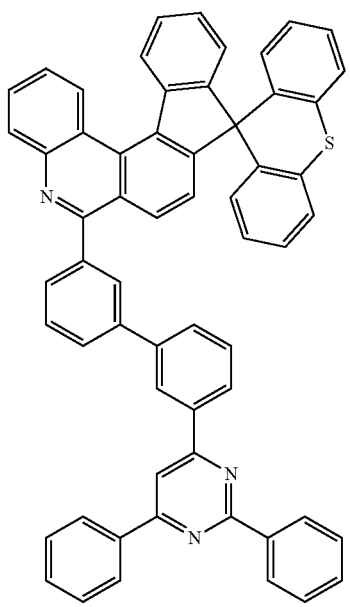

356
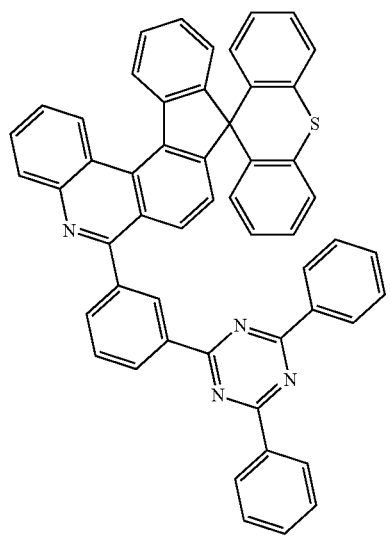
357
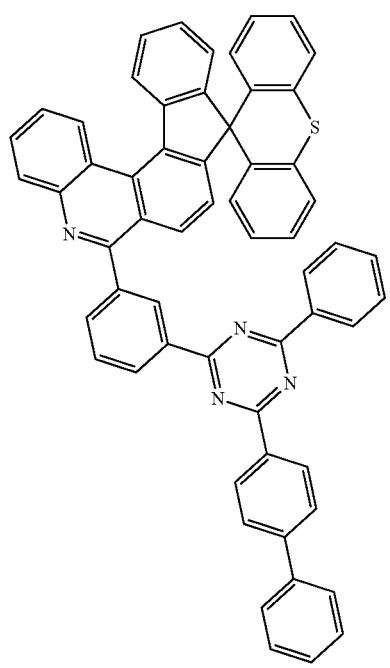
358
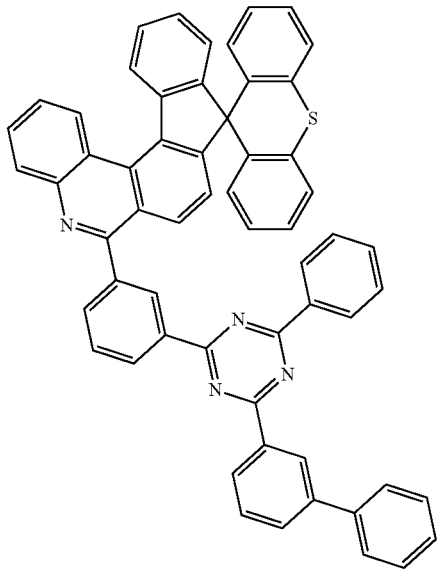
359
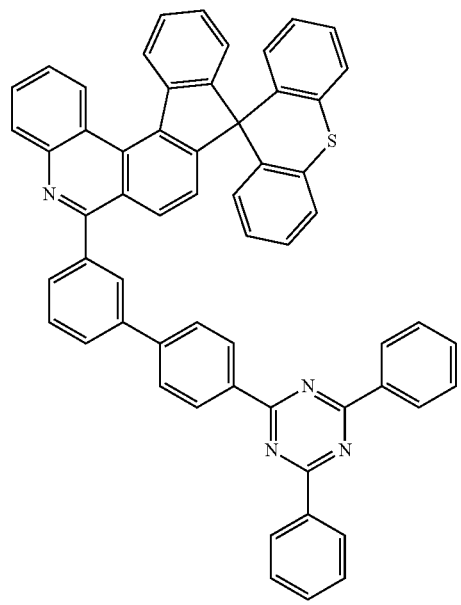

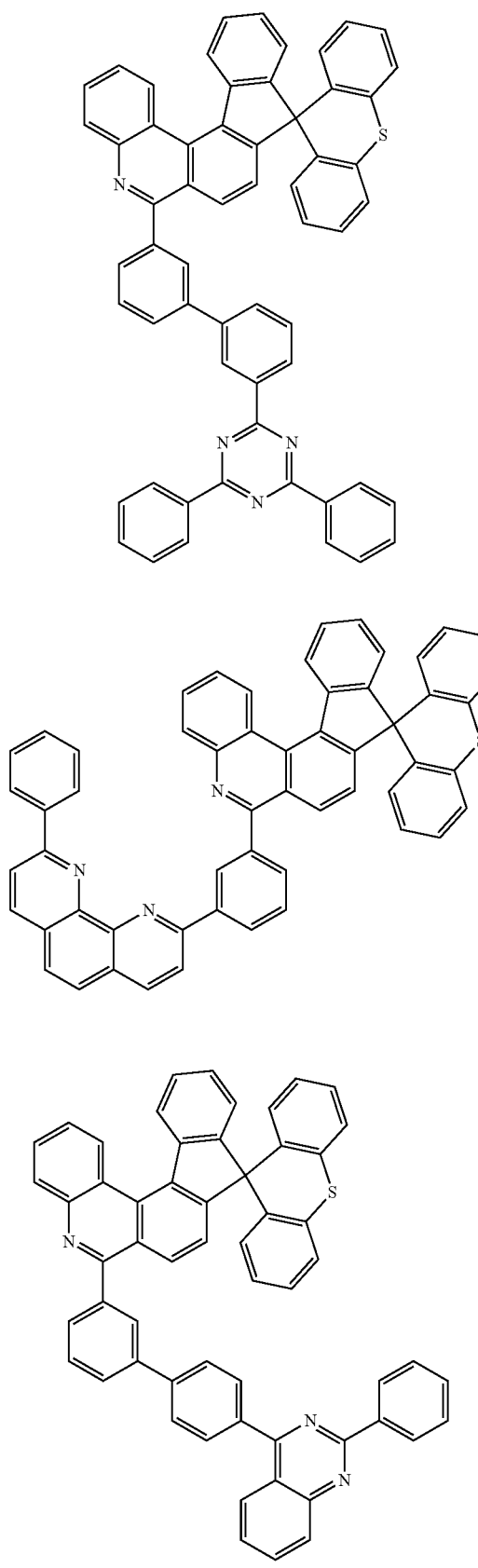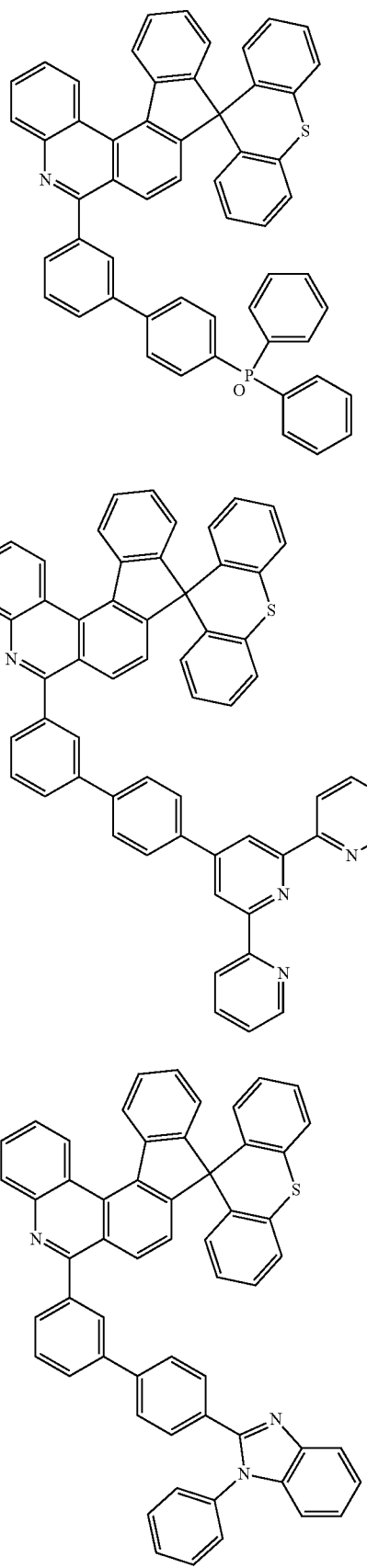

497
-continued
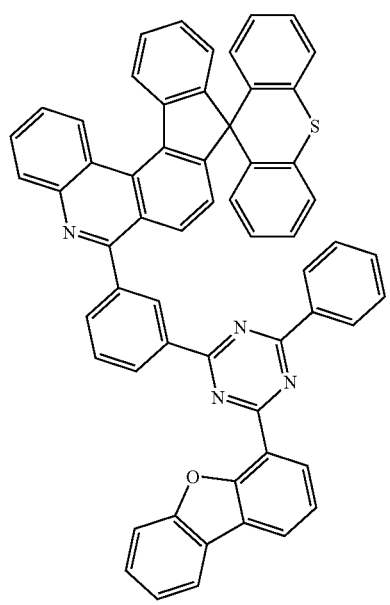
366
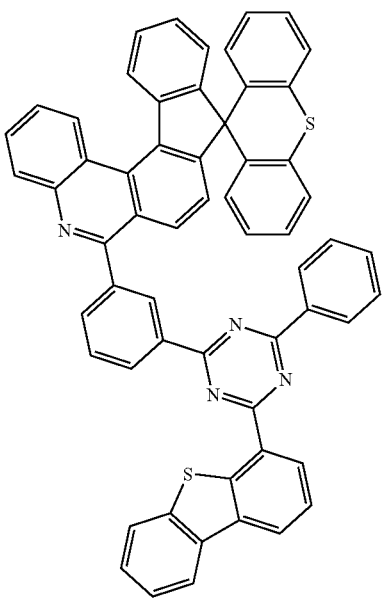
368
367
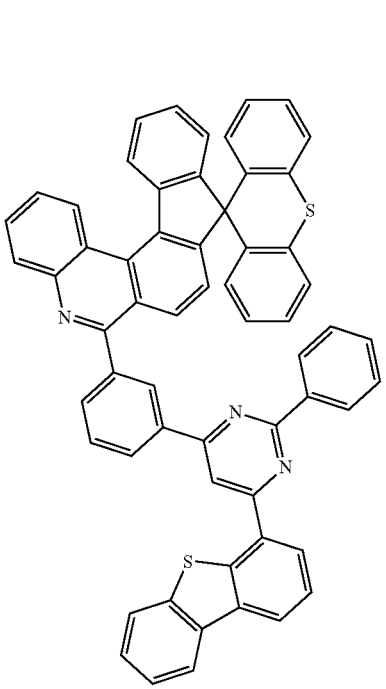
369
498
-continued 499
-continued
370
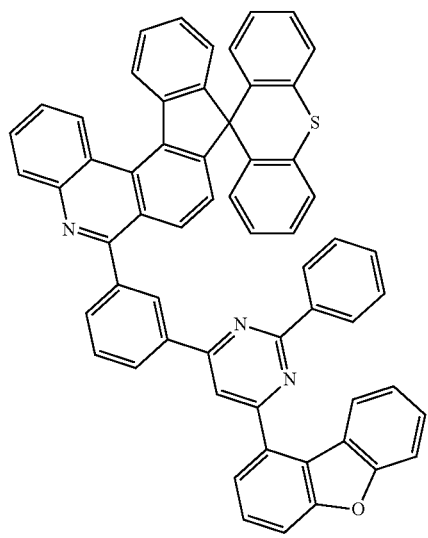
371
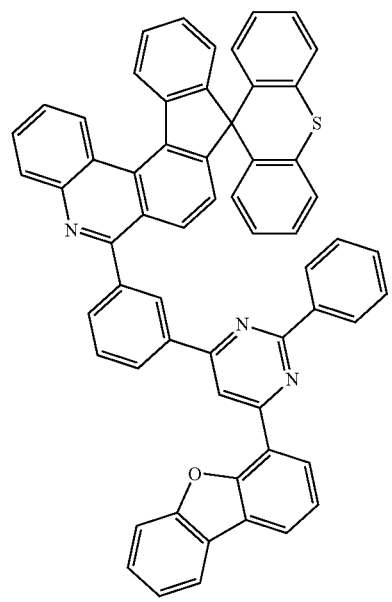
500
-continued
372
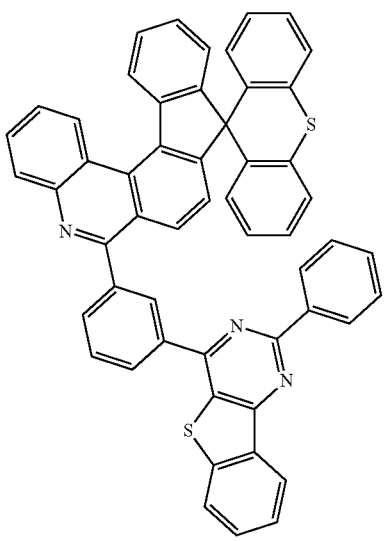
373
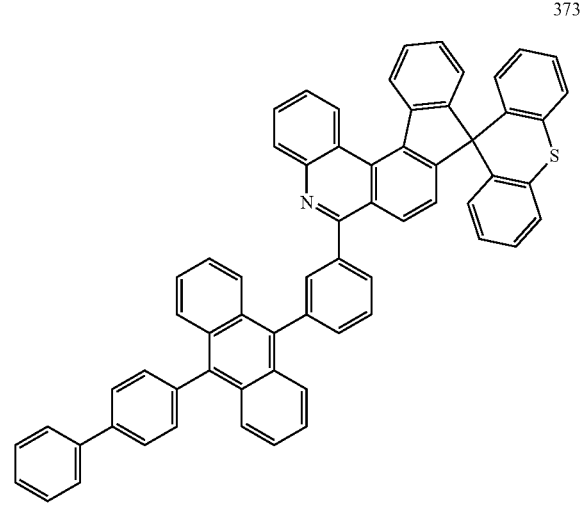
374
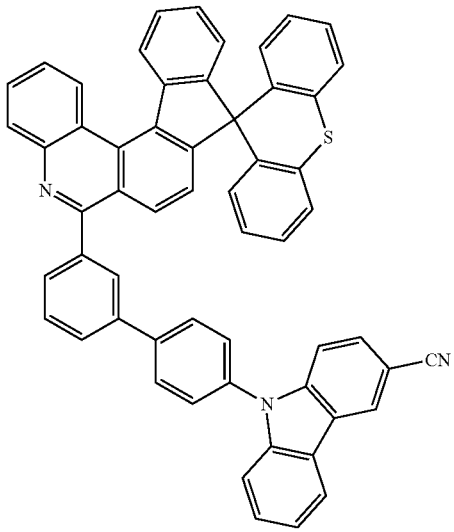

501
-continued
375
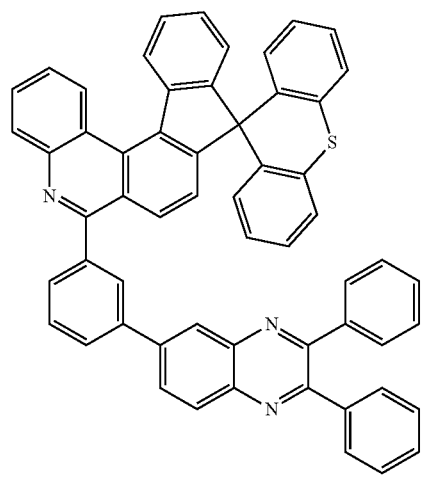
376
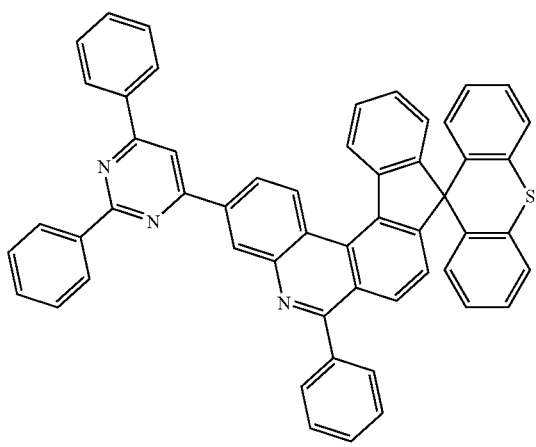
377
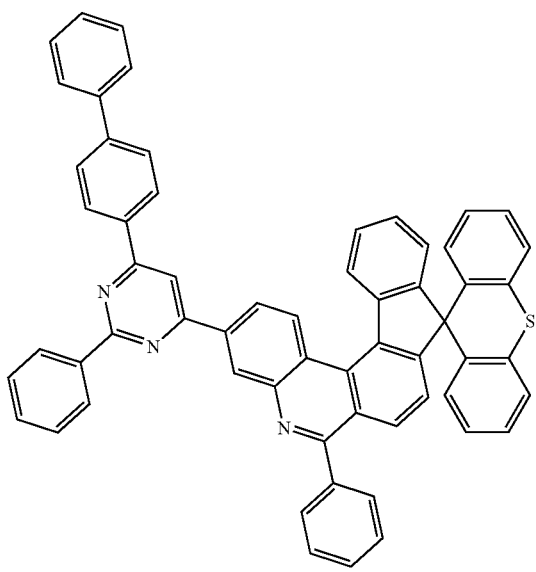
502
-continued
378
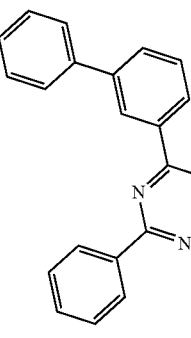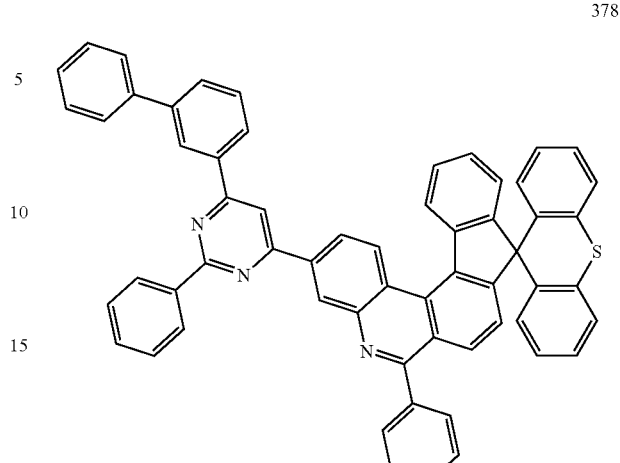
379
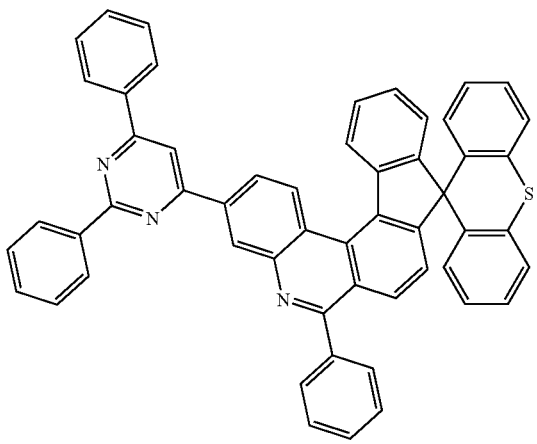
380
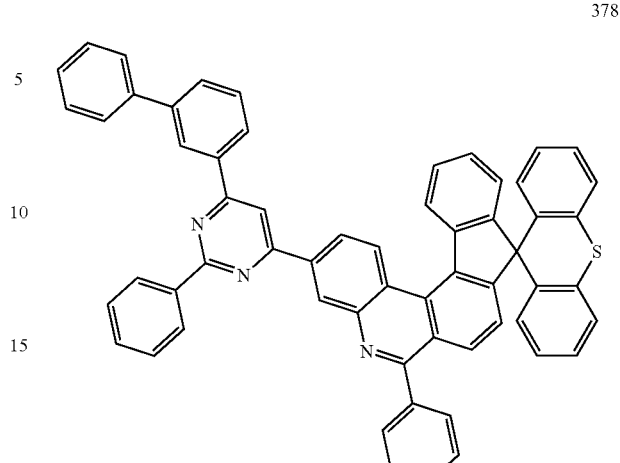

503
-continued
381
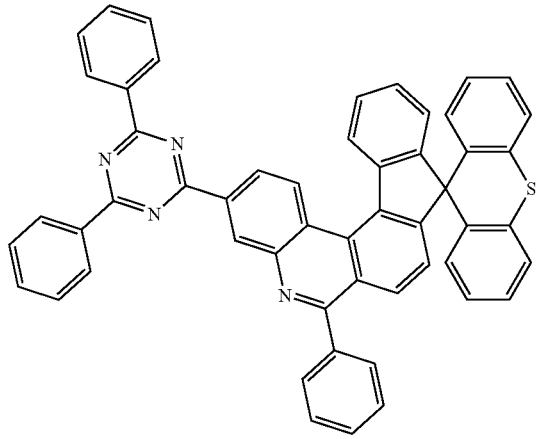
382
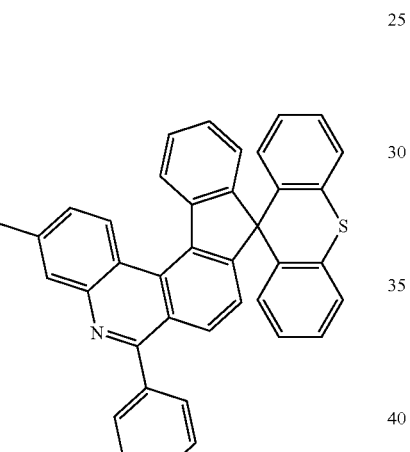
383
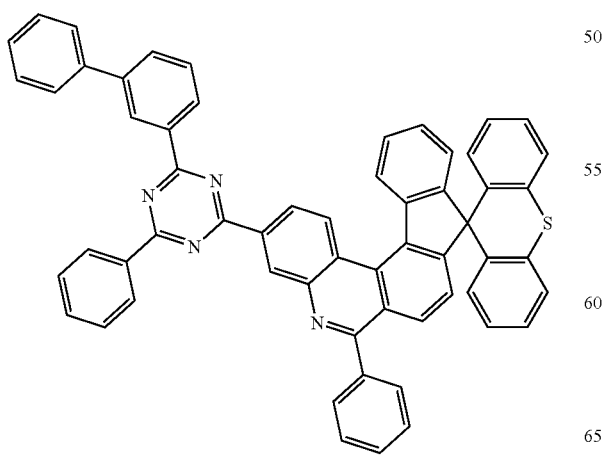
504
-continued
384
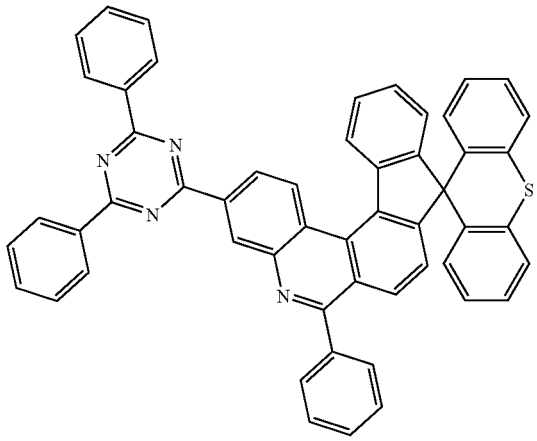
385
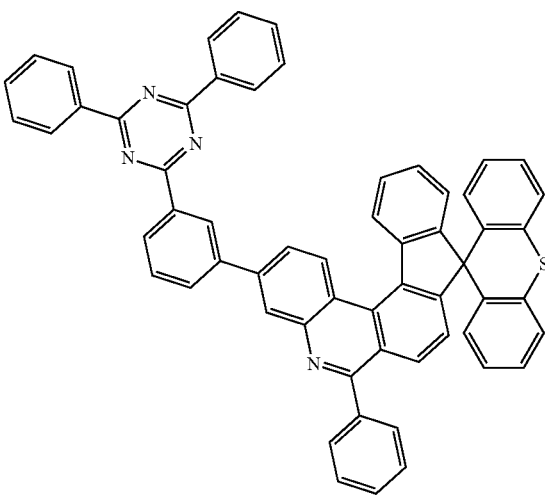
386
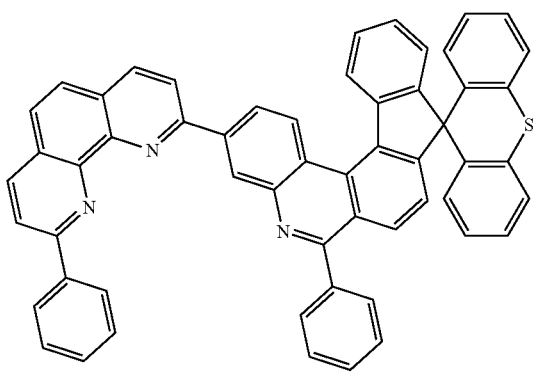

505
-continued
387
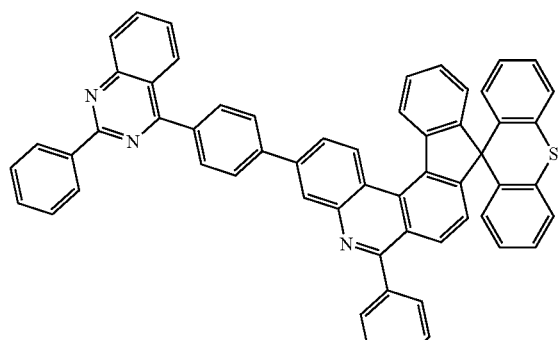
388
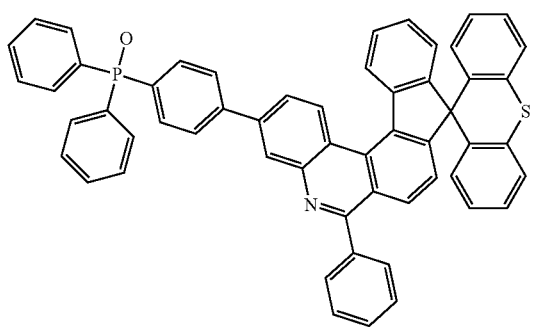
389
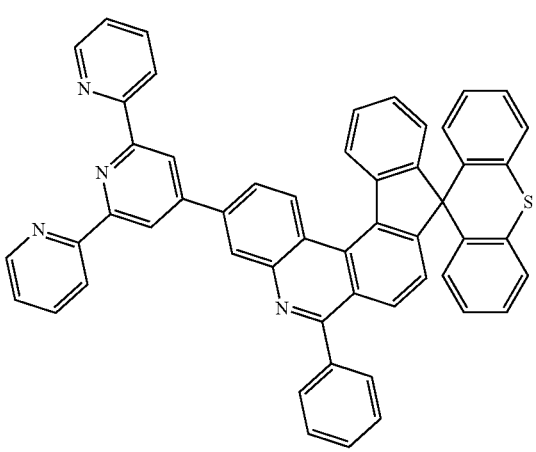
390
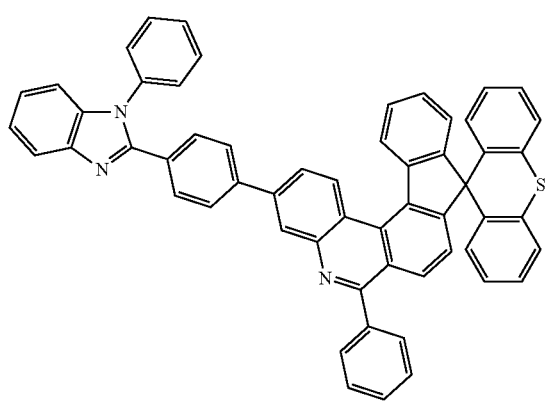
506
-continued
391
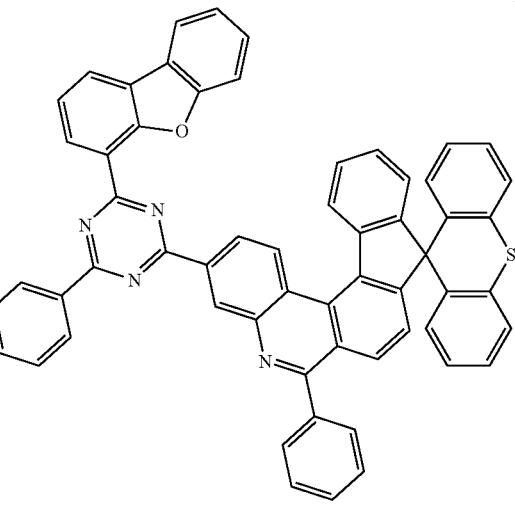
392
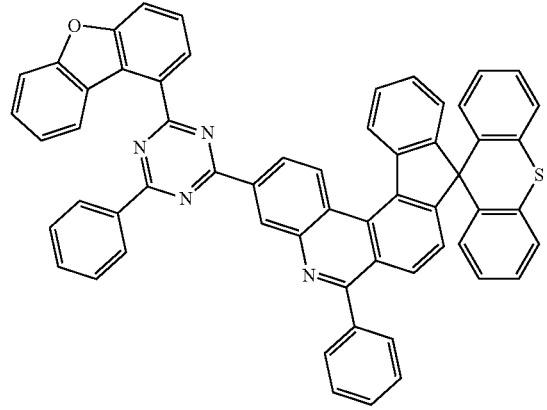
393
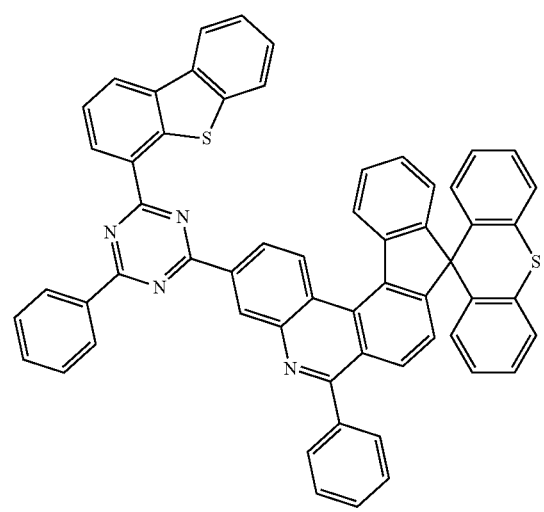

507
-continued
394
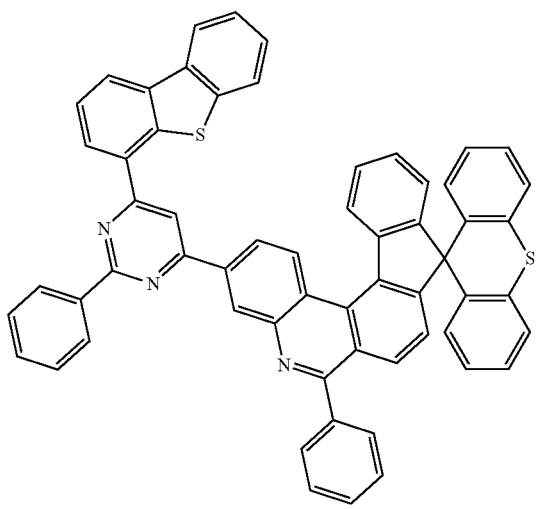
395
396
508
-continued
397
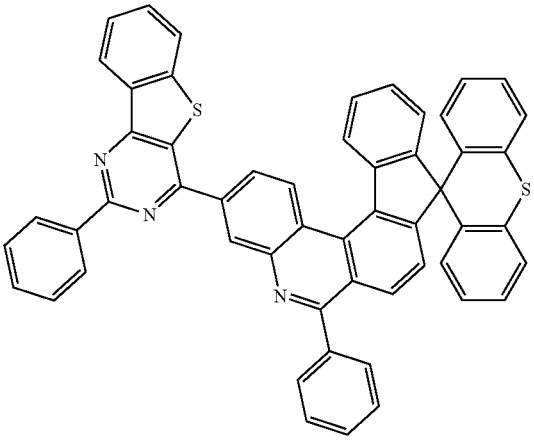
398
399
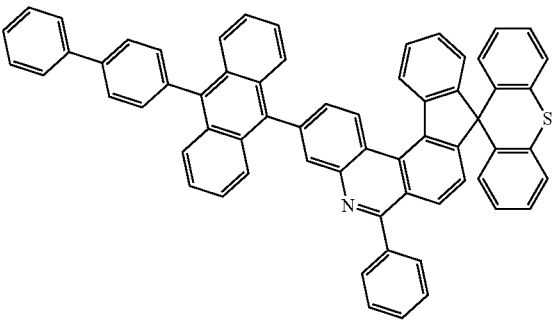
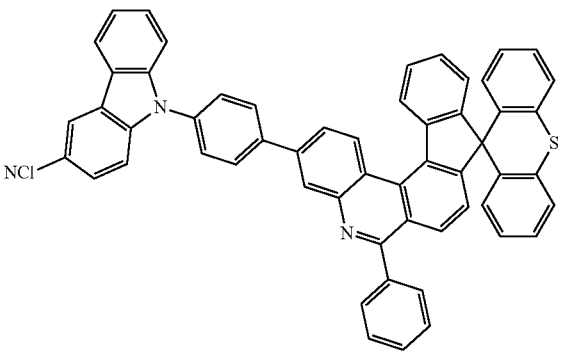
400
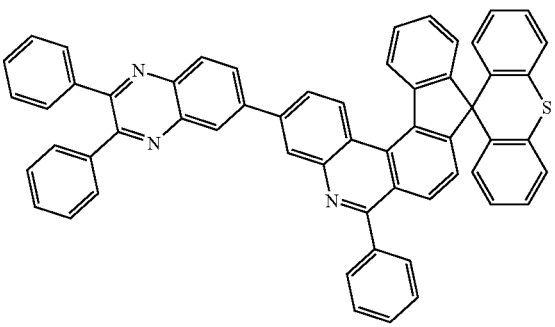

509
-continued
401
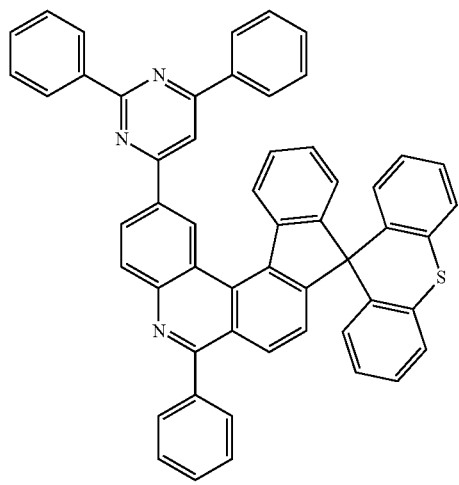
402
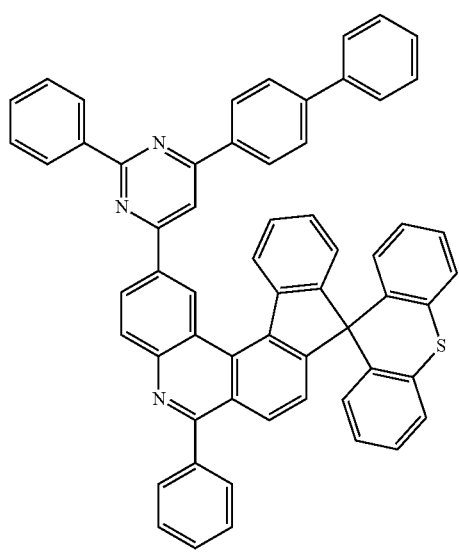
403
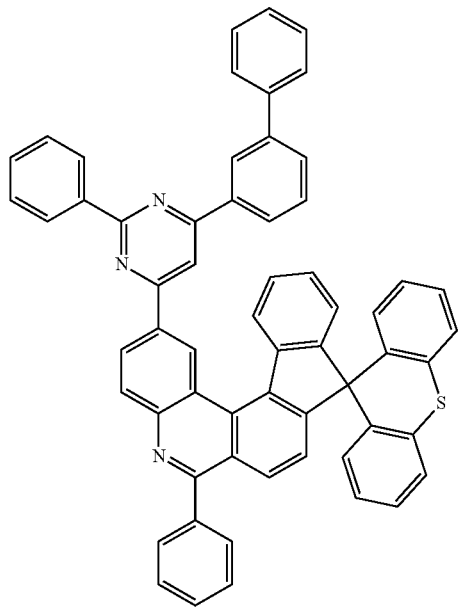
510
-continued
404
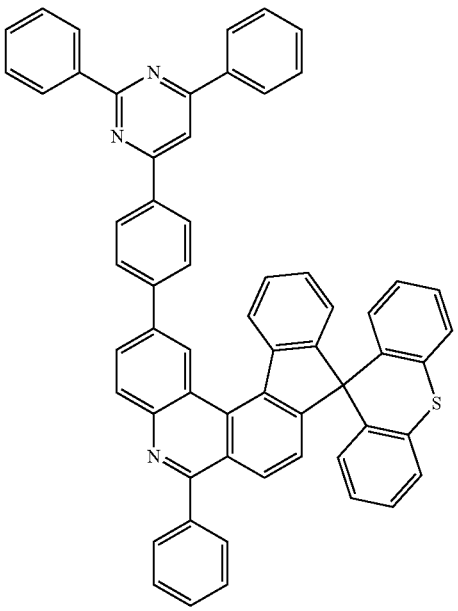
405
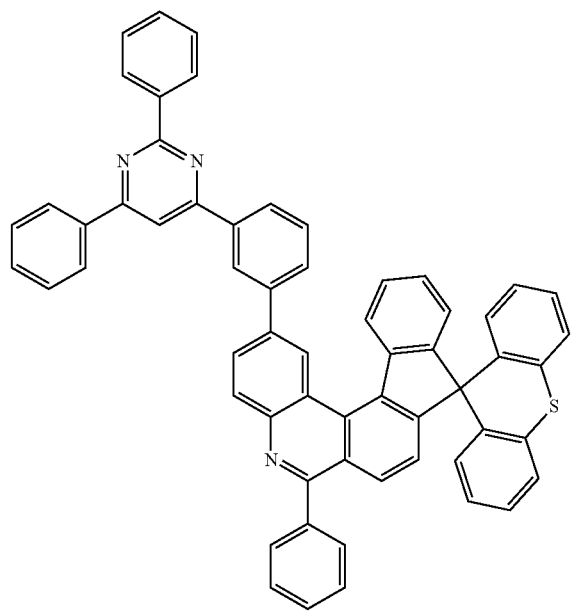

511
-continued
512
-continued
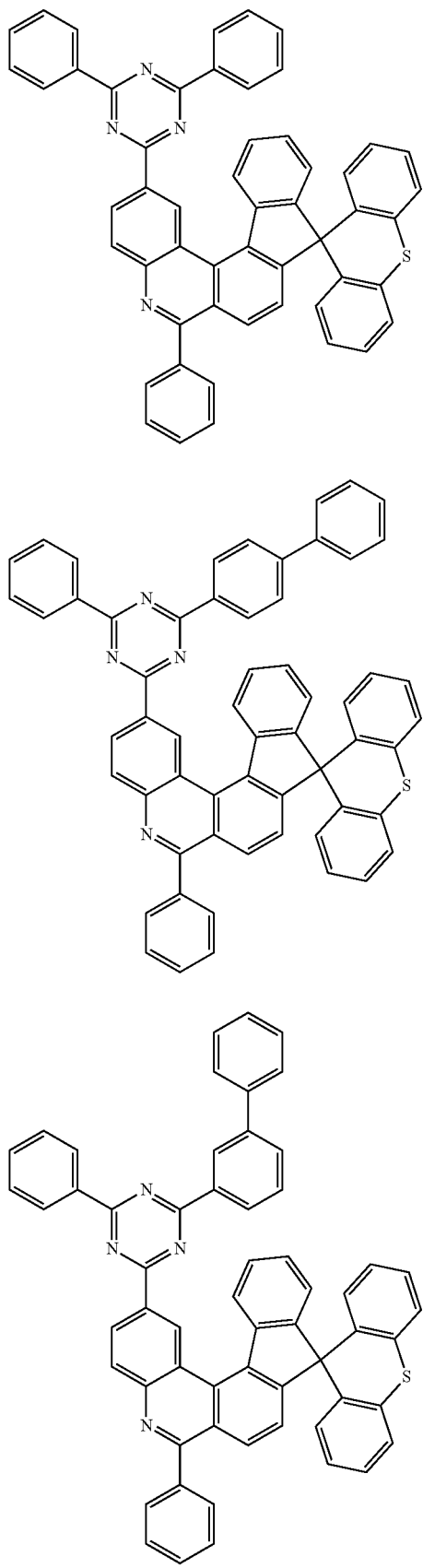
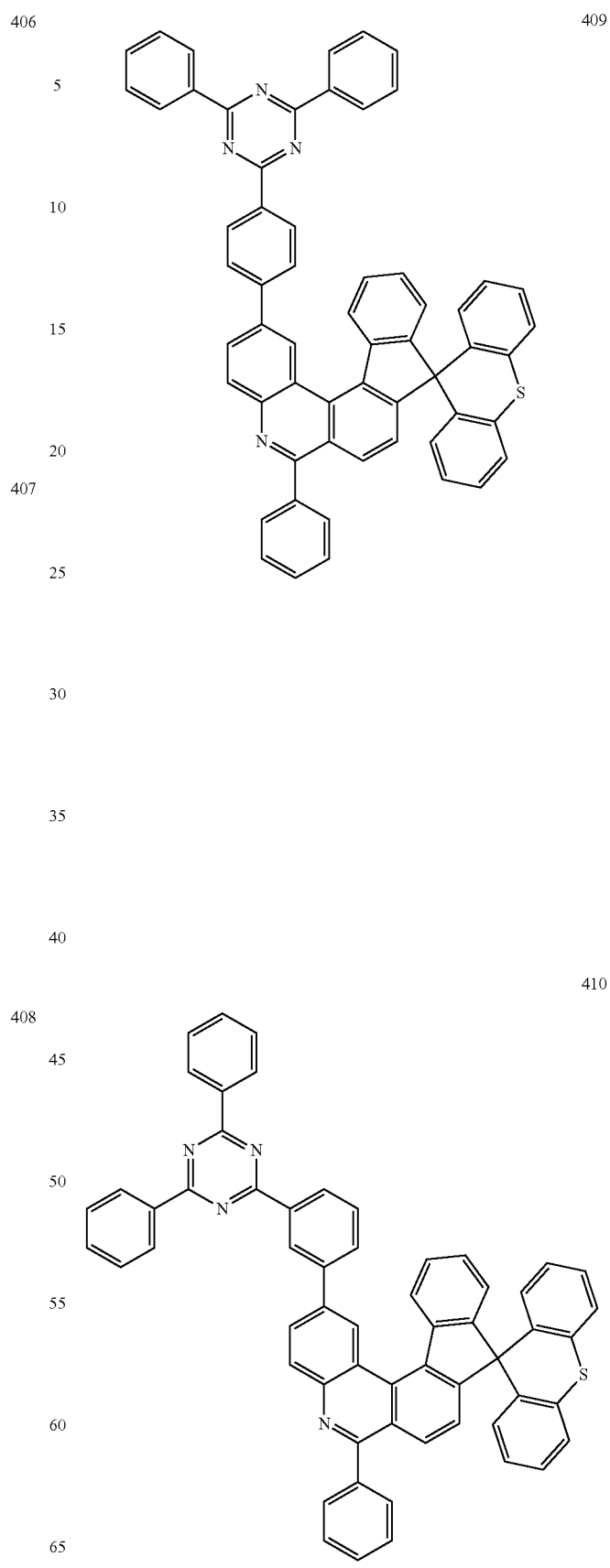

513
-continued
411
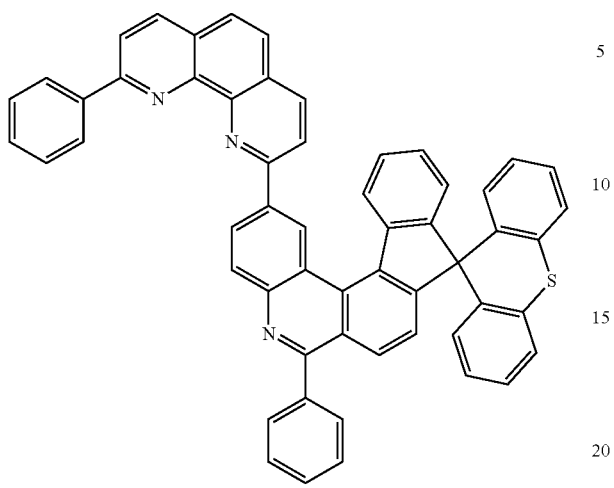
412
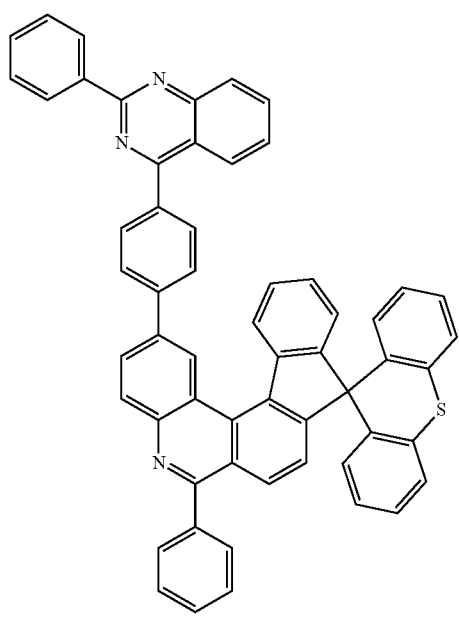
514
-continued
413
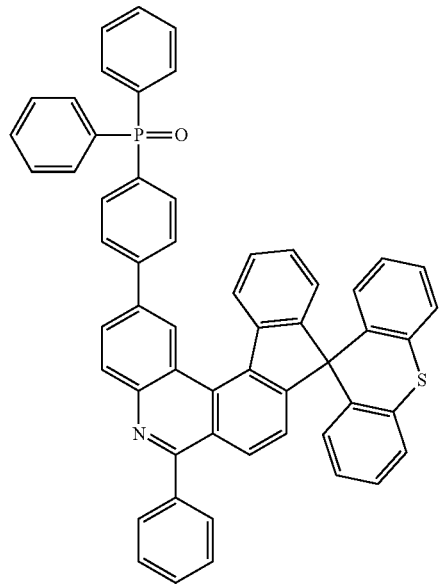
414

515
-continued
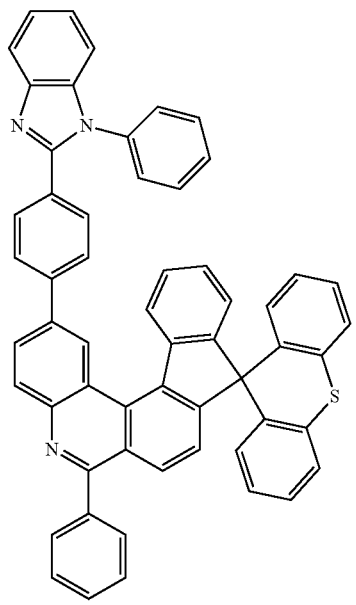
415
516
-continued
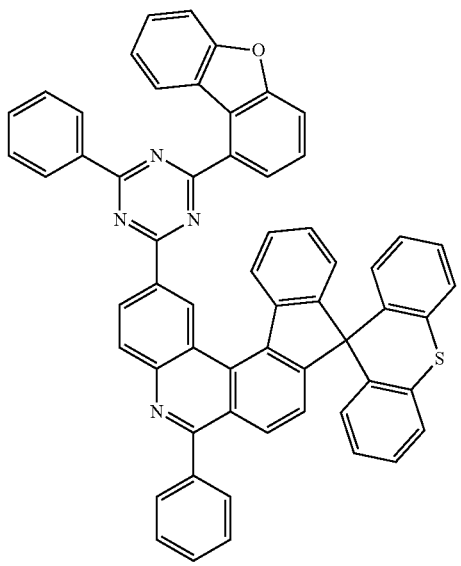
417
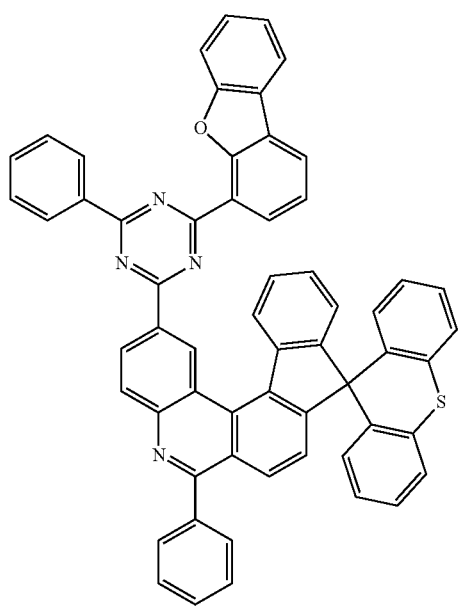
416
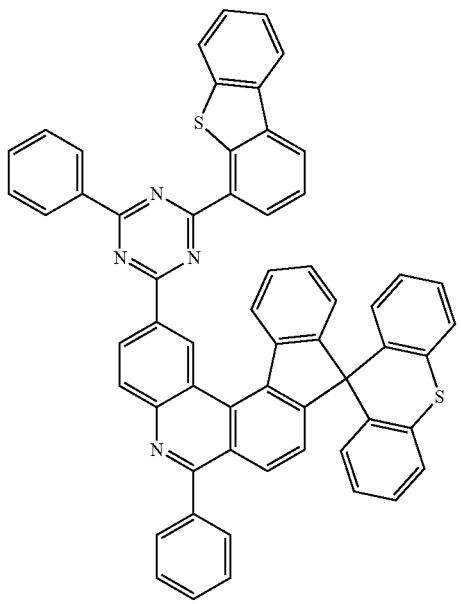
418

517
-continued
419
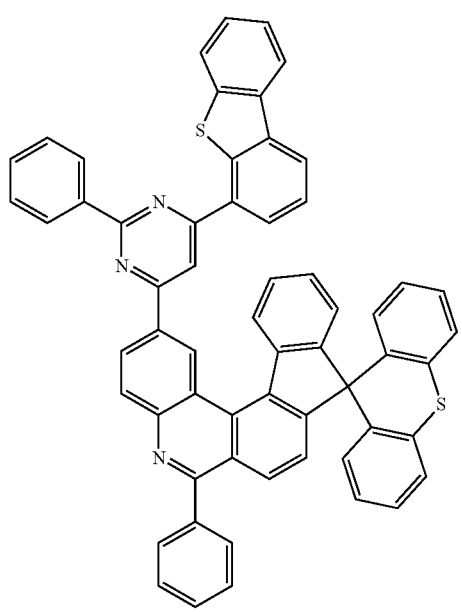
420
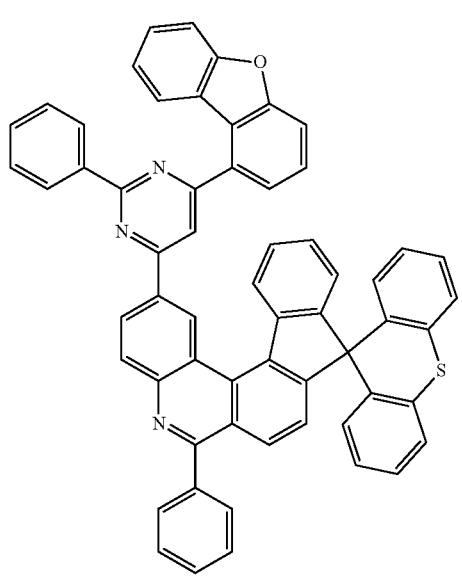
518
-continued
421
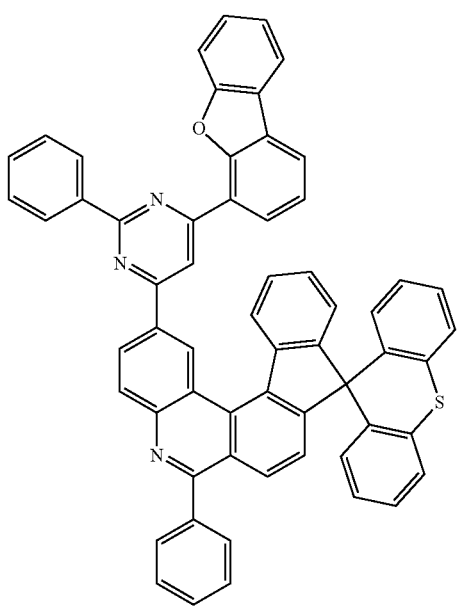
422
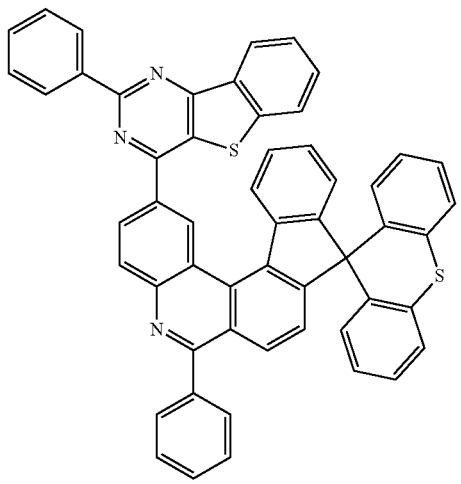

519
-continued
423
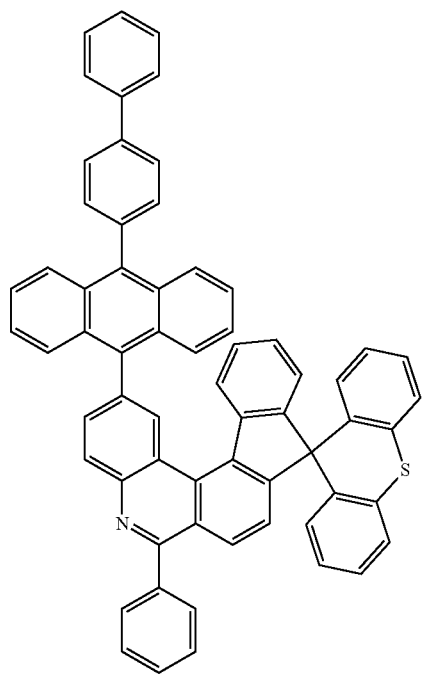
424
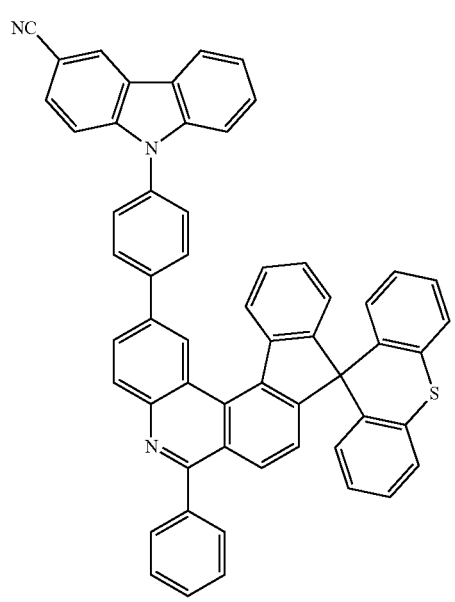
520
-continued
425
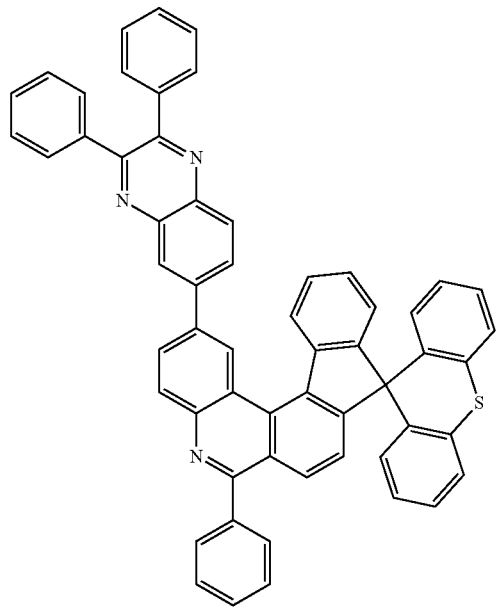
426
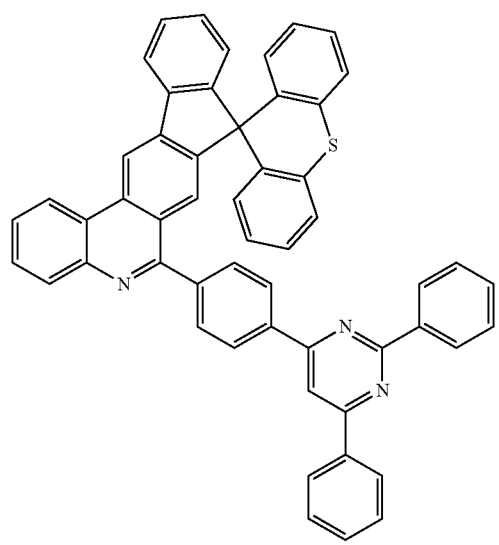

521
-continued
427
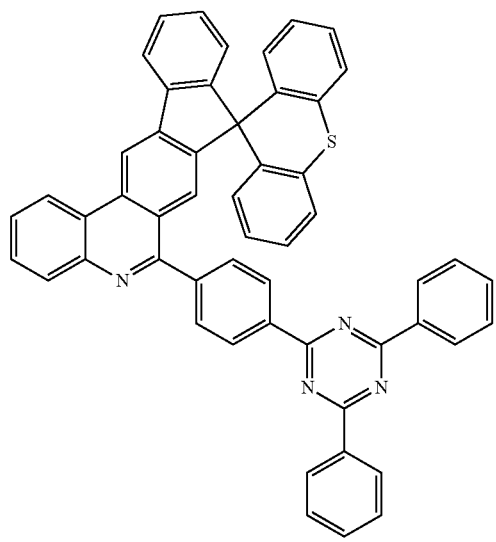
428
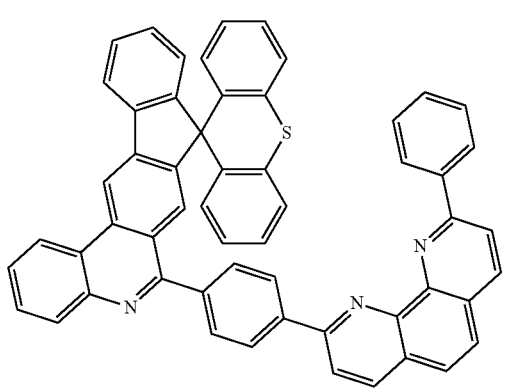
429
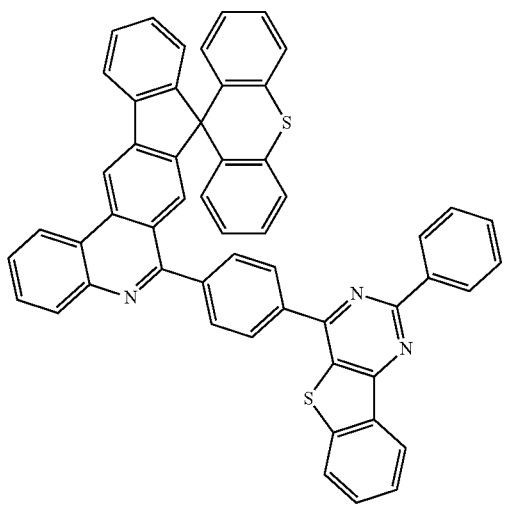
522
-continued
430
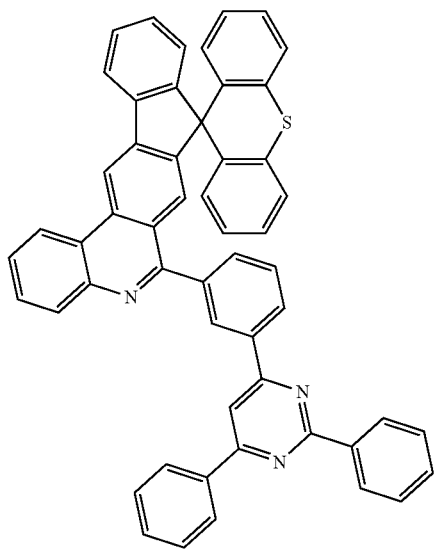
431
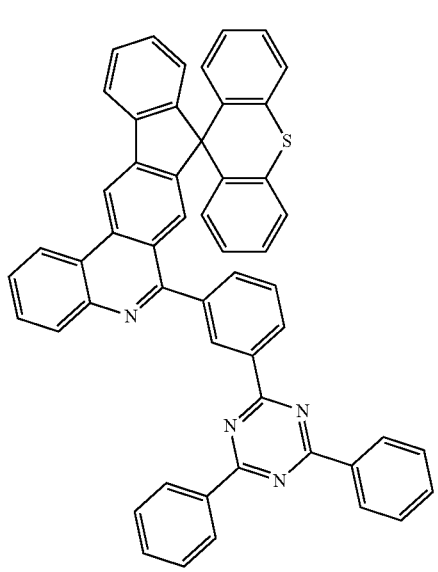
432
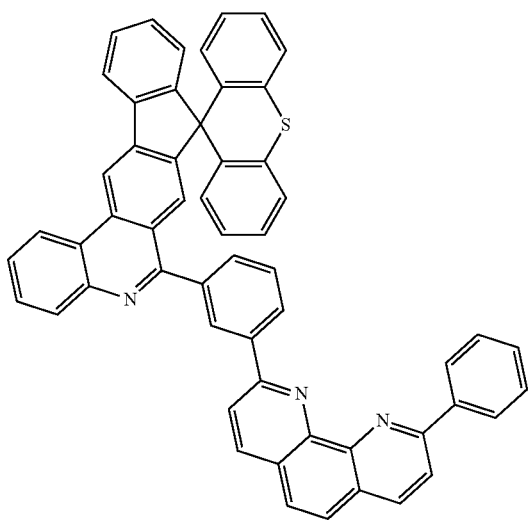

523
-continued
433
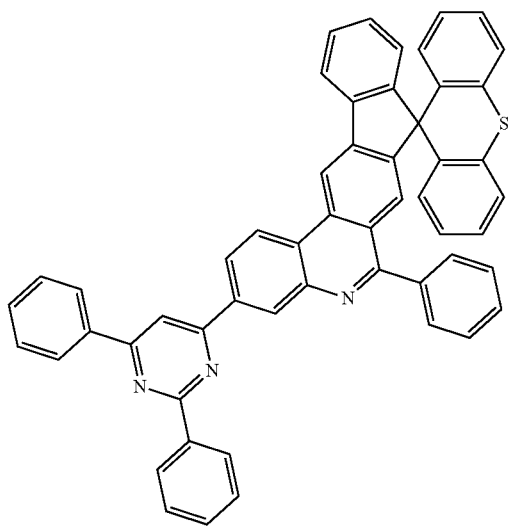
434
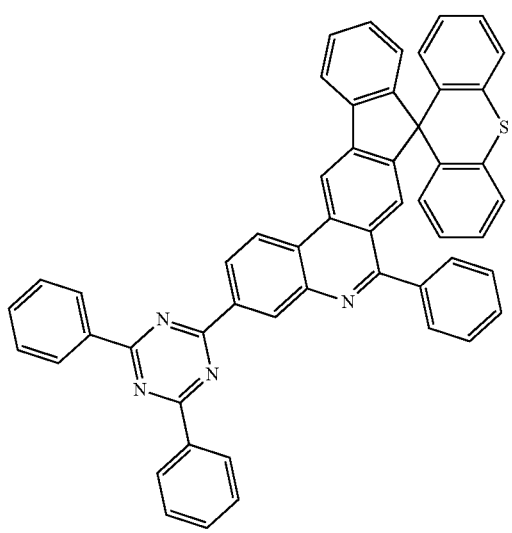
435
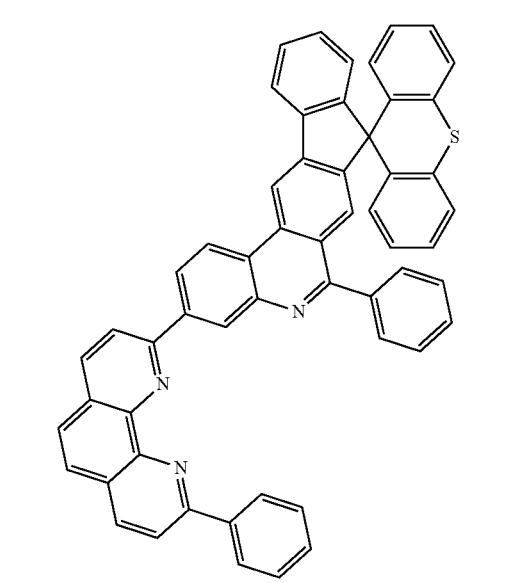
524
-continued
436
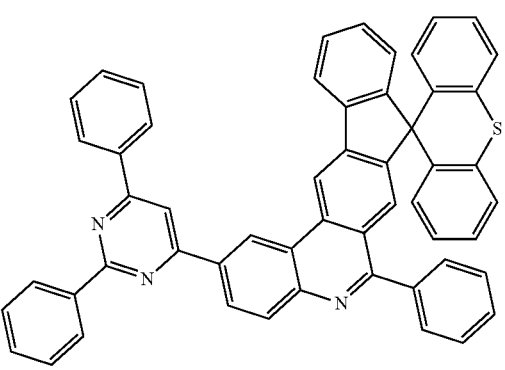
437
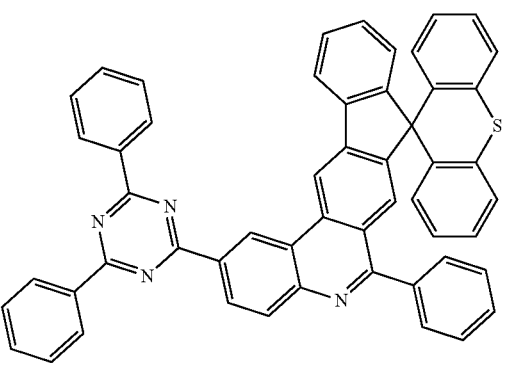
438
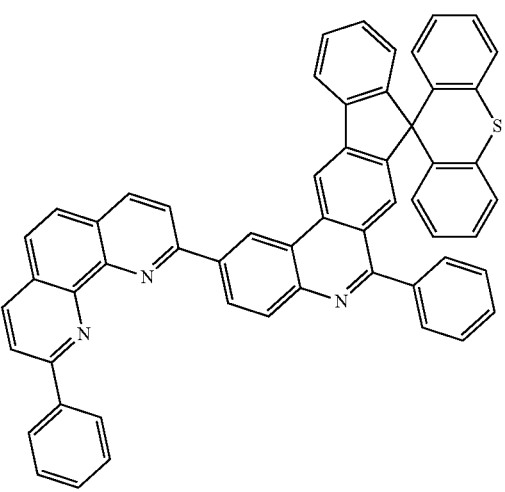

525
-continued
439
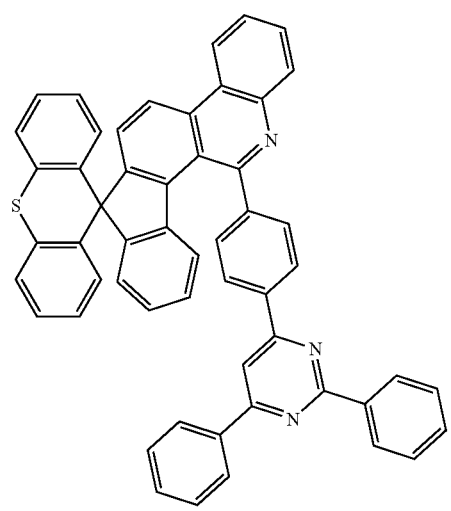
440
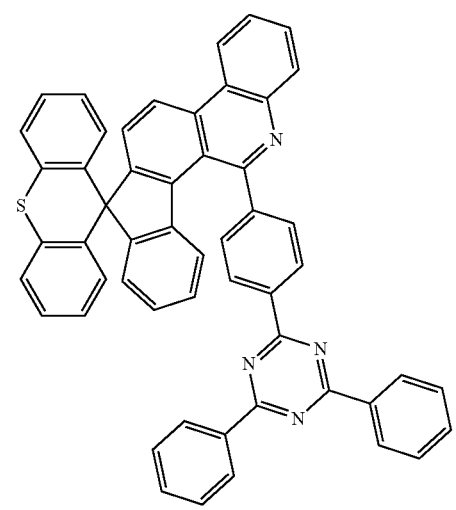
441
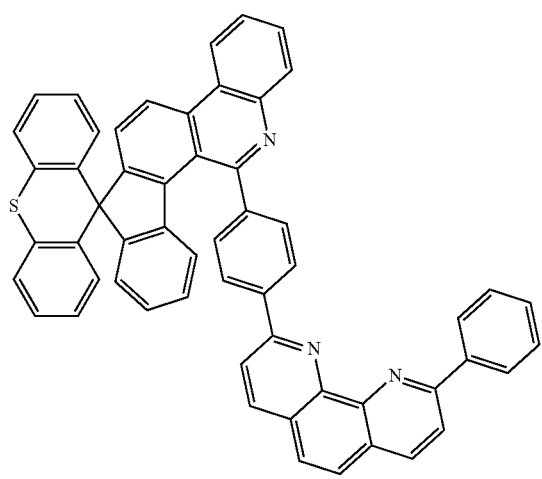
526
-continued
442
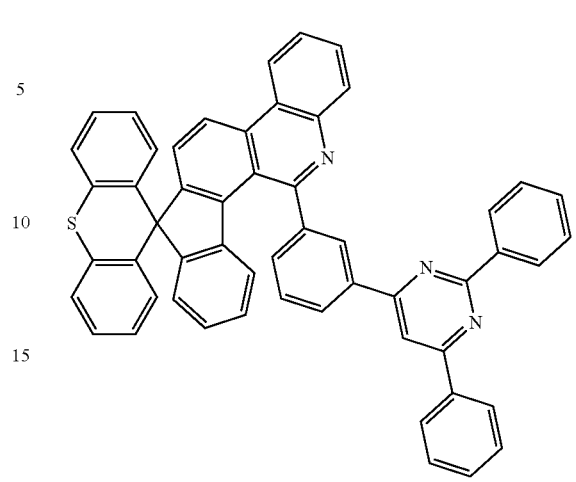
443
444
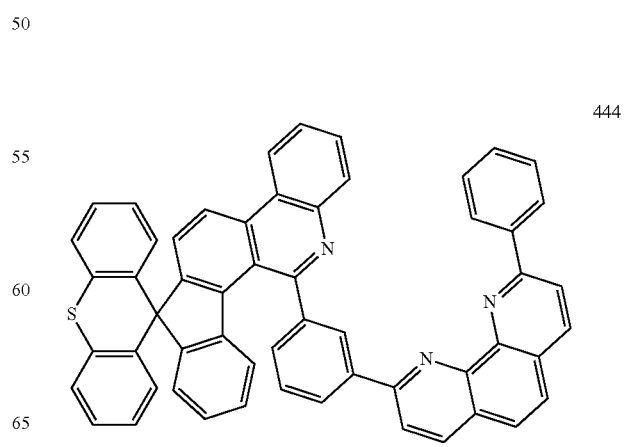

527
-continued
445
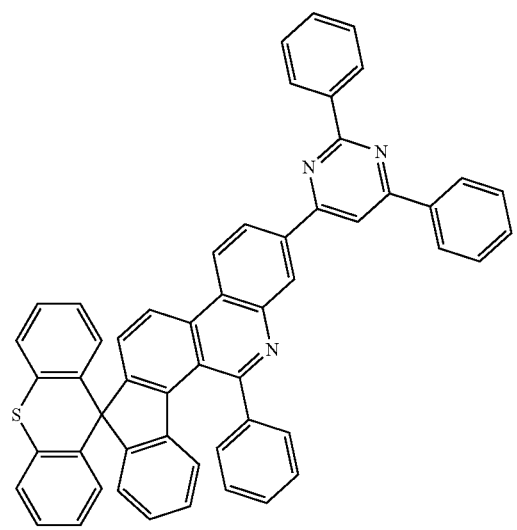
446
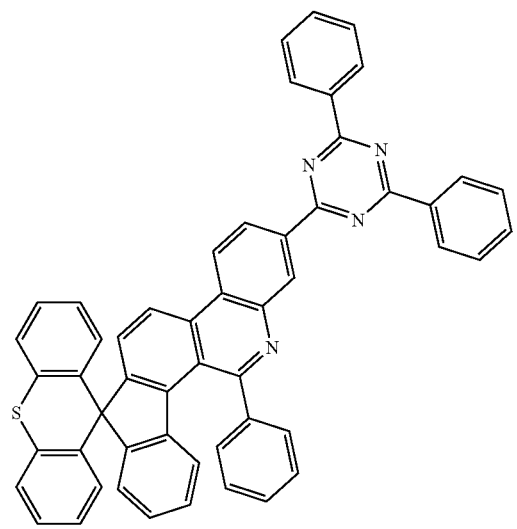
447
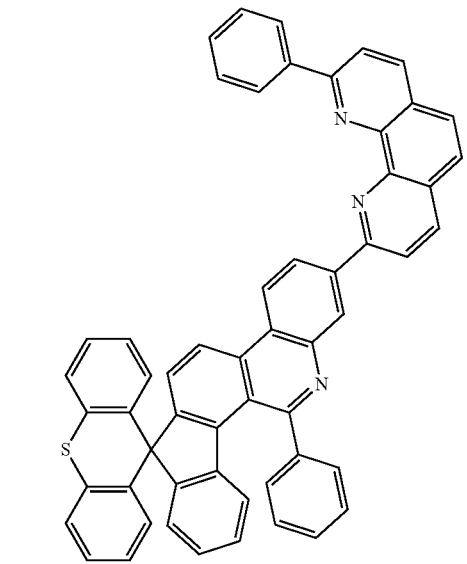
528
-continued
448
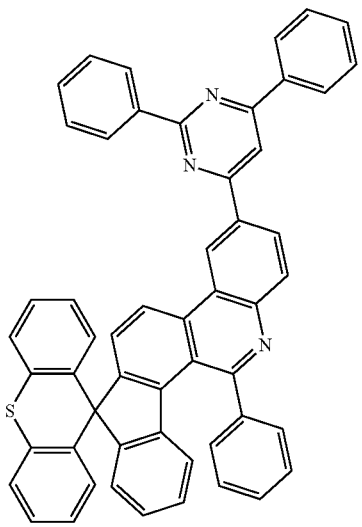
449
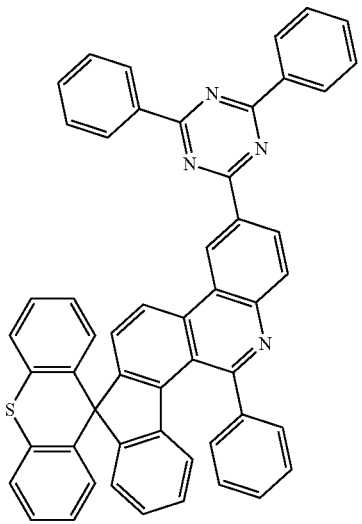
450
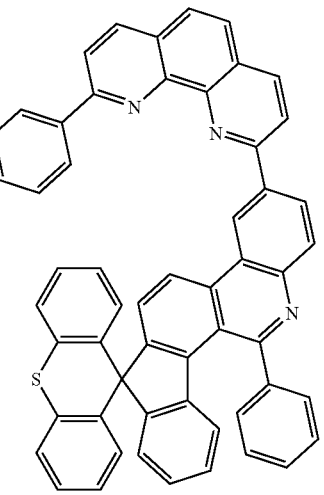

529
-continued
451
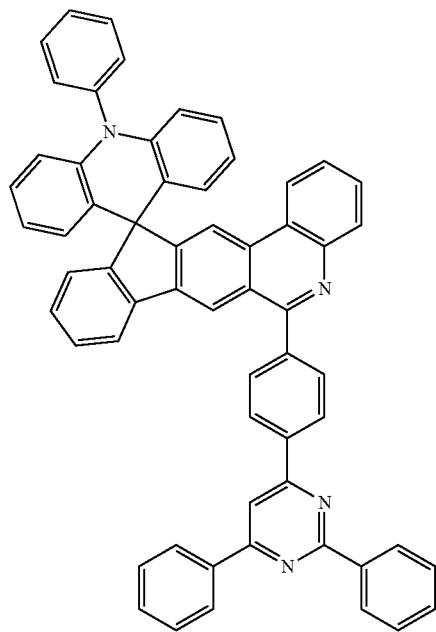
452
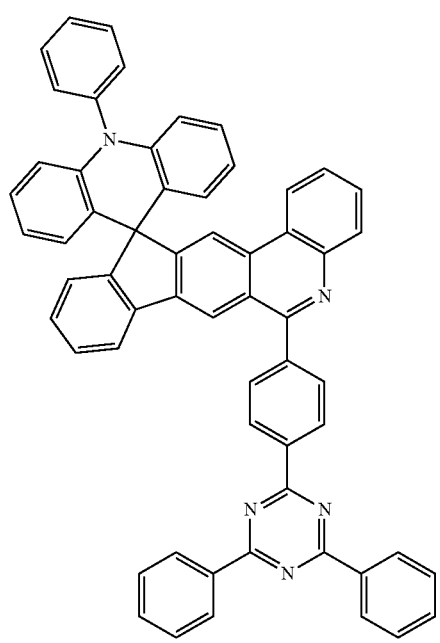
530
-continued
453
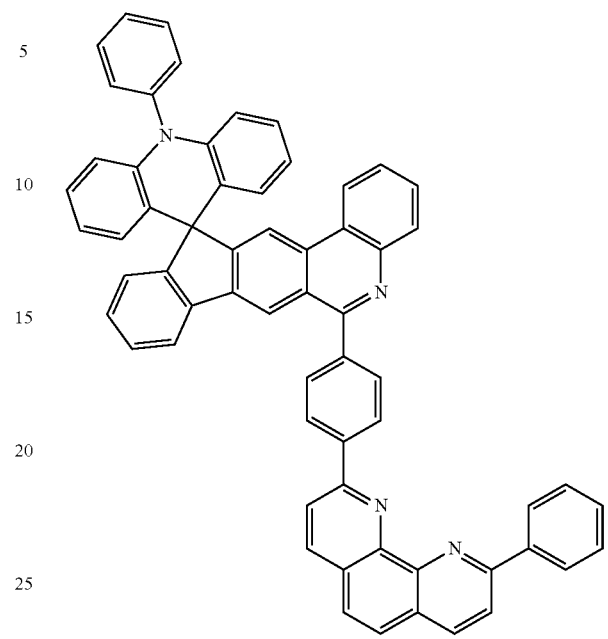
454
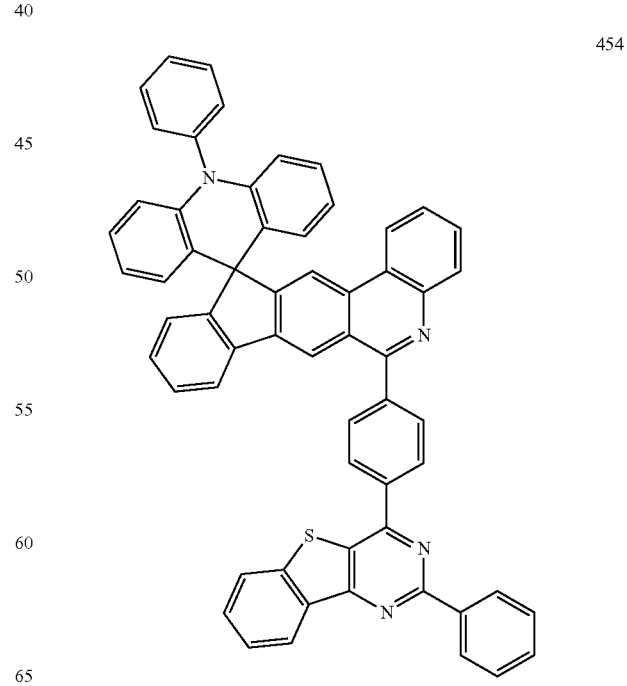

-continued
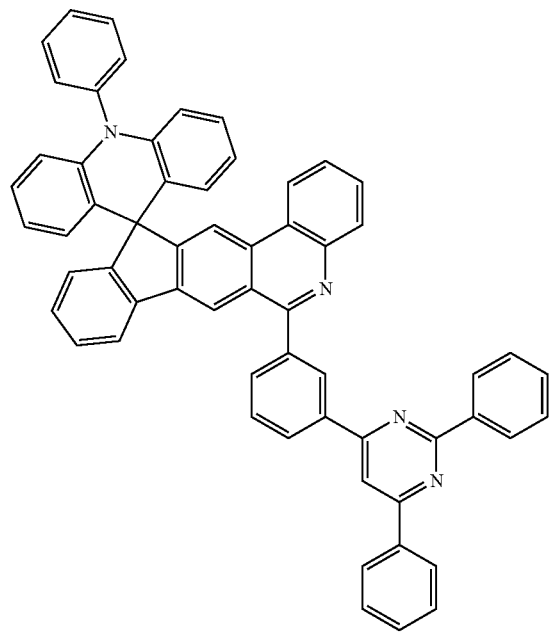
455
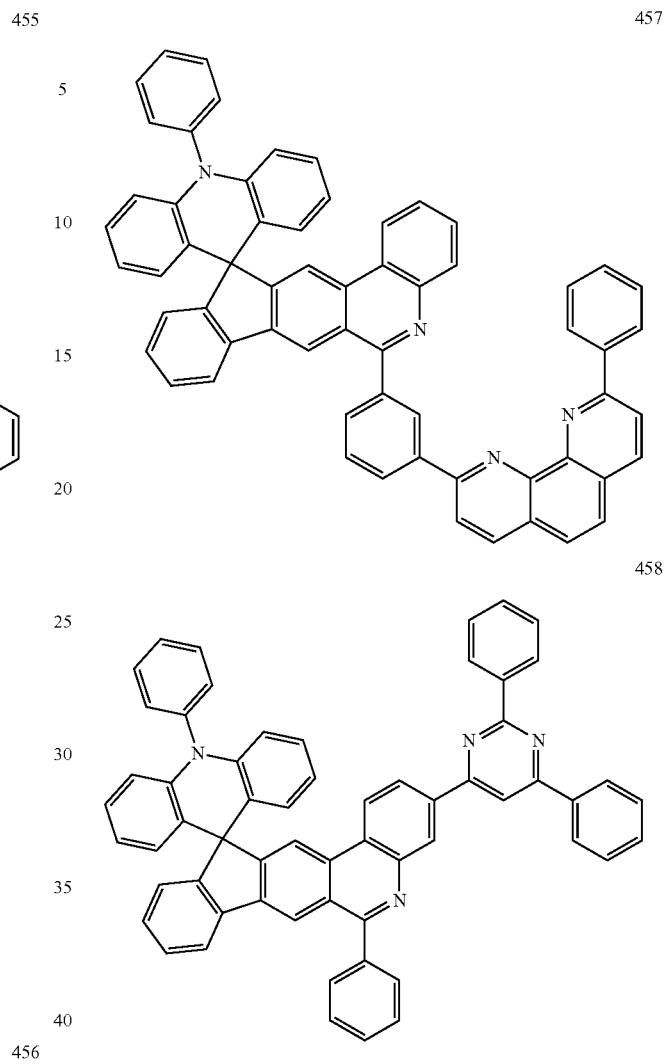
457
458
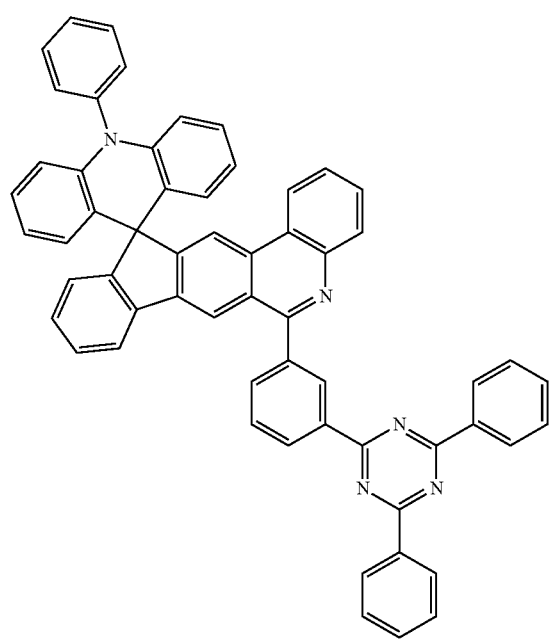
456
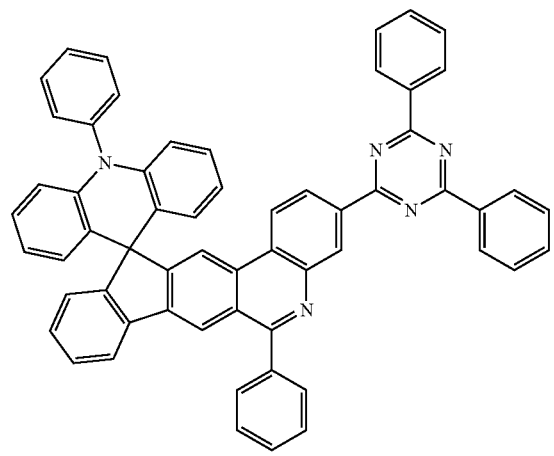
459

533
-continued
460
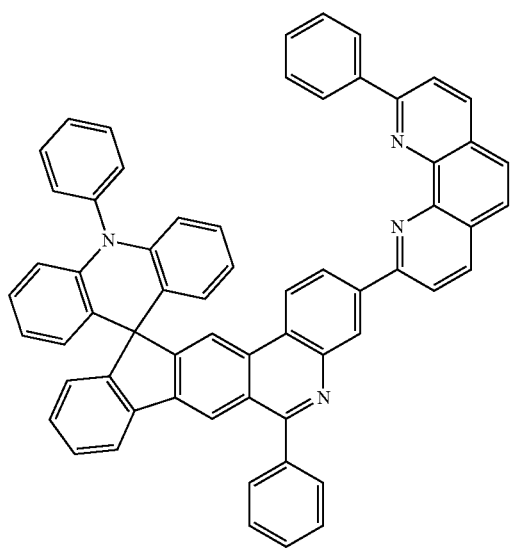
461
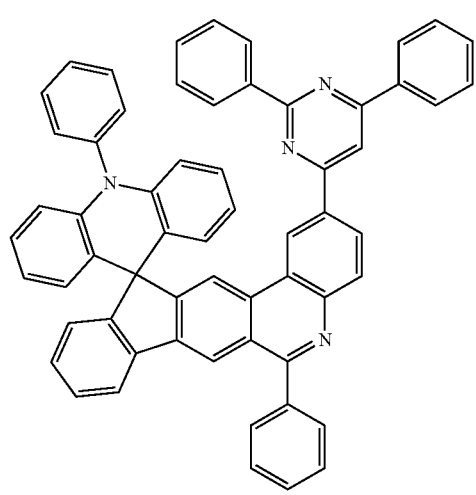
462
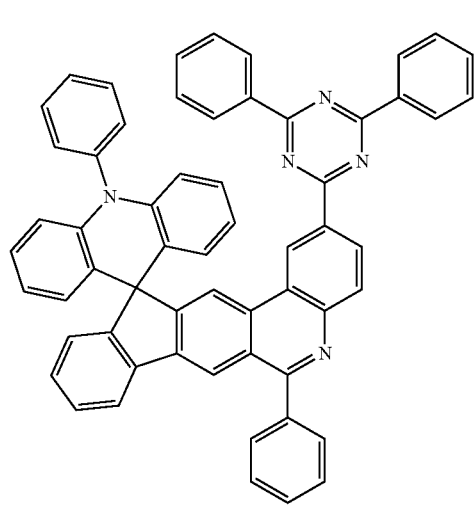
534
-continued
463
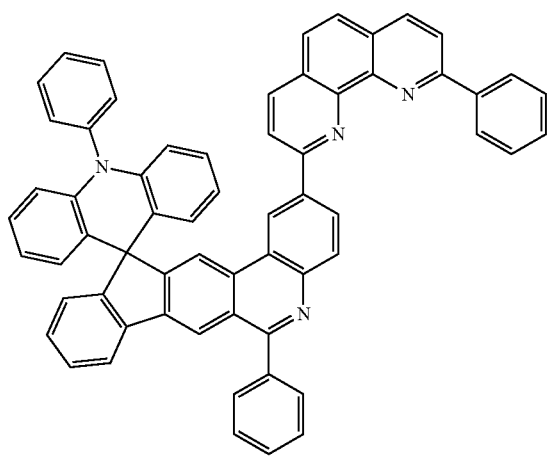
464
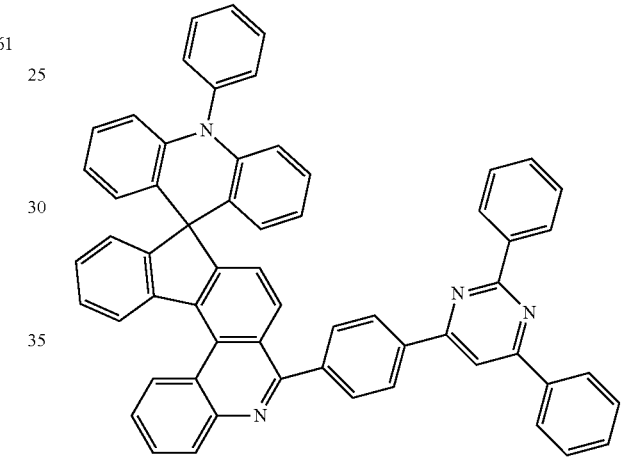
465
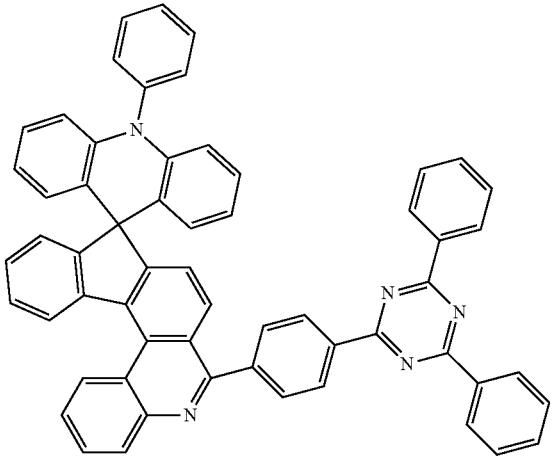

535
-continued
466
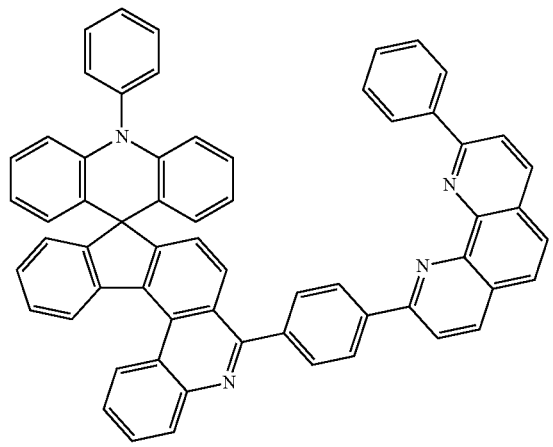
467
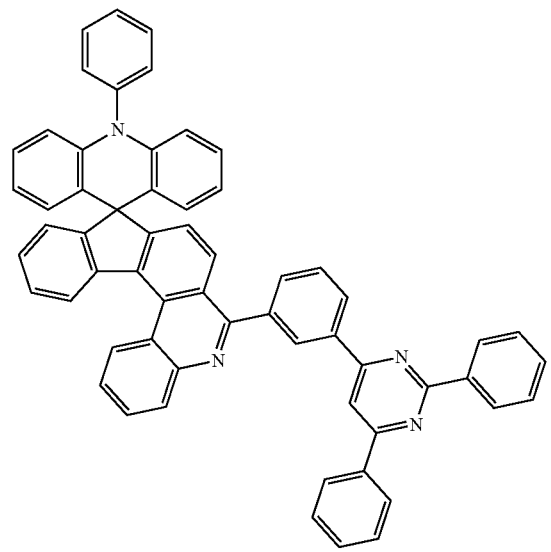
468
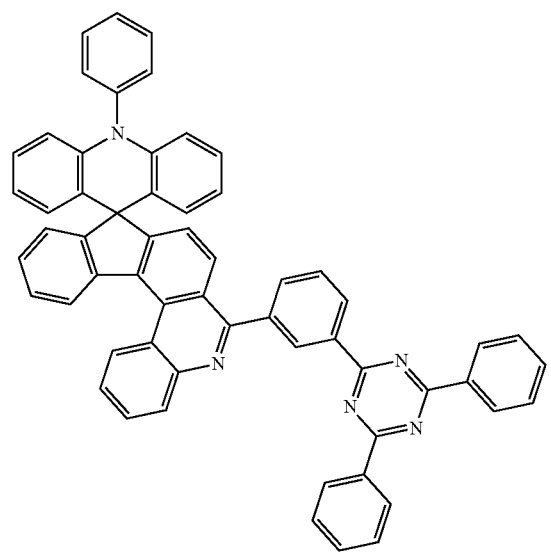
536
-continued
469
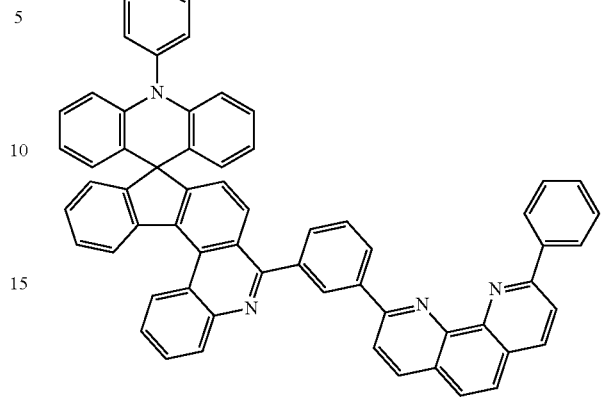
470
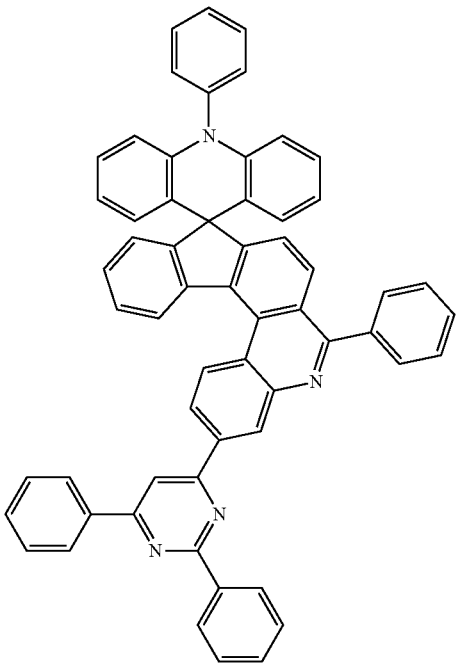

537
-continued
471
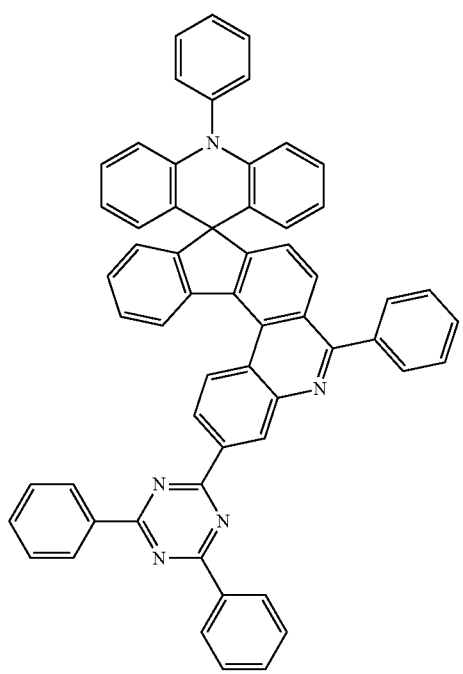
472
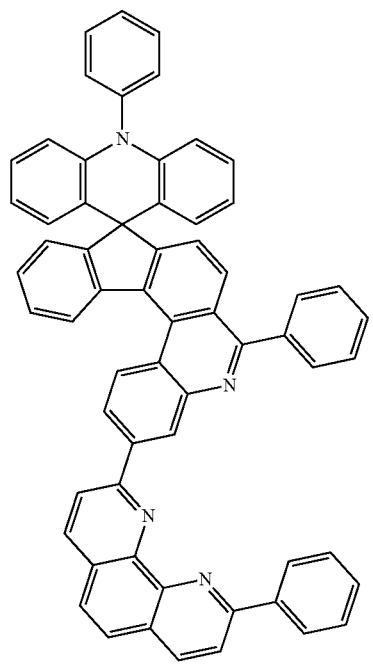
538
-continued
473
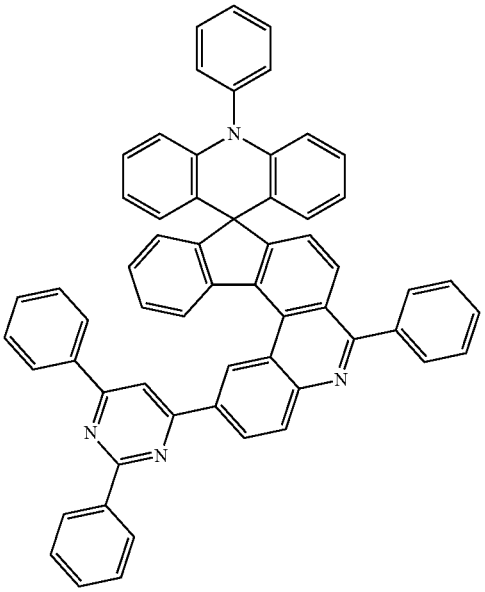
474
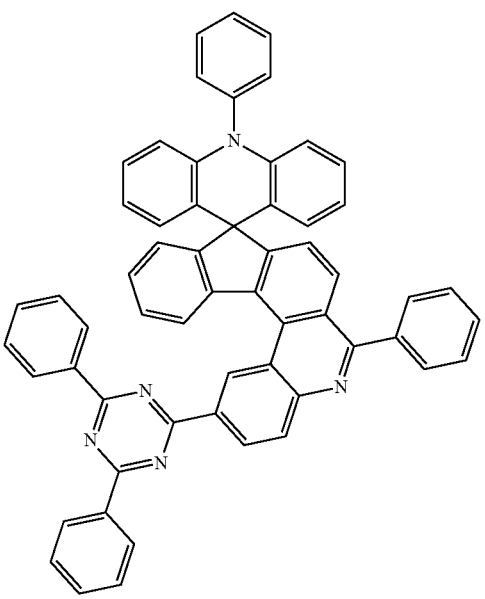

475
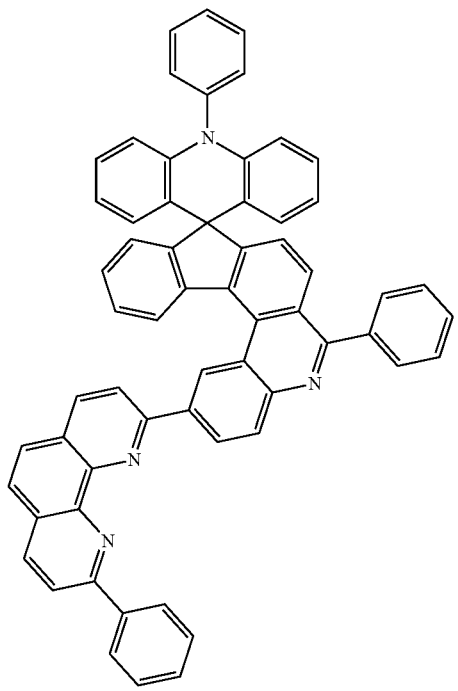
476
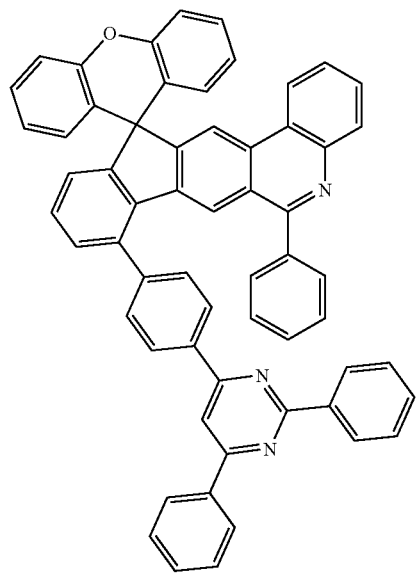
477
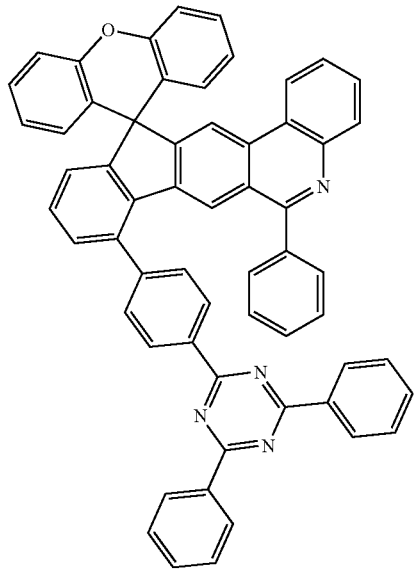
478
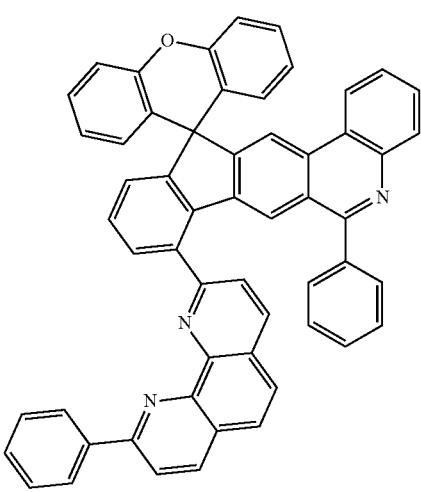
479
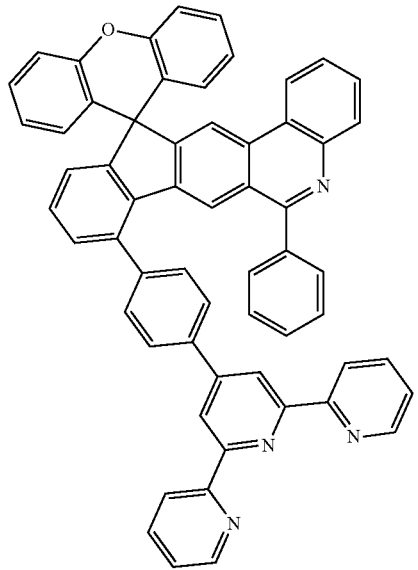

541
-continued
542
-continued
480
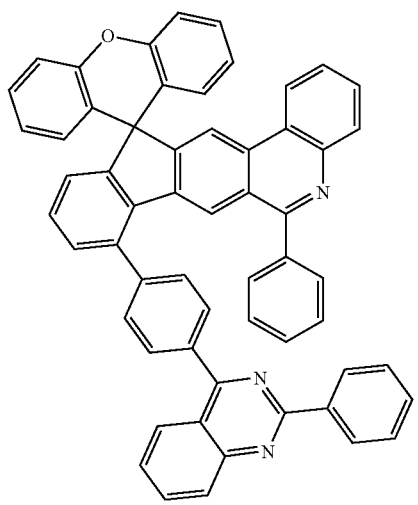
482
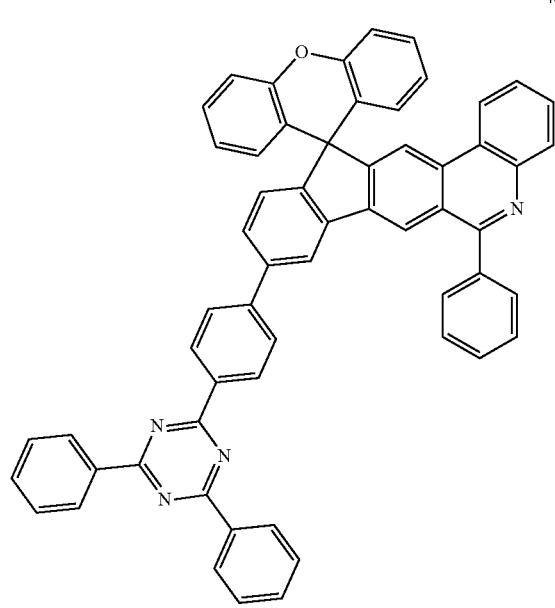
481
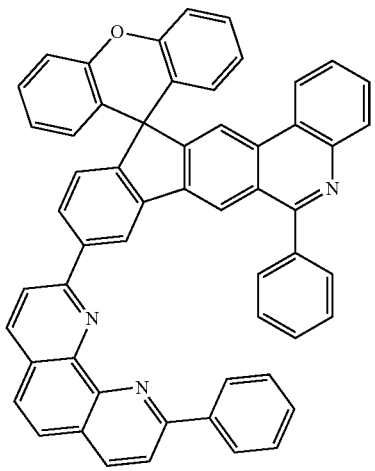
483

543
-continued
484
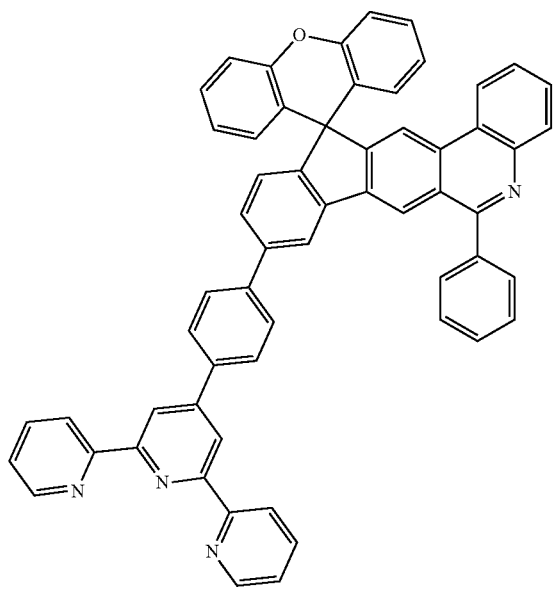
485
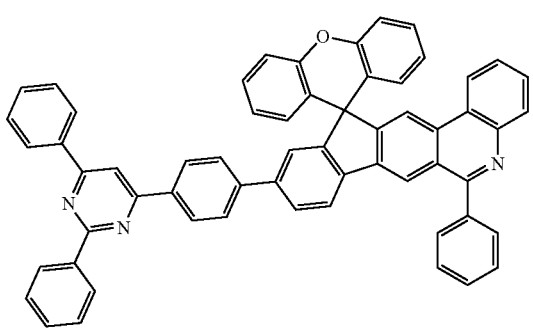
486
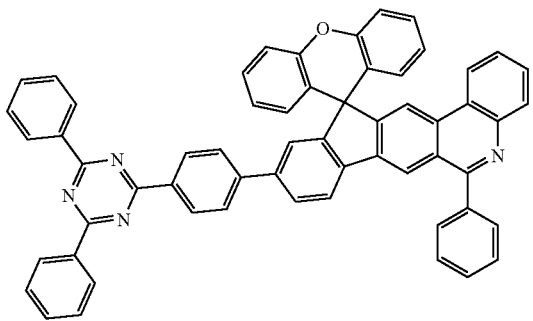
544
-continued
487
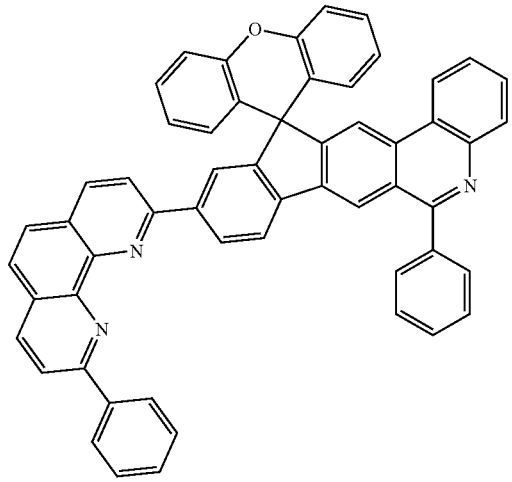
488
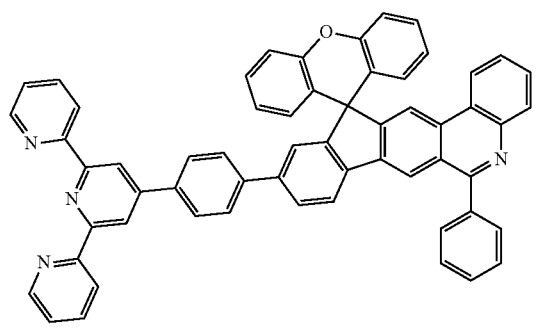
489
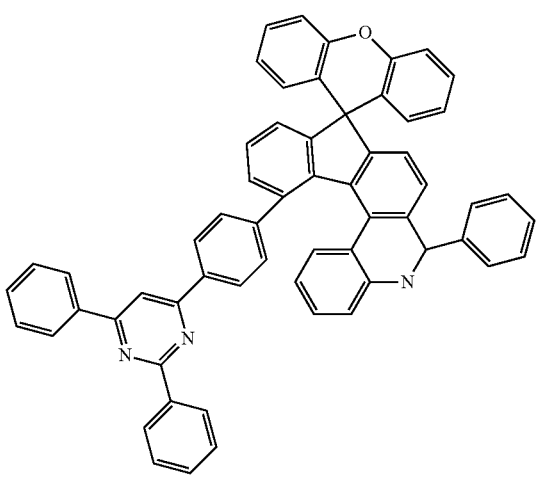

490
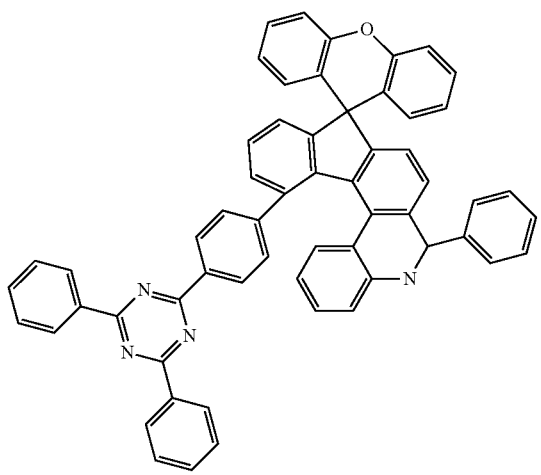
491
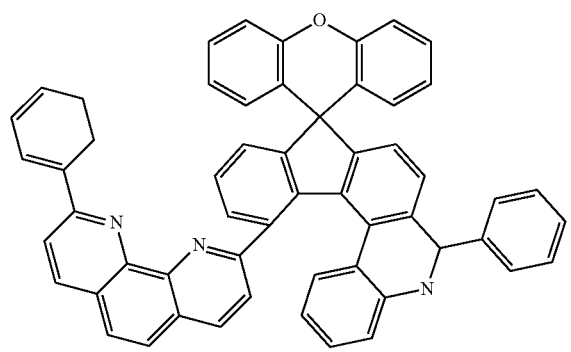
492
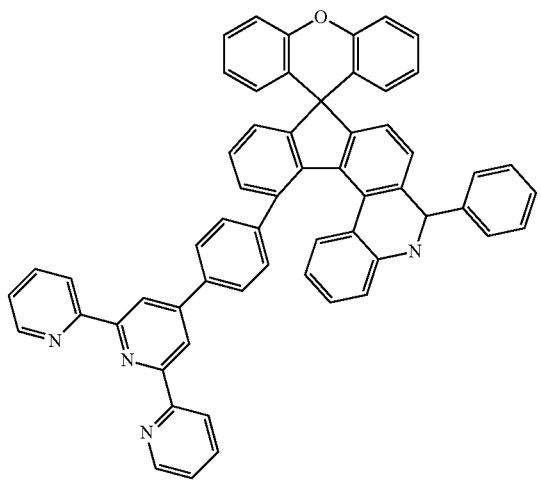
493
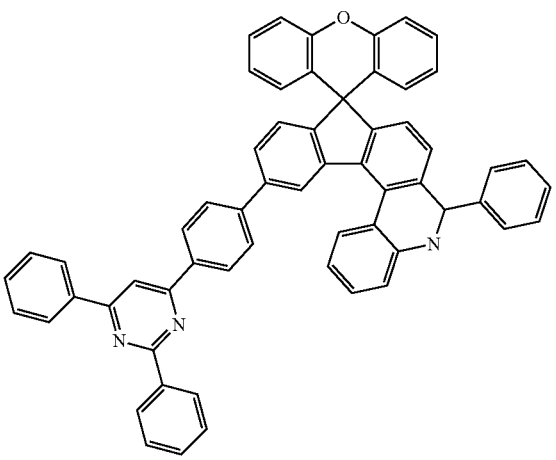
494
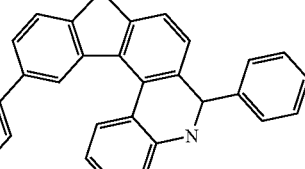
495
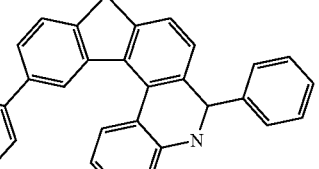

-continued
496
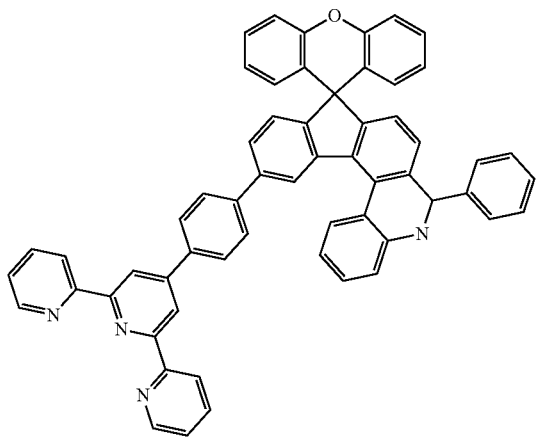
497
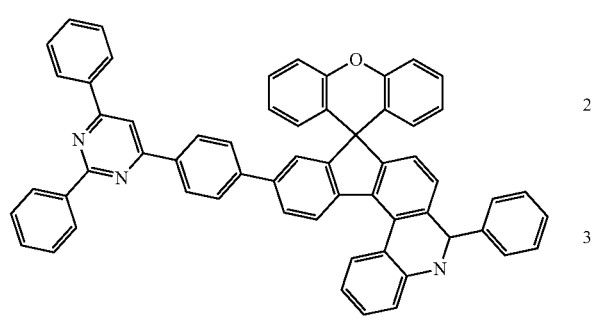
498
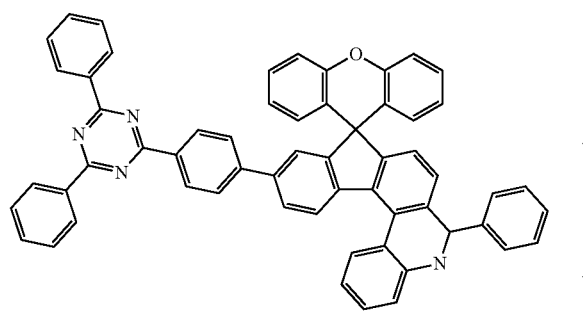
499
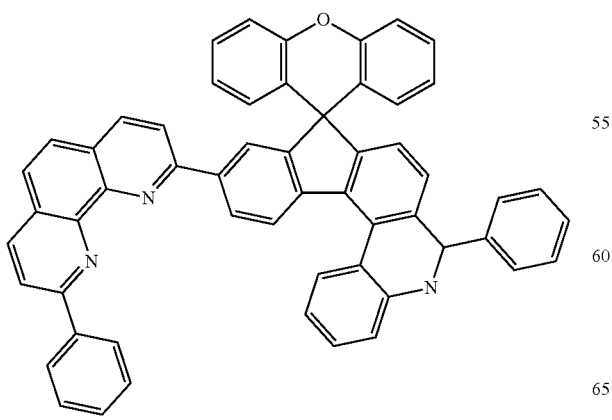
-continued
500
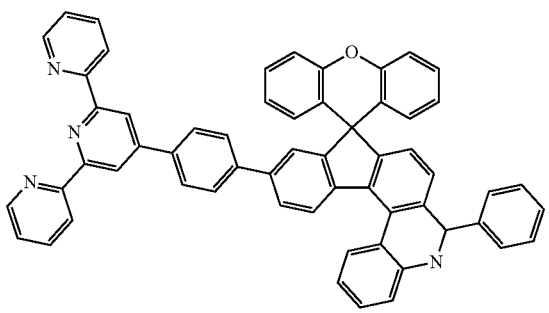
501
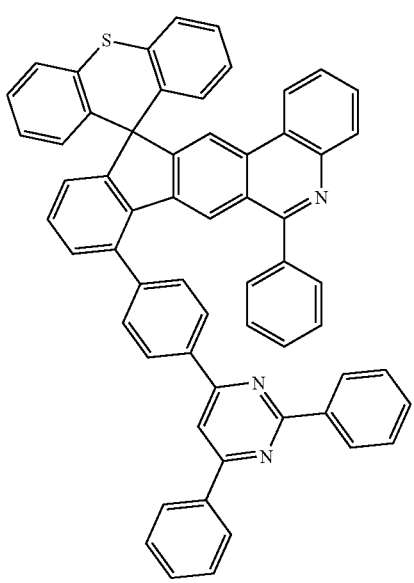
502
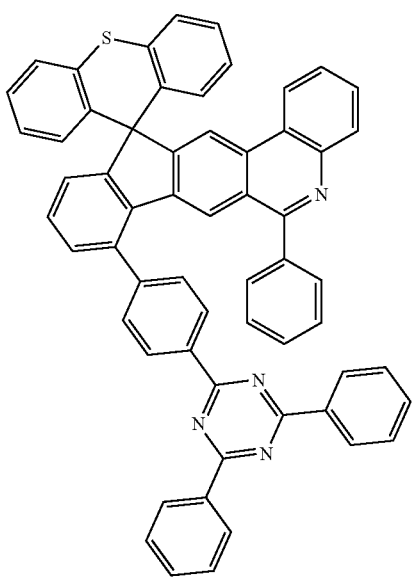

549
-continued
503
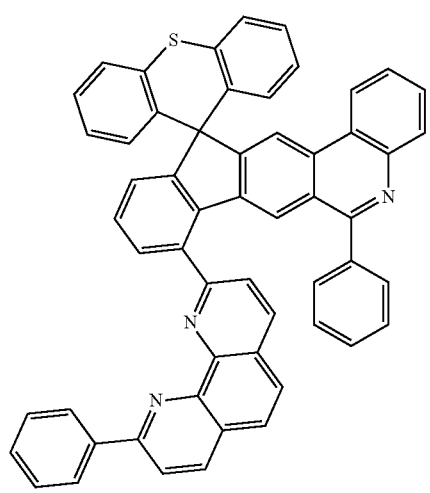
504
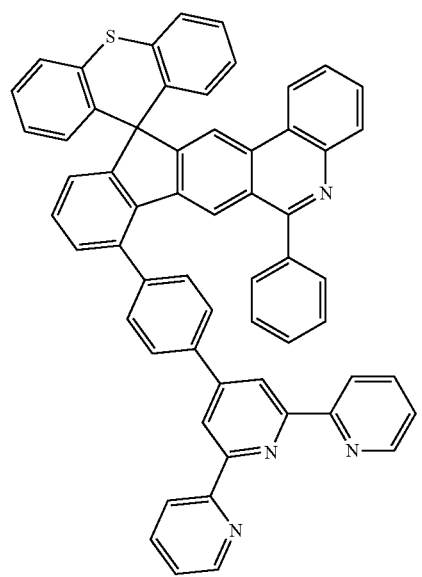
505
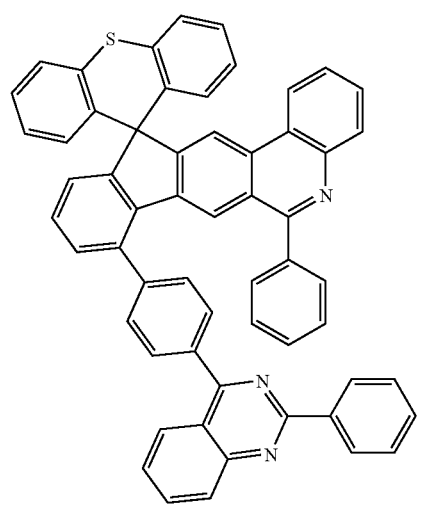
550
-continued
506
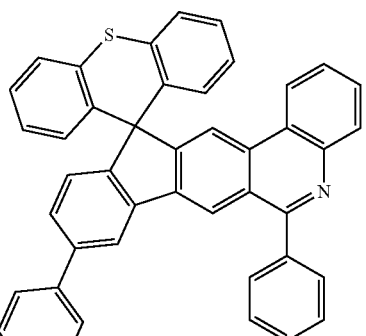
507
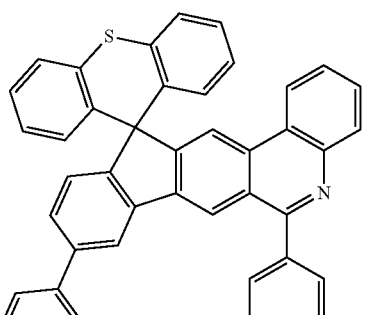

551
-continued
508
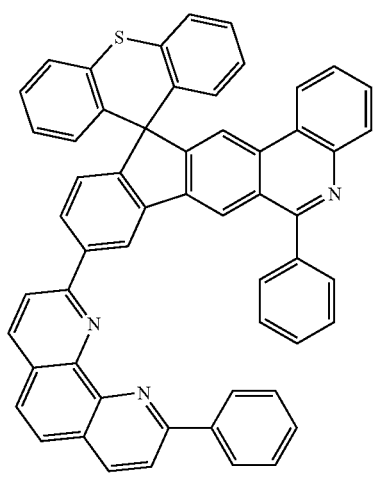
509
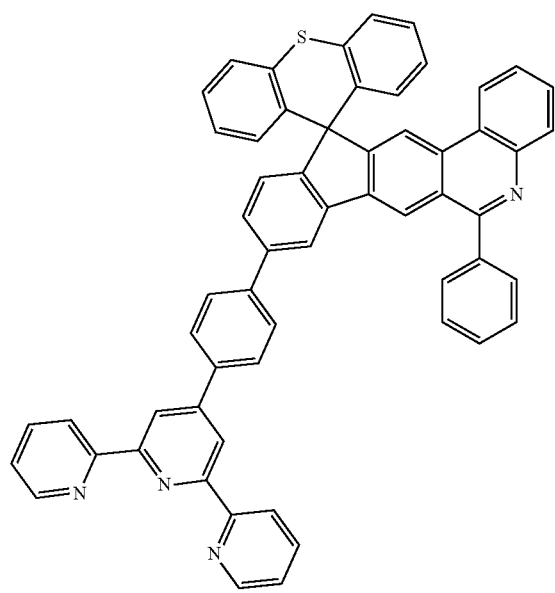
510
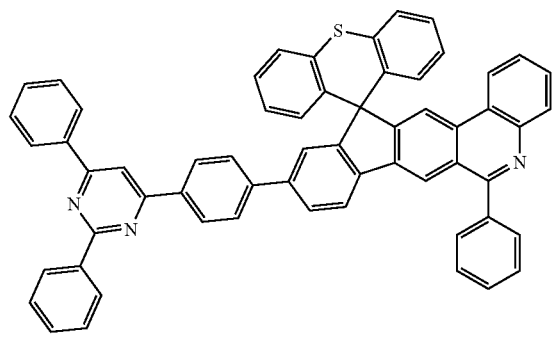
552
-continued
511
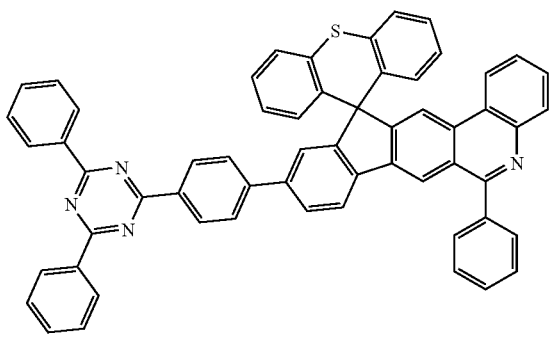
512
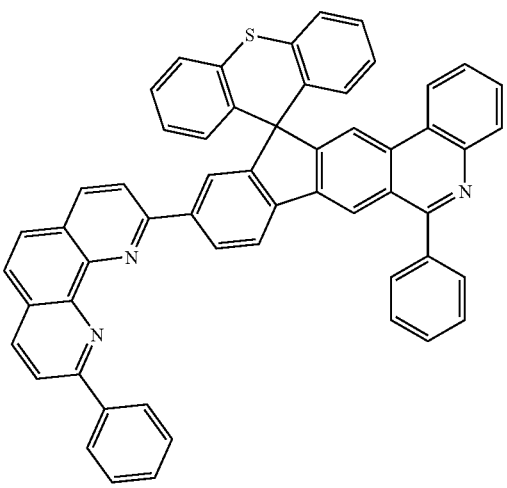
513

514 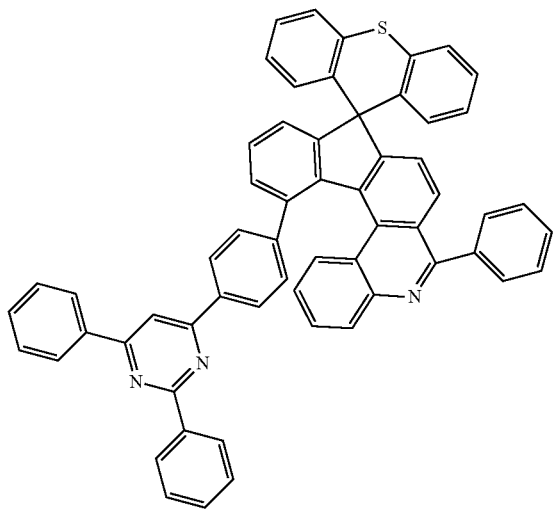
515 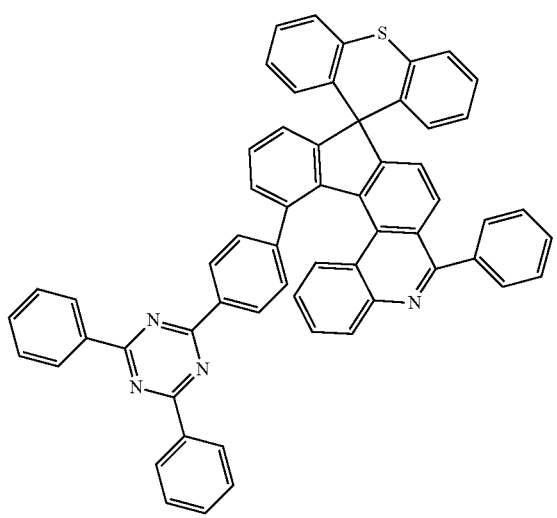
516 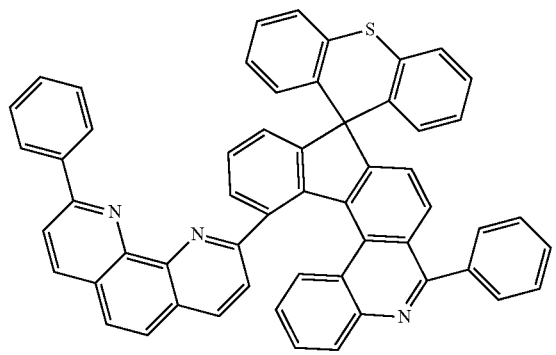
517 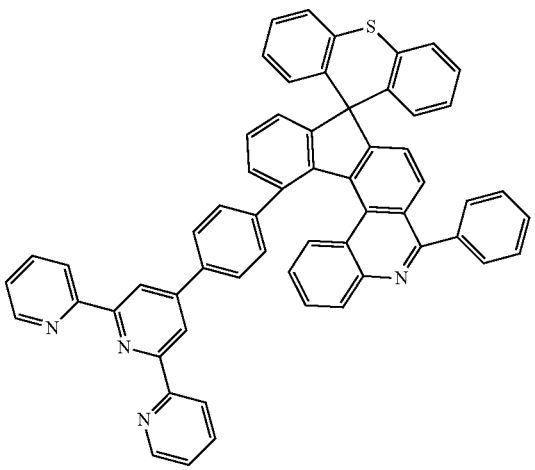
518 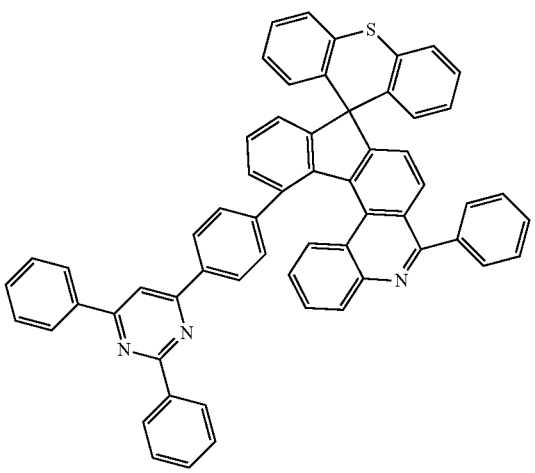
519 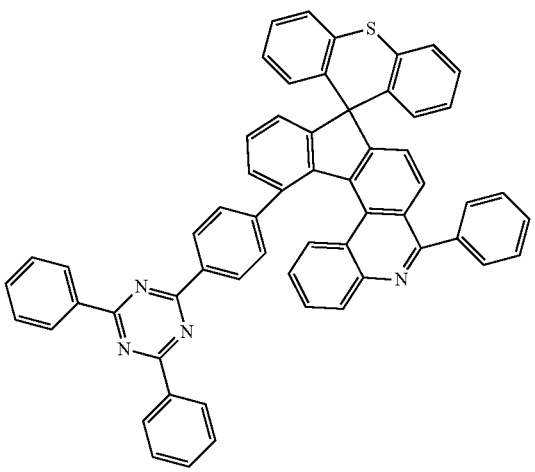

-continued
520
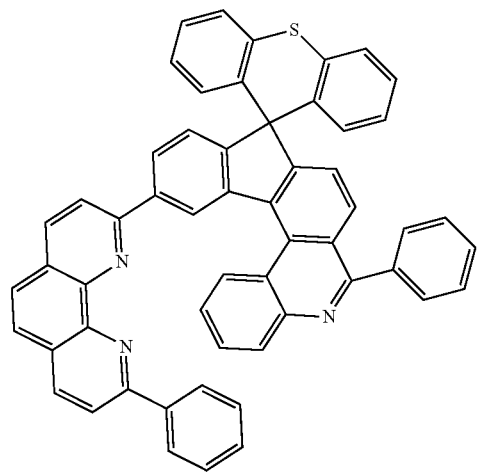
521
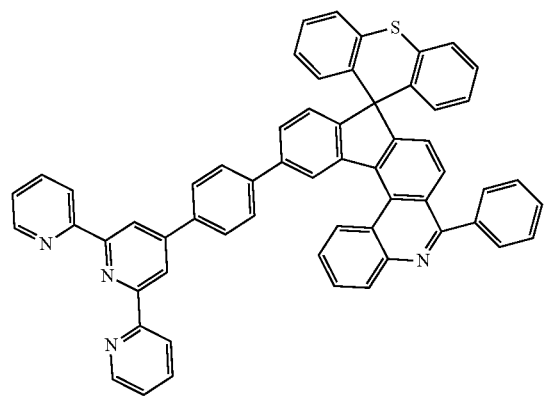
522
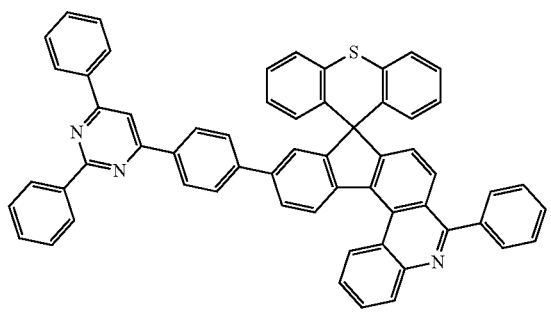
523
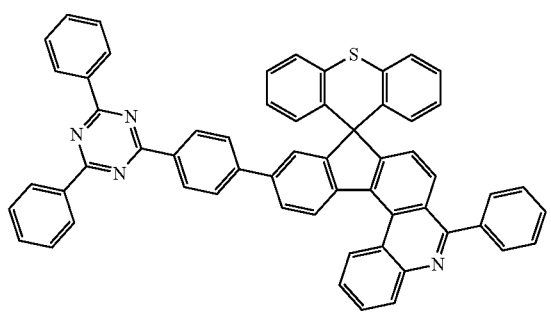
-continued
524
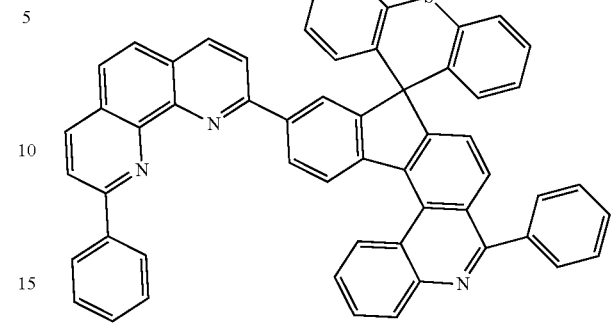
525
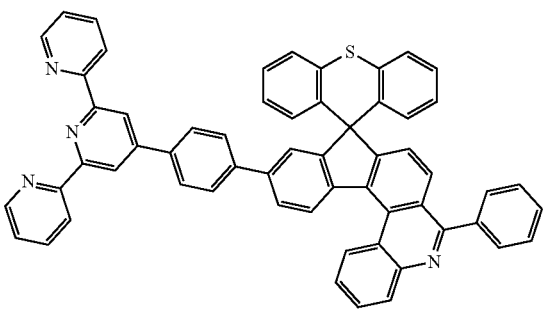
526
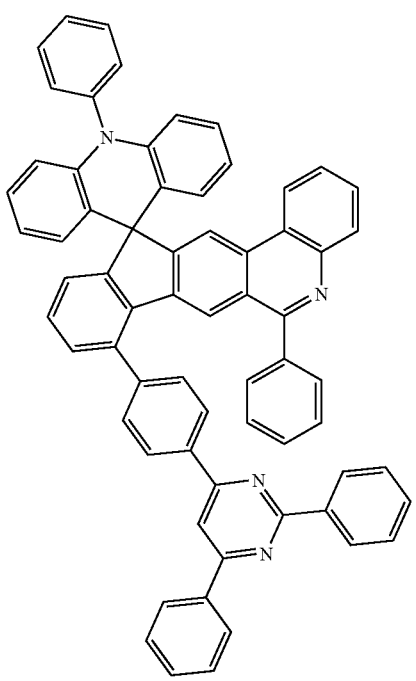

557
-continued
527
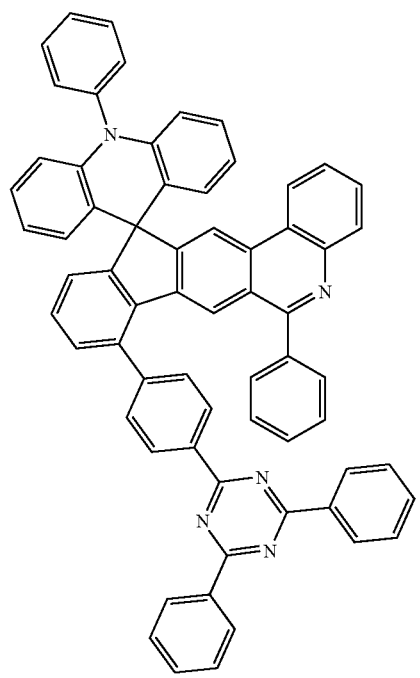
558
-continued
529
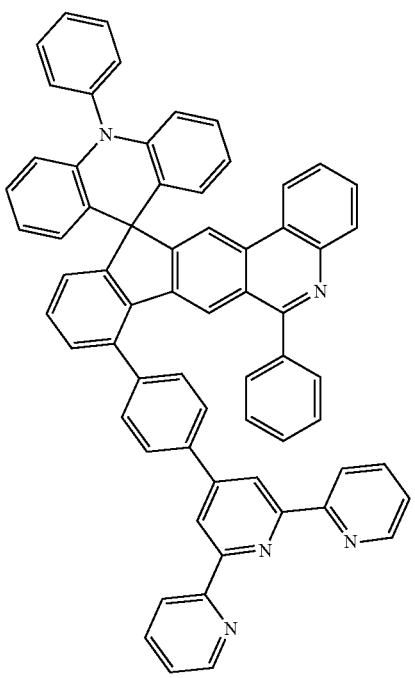
528
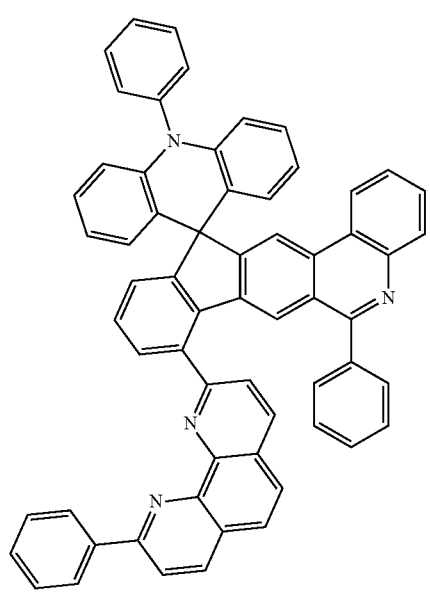
530
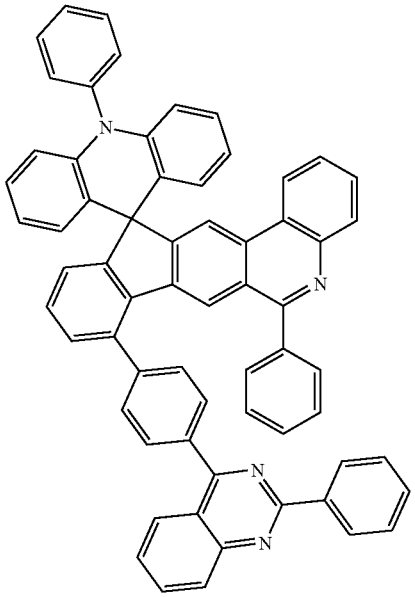

559
-continued
531
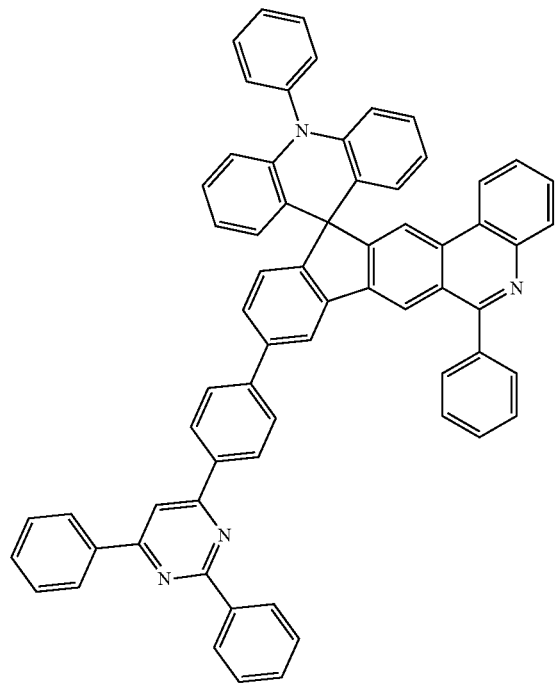
532
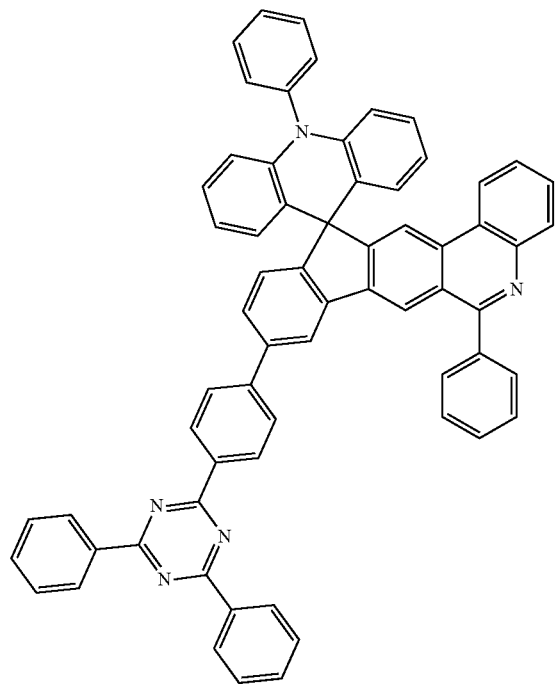
560
-continued
533
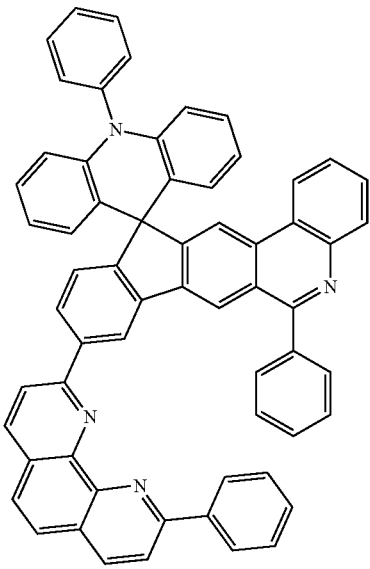
534
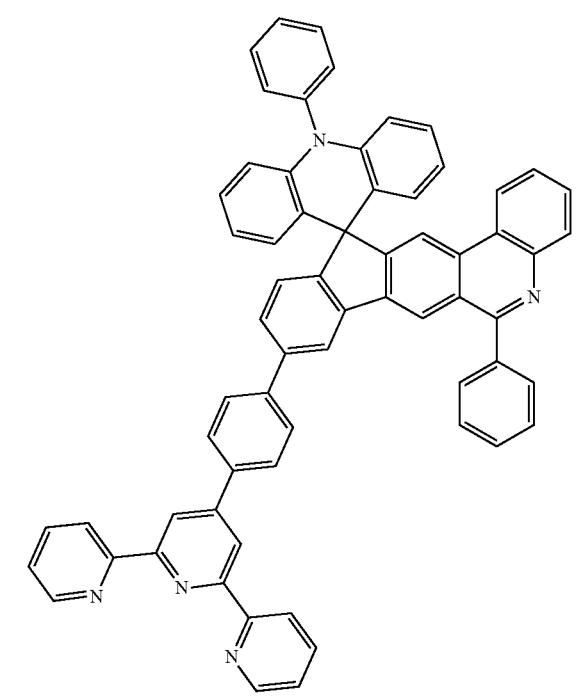

-continued
535
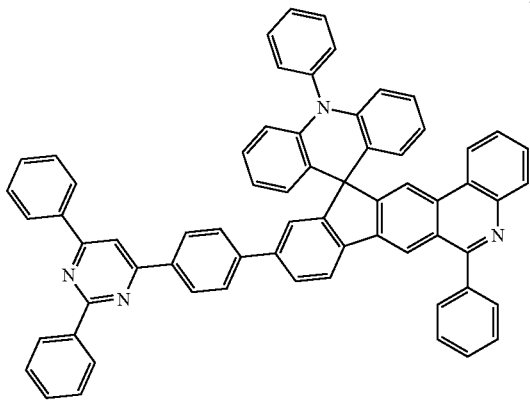
536
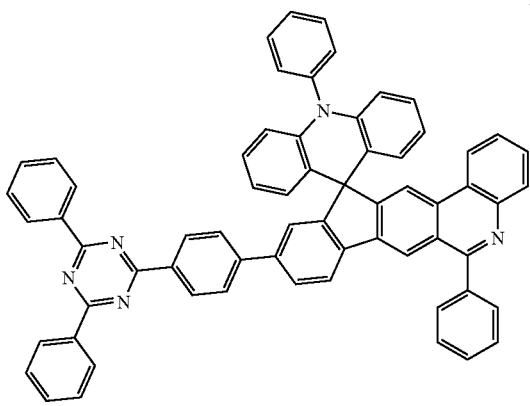
537
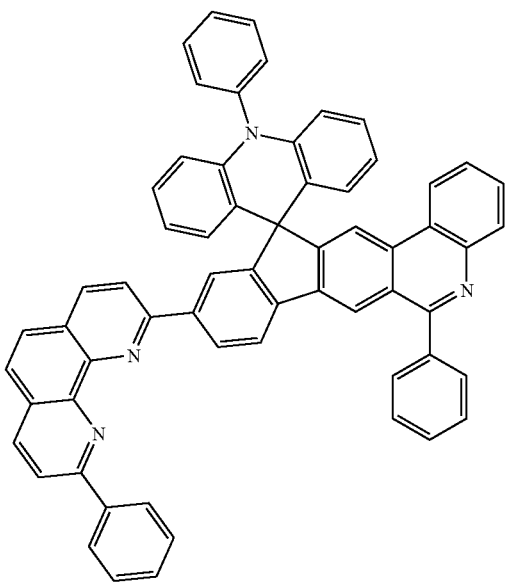
-continued
538
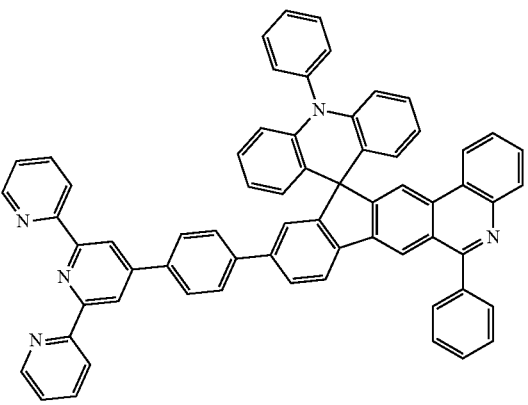
539
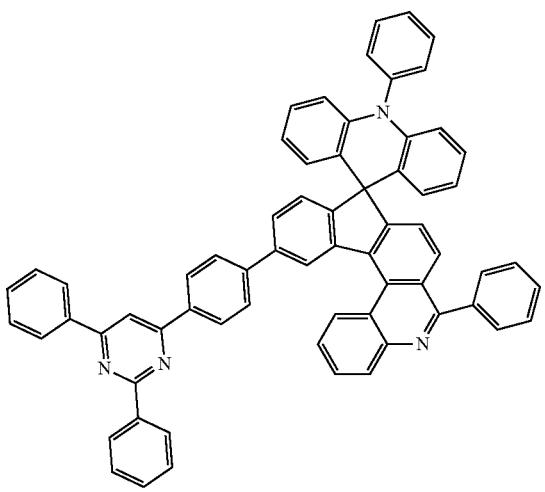
540
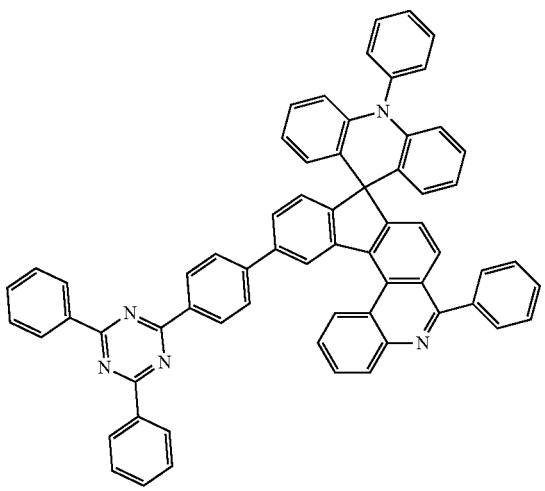

563
-continued
564
-continued
541
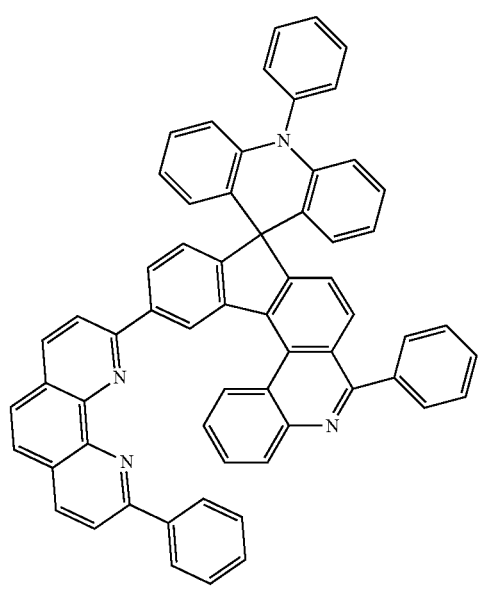
544
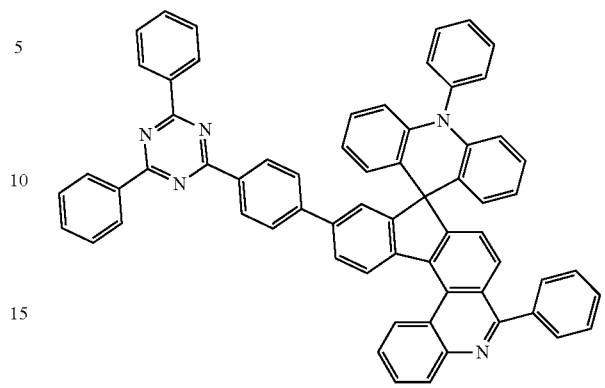
542
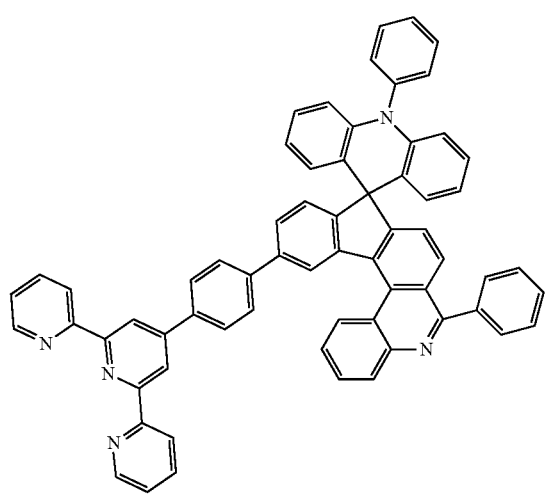
545
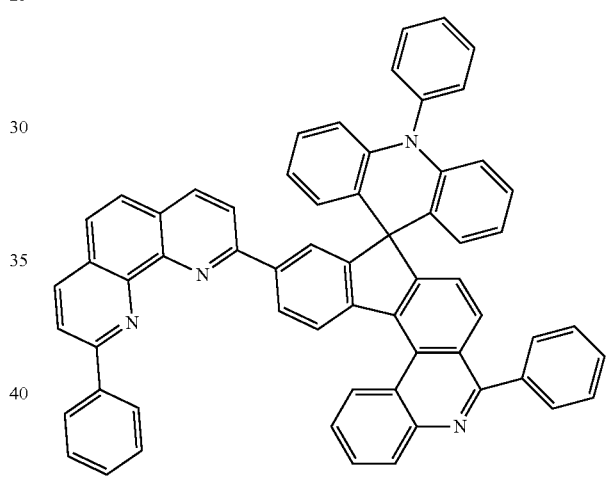
543
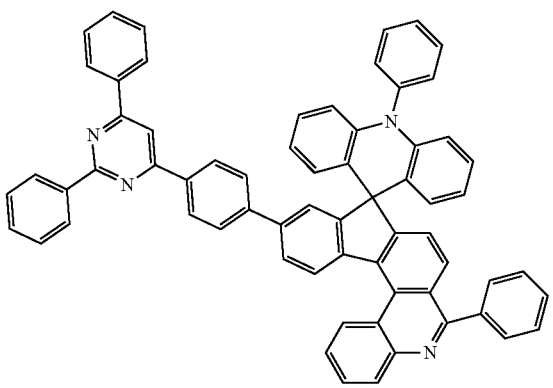
546
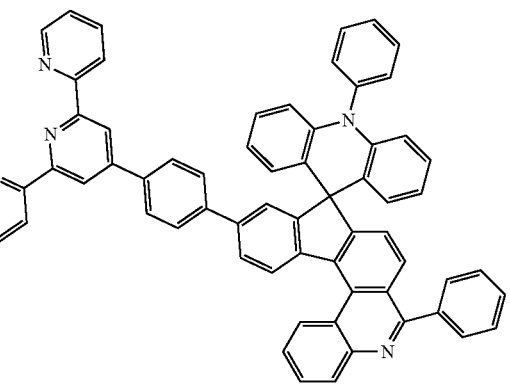

547

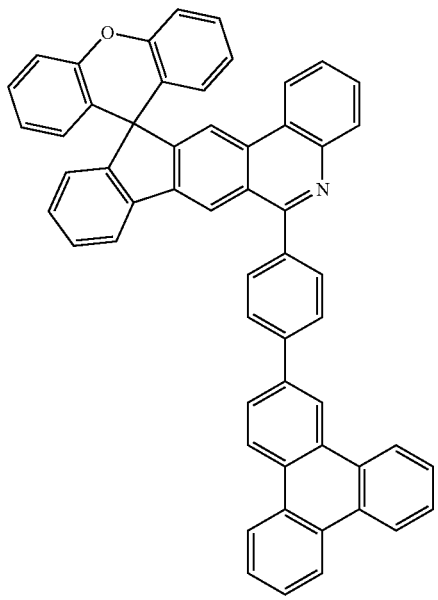

549

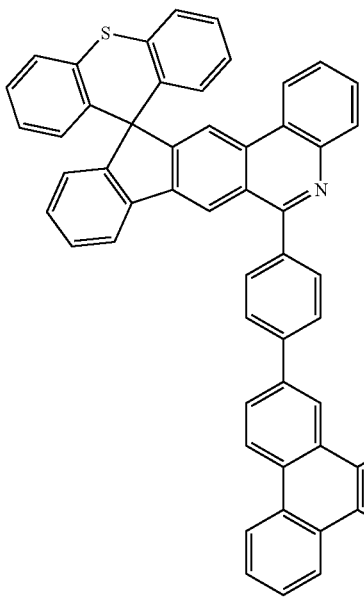

550

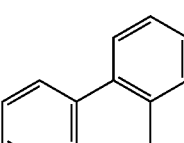

548

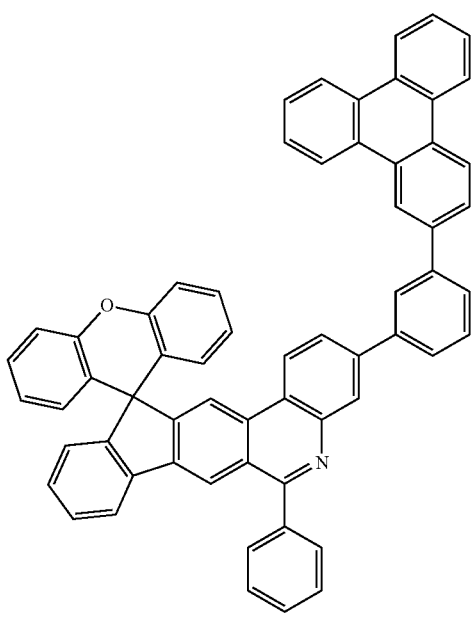

7. An organic light emitting device comprising:
   a first electrode;
   a second electrode; and
   one or more organic material layers provided between the first electrode and the second electrode,
   wherein one or more layers of the organic material layers comprise the heterocyclic compound of claim 1.

8. The organic light emitting device of claim 7, wherein the one or more organic material layers comprise an electron transfer layer, and the electron transfer layer comprises the heterocyclic compound.

9. The organic light emitting device of claim 7, wherein the one or more organic material layers comprise a hole blocking layer, and the hole blocking layer comprises the heterocyclic compound.

10. The organic light emitting device of claim 7, further comprising one, two or more layers selected from the group consisting of a light emitting layer, a hole injection layer, a hole transfer layer, an electron injection layer, an electron transfer layer, an electron blocking layer and a hole blocking layer.

11. The organic light emitting device of claim 7, comprising:
- a first electrode;
- a first stack provided on the first electrode and comprising a first light emitting layer;
- a charge generation layer provided on the first stack;
- a second stack provided on the charge generation layer and comprising a second light emitting layer; and
- a second electrode provided on the second stack.

12. The organic light emitting device of claim 11, wherein the charge generation layer comprises the heterocyclic compound represented by Chemical Formula 1.

13. The organic light emitting device of claim 11, wherein the charge generation layer is an N-type charge generation layer, and the charge generation layer comprises the heterocyclic compound represented by Chemical Formula 1.

* * * * *